(12) United States Patent
Takemoto et al.

(10) Patent No.: US 7,582,665 B2
(45) Date of Patent: Sep. 1, 2009

(54) COMPOUNDS EXHIBITING THROMBOPOIETIN RECEPTOR AGONISM

(75) Inventors: Hiroshi Takemoto, Osaka (JP); Takeshi Shiota, Osaka (JP); Masami Takayama, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 403 days.

(21) Appl. No.: 10/169,362

(22) PCT Filed: Jan. 23, 2001

(86) PCT No.: PCT/JP01/00411

§ 371 (c)(1),
(2), (4) Date: Jul. 2, 2002

(87) PCT Pub. No.: WO01/53267

PCT Pub. Date: Jul. 26, 2001

(65) Prior Publication Data

US 2003/0195231 A1 Oct. 16, 2003

(30) Foreign Application Priority Data

Jan. 24, 2000 (JP) ............... 2000-13770
Feb. 8, 2000 (JP) ............... 2000-30593

(51) Int. Cl.
A61K 31/425 (2006.01)
C07D 277/593 (2006.01)
A01N 43/78 (2006.01)

(52) U.S. Cl. .................. 514/366; 514/371; 548/150; 548/190; 548/198

(58) Field of Classification Search ............. 514/366, 514/371; 548/150, 190, 195, 198
See application file for complete search history.

(56) References Cited

U.S. PATENT DOCUMENTS

| 5,112,867 | A | * | 5/1992 | Kinoshita et al. | ........... 514/617 |
|---|---|---|---|---|---|
| 5,413,997 | A | * | 5/1995 | Kinoshita et al. | ........... 514/183 |
| 5,607,952 | A | | 3/1997 | Badorc et al. | ........... 514/326 |
| 5,654,622 | A | | 8/1997 | Toya et al. | ........... 320/21 |
| 5,869,451 | A | | 2/1999 | Dower et al. | |
| 6,140,330 | A | * | 10/2000 | Mori et al. | ........... 514/254.03 |
| 6,225,323 | B1 | * | 5/2001 | Yatscoff et al. | ........... 514/292 |
| 6,306,871 | B1 | * | 10/2001 | Yatscoff et al. | ........... 514/292 |
| 6,555,519 | B2 | * | 4/2003 | Washburn | ........... 514/3 |
| 6,670,387 | B1 | | 12/2003 | Luengo et al. | |
| 6,737,382 | B1 | * | 5/2004 | Iwataki et al. | ........... 504/252 |
| 2004/0063764 | A1 | | 4/2004 | Takemoto et al. | |
| 2004/0082626 | A1 | | 4/2004 | Takemoto et al. | |
| 2005/0153977 | A1 | | 7/2005 | Sugasawa et al. | |

2007/0043087 A1 2/2007 Takayama et al.

FOREIGN PATENT DOCUMENTS

| EP | 0 295656 B1 | 12/1988 |
|---|---|---|
| EP | 0 656355 A1 | 7/1995 |
| EP | 0 719775 B1 | 7/1996 |
| EP | 1 207 155 A1 | 5/2002 |
| EP | 1 253 142 A1 | 10/2002 |
| EP | 1 466 912 A1 | 10/2004 |
| JP | 7/112975 | 5/1995 |
| JP | 10072492 | 3/1998 |
| JP | 10287634 | 10/1998 |
| JP | 11001477 | 1/1999 |
| JP | 11152276 | 6/1999 |
| WO | WO 94/04516 | 6/1995 |
| WO | WO 96/40750 | 12/1996 |
| WO | WO 00/35446 | 6/2000 |
| WO | WO 01/07423 A1 | 2/2001 |
| WO | WO 01/53267 A1 | 7/2001 |
| WO | WO 02/059099 A1 | 8/2002 |
| WO | WO 02/059100 A1 | 8/2002 |
| WO | WO 03/062233 A1 | 7/2003 |

OTHER PUBLICATIONS

Vippagunta, S.R. et. al., "Crystalline solids", Adv. Drug Del. Rev., 2001, Vol. 48, pp. 3-26.*
Vigon et al., Molecular cloning and characterization of *MPL*, the human homolog of the *v-mpl* oncogene: Identification of a member of the hematopoietic growth factor receptor superfamily, *P.N.A.S.* 89:5640-5644 (1992).

* cited by examiner

*Primary Examiner*—James O Wilson
*Assistant Examiner*—Tamthom N Truong
(74) *Attorney, Agent, or Firm*—Finnegan, Henderson, Farabow, Garrett & Dunner, LLP

(57) ABSTRACT

Pharmaceutical compositions containing as an active ingredient compounds of the general formula (I), prodrugs of the same, pharmaceutically acceptable salts of both, or solvates of them and exhibiting thrombopoietin receptor agonism:

$$X^1-Y^1-Z^1-W^1 \qquad (I)$$

wherein $X^1$ is optionally substituted aryl, optionally substituted heteroaryl or the like; $Y^1$ is $-NR^4CO-(CH_2)_{0-2}-$ or the like (wherein $R^4$ is a hydrogen or the like); $Z^1$ is optionally substituted phenylene or the like; and $W^1$ is a group represeted by the below formula:

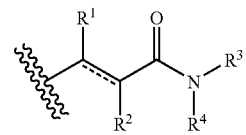

wherein $R^1$, $R^2$, $R^3$, and $R^4$ are each independently a hydrogen atom, optionally substituted lower alkyl or the like, a broken line ( - - - ) represents the presence or absence of bond.

6 Claims, 3 Drawing Sheets

COMPOUNDS EXHIBITING THROMBOPOIETIN RECEPTOR AGONISM

TECHNICAL FIELD

The present invention relates to compounds exhibiting thrombopoietin receptor agonism.

BACKGROUND ART

Thrombopoietin, polypeptide cytokine composed of 332 amino acids, activates the production of platelets by stimulating the differentiation and proliferation of megakaryocytes through the receptor and is expected as a medicine for hemopathy accompanied with the unusual number of platelets, for example, thrombocytopenia and the like. DNA sequences encoding the thrombopoietin receptor have been described in Proc. Natl. Acad. Sci., 89, 5640-5644 (1992). Low molecular peptides having an affinity for the thrombopoietin receptor is also known (JP98/72492A and WO96/40750), but these peptide derivatives are not generally practical for oral administration.

1,4-Benzodiazepine derivatives as a low molecule compound having an affinity to the thrombopoietin receptor is described in JP99/1477A and JP99/152276A.

The compounds having a similar structure of the present invention compound are described in JP98/287634A and the like, but the affinity for thrombopoietin receptor is not described therein.

DISCLOSURE OF INVENTION

The object of the present invention is to prepare pharmaceutical compositions exhibiting thrombopoietin receptor agonism and provide orally administrable platelet production modifiers.

In the above situation, the inventors of the present invention have found that the following compounds exhibit strong thrombopoietin receptor agonism.

The present invention relates to:

I) A pharmaceutical composition exhibiting thrombopoietin receptor agonism which contains as an active ingredient a compound of the general formula (I):

$$X^1-Y^1-Z^1-W^1 \qquad (I)$$

wherein $X^1$ is optionally substituted aryl, optionally substituted aralkyl, optionally substituted heteroaryl, or optionally substituted heteroarylalkyl; $Y^1$ is —$NR^A$CO—$(CR^C R^D)_{0-2}$—, —$NR^A$CO—$(CH_2)_{0-2}$—V—, —$NR^A$CO—$CR^C$=$CR^D$—, —V—$(CH_2)_{1-5}$—$NR^A$CO—$(CH_2)_{0-2}$—, —V—$(CH_2)_{1-5}$—$CONR^A$—$(CH_2)_{0-2}$—, —$CONR^A$—$(CH_2)_{0-2}$—, —$(CH_2)_{0-2}$—$NR^A$—$SO_2$-$(CH_2)_{0-2}$—, —$(CH_2)_{0-2}$—$SO_2$—$NR^A$—$(CH_2)_{0-2}$—, —$NR^A$—$(CH_2)_{0-2}$—, —$NR^A$—CO—$NR^A$—, —$NR^A$—CS—$NR^A$—, —N=C(—$SR^A$)—$NR^A$—, —$NR^A$CSNR^A$CO—, —N=C(—$SR^A$)—$NR^A$CO—, —$NR^A$—$(CH_2)_{1-2}$—$NR^A$—CO—, —$NR^A$CONR^A NR^B$CO—, or —N=C(—$NR^A R^A$)—$NR^A$—CO—, wherein $R^A$ is each independently a hydrogen atom or lower alkyl; $R^B$ is a hydrogen atom or phenyl; $R^C$ and $R^D$ are each independently a hydrogen atom, halogen atom, optionally substituted lower alkyl, optionally substituted lower alkyloxy, optionally substituted lower alkylthio, optionally substituted lower alkenyl, optionally substituted lower alkynyl, optionally substituted aryl, optionally substituted heteroaryl, optionally substituted cycloalkyl, optionally substituted aralkyl, optionally substituted heteroarylalkyl, optionally substituted non-aromatic heterocyclic group, or optionally substituted amino; V is an oxygen atom or a sulfur atom;

$Z^1$ is optionally substituted phenylene, optionally substituted monocyclic heteroarylene, optionally substituted monocyclic non-aromatic heterocycle-diyl, or optionally substituted monocyclic cycloalkane-diyl;

$W^1$ is a group represented by the formula:

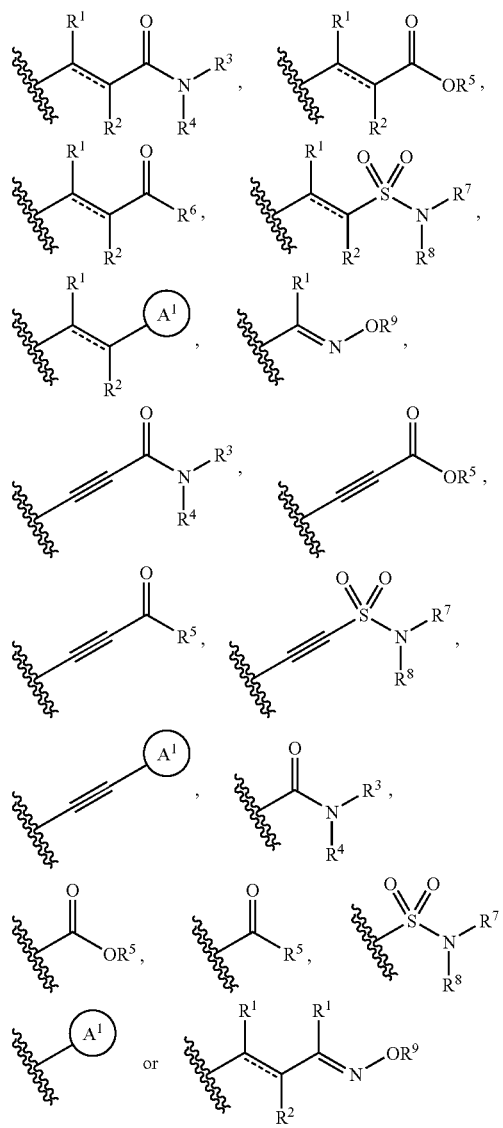

wherein $R^1$, $R^2$, $R^3$, $R^4$, $R^7$, and $R^8$ are each independently a hydrogen atom, halogen atom, optionally substituted lower alkyl, optionally substituted lower alkyloxy, optionally substituted lower alkylthio, optionally substituted lower alkenyl, optionally substituted lower alkynyl, optionally substituted aryl, optionally substituted heteroaryl, optionally substituted cycloalkyl, optionally substituted aralkyl, optionally substituted heteroarylalkyl, optionally substituted non-aromatic heterocyclic group, or optionally substituted amino;

$R^5$, $R^6$, and $R^9$ are each independently a hydrogen atom, optionally substituted lower alkyl, optionally substituted lower alkenyl, optionally substituted lower alkynyl, optionally substituted aryl, optionally substituted heteroaryl, optionally substituted cycloalkyl, optionally substituted aralkyl, optionally substituted heteroarylalkyl, or optionally substituted non-aromatic heterocyclic group;

$A^1$ is a optionally substituted aryl or optionally substituted heteroaryl;

a broken line ( - - - ) represents the presence or absence of a bond, its prodrug, or their pharmaceutically acceptable salt, or solvate thereof.

In more detail, the invention relates to the following II) to XXIX).

II) A pharmaceutical composition exhibiting thrombopoietin receptor agonism of I), wherein $X^1$ is optionally substituted heteroaryl.

III) A pharmaceutical composition exhibiting thrombopoietin receptor agonism of I), wherein $X^1$ is a group represented by the formula:

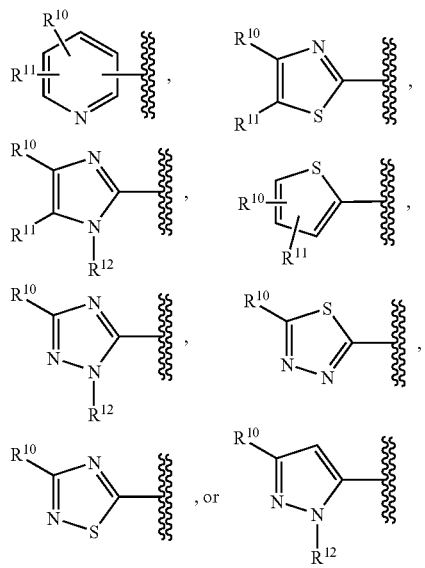

wherein $R^{10}$ and $R^{11}$ are each independently a hydrogen atom, optionally substituted lower alkyl, carboxy, lower alkyloxycarbonyl, halogen atom, optionally substituted aminocarbonyl, optionally substituted heteroaryl, or optionally substituted aryl;

$R^{12}$ is a hydrogen atom or lower alkyl.

IV) A pharmaceutical composition exhibiting thrombopoietin receptor agonism which contains a compound of I), wherein $X^1$ is a group represented by the formula:

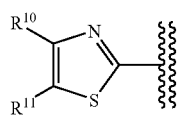

V) A pharmaceutical composition exhibiting thrombopoietin receptor agonism of any one of I) to IV), wherein $Y^1$ is —NHCO—, —CONH—, —NHCH$_2$—, —NHCO—CH=CH—, or —NHSO$_2$—.

VI) A pharmaceutical composition exhibiting thrombopoietin receptor agonism of any one of I) to IV), wherein $Y^1$ is —NHCO—.

VII) A pharmaceutical composition exhibiting thrombopoietin receptor agonism of any one of I) to VI), wherein $Z^1$ is 1,4-phenylene optionally substituted with halogen atom or lower alkyl.

VIII) A pharmaceutical composition exhibiting thrombopoietin receptor agonism of any one of I) to VII), wherein $R^1$ is a hydrogen atom or lower alkyl.

IX) A pharmaceutical composition exhibiting thrombopoietin receptor agonism of any one of I) to VIII), wherein $R^2$ is a hydrogen atom, lower alkyl, halogen atom, lower alkyloxy, lower alkylthio, or optionally substituted amino.

X) A pharmaceutical composition exhibiting thrombopoietin receptor agonism of any one of I) to IX), wherein $W^1$ is a group represented by the formula:

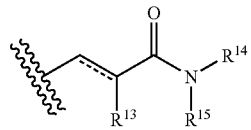

wherein $R^{13}$ is a hydrogen atom, lower alkyl, lower alkyloxy, lower alkylthio, or halogen atom;

$R^{14}$ and $R^{15}$ are each independently a hydrogen atom, or optionally substituted lower alkyl, optionally substituted lower alkenyl, optionally substituted lower alkynyl, optionally substituted cycloalkyl, optionally substituted aryl, optionally substituted heteroaryl, or optionally substituted heteroarylalkyl, each substituted by one or more substituent(s) selected from substituent group A;

a broken line ( - - - ) is as defined in I);

substituent group A consists of a halogen atom, halo(lower)alkyl, optionally substituted amino, carboxy, lower alkylthio, lower alkylsilyl, or lower alkyloxy.

XI) A pharmaceutical composition exhibiting thrombopoietin receptor agonism of any one of I) to IX), wherein $W^1$ is a group represented by the formula:

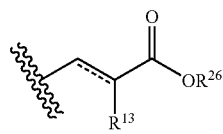

$R^{13}$ is a hydrogen atom, lower alkyl, lower alkyloxy, lower alkylthio, or halogen atom;

$R^{26}$ is a hydrogen atom or lower alkyl;

a broken line ( - - - ) is as defined in I);

XII) A pharmaceutical composition exhibiting thrombopoietin receptor agonism of any one of I) to XI), which is a platelet production modifier.

XIII) Use of a compound of any one of I) to XI), for preparation of a medicine for modifiering a platelet production.

XIV) A method for modifiering a platelet production of a mammal, including a human, which comprises administration to said mammal of a compound of any one of I) to XI) in a pharmaceutically effective amount.

XV) A compound represented by the general formula (II):

$$X^2-Y^2-Z^2-W^2 \qquad (II)$$

wherein $X^2$ is optionally substituted 5-member heteroaryl or optionally substituted pyridyl:

$Y^2$ is —$NR^ACO$—$(CR^CR^D)_{0-2}$—, —$NR^ACO$—$(CH_2)_{0-2}$—V—, —$NR^ACO$—$CR^C$=$CR^D$—, —V—$(CH_2)_{1-5}$—$NR^ACO$—$(CH_2)_{0-2}$—, —V—$(CH_2)_{1-5}$—$CONR^A$—$(CH_2)_{0-2}$—, —$CONR^A$—$(CH_2)_{0-2}$—, —$(CH_2)_{0-2}$—$NR^A$—$SO_2$—$(CH_2)_{0-2}$—, —$(CH_2)_{0-2}$—$SO_2$—$NR^A$—$(CH_2)_{0-2}$—, —$NR^A$—$(CH_2)_{0-2}$—, —$NR^A$—$CO$—$NR^A$—, —$NR^A$—$CS$—$NR^A$—, —N=C(—$SR^A$)—$NR^A$—, —$NR^A$CSN-$R^A$CO—, —N=C(—$SR^A$)—$NR^A$CO—, —$NR^A$—$(CH_2)_{1-2}$—$NR^A$—CO—, —$NR^A$CONR$^A$NR$^B$CO—, or —N=C(—$NR^AR^A$)—$NR^A$—CO—, wherein $R^A$ is each independently a hydrogen atom or lower alkyl; $R^B$ is a hydrogen atom or phenyl; $R^C$ and $R^D$ are each independently a hydrogen atom, halogen atom, optionally substituted lower alkyl, optionally substituted lower alkyloxy, optionally substituted lower alkylthio, optionally substituted lower alkenyl, optionally substituted lower alkynyl, optionally substituted aryl, optionally substituted heteroaryl, optionally substituted cycloalkyl, optionally substituted aralkyl, optionally substituted heteroarylalkyl, optionally substituted non-aromatic heterocyclic group, or optionally substituted amino; V is an oxygen atom or a sulfur atom;

$Z^2$ is optionally substituted phenylene, optionally substituted 2,5-pyridine-diyl, optionally substituted 2,5-thiophene-diyl, or optionally substituted 2,5-furan-diyl;

$W^2$ is a group represented by the formula:

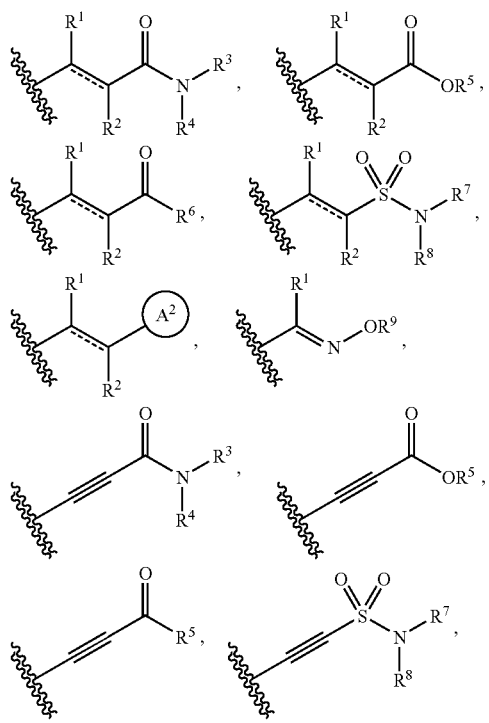

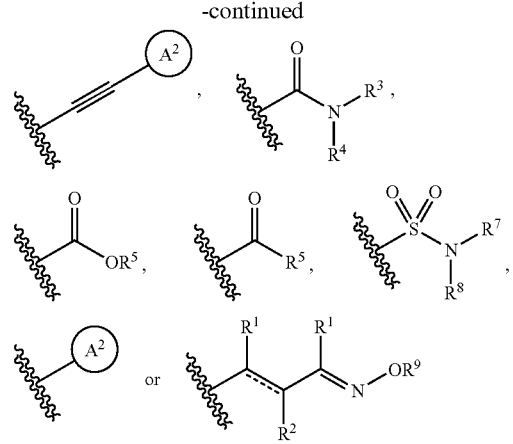

wherein $R^1$, $R^2$, $R^3$, $R^4$, $R^7$, and $R^8$ are each independently a hydrogen atom, halogen atom, optionally substituted lower alkyl, optionally substituted lower alkyloxy, optionally substituted lower alkylthio, optionally substituted lower alkenyl, optionally substituted lower alkynyl, optionally substituted aryl, optionally substituted heteroaryl, optionally substituted cycloalkyl, optionally substituted aralkyl, optionally substituted heteroarylalkyl, optionally substituted non-aromatic heterocyclic group, or optionally substituted amino;

$R^5$, $R^6$, and $R^9$ are each independently a hydrogen atom, optionally substituted lower alkyl, optionally substituted lower alkenyl, optionally substituted lower alkynyl, optionally substituted aryl, optionally substituted heteroaryl, optionally substituted cycloalkyl, optionally substituted aralkyl, optionally substituted heteroarylalkyl, or optionally substituted non-aromatic heterocyclic group;

$A^2$ is a optionally substituted aryl or optionally substituted heteroaryl;

a broken line ( - - - ) represents the presence or absence of a bond, its prodrug, or their pharmaceutically acceptable salt, or solvate thereof.

XVI) A compound described in XV), wherein $X^2$ is a group represented by the formula:

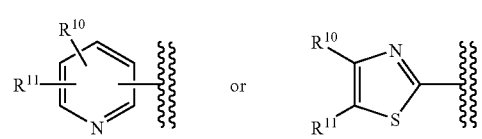

wherein $R^{10}$ and $R^{11}$ are each independently a hydrogen atom, optionally substituted lower alkyl, carboxy, lower alkyloxycarbonyl, halogen atom, optionally substituted aminocarbonyl, optionally substituted heteroaryl, or optionally substituted aryl, its prodrug, or their pharmaceutically acceptable salt, or solvate thereof.

XVII) A compound described in XV) or XVI), wherein $X^2$ is a group represented by the formula:

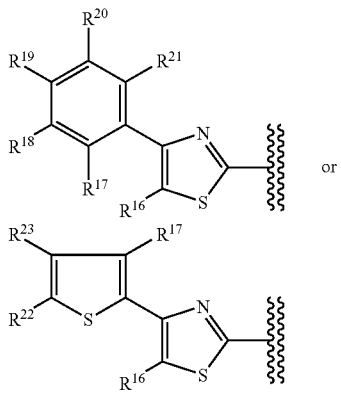

or wherein $R^{16}$ is a hydrogen atom, optionally substituted lower alkyl, carboxy, lower alkyloxycarbonyl, halogen atom, or optionally substituted aminocarbonyl;

$R^{17}$, $R^{18}$, $R^{19}$, $R^{20}$, $R^{21}$, $R^{22}$, and $R^{23}$ are each independently a hydrogen atom, optionally substituted lower alkyl by one or more substituent(s) selected from substituent group B, cycloalkyl, optionally substituted alkyoxy by one or more substituent(s) selected from substituent group B, alkylthio, halogen atom, optionally substituted phenyl by one or more substituent(s) selected from substituent group C, optionally substituted heteroaryl by one or more substituent(s) selected from substituent group C, or optionally substituted nonaromatic heterocyclic group by one or more substituent(s) selected from substituent group C;

substituent group B consists of hydroxy, alkyloxy, halogen atom, carboxy, lower alkyloxycarbonyl, aryloxycarbonyl, optionally substituted amino, optionally substituted phenyl by one or more substituent(s) selected from substituent group C, non-aromatic heterocyclic group, or heteroaryl;

substituent group C consisits of hydroxy, alkyl, halogen atom, halo(lower)alkyl, carboxy, lower alkyloxycarbonyl, alkyloxy, optionally substituted amino, non-aromatic heterocyclic group, or heteroaryl;

$R^{16}$ and $R^{17}$ taken together may form —$CH_2$—, —$CH_2CH_2$—, —$CH_2CH_2CH_2$—, —$OCH_2$—, or —$SCH_2$—;

its prodrug, or their pharmaceutically acceptable salt, or solvate thereof.

XVIII) A compound of any one of XV) to XVII), wherein $Y_2$ is —NHCO—;

its prodrug, or their pharmaceutically acceptable salt, or solvate thereof.

XIX) A compound of any one of XV) to XVIII), wherein $Z^2$ is 1,4-phenylene optionally substituted with halogen atom or lower alkyl;

its prodrug, or their pharmaceutically acceptable salt, or solvate thereof.

XX) A compound of any one of XV) to XIX), wherein $R^1$ is a hydrogen atom or lower alkyl;

its prodrug, or their pharmaceutically acceptable salt, or solvate thereof.

XXI) A compound of any one of XV) to XX), wherein $R^2$ is a hydrogen atom, lower alkyl, halogen atom, lower alkyloxy, lower alkylthio, or optionally substituted amino;

its prodrug, or their pharmaceutically acceptable salt, or solvate thereof.

XXII) A compound of any one of XV) to XXI), wherein $W^2$ is a group represented by the formula:

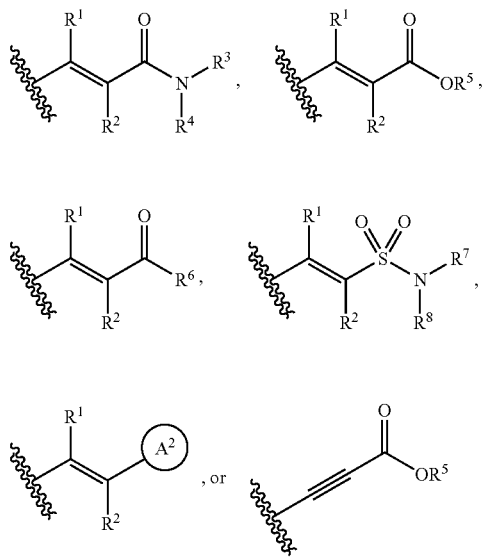

wherein, $R^1$, $R^2$, $R^3$, $R^4$, $R^5$, $R^6$, $R^7$, $R^8$ and $A^2$ are as defined in claim XV); provided that $R^2$ is not imidazolyl, triazolyl, or tetrazolyl;

its prodrug, or their pharmaceutically acceptable salt, or solvate thereof.

XXIII) A compound of any one of XV) to XXII), wherein $W^2$ is a group represented by the formula:

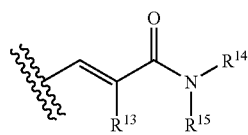

wherein $R^{13}$ is a hydrogen atom, lower alkyl, lower alkyloxy, lower alkylthio, or halogen atom;

$R^{14}$ and $R^{15}$ are each independently a hydrogen atom, or optionally substituted lower alkyl, optionally substituted lower alkenyl, optionally substituted lower alkynyl, optionally substituted cycloalkyl, optionally substituted aryl, optionally substituted heteroaryl, or optionally substituted heteroarylalkyl, each substituted by one or more substituent(s) selected from substituent group A;

substituent group A consists of a halogen atom, halo(lower)alkyl, optionally substituted amino, carboxy, lower alkylthio, lower alkylsilyl, or lower alkyloxy;

its prodrug, or their pharmaceutically acceptable salt, or solvate thereof.

XXIV) A compound of any one of XV) to XXII), wherein $W^2$ is a group represented by the formula:

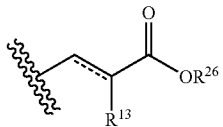

wherein $R^{13}$ is a hydrogen atom, lower alkyl, lower alkyloxy, lower alkylthio, or halogen atom;

$R^{26}$ is a hydrogen atom or lower alkyl;

a broken line ( - - - ) as defined in XV);

its prodrug, or their pharmaceutically acceptable salt, or solvate thereof.

XXV) A compound represented by the general formula (III):

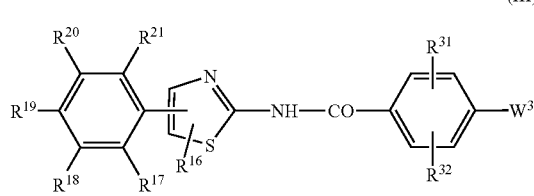

(III)

wherein $R^{16}$ is a hydrogen atom, optionally substituted lower alkyl, carboxy, lower alkyloxycarbonyl, halogen atom, or optionally substituted aminocarbonyl;

$R^{17}$, $R^{18}$, $R^{19}$, $R^{20}$, and $R^{21}$ are each independently a hydrogen atom, optionally substituted lower alkyl by one or more substituent(s) selected from substituent group B, cycloalkyl, optionally substituted alkyoxy by one or more substituent(s) selected from substituent group B, alkylthio, halogen atom, optionally substituted phenyl by one or more substituent(s) selected from substituent group C, optionally substituted heteroaryl by one or more substituent(s) selected from substituent group C, or optionally substituted nonaromatic heterocyclic group by one or more substituent(s) selected from substituent group C;

substituent group B consists of hydroxy, alkyloxy, halogen atom, carboxy, lower alkyloxycarbonyl, aryloxycarbonyl, optionally substituted amino, optionally substituted phenyl by one or more substituent(s) selected from substituent group C, non-aromatic heterocyclic group, or heteroaryl;

substituent group C consists of hydroxy, alkyl, halogen atom, halo(lower)alkyl, carboxy, lower alkyloxycarbonyl, alkyloxy, optionally substituted amino, non-aromatic heterocyclic group, or heteroaryl;

$R^{16}$ and $R^{17}$ taken together may form —CH$_2$—, —CH$_2$CH$_2$—, —CH$_2$CH$_2$CH$_2$—, —OCH$_2$—, or —SCH$_2$—;

$R^{31}$ and $R^{32}$ are each independently a hydrogen atom, lower alkyl, halogen atom, halo(lower)alkyl, lower alkyloxy, halo(lower)alkyloxy, or hydroxy;

$W^3$ is represented by the formula:

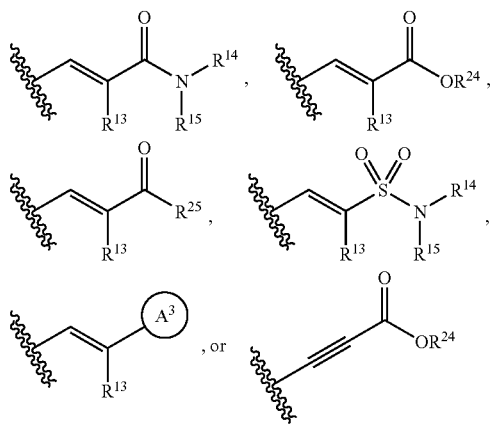

wherein $R^{13}$ is a hydrogen atom, lower alkyl, lower alkyloxy, lower alkylthio, or halogen atom;

$R^{14}$ and $R^{15}$ are each independently a hydrogen atom, or optionally substituted lower alkyl, optionally substituted lower alkenyl, optionally substituted lower alkynyl, optionally substituted cycloalkyl, optionally substituted aryl, optionally substituted aralkyl, optionally substituted heteroaryl, optionally substituted heteroarylalkyl, or optionally substituted non-aromatic heterocyclic group, each substituted by one or more substituent(s) selected from substituent group A;

substituent group A consists of a halogen atom, halo(lower)alkyl, optionally substituted amino, carboxy, lower alkylthio, lower alkylsilyl, or lower alkyloxy;

$R^{24}$ is a hydrogen atom or lower alkyl;

$R^{25}$ is lower alkyl, optionally substituted aryl, or optionally substituted non-aromatic heterocyclic group;

$A^3$ is heteroaryl;

its prodrug, or their pharmaceutically acceptable salt, or solvate thereof.

XXVI) A compound represented by the general formula (IV-A):

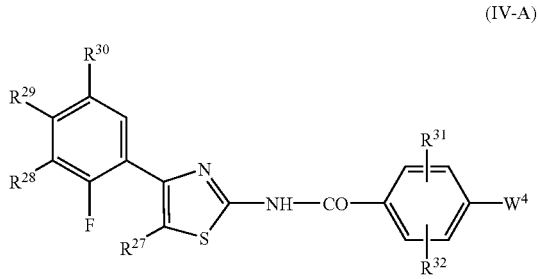

(IV-A)

wherein $R^{27}$ is a hydrogen atom, C1-C3 alkyl, trifluoromethyl, or halogen atom;

$R^{28}$, $R^{29}$, and $R^{30}$ are independently a hydrogen atom, optionally substituted lower alkyl by one or more substituent(s) selected from substituent group B, cycloalkyl, optionally substituted alkyoxy by one or more substituent(s) selected from substituent group B, alkylthio, halogen atom, optionally substituted phenyl by one or more substituent(s) selected from substituent group C, optionally substituted heteroaryl by one or more substituent(s) selected from substituent group C, or optionally substituted nonaromatic heterocyclic group by one or more substituent(s) selected from substituent group C;

substituent group B consists of hydroxy, alkyloxy, halogen atom, carboxy, lower alkyloxycarbonyl, aryloxycarbonyl, optionally substituted amino, optionally substituted phenyl by one or more substituent(s) selected from substituent group C, non-aromatic heterocyclic group, or heteroaryl;

substituent group C consists of hydroxy, alkyl, halogen atom, halo(lower)alkyl, carboxy, lower alkyloxycarbonyl, alkyloxy, optionally substituted amino, non-aromatic heterocyclic group, or heteroaryl;

$R^{31}$ and $R^{32}$ are each independently a hydrogen atom, lower alkyl, halogen atom, haro(lower)alkyl, lower alkyloxy, halo(lower)alkyloxy, or hydroxy;

$W^4$ is a group represented by the formula:

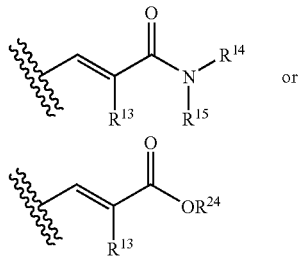

wherein $R^{13}$ is a hydrogen atom, lower alkyl, lower alkyloxy, lower alkylthio, or halogen atom;

$R^{14}$ and $R^{15}$ are each independently a hydrogen atom, optionally substituted lower alkyl, optionally substituted lower alkenyl, optionally substituted lower alkynyl, optionally substituted cycloalkyl, optionally substituted aryl, optionally substituted aralkyl, optionally substituted heteroaryl, optionally substituted heteroarylalkyl, or optionally substituted non-aromatic heterocyclic group, each substituted by one or more substituent(s) selected from substituent group A;

substituent group A consists of a halogen atom, halo(lower)alkyl, optionally substituted amino, carboxy, lower alkylthio, lower alkylsilyl, or lower alkyloxy;

$R^{24}$ is a hydrogen atom or lower alkyl;

its prodrug, or their pharmaceutically acceptable salt, or solvate thereof.

XXVII) A compound represented by the general formula (IV-B):

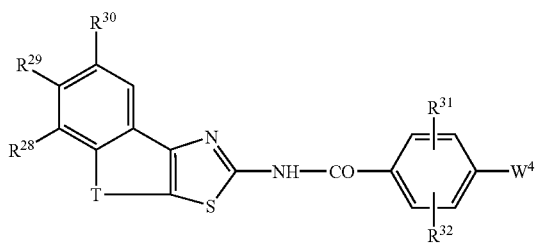

(IV-B)

wherein $R^{28}$, $R^{29}$, and $R^{30}$ are each independently a hydrogen atom, optionally substituted lower alkyl by one or more substituent(s) selected from substituent group B, cycloalkyl, optionally substituted alkyoxy by one or more substituent(s) selected from substituent group B, alkylthio, halogen atom, optionally substituted phenyl by one or more substituent(s) selected from substituent group C, optionally substituted heteroaryl by one or more substituent(s) selected from substituent group C, or optionally substituted nonaromatic heterocyclic group by one or more substituent(s) selected from substituent group C;

substituent group B consists of hydroxy, alkyloxy, halogen atom, carboxy, lower alkyloxycarbonyl, aryloxycarbonyl, optionally substituted amino, optionally substituted phenyl by one or more substituent(s) selected from substituent group C, non-aromatic heterocyclic group, or heteroaryl;

substituent group C consists of hydroxy, alkyl, halogen atom, halo(lower)alkyl, carboxy, lower alkyloxycarbonyl, alkyloxy, optionally substituted amino, non-aromatic heterocyclic group, or heteroaryl;

$R^{31}$ and $R^{32}$ are each independently a hydrogen atom, lower alkyl, halogen atom, haro(lower)alkyl, lower alkyloxy, halo(lower)alkyloxy, or hydroxy;

$W^4$ is a group represented by the formula:

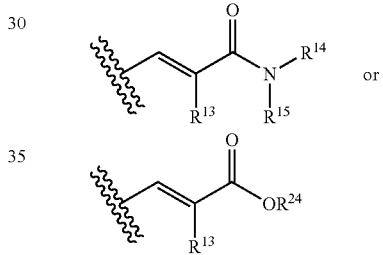

wherein $R^{13}$ is a hydrogen atom, lower alkyl, lower alkyloxy, lower alkylthio, or halogen atom;

$R^{14}$ and $R^{15}$ are each independently a hydrogen atom, optionally substituted lower alkyl, optionally substituted lower alkenyl, optionally substituted lower alkynyl, optionally substituted cycloalkyl, optionally substituted aryl, optionally substituted aralkyl, optionally substituted heteroaryl, optionally substituted heteroarylalkyl, or optionally substituted non-aromatic heterocyclic group, each substituted by one or more substituent(s) selected from substituent group A;

substituent group A consists of a halogen atom, halo(lower)alkyl, optionally substituted amino, carboxy, lower alkylthio, lower alkylsilyl, or lower alkyloxy;

$R^{24}$ is a hydrogen atom or lower alkyl;

T is —$CH_2$—, —$CH_2CH_2$—, —$CH_2CH_2CH_2$—, —$OCH_2$—, or —$SCH_2$—;

its prodrug, or their pharmaceutically acceptable salt, or solvate thereof.

XXVIII) A pharmaceutical composition containing as the active ingredient a compound of any one of XV) to XXVII).

XXIX) A pharmaceutical composition containing as the active ingredient a compound of any one of XV) to XXVII), which is exhibiting thrombopoietin receptor agonism.

XXX) A platelet production modifier which contains as the active ingredient a compound of any one of XV) to XXVII).

XXXI) Use of a compound of any one of XV) to XXVII) for preparation of a pharmaceutical composition for modifiering a platelet production.

XXXII) A method for modifiering a platelet production of a mammal, including a human, which comprises administration to said mammal of a compound of any one of XV) to XXVII) in a pharmaceutically effective amount.

In the present specification, the term "halogen" means fluoro, chloro, bromo, and iodo.

In the present specification, the term "alkyl" employed alone or in combination with other terms means a straight- or branched chain monovalent hydrocarbon group having 1 to 15 carbon atom(s). Examples of alkyl include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl, n-nonanyl, n-decanyl, n-undecanyl, n-dodecanyl, n-tridecanyl, n-tetradecanyl, n-pentadecanyl, and the like. C1 to C10 alkyl is preferred. C1 to C6 alkyl is more preferred.

In the present specification, the term "lower alkyl" employed alone or in combination with other terms means a straight- or branched chain monovalent hydrocarbon group having 1 to 8 carbon atom(s). Examples of alkyl include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl, and the like. C1 to C6 alkyl is preferred. C1 to C3 alkyl is more preferred.

In the present specification, the term "C1 to C3 alkylene" include methylene, ethylene, propylene, and the like.

In the present specification, the term "cycloalkane" employed alone or in combination with other terms means a mono cycloalkane having 3 to 8 carbon atom. Examples of cycloalkane include cyclopropane, cyclobutane, cyclopentane, cyclohexane, cycloheptane, cyclooctane, and the like. C3 to C6 cycloalkane is preferred.

In the present specification, the term "cycloalkyl" employed alone or in combination with other terms means a mono cycloalkane having 3 to 8 carbon atom. Examples of cycloalkyl include cyclopropyl, cyclobutyl, cyclopentyl, cyclohexyl, cycloheptyl, cyclooctyl, and the like. C3 to C6 cycloalkyl is preferred.

The term "lower alkenyl" in the present specification means a straight- or branched chain monovalent hydrocarbon group having 2 to 8 carbon atoms and one or more double bond. Examples of the alkenyl include vinyl, allyl, 1-propenyl, 2-propenyl, a variety of butenyl isomers and the like. C2 to C6 alkenyl is preferred. C2 to C4 alkenyl is more preferred.

The term "lower alkynyl" used in the present specification means a straight or branched chain monovalent hydrocarbon group having 2 to 8 carbon atoms and one or more than two triple bond. Examples of the alkynyl include ethynyl, 1-propynyl, 2-propynyl, 1-propenyl, 2-propenyl, crotonyl, isopentenyl, a variety of butenyl isomers and the like. C2 to C6 alkynyl is preferred. C2 to C4 alkynyl is more preferred.

In the present specification, the term "aryl" employed alone or in combination with other terms means monocyclic or condensed ring aromatic hydrocarbons. Examples of aryl include phenyl, 1-naphtyl, 2-naphtyl, anthryl, and the like.

The term "aralkyl" herein used means the above mentioned "lower alkyl" substituted with the above mentioned "aryl" at any possible position. Examples of the aralkyl are benzyl, phenethyl (e.g., 2-phenethyl), phenylpropyl (e.g., 3-phenylpropyl), naphthylmethyl (e.g., 1-naphthylmethyl and 2-naphthylmethyl), anthrylmethyl (e.g., 9-anthrylmethyl), and the like. Benzyl and phenylethy are preferred.

In the present specification, the term "non-aromatic heterocyclic group" employed alone or in combination with other terms means a 5 to 7 membered non-aromatic ring which contains one or more hetero atoms selected from the group consisting of oxygen, sulfur, and nitrogen atoms in the ring and the 5 to 7 membered non-aromatic ring may be condensed with two or more rings. Examples of the non-aromatic heterocyclic group are pyrrolidinyl (e.g., 1-pyrrolidinyl, 2-pyrrolidinyl), pyrrolinyl (e.g., 3-pyrrolinyl), imidazolidinyl (e.g., 2-imidazolidinyl), imidazolinyl (e.g., imidazolinyl), pyrazolidinyl (e.g., 1-pyrazolidinyl, 2-pyrazolidinyl), pyrazolinyl (e.g., pyrazolinyl), piperidinyl (e.g., piperidino, 2-piperidinyl), piperazinyl (e.g., 1-piperazinyl), indolynyl (e.g., 1-indolynyl), isoindolinyl (e.g., isoindolinyl), morpholinyl (e.g., morpholino, 3-morpholinyl), tetrahydrofuranyl, tetrahydropyranyl, and the like.

Preferable are morpholino, piperazino, pyrrolidino, teterahydrofuranyl, tetrahydropyranyl, and the like as "non-aromatic heterocyclic group" of $R^{17}$, $R^{18}$, $R^{19}$, $R^{20}$, $R^{21}$, $R^{22}$, $R^{23}$, $R^{28}$, $R^{29}$, and $R^{30}$.

Preferable are morpholino, piperazino, piperidino, teterahydrofuranyl, tetrahydropyranyl, and the like as "non-aromatic heterocyclic group" of substituent group B.

Preferable are morpholino, piperazino, piperidino, pyrrolidino, teterahydrofuranyl, tetrahydropyranyl, and the like as "non-aromatic heterocyclic group" of substituent group C.

In the present specification, the term "heteroaryl" employed alone or in combination with other terms means a 5 to 6 membered aromatic heterocyclic group which contains one or more hetero atoms selected from the group consisting of oxygen, sulfur, and nitrogen atoms in the ring and may be fused with above mentioned cycloalkyl, above mentioned aryl, above mentioned non-aromatic heterocyclic group, and other heteroaryl at any possible position. Examples of the heteroaryl are pyrrolyl (e.g., 1-pyrrolyl, 2-pyrrolyl, 3-pyrrolyl), furyl (e.g., 2-furyl, 3-furyl), thienyl (e.g., 2-thienyl 3-thienyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl(e.g., 1H-tetrazolyl), oxadiazolyl (e.g., 1,3,4-oxadiazolyl), thiadiazolyl (e.g., 1,3,4-thiadiazolyl), indolizinyl (e.g., 2-indolizinyl, 6-indolizinyl), isoindolyl (2-isoindolyl), indolyl (e.g., 1-indolyl, 2-indolyl, 3-indolyl), indazolyl (e.g., 3-indazolyl), puriyl (e.g., 8-puriyl), quinolizinyl ( e.g., 2-quinolizinyl), isoquinolyl (e.g., 3-isoquinolyl), quinolyl (e.g., 3-quinolyl, 5-quinolyl), phthalazinyl (e.g., 1-phthalazinyl), naphthyridinyl (e.g., 2-naphthyridinyl), quinolanyl (2-quinolanyl), quinazolinyl (e.g., 2-quinazolinyl), cinnolinyl (e.g., 3-cinnolinyl), pteridinyl (e.g., 2-pteridinyl), carbazolyl (e.g., 2-carbazolyl, 4-carbazolyl), phenanthridinyl (e.g., 2-phenanthridinyl, 3-phenanthridinyl), acridinyl (e.g., 1-acridinyl, 2-acridinyl), dibenzofuranyl (e.g., 1-dibenzofuranyl, 2-dibenzofuranyl), benzimidazolyl (e.g., 2-benzimidazolyl), benzisoxazolyl (e.g., 3-benzisoxazolyl), benzoxazolyl (e.g., 2-benzoxazolyl), benzoxadiazolyl (e.g., 4-benzoxadiazolyl), benzisothiazolyl (e.g., 3-benzisothiazolyl), benzothiazolyl (e.g., 2-benzothiazolyl), benzofuryl (e.g., 3-benzofuryl), benzothienyl (e.g., 2-benzothienyl), 4,5-dihydronaphtho[1,2-d]thiazolyl, 4H-chromeno[4,3-d]thiazolyl, 4H-thiochromeno[4,3-d]thiazolyl, 4,5-dihydrothiazo[5,4-c]quinolyl, 8H-indeno[1,2-d]thiazolyl, 5,6-dihydro-4H-3-thia-1-azabenzo[e]azurenyl and the like.

Preferable are thiazolyl, isoxazolyl, thienyl, carbazolyl, benzothiazolyl, pyridyl, pyrazolyl, and the like as "heteroaryl" for $X^1$. More preferable are thiazolyl, pyridyl, and the like.

Preferable are pyridyl, thiazolyl, benzothiazolyl, and the like as "heteroaryl" for $R^1$, $R^2$, $R^3$, $R^4$, $R^7$, and $R^8$.

Preferable are pyridyl, thienyl, furyl, pyrimidinyl, imidazolyl, thiazolyl, oxazolyl, triazolyl, and the like as "heteroaryl" for $R^{10}$ and $R^{11}$.

Preferable are imidazolyl, triazolyl, tetrazolyl, pyridyl, pyrimidinyl, and the like as "heteroaryl" for $A^1$, $A^2$, and $A^3$.

Preferable are pyridyl, thienyl, furyl, pyrimidinyl, imidazolyl, thiazolyl, oxazolyl, triazolyl, and the like as "heteroaryl" for $R^{17}$, $R^{18}$, $R^{19}$, $R^{20}$, $R^{21}$, $R^{22}$, $R^{23}$, $R^{28}$, $R^{19}$, and $R^{30}$.

Preferable are pyridyl, pyrazolyl, pyrimidinyl, imidazolyl, oxazolyl, triazolyl, furyl, thienyl and the like as "heteroaryl" for substituent group B.

Preferable are pyridyl, pyrazolyl, imidazolyl, and the like as "heteroaryl" for substituent group C.

In the present specification, the term "5-membered heteroaryl" measns a 5 membered aromatic heterocyclic group which contains one or more hetero atoms selected from the group consisting of oxygen, sulfur, and nitrogen atoms. Examples of the 5-membered heteroaryl are thienyl, furyl, pyrrolyl, imidazolyl, pyrazolyl, isothiazolyl, isoxazolyl, thiazolyl, oxazolyl, 1,2,3-triazolyl, 1,2,4-triazolyl, 1,2,4-thiadiazolyl, 1,3,4-thiadiazolyl, 1,2,4-oxadiazolyl, 1,3,4-oxadiazolyl, and the like. Preferable is thiazolyl.

The term "heteroarylalkyl" herein used means the above-mentioned "lower alkyl" substituted with the above-mentioned "heteroaryl" at any possible position. Examples of the heteroarylalkyl are thienylmethyl (e.g., 2-thienylmethyl), thienylethyl (e.g., 2-(thiophen-2-yl)ethyl), furylmethyl (e.g., 2- furylmethyl), furylethyl (e.g., 2-(furan-2-yl)ethyl), pyrrolylmethyl (e.g., 2-pyrrolylmethyl), pyrrolylethyl (e.g., 2-(pyrrol-2-yl)ethyl), imidazolylmethyl (e.g., 2-imidazolylmethyl, 4-imidazolylmethyl), imidazolylethyl (e.g., 2-(imidazol-2-yl)ethyl), pyrazolylmethyl (e.g., 3-pyrazolylmethyl), pyrazolylethyl (e.g., 2-(pyrazol-3-yl)ethyl), thiazolylmethyl (e.g., 2-thiazolylmethyl), thiazolylethyl (e.g., 2-(thiazol-2-yl) ethyl), isothiazolylmethyl (e.g., 3-thiazolylmethyl), isoxazolylmethyl (e.g., 3-isoxazolylmethyl), oxazolylmethyl (e.g., 2-oxazolylmethyl), oxazolylethyl (e.g., 2-(oxazol-2-yl) ethyl), pyridylmethyl (e.g., 2-pyridylmethyl, 3-pyridylmethyl, 4-pyridylmethyl), pyridylethyl (e.g., 2-pyridylethyl) and the like.

Preferable are 2-thienylmethyl, 2-furylmethyl, and the like as "heteroarylalkyl" for $R^1$, $R^2$, $R^3$, $R^4$, $R^7$, and $R^8$.

The term "phenylene" herein used means a divalent group of the above-mentioned "phenyl". Examples of the phenylene are 1,2-phenylene, 1,3-phenylen, 1,4-phenylene, and the like. Preferable is 1,4-phenylene.

The term "monocyclic heteroarylene" herein used means a monocyclic heteroaryl divalent group of the above-mentioned "heteroaryl". Examples of the heteroarylene are thionphene-diyl, furan-diyl, pyridine-diyl, and the like. Mentioned in more detail, it is exemplified by 2,5-thionphene-diyl, 2,5-furan-diyl, 2,5-pyridine-diyl, 2,5-thiazole-diyl, 2,5-(1,3,4-thiadiazole)-diyl, 2,5-piridine-diyl, 2,5-pirazine-diyl, 3,6-pyridazine-diyl, 2,5-(4H-pyrane)-diyl, and the like. Preferable are 2,5-thionphene-diyl, 2,5-furan-diyl, 2,5-pyridine-diyl.

The term "monocyclic non-aromatic heterocycle-diyl" herein used means a divalent group of an above-mentioned "monocyclic non-aromatic heterocyclic group". Examples of the non-aromatic heterocycle-diyl are pyrrolidine-diyl, piperidine-diyl, pyrazine-diyl and the like.

The term "monocyclic cycloalkane-diyl" herein used means a divalent group of the above-mentioned "monocyclic cycloalkyl". Examples of the cycloalkyl-diyl are 1,4-cylopentane-diyl, 1,4-cyclohexane-diyl and the like.

The term "alkyloxy" herein used are methyloxy, ethyloxy, n-propyloxy, i-propyloxy, n-butyloxy, i-butyloxy, sec-butyloxy, tert-butyloxy, n-pentyloxy, n-hexyloxy, n-heptyloxy, n-octyloxy, n-nonanyloxy, n-decanyloxy, and the like. Methyloxy, ethyloxy, n-propyloxy, i-propyloxy and n-butyloxy are preferred.

The term "lower alkyloxy" herein used are methyloxy, ethyloxy, n-propyloxy, i-propyloxy, n-butyloxy, i-butyloxy, sec-butyloxy, tert-butyloxy, and the like. Methyloxy, ethyloxy, n-propyloxy, i-propyloxy and n-butyloxy are preferred.

The term "lower alkylthio" herein used are methylthio, ethylthio, and the like.

The term "lower alkyloxycarbonyl" herein used are methyloxycarbonyl, ethyloxycarbonyl, n-propyloxycarbonyl, isopropyloxycarbonyl, n-butyloxycarbonyl, t-butyloxycarbonyl, n-pentyloxycarbonyl and the like.

The term "aryloxycarbonyl" herein used are phenyloxycarbonyl, 1-naphthyloxycarbonyl, 2-naphthyloxycarbonyl, and the like.

In the present specification, the term "acyl" employed alone or in combination with other terms means alkylcarbonyl in which alkyl group is the above-mentioned "lower alkyl" and arylcarbonyl in which aryl group is the above-mentioned "aryl". Examples of the acyl are acetyl, propyonyl, benzoyl, and the like. "Lower alkyl" and "aryl" may be substituted respectively with substituents mentioned below.

In the present specification, the term "halo(lower)alkyl" employed alone or in combination with other terms means the above-mentioned "lower alkyl" which is substituted with the above mentioned "halogen" at 1 to 8 positions, preferably, at 1 to 5. Examples of the halo(lower)alkyl are trifluoromethyl, trichloromethyl, difluoroethyl, trifluoroethyl, dichloroethyl, trichloroethyl, and the like. Preferable is trifluoromethyl.

The term "halo(lower)alkyl" herein used are trifluoromethyl, trichloromethyl, difluoroethyl, trifluoroethyl, dichloroethyl, trichloroethyl, and the like. Preferable is trifluoromethyl.

Examples of the term "acyloxy" herein used are acetyloxy, propionyloxy, benzoyloxy and the like.

Examples of the term "lower alkylsilyl" herein used are triethylsilyl, t-butyldimethylsilyl, and the like.

In the present specification, the term "optionally substituted amino" employed alone or in combination with other terms includes amino substituted with one or two of the above mentioned "lower alkyl", "aralkyl", "heteroarylalkyl" or "acyl". Examples of the optionally substituted amino are amino, methylamino, dimethylamino, ethylmethylamino, diethylamino, benzylamino, acetylamino, benzoylamino and the like. Preferable are amino, methylamino, dimethylamino, ethylmethylamino, diethylamino and acetylamino.

Examples of the term "optionally substituted aminocarbonyl" herein used are aminocarbonyl, methylaminocarbonyl, dimethylaminocarbonyl, ethylmethylaminocarbonyl, diethylaminocarbonyl and the like. Preferable are aminocarbonyl, methylaminocarbonyl, and dimethylaminocarbonyl.

In the present specification, the term "optionally substituted ureide" includes ureide substituted with one or more than two of the above mentioned "lower alkyl", "aryl", "aralkyl", "heteroaryl", "heteroarylalkyl" or "acyl".

The substituents of "optionally substituted lower alkyl" are cycloalkyl, lower alkenyl, lower alkyliden, hydroxy, lower alkyloxy, mercapto, lower alkylthio, halogen, nitro, cyano, carboxy, lower alkyloxycarbonyl, halo(lower)alkyl, halo (lower)alkyloxy, optionally substituted amino, optionally substituted aminocarbonyl, acyl, acyloxy, optionally substituted non-aromatic heterocyclic group, aryloxy (e.g., phenyloxy), aralkyloxy (e.g., benzyloxy), lower alkylsulfonyl, guanidino, azo group, optionally substituted ureide, =N—O— (acyl) and the like. These substituents are able to locate at one or more of any possible positions.

Preferable are halogen atom, or halo(lower)alkyl, as substituents of "optionally substituted lower alkyl" for $R^C$ and $R^D$.

Preferable are hydroxy, carboxy, halogen atom, alkyloxy, alkylthio, alkylsilyl, optionally substituted amino, cyano, acyl, and the like as substituents of "optionally substituted lower alkyl" for $R^1$, $R^2$, $R^3$, $R^4$, $R^5$, $R^6$, $R^7$, $R^8$, and $R^9$.

Preferable are lower alkyloxycarbonyl and halogen atom as substituents of "optionally substituted lower alkyl" for $R^{10}$, $R^{11}$, and $R^{16}$.

Preferable are cycloalkyl, lower alkenyl, lower alkylidene as substituents of "optionally substituted lower alkyl" for $R^{12}$.

The substituents of "optionally substituted lower alkyloxy" and "optionally substituted lower alkylthio" are cycloalkyl, lower alkenyl, lower alkyliden, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy, optionally substituted non-aromatic heterocyclic group, aryloxy (e.g., phenyloxy), aralkyloxy (e.g., benzyloxy), lower alkylsulfonyl, guanidino, azo group, optionally substituted ureide, =N—O— (acyl) and the like. These substituents are able to locate at one or more of any possible positions.

The substituents of "optionally substituted lower alkenyl" and "optionally substituted lower alkylthio" are cycloalkyl, lower alkenyl, lower alkyliden, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy, optionally substituted non-aromatic heterocyclic group, aryloxy (e.g., phenyloxy), aralkyloxy (e.g., benzyloxy), lower alkylsulfonyl, guanidino, azo group, optionally substituted ureide, and the like. These substituents are able to locate at one or more of any possible positions.

The substituents of "optionally substituted phenylene", "optionally substituted heteroarylene", "optionally substituted 2,5-pyridine-diyl", "optionally substituted 2,5-thiophene-diyl", "optionally substituted 2,5-furan-diyl", "optionally substituted monocyclic non-aromatic heterocycle-diyl", "optionally substituted monocyclic cycloalkane-diyl", "optionally substituted aryl", "optionally substituted phenyl", "optionally substituted heteroaryl", "optionally substituted 5-membered heteroaryl", "optionally substituted pyridyl", "optionally substituted non-aromatic heterocyclic group", "optionally substituted cycloalkyl", "optionally substituted aralkyl", and "optionally substituted heteroarylalkyl" herein used are optionally substituted alkyl, cycloalkyl, lower alkenyl, lower alkynyl, hydroxy, alkyloxy,aralkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy, optionally substituted aryl (which is substituted by halogen atom, carboxy, alkyl, or alkyloxy, and the like), optionally substituted heteroaryl (which is substituted by halogen atom, carboxy, alkyl, or alkyloxy, and the like), optionally substituted non-aromatic heterocyclic group, optionally substituted aralkyl, lower alkylsulfonyl, guanidino, azo group, —N=N— (optionally substituted phenyl) or optionally substituted ureide and the like. These substituents are able to locate at one or more of any possible positions.

Preferable are halogen, nitro, cyano, lower alkyl, lower alkyloxy, and the like as substituents of "optionally substituted phenylene", "optionally substituted heteroarylene", "optionally substituted 2,5-pyridine-diyl", "optionally substituted 2,5-thiophene-diyl", "optionally substituted 2,5-furan-diyl", "optionally substituted monocyclic non-aromatic heterocycle-diyl", "optionally substituted monocyclic cycloalkyl-diyl". Their unsubstituted one is preferred.

The examples of substituents of "optionally substituted aryl" and "optionally substituted aralkyl" for $X^1$ are lower alkyl, hydroxy lower alkyl, hydroxy, lower alkyloxy, lower alkylthio, halogen, nitro, cyano, carboxy, lower halo(lower)alkyl, halo(lower)alkyloxy, aralkyloxy, unsubstituted or substituted amino, unsubstituted or substituted aminocarbonyl, aryl, heteroaryl, non-aromatic heterocyclic group, arylazo (e.g., phenylazo), and the like. Preferable substituents are lower alkyl, hydroxy, lower alkyloxy, lower alkylthio, halogen, halo(lower)alkyl, halo(lower)alkyloxy, aralkyloxy, —N=N— (phenyl), alkylendioxy, and the like.

The examples of "optionally substituted aryl" for $X^1$ are phenyl, 3-methylphenyl, 4-methylphenyl, 3,4-dimethylphenyl, 4-ethylphenyl, 4-t-buylphenyl, 4-n-buylphenyl, 4-n-hexylphenyl, 4-n-octylphenyl, 3,5-di-t-butyl-4-hydroxyphenyl, 4-ethyloxyphenyl, 4-fluorophenyl, 3,4-dichlorophenyl, 3,5-dichlorophenyl, 4-iodophenyl, 4-trifluoromethylphenyl, 4-methylthiophenyl, 4-phenylmethyloxyphenyl, 4-phenyazophenyl, 4-phenylphenyl, 2-naphtyl, benzodioxoryl (e.g., 1,3-benzodioxoryl), and the like.

The substituents of "optionally substituted aryl" for $R^{10}$ and $R^{11}$ are halogen atom, optionally substituted alkyl, cycloalkyl, lower alkenyl, lower alkynyl, hydroxy, lower alkyloxy, mercapto, lower alkylthio, nitro, cyano, carboxy, lower alkyloxycarbonyl, halo(lower)alkyl, halo(lower)alkyloxy, optionally substituted amino, optionally substituted aminocarbonyl, acyl, formyl, acyloxy, optionally substituted aryl, optionally substituted heteroaryl (e.g., pyridyl, imidazolyl), non-aromatic heterocyclic group (e.g., morpholino, piperazinyl), aralkyl, and the like. Preferable are optionally substituted alkyl by one or more substituent(s) selected from substituent group B, cycloalkyl, optionally substituted alkyloxy by one or more substituent(s) selected from substituent group B, alkylthio, halogen atom, optionally substituted phenyl by one or more substituent(s) selected from substituent group C, optionally substituted heteroaryl by one or more substituent(s) selected from substituent group C, optionally substituted non-aromatic heterocyclic group by one or more substituent(s) selected from substituent group C, and the like.

Substituent group B consists of hydroxy, alkyloxy, halogen atom, carboxy, lower alkyloxycarbonyl, aryloxycarbonyl, optionally substituted amino, optionally substituted phenyl by one or more substituent(s) selected from substituent group C, non-aromatic heterocyclic group, and heteroaryl.

Substituent group C consists of hydroxy, alkyl, halogen atom, halo(lower)alkyl, carboxy, lower alkyloxycarbonyl, alkyloxy, optionally substituted amino, non-aromatic heterocyclic group, and heteroaryl.

The aryl may be fused with C5-C7 cycloalkane (e.g., cyclopentane, cyclohexane) and non-aromatic heterocyclic group (e.g., tetrahydrofuranyl, 1,3-dioxolyl, 1,4-dioxynyl, pyrrolidinyl) to form indane, 1,2,3,4-tetrahydronaphthalene, 1,2,3,4-tetrahydroquinoline, 2,3-dihydrobenzo[1,4]dioxyine, benzo[1,3]dioxsole, 2,3-dihydrobenzofuran, 2,3-dihydro-1H-indole.

The substituents of "optionally substituted heteroaryl" and "optionally substituted heteroarylalkyl" for $X^1$ are optionally substituted alkyl, lower alkenyl (e.g., =CH—CH$_3$), lower alknyl, hydroxy, lower alkyloxy, mercapto, lower alkylthio, halogen, nitro, cyano, carboxy, lower alkyloxycarbonyl, halo (lower)alkyl, halo(lower)alkyloxy, optionally substituted amino, optionally substituted aminocarbonyl, acyl (e.g., optionally substituted aryloxycarbonyl by halogen atom nitro, cyano, and the like) acyloxy, optionally substituted aryl, optionally substituted heteroaryl (e.g., 2-pyridyl, 3-pyridyl, 4-pyridyl, 3-thienyl, 5-methylpyridin-2-yl, 3-quinolyl, 5-chlorothiophen-2-yl, 5-bromothiophen-2-yl), non-aromatic heterocyclic group, aralkyl, =N—O— (acyl) and the like. Preferable are optionally substituted lower alkyl, lower alkenyl, lower alkyloxycarbonyl, optionally substituted phenyl, heteroaryl, =N—O— (acyl) and the like.

In the case of heteroatom is nitrogen atom, the nitrogen atom may be substituted by alkyl, oxo, and the like.

The substituents of "optionally substituted 5-membered heteroaryl" for $X^2$ are optionally substituted lower alkyl, lower alkenyl (e.g., =CH—CH$_3$), lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl (e.g., aryloxycarbonyl optionally substituted with halogen, nitro, cyano and the like), acyloxy, optionally substituted phenyl, aryl, optionally substituted heteroaryl (e.g., 2-pyridyl, 3-pyridyl, 4-pyridyl, 3-thienyl, 5-methylpyridine-2-yl, 3-quinolyl, 5-chlorothiophene-2-yl, 5-bromothiophene-2-yl), non-aromatic heterocyclic group, aralkyl, =N—O— (acyl), and the like. Preferable are optionally substituted alkyl by one or more substituent(s) selected from substituent group B, cycloalkyl, optionally substituted alkyloxy by one or more substituent(s) selected from substituent group B, alkylthio, halogen atom, optionally substituted phenyl by one or more substituent(s) selected from substituent group C, optionally substituted heteroaryl by one or more substituent(s) selected from substituent group C, or optionally substituted non-aromatic heterocyclic group by one or more substituent(s) selected from substituent group C, and the like.

Substituent group B consists of hydroxy, alkyloxy, halogen atom, carboxy, lower alkyloxycarbonyl, aryloxycarbonyl, optionally substituted amino, optionally substituted phenyl by one or more substituent(s) selected from substituent group C, non-aromatic heterocyclic group, and heteroaryl, Substituent group C consists of hydroxy, alkyl, halogen atom, halo(lower)alkyl, carboxy, lower alkyloxycarbonyl, alkyloxy, optionally substituted amino, non-aromatic heterocyclic group, and heteroaryl, The substituents of "optionally substituted aryl" for $R^{10}$ and $R^{11}$ are halogen atom, optionally substituted alkyl, cycloalkyl, lower alkenyl, lower alkynyl, hydroxy, lower alkyloxy, mercapto, lower alkylthio, nitro, cyano, carboxy, lower alkyloxycarbonyl, halo(lower)alkyl, halo(lower)alkyloxy, optionally substituted amino, optionally substituted aminocarbonyl, acyl, formyl, acyloxy, optionally substituted aryl, optionally substituted heteroaryl (e.g., pyridyl, imidazolyl), non-aromatic heterocyclic group (e.g., morpholino, piperazinyl), aralkyl, and the like. Preferable are optionally substituted alkyl by one or more substituent(s) selected from substituent group B, cycloalkyl, optionally substituted alkyloxy by one or more substituent(s) selected from substituent group B, alkylthio, halogen atom, optionally substituted phenyl by one or more substituent(s) selected from substituent group C, optionally substituted heteroaryl by one or more substituent(s) selected from substituent group C, optionally substituted non-aromatic heterocyclic group by one or more substituent(s) selected from substituent group C, and the like, Substituent group B consists of hydroxy, alkyloxy, halogen atom, carboxy, lower alkyloxycarbonyl, aryloxycarbonyl, optionally substituted amino, optionally substituted phenyl by one or more substituent(s) selected from substituent group C, non-aromatic heterocyclic group, and heteroaryl.

Substituent group C consists of hydroxy, alkyl, halogen atom, halo(lower)alkyl, carboxy, lower alkyloxycarbonyl, alkyloxy, optionally substituted amino, non-aromatic heterocyclic group, and heteroaryl.

In the present specification, the term "$(\alpha)_{\beta\text{-}\gamma}$" means that α is present of number of β to γ. Examples of "$(\alpha)_{\beta\text{-}\gamma}$" are $(CR^C R^D)_{0\text{-}2}$, $(CH_2)_{0\text{-}2}$, $(CH_2)_{0\text{-}5}$ mean that $CR^C R^D$ is present of number of 0 to 2, $CH_2$ is present of number of 0 to 2, $CH_2$ is present of number of 0 to 5, respectively.

In the present specification, the term "hemopathy" means hemopathy accompanied with the unusual number of platelet. For example the hemopathy is thrombocytopenia (after bone marrow transplantation, after chemotherapy, anaplastic anemia, bone marrow dysplasia syndrome, acquired thrombopenia of intractable sudden thrombocy topenic purpura and the like, congenital thrombopenia of thrombopoietin deficiency and the like) and the like. For example this medicine can be used as treating agent in the case of decreacing number of platelet by administrating antitumor agent, or as protecting agent in the case of expecting the decreace of number of platelet by administrating antitumor agent.

In the present specification, the term "modifiering a platelet production" means 1) increasing a number of platelet decreased by administrating antitumor agent and the like. 2) maintaining a number of platelet which may be decreased by administrating antitumor agent and the like. 3) reducing the ratio of the platelet number of decrease caused by administrating antitumor agent and the like.

BEST MODE CARRYING OUT THE INVENTION

Figure 1:
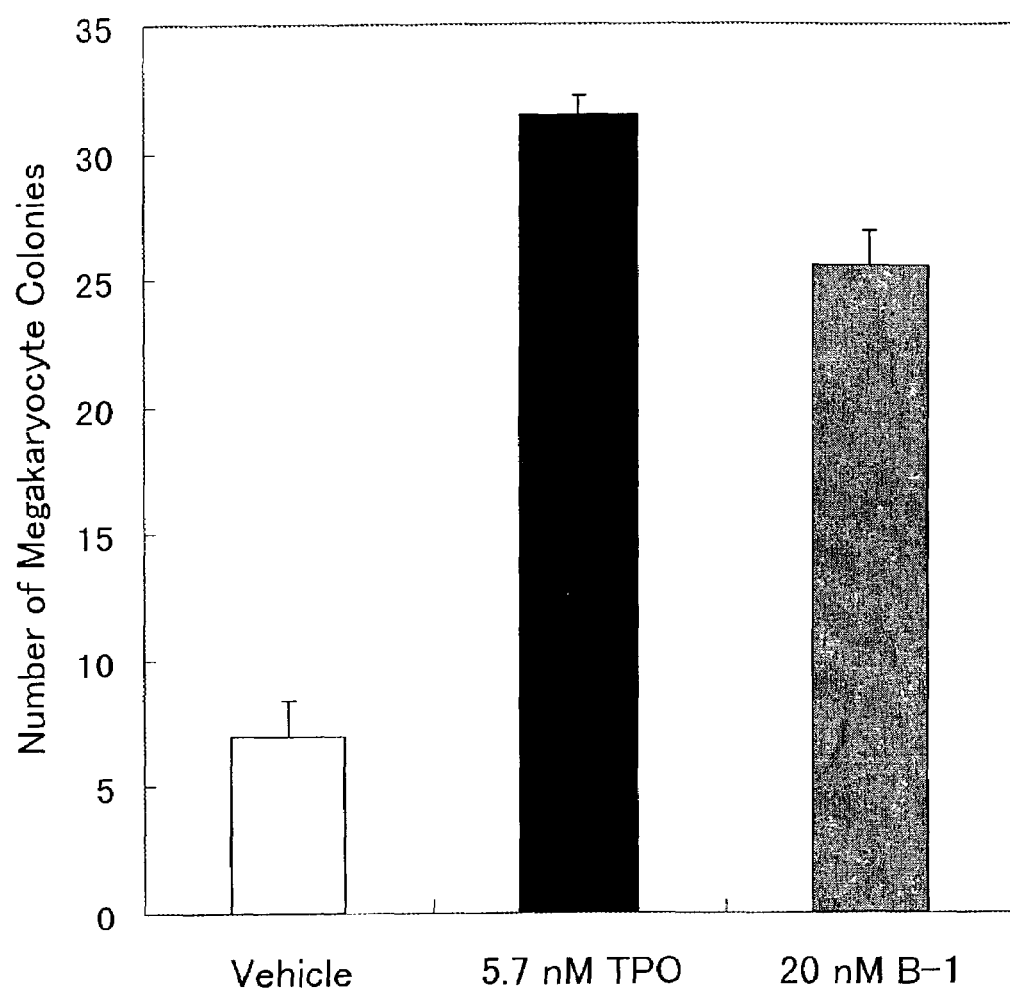
FIG. 1: The chart shows the stimulation activity of a present invention for the proliferation and differentiation of megakaryocyte precursor cells, by counting megakaryocyte colonies formed from human bone marrow cells.

Compounds (I) of the invention can be synthesized by the following methods A to B and the similar process.

(Method A)

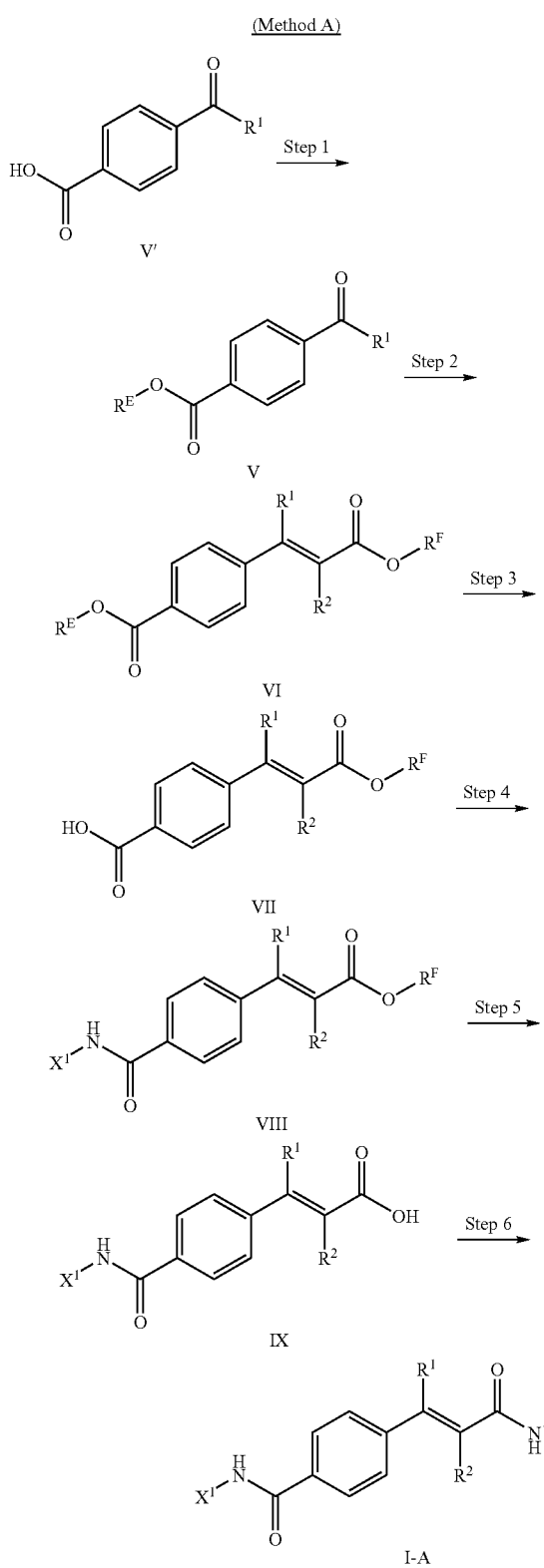

wherein $R^1$, $R^2$, $R^3$, and X are as defined above mentioned.

(Step 1)

This step is a process of protecting of carboxylic acid of 4-formyl-substituted or 4-acyl-substitutedbenzoic acid derivatives by $R^E$. In step 3 combination of $R^E$ and $R^F$ is important in order to remove selectively protecting group of two carboxylic acid. In the case of $R^F$ is protecting group such as methyl and ethyl, which can be removed by basic condition, it is necessary that protecting group of $R^E$ can be removed by another condition except basic condition. Examples of $R^E$ are allyl (removed by palladium (0) complex), tert-butyl, p-methoxybenzyl, triphenylmethyl, diphenylmethyl (removed by acidic condition), trimethylsilylethyl, trimethylsilylethoxymethyl, tert-butyldimethylsilyl (removed by fluoride ion) and the like.

Esterification condition can be used the method of reacting with considerable halo-compound in the presence of suitable base. And it can be synthesized by condensation reaction using a alcohol derivative as starting material.

(Step 2)

This step is a process of converting aldehyde or ketone to olefin. For examples, the olefin can be syntesized by the reaction using phosphineylide such as Wittig reaction, Horner-Emmons reaction, or by dehydrated condensation reaction such as Knoevenagel reaction.

(Step 3)

This step is a process of removing the protecting group $R^E$. The removal of protecting group $R^E$ is carried out under suitable reaction condition as described in Protective Groups in Organic Synthesis, Theodora W Green (John Wiley & Sons).

(Step 4)

This step is a process of preparing amide derivative (VIII) from carboxylic acid derivative (VII) and amine derivative ($X^1$—$NH_2$) by the method such as active esterification, acid chloride, mixed acid anhydride. This step is reacted in the solvent such as tetrahydrofuran, dioxane, dichloromethane, toluene, benzene. At active esterification method it can be carried out by using 1-hydroxybenzotriazole, hydroxysuccinimide, dimethylaminopyridine, and the like and dicyclohexylcarbodiimide, 1-ethyl-3-(3-dimethylaminopropyl)carbodiimide hydrochloride salt, and the like as condensation reagent. At acid halide method it can be carried out by converting free carboxylic acid which is reacted with thionyl chloride or oxalyl chloride to acid chloride. At mixed acid anhydride method it can be carried out by converting carboxylic acid which is reacted with ethylchloroformate, isobutylchloroformate or the like to mixed acid anhydride. Triethylamine, pyridine or the like are used as base in these reaction according to be necessary.

(Step 5)

This step is a process of removing protecting group $R^F$. The protecting group $R^F$ is removed under suitable reaction condition by using the method as described in Protective Groups in Organic Synthesis, Theodora W Green (John Wiley & Sons).

(Step 6)

This step is a process of preparing amide derivative (I-A) from carboxylic acid derivative (IX) and amine derivative ($R^3$—$NH_2$) by the method such as active esterification, acid chloride, mixed acid anhydride method. This step is reacted in the solvent such as tetrahydrofuran, dioxane, dichloromethane, toluene, benzene. At active esterification method it can be carried out by using 1-hydroxybenzotriazole, hydroxysuccinimide, dimethylaminopyridine, and the like and dicyclohexylcarbodiimide, 1-ethyl-3-(3-dimethylaminopropyl)carbodiimide hydrochloride salt, and the like as condensation reagent. At acid halide method it can be carried out by converting free carboxylic acid which is reacted with thionyl chloride or oxalyl chloride to acid chloride. At mixed acid anhydride method it can be carried out by converting carboxylic acid which is reacted with ethylchloroformate, isobutylchloroformate or the like to mixed acid anhydride. Triethylamine, pyridine or the like are used as base in these reaction according to be necessary.

(Method B)

This method is another method for preparing compound (VIII) as described method A.

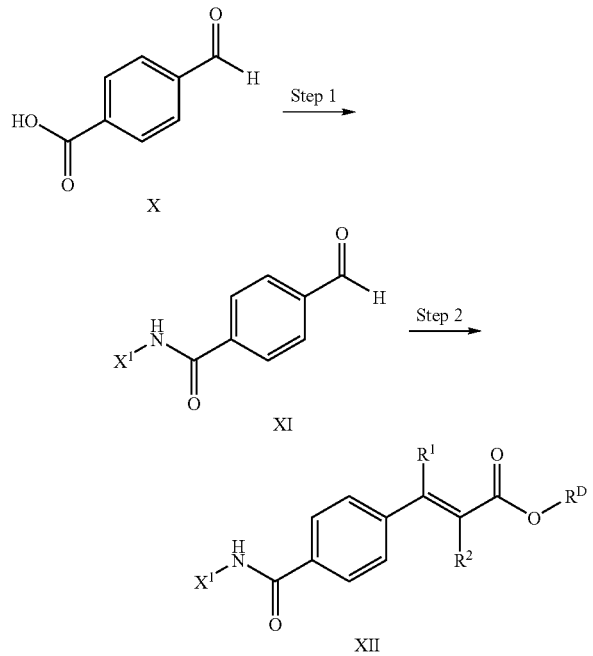

wherein $R^1$, $R^2$ and $X^1$ are as defined above mentioned.

(Step 1)

This step is a process of preparing carboamide derivative (XI) in a manner similar to Step 4 of Method A.

(Step 2)

This step is a process of converting aldehyde derivative (XI) to olefin derivative (XII) in a manner similar to Step 2 of Method A. Compound (XII) can be converted to compound (I-A) in a manner similar to Step 5 and 6 of Metod A.

A compound is represented by the formula wherein $Y^1$ is —N(-alkyl)-CO—; $Z^1$ is optionally substituted thiazole or the like:

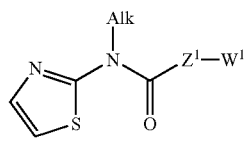

wherein $W^1$ and $Z^1$ are as defined above mentioned; Alk is lower alkyl.

Under alkylation condition for preparing the above mentioned compound may be obtained below mentioned compound.

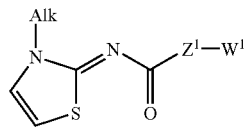

wherein $W^1$, $Z^1$ and Alk are as defined above mentioned.

Compound in formula (I), (II) and (III) wherein a broken line ( - - - ) represents the presence of a bond, contains cis-isomer, trans-isomer and their mixture. For example, compound wherein $W^1$ is amide type possesses cisisomer and trans-isomer blow mentioned.

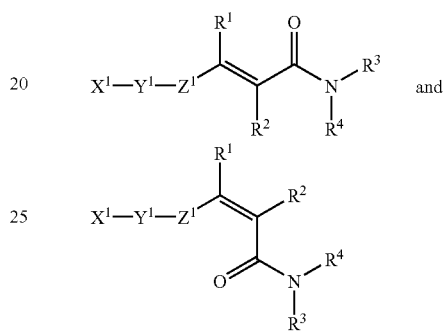

wherein $R^1$, $R^2$, $R^3$, $R^4$, $X^1$, $Y^1$, and $Z^1$ are as defined above mentioned.

The term "solvate" includes, for example, solvates with organic solvents, hydrates, and the like.

The term "compound of the present invention" herein used includes a pharmaceutically acceptable salt or solvate thereof. The salt is exemplified by a salt with alkali metals (e.g., lithium, sodium, potassium, and the like), alkaline earth metals (e.g., magnesium, calcium, and the like), ammonium, organic bases, amino acids, mineral acids (e.g., hydrochloric acid, hydrobromic acid, phosphoric acid, sulfuric acid, and the like), or organic acids (e.g., acetic acid, citric acid, maleic acid, fumaric acid, benzenesulfonic acid, p-toluenesulfonic acid, and the like). These salts can be formed by the usual method. These hydrates can coordinate with any water molecules when hydrates are formed.

Prodrug is a derivative of the compound having a group which can be decomposed chemically or metabolically, and such prodrug is a compound according to the present invention which becomes pharmaceutically active by means of solvolysis or by placing the compound in vivo under a physiological condition. The method of both selection and manufacture of appropriate prodrug derivatives is described in, for example. Design of Prodrugs, Elsevier, Amsterdam, 1985). For instance, prodrugs such as an ester derivative which is prepared by reacting a basal acid compound with a suitable alcohol, or an amide derivative which is prepared by reacting a basal acid compound with a suitable amine are exemplified when the compounds according to present invention have a carboxylic group. Particularly preferred esters as prodrugs are methyl, ethyl, n-propyl, isopropyl, n-butyl, isobutyl, tert-butyl, morpholinoethyl, and N,N-diethylglycolamido, and the like. For instance, prodrugs such as an acyloxy derivative which is prepared by reacting a basal hydroxy compound with a suitable acyl halide or a suitable acid anhydride, or an amide derivative which is prepared by reacting a basal acid compound with a suitable amine are exemplified when the compounds according to present invention have a hydroxy group. Particularly preferred acyloxy derivatives as prodrugs —OCOC$_2$H$_5$, —OCO(t-Bu), —OCOC$_{15}$H$_{31}$, —OCO(m-COONa—Ph), —COCH$_2$CH$_2$COONa, —OCOCH(NH$_2$)CH$_3$, —OCOCH$_2$N(CH$_3$)$_2$, and the like. For instance, prodrugs such as an amide derivative which is prepared by reacting a basal amino compound with a suitable acid halide or a suitable acid anhydride are exemplified when the compounds according to present invention have an amino group. Particularly preferred amide as prodrugs are —NHCO(CH$_2$)$_{20}$CH$_3$, —NHCOCH(NH$_2$)CH$_3$, and the like.

The compound of the present invention is not restricted to any particular isomers but includes all possible isomers and racemic modifications.

The present invention compounds show excellent thrombopoietin receptor agonism as described in examples mentioned later, and may be used as a pharmaceutical composition (platelet production modifier) for hemopathy accompanied with the unusual number of platelet, for example thrombocytopenia and the like. And the present compound may be used as a peripheral blood stem cell releasing promoter, a differetiation-inducer of megakaryocytic leukemic cell, a platelet increasing agent of a platelet donor and the like.

When the compound of the present invention is administered to a person for the treatment of the above diseases, it can be administered orally as powder, granules, tablets, capsules, pilulae, and liquid medicines, or parenterally as injections, suppositories, percutaneous formulations, insufflation, or the like. An effective dose of the compound is formulated by being mixed with appropriate medicinal admixtures such as excipient, binder, penetrant, disintegrators, lubricant, and the like if necessary. Parenteral injections are prepared by sterilizing the compound together with an appropriate carrier.

The dosage varies with the conditions of the patients, administration route, their age, and body weight. In the case of oral administration, the dosage can generally be between 0.1 to 100 mg/kg/day, and preferably 1 to 20 mg/kg/day for adult.

The following examples are provided to further illustrate the present invention and are not to be constructed as limiting the scope thereof.

Abbreviations described below are used in the following examples.
Me: methyl
Et: ethyl
n-Pr: n-propyl
i-Pr: isopropyl
c-Pr: cyclopropyl
n-Bu: n-butyl
i-Bu: i-butyl
sec- Bu:sec-butyl
t-Bu: tert-butyl
i-Bu: i-butyl
n-Pen: n-pentyl
c-Pen: cyclopentyl
n-Hex: n-hexyl
c-Hex: cyclohexyl
i-Hex: i-hexyl
Ph: phenyl
Bn: benzyl
Bz: benzoyl
Py: pyridyl
Th: thienyl
Ac: acetyl
Z: benzyloxycarbonyl
DMF: N,N-dimethylformamide
THF: tetrahydrofuran proppargyl, allyl, pyrazole, pyrimidine, piperidine, methyl, cyclohexylmethyl

EXAMPLE

Example 1

The Preparation of Compound (A-1, A-2, and B-1)

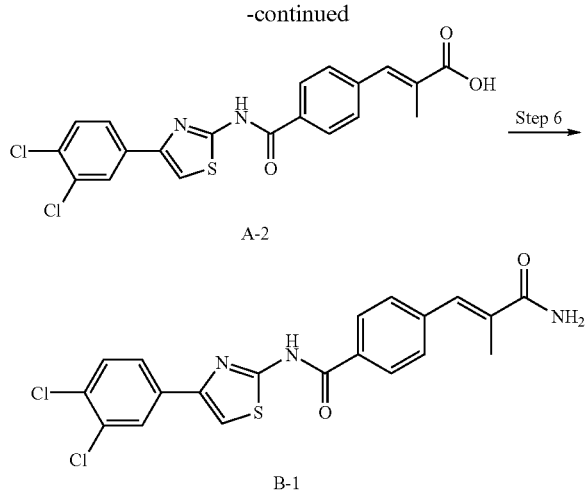

A-2

B-1

(Step 1)

A solution of terephthaladehydic acid (7.5 g), allyl bromide (4.41 ml), and potassium carbonate (7.0 g) in DMF (100 ml) was stirred at 60° C. for 16 h. The reaction solvent was removed under reduced pressure, and the residue was partitioned between ethyl acetate and water. The ethyl acetate layer was washed with sodium bicarbonate aqueous solution, water, and brine, and dried over magnesium sulfate. The solvent was removed under reduced pressure to obtain compound (2) 9.2 g as colorless clear oil.

1H NMR(CDCl$_3$, δ ppm): 4.87 (2H, dt, J=1.2, 5.7 Hz), 5.30-5.47 (2H, m), 5.99-6.12 (1H, m), 7.94-7.98 (2H, m), 8.20-8.25 (2H, m), 10.11 (1H, s).

(Step 2)

A solution of compound (2) (4.37 g) and ethyl 2-(triphenylphosphoranilidene)propionate (10.63 g) in toluene (100 ml) was heated with stirring at 70° C. for 1 h. The reaction solvent was concentrated to ca. 30 to 40 ml, the precipitated triphenylphosphineoxide was filtered off. The filtrate was concentrated, and the residue was purified by silica gel column chromatography (ethyl acetate/n-hexane=1/10) to obtain compound (3) 6.9 g as colorless clear oil.

$^1$H NMR (CDCl$_3$, δ ppm): 1.36 (3H, t, J=7.2 Hz), 2.11 (3H, d, J=1.5 Hz), 4.29 (2H, q, J=7.2 Hz), 4.84 (2H, dt, J=1.2, 5.7 Hz), 5.28-5.46 (2H, m), 5.98-6.11 (1H, m), 7.43-7.47 (2H, m), 7.69 (1H, d, J=1.5 Hz), 8.06-8.10 (2H, m).

(Step 3)

A solution of compound (3) (6 g), tetrakistriphenylphosphinpalladium (1.27 g), and morpholine (2.68 g) in THF (100 ml) was stirred at 60° C. for 30 min. The reaction solvent was concentrated to ca. 30 to 40 ml, and ethyl acetate was added to the residue. The mixture was extracted with sodium bicarbonate aqueous solution three times. The combined sodium bicarbonate extract was acidified with 3M hydrocholic acid, and the precipitated crystals were extracted with ethyl acetate. The ethyl acetate layer was washed with brine, dried over magnesium sulfate. The solvent was removed under reduced pressure to obtain compound (4) 4.5 g as white crystals.

$^1$H NMR (CDCl$_3$, δ ppm): 1.37 (3H, t, J=7.2 Hz), 2.13 (3H, d, J=1.2 Hz), 4.30 (2H, q, J=7.2 Hz), 7.49 (2H, d, J=8.4 Hz), 7.71 (1H, s), 8.14 (2H, d, J=8.4 Hz).

(Step 4)

To a solution of compound (4) (5.67 g), oxalyl chloride (1.3 ml) in THF (100 ml) was added catalytic amount of DMF, and then the reaction mixture was stirred at room temperature for 2 h. The reaction solution was removed under reduced pressure, toluene was added to the resulting residue, and toluene was removed under reduced pressure. The obtained carboxylic acid chloride was dissolved with dioxane (70 ml), was added 2-amino-4-(3,4-dichlorophenyl)thiazole (1 g), and pyridine (970 μl) to the mixture. The reaction solution was heated with stirring at 100° C. for 16 h, and partitioned between ethyl acetete and water. The ethyl acetate layer was washed with sodium bicarbonate aqueous solution, water, and brine, and drided over magnesium sulfate. The solvent was removed under reduced pressure to obtain compound (A-1) 1.5 g as white crystals.

$^1$H NMR (DMSO-d$_6$, δ ppm): 1.29 (3H, t, J=7.2 Hz), 2.10 (3H, d, J=1.2 Hz), 4.23 (2H, q, J=7.2 Hz), 7.62-7.68 (3H, m), 7.72 (1H, d, J=8.4 Hz), 7.91 (1H, s), 7.94 (1H, dd, J=1.8, 8.4 Hz), 8.15-8.20 (2H, m), 8.21 (1H, d, J=1.8 Hz), 12.84 (1H, br).

(Step 5)

A solution of compound (A-1) (1.7 g), 4M sodium hydroxide aqueous solution (5.5 ml) in THF (150 ml) was heated with stirring 85° C. for 18 h. The reacton solution was acidified with diluted hydrochloric acid, and the precipitated crystals were filtered. The obtained powder was washed methanol and ethyl acetate to obtain compound (A-2) (1.5 g) as white powder.

$^1$H NMR (DMSO-d$_6$, δ ppm): 2.08 (3H, d, J=0.9 Hz), 7.62-7.68 (3H, m), 7.72 (1H, d, J=8.7 Hz), 7.92 (1H, s), 7.95 (1H, dd, J=2.1, 8.7 Hz), 8.16-8.20 (2H, m), 8.22 (1H, d, J=1.8 Hz), 12.84 (1H, br).

(Step 6)

To a solution of compound (A-2) (690 mg), oxalyl chloride (420 μl) in THF (150 ml) was added catalytic amount of DMF, and then the reaction solution was stirred at 70° C. for 1 h. The reaction solution was removed under reduced pressure, toluene was added to the resulting residue, and toluene was removed under reduced pressure. To the obtained carboxylic acid chloride was added THF (100 ml), and cooled at ice-cooling. To a solution of 28% ammonia aqueous solution (20 ml) was added ether and sodium hydroxide (5 g) at ice-cooling, and stirred for 10 min, and standed. This ether solution was added to a THF solution of the acid chloride, and sitrred at ice-cooling for 1 h. The reaction solution was partitioned between ethyl acetete and water. The organic layer was successively washed with sodium bicarbonate aqueous solution, water, and brine, and drided over magnesium sulfate. The solvent was removed under reduced pressure, the residue was purified by silica gel column chromatography (ethyl acetate/n-hexane=10/1 to ethyl acetate) to obtain compound (B-1) (400 mg) as colorless crystals.

$^1$H NMR (DMSO-d$_6$, δ ppm): 2.04 (3H, d, J=1.5 Hz), 7.18 (1H, br), 7.32 (1H, s), 7.52-7.58 (2H, m), 7.60 (1H, br), 7.72 (1H, d, J=8.1 Hz), 7.91 (1H, s), 7.94 (1H, dd, J=2.1, 8.4 Hz), 8.14-8.19 (2H, m), 8.22 (1H, d, J=2.4 Hz), 12.81 (1H, br).

Example 2

The Preparation of Compound (A-7)

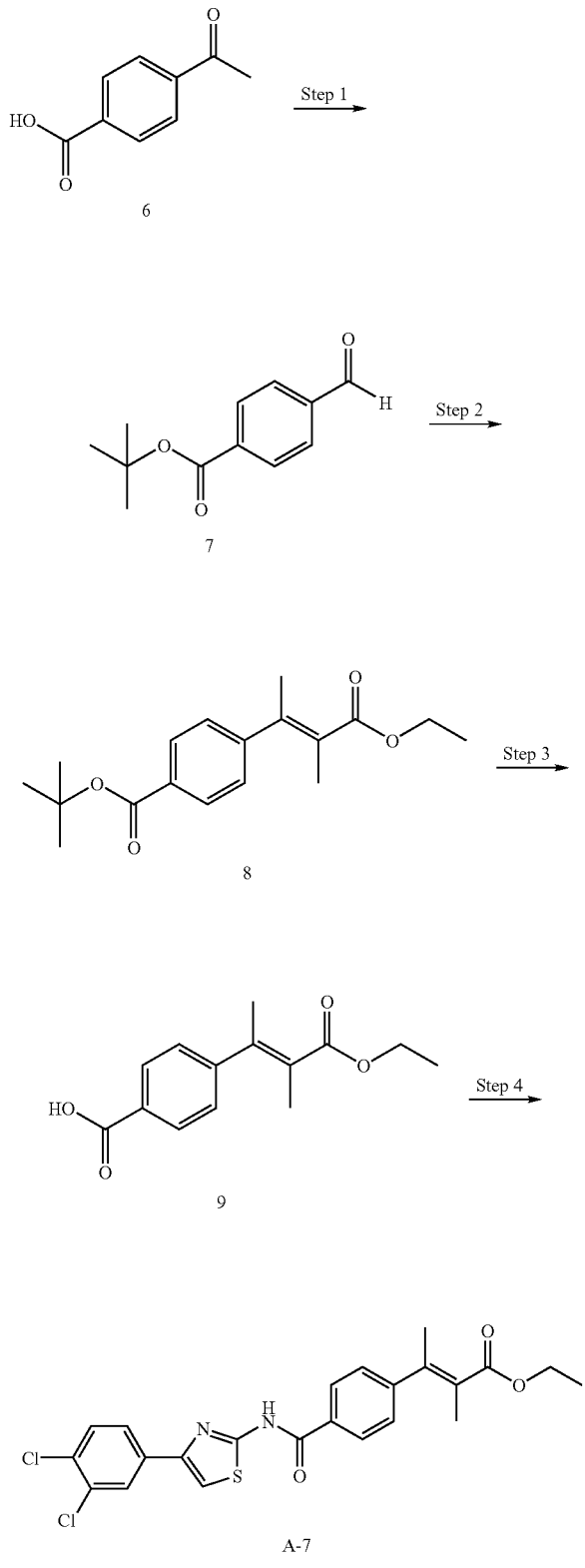

(Step 1)

To a solution of 4-acetylbenzoic acid (1.64 g), oxalyl chloride (1.31 ml) in THF (100 ml) was added catalytic amount of DMF, and then the reaction mixture was stirred at room temperature for 2 h. The reaction solution was removed under reduced pressure, toluene was added to the resulting residue, and toluene was removed under reduced pressure. To the obtained carboxylic acid chloride was added THF (50 ml), tert-butyl alchol (1.15 ml), and pyridine (1.21 ml), and the reaction mixture was heated under reflux for 40 h, and partitioned between ice-water acidified with hydrochloric acid and ethyl acetate. The ethyl acetate layer was washed with sodium bicarbonate aqueous solution, water, and brine, and drided over magnesium sulfate. The solvent was removed under reduced pressure, the residue was purified by silica gel column chromatography (ethyl acetate/n-hexane=/1/5) to obtain compound (7) (2.0 g) as white crystals.

$^1$H NMR(CDCl$_3$, δ ppm): 1.61 (9H, s), 2.64 (3H, s), 7.96-7.00 (2H, m), 8.04-8.09 (2H, m).

(Step 2)

To a suspension of 60% sodium hydride (360 mg) in THF (100 ml) was added 2-phosphonopropionic acid triethyl (2.14 g) at ice-cooling. After the reacton mixture was stirred for 30 min, added dropwise a solution of compound (7) (1.9 g) in THF (15 ml) at ice-cooling. The reaction solution was stirred at 50° C. for 3 h, and partitioned between ice-water acidified with hydrochloric acid and ethyl acetate. The ethyl acetate layer was washed with sodium bicarbonate aqueous solution, water, and brine, and drided over magnesium sulfate. The solvent was removed under reduced pressure, the residue was purified by silica gel column chromatography (ethyl acetate/n-hexane=1/15) to obtain compound (8) (1.0 g) as a colorless oil.

$^1$H NMR(CDCl$_3$, δ ppm): 1.35 (3H, t, J=7.2 Hz), 1.60 (9H, s), 1.74 (3H, q, J=1.5 Hz), 2.24 (3H, q, J=1.5 Hz), 4.27 (2H, q, J=6.9 Hz), 7.18-7.22 (2H, m), 7.97-8.10 (2H, m).

(Step 3)

A solution of compound (8) (900 mg) in formic acid (98-100%, 10 ml) was stirred at room temperature for 3 h. The reaction solution was concentrated, toluene was added to the residure, and concentrated again. The obtained residue was washed with n-hexane to obtain compound (9) (680 mg) as white crystals.

$^1$H NMR(CDCl$_3$, δ ppm): 1.36 (3H, t, J=7.2 Hz), 1.74 (3H, q, J=1.5 Hz), 2.26 (3H, q, J=1.5 Hz), 4.28 (2H, q, J=7.2 Hz), 7.25-7.29 (2H, m), 8.10-8.14 m).

(Step 4)

Compound (A-7) was synthsized from compound (9) as starting material in a manner similar to Step 4 of Example 1.

$^1$H NMR(CDCl$_3$, δ ppm): 1.36 (3H, t, J=7.2 Hz), 1.74 (3H, q, J=1.5 Hz), 2.25 (3H, q, J=1.5 Hz), 4.28 (2H, q, J=7.2 Hz), 7.26-7.29 (2H, m), 7.44 (1H, d, J=8.4 Hz), 7.61 (1H, dd, J=2.1, 8.4 Hz), 7.91 (1H, d, J=2.1 Hz), 7.91-7.95 (2H, m), 10.09 (1H, br).

Compound (A-3) to (A-6), (A-8) to (A-107), (B-2) to (B-46), (C-1) to (C-5), (D-1), (E-1) to (E-2), (F-1) to (F-3), (G-1) to (G-8), (H-1) to (H-8) and (I-1) to (I-6) were synthsized in a manner similar to Example 1 and 2.

Their physical data of compound group A were shown in Tables 1 to 10, compound group B in Tables 11 to 17, compound group C in Tables 18, compound group D in Tables 19, compound group E in Tables 20, compound group F in Tables 21, compound group G in Tables 22 to 23, compound group H in Tables 24 to 25, and compound group I in Tables 26.

TABLE 1

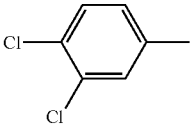

| Compound No. | R⁶ | R¹ | R² | R⁵ | ¹H-NMR(DMSO d-6) |
|---|---|---|---|---|---|
| A-3 | 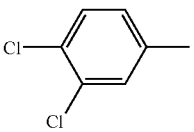 3,4-diClPh | H | H | Et | 1.28(3H, t, J=7.2Hz), 4.22(2H, q, J=7.2Hz), 6.80(1H, d, J=16.5Hz), 7.72(1H, d, J=8.4Hz), 7.73(1H, d, J=15.9Hz), 7.88-7.93(3H, m), 7.94(1H, dd, J=2.1, 8.7Hz), 8.12-8.18(2H, m), 8.21(1H, d, J=1.8Hz), 12.84(1H, s). |
| A-4 | 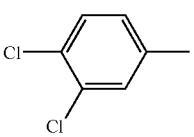 3,4-diClPh | H | H | H | 6.70(1H, d, J=15.9Hz), 7.67(1H, d, J=15.9Hz), 7.72(1H, d, J=8.7Hz), 7.84(2H, m), 7.92(1H, s), 7.95(1H, dd, J=1.8, 8.1Hz), 8.12-8.18(2H, m), 8.21(1H, d, J=2.1Hz). 12.57(1H, br), 12.84(1H, s). |
| A-5 | 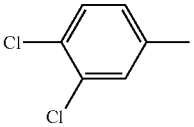 3,4-diClPh | H | Et | Et | 1.13(3H, t, J=7.2Hz), 1.30(3H, t, J=7.2Hz), 2.50(2H, q, J=7.2Hz), 4.24(2H, q, J=7.2Hz), 7.577(1H, s), 7.60-7.63(2H, m), 7.72(1H, d, J=8.7Hz), 7.92(1H, s), 7.95(1H, dd, J=1.8, 8.4Hz), 8.16-8.20(2H, m), 8.21(1H, d, J=1.8Hz) 12.85(1H, br). |
| A-6 | 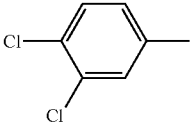 3,4-diClPh | H | Et | H | 1.13(3H, t, J=7.5Hz), 2.47(2H, q, J=7.2Hz), 7.55-7.60(2H, m), 7.61(1H, s), 7.72(1H, d, J=8.4Hz), 7.91(1H, s), 7.95(1H, dd, J=2.1, 8.4Hz), 8.15-8.20(2H, m), 8.21(1H, d, J=2.1Hz), 12.76(1H, br). |
| A-8 | 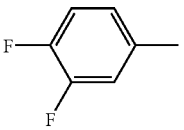 3,4-diClPh | Me | Me | H | 1.71(3H, d, J=1.5Hz), 2.22(3H, d, J=1.2Hz), 7.37-7.42(2H, m), 7.73(1H, d, J=8.4Hz), 7.92(1H, s), 7.95(1H, dd, J=2.1, 8.4Hz), 8.13-8.18(2H, m), 8.22(1H, d, J=2.1Hz), 12.77(1H, br). |
| A-9 | 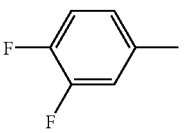 3,4-diFPh | H | Me | Et | 1.29(3H, t, J=6.9Hz), 2.10(3H, d, J=1.8Hz), 4.23(2H, q, J=6.9Hz), 7.48-7.57(1H, m), 7.62-7.68(3H, m), 7.78-7.85(2H, m), 7.93-8.10(1H, m), 8.15-8.20(2H, m), 12.85(1H, br). |
| A-10 | 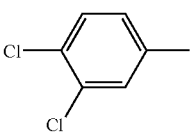 3,4-diFPh | H | Me | H | 2.07(3H, d, J=1.5Hz), 7.47-7.57(1H, m), 7.62-7.67(3H, m), 7.79-7.85(2H, m), 7.93-8.01(1H, m), 8.15-8.20(2H, m), 12.81(1H, br). |
| A-11 | 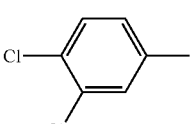 3,4-diClPh | H | Cl | Et | 1.33(3H, t, J=7.2Hz), 4.33(2H, q, J=7.2Hz), 7.72(1H, d, J=8.1Hz), 7.93(3H, s), 7.94(1H, dd, J=2.1, 8.1Hz), 8.04(2H, d, J=8.7Hz), 8.08(1H, s), 8.21(1H, d, J=2.4Hz), 8.21(2H, d, J=8.7Hz), 12.91(1H, s). |
| A-12 | 3,4-diClPh | H | F | Et | 1.26(3H, t, J=7.5Hz), 4.27(2H, q, J=7.5Hz), 6.91(1H, d, J=21Hz), 7.22(1H, s), 7.42(1H, d, J=8.1Hz), 7.55(2H, d, J=8.1Hz), 7.69(1H, dd, J=1.8Hz, 8.1Hz), 7.87(1H, d, J=2.1Hz), 7.87(2H, d, J=8.1Hz), 10.15(1H, s) |

TABLE 2

| Compound No. | R⁶ | R¹ | R² | R⁵ | ¹H-NMR(DMSO d-6) |
|---|---|---|---|---|---|
| A-13 | 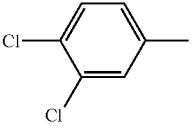 3,4-diCl-phenyl | H | NHZ | Me | 3.64(1H, s), 5.12(2H, s), 6.55(1H, s), 7.32(2H, d, J=8.4Hz), 7.35-7.42(5H, m), 7.72(1H, d, J=8.7Hz), 7.94(1H, dd, J=1.8Hz, 8.7Hz), 8.06(2H, d, J=8.4Hz), 8.21(1H, d, J=1.8Hz), 9.39(1H, s), 9.39(1H, s), 12.86(1H, s) |
| A-14 | 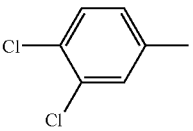 3,4-diCl-phenyl | H | Cl | H | 7.73(1H, d, J=8.4Hz), 7.94(1H, s), 7.95(1H, dd, J=2.1, 8.4Hz), 8.04(2H, d, J=8.1Hz), 8.05(1H, s), 8.21(2H, d, J=8.1Hz), 8.22(1H, d, J=2.1Hz), 12.90(1H, s), 13.84(1H, bs) |
| A-15 | 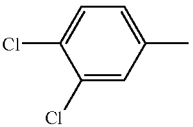 3,4-diCl-phenyl | H | Br | Me | 3.55(3H, s), 6.84(1H, s), 7.56(2H, d, J=8.4Hz), 7.72(1H, d, J=8.1Hz), 7.93(1H, s), 7.95(1H, dd, J=8.4, 2.1Hz), 8.15(2H, d, J=8.4Hz), 8.22(1H, d, J=2.1Hz), 12.90(1H, s) |
| A-16 | 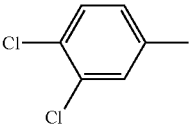 3,4-diCl-phenyl | H | Br | H | 6.72(1H, s), 7.58(2H, d, J=8.4Hz), 7.72(1H, d, J=8.4Hz), 7.93(1H, s), 7.95(1H, dd, J=8.4Hz, 1.8Hz), 8.12(2H, d, J=8.4Hz), 8.22(1H, d, J=2.4Hz), 12.88(1H, bs) |
| A-17 | 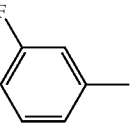 3-F-phenyl | H | Me | Et | 7.15-7.21(1H, m), 7.26-7.84(6H, m), 7.47-7.54(1H, m), 7.87(1H, s), 8.24(2H, d, J=8.5Hz), 12.97(1H, s), 13.97(1H, bs) |
| A-18 | 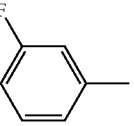 3-F-phenyl | H | Me | H | 2.07(3H, d, J=1.4Hz), 7.12-7.21(1H, m), 7.47-7.54(1H, m), 7.64(2H, d, J=8.5Hz), 7.66(1H, s), 7.74-7.78(1H, m), 7.80-7.84(1H, m), 7.85(1H, s), 8.18(2H, d, J=8.5Hz), 12.63(1H, bs), 12.85(1H, s) |
| A-19 | 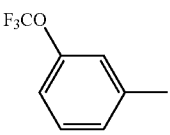 3-F₃CO-phenyl | H | Me | Et | 1.30(3H, t, J=7.1Hz), 2.10(3H, d, J=1.4Hz), 4.23(2H, q, J=7.1Hz), 7.33-7.36(1H, m), 7.58(1H, t, J=8.0Hz), 7.65(2H, d, J=8.5Hz), 7.67(1H, s), 7.91(1H, s), 7.93(1H, bs), 7.99-8.02(1H, m), 8.19(2H, d, J=8.5Hz), 12.85(1H, s) |
| A-20 | 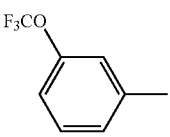 3-F₃CO-phenyl | H | Me | H | 2.07(3H, d, J=1.4Hz), 7.33-7.36(1H, m), 7.57-7.66(4H, m), 7.91(1H, s), 7.94(1H, m), 7.99-8.02(1H, m), 8.18(2H, d, J=8.5Hz), 12.68(1H, bs), 12.85(1H, s) |
| A-21 | 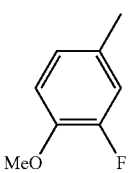 3-MeO-4-F-phenyl | H | Me | Et | 1.29(3H, t, J=7.1Hz), 2.10(3H, d, J=1.7Hz), 3.89(3H, s), 4.23(2H, q, J=7.1Hz), 7.22-7.28(1H, m), 7.63-7.66(4H, m), 7.74-7.80(2H, m), 8.18(2H, d, J=8.5Hz), 12.80(1H, bs) |
| A-22 | 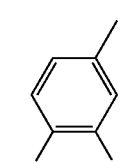 3-MeO-4-F-phenyl | H | Me | H | 2.07(3H, d, J=1.4Hz), 3.89(3H, s), 7.22-7.28(1H, m), 7.63-7.67(4H, m), 7.75-7.81(2H, m), 8.18(2H, d, J=8.5Hz), 12.80(1H, bs) |

TABLE 2-continued

| Compound No. | R$^6$ | R$^1$ | R$^2$ | R$^5$ | $^1$H-NMR(DMSO d-6) |
|---|---|---|---|---|---|
| A-23 | 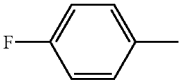 | H | Me | Et | 1.29(3H, t, J=7.1Hz), 2.10(3H, d, J=1.4Hz), 4.23(2H, q, J=7.1Hz), 7.26-7.32(4H, m), 7.63-7.66(3H, m), 7.69(1H, s), 7.97-8.02(2H, m), 8.18(2H, d, J=8.5Hz), 12.83(1H, bs) |
| A-24 |  | H | Me | H | 2.08(3H, d, J=1.1Hz), 7.26-7.32(2H, m), 7.64(2H, d, J=8.5Hz), 7.66(1H, s), 7.704(1H, s), 7.98-8.03(2H, m), 8.18(2H, d, J=8.5Hz), 12.85(1H, bs) |

TABLE 3

| Compound No. | R$^6$ | R$^1$ | R$^2$ | R$^5$ | $^1$H-NMR(DMSO d-6) |
|---|---|---|---|---|---|
| A-25 | 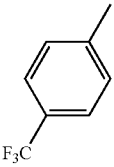 | H | Me | Et | 1.29(3H, t, J=7.1Hz), 2.10(3H, d, J=1.4Hz), 4.23(2H, q, J=7.1Hz), 7.64-7.67(3H, m), 7.83(2H, d, J=8.5Hz), 7.95(1H, s), 8.17-8.20(4H, m), 12.93(1H, bs) |
| A-26 | 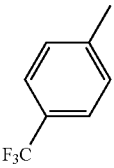 | H | Me | H | 2.07(3H, d, J=1.1Hz), 7.65(2H, d, J=8.2Hz), 7.66(1H, s), 7.83(2H, d, J=8.5Hz), 7.96(1H, s), 8.17(2H, d, J=8.2Hz), 8.18(2H, d, J=8.5Hz), 12.93(1H, s) |
| A-27 | 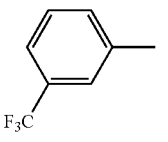 | H | Me | Et | 1.29(3H, t, J=7.1Hz), 2.10(3H, d, J=1.4Hz), 4.23(2H, q, J=7.1Hz), 7.64-7.72(5H, m), 7.97(1H, s), 8.19(2H, d, J=8.5Hz), 8.25-8.28(1H, m), 8.33(1H, s), 12.80(1H, bs) |
| A-28 | 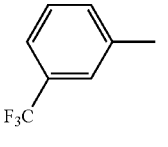 | H | Me | H | 2.08(3H, d, J=1.1Hz), 7.68(2H, d, J=8.2Hz), 7.66(1H, s), 7.71(1H, d, J=5.2Hz), 7.91(1H, s), 8.18(2H, d, J=8.2Hz), 8.26-8.28(1H, m), 8.33(1H, bs), 12.87(1H, s) |
| A-29 | 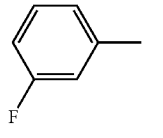 | H | Cl | Et | 1.33(3H, t, J=7.1Hz), 4.32(2H, q, J=7.1Hz), 7.15-7.21(1H, m), 7.47-7.54(1H, m), 7.81-7.83(1H, m), 7.86(1H, s), 8.05(2H, d, J=8.5Hz), 8.09(1H, s), 8.22(2H, d, J=8.5Hz), 12.92(1H, bs) |
| A-30 | 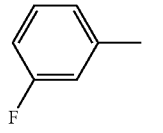 | H | Cl | H | 7.16-7.21(1H, m), 7.47-7.54(1H, m), 7.75-7.78(1H, m), 7.81-7.84(1H, m), 7.86(1H, s), 8.04(2H, d, J=8.2Hz), 8.06(1H, s), 8.21(2H, d, J=8.2Hz), 12.91(1H, s) |
| A-31 | 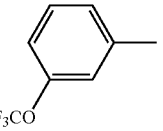 | H | Cl | Et | 1.33(3H, t, J=7.1Hz), 4.33(2H, q, J=7.1Hz), 7.34-7.36(1H, m), 7.57-7.63(1H, m), 7.92(1H, s), 7.94(1H, s), 7.99-8.02(1H, m), 8.05(2H, d, J=8.5Hz), 8.08(1H, s), 8.22(2H, d, J=8.5Hz), 12.92(1H, bs) |
| A-32 | 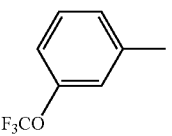 | H | Cl | H | 7.33-7.36(1H, m), 7.57-7.63(1H, m), 7.93(1H, s), 7.93(1H, m), 8.04-8.06(4H, m), 8.21(2H, d, J=8.2Hz), 12.92(1H, s) |

TABLE 3-continued

| Compound No. | R⁶ | R¹ | R² | R⁵ | ¹H-NMR(DMSO d-6) |
|---|---|---|---|---|---|
| A-33 | 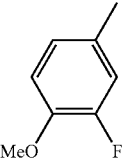 | H | Cl | Et | 1.33(3H, t, J=7.1Hz), 3.88(3H, s), 4.33(2H, q, J=7.1Hz), 7.22-7.28(1H, m), 7.67(1H, s), 7.74-7.80(2H, m), 8.05(2H, d, J=8.5Hz), 8.09(1H, s), 8.21(2H, d, J=8.5Hz), 12.88(1H, bs) |
| A-34 | 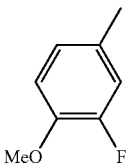 | H | Cl | H | 3.89(3H, s), 7.22-7.28(1H, m), 7.67(1H, s), 7.76-7.81(2H, m), 8.04(2H, d, J=8.5Hz), 8.05(1H, s), 8.21(2H, d, J=8.5Hz), 12.87(1H, bs) |
| A-35 | 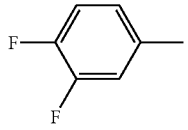 | H | Cl | Et | 1.33(3H, t, J=7.1Hz), 4.32(2H, q, J=7.1Hz), 7.48-7.57(1H, m), 7.80-7.85(1H, m), 7.83(1H, s), 7.94-8.01(1H, m), 8.05(2H, d, J=8.5Hz), 8.08(1H, s), 8.21(2H, d, J=8.5Hz), 12.91(1H, bs) |
| A-36 | 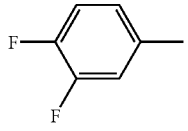 | H | Cl | H | 7.48-7.58(1H, m), 7.80-7.85(1H, m), 7.83(1H, s), 7.94-8.01(1H, m), 8.04(2H, d, J=8.5Hz), 8.05(1H, s), 8.21(2H, d, J=8.5Hz), 12.92(1H, bs) |

TABLE 4

| Compound No. | R⁶ | R¹ | R² | R⁵ | ¹H-NMR(DMSO d-6) |
|---|---|---|---|---|---|
| A-37 | 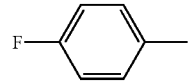 | H | Cl | Et | 1.33(3H, t, J=7.1Hz), 4.32(2H, q, J=7.1Hz), 7.26-7.32(2H, m), 7.71(1H, s), 7.98-8.02(2H, m), 8.04(2H, d, J=8.5Hz), 8.09(1H, s), 8.21(2H, d, J=8.5Hz), 12.91(1H, bs) |
| A-38 | 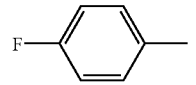 | H | Cl | H | 7.26-7.33(2H, m), 7.72(1H, s), 7.98-8.03(2H, m), 8.04(2H, d, J=8.5Hz), 8.05(1H, s), 8.21(2H, d, J=8.5Hz), 12.92(1H, bs) |
| A-39 | 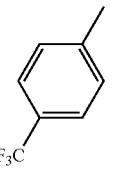 | H | Cl | Et | 1.33(3H, t, J=7.1Hz), 4.32(2H, q, J=7.1Hz), 7.83(2H, d, J=8.4Hz), 7.97(1H, s), 8.05(2H, d, J=8.5Hz), 8.09(1H, s), 8.18(2H, d, J=8.4Hz), 8.22(2H, d, J=8.5Hz), 13.00(1H, s) |
| A-40 | 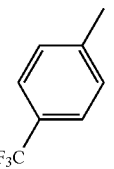 | H | Cl | H | 7.83(2H, d, J=8.5Hz), 7.96(1H, s), 8.04(2H, d, J=8.5Hz), 8.06(1H, s), 8.18(2H, d, J=8.5Hz), 8.22(2H, d, J=8.5Hz), 12.97(1H, bs) |
| A-41 | 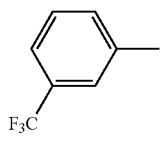 | H | Cl | Et | 1.33(3H, t, J=7.1Hz), 4.33(2H, q, J=7.1Hz), 7.70-7.72(2H, m), 7.98(1H, s), 8.05(2H, d, J=8.5Hz), 8.09(1H, s), 8.22(2H, d, J=8.5Hz), 8.25-8.28(1H, m), 8.33(1H, bs), 12.92(1H, s) |

TABLE 4-continued

| Compound No. | R⁶ | R¹ | R² | R⁵ | ¹H-NMR(DMSO d-6) |
|---|---|---|---|---|---|
| A-42 | 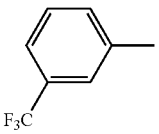 | H | Cl | H | 7.70-7.72(2H, m), 7.98(1H, s), 8.04(2H, d, J=8.5Hz), 8.06(1H, s), 8.22(2H, d, J=8.5Hz), 8.24-8.28(1H, m), 8.33(1H, bs), 12.92(1H, bs) |
| A-43 | 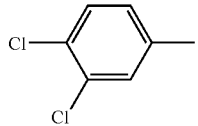 | H | F | H | 7.15(1H, d, J=36.3Hz), 7.73(1H, d, J=8.4Hz), 7.86(2H, d, J=8.7Hz), 7.97-7.94(2H, m), 8.18(2H, d, J=8.4Hz), 8.22(1H, d, J=2.1Hz), 12.89(1H, s) |
| A-44 | 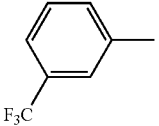 | H | F | H | 7.20(1H, d, J=23.1Hz), 7.68(2H, d, J=8.5Hz), 7.70(1H, s), 7.97(1H, s), 8.12(2H, d, J=8.5Hz), 8.25-8.28(1H, m), 8.33(1H, bs), 12.84(1H, bs) |
| A-45 | 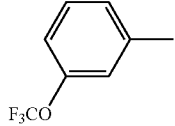 | H | F | H | 7.19(1H, d, J=22.8Hz), 7.33-7.56(1H, m), 7.57-7.63(1H, m), 7.68(2H, d, J=8.5Hz), 7.91(1H, s), 7.94(1H, bs), 7.99-8.02(1H, m), 8.11(2H, d, J=8.5Hz), 12.83(1H, bs) |
| A-46 | 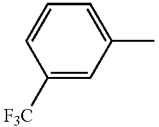 | H | F | H | 7.20(1H, d, J=22.9Hz), 7.68(2H, d, J=8.5Hz), 7.83(2H, d, J=8.5Hz), 7.96(1H, s), 8.12(2H, d, J=8.5Hz), 8.18(2H, d, J=8.5Hz), 12.91(1H, s), 13.87(1H, bs) |
| A-47 | 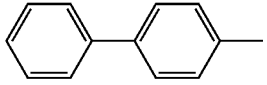 | H | Cl | H | 7.39-7.45(1H, m), 7.48-7.54(2H, m), 7.67-7.73(3H, m), 7.77-7.81(2H, m), 8.03-8.07(3H, m), 8.19-8.25(3H, m) |
| A-48 | 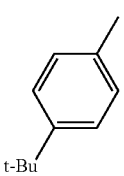 | H | Cl | H | 1.32(9H, s), 7.47(2H, d, J=9.0Hz), 7.64(1H, s), 7.89(2H, d, J=9.0Hz), 8.01-8.06(3H, m), 8.22(2H, d, J=8.1Hz), 12.89(1H, s), 13.90(1H, bs) |
| A-49 | 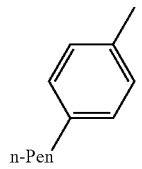 | H | Cl | H | 0.87(3H, t, J=7.2Hz), 1.26-1.36(4H, m), 1.60(2H, quint, J=7.8Hz), 2.60(2H, t, J=7.5Hz), 7.27(2H, d, J=8.4Hz), 7.64(1H, s), 7.87(2H, d, J=8.1Hz), 8.02-8.05(3H, m), 8.21(2H, d, J=8.4Hz), 12.88(1H, s), 13.79(1H, bs) |

TABLE 5

| Compound No. | R⁶ | R¹ | R² | R⁵ | ¹H-NMR(DMSO d-6) |
|---|---|---|---|---|---|
| A-50 | 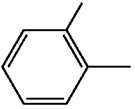 | H | Cl | H | 7.30-7.46(3H, m), 7.63(1H, d, J=2.4Hz), 8.03-8.07(3H, m), 8.12(1H, td, J=1.8Hz, 7.8Hz), 8.22(2H, d, J=8.7Hz), 12.93(1H, s), 13.85(1H, bs) |

TABLE 5-continued

| Compound No. | R⁶ | R¹ | R² | R⁵ | ¹H-NMR(DMSO d-6) |
|---|---|---|---|---|---|
| A-51 | 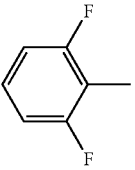 | H | Cl | H | 7.19-7.28(2H, m), 7.47-7.57(2H, m), 8.01-8.05(3H, m), 8.21(2H, d, J=8.4Hz), 12.97(1H, s), 13.80(1H, bs) |
| A-52 | 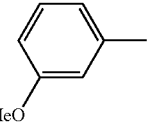 | H | Cl | H | 3.82(3H, s), 6.89-6.94(1H, m), 7.36(1H, t, J=8.1Hz), 7.53-7.56(2H, m), 7.75(1H, s), 8.02-8.06(3H, m), 8.21(2H, d, J=8.4Hz), 12.88(1H, s), 13.82(1H, bs) |
| A-53 | 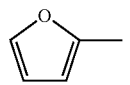 | H | Cl | H | 6.60(1H, dd, J=1.8Hz, 3.3Hz), 6.75(1H, d, J=3.3Hz), 7.44(1H, s), 7.75(1H, d, J=1.8Hz), 8.01-8.04(3H, m), 8.21(2H, d, J=8.7Hz) |
| A-54 | 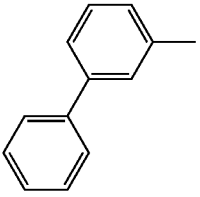 | H | Cl | H | 7.37(1H, m), 7.49-7.58(3H, m), 7.65(1H, dt, J=1.8Hz, 8.1Hz), 7.71-7.76(2H, m), 7.88(1H, s), 7.97(1H, dt, J=1.8Hz, 7.5Hz), 8.03-8.06(3H, m), 8.23(2H, d, J=7.8Hz), 8.28(1H, t, J=1.8Hz), 12.90(1H, s), 13.82(1H, bs) |
| A-55 | 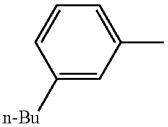 | H | Cl | H | 0.92(3H, t, J=7.5Hz), 1.34(2H, sext, J=7.5Hz), 1.60(2H, quint, J=7.5Hz), 2.64(2H, t, J=7.5Hz), 7.17(1H, d, J=7.8Hz), 7.35(1H, t, J=7.5Hz), 7.70(1H, s), 7.76(1H, d, J=7.8Hz), 7.81(1H, s), 8.02-8.05(3H, m), 8.22(2H, d, J=8.4Hz) 12.86(1H, s), 13.84(1H, bs) |
| A-56 | 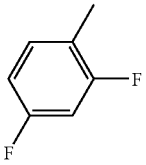 | H | Cl | H | 7.24(1H, dt, J=5.8Hz, 2.5Hz), 7.40(1H, ddd, J=11.9Hz, 9.4Hz, 2.5Hz), 7.59(1H, d, J=2.5Hz), 8.04(2H, d, J=8.5Hz), 8.05(1H, s), 8.09-8.20(1H, m), 8.21(2H, d, J=8.5Hz), 12.93(1H, s), 13.82(1H, bs) |
| A-57 | 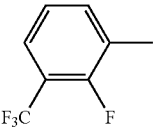 | H | Cl | H | 7.55(1H, t, J=8.0Hz), 7.77-7.81(2H, m), 8.04(2H, d, J=8.5Hz), 8.06(1H, s), 8.22(2H, d, J=8.5Hz), 8.37-8.42(1H, m), 12.99(1H, s), 13.85(1H, bs) |
| A-58 | 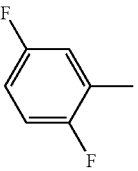 | H | Cl | H | 7.22-7.30(1H, m), 7.37-7.46(1H, m), 7.72(1H, d, J=2.5Hz), 8.04(2H, d, J=8.5Hz), 8.05(1H, s), 8.21(2H, d, J=8.5Hz), 12.92(1H, s), 13.82(1H, bs) |
| A-59 | 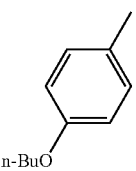 | H | Cl | H | 0.92-0.97(3H, m), 1.41-1.49(2H, m), 1.67-1.75(2H, m), 4.01(2H, t, J=6.3Hz), 7.00(2H, d, J=8.5Hz), 7.54(1H, s), 7.87(2H, d, J=8.5Hz), 8.04(2H, d, J=8.5Hz), 8.05(1H, s), 8.21(2H, d, J=8.5Hz), 12.85(1H, s), 13.76(1H, bs) |

TABLE 5-continued

| Compound No. | R⁶ | R¹ | R² | R⁵ | ¹H-NMR(DMSO d-6) |
|---|---|---|---|---|---|
| A-60 | 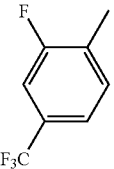 | H | Cl | H | 7.74-7.76(1H, m), 7.82(1H, d, J=2.7Hz), 7.80-7.84(1H, m), 8.03-8.05(3H, m), 8.22(2H, d, J=8.5Hz), 8.31(1H, t, J=7.6Hz), 13.01(1H, s), 13.79(1H, bs) |
| A-61 | 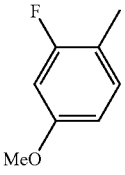 | H | Cl | H | 3.83(3H, s), 6.91-6.98(2H, m), 7.45(1H, d, J=2.5Hz), 8.00(4H, m), 8.21(2H, d, J=8.5Hz), 12.88(1H, s), 13.81(1H, bs) |

TABLE 6

| Compound No. | R⁶ | R¹ | R² | R⁵ | ¹H-NMR(DMSO d-6) |
|---|---|---|---|---|---|
| A-62 | 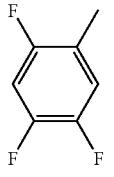 | H | Cl | H | 7.68(1H, d, J=2.5Hz), 7.68-7.76(1H, m), 7.80-8.07(4H, m), 8.20(2H, d, J=8.5Hz), 12.92(1H, s) |
| A-63 | 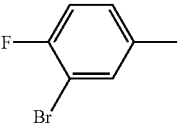 | H | Cl | H | 7.48(1H, t, J=8.8Hz), 7.85(1H, s), 7.98-8.03(1H, m), 8.04(2H, d, J=8.5Hz), 8.05(1H, s), 8.21(2H, d, J=8.5Hz), 8.30(1H, dd, J=6.9Hz, 2.2Hz), 12.88(1H, s), 13.82(1H, bs) |
| A-64 | 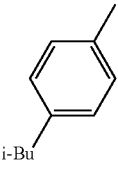 | H | Cl | H | 0.89('6H, d, J=6.7Hz), 1.87(1H, seven, J=6.7Hz), 2.48(2H, d, J=7.3Hz), 7.23(2H, d, J=8.2Hz), 7.64(1H, s), 7.87(2H, d, J=8.2Hz), 8.04(2H, d, J=8.5Hz), 8.05(1H, s), 8.21(2H, d, J=8.5Hz), 12.88(1H, s), 13.79(1H, bs) |
| A-65 | 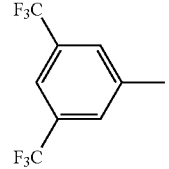 | H | Cl | H | 8.02-8.05(4H, m), 8.05(1H, s), 8.22(2H, d, J=8.5Hz), 8.27(1H, s), 8.64(2H, s), 12.94(1H, s), 13.84(1H, bs) |
| A-66 | 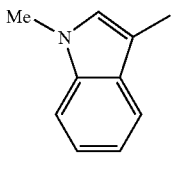 | H | Cl | H | 3.86(3H, s), 7.17(1H, t, J=7.5Hz), 7.25(1H, t, J=7.5Hz), 7.38(1H, s), 7.50(1H, d, J=8.4Hz), 7.78(1H, s), 8.03-8.06(3H, m), 8.17(1H, d, J=7.8Hz), 8.22(2H, d, J=8.4Hz), 12.79(1H, bs) |

TABLE 6-continued

| Compound No. | R⁶ | R¹ | R² | R⁵ | ¹H-NMR(DMSO d-6) |
|---|---|---|---|---|---|
| A-67 | (4-(2-(dimethylamino)ethoxy)phenyl, methyl-substituted) | H | Cl | H | 2.85(6H, s), 3.52(2H, t, J=5.4Hz), 4.41(2H, t, J=5.4Hz), 7.09(2H, d, J=8.7Hz), 7.60(1H, s), 7.93(2H, d, J=8.7Hz), 8.01-8.05(3H, m), 8.21(2H, d, J=8.7Hz), 12.84(1H, bs) |
| A-68 | (4-fluoro-methylphenyl) | H | F | H | 7.15(1H, d, J=36Hz), 7.24-7.33(2H, m), 7.70(1H, s), 7.86(2H, d, J=8.4Hz), 7.96-8.03(2H, m), 8.18(2h, d, J=8.7Hz), 12.86(1H, s) |
| A-69 | (4-bromo-2-fluoro-methylphenyl) | H | Cl | H | 7.57(1H, dd, J=8.7Hz, 1.8Hz), 7.67(1H, d, J=2.4Hz), 7.70(1H, dd, J=11.4Hz, 2.1Hz), 8.02-8.09(4H, m), 8.21(2H, d, J=8.7Hz), 12.97(1H, s), 13.69(1H, bs) |
| A-70 | (2-fluoro-4-methyl-methylphenyl) | H | Cl | H | 2.36(3H, s), 7.13-7.19(2H, m), 7.54-7.55(1H, m), 7.98-8.06(4H, m), 8.22(2H, d, J=8.4Hz), 12.89(1H, s), 13.80(1H, bs) |
| A-71 | (3-fluoro-4-methylbiphenyl) | H | Cl | H | 7.39-7.45(1H, m), 7.51(2H, t, J=7.8Hz), 7.67-7.72(3H, m), 7.79(2H, d, J=8.4Hz), 8.03-8.07(3H, m), 8.19-8.25(3H, m), 12.97(1H, s), 13.86(1H, bs) |
| A-72 | (2,3-difluoro-methylphenyl) | H | Cl | H | 7.30-7.48(2H, m), 7.72(1H, d, J=2.4Hz), 7.88-7.93(1H, m), 8.04(2H, d, J=8.5Hz), 8.05(1H, s), 8.22(2H, d, J=8.5Hz), 12.96(1H, s), 13.83(1H, bs) |
| A-73 | (5-methyl-2,3-dihydro-1H-indenyl) | H | Cl | H | 2.00-2.10(2H, m), 2.86-2.94(4H, m), 7.29(1H, d, J=7.7Hz), 7.61(1H, s), 7.72-7.75(1H, m), 7.82(1H, s), 8.04(2H, d, J=8.5Hz), 8.05(1H, s), 8.21(2H, d, J=8.5Hz), 12.84(1H, s), 13.84(1H, bs) |

TABLE 7

| Compound No. | R⁶ | R¹ | R² | R⁵ | ¹H-NMR(DMSO d-6) |
|---|---|---|---|---|---|
| A-74 | (5-methyl-2,3-dihydrobenzofuranyl) | H | Cl | H | 3.24(2H, t, J=8.5Hz), 4.57(2H, t, J=8.8Hz), 6.83(1H, d, J=8.2Hz), 7.49(1H, s), 7.73(1H, dd, J=8.2Hz, 1.6Hz), 7.82(1H, s), 8.04(2H, d, J=8.5Hz), 8.05(1H, s), 8.20(2H, d, J=8.5Hz), 12.83(1H, bs) |

TABLE 7-continued

| Compound No. | R⁶ | R¹ | R² | R⁵ | ¹H-NMR(DMSO d-6) |
|---|---|---|---|---|---|
| A-75 | 3-Cl-4-F-phenyl | H | Cl | H | 7.51(1H, t, J=9.1Hz), 7.86(1H, s), 7.95-8.00(1H, m), 8.04(2H, d, J=8.5Hz), 8.05(1H, s), 8.16(1H, dd, J=7.4Hz, 2.2Hz), 8.22(2H, d, J=8.5Hz), 12.90(1H, bs) |
| A-76 | 4-(F₃CO)-phenyl | H | Cl | H | 7.46(2H, d, J=8.8Hz), 7.72(1H, s), 8.04(2H, d, J=8.5Hz), 8.06(1H, s), 8.09(2H, d, J=8.8Hz), 8.22(2H, d, J=8.5Hz), 12.96(1H, s), 13.86(1H, bs) |
| A-77 | 3,4,5-trifluorophenyl | H | Cl | H | 7.76(1H, d, J=2.4Hz), 7.81-7.91(1H, m), 8.03(2H, d, J=8.5Hz), 8.04(1H, s), 8.20(2H, d, J=8.5Hz), 12.95(1H, s), 13.81(1H, s) |
| A-78 | 4-(MeS)-phenyl | H | Cl | H | 2.52(3H, s), 7.34(2H, d, J=8.5Hz), 7.69(1H, s), 7.91(2H, d, J=8.5Hz), 8.04(2H, d, J=8.8Hz), 8.06(1H, s), 8.21(2H, d, J=8.5Hz), 12.91(1H, bs) |
| A-79 | 3-(F₃C)-4-F-phenyl | H | Cl | H | 7.58-7.64(1H, m), 7.79(1H, d, J=2.5Hz), 7.79-7.83(1H, m), 8.04(2H, d, J=8.5Hz), 8.06(1H,s), 8.22(2H, d, J=8.5Hz), 8.52(1H, dd, J=6.9Hz, 2.2Hz), 12.93(1H, s), 13.72(1H, bs) |
| A-80 | 2-phenyl-3-F-phenyl | H | Cl | H | 7.39-7.55(5H, m), 7.56-7.62(2H, m), 8.05(2H, d, J=8.5Hz), 8.06(1H, s), 8.13(1H, td, J=7.8Hz, 1.8Hz), 8.23(2H, d, J=8.5Hz), 12.96(1H, s), 13.82(1H, bs) |
| A-81 | 2-F-3-Br-phenyl | H | Cl | H | 7.30(1h, t, J=8.1Hz), 7.68-7.74(2H, m), 8.02-8.05(3H, m), 8.10(1H, td, J=7.8Hz, 1.8Hz), 8.21(2H, d, J=8.7Hz), 12.96(1H, s), 13.82(1h, bs) |
| A-82 | 2-F-3-(MeO)-phenyl | H | Cl | H | 3.89(2H, s), 7.14-7.27(2H, m), 7.60-7.68(2H, m), 8.02-8.06(3H, m), 8.21(2H, d, J=8.4Hz), 12.92(1H, s), 13.80(1H, bs) |
| A-83 | 2-F-3-Me-phenyl | H | Cl | H | 2.32(3H, d, J=1.8Hz), 7.21(1H, t, J=7.5Hz), 7.25-7.31(1H, m), 7.61(1H, d, J=2.7Hz), 7.94(1H, td, J=7.5Hz, 1.8Hz), 8.02-8.06(3H, m), 8.21(2H, d), 12.91(1H, s), 13.80(1H, bs) |

TABLE 7-continued

| Compound No. | R⁶ | R¹ | R² | R⁵ | ¹H-NMR(DMSO d-6) |
|---|---|---|---|---|---|
| A-84 | 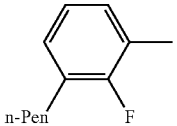 n-Pen, F | H | Cl | H | 0.84-0.90(3H, m), 1.30-1.37(4H, m), 1.56-1.66(2H, m), 2.68(2H, t, J=7.3Hz), 7.20-7.30(2H, m), 7.61(1H, d, J=2.7Hz), 7.95(1H, td, J=7.3Hz, 2.1Hz), 8.04(2H, d, J=8.5Hz), 8.06(1H, s), 8.21(2H, d, J=8.5Hz), 12.88(1H, s), 13.89(1H, bs) |

TABLE 8

| Compound No. | R⁶ | R¹ | R² | R⁵ | ¹H-NMR(DMSO d-6) |
|---|---|---|---|---|---|
| A85 | 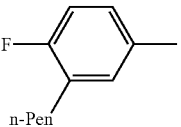 F, n-Pen | H | Cl | H | 0.86-0.90(3H, m), 1.30-1.37(4H, m), 1.56-1.66(2H, m), 2.65(2H, t, J=7.6Hz), 7.18-7.24(1H, m), 7.69(1H, s), 7.79-7.84(1H, m), 7.87-7.91(1H, m), 8.03(2H, d, J=8.5Hz), 8.06(1H, s), 8.22(2H, d, J=8.5Hz), 12.92(1H, s), 14.00(1H, bs) |
| A-86 | 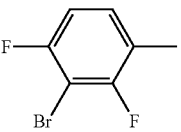 F, Br, F | H | Cl | H | 7.28(1H, td, J=9.1Hz, 1.8Hz), 7.64(1H, s), 7.81-7.89(1H, m), 8.04(2H, d, J=8.5Hz), 8.05(1H, s), 8.20(2H, d, J=8.5Hz), 13.01(1H, s), 13.93(1H, bs) |
| A-87 | 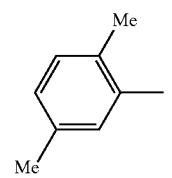 Me, Me | H | Cl | H | 2.31(3H, s), 2.41(3H, s), 7.08(1H, dd, J=7.7Hz, 1.4Hz), 7.18(1H, d, J=7.7Hz), 7.33(1H, s), 7.49(1H, d, J=1.4Hz), 8.05(2H, d, J=8.5Hz), 8.20(2H, d, J=8.5Hz), 12.85(1H, bs) |
| A-88 | 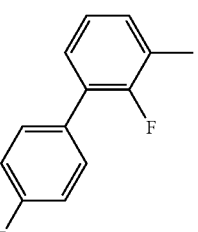 F, F | H | Cl | H | 7.31-7.44(3H, m), 7.49(td, J=7.5Hz, 1.8Hz), 7.62-7.68(3H, m), 8.03-8.06(3H, m), 8.12(1H, td, J=7.5Hz, 1.8Hz), 8.22(2H, d, J=8.4Hz), 12.96(1H, s), 13.81(1H, bs) |
| A-89 | 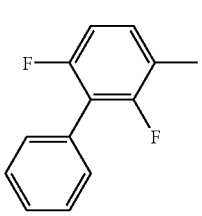 F, F | H | Cl | H | 7.31-7.37(1H, m), 7.41-7.66(7H, m), 8.03(2H, d, J=8.5Hz), 8.05(1H, s), 8.21(2H, d, J=8.5Hz), 13.00(1H, bs) |
| A-90 | 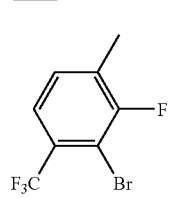 F₃C, F, Br | H | Cl | H | 7.49(1H, s), 7.70(1H, d, J=8.5Hz), 8.02-8.10(4H, m), 8.19(2H, d, J=8.5Hz), 12.97(1H, s), 13.82(1H, bs) |
| A-91 | 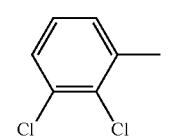 Cl, Cl | H | Cl | H | 7.48(1H, t, J=7.9Hz), 7.69(1H, dd, J=7.9Hz, 1.5Hz), 7.74(1H, s), 7.81(1H, dd, J=7.9Hz, 1.8Hz), 8.04(2H, d, J=8.5Hz), 8.06(1H, s), 8.21(2H, d, J=8.5Hz), 12.99(1H, s), 13.87(1H, bs) |

TABLE 8-continued

| Compound No. | R⁶ | R¹ | R² | R⁵ | ¹H-NMR(DMSO d-6) |
|---|---|---|---|---|---|
| A-92 | 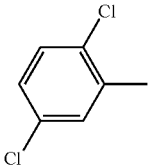 | H | Cl | H | 7.47(1H, dd, J=8.6Hz, 2.7Hz), 7.62(1H, d, J=8.4Hz), 7.88(1H, s), 8.02-8.05(4H, m), 8.21(2H, d, J=8.4Hz), 12.93(1H, s), 13.88(1H, bs) |
| A-93 | 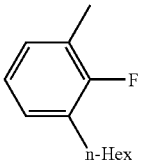 | H | Cl | H | 0.86(3H, t, J=6.9Hz), 1.27-1.30(6H, m), 1.55-1.62(2H, m), 2.68(2H, t, J=7.5Hz), 7.19-7.30(2H, m), 7.61(1H, d, J=2.7Hz), 7.94(1H, dt, J=7.0Hz, 2.0Hz), 8.03(2H, d, J=8.5Hz), 8.05(1H, s), 8.21(2H, d, J=8.5Hz), 12.92(1H, s), 13.86(1H, bs) |
| A-94 | 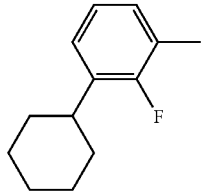 | H | Cl | H | 13.70(bs, 1H), 12.93(bs, 1H), 8.21(d, 2H, J=8.2Hz), 8.06(s, 1H), 8.04(d, 2H, J=8.2Hz), 7.94(dt, 1H, J=7.5, 2.0Hz), 7.61(d, 1H, J=2.7Hz), 7.32(m, 1H), 7.25(t, 1H, J=7.5Hz), 2.90(m, 1H), 1.20-1.90(m, 10H) |
| A-95 | 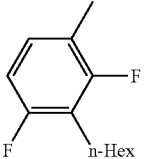 | H | Cl | H | 0.85-0.89(3H, m), 1.27-1.35(4H, m), 1.53-1.60(2H, m), 2.63(2H, t, J=7.7Hz), 7.11-7.17(1H, m), 7.34-7.41(1H, m), 7.51(1H, s), 8.03(2H, d, J=8.5Hz), 8.05(1H, s), 8.20(2H, d, J=8.5Hz), 12.96(1H, s), 13.78(1H, bs) |

TABLE 9

| Compound No. | R⁶ | R¹ | R² | R⁵ | ¹H-NMR(DMSO d-6) |
|---|---|---|---|---|---|
| A-96 | 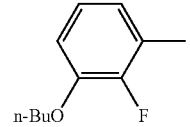 | H | Cl | H | 0.96(3H, t, J=7.4Hz), 1.41-1.54(2H, m), 1.70-1.78(2H, m), 4.08(2H, t, J=6.4Hz), 7.13-7.24(2H, m), 7.61-7.66(2H, m), 8.03(2H, d, J=8.6Hz), 8.05(1H, s), 8.21(2H, d, J=8.6Hz), 12.92(1H, s), 13.81(1H, bs) |
| A-97 | 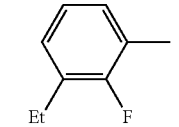 | H | Cl | H | 1.23(3H, t, J=7.5Hz), 2.72(2H, q, J=7.5Hz), 7.21-7.33(2H, m), 7.61(1H, d, J=2.5Hz), 7.95(1H, dd, J=7.5Hz, 2.0Hz), 8.04(2H, d, J=8.5Hz), 8.05(1H, s), 8.21(2H, d, J=8.5Hz), 12.92(1H, s), 13.85(1H, bs) |
| A-98 | 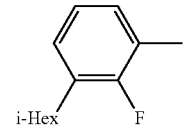 | H | Cl | H | 0.88(6H, d, J=6.6Hz), 1.19-1.26(2H, m), 1.53-1.66(3H, m), 2.66(2H, t, J=7.7Hz), 7.20-7.30(2H, m), 7.61(1H, d, J=2.7Hz), 7.95(1H, dd, J=7.5Hz, 2.2Hz), 8.04(2H, d, J=8.4Hz), 8.05(1H, s), 8.21(2H, d, J=8.4Hz), 12.92(1H, s), 13.86(1H, bs) |
| A-99 | 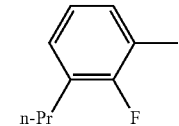 | H | Cl | H | 0.94(3H, t, J=7.5Hz), 1.63(2H, sext, J=7.5Hz), 2.67(2H, t, J=2.67Hz), 7.20-7.31(2H, m), 7.61(1H, d, J=2.7Hz), 7.95(1H, td, J=7.5Hz, 2.4Hz), 8.02-8.06(3H, m), 8.22(2H, d, J=8.4Hz), 12.92(1H, s), 13.79(1H, bs) |
| A-100 | 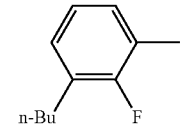 | H | Cl | H | 0.92(3H, t, J=7.5Hz), 1.35(2H, sext, J=7.5Hz), 1.59(2H, quint, J=7.5Hz), 2.69(2H, t, J=7.5Hz), 7.19-7.30(2H, m), 7.61(1H, d, J=2.7Hz), 7.94(1H, td, J=8.2Hz, 2.4Hz), 7.99-8.06(3H, m), 8.21(2H, d, J=8.4Hz), 12.92(1H, s), 13.80(1H, bs) |

TABLE 9-continued

| Compound No. | R⁶ | R¹ | R² | R⁵ | ¹H-NMR(DMSO d-6) |
|---|---|---|---|---|---|
| A-101 | 2-Br, 6-n-Pr, 3-F phenyl | H | Cl | H | 0.98(1H, t, J=7.5Hz), 1.60(2H, sext, J=7.5Hz), 2.77-2.83(2H, m), 7.59(1H, d, J=8.4Hz), 7.66(1H, d, J=3.0Hz), 7.91(1H, t, J=8.4Hz), 8.01-8.07(3H, m), 8.21(2H, d, J=8.7Hz), 12.94(1H, s), 13.80(1H, bs) |
| A-102 | 2-F, 6-(pyridin-3-yl) phenyl | H | Cl | H | 7.46(1H, t, J=8.1Hz), 7.54-7.60(2H, m), 7.70(1H, d, J=2.7Hz), 7.99-8.07(4H, m), 8.17(1H, dd, J=8.2Hz, 1.8Hz), 8.21(2H, d, J=8.4Hz), 8.66(1H, bs), 8.83(1H, bs), 12.97(1H, s) |
| A-103 | 2-F, 6-EtO phenyl | H | Cl | H | 1.39(3H, t, J=7.0Hz), 4.15(2H, q, J=7.0Hz), 7.13-7.25(2H, m), 7.62-7.67(2H, m), 8.04(2H, d, J=8.5Hz), 8.06(1H, s), 8.22(2H, d, J=8.5Hz), 12.94(1H, s), 13.86(1H, bs) |
| A-104 | 2-F, 6-(2-phenylethyl) phenyl | H | Cl | H | 2.89-2.98(4H, m), 7.17-7.61(7H, m), 7.61(1H, d, J=2.5Hz), 7.95(1H, dt, J=7.4Hz, 2.2Hz), 8.04(2H, d, J=8.6Hz), 8.05(1H, s), 8.21(2H, d, J=8.6Hz), 12.92(1H, s), 13.86(1H, bs) |
| A-105 | 2-F, 6-(3,3-dimethylbutyl) phenyl | H | Cl | H | 0.97(9H, s), 1.45-1.50(2H, m), 2.62-2.68(2H, m), 7.19-7.30(2H, m), 7.62(1H, d, J=2.4Hz), 7.94(1H, dt, J=7.5Hz, 2.1Hz), 8.04(2H, d, J=8.5Hz), 8.06(1H, s), 8.22(2H, d, J=8.5Hz), 12.92(1H, s), 13.85(1H, bs) |

TABLE 10

| Compound No. | R⁶ | R¹ | R² | R⁵ | ¹H-NMR(DMSO d-6) |
|---|---|---|---|---|---|
| A-106 | 2-F, 6-(2-ethoxyethyl) phenyl | H | Cl | H | 1.10(3H, t, J=6.9Hz), 2.93(2H, t, J=6.9Hz), 3.46(2H, q, J=6.9Hz), 3.62(2H, t, J=6.9Hz), 7.24(1H, t, J=7.5Hz), 7.33(1H, td, J=7.2Hz, 1.8Hz), 7.61(1H, d, J=2.7Hz), 7.97(1H, td, J=7.2Hz, 1.8Hz), 8.02-8.06(3H, m), 8.21(2H, d, J=8.4Hz), 12.93(1H, s), 13.89(1H, bs) |
| A-107 | 2-F, 6-benzyl phenyl | H | Cl | H | 4.06(2H, s), 7.18-7.35(7H, m), 7.61(1H, d, J=2.7Hz), 7.98(1H, td, J=7.5Hz, 2.1Hz), 8.02-8.05(3H, m), 8.21(2H, d, J=8.7Hz), 12.92(1H, s), 13.86(1H, bs) |

TABLE 11

[Structure: R6-thiazole-NH-C(O)-phenyl-C(R1)=C(R2)-C(O)-R]

| Compound No. | R6 | R1 | R2 | R | 1H-NMR (DMSO d-6) |
|---|---|---|---|---|---|
| B-2 | 3,4-dichlorophenyl | H | H | —NH2 | 6.77 (1H, d, J=15.9 Hz), 7.20 (1H, br), 7.50 (1H, d, J=15.9 Hz), 7.60 (1H, br), 7.72 (1H, d, J=8.7 Hz), 7.72-7.76 (2H, m), 7.91 (1H, s), 7.95 (1H, dd, J=1.8, 8.4 Hz), 8.14-8.18 (2H, m), 8.22 (1H, d, J=1.8 Hz), 12.82 (1H, br). |
| B-3 | 3,4-dichlorophenyl | H | H | —NHMe | 2.73 (3H, d, J=4.8 Hz), 6.75 (1H, d, J=15.6 Hz), 7.50 (1H, d, J=15.6 Hz), 7.72 (1H, d, J=8.1 Hz), 7.72-7.75 (2H, m), 7.91 (1H, s), 7.95 (1H, dd, J=2.1, 8.4 Hz), 8.09-8.18 (3H, m), 8.21 (1H, d, J=2.1 Hz), 12.81 (1H, br). |
| B-4 | 3,4-dichlorophenyl | H | Me | —NHme | 2.06 (3H, d, J=1.5 Hz), 2.72 (3H, t, J=4.5 Hz), 7.27 (1H, s), 7.53-7.58 (2H, m), 7.72 (1H, d, J=8.7Hz), 7.92 (1H, s), 7.95 (1H, dd, J=1.8, 8.1 Hz), 8.07 (1H, q, J=4.2Hz), 8.13-8.18 (2H, m), 8.22 (1H, d, J=2.1 Hz), 12.81 (1H, s). |
| B-5 | 3,4-dichlorophenyl | H | Me | —N(Me)2 | 2.05 (3H, d, J=1.5 Hz), 3.32 (6H, s), 6.57 (1H, s), 7.54-7.58 (2H, m), 7.72 (1H, d, J=8.4 Hz), 7.91 (1H, s), 7.95 (1H, dd, J=1.8, 8.4 Hz), 8.13-8.18 (2H, m), 8.22 (1H, d, J 1.8 Hz), 12.79 (1H, br). |
| B-6 | 3,4-dichlorophenyl | H | Me | —NHEt | 1.10 (3H, t, J=7.2 Hz), 2.05 (3H, d, J=1.2 Hz), 3.17-3.26 (1H, m), 7.25 (1H, s), 7.54-7.58 (2H, m), 7.72 (1H, d, J=8.4 Hz), 7.91 (1H, s), 7.95 (1H, dd, J=2.1, 8.1 Hz), 8.09 (1H, t, J=5.4 Hz), 8.13-8.18 (2H, m), 8.21 (1H, d, J=2.1 Hz), 12.80 (1H, s). |
| B-7 | 3,4-dichlorophenyl | H | Me | —NH(n-Pr) | 0.89 (3H, t, J=7.2 Hz), 1.51 (2H, sextet, d=7.2 Hz), 2.06 (3H, d,J=1.5 Hz), 3.11-3.18 (2H, m), 7.25 (1H, s), 7.54-7.59 (2H, m), 7.72 (1H, d, J=8.4 Hz), 7.92 (1H, s), 7.95 (1H, dd, J=2.1, 8.4 Hz), 8.10 (1H, t, J=5.4 Hz), 8.14-8.19 (2H, m), 8.22 (1H, d, J=2.1 Hz), 12.82 (1H, s). |
| B-8 | 3,4-dichlorophenyl | H | Me | morpholino | 2.06 (3H, d, J=1.2 Hz), 3.53-3.58 (4H, m), 3.60-3.64 (4H, m), 6.60 (1H, s), 7.54-7.61 (2H, m), 7.72 (1H, d, J=8.7 Hz), 7.91 (1H, s), 7.95 (1H, dd, J=2.1, 8.7 Hz), 8.13-8.19 (2H, m), 8.22 (1H, d, J=2.1 Hz), 12.80 (1H, br). |

TABLE 12

| Compound No. | R6 | R1 | R2 | R | 1H-NMR (DMSO d-6) |
|---|---|---|---|---|---|
| B-9 | 3,4-dichlorophenyl | H | Me | —NHBn | 2.10 (3H, d, J=1.5 Hz), 4.41 (2H, d, J=6.0 Hz), 7.52-7.38 (6H, m), 7.56-7.61 (2H, m), 7.72 (1H, d, J=8.4 Hz), 7.92 (1H, s), 7.95 (1H, dd, J=2.1, 8.4 Hz), 8.14-8.20 (2H, m), 8.22 (1H, d, J=2.4 Hz), 12.82 (1H, br). |

TABLE 12-continued

| Compound No. | R⁶ | R¹ | R² | R | ¹H-NMR (DMSO d-6) |
|---|---|---|---|---|---|
| B-10 | 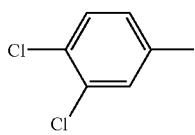 | H | Me | 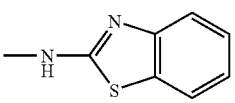 | 2.22 (3H, t, J=1.2 Hz), 7.34 (1H, dt, J=1.2, 8.1 Hz), 7.47 (1H, dt, Jz=1.2, 8.4 Hz), 7.65-7.71 (3H, m), 7.73 (1H, d, J=8.4 Hz), 7.78 (1H, d, J=7.8 Hz), 7.94 (1H, s), 7.96 (1H, dd, J=2.1, 8.4 Hz), 8.02 (1H, d, J=8.2 Hz), 8.19-8.24 (3H, m), 12.63 (1H, br), 12.89 (1H, br). |
| B-11 | 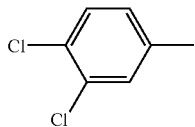 | H | Me | 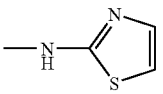 | 2.18 (3H, d, J=1.5 Hz), 7.27 (1H, d, J=2.4 Hz), 7.56 (1H, d, J=3.3 Hz), 7.59 (1H, br), 7.63-7.68 (2H, m), 7.73 (1H, d, J=8.4 Hz), 7.93 (1H, s), 7.96 (1H, dd, J=2.1, 8.4 Hz), 8.17-8.22 (2H, m), 8.23 (1H, d, J=2.1 Hz), 12.36 (1H, br), 12.87 (1H, br). |
| B-12 | 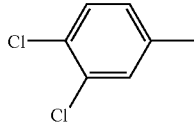 | H | Me | 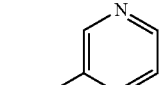 | 2.18 (3H, d, J=1.2 Hz), 7.37-7.43 (2H, m), 7.64-7.69 (2H, m), 7.73 (1H, d, J=8.4 hz), 7.94 (1H, s), 7.96 (1H, dd, J=1.8, 8.4 Hz), 8.15 (1H, td, J=1.5, 6.9 Hz), 8.18-8.24 (3H, m), 8.31(1H, dd, J=1.5, 4.5 Hz)8.89 (1H, d, J=2.4 Hz), 12.87 (1H, br). |
| B-13 | 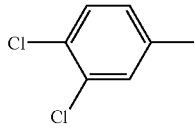 | H | Me | 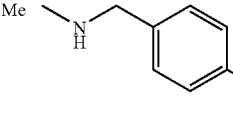 | 2.11 (3H, d, J=1.2 Hz), 4.49 (2H, d, J=6.0 Hz), 7.36 (1H, br), 7.52-7.62 (4H, m), 7.69-7.74 (3H, m), 7.92 (1H, s), 7.95 (1H, dd, J=2.1, 8.1 Hz), 8.15-8.20 (2H, m), 8.22 (1H, d, J=2.1 Hz), 8.79 (1H, t, J=6.3 Hz), 12.83 (1H, br). |
| B-14 | 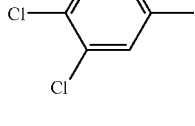 | H | Me | 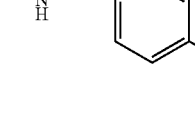 | 2.09 (3H, d, J=1.2 Hz), 4.38 (2H, d, J=5.7 Hz), 7.13-7.20 (2H, m), 7.32-7.39 (3H, m), 7.55-7.61 (2H, m), 7.73 (1H, d, J=8.4 Hz), 7.92 (1H, s), 7.95 (1H, dd, J=2.1, 8.4 Hz), 8.14-8.19 (2H, m), 8.22 (1H, d, J=2.1 Hz), 8.71 (1H, t, J=6.0 Hz), 12.84 (1H, br). |
| B-15 | 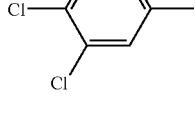 | H | Me | 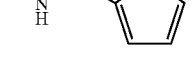 | 2.08 (3H, d, J=1.5 Hz), 4.55 (2H, d, J=5.7 Hz), 6.96-7.03 (2H, m), 7.31 (1H, br), 7.40 (1H, dd, J=1.5, 5.4 Hz), 7.55-7.60 (2H, m), 7.73 (1H, d, J=8.4 Hz), 7.92 (1H, s), 7.95 (1H, dd, J=2.1, 8.4 Hz), 8.14-8.19 (2H, m), 8.22 (1H, d, J=2.1 Hz), 8.80 (1H, t, J=6.0 Hz), 12.84 (1H, br). |

TABLE 13

| Compound No. | R⁶ | R¹ | R² | R | ¹H-NMR (DMSO d-6) |
|---|---|---|---|---|---|
| B-16 | 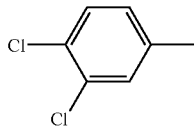 | H | Me | 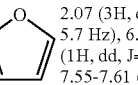 | 2.07 (3H, d, J=1.2 Hz), 4.39 (2H, d, J=5.7 Hz), 6.28 (1H, d, J=3.6 Hz), 6.41 (1H, dd, J=1.8, 3.3 Hz), 7.30 (1H, br), 7.55-7.61 (3H, m), 7.73 (1H, d, J=8.1 Hz), 7.92 (1H, s), 7.95 (1H, dd, J=2.1, 8.4 Hz), 8.14-8.18 (2H, m), 8.22 (1H, d, J=2.1 Hz), 8.63 (1H, t, J=6.0 Hz), 12.84 (1H, br). |
| B-17 | 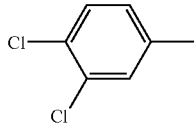 | H | Et | —NH₂ | 1.07 (3H, t, J=7.2 Hz), 2.47 (2H, q, J=7.2 Hz), 7.20 (2H, br), 7.48-7.53 (2H, m), 7.65 (1H, br), 7.73 (1H, d, J=8.1 Hz), 7.93 (1H, s), 7.95 (1H, dd, J=2.1, 8.4 Hz), 8.13-8.18 (2H, m), 8.22 (1H, d, J=2.1 Hz), 12.83 (1H, br). |

TABLE 13-continued

| Compound No. | R⁶ | R¹ | R² | R | ¹H-NMR (DMSO d-6) |
|---|---|---|---|---|---|
| B-18 | 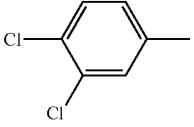 | H | Et | —NHMe | 1.05 (3H, t, J=7.5 Hz), 2.48 (2H, q, J=7.5 Hz), 2.72 (2H, d, J=4.5 Hz), 7.11 (1H, s), 7.48-7.53 (2H, m), 7.73 (1H, d, J=8.4 Hz), 7.92 (1H, s), 7.95 (1H, dd, J=2.4, 8.1 Hz), 8.08-8.18 (3H, m), 8.22 (1H, d, J=2.4 Hz), 12.82 (1H, br). |
| B-19 | 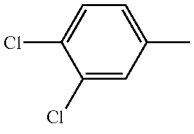 | H | Et | —NHEt | 1.05 (3H, t, J=7.5 Hz), 1.10 (3H, t, J=7.2 Hz), 2.48 (2H, q, J=7.2 Hz), 3.16-3.26 (2H, m), 7.09 (1H, s), 7.48-7.53 (2H, m), 7.73 (1H, d, J=8.4 Hz), 7.93 (1H, s), 7.95 (1H, dd, J=2.1, 8.4 Hz), 8.14-8.20 (2H, m), 8.22 (1H, d, J = 2.1 Hz), 12.84 (1H, br). |
| B-20 | 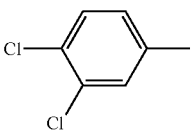 | H | Et | —NHBn | 1.08 (3H, t, J=7.5 Hz), 2.52 (2H, q, J=7.8 Hz), 4.41 (2H, d, J=6.3 Hz), 7.18 (1H, s), 7.22-7.40 (5H, m), 7.50-7.54 (2H, m), 7.73 (1H, d, J=8.4 Hz), 7.93 (1H, s), 7.95 (1H, dd, J=1.8, 8.4 Hz), 8.14-8.18 (2H, m), 8.22 (1H, d, J=1.8 Hz), 8.75 (1H, t, J=6.0 Hz), 12.84 (1H, br). |
| B-21 | 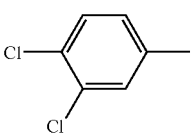 | Me | Me | —NH₂ | 1.70 (3H, d, J=1.2 Hz), 2.04 (3H, d, J=1.2 Hz), 7.21 (1H, br), 7.35-7.41 (2H, m), 7.52 (1H, br), 7.73 (1H, d, J=8.4 Hz), 7.92 (1H, s), 7.95 (1H, dd, J=2.1, 8.4 Hz), 8.13-848 (2H, m), 8.22 (1H, d, J=1.8 Hz), 12.80 (1H, br). |
| B-22 | 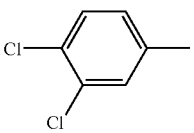 | Me | Me | —NHMe | 1.69 (3H, d, J=1.2 Hz), 1.99 (3H, d, J=1.5 Hz), 2.69 (3H, d, J=4.5 Hz), 7.36-7.41 (2H, m), 7.73 (1H, d, J=8.4 Hz), 7.92 (1H, s), 7.95 (1H, dd, J=2.1, 8.4 Hz), 7.99 (1H, q, J=4.8 Hz), 8.13-8.18 (2H, m), 8.22 (1H, d, J=2.1 Hz), 12.80 (1H, br). |

TABLE 14

| Compound No. | R⁶ | R¹ | R² | R | ¹H-NMR (DMSO d-6) |
|---|---|---|---|---|---|
| B-23 | 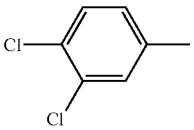 | Me | Me | —NHEt | 1.10 (3H, t, J=7.2 Hz), 1.69 (3H, d, J=1.2 Hz), 2.00 (3H, d, J=1.5 Hz), 3.14-3.23 (2H, m), 7.36-7.41 (2H, m), 7.73 (1H, d, J=8.4 Hz), 7.92 (1H, s), 7.95 (1H, dd, J=2.1, 8.4 Hz), 8.06 (1H, t, J=5.4 Hz), 8.13-8.17 (2H, m), 8.22 (1H, d, J=2.1 Hz), 12.80 (1H, br). |
| B-24 | 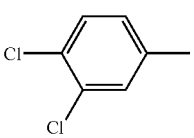 | Me | Me | —NHBn | 1.73 (3H, d, J=1.5 Hz), 2.00 (3H, d, J=1.5 Hz), 4.39 (2H, d, J=5.7 Hz), 7.22-7.42 (7H, m), 7.73 (1H, d, J=8.4 Hz), 7.92 (1H, s), 7.95 (1H, dd, J=1.8, 8.4 Hz), 8.12-8.18 (2H, m), 8.22 (1H, d, J=1.8 Hz), 8.62 (1H, t, J=6.3 Hz), 12.80 (1H, br). |
| B-25 | 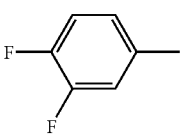 | H | Me | —NH₂ | 2.04 (3H, d, J=1.2 Hz), 7.20 (1H, br), 7.32 (1H, br), 7.48-7.64 (4H, m), 7.79-7.86 (2H, m), 7.94-8.02 (1H, m), 8.14-8.18 (2H, m), 12.83 (1H, br). |
| B-26 | 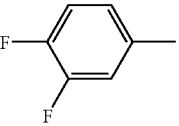 | H | Me | —NHMe | 2.06 (3H, d, J=1.2 Hz), 2.72 (3H, d, J=4.8 Hz), 7.26 (1H, s), 7.47-7.58 (3H, m), 7.78-7.87 (2H, m), 7.94-8.02 (1H, m), 8.08 (1H, q, J=4.5 Hz)8.13-8.18 (2H, m), 12.82 (1H, br). |

TABLE 14-continued

| Compound No. | R⁶ | R¹ | R² | R | ¹H-NMR (DMSO d-6) |
|---|---|---|---|---|---|
| B-27 | 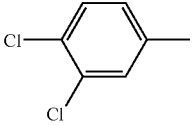 | H | Me | —NH(CH₂)₂-N(CH₃)₂ | 2.05 (3H, d, J=1.2 Hz), 2.19 (6H, s), 2.39 (2H, t, J=6.9 Hz), 3.28 (2H, q, J= 6.9 Hz), 7.26 (1H, br), 7.55 (2H, d, J= 8.7 Hz), 7.72 (1H, d, J=8.1 Hz), 7.91(1H, s), 7.95 (1H, dd, J=2.1 Hz, 8.1 Hz), 8.01 (1H, t, J=5.7 Hz), 8.16 (2H, d, J =8.7 Hz),. 8.22 (1H, d, J=2.1 Hz), 12.83 (1H, br) |
| B-28 | 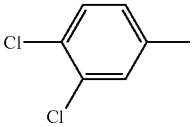 | H | Me | —NH(CH₂)₂-COOH | 2.05 (3H, d, J=1.5 Hz), 2.49 (3H, t, J= 7.5 Hz), 3.39 (2H, q, J=6.0 Hz), 7.26 (1H, br), 7.56 (2H, d, J=8.7 Hz), 7.73 (1H, d, J=8.4 Hz), 7.93 (1H, s), 7.95 (1H, dd, J=1.8 Hz, 8.4 Hz), 8.16 (2H, d, J=8.7 Hz),. 8.22 (1H, d, J=1.8 Hz), 12.90 (2H, br) |
| B-29 | 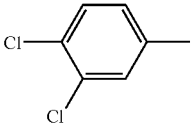 | H | Me | —NHN(CH₃)₂ | 2.05 (3H, s), 2.56 (6H, s), 7.14 (1H, s), 7.56 (2H, d, J=8.1 Hz), 7.73(1H, d, J= 8.1 Hz), 7.93 (1H, s), 7.95 (1H, dd, J= 1.8 Hz, 8.1 Hz), 8.16 (2H, d, J=8.1 Hz),. 8.22 (1H, d, J=1.8 Hz), 9.08 (1H, s), 12.83 (1H, br) |
| B-30 | 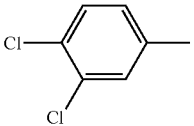 | H | Me | —NHPh | 2.17 (3H, d, J=1.1 Hz), 7.07-7.11 (1H, m), 7.32-7.37 (3H, m), 7.65 (2H, d, J= 8.5 Hz), 7.73 (3H, d, J=8.5 Hz), 7.93(1H, s), 7.96 (1H, dd, J=2.2 Hz, 8.5 Hz), 8.20 (2H, d, J=8.5 Hz), 8.22 (1H, d, J=2.2 Hz), 10.01 (1H, s), 12.85 (1H, s) |

TABLE 15

| Compound No. | R⁶ | R¹ | R² | R | ¹H-NMR (DMSO d-6) |
|---|---|---|---|---|---|
| B-31 | 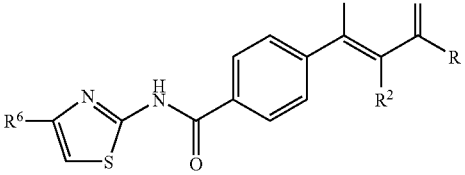 | H | Me | —NHCH₂CF₃ | 2.09 (3H, d, J=1.1 Hz), 4.02 (2H, m), 7.34 (1H, s), 7.60 (2H, d, J=8.4 Hz), 7.73 (1H, d, J=8.5 Hz), 7.93 (1H, s), 7.95 (1H, dd, J=2.2 Hz, 8.5 Hz), 8.18 (2H, d, J=8.4 Hz),. 8.22 (1H, d, J=2.2 Hz), 8.75 (1H, t, J=6.0 Hz), 12.85 (1H, s) |
| B-32 | 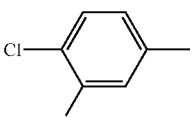 | H | Me | —NH(CH₂)₃—SCH₃ | 1.76 (2H, qn, J=6.9 Hz), 2.06 (6H, s), 2.49-2.53 (2H, m), 3.26 (2H, q, J=5.7 Hz), 7.26 (1H, s), 7.57 (2H, d, J=8.4 Hz), 7.73 (1H, d, J=8.4 Hz), 7.92(1H, s), 7.95(1H, dd, J=2.1 Hz, 8.4 Hz), 8.15 (1H, t, J=4.8 Hz), 8.16 (2H, d, J=8.4 Hz), 8.22 (1H, d, J=2.1 Hz), 12.83 (1H, br) |
| B-33 | 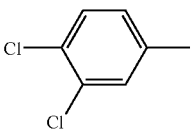 | H | Me | —NHCH(CH₃)-Ph | 1.46 (3H, d, J=7.2 Hz), 2.08 (2H, d, J= 1.5 Hz), 5.08 (1H, qn, J =7.2 Hz), 7.21-7.41 (6H, m), 7.69 (2H, d, J=8.4 Hz), 7.72 (1H, d, J=8.4 Hz), 7.92 (1H, s), 7.95 (1H, dd, J=2.1 Hz, 8.4 Hz), 8.17 (2H, d, J=8.4 Hz), 8.22 (1H, d, J=2.1 Hz), 8.48 (1H, d, J=8.4 Hz), 12.83 (1H, br) |
| B-34 | 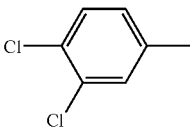 | H | Me | —NHCH₂Si-(CH₃)₃ | 0.06 (9H, s), 2.06 (3H, d, J=1.2 Hz), 2.72 (2H, d, J=5.4 Hz), 7.18 (1H, s), 7.57 (2H, d, J=8.4 Hz), 7.73 (1H, d, J= 8.4 Hz), 7.93 (1H, s), 7.95 (1H, dd, J= 2.1 Hz, 8.4 Hz), 7.99(1H, t, J=5.4 Hz), 8.16 (2H, d, J=8.4 Hz), 8.22 (1H, d, J= 2.1 Hz), 12.83 (1H, s) |

TABLE 15-continued

| Compound No. | R⁶ | R¹ | R² | R | ¹H-NMR (DMSO d-6) |
|---|---|---|---|---|---|
| B-35 | 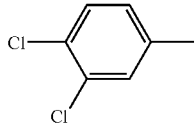 | H | Me | —NH(i-Bu) | 0.87 (3H, t, J=7.1 Hz), 1.11 (3H, d, J= 6.6 Hz), 1.41-1.57 (2H, m), 2.06 (3H, d, J=1.4 Hz), 3.83 (1H, sexth, J=6.6 Hz), 7.21 (1H, s), 7.57 (2H, d, J=8.4 Hz), 7.72 (1H, d, J=8.4 Hz), 7.80 (1H, d, J= 8.1 Hz), 7.92 (1H, s), 7.95 (1H, dd, J= 2.1 Hz, 8.4 Hz), 8.17 (2H, d, J=8.4 Hz), 8.22 (1H, d, J=2.1 Hz), 12.82 (1H, s) |
| B-36 | 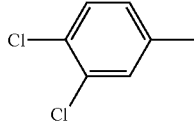 | H | Me | —NH(c-Pr) | 0.52-0.70 (4H, m), 2.04 (3H, d, J=0.8 Hz), 2.74-2.80 (1H, m), 7.56 (2H, d, J= 8.1 Hz), 7.72 (1H, d, J=8.4 Hz), 7.92 (1H, s), 7.95 (1H, dd, J=2.1 Hz, 8.4 Hz), 8.11 (1H, d, J=4.2 Hz), 8.16(2H, d, J= 8.1 Hz), 8.22 (1H, d, J=2.1 Hz), 12.82 (1H, s) |

TABLE 16

| Compound No. | R⁶ | R¹ | R² | R | ¹H-NMR (DMSO d-6) |
|---|---|---|---|---|---|
| B-37 | 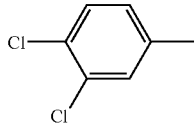 | H | Me | —NH(CH₂)₃O—CH₃ | 0.87 (3H, t, J=7.1 Hz), 1.11 (3H, d, J= 6.6 Hz), 1.41-1.57 (2H, m), 2.06 (3H, d, J=1.4 Hz), 3.83 (1H, sexth, J=6.6 Hz), 7.25 (1H, s), 7.57 (2H, d, J=8.7 Hz), 7.73 (1H, d, J=8.1 Hz), 7.95 (1H, dd, J= 2.1 Hz, 8.1 Hz), 8.11 (1H, t, J=6.0 Hz), 8.16 (2H, d, J=8.7 Hz), 8.22 (1H, d, J=2.1 Hz), 12.83 (1H, s) |
| B-38 | 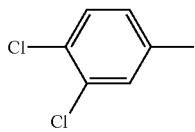 | H | Me | —NH(c-Pen) | 1.46-1.58 (4H, m), 1.63-1.71 (2H, m), 1.81-1.90 (2H, m), 2.05 (3H, s), 4.10-4.15 (1H, m), 7.20 (1H, s), 7.57 (2H, d, J= 8.4 Hz), 7.73 (1H, d, J=8.1 Hz), 7.92-7.96 (3H, m), 8.16 (2H, d, J=8.4 Hz), 8.22 (1H, d, J=1.8 Hz, 12.82 (1H, s) |
| B-39 | 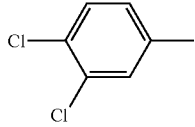 | H | Me | —NH(t-Bu) | 1.35 (9H, s), 2.03 (3H, d, J=1.5 Hz), 7.13 (1H, s), 7.56 (2H, d, J=8.4 Hz), 7.72 (1H, d, J=8.4 Hz), 7.92 (1H, s), 7.95 (1H, dd, J=2.1 Hz, 8.4 Hz), 8.16 (2H, d, J=8.4 Hz), 8.22 (1H, d, J=2.1 Hz), 12.82 (1H, s) |
| B-40 | 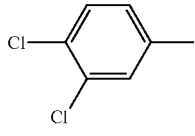 | H | Me | —NHpropargyl | 2.06 (3H, d, J=1.2 Hz), 3.12 (1H, t, J= 2.4 Hz), 3.98 (2H, dd, J=5.4 HZ, 2.4 Hz), 7.30 (1H, s), 7.58 (2H, d, J=8.4 Hz), 7.73 (1H, d, J=8.4 Hz), 7.20 (1H, s), 7.95 (1H, dd, J=8.4 Hz, 2.1 Hz), 8.16 (2H, d, J=8.4 Hz), 8.22 (1H, d, J=2.1 Hz), 8.57 (1H, t, J=5.4 Hz), 12.83 (1H, s) |
| B-41 | 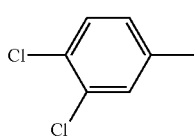 | H | Me | —NHallyl | 2.08 (3H, d, J=1.2 Hz), 3.83 (2H, t, J= 5.7 Hz), 5.07-5.21 (2H, m), 5.94-5.81 (1H, m), 7.29 (1H, s), 7.58 (2H, d, J=8.4 Hz), 7.73 (1H, d, J=8.7 Hz), 7.92 (1H, s), 7.94 (1H, dd, J=8.4 Hz, 1.8 Hz), 8.17 (2H, d, J=8.4 Hz), 8.22 (1H, d, J=1.8 Hz), 8.31 (1H, t, J=5.7 Hz), 12.83 (1H, s) |
| B-42 | 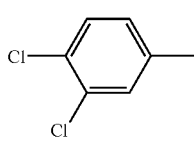 | H | Me | —NH(CH₂)₂O—CH₃ | 2.06 (3H, d, J=1.2 Hz), 3.28 (3H, s), 3.37-3.46 (4H, m), 7.27 (1H, s), 7.57 (2H, d, J=8.7 Hz), 7.72 (1H, d, J=8.4 Hz), 7.92 (1H, s), 7.95 (1H, dd, J=8.4 Hz, 2.1 Hz), 8.15 (1H, s), 8.17 (2H, d, J= 8.7 Hz), 8.22 (1H, d, J=2.1 Hz), 12.83 (1H, s) |

TABLE 16-continued

| Compound No. | R⁶ | R¹ | R² | R | ¹H-NMR (DMSO d-6) |
|---|---|---|---|---|---|
| B-43 | 3,4-diCl-phenyl | H | Me | —NHNHAc | 1.91 (3H, s), 2.08 (3H, d, J=1.5 Hz), 7.32 (1H, s), 7.59 (2H, d, J=8.4 Hz), 7.73 (1H, d, J=8.4 Hz), 7.95 (1H, dd, J=8.4 Hz, 1.8 Hz), 8.18 (2H, d, J=8.4 Hz), 8.22 (1H, d, J=1.8 Hz), 9.81(1H, s), 9.95 (1H, s), 12.85 (1H, s) |

TABLE 17

| Compound No. | R⁶ | R¹ | R² | R | ¹-NMR (DMSO d-6) |
|---|---|---|---|---|---|
| B-44 | 3,4-diCl-phenyl | H | Me | —NHNHPh | 2.13 (3H, d, J=1.2 Hz), 6.73 (1H, t, J=7.5 Hz), 6.80 (2H, d, J=7.8 Hz), 7.17 (2H, t, J=8.1 Hz), 7.38 (1H, s), 7.63 (2H, d,J=8.4 Hz), 7.73 (1H, d,J=8.1 Hz), 7.82 (1H, d, J=2.7 Hz), 7.93 (1H, s), 7.96 (1H, dd, J=8.1 Hz, 1.8 Hz), 8.19 (2H, d, J=8.4 Hz), 8.23 (1H, d, J=1.8 Hz), 10.04 (1H, d, J=2.7 Hz), 12.86 (1H, s) |
| B-45 | 3,4-diCl-phenyl | H | Me | —N(CH₃)NH₂ | 2.10 (3H, s), 3.11 (3H, s), 4.84 (2H, bs), 6.59(1H, s), 7.53 (2H, d, J=8.1 Hz), 7.71 (1H, d, J=8.1 Hz), 7.85 (1H, s), 7.94 (1H, dd, J=8.1 Hz, 1.8 Hz), 8.15 (2H, d, J=8.1 Hz), 8.21 (1H, d, J=1.8 Hz), 12.63 (1H, br) |
| B-46 | 3,4-diCl-phenyl | H | Me | —NHOCH₃ | 2.03 (3H, d, J=1.5 Hz), 3.68 (3H, s), 7.20 (1H, s), 7.57 (2H, d, J=8.4 Hz), 7.72 (1H, d, J=8.1 Hz), 7.95 (1H, dd, J=8.1 Hz, 2.1 Hz), 8.16 (2H, d, J=8.4 Hz), 8.22 (1H, d, J=2.1 Hz), 11.43 (1H, s), 12.84 (1H, s) |

TABLE 18

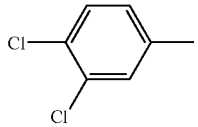

| Compound No. | R¹⁰ | R¹ | R² | R⁵ | ¹H-NMR (DMSO d-6) |
|---|---|---|---|---|---|
| C-1 | 3,4-diCl-phenyl | H | Me | Me | 2.08 (3h, d, J=1.2 Hz), 3.64 (3H, s), 6.87 (1H, s), 7.38 (2H, d, J=8.7 Hz), 7.72 (1H, d, J=8.7 Hz), 7.91 (1H, s), 7.95 (1H, dd, J=8.7 Hz, 2.1 Hz), 8.08 (2H, d, J=8.4 Hz), 8.21 (1H, d, J=2.1 Hz), 12.79 (1H, s) |
| C-2 | 3,4-diCl-phenyl | H | Me | H | 2.06 (3H, d, J=1.2 Hz), 6.69 (1H, s), 7.46 (2H, d, J=9.0 Hz), 7.72 (1H, d, J=8.7 Hz), 7.92 (1H, s), 7.94 (1H, dd, J=8.4 Hz, 1.8 Hz), 8.08 (2H, d, J=8.7 Hz), 8.22 (1H, d, J=2.1 Hz), 12.77 (1H, s), 12.91 (1H, s) |
| C-3 | 3,4-diCl-phenyl | H | Br | Me | 3.76 (3H, s), 7.48 (2H, d, J=8.7 Hz), 7.69 (1H, s), 7.72 (1H, d, J=8.4 Hz), 7.93 (1H, s), 7.95 (1H, dd, J=8.4 Hz, 2.1 Hz), 8.11 (2H, d, J=8.4 Hz), 8.21 1H, d, J=2.1 Hz), 12.86 (1H, s) |

TABLE 18-continued

Structure: R10-thiazole-NH-C(=O)-C6H4-C(R1)=C(R2)-C(=O)-O-R5

| Compound No. | R10 | R1 | R2 | R5 | ¹H-NMR (DMSO d-6) |
|---|---|---|---|---|---|
| C-4 | 3,4-dichlorophenyl | H | Br | H | 7.47 (1H, s), 7.54 (2H, d, J=8.7 Hz), 7.92 (1H, s), 7.95 (1H, dd, J=8.4 Hz, 2.1 Hz), 8.11 (2H, d, J=8.4 Hz), 8.21 (1H, d, J=1.8 Hz), 12.83 (1H, s) |
| C-5 | 3,4-dichlorophenyl | H | F | H | 7.19 (1H, d, J=23.1 Hz), 7.68 (2H, d, J=8.4 Hz), 7.73 (1H, d, J=8.1 Hz), 7.93 (1H, s), 7.95 (1H, dd, J=8.1 Hz, 2.1 Hz), 8.11 (2H, d, J=8.1 Hz), 8.22 (1H, d, J=1.8 Hz), 12.84 (1H, s) |

TABLE 19

Structure: R10-thiazole-NH-C(=O)-C6H4-C(R1)=C(R2)-Het

| Compound No. | R10 | R1 | R2 | Het | ¹H-NMR (DMSO d-6) |
|---|---|---|---|---|---|
| D-1 | 3,4-dichlorophenyl | H | Me | 2-methylimidazol-1-yl | 2.35 (3H, d, J=0.9 Hz), 7.12 (2H, bs), 7.32 (1H, s), 7.58 (2H, d, J=8.1 Hz), 7.72 (1H, d, J=7.8 Hz), 7.92 (1H, s), 795 (1H, dd, J=8.4 Hz, 2.1 Hz), 8.17 (2H, d, J=8.4 Hz), 8.22(1H, d, J=1.8 Hz), 12.31 (1H, s), 12.79 (1H, s) |

TABLE 20

Structure: R10-thiazole-NH-C(=O)-C6H4-C(R1)=C(R2)-CH=N-R

| Compound No. | R10 | R1 | R2 | R | ¹H-NMR (d-6) |
|---|---|---|---|---|---|
| E-1 | 3,4-dichlorophenyl | H | Me | anti OH | 12.80(bs, 1H), 11.20(s, 1H), 8.21(s, 1H), 815(d, 2H, J=8.3 Hz), 7.95(m, 1H), 7.93(s, 1H), 7.90(s, 1H), 7.72(d, 1H, J=8.5 Hz), 7.57(d, 2H, J=8.3 Hz), 6.83(s, 1H), 2.10(s, SH) |

TABLE 20-continued

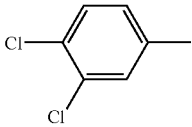

| Compound No. | R10 | R1 | R2 | R | 1H-NMR (d-6) |
|---|---|---|---|---|---|
| E-2 | 3,4-dichlorophenyl | H | Me | syn OH | 10.60(bs, 1H), 8.12(d, 1H, J=1.9 Hz), 8.03 (d, 2H, J=8.5 Hz), 7.87(dd, 1H, J=8.5, 1.9 Hz), 7.58(d, 1H, J=8.5 Hz), 7.26(s, 1H), 7.16(d, 2H, J=8.2 Hz), 6.56(d, 1H, J=7.1 Hz), 3.20(m, 1H), 2.51-2.80(m, 2H), 0.98(d, 3H, J=6.9 Hz) |

TABLE 21

| Compound No. | R10 | R1 | R2 | R | 1H-NMR (DMSO d-6) |
|---|---|---|---|---|---|
| F-1 | 3,4-dichlorophenyl | H | Me | —N(Me)2 | (CDCl3) 2.24(d, 3H, J=1.5 Hz), 2.92(s, 6H), 7.24(s, 1H), 7.47(d, 1H, J=8.2 Hz), 7.52 (s, 1H), 7.53(d, 2H, J=8.5 Hz), 7.64(dd, 1H, J=8.2, 1.8 Hz), 7.93(d, 1H, J=1.8 Hz), 8.00(d, 2H, J=8.5 Hz), 9.85(brs, 1H). |
| F-2 | 3,4-dichlorophenyl | H | Me | —NH(t-Bu) | (CDCl3) 1.38(s, 9H), 2.28(d 3H, J=1.4 Hz), 4.19(s, 1H), 7.24(s, 1H), 7.49(d, 1H, J= 8.2 Hz), 7.53(d, 2H, J=8.5 Hz), 7.62(brs, 1H), 7.66(dd, 1H, J=8.2, 1.9 Hz), 7.96(d, 1H, J=1.9 Hz), 8.03(d, 2H, J=8.5 Hz), 9.80(brs, 1H). |
| F-3 | 3,4-dichlorophenyl | H | Me | —NH2 | 2.25(d, 3H, J=1.2 Hz), 7.17(s, 2H), 7.42(brs, 1H), 7.64(d, 2H, J=8.2 Hz), 7.73(d, 2H, J=8.2 Hz), 7.92(s, 1H), 7.95(dd, 1H, J= 8.2, 2.1 Hz), 8.18(d, 2H, J= 8.2 Hz), 8.22(d, 1H, J=2.1 Hz), 12.90(brs, 1H). |

TABLE 22

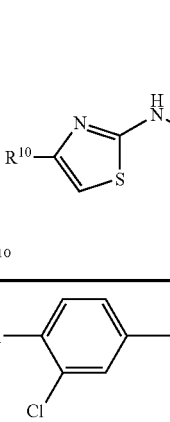

| Compound No. | R10 | R1 | R2 | R3 | 1H-NMR (DMSO d-6) |
|---|---|---|---|---|---|
| G-1 | 3,4-dichlorophenyl | H | H | Me | 2.67 (2H, t, J=7.7 Hz), 3.02 (2H, t, J=7.7 Hz), 3.69 (3H, s), 7.20 (1H, s), 7.26 (1H, s), 7.29 (2H, d, J=8.2 Hz), 7.41 (1H, d, J = 8.5 Hz), 7.58 (1H, dd, J=8.5 Hz, 2.2 Hz), 7.82 (2H, d, J=8.2 Hz), 7.86 (1H, d, J=2.2 Hz), 10.15 (1H, bs) (CDCl3) |
| G-2 | 3,4-dichlorophenyl | H | H | H | 2.61 (2H, t, J=7.3 Hz), 2.92 (2H, t, J=7.3 Hz), 7.42 (2H, d, J=8.5 Hz), 7.41(1H, d, J=8.5 Hz), 7.92 (1H, s), 7.95 (1H, dd, J=8.5 Hz, 2.1 Hz), 8.05 (2H, d, J=8.5 Hz), 8.22 (1H, d, J=2.1 Hz), 12.27 (1H, bs), 14.73 (1H, bs) |
| G-3 | 3,4-dichlorophenyl | H | Me | H | 1.07 (3H, d, J=6.6 Hz), 2.68-2.77 (2H, m), 2.94-3.03 (1H, m), 7.39 (2H, d, J=8.5 Hz), 7.72(1H, d, J=8.5 Hz), 7.95 (1H, dd, J=8.5 Hz, 2.2 Hz), 8.06 (2H, d, J=8.5 Hz), 8.21 (1H, d, J=2.2 Hz), 12.19 (1H, bs), 12.69 (1H, bs) |
| G-4 | 3,4-dichlorophenyl | H | Cl | H | 3.19 (1H, dd, J=14.3 Hz, 8.2 Hz), 3.42 (1H, dd, J=14.3 Hz, 6.3 Hz), 4.83 (1H, dd, J=8.2 Hz, 6.3 Hz), 7.48 (2H, d, J=8.2 Hz), 7.72 (1H, d, J=8.5 Hz), 7.92 (1H, s), 7.95 (1H, dd, J=8.5 Hz, 1.9 Hz), 8.08 (2H, d, J=8.2 Hz), 8.22 (1H, d, J=1.9 Hz), 12.77 (1H, bs), 13.46 (1H, bs) |
| G-5 | 3,4-dichlorophenyl | H | Cl | Me | 3.21 (1H, dd, J=14.3 Hz, 8.0 Hz), 3.41 (1H, dd, J=14.3 Hz, 6.6 Hz), 3.77 (3H, s), 4.46 (1H, dd, J=8.0 Hz, 6.6 Hz), 7.20 (1H, s), 7.26 (2H, d, J=8.5 Hz), 7.35 (1H, d, J=8.5 Hz), 7.52 (1H, dd, J=8.5 Hz, 2.2 Hz), 7.78-7.81 (3H, m), 10.71 (1H, bs) (CDCl3) |
| G-6 | 3,4-dichlorophenyl | H | F | H | 3.11-3.39 (2H, m), 5.23-5.44 (1H, m), 7.46 (2H, d, J=8.2 Hz), 7.72 (1H, d, J=8.2 Hz), 7.92 (1H, s), 7.95 (1H, dd, J=8.2 Hz, 2.1 Hz), 8.09 (2H, d, J=8.2 Hz), 8.22 (1H, d, J=2.1 Hz), 13.45 (1H, bs) |

TABLE 23

| Compound No. | R10 | R1 | R2 | R5 | 1H-NMR (DMSO d-6) |
|---|---|---|---|---|---|
| G-7 | 3,4-dichlorophenyl | H | F | Et | 1.20 (3H, t, J=7.1 Hz), 3.14-3.39 (2H, m), 4.17 (2H, q, J=7.1 Hz), 5.36-5.56 (1H, m), 7.45 (2H, d, J=8.5 Hz), 7.72 (1H, d, J=8.2 Hz), 7.92 (1H, s), 7.95 (1H, dd, J=8.2 Hz, 1.9 Hz), 8.08 (2H, d, J=8.2 Hz), 8.22 (1H, d, J=1.9 Hz), 12.78 (1H, bs) |

TABLE 23-continued

| Compound No. | R^10 | R^1 | R^2 | R^5 | $^1$H-NMR (DMSO d-6) |
|---|---|---|---|---|---|
| G-8 | 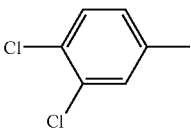 3,4-dichlorophenyl | Me | Cl | G | 1.39 (3H, d, J=7.1 Hz), 3.41-3.49 (1H, m), 4.78 (1H, d, J=8.5 Hz), 7.52 (2H, d, J=8.5 Hz), 7.72 (1H, d, J=8.5 Hz), 7.92 (1H, s), 7.95 (1H, dd, J=8.5 Hz, 1.9 Hz), 8.09 (2H, d, J=8.2 Hz), 8.22 (1H, d, J=1.9 Hz), 12.76 (1H, bs) |

TABLE 24

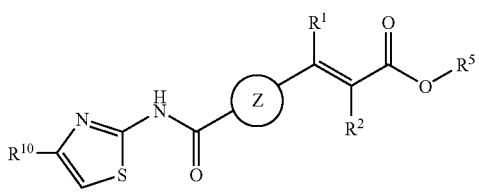

| Compound No. | R^10 | Z | R^1 | R^2 | R^5 | $^1$H-NMR (DMSO d-6) |
|---|---|---|---|---|---|---|
| H-1 | 3,4-dichlorophenyl | 1,3-phenylene | H | H | Et | (CDCl$_3$) 10.10(bs, 1H), 8.06(s, 1H), 7.91(d, 1H, J=8.0 Hz), 7.89(d, 1H, J=2.0 Hz), 7.72(d, 1H, J=8.0 Hz), 7.69(d, 1H, J=16.0 Hz), 7.61(dd, 1H, J=8.5, 2.0 Hz), 7.53(t, 1H, J=8.0 Hz), 7.43(d, 1H, J=8.5 Hz), 7.23(s, 1H), 6.51(d, 1H, J=16.0 Hz), 4.30(q, 2H, J=7.0 Hz), 1.35(t, 3H, J=7.0 Hz) |
| H-2 | 3,4-dichlorophenyl | 1,3-phenylene | H | H | H | 12.90(s, 1H), 12.50(s, 1H), 8.57(s, 1H), 8.23(d, 1H, J=2.0 Hz), 8.10(d, 1H, J=8.0 Hz), 7.96(dd, 1H, J=8.5, 2.0 Hz), 7.94(s, 1H), 7.92(d, 1H, J=8.0 Hz), 7.73(d, 1H, J=8.0 Hz), 7.68(d, 1H, J=16.0 Hz), 7.62(t, 1H, J=8.0 Hz), 6.76(d, 1H, J=16.0 Hz) |
| H-3 | 3,4-dichlorophenyl | 2,5-dimethyl-1,4-phenylene | H | H | Me | 2.22 (3H, s), 2.42 (3H, s), 3.85 (3H, s), 6.37 (1H, d, J=15.9 Hz), 7.10 (1H, s), 7.18 (1H, s), 7.25 (1H, s), 7.31 (1H, d, J=8.5 Hz), 7.40 (1H, dd, J=8.5 Hz, 1.9 Hz), 7.63 (1H, d, J=1.9 Hz), 7.82 (1H, d, J=15.9 Hz), 11.30 (1H, bs) (CDCl3) |
| H-4 | 3,4-dichlorophenyl | 2,5-dimethyl-1,4-phenylene | H | H | H | 2.41 (6H, s), 6.55 (1H, d, J=15.9 Hz), 7.53 (1H, s), 7.69 (1H, s), 7.72 (1H, d, J=8.4Hz), 7.79 (1H, d, J=15.9 Hz), 7.73 (1H, dd, J=8.4 Hz, 1.9 Hz), 8.18 (1H, d, J=1.9 Hz), 12.70 (1H, s) |
| H-5 | 3,4-dichlorophenyl | 2,5-dimethyl-1,4-phenylene | H | Cl | Et | 1.42 (3H, t, J=6.9 Hz), 2.16 (3H, s), 2.43 (3H, s), 4.39 (q, 2H, J=6.9 Hz), 7.17 (1H, s), 7.19 (1H, s), 7.26 (1H, s), 7.34 (1H, d, J=8.7 Hz), 7.45 (1H, dd, J=8.7 Hz, 2.1 Hz), 7.47 (1H, s), 7.69 (1H, d, J=2.1 Hz), 7.91 (1H, s), 11.09 (1H, s) (CDCl3) |
| H-6 | 3,4-dichlorophenyl | 2,5-dimethyl-1,4-phenylene | H | Cl | H | 2.31 (3H, s), 2.42 (3H, s), 7.56 (1H, s), 7.57 (1H, s), 7.72 (1H, d, J=8.5 Hz), 7.91-7.94 (2H, m), 8.04 (1H, s), 8.18 (1H, d, J=1.9 Hz), 12.71 (1H, s) |

TABLE 25

| Compound No. | R¹⁰ | Z | R¹ | R² | R⁵ | ¹H-NMR (DMSO d-6) |
|---|---|---|---|---|---|---|
| H-7 | 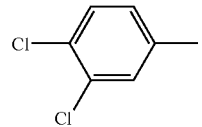 | 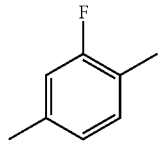 | H | Cl | H | 7.73(d, 1H, J=8.6 Hz), 7.95(dd, 1H, J=8.6, 1.8 Hz), 7.97(s, 1H), 8.03(s, 1H), 8.04-8.10(m, 2H), 8.17(t, 1H, J=7.7 Hz), 8.02(d, 1H, J=1.8 Hz), 13.01(s, 1H), 14.09(s, 1H) |
| H-8 | 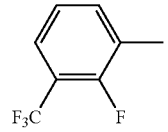 | 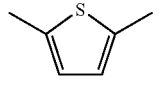 | H | Cl | H | 7.55(t, 1H, J=7.7 Hz), 7.78(m, 1H), 7.79(d, 1H, J =2.7 Hz), 7.86(d, 1H, J=4.5 Hz), 8.32(s, 1H), 8.35(d, 1H, J=4.5 Hz), 8.39(t, 1H, J=7.7 Hz), 13.18(s, 1H), 13.87(br, 1H) |

TABLE 26

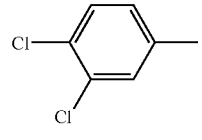

| Compound No. | R¹⁰ | Y | R¹ | R² | R⁵ | ¹H-NMR (DMSO d-6) |
|---|---|---|---|---|---|---|
| I-1 | 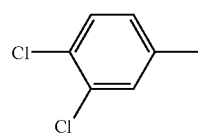 | —NHCH₂— | H | Me | Et | (CDCl₃) 7.91(d, 1H, J=1.9 Hz), 7.67(d, 1H, J=1.3 Hz), 7.62(dd, 1H, J=8.3, 1.9 Hz), 7.43(d, 1H, J=8.3 Hz), 7.41(s, 4H), 6.73(s, 1H), 5.57(m, 1H), 4.57(d, 2H, J=5.8 Hz), 4.27(q, 2H, J=7.1 Hz), 2.11(d, 3H, J=1.3 Hz), 1.35(t, 3H, J=7.1 Hz) |
| I-2 | 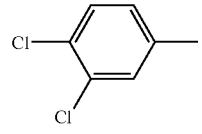 | —NHCH₂— | H | Me | H | 12.50(bs, 1H), 8.29(t, 1H, J=5.5 Hz), 8.03(d, 1H, J=2.0 Hz), 7.80(dd, 1H, J=8.5, 2.0 Hz), 7.61(d, 1H, J=8.5 Hz), 7.57(s, 1H), 7.45(s, 4H), 7.30(s, 1H), 4.54(d, 2H, J=5.5 Hz), 2.02(d, 3H, J=0.5 Hz) |
| I-3 | 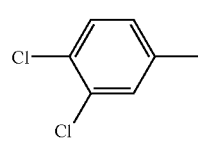 | —NHCOCH₂— | H | Me | Et | (CDCl₃) 8.82(bs, 1H), 7.88(d, 1H, J=2.0 Hz), 7.68(s, 1H), 7.58(dd, 1H, J=8.0, 2.0 Hz), 7.45(d, 2H, J=8.2 Hz), 7.44(d, 1H, J=8.5 Hz), 7.35(d, 1H, J=8.2 Hz), 7.15(s, 1H), 4.29(q, 2H, J=7.0 Hz), 3.85(s, 2H), 2.14(d, 3H, J=1.4 Hz), 1.36(t, 3H, J=7.0 Hz) |
| I-4 |  | —NHCOCH₂— | H | Me | H | 12.60(bs, 1H), 12.50(bs, 1H), 8.14(d, 1H, J=2.0 Hz), 7.88(dd, 1H, J=8.5, 2.0 Hz), 7.84(s, 1H), 7.70(d, 1H, J=8.5 Hz), 7.58(s, 1H), 7.45(d, 2H, J=8.5 Hz), 7.40(d, 2H, J=8.5 Hz), 3.84(s, 2H), 2.03(d, 3H, J=1.5 Hz) |

TABLE 26-continued

| Compound No. | R¹⁰ | Y | R¹ | R² | R⁵ | ¹H-NMR (DMSO d-6) |
|---|---|---|---|---|---|---|
| I-5 | 3,4-dichlorophenyl | —NHSO₂— | H | Me | Et | (CDCl3) 1.35(t, 3H, J = 7.2 Hz), 2.06(d, 3H, J=1.5 Hz), 4.27(q, 2H, J=7.2 Hz), 6.64(s, 1H), 7.35(dd, 1H, J=8.2, 2.1 Hz), 7.42 (d, 2H, J=8.2 Hz), 7.44(d, 1H, J=8.2 Hz), 7.58(d, 1H, J=2.1 Hz), 7.62(s, 1H), 7.98(d, 2H, J=8.2 Hz). |
| I-6 | 3,4-dichlorophenyl | —NHSO₂— | H | Me | H | (CDCl3+CD3OD) 2.09(d, 3H, J = 1.5 Hz), 6.66(s, 1H), 7.40(dd, 1H, J=8.2, 2.4 Hz), 7.49 (d, 2H, J=8.5 Hz), 7.52(d, 1H, J=8.2 Hz), 7.66(d, 1H, J=2.4 Hz), 7.69(s, 1H), 7.97(d, 2H, J=8.5 Hz). |

Example 3

The Preparation of Compound (A-15)

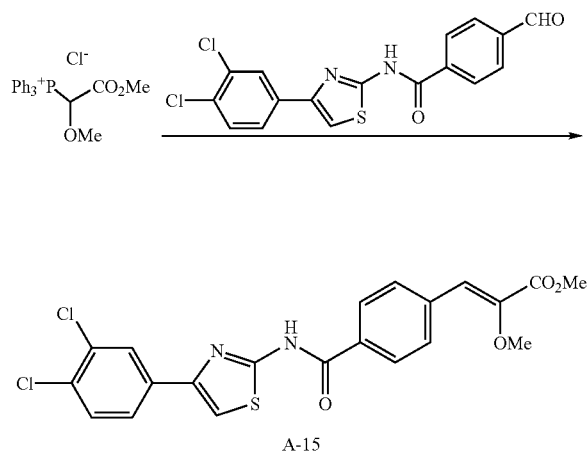

To a suspension of methoxy-methoxycarbonylmethyl-triphenylphosphonium chloride (152 mg) and 2-(4-formyl-benzoylamino)-4-(3,4-dichlorophenyl)thiazole (57 mg) in methylene chloride (3 ml) was added triethylamine (38 mg), and the reaction mixture was stirred at room temperature for overnight. The mixture was concentrated, purified by silica gel column chromatography to obtain compound (A-15) 30 mg.

Melting point: 203~205° C. ¹H-NMR (CDCl₃) δ ppm: 3.85 (s, 3H), 3.89 (s, 3H), 6.96 (s, 1H), 7.22 (s, 1H), 7.46 (dd, 1H, J=8.2, 1.9 Hz), 7.63 (d, 1H, J=8.2 Hz) 7.86 (d, 2H, J=8.6 Hz), 7.92 (d, 1H, J=1.9 Hz), 7.94 (d, 2H, J=8.6 Hz), 9.82 (brs, 1H).

Example 4

The Preparation of Compound (J-3)

A solution of (E)-3-(4-iodophenyl)-2-methylacrylic acid ethyl ester (200 mg), dichlorobis(triphenylphosphine)palladium (II) (22 mg), 2-amino-4-(4'-chlorophenyl)-1H-imidazole (277 mg), and triethylamine (0.27 ml) in DMF (7 ml) was stirred under carbon monooxide atmosphere at 90° C. for 15 min. The reaction mixture was cooled, poured into water. The precipitated crystals were filterd, recrystalaized with DMF to obtain compound (J-3) 117 mg as light yellow crystals.

Example 5

The Preparation of Compound (J-16)

To a solution of ethyl ester of compound (A-53) (300 mg) in acetonitrile/tetrahydrofuran (1/1, 80 ml), was added 1-fluoro-4-hydroxy-1,4-diazoniabicyclo[2.2.2]octane bistetrafluoroborate (50% on alumina 1.24 g), was stirred at 80° C. for 30 min. Alumina was filtered off, the filtrate was concentrated under reduced pressure, and added chloroform. The insoluble materials was filtered off again, and the filtrate was concentrated. The residue was purified by preparative TLC plate to obtain fluoro derivative 20 mg as yellow crystals. The obtained ester derivative was solvolized in a manner similar to preparing compound (A-2) to obtain compound (J-16).

Compound (J-1) to (J-2), (J-4) to (J-15), and (J-17) were synthsized in a manner similar to Example 4 and 5. Their physical data of compound were shown in Tables 27 to 28.

TABLE 27

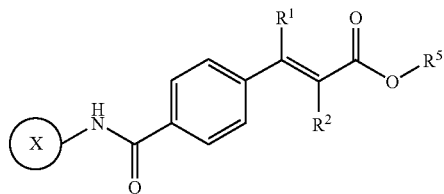

| Compound No. | X | R¹ | R² | R⁵ | ¹H-NMR (DMSO d-6) |
|---|---|---|---|---|---|
| J-1 | phenyl-pyrazole with 3-Me and 5-OH | H | Cl | Et | 1.33 (3H, t, J=7.2 Hz), 4.32 (2H, q, J=7.2 Hz), 6.13 (1H, s), 7.24 (1H, t, J=7.5 Hz), 7.46 (2H, t, J=8.1 Hz), 7.76 (2H, d, J=7.8 Hz), 7.98-8.12 (5H, m), 11.02 (1H, s), 11.89(1H, s) |
| J-2 | phenyl-pyrazole with 3-Me and 5-OH | H | Cl | H | 6.13 (1H, s), 7.24(1H, t, J=7.2 Hz), 7.46 (2H, t, J=8.1 Hz), 7.75 (2H, d, J=8.4 Hz), 7.96-8.12 (5H, m), 11.01 (1H, s), 11.86 (1H, s), 13.80 (1H, bs) |
| J-3 | 4-chlorophenyl-imidazole-Me | H | Me | Et | 12.07(bs, 1H), 11.74(bs, 1H), 8.13(d, 2H, J=8.5 Hz), 7.79(d, 2H, J =8.5 Hz), 7.67(s, 1H), 7.63(d, 2H, J=8.5 Hz), 7.44(s, 1H), 7.40(d, 2H, J=8.5 Hz), 4.22(q, 2H, J=7.0 Hz), 2.09(d, 3H, J=1.2 Hz), 1.29(t, 3H, J = 7.0 Hz) |
| J-4 | 4-chlorophenyl-imidazole-Me | H | Me | H | 12.10(bs, 3H), 8.12(d, 2H, J=8.5 Hz), 7.80(d, 2H, J=8.5 Hz), 7.65(s, 1H), 7.62(d, 2H, J=8.5 Hz), 7.45(s, 1H), 7.40(d, 2H, J=8.5 Hz), 2.07(d, 3H, J=1.5 Hz) |
| J-5 | 3,4-dichlorophenyl-1,2,4-triazole-Me | H | Me | Et | 14.00(bs, 1H), 12.20(bs, 1H), 8.10-8.20(m, 3H), 7.95(dd, 1H, J=8.2, 1.9 Hz), 7.77(d, 1H, J=8.2 Hz), 7.60-7.70(m, 3H), 4.23(q, 2H, J=7.0 Hz), 2.10(s, 3H), 1.29(t, 3H, J=7.0 Hz) |
| J-6 | phenyl-1,3,4-thiadiazole-Me | H | Me | H | 13.95(bs, 1H), 12.69(bs, 1H), 12.22(bs, 1H), 8.10-8.18(m, 3H), 7.95(dd, 1H, J=8.2, 2.0 Hz), 7.77(d, 1H, J=8.2 Hz), 7.61-7.68(m, 3H), 2.07(d, 3H, J=1.2 Hz) |
| J-7 | phenyl-1,3,4-thiadiazole-Me | H | Me | Et | 13.24(bs, 1H), 8.20(d, 2H, J=8.2 Hz), 7.96-8.04(m, 2H), 7.64-7.70(m, 3H), 7.52-7.60(m, 3H), 4.23(q, 2H, J=7.0 Hz), 2.10(d, 3H, J=1.4 Hz), 1.29(t, 3H, J=7.0 Hz) |
| J-8 | phenyl-1,2,4-thiadiazole-Me | H | Me | Et | 13.72(bs, 1H), 8.20-8.30(m, 4H), 7.66-7.74(m, 3H), 7.50-7.58(m, 3H), 4.23(q, 2H, J=7.0 Hz), 2.10(s, 3H), 1.30(t, 3H, J=7.0 Hz) |
| J-9 | phenyl-pyrazole-N-Me, 5-Me | H | Me | Et | 10.50(s, 1H), 8.06(d, 2H, J=8.2 Hz), 7.79(d, 2H, J=7.1 Hz), 7.62-7.70(m, 3H), 7.41(t, 2H, J=7.5 Hz), 7.30(t, 1H, J=7.5 Hz), 6.74(s, 1H), 4.23(q, 2H, J=7.1 Hz), 3.77(s, 3H), 2.09(d, 3H, J=1.1 Hz), 1.29(t, 3H, J=7.1 Hz) |

TABLE 28

| Compound No. | X | R¹ | R² | R⁵ | ¹H-NMR (DMSO d-6) |
|---|---|---|---|---|---|
| J-10 | (phenyl-thiophene with HOOC) | H | Me | H | 12.64(bs, 1H), 7.99(d, 2H, J=8.2 Hz), 7.72(d, 2H, J=8.5 Hz), 7.66(s, 1H), 7.28-7.38(m, 5H), 6.95(s, .1H), 2.07(d, 3H, J = 1.2 Hz) |
| J-11 | (2,4-difluorophenyl-thiazole-Me) | H | Cl | H | 2.31 (3H, d, J=1.9 Hz), 7.18-7.24 (1H, m), 7.35-7.42 (1H, m), 7.56-7.64 (1H, m), 8.03 (2H, d, J=8.5 Hz), 8.04 (1H, s), 8.18 (2H, d, J=8.5 Hz), 12.79 (1H, bs) |
| J-12 | (F₃C, F-phenyl-thiazole-Me) | H | Cl | H | 2.35 (3H, d, J=1.6 Hz), 7.51-7.56 (1H, m), 7.84-7.92 (1H, m), 8.03 (2H, d, J=8.5 Hz), 8.04 (1H, s), 8.19 (2H, d, J=8.5 Hz), 12.83 (1H, s), 13.84 (1H, bs) |
| J-13 | (Br-phenyl-thiazole-Me) | H | Cl | H | 2.53 (3H, s), 7.44(1H, t, J=7.9 Hz), 7.55-7.59 (1H, m), 7.69-7.72 (1H, m), 7.92 (1H, t, J=1.8 Hz), 8.02 (2H, d, J=8.5 Hz), 8.04 (1H, s), 8.19 (2H, d, J=8.5 Hz), 12.76 (1H, bs), 13.80 (1H, bs) |
| J-14 | (F₃C-phenyl-thiazole-Me) | H | Cl | H | 2.56 (3H, s), 7.72-7.74 (2H, m), 8.00-8.06 (5H, m), 8.20 (2H, d, J=8.5 Hz), 12.77 (1H, s), 13.75 (1H, bs) |
| J-15 | (n-Pen-naphthothiazole) | H | Cl | H | 0.86-0.90 (3H, m), 1.33-1.35 (4H, m), 1.48-1.58 (2H, m),. 2.64 (2H, t, J=7.5 Hz), 2.98 (4H, s), 7.07-7.09 (1H, m), 7.20 (1H, t, J=7.6 Hz), 7.63-7.66(1H, m), 8.03 (2H, d, J=8.5 Hz), 8.05 (1H, s), 8.20 (2H, d, J=8.5 Hz), 12.81 (1H, s), 13.79 (1H, bs) |
| J-16 | (n-Bu-phenyl-thiazole-F) | H | Cl | H | 13.80(bs, 1H), 13.20(s, 1H), 8.20(d, 2H, J= 8.5 Hz), 8.06(s, 1H), 8.04(d, 2H, J=8.0 Hz), 7.75(m, 1H), 7.68(m, 1H), 7.42(dd, 1H, J=8.2, 7.6 Hz), 7.26(d, 1H, J=7.6 Hz), 2.65(t, 2H, J=7.8 Hz), 1.50-1.70(m, 2H), 1.20-1.40(m, 2H), 0.92(t, 3H, J=7.3 Hz) |
| J-17 | (F₃C-phenyl-thiazole-F) | H | Cl | H | 13.88(bs, 1H), 13.01(s, 1H), 8.10-8.24(m, 4H), 8.00-8.08(m, 3H), 7.74-7.80(m, 2H) |

Example 6

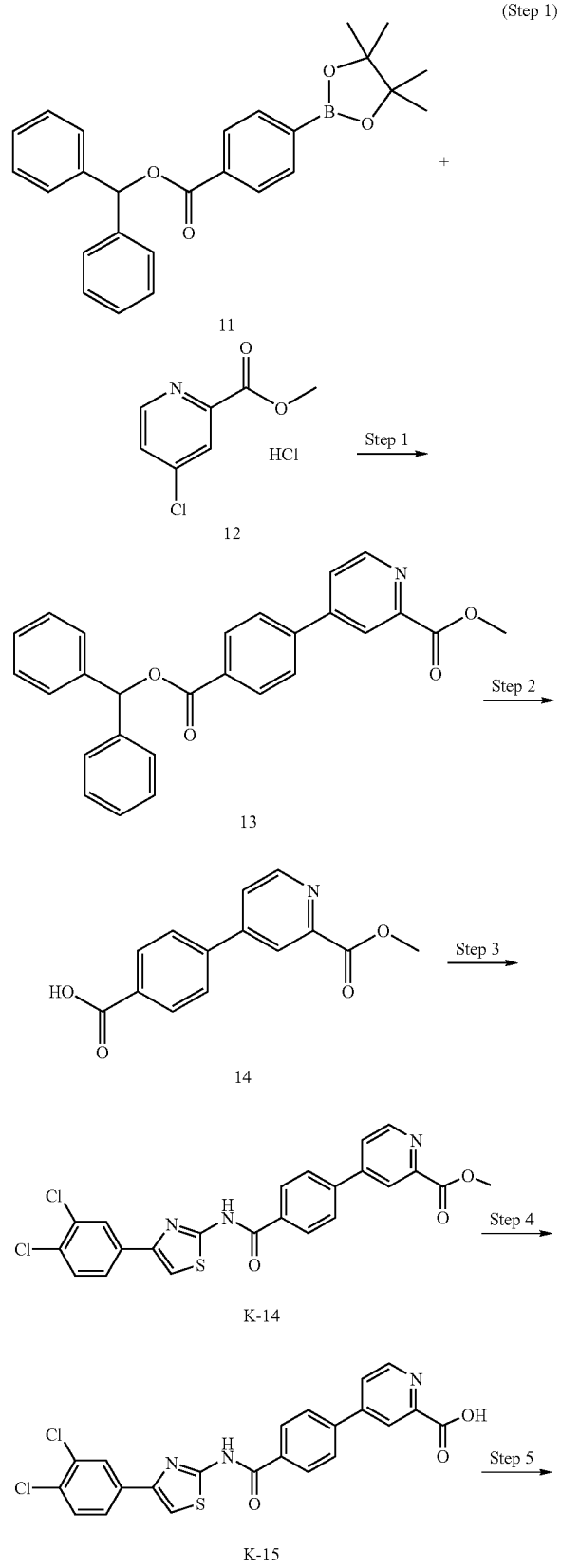

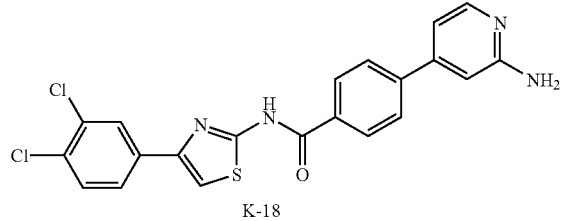

A solution of compound (11) (1.1 g), compound (12) (760 mg), potassium carbonate (1.44 g), tetrakistriphenylphosphinepalladium (250 mg) in DMF was stirred at 110° C. for 2 h. The reaction solution was poured into ethyl acetate, and the mixture was washed with water four times and brine, dried over magnesium sulfate. The solvent was concentrated, the residue was purified by silica gel column chromatography (ethyl acetate/n-hexane=2/3) to obtain compound (13) (870 mg) as a amorphous.

$^1$H NMR(CDCl$_3$, δ ppm): 4.06 (3H, s), 7.16 (1H, s), 7.28-7.50 (10H, m), 7.72 (1H, dd, J=4.8 Hz, 1.8 Hz), 7.75-7.80 (2H, m), 8.25-8.30 (2H, m), 8.40 (1H, d, J=2.1 Hz).

(Step 2)

A solution of compound (13) (870 mg) in formic acid (98-100%, 20 ml) was stirred at 50° C. for 3 h. The reaction solution was concentrated, toulene was added to the residure, and concentrated again. The obtained residue was washed with isopropyl ether to obtain compound (4) (473 mg) as white crystals.

$^1$H NMR(CDCl$_3$, δ ppm): 3.93 (3H, s), 7.97-8.02 (2H, m), 8.04 (1H, dd, J=7.8 Hz, 1.8 Hz), 8.07-8.12 (2H, m), 8.35 (1H, d, J=1.5 Hz), 8.82 (1H, d, J=4.8 Hz).

(Step 3)

Compound (K-14) was synthesized form compound (4) as starting material in a manner similar to Step 4 of Example 1. Its physical data was shown in Table 29.

(Step 4)

Compound (K-15) was synthesized form compound (K-14) as starting material in a manner similar to Step 5 of Example 1. Its physical data was shown in Table 29.

(Step 5)

A solution of compound (K-15) (100 mg), diphenylphosporoazide (55 μl), triethylamine (351 μl), and tert-butanol (1 ml) in DMF (15 ml) was stirred at 100° C. for 1 h. The reaction solution was poured into ethyl acetate, THF was added according to necessity when the precipitate was produced, and the mixture was washed with water two times, sodium bicarbonate aqueous solution and brine, dried over magnesium sulfate. The solvent was concentrated, the residue was purified by silica gel column chromatography (ethyl acetate/n-hexane=1/1) to obtain compound (K-18) (60 mg) as white crystals.

Compound (K-16) to (K-17), and (K-19) were synthesized in a manner similar to Example 6 and compound (K-1) to (K-13) in a manner similar to Example 1. Their physical date were shown in Table 29 to 31.

TABLE 29

[Structure: R^10—[thiazole]—Y—[phenyl]—W]

| Compound No. | R^10 | Y | W | $^1$H-NMR (DMSO d-6) |
|---|---|---|---|---|
| K-1 | 3,4-dichlorophenyl | —NH-C(=O)-CH=CH-CH— (trans crotonamide, N-linked) | —CONHMe | 2.80 (3H, d, J=4.5 Hz), 7.00 (1H, d, J=15.8 Hz), 7.70-7.81 (4H, m), 7.89-7.93 (4H, m),. 8.16 (1H, d, J=2.0 Hz), 8.53 (1H, q, J=4.5 Hz), 12.62 (1H, bs) |
| K-2 | 3,4-difluorophenyl | —NH-C(=O)-CH=CH-CH— | —CONHMe | 2.81 (3H, d, J=4.4 Hz), 7.02 (1H, d, J=15.8 Hz), 7.47-7.56 (1H, m), 7.71-7.81 (5H, m),. 7.90-7.97 (3H, m), 8.54 (1H, q, J=4.5 Hz), 12.60 (1H, bs) |
| K-3 | 3,4-dichlorophenyl | —NH-C(=O)-CH=CH-CH— | —COOMe | 3.88 (3H, s), 7.03 (1H, d, J=15.9 Hz), 7.71 (1H, d, J=8.2 Hz), 7.76-7.83 (3H, m), 7.89-7.92 (2H, m),. 8.03 (2H, d, J=8.2 Hz), 8.15 (1H, d, J=1.8 Hz), 12.66 (1H, bs) |
| K-4 | 3,4-dichlorophenyl | —NH-C(=O)-C(Me)=CH-CH— | —CONHMe | 2.17 (3H, d, J=1.1 Hz), 2.80 (3H, d, J=4.5 Hz), 7.58 (2H, d, J=8.3 Hz), 7.62 (1H, bs), 7.72 (1H, d, J=8.4 Hz),. 7.89-7.95 (4H, m), 8.20 (1H, d, J=2.0 Hz), 8.53 (1H, q, J=4.5 Hz), 12.46 (1H, bs) |
| K-5 | 3,4-dichlorophenyl | —NH-C(=O)-C(F)=CH-CH— | —CONHMe | 2.79 (3H, d, J=4.5 Hz), 7.16 (1H, d, J=24.2 Hz), 7.64 (2H, d, J=8.3 Hz), 7.71 (1H, d, J=8.5 Hz),. 7.81-7.83 (m, 2H), 7.90-7.97 (m, 2H), 8.18 (1H, d, J=1.7 Hz), 8.49 (1H, q, J=4.5 Hz), 13.01 (1H, bs) |
| K-6 | 3,4-dichlorophenyl | —NH-C(=O)-CH=CH-CH— | —COOH | 7.11 (1H, d, J=15.8 Hz), 7.69-7.82 (4H, m), 7.89-7.93 (2H, m),. 8.02 (2H, d, J=8.1 Hz), 8.16 (1H, d, J=1.6 Hz), 12.72 (1H, bs) |
| K-7 | 3,4-dichlorophenyl | —NH-C(=O)-CH2-CH2-CH— | —COOMe | 2.59 (2H, t, J=7.5 Hz), 3.04 (2H, t, J=7.5 Hz), 3.91(3H, s), 7.14-7.17 (3H, m), 7.43 (2H, d, J=8.7 Hz), 7.58 (1H, dd, J=8.7 Hz, 2.0 Hz), 7.87 (1H, d, J=2.0 Hz), 7.94 (2H, d, J=8.7 Hz),. 9.87 (1H, s) (CDCl3) |

TABLE 30

| Compound No | R¹⁰ | Y | W | ¹H-NMR (DMSO d-6) |
|---|---|---|---|---|
| K-8 | 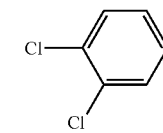 | 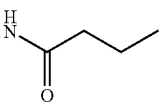 | —COOH | 2.82 (2H, t, J=7.2 Hz), 3.02 (2H, t, J=7.2 Hz), 7.38 (2H, d, J=8.5 Hz), 7.68 (1H, d, J=8.4 Hz), 7.83-7.89 (4H, m), 8.12 (1H, d, J=2.0 Hz), 12.33 (1H, s), 12.82 (1H, s) |
| K-9 | 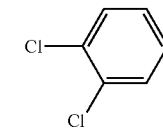 | 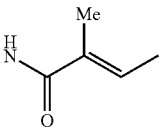 | —SO₂NH(t-Bu) | (CDCl3) 1.26(s, 9H), 2.25(d, 3H, J=1.5 Hz), 4.61(s, 1H), 7.21(s, 1H), 7.45(d, 2H, J=8.5 Hz), 7.47(d, 1H, J=8.2 Hz), 7.60(brs, 1H), 7.63(dd, 1H, J=8.2, 1.8 Hz), 7.94(d, 1H, J=1.8 Hz), 7.95(d, 2H, J=8.5 Hz), 9.58(brs, 1H). |
| K-10 | 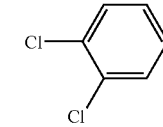 | 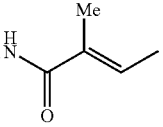 | —SO₂NH₂ | 2.14(d, 3H, J=1.5 Hz), 7.42(brs, 2H), 7.59(brs, 1H), 7.65(d, 2H, J=8.2 Hz), 7.69(d, 1H, J=8.2 Hz), 7.86(s, 1H), 7.87(d, 2H, J=8.2 Hz), 7.91(dd, 1H, J=8.2, 2.1 Hz), 8.18(d, 1H, J=2.1 Hz), 12.47(brs, 1H). |
| K-11 | 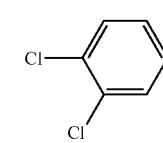 | 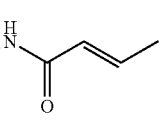 | —SO₂NH(t-Bu) | 1.11(s, 9H), 7.03(d, 1H, J=16.2 Hz), 7.65(s, 1H), 7.67(d, 1H, J=8.5 Hz), 7.80(d, 1H, J=16.2 Hz), 7.81(d, 2H, J=8.5 Hz), 7.89-7.93(m, 4H), 8.17(d, 1H, J=1.8 Hz), 12.67(s, 1H). |
| K-12 | 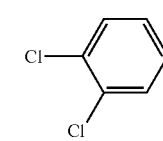 | 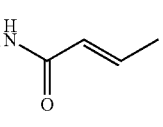 | —SO₂NH₂ | 7.03(d, 1H, J=16.0 Hz), 7.47(2H, s), 7.72(d, 1H, J=8.5 Hz), 7.81(d, 1H, J=16.0 Hz), 7.83(d, 2H, J=8.4 Hz), 7.89(d, 2H, J=8.4 Hz), 7.91(s, 1H), 7.91(dd, 1H, J=8.5, 2.1 Hz), 8.17(d, 2H, J=2.1 Hz), 12.67(s, 1H). |
| K-13 | 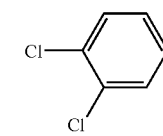 | 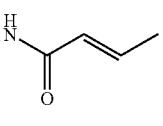 | —SO₃H | 6.94(d, 1H, J=15.8 Hz), 7.60(d, 2H, J=8.2 Hz), 7.67(d, 2H, J=8.2 Hz), 7.72(d, 1H, J=8.2 Hz), 7.74(d, 1H, J=15.8 Hz), 7.89(s, 1H), 7.91(dd, 1H, J=8.2, 1.9 Hz), 8.16(d, 1H, J=1.9 Hz), 12.57(brs, 1H). |
| K-14 | 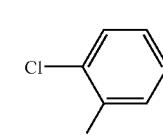 | —NHCO— | 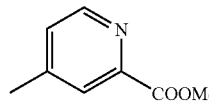 | 3.94 (3H, s), 7.72 (1H, d, J=8.7 Hz), 7.93 (1H, s), 7.95 (1H, dd, J=8.4 Hz, 1.8 Hz), 8.04-8.10 (3H, m), 8.22 (1H, d, J=2.4 Hz), 8.30 (2H, d, J=8.4 Hz), 8.39 (1H, d, J=1.2 Hz), 12.93 (1H, s) |
| K-15 | 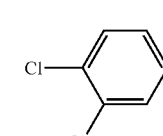 | —NHCO— | 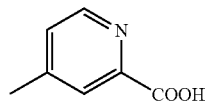 | 7.71 (1H, d, J=8.4 Hz), 7.82 (1H, bs), 7.89 (1H, s), 7.93-8.01 (3H, m), 8.22 (1H, d, J=2.1 Hz), 8.26-8.34 (3H, m), 8.65 (1H, bs) |

TABLE 31
| Compound No. | R¹⁰ | Y | W | ¹H-NMR (DMSO d-6) |
|---|---|---|---|---|
| K-16 | 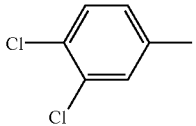 | —NHCO— | 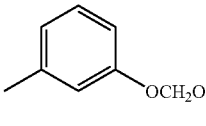 | 3.53(3H, s), 5.26(s, 1H), 7.10 (1H, ddd, J=8.2Hz, 2.5Hz, 0.9 Hz), 7.21(1H, s), 7.22-7.28(2H, m), 7.36-7.40(2H, m), 7.55(1H, dd, J=8.4Hz, 2.0Hz), 7.63(2H, d, J=8.4Hz), 7.83(1H, d, J= 2.0Hz), 7.93(2H, d, J=8.4Hz), 10.86(1H, bs) (CDCl3) |
| K-17 | 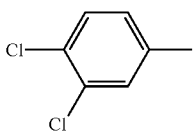 | —NHCO— | 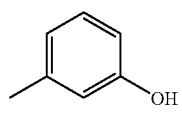 | 6.82-6.86(1H, m), 7.12-7.13 (1H, m), 7.17-7.20(1H, m), 7.28-7.37(1H, m), 7.73(1H, d, J= 8.2Hz), 7.89(2H, d, J=8.5Hz), 7.93(1H, s), 7.95(1H, dd, J=8.2 Hz, 2.0Hz), 8.21(2H, d, J=8.5 Hz), 8.23(1H, d, J=2.0Hz), 9.62(1H, s), 12.83(1H, s) |
| K-18 | 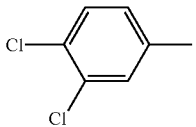 | —NHCO— | 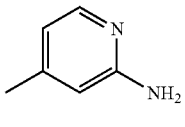 | 6.06(2H, s), 6.79(1H, s), 6.87 (1H, d, J=4.8Hz), 7.73(1H, d, J= 8.4Hz), 7.82(2H, d, J=8.4 Hz), 7.93(1H, s), 7.96(1H, dd, J= 8.1Hz, 1.5Hz), 8.02(1H, d, J= 5.1Hz), 8.21-8.27(3H, m), 12.88(1H, s) |
| K-19 | 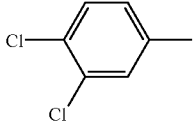 | —NHCO— | 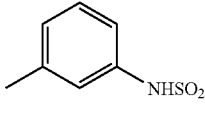 | 3.06(2H, s), 7.28(1H, dt, 7.2Hz, 2.1Hz), 7.45-7.57(3H, m), 7.73 (1H, d, J=8.1Hz), 7.81(2H, d, J= 8.4Hz), 7.93(1H, s), 7.96(1H, dd, J=8.4Hz, 2.1Hz), 8.21-8.27(3H, m), 9.88(1H, bs), 12.84 (1H, bs) |
Example 7
The Preparation of Compounds (L-1, L-2)
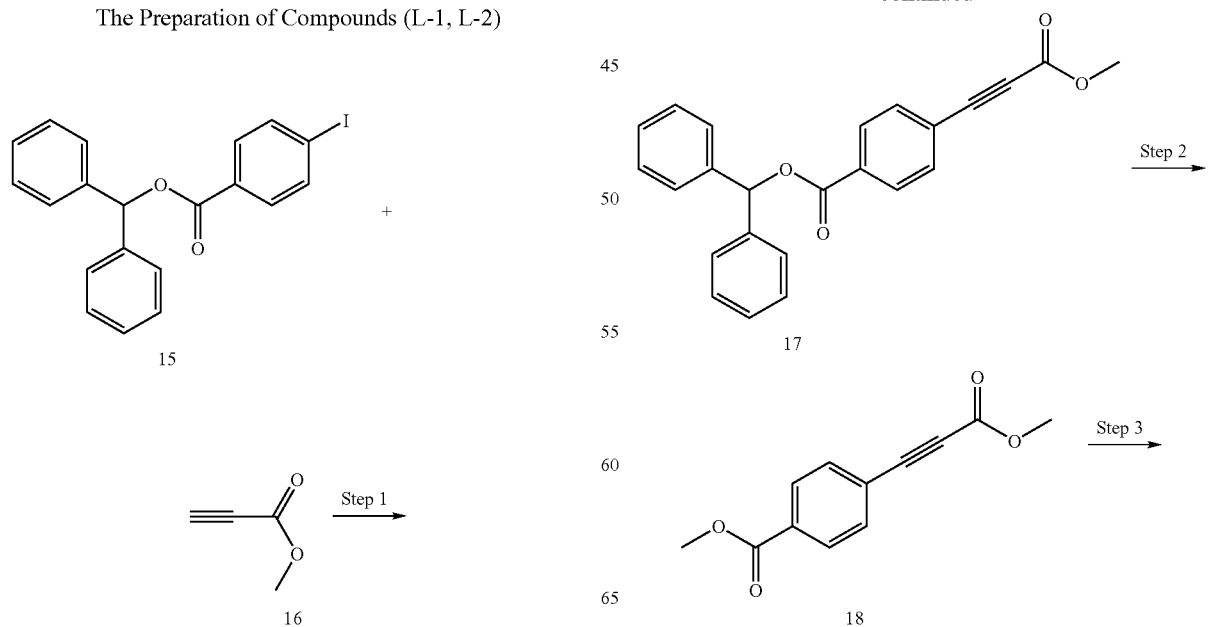

-continued

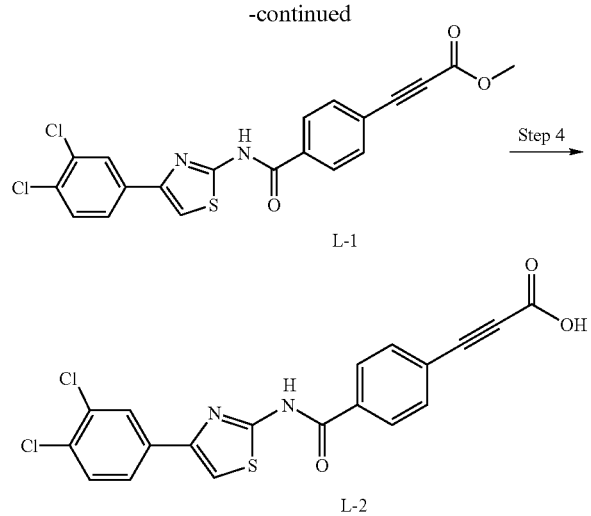

L-1

L-2

(Step 1)

(Step 1)

A solution of compound (15) (6.3 g), compound (16) (2.0 ml), triethylamine (6.3 ml), tetrakistriphenylphosphine-palladium (870 mg), and copper (I) iodide (290 mg) in DMF (70 ml) was stirred at 90° C. for 4 h. The reaction solution was poured into ethyl acetate, and the mixture was washed with water four times and brine, dried over magnesium sulfate. The solvent was concentrated, the residue was purified by silica gel column chromatography (ethyl acetate/n-hexane=1/4) to obtain compound (17) (2.25 g) as a amorphous.

$^1$H NMR(CDCl$_3$, δ ppm): 3.81 (3H, s), 7.06 (1H, s), 7.28-7.42 (6H, m), 7.51-7.55 (4H, m), 7.85 (2H, d, J=8.7 Hz), 8.17 (2H, d, J=8.7 Hz).

(Step 2)

A solution of compound (17) (180 mg) and formic acid (98-100%, 4 ml) in THF (4 ml) was stirred at room temperature for 18 h. The reaction solution was concentrated, toulene was added to the residure, and concentrated again. The obtained residure was washed with isopropyl ether to obtain compound (18) (95 mg) as white needles.

$^1$H NMR(CDCl$_3$, δ ppm): 3.80 (3H, s), 7.79 (2H, d, J=8.1 Hz), 8.00 (2H, d, J=8.1 H z), 13.33 (1 H, bs).

(Step 3)

Compound (L-1) was synthesized form compound (4) as starting material in a manner similar to Step 4 of Example 1. Its physical data was shown in Table 32.

(Step 4)

Compound (L-2) was synthesized form compound (L-1) as starting material in a manner similar to Step 5 of Example 1. Its physical data was shown in Table 32.

Compound (L-3) to (L-4) were synthesized in a manner similar to Example. Their physical date were shown in Table 32.

TABLE 32

| Compound No. | R$^{10}$ | Z | R$^5$ | $^1$H-NMR (DMSO d-6) |
|---|---|---|---|---|
| L-1 | 3,4-dichlorophenyl | 1,4-phenylene | Me | 3.82(3H, s), 7.72(1H, s), 7.85(2H, d, J=8.7Hz), 7.94(1H, dd, J=8.4Hz, 2.1Hz), 7.94(1H, s), 8.16-8.22(3H, m), 12.97 (1H, s) |
| L-2 | 3,4-dichlorophenyl | 1,4-phenylene | H | 7.72(1H, d, J=8.4Hz), 7.81(2H, d, J=8.4Hz), 7.95(1H, dd, J=8.4Hz, 2.1Hz), 7.94(1H, s), 8.18(2H, d, J=8.4Hz), 8.21(1H, d, J=2.1Hz), 12.96(1H, s) |
| L-3 | 3,4-dichlorophenyl | 2-methoxy-1,4-phenylene | Me | 3.80(3H, s), 4.01(3H, s), 7.70-7.74(3H, m), 7.88(1H, s), 7.92-7.96(2H, m), 8.21 (1H, d, J=1.8Hz), 12.99(1H, s) |
| L-4 | 3,4-dichlorophenyl | 2-methoxy-1,4-phenylene | H | 4.01(3H, s), 7.70-7.74(3H, m), 7.88 (1H, s), 7.93-7.97(2H, m), 8.22(1H, d, J=2.1Hz), 12.98(1H, s), 13.75(1H, bs) |

The below mentioned compounds were synthesized in a manner similar to above described method.

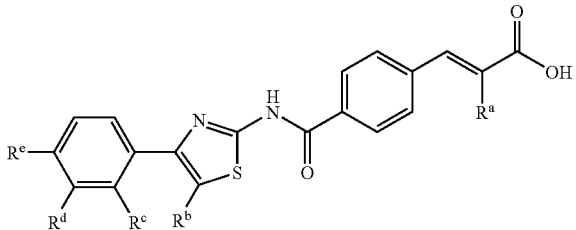

(Compound No., $R^a$, $R^b$, $R^c$, $R^d$, $R^e$)=(M-1, H, H, H, H, H), (M-2, H, H, H, H, Cl), (M-3, H, H, H, H, F), (M-4, H, H, H, H, CF$_3$), (M-5, H, H, H, H, Br), (M-6, H, H, H, H, CH$_3$), (M-7, H, H, H, F, H), (M-8, H, H, H, F, Cl), (M-9, H, H, H, F, F), (M-10, H, H, H, F, CF$_3$), (M-11, H, H, H, F, Br), (M-12, H, H, H, F, CH$_3$), (M-13, H, H, H, Cl, H), (M-14, MeO, H, H, Cl, Cl), (M-15, H, H, H, Cl, F), (M-16, H, H, H, Cl, CF$_3$), (M-17, H, H, H, Cl, Br), (M-18, H, H, H, Cl, CH$_3$), (M-19, H, H, H, CH$_3$, H), (M-20, H, H, H, CH$_3$, Cl), (M-21, H, H, H, CH$_3$, F), (M-22, H, H, H, CH$_3$, CF$_3$), (M-23, H, H, H, CH$_3$, Br), (M-24, H, H, H, CH$_3$, CH$_3$), (M-25, H, H, H, Et, H), (M-26, H, H, H, Et, Cl), (M-27, H, H, H, Et, F), (M-28, H, H, H, Et, CF$_3$), (M-29, H, H, H, Et, Br), (M-30, H, H, H, Et, CH$_3$), (M-31, H, H, H, n-Pr, H), (M-32, H, H, H, n-Pr, Cl), (M-33, H, H, H, n-Pr, F), (M-34, H, H, H, n-Pr, CF$_3$), (M-35, H, H, H, n-Pr, Br), (M-36, H, H, H, n-Pr, CH$_3$), (M-37, H, H, H, c-Pr, H), (M-38, H, H, H, c-Pr, Cl), (M-39, H, H, H, c-Pr, F), (M-40, H, H, H, c-Pr, CF$_3$), (M-41, H, H, H, c-Pr, Br), (M-42, H, H, H, c-Pr, CH$_3$), (M-43, H, H, H, i-Pr, H), (M-44, H, H, H, i-Pr, Cl), (M-45, H, H, H, i-Pr, F), (M-46, H, H, H, i-Pr, CF$_3$), (M-47, H, H, H, i-Pr, Br), (M-48, H, H, H, i-Pr, CH$_3$), (M-49, H, H, H, n-Bu, H), (M-50, H, H, H, n-Bu, Cl), (M-51, H, H, H, n-Bu, F), (M-52, H, H, H, n-Bu, CF$_3$), (M-53, H, H, H, n-Bu, Br), (M-54, H, H, H, n-Bu, CH$_3$), (M-55, H, H, H, i-Bu, H), (M-56, H, H, H, i-Bu, Cl), (M-57, H, H, H, i-Bu, F), (M-58, H, H, H, i-Bu, CF$_3$), (M-59, H, H, H, i-Bu, Br), (M-60, H, H, H, i-Bu, CH$_3$), (M-61, H, H, H, sec-Bu, H), (M-62, H, H, H, sec-Bu, Cl), (M-63, H, H, H, sec-Bu, F), (M-64, H, H, H, sec-Bu, CF$_3$), (M-65, H, H, H, sec-Bu, Br), (M-66, H, H, H, sec-Bu, CH$_3$), (M-67, H, H, H, n-Pen, H), (M-68, H, H, H, n-Pen, Cl), (M-69, H, H, H, n-Pen, F), (M-70, H, H, H, n-Pen, CF$_3$), (M-71, H, H, H, n-Pen, Br), (M-72, H, H, H, n-Pen, CH$_3$), (M-73, H, H, H, c-Pen, H), (M-74, H, H, H, c-Pen, Cl), (M-75, H, H, H, c-Pen, F), (M-76, H, H, H, c-Pen, CF$_3$), (M-77, H, H, H, c-Pen, Br), (M-78, H, H, H, c-Pen, CH$_3$), (M-79, H, H, H, n-Hex, H), (M-80, H, H, H, n-Hex, Cl), (M-81, H, H, H, n-Hex, F), (M-82, H, H, H, n-Hex, CF$_3$), (M-83, H, H, H, n-Hex, Br), (M-84, H, H, H, n-Hex, CH$_3$), (M-85, H, H, H, c-Hex, H), (M-86, H, H, H, c-Hex, Cl), (M-87, H, H, H, c-Hex, F), (M-88, H, H, H, c-Hex, CF$_3$), (M-89, H, H, H, c-Hex, Br), (M-90, H, H, H, c-Hex, CH$_3$), (M-91, H, H, H, OH, H), (M-92, H, H, H, OH, Cl), (M-93, H, H, H, OH, F), (M-94, H, H, H, OH, CF$_3$), (M-95, H, H, H, OH, Br), (M-96, H, H, H, OH, CH$_3$), (M-97, H, H, H, EtO, H), (M-98, H, H, H, EtO, Cl), (M-99, H, H, H, EtO, F), (M-100, H, H, H, EtO, CF$_3$), (M-101, H, H, H, EtO, Br), (M-102, H, H, H, EtO, CH$_3$), (M-103, H, H, H, n-PrO, H), (M-104, H, H, H, n-PrO, Cl), (M-105, H, H, H, n-PrO, F), (M-106, H, H, H, n-PrO, CF$_3$), (M-107, H, H, H, n-PrO, Br), (M-108, H, H, H, n-PrO, CH$_3$), (M-109, H, H, H, PhO, H), (M-110, H, H, H, PhO, Cl), (M-111, H, H, H, PhO, F), (M-112, H, H, H, PhO, CF$_3$), (M-113, H, H, H, PhO, Br), (M-114, H, H, H, PhO, CH$_3$), (M-115, H, H, H, BnO, H), (M-116, H, H, H, BnO, Cl), (M-117, H, H, H, BnO, F), (M-118, H, H, H, BnO, CF$_3$), (M-119, H, H, H, BnO, Br), (M-120, H, H, H, BnO, CH$_3$), (M-121, H, H, H, PhCH$_2$CH$_2$O, H), (M-122, H, H, H, PhCH$_2$CH$_2$O, Cl), (M-123, H, H, H, PhCH$_2$CH$_2$O, F), (M-124, H, H, H, PhCH$_2$CH$_2$O, CF$_3$), (M-125, H, H, H, PhCH$_2$CH$_2$O, Br), (M-126, H, H, H, PhCH$_2$CH$_2$O, CH$_3$), (M-127, H, H, H, CF$_3$O, H), (M-128, H, H, H, CF$_3$O, Cl), (M-129, H, H, H, CF$_3$O, F), (M-130, H, H, H, CF$_3$O, CF$_3$), (M-131, H, H, H, CF$_3$O, Br), (M-132, H, H, H, CF$_3$O, CH$_3$), (M-133, H, H, H, Ph, H), (M-134, H, H, H, Ph, Cl), (M-135, H, H, H, Ph, F), (M-136, H, H, H, Ph, CF$_3$), (M-137, H, H, H, Ph, Br), (M-138, H, H, H, Ph, CH$_3$), (M-139, H, H, H, 4-F-Ph, H), (M-140, H, H, H, 4-F-Ph, Cl), (M-141, H, H, H, 4-F-Ph, F), (M-142, H, H, H, 4-F-Ph, CF$_3$), (M-143, H, H, H, 4-F-Ph, Br), (M-144, H, H, H, 4-F-Ph, CH$_3$), (M-145, H, H, H, 4-CF$_3$-Ph, H), (M-146, H, H, H, 4-CF$_3$-Ph, Cl), (M-147, H, H, H, 4-CF$_3$-Ph, F), (M-148, H, H, H, 4-CF$_3$-Ph, CF$_3$), (M-149, H, H, H, 4-CF$_3$-Ph, Br), (M-150, H, H, H, 4-CF$_3$-Ph, CH$_3$), (M-151, H, H, H, 4-(Me)$_2$N-Ph, H), (M-152, H, H, H, 4-(Me)$_2$N-Ph, Cl), (M-153, H, H, H, 4-(Me)$_2$N-Ph, F), (M-154, H, H, H, 4-(Me)$_2$N-Ph, CF$_3$), (M-155, H, H, H, 4-(Me)$_2$N-Ph, Br), (M-156, H, H, H, 4-(Me)$_2$N-Ph, CH$_3$), (M-157, H, H, H, 4-OH-Ph, H), (M-158, H, H, H, 4-OH-Ph, Cl), (M-159, H, H, H, 4-OH-Ph, F), (M-160, H, H, H, 4-OH-Ph, CF$_3$), (M-161, H, H, H, 4-OH-Ph, Br), (M-162, H, H, H, 4-OH-Ph, CH$_3$), (M-163, H, H, H, 3,4-di-F-Ph, H), (M-164, H, H, H, 3,4-di-F-Ph, Cl), (M-165, H, H, H, 3,4-di-F-Ph, F), (M-166, H, H, H, 3,4-di-F-Ph, CF$_3$), (M-167, H, H, H, 3,4-di-F-Ph, Br), (M-168, H, H, H, 3,4-di-F-Ph, CH$_3$), (M-169, H, H, H, 4-COOH-Ph, H), (M-170, H, H, H, 4-COOH-Ph, Cl), (M-171, H, H, H, 4-COOH-Ph, F), (M-172, H, H, H, 4-COOH-Ph, CF$_3$), (M-173, H, H, H, 4-COOH-Ph, Br), (M-174, H, H, H, 4-COOH-Ph, CH$_3$), (M-175, H, H, H, Bn, H), (M-176, H, H, H, Bn, Cl), (M-177, H, H, H, Bn, F), (M-178, H, H, H, Bn, CF$_3$), (M-179, H, H, H, Bn, Br), (M-180, H, H, H, Bn, CH$_3$), (M-181, H, H, H, 4-F-Bn, H), (M-182, H, H, H, 4-F-Bn, Cl), (M-183, H, H, H, 4-F-Bn, F), (M-184, H, H, H, 4-F-Bn, CF$_3$), (M-185, H, H, H, 4-F-Bn, Br), (M-186, H, H, H, 4-F-Bn, CH$_3$), (M-187, H, H, H, 2-Py, H), (M-188, H, H, H, 2-Py, Cl), (M-189, H, H, H, 2-Py, F), (M-190, H, H, H, 2-Py, CF$_3$), (M-191, H, H, H, 2-Py, Br), (M-192, H, H, H, 2-Py, CH$_3$), (M-193, H, H, H, 3-Py, H), (M-194, H, H, H, 3-Py, Cl), (M-195, H, H, H, 3-Py, F), (M-196, H, H, H, 3-Py, CF$_3$), (M-197, H, H, H, 3-Py, Br), (M-198, H, H, H, 3-Py, CH$_3$), (M-199, H, H, H, 4-Py, H), (M-200, H, H, H, 4-Py, Cl), (M-201, H, H, H, 4-Py, F), (M-202, H, H, H, 4-Py, CF$_3$), (M-203, H, H, H, 4-Py, Br), (M-204, H, H, H, 4-Py, CH$_3$), (M-205, H, H, H, 2-Th, H), (M-206, H, H, H, 2-Th, Cl), (M-207, H, H, H, 2-Th, F), (M-208, H, H, H, 2-Th, CF$_3$), (M-209, H, H, H, 2-Th, Br), (M-210, H, H, H, 2-Th, CH$_3$), (M-211, H, H, H, 3-Th, H), (M-212, H, H, H, 3-Th, Cl), (M-213, H, H, H, 3-Th, F), (M-214, H, H, H, 3-Th, CF$_3$), (M-215, H, H, H, 3-Th, Br), (M-216, H, H, H, 3-Th, CH$_3$), (M-217, H, H, H, pyrrazol-2-yl, H), (M-218, H, H, H, pyrrazol-2-yl, Cl), (M-219, H, H, H, pyrrazol-2-yl, F), (M-220, H, H, H, pyrrazol-2-yl, CF$_3$), (M-221, H, H, H, pyrrazol-2-yl, Br), (M-222, H, H, H, pyrrazol-2-yl, CH$_3$), (M-223, H, H, H, pyrrazol-3-yl, H), (M-224, H, H, H, pyrrazol-3-yl, Cl), (M-225, H, H, H, pyrrazol-3-yl, F), (M-226, H, H, H, pyrrazol-3-yl, CF$_3$), (M-227, H, H, H, pyrrazol-3-yl, Br), (M-228, H, H, H, pyrrazol-3-yl, CH$_3$), (M-229, H, H, H, pyrimidin-2-yl, H), (M-230, H, H, H, pyrimidin-2-yl, Cl), (M-231, H, H, H, pyrimidin-2-yl, F), (M-232, H, H, H, pyrimidin-2-yl, CF$_3$), (M-233, H, H, H, pyrimidin-2-yl, Br), (M-234, H, H, H, pyrimidin-2-yl, CH$_3$), (M-235, H, H, H, pyrimidin-4-yl, H), (M-236, H, H, H, pyrimidin-4-yl, Cl), (M-237, H, H, H, pyrimidin-4-yl, F), (M-238, H, H, H, pyrimidin-4-yl, CF₃), (M-239, H, H, H, pyrimidin-4-yl, Br), (M-240, H, H, H, pyrimidin-4-yl, CH₃), (M-241, H, H, H, pyrimidin-5-yl, H), (M-242, H, H, H, pyrimidin-5-yl, Cl), (M-243, H, H, H, pyrimidin-5-yl, F), (M-244, H, H, H, pyrimidin-5-yl, CF₃), (M-245, H, H, H, pyrimidin-5-yl, Br), (M-246, H, H, H, pyrimidin-5-yl, CH₃), (M-247, H, H, H, HOOCCH₂CH₂CH₂, H), (M-248, H, H, H, HOOCCH₂CH₂CH₂, Cl), (M-249, H, H, H, HOOCCH₂CH₂CH₂, F), (M-250, H, H, H, HOOCCH₂CH₂CH₂, CF₃), (M-251, H, H, H, HOOCCH₂CH₂CH₂, Br), (M-252, H, H, H, HOOCCH₂CH₂CH₂, CH₃), (M-253, H, H, H, HOOCCH₂CH₂CH₂CH₂, H), (M-254, H, H, H, HOOCCH₂CH₂CH₂CH₂, Cl), (M-255, H, H, H, HOOCCH₂CH₂CH₂CH₂, F), (M-256, H, H, H, HOOCCH₂CH₂CH₂CH₂, CF₃), (M-257, H, H, H, HOOCCH₂CH₂CH₂CH₂, Br), (M-258, H, H, H, HOOCCH₂CH₂CH₂CH₂, CH₃), (M-259, H, H, H, (Me)₂NCOCH₂CH₂CH₂, H), (M-260, H, H, H, (Me)₂NCOCH₂CH₂CH₂, Cl), (M-261, H, H, H, (Me)₂NCOCH₂CH₂CH₂, F), (M-262, H, H, H, (Me)₂NCOCH₂CH₂CH₂, CF₃), (M-263, H, H, H, (Me)₂NCOCH₂CH₂CH₂, Br), (M-264, H, H, H, (Me)₂NCOCH₂CH₂CH₂, CH₃), (M-265, H, H, H, (Me)₂NCOCH₂CH₂CH₂CH₂, H), (M-266, H, H, H, (Me)₂NCOCH₂CH₂CH₂CH₂, Cl), (M-267, H, H, H, (Me)₂NCOCH₂CH₂CH₂CH₂, F), (M-268, H, H, H, (Me)₂NCOCH₂CH₂CH₂CH₂, CF₃), (M-269, H, H, H, (Me)₂NCOCH₂CH₂CH₂CH₂, Br), (M-270, H, H, H, (Me)₂NCOCH₂CH₂CH₂CH₂, CH₃), (M-271, H, H, H, MeOCH₂, H), (M-272, H, H, H, MeOCH₂, Cl), (M-273, H, H, H, MeOCH₂, F), (M-274, H, H, H, MeOCH₂, CF₃), (M-275, H, H, H, MeOCH₂, Br), (M-276, H, H, H, MeOCH₂, CH₃), (M-277, H, H, H, EtOCH₂, H), (M-278, H, H, H, EtOCH₂, Cl), (M-279, H, H, H, EtOCH₂, F), (M-280, H, H, H, EtOCH₂, CF₃), (M-281, H, H, H, EtOCH₂, Br), (M-282, H, H, H, EtOCH₂, CH₃), (M-283, H, H, H, EtOCH₂CH₂, H), (M-284, H, H, H, EtOCH₂CH₂, Cl), (M-285, H, H, H, EtOCH₂CH₂, F), (M-286, H, H, H, EtOCH₂CH₂, CF₃), (M-287, H, H, H, EtOCH₂CH₂, Br), (M-288, H, H, H, EtOCH₂CH₂, CH₃), (M-289, H, H, H, MeOCH₂CH₂OCH₂CH₂, H), (M-290, H, H, H, MeOCH₂CH₂OCH₂CH₂, Cl), (M-291, H, H, H, MeOCH₂CH₂OCH₂CH₂, F), (M-292, H, H, H, MeOCH₂CH₂OCH₂CH₂, CF₃), (M-293, H, H, H, MeOCH₂CH₂OCH₂CH₂, Br), (M-294, H, H, H, MeOCH₂CH₂OCH₂CH₂, CH₃), (M-295, H, H, H, MeOCH₂CH₂, H), (M-296, H, H, H, MeOCH₂CH₂, Cl), (M-297, H, H, H, MeOCH₂CH₂, F), (M-298, H, H, H, MeOCH₂CH₂, CF₃), (M-299, H, H, H, MeOCH₂CH₂, Br), (M-300, H, H, H, MeOCH₂CH₂, CH₃), (M-301, H, H, H, HOCH₂, H), (M-302, H, H, H, HOCH₂, Cl), (M-303, H, H, H, HOCH₂, F), (M-304, H, H, H, HOCH₂, CF₃), (M-305, H, H, H, HOCH₂, Br), (M-306, H, H, H, HOCH₂, CH₃), (M-307, H, H, H, HOCH₂CH₂, H), (M-308, H, H, H, HOCH₂CH₂, Cl), (M-309, H, H, H, HOCH₂CH₂, F), (M-310, H, H, H, HOCH₂CH₂, CF₃), (M-311, H, H, H, HOCH₂CH₂, Br), (M-312, H, H, H, HOCH₂CH₂, CH₃), (M-313, H, H, H, HOCH₂CH₂CH₂, H), (M-314, H, H, H, HOCH₂CH₂CH₂, C), (M-315, H, H, H, HOCH₂CH₂CH₂, F), (M-316, H, H, H, HOCH₂CH₂CH₂, CF₃), (M-317, H, H, H, HOCH₂CH₂CH₂, Br), (M-318, H, H, H, HOCH₂CH₂CH₂, CH₃), (M-319, H, H, H, HOCH₂CH₂CH₂CH₂, H), (M-320, H, H, H, HOCH₂CH₂CH₂CH₂, Cl), (M-321, H, H, H, HOCH₂CH₂CH₂CH₂, F), (M-322, H, H, H, HOCH₂CH₂CH₂CH₂, CF₃), (M-323, H, H, H, HOCH₂CH₂CH₂CH₂, Br), (M-324, H, H, H, HOCH₂CH₂CH₂CH₂, CH₃), (M-325, H, H, H, HOCH₂CH₂CH₂CH₂CH₂, H), (M-326, H, H, H, HOCH₂CH₂CH₂CH₂CH₂, Cl), (M-327, H, H, H, HOCH₂CH₂CH₂CH₂CH₂, F), (M-328, H, H, H, HOCH₂CH₂CH₂CH₂CH₂, CF₃), (M-329, H, H, H, HOCH₂CH₂CH₂CH₂CH₂, Br), (M-330, H, H, H, HOCH₂CH₂CH₂CH₂CH₂, CH₃), (M-331, H, H, H, HOCH₂CH₂OCH₂CH₂, H), (M-332, H, H, H, HOCH₂CH₂OCH₂CH₂, Cl), (M-333, H, H, H, HOCH₂CH₂OCH₂CH₂, F), (M-334, H, H, H, HOCH₂CH₂OCH₂CH₂, CF₃), (M-335, H, H, H, HOCH₂CH₂OCH₂CH₂, Br), (M-336, H, H, H, HOCH₂CH₂OCH₂CH₂, CH₃), (M-337, H, H, H, (Me)₂N, H), (M-338, H, H, H, (Me)₂N, Cl), (M-339, H, H, H, (Me)₂N, F), (M-340, H, H, H, (Me)₂N, CF₃), (M-341, H, H, H, (Me)₂N, Br), (M-342, H, H, H, (Me)₂N, CH₃), (M-343, H, H, H, piperidin-4-yl-methyl, H), (M-344, H, H, H, piperidin-4-yl-methyl, Cl), (M-345, H, H, H, piperidin-4-yl-methyl, F), (M-346, H, H, H, piperidin-4-yl-methyl, CF₃), (M-347, H, H, H, piperidin-4-yl-methyl, Br), (M-348, H, H, H, piperidin-4-yl-methyl, CH₃), (M-349, H, H, H, cyclohexylmethyl, H), (M-350, H, H, H, cyclohexylmethyl, Cl), (M-351, H, H, H, cyclohexylmethyl, F), (M-352, H, H, H, cyclohexylmethyl, CF₃), (M-353, H, H, H, cyclohexylmethyl, Br), (M-354, H, H, H, cyclohexylmethyl, CH₃), (M-355, H, H, F, H, H), (M-356, H, H, F, H, Cl), (M-357, H, H, F, H, F), (M-358, H, H, F, H, CF₃), (M-359, H, H, F, H, Br), (M-360, H, H, F, H, CH₃), (M-361, H, H, F, F, H), (M-362, H, H, F, F, Cl), (M-363, H, H, F, F, F), (M-364, H, H, F, F, CF₃), (M-365, H, H, F, F, Br), (M-366, H, H, F, F, CH₃), (M-367, H, H, F, Cl, H), (M-368, H, H, F, Cl, Cl), (M-369, H, H, F, Cl, F), (M-370, H, H, F, Cl, CF₃), (M-371, H, H, F, Cl, Br), (M-372, H, H, F, Cl, CH₃), (M-373, H, H, F, CH₃, H), (M-374, H, H, F, CH₃, Cl), (M-375, H, H, F, CH₃, F), (M-376, H, H, F, CH₃, CF₃), (M-377, H, H, F, CH₃, Br), (M-378, H, H, F, CH₃, CH₃), (M-379, H, H, F, Et, H), (M-380, H, H, F, Et, Cl), (M-381, H, H, F, Et, F), (M-382, H, H, F, Et, CF₃), (M-383, H, H, F, Et, Br), (M-384, H, H, F, Et, CH₃), (M-385, H, H, F, n-Pr, H), (M-386, H, H, F, n-Pr, Cl), (M-387, H, H, F, n-Pr, F), (M-388, H, H, F, n-Pr, CF₃), (M-389, H, H, F, n-Pr, Br), (M-390, H, H, F, n-Pr, CH₃), (M-391, H, H, F, c-Pr, H), (M-392, H, H, F, c-Pr, Cl), (M-393, H, H, F, c-Pr, F), (M-394, H, H, F, c-Pr, CF₃), (M-395, H, H, F, c-Pr, Br), (M-396, H, H, F, c-Pr, CH₃), (M-397, H, H, F, i-Pr, H), (M-398, H, H, F, i-Pr, Cl), (M-399, H, H, F, i-Pr, F), (M-400, H, H, F, i-Pr, CF₃), (M-401, H, H, F, i-Pr, Br), (M-402, H, H, F, i-Pr, CH₃), (M-403, H, H, F, n-Bu, H), (M-404, H, H, F, n-Bu, Cl), (M-405, H, H, F, n-Bu, F), (M-406, H, H, F, n-Bu, CF₃), (M-407, H, H, F, n-Bu, Br), (M-408, H, H, F, n-Bu, CH₃), (M-409, H, H, F, i-Bu, H), (M-410, H, H, F, i-Bu, Cl), (M-411, H, H, F, i-Bu, F), (M-412, H, H, F, i-Bu, CF₃), (M-413, H, H, F, i-Bu, Br), (M-414, H, H, F, i-Bu, CH₃), (M-415, H, H, F, sec-Bu, H), (M-416, H, H, F, sec-Bu, Cl), (M-417, H, H, F, sec-Bu, F), (M-418, H, H, F, sec-Bu, CF₃), (M-419, H, H, F, sec-Bu, Br), (M-420, H, H, F, sec-Bu, CH₃), (M-421, H, H, F, n-Pen, H), (M-422, H, H, F, n-Pen, Cl), (M-423, H, H, F, n-Pen, F), (M-424, H, H, F, n-Pen, CF₃), (M-425, H, H, F, n-Pen, Br), (M-426, H, H, F, n-Pen, CH₃), (M-427, H, H, F, c-Pen, H), (M-428, H, H, F, c-Pen, Cl), (M-429, H, H, F, c-Pen, F), (M-430, H, H, F, c-Pen, CF₃), (M-431, H, H, F, c-Pen, Br), (M-432, H, H, F, c-Pen, CH₃), (M-433, H, H, F, n-Hex, H), (M-434, H, H, F, n-Hex, Cl), (M-435, H, H, F, n-Hex, F), (M-436, H, H, F, n-Hex, CF₃), (M-437, H, H, F, n-Hex, Br), (M-438, H, H, F, n-Hex, CH₃), (M-439, H, H, F, c-Hex, H), (M-440, H, H, F, c-Hex, Cl), (M-441, H, H, F, c-Hex, F), (M-442, H, H, F, c-Hex, CF₃), (M-443, H, H, F, c-Hex, Br), (M-444, H, H, F, c-Hex, CH₃), (M-445, H, H, F, OH, H), (M-446, H, H, F, OH, Cl), (M-447, H, H, F, OH, F), (M-448, H, H, F, OH, CF$_3$), (M-449, H, H, F, OH, Br), (M-450, H, H, F, OH, CH$_3$), (M-451, H, H, F, EtO, H), (M-452, H, H, F, EtO, Cl), (M-453, H, H, F, EtO, F), (M-454, H, H, F, EtO, CF$_3$), (M-455, H, H, F, EtO, Br), (M-456, H, H, F, EtO, CH$_3$), (M-457, H, H, F, n-PrO, H), (M-458, H, H, F, n-PrO, Cl), (M-459, H, H, F, n-PrO, F), (M-460, H, H, F, n-PrO, CF$_3$), (M-461, H, H, F, n-PrO, Br), (M-462, H, H, F, n-PrO, CH$_3$), (M-463, H, H, F, PhO, H), (M-464, H, H, F, PhO, Cl), (M-465, H, H, F, PhO, F), (M-466, H, H, F, PhO, CF$_3$), (M-467, H, H, F, PhO, Br), (M-468, H, H, F, PhO, CH$_3$), (M-469, H, H, F, BnO, H), (M-470, H, H, F, BnO, Cl), (M-471, H, H, F, BnO, F), (M-472, H, H, F, BnO, CF$_3$), (M-473, H, H, F, BnO, Br), (M-474, H, H, F, BnO, CH$_3$), (M-475, H, H, F, PhCH$_2$CH$_2$O, H), (M-476, H, H, F, PhCH$_2$CH$_2$O, Cl), (M-477, H, H, F, PhCH$_2$CH$_2$O, F), (M-478, H, H, F, PhCH$_2$CH$_2$O, CF$_3$), (M-479, H, H, F, PhCH$_2$CH$_2$O, Br), (M-480, H, H, F, PhCH$_2$CH$_2$O, CH$_3$), (M-481, H, H, F, CF$_3$O, H), (M-482, H, H, F, CF$_3$O, Cl), (M-483, H, H, F, CF$_3$O, F), (M-484, H, H, F, CF$_3$O, CF$_3$), (M-485, H, H, F, CF$_3$O, Br), (M-486, H, H, F, CF$_3$O, CH$_3$), (M-487, H, H, F, Ph, H), (M-488, H, H, F, Ph, Cl), (M-489, H, H, F, Ph, F), (M-490, H, H, F, Ph, CF$_3$), (M-491, H, H, F, Ph, Br), (M-492, H, H, F, Ph, CH$_3$), (M-493, H, H, F, 4-F-Ph, H), (M-494, H, H, F, 4-F-Ph, Cl), (M-495, H, H, F, 4-F-Ph, F), (M-496, H, H, F, 4-F-Ph, CF$_3$), (M-497, H, H, F, 4-F-Ph, Br), (M-498, H, H, F, 4-F-Ph, CH$_3$), (M-499, H, H, F, 4-CF$_3$-Ph, H), (M-500, H, H, F, 4-CF$_3$-Ph, Cl), (M-501, H, H, F, 4-CF$_3$-Ph, F), (M-502, H, H, F, 4-CF$_3$-Ph, CF$_3$), (M-503, H, H, F, 4-CF$_3$-Ph, Br), (M-504, H, H, F, 4-CF$_3$-Ph, CH$_3$), (M-505, H, H, F, 4-(Me)$_2$N-Ph, H), (M-506, H, H, F, 4-(Me)$_2$N-Ph, Cl), (M-507, H, H, F, 4-(Me)$_2$N-Ph, F), (M-508, H, H, F, 4-(Me)$_2$N-Ph, CF$_3$), (M-509, H, H, F, 4-(Me)$_2$N-Ph, Br), (M-510, H, H, F, 4-(Me)$_2$N-Ph, CH$_3$), (M-511, H, H, F, 4-OH-Ph, H), (M-512, H, H, F, 4-OH-Ph, Cl), (M-513, H, H, F, 4-OH-Ph, F), (M-514, H, H, F, 4-OH-Ph, CF$_3$), (M-515, H, H, F, 4-OH-Ph, Br), (M-516, H, H, F, 4-OH-Ph, CH$_3$), (M-517, H, H, F, 3,4-di-F-Ph, H), (M-518, H, H, F, 3,4-di-F-Ph, Cl), (M-519, H, H, F, 3,4-di-F-Ph, F), (M-520, H, H, F, 3,4-di-F-Ph, CF$_3$), (M-521, H, H, F, 3,4-di-F-Ph, Br), (M-522, H, H, F, 3,4-di-F-Ph, CH$_3$), (M-523, H, H, F, 4-COOH-Ph, H), (M-524, H, H, F, 4-COOH-Ph, Cl), (M-525, H, H, F, 4-COOH-Ph, F), (M-526, H, H, F, 4-COOH-Ph, CF$_3$), (M-527, H, H, F, 4-COOH-Ph, Br), (M-528, H, H, F, 4-COOH-Ph, CH$_3$), (M-529, H, H, F, Bn, H), (M-530, H, H, F, Bn, Cl), (M-531, H, H, F, Bn, F), (M-532, H, H, F, Bn, CF$_3$), (M-533, H, H, F, Bn, Br), (M-534, H, H, F, Bn, CH$_3$), (M-535, H, H, F, 4-F-Bn, H), (M-536, H, H, F, 4-F-Bn, Cl), (M-537, H, H, F, 4-F-Bn, F), (M-538, H, H, F, 4-F-Bn, CF$_3$), (M-539, H, H, F, 4-F-Bn, Br), (M-540, H, H, F, 4-F-Bn, CH$_3$), (M-541, H, H, F, 2-Py, H), (M-542, H, H, F, 2-Py, Cl), (M-543, H, H, F, 2-Py, F), (M-544, H, H, F, 2-Py, CF$_3$), (M-545, H, H, F, 2-Py, Br), (M-546, H, H, F, 2-Py, CH$_3$), (M-547, H, H, F, 3-Py, H), (M-548, H, H, F, 3-Py, Cl), (M-549, H, H, F, 3-Py, F), (M-550, H, H, F, 3-Py, CF$_3$), (M-551, H, H, F, 3-Py, Br), (M-552, H, H, F, 3-Py, CH$_3$), (M-553, H, H, F, 4-Py, H), (M-554, H, H, F, 4-Py, Cl), (M-555, H, H, F, 4-Py, F), (M-556, H, H, F, 4-Py, CF$_3$), (M-557, H, H, F, 4-Py, Br), (M-558, H, H, F, 4-Py, CH$_3$), (M-559, H, H, F, 2-Th, H), (M-560, H, H, F, 2-Th, Cl), (M-561, H, H, F, 2-Th, F), (M-562, H, H, F, 2-Th, CF$_3$), (M-563, H, H, F, 2-Th, Br), (M-564, H, H, F, 2-Th, CH$_3$), (M-565, H, H, F, 3-Th, H), (M-566, H, H, F, 3-Th, Cl), (M-567, H, H, F, 3-Th, F), (M-568, H, H, F, 3-Th, CF$_3$), (M-569, H, H, F, 3-Th, Br), (M-570, H, H, F, 3-Th, CH$_3$), (M-571, H, H, F, pyrrazol-2-yl, H), (M-572, H, H, F, pyrrazol-2-yl, Cl), (M-573, H, H, F, pyrrazol-2-yl, F), (M-574, H, H, F, pyrrazol-2-yl, CF$_3$), (M-575, H, H, F, pyrrazol-2-yl, Br), (M-576, H, H, F, pyrrazol-2-yl, CH$_3$), (M-577, H, H, F, pyrrazol-3-yl, H), (M-578, H, H, F, pyrrazol-3-yl, Cl), (M-579, H, H, F, pyrrazol-3-yl, F), (M-580, H, H, F, pyrrazol-3-yl, CF$_3$), (M-581, H, H, F, pyrrazol-3-yl, Br), (M-582, H, H, F, pyrrazol-3-yl, CH$_3$), (M-583, H, H, F, pyrimidin-2-yl, H), (M-584, H, H, F, pyrimidin-2-yl, Cl), (M-585, H, H, F, pyrimidin-2-yl, F), (M-586, H, H, F, pyrimidin-2-yl, CF$_3$), (M-587, H, H, F, pyrimidin-2-yl, Br), (M-588, H, H, F, pyrimidin-2-yl, CH$_3$), (M-589, H, H, F, pyrimidin-4-yl, H), (M-590, H, H, F, pyrimidin-4-yl, Cl), (M-591, H, H, F, pyrimidin-4-yl, F), (M-592, H, H, F, pyrimidin-4-yl, CF$_3$), (M-593, H, H, F, pyrimidin-4-yl, Br), (M-594, H, H, F, pyrimidin-4-yl, CH$_3$), (M-595, H, H, F, pyrimidin-5-yl, H), (M-596, H, H, F, pyrimidin-5-yl, Cl), (M-597, H, H, F, pyrimidin-5-yl, F), (M-598, H, H, F, pyrimidin-5-yl, CF$_3$), (M-599, H, H, F, pyrimidin-5-yl, Br), (M-600, H, H, F, pyrimidin-5-yl, CH$_3$), (M-601, H, H, F, HOOCCH$_2$CH$_2$, H), (M-602, H, H, F, HOOCCH$_2$CH$_2$, Cl), (M-603, H, H, F, HOOCCH$_2$CH$_2$, F), (M-604, H, H, F, HOOCCH$_2$CH$_2$, CF$_3$), (M-605, H, H, F, HOOCCH$_2$CH$_2$, Br), (M-606, H, H, F, HOOCCH$_2$CH$_2$, CH$_3$), (M-607, H, H, F, HOOCCH$_2$CH$_2$CH$_2$, H), (M-608, H, H, F, HOOCCH$_2$CH$_2$CH$_2$, Cl), (M-609, H, H, F, HOOCCH$_2$CH$_2$CH$_2$, F), (M-610, H, H, F, HOOCCH$_2$CH$_2$CH$_2$, CF$_3$), (M-611, H, H, F, HOOCCH$_2$CH$_2$CH$_2$, Br), (M-612, H, H, F, HOOCCH$_2$CH$_2$CH$_2$, CH$_3$), (M-613, H, H, F, (Me)$_2$NCOCH$_2$CH$_2$CH$_2$, H), (M-614, H, H, F, (Me)$_2$NCOCH$_2$CH$_2$CH$_2$, Cl), (M-615, H, H, F, (Me)$_2$NCOCH$_2$CH$_2$CH$_2$, F), (M-616, H, H, F, (Me)$_2$NCOCH$_2$CH$_2$CH$_2$, CF$_3$), (M-617, H, H, F, (Me)$_2$NCOCH$_2$CH$_2$CH$_2$, Br), (M-618, H, H, F, (Me)$_2$NCOCH$_2$CH$_2$CH$_2$, CH$_3$), (M-619, H, H, F, (Me)$_2$NCOCH$_2$CH$_2$CH$_2$CH$_2$, H), (M-620, H, H, F, (Me)$_2$NCOCH$_2$CH$_2$CH$_2$CH$_2$, Cl), (M-621, H, H, F, (Me)$_2$NCOCH$_2$CH$_2$CH$_2$CH$_2$, F), (M-622, H, H, F, (Me)$_2$NCOCH$_2$CH$_2$CH$_2$CH$_2$, CF$_3$), (M-623, H, H, F, (Me)$_2$NCOCH$_2$CH$_2$CH$_2$CH$_2$, Br), (M-624, H, H, F, (Me)$_2$NCOCH$_2$CH$_2$CH$_2$CH$_2$, CH$_3$), (M-625, H, H, F, MeOCH$_2$, H), (M-626, H, H, F, MeOCH$_2$, Cl), (M-627, H, H, F, MeOCH$_2$, F), (M-628, H, H, F, MeOCH$_2$, CF$_3$), (M-629, H, H, F, MeOCH$_2$, Br), (M-630, H, H, F, MeOCH$_2$, CH$_3$), (M-631, H, H, F, EtOCH$_2$, H), (M-632, H, H, F, EtOCH$_2$, Cl), (M-633, H, H, F, EtOCH$_2$, F), (M-634, H, H, F, EtOCH$_2$, CF$_3$), (M-635, H, H, F, EtOCH$_2$, Br), (M-636, H, H, F, EtOCH$_2$, CH$_3$), (M-637, H, H, F, EtOCH$_2$CH$_2$, H), (M-638, H, H, F, EtOCH$_2$CH$_2$, Cl), (M-639, H, H, F, EtOCH$_2$CH$_2$, F), (M-640, H, H, F, EtOCH$_2$CH$_2$, CF$_3$), (M-641, H, H, F, EtOCH$_2$CH$_2$, Br), (M-642, H, H, F, EtOCH$_2$CH$_2$, CH$_3$), (M-643, H, H, F, MeOCH$_2$CH$_2$OCH$_2$CH$_2$, H), (M-644, H, H, F, MeOCH$_2$CH$_2$OCH$_2$CH$_2$, Cl), (M-645, H, H, F, MeOCH$_2$CH$_2$OCH$_2$CH$_2$, F), (M-646, H, H, F, MeOCH$_2$CH$_2$OCH$_2$CH$_2$, CF$_3$), (M-647, H, H, F, MeOCH$_2$CH$_2$OCH$_2$CH$_2$, Br), (M-648, H, H, F, MeOCH$_2$CH$_2$OCH$_2$CH$_2$, CH$_3$), (M-649, H, H, F, MeOCH$_2$CH$_2$, H), (M-650, H, H, F, MeOCH$_2$CH$_2$, Cl), (M-651, H, H, F, MeOCH$_2$CH$_2$, F), (M-652, H, H, F, MeOCH$_2$CH$_2$, CF$_3$), (M-653, H, H, F, MeOCH$_2$CH$_2$, Br), (M-654, H, H, F, MeOCH$_2$CH$_2$, CH$_3$), (M-655, H, H, F, HOCH$_2$, H), (M-656, H, H, F, HOCH$_2$, Cl), (M-657, H, H, F, HOCH$_2$, F), (M-658, H, H, F, HOCH$_2$, CF$_3$), (M-659, H, H, F, HOCH$_2$, Br), (M-660, H, H, F, HOCH$_2$, CH$_3$), (M-661, H, H, F, HOCH$_2$CH$_2$, H), (M-662, H, H, F, HOCH$_2$CH$_2$, Cl), (M-663, H, H, F, HOCH$_2$CH$_2$, F), (M-664, H, H, F, HOCH$_2$CH$_2$, CF$_3$), (M-665, H, H, F, HOCH$_2$CH$_2$, Br), (M-666, H, H, F, HOCH$_2$CH$_2$, CH$_3$), (M-667, H, H, F, HOCH₂CH₂CH₂, H), (M-668, H, H, F, HOCH₂CH₂CH₂, Cl), (M-669, H, H, F, HOCH₂CH₂CH₂, F), (M-670, H, H, F, HOCH₂CH₂CH₂, CF₃), (M-671, H, H, F, HOCH₂CH₂CH₂, Br), (M-672, H, H, F, HOCH₂CH₂CH₂, CH₃), (M-673, H, H, F, HOCH₂CH₂CH₂CH₂, H), (M-674, H, H, F, HOCH₂CH₂CH₂CH₂, Cl), (M-675, H, H, F, HOCH₂CH₂CH₂CH₂, F), (M-676, H, H, F, HOCH₂CH₂CH₂CH₂, CF₃), (M-677, H, H, F, HOCH₂CH₂CH₂CH₂, Br), (M-678, H, H, F, HOCH₂CH₂CH₂CH₂, CH₃), (M-679, H, H, F, HOCH₂CH₂CH₂CH₂CH₂, H), (M-680, H, H, F, HOCH₂CH₂CH₂CH₂CH₂, Cl), (M-681, H, H, F, HOCH₂CH₂CH₂CH₂CH₂, F), (M-682, H, H, F, HOCH₂CH₂CH₂CH₂CH₂, CF₃), (M-683, H, H, F, HOCH₂CH₂CH₂CH₂CH₂, Br), (M-684, H, H, F, HOCH₂CH₂CH₂CH₂CH₂, CH₃), (M-685, H, H, F, HOCH₂CH₂OCH₂CH₂, H), (M-686, H, H, F, HOCH₂CH₂OCH₂CH₂, Cl), (M-687, H, H, F, HOCH₂CH₂OCH₂CH₂, F), (M-688, H, H, F, HOCH₂CH₂OCH₂CH₂, CF₃), (M-689, H, H, F, HOCH₂CH₂OCH₂CH₂, Br), (M-690, H, H, F, HOCH₂CH₂OCH₂CH₂, CH₃), (M-691, H, H, F, (Me)₂N, H), (M-692, H, H, F, (Me)₂N, Cl), (M-693, H, H, F, (Me)₂N, F), (M-694, H, H, F, (Me)₂N, CF₃), (M-695, H, H, F, (Me)₂N, Br), (M-696, H, H, F, (Me)₂N, CH₃), (M-697, H, H, F, piperidin-4-yl-methyl, H), (M-698, H, H, F, piperidin-4-yl-methyl, Cl), (M-699, H, H, F, piperidin-4-yl-methyl, F), (M-700, H, H, F, piperidin-4-yl-methyl, CF₃), (M-701, H, H, F, piperidin-4-yl-methyl, Br), (M-702, H, H, F, piperidin-4-yl-methyl, CH₃), (M-703, H, H, F, cyclohexylmethyl, H), (M-704, H, H, F, cyclohexylmethyl, Cl), (M-705, H, H, F, cyclohexylmethyl, F), (M-706, H, H, F, cyclohexylmethyl, CF₃), (M-707, H, H, F, cyclohexylmethyl, Br), (M-708, H, H, F, cyclohexylmethyl, CH₃), (M-709, H, H, Cl, H, H), (M-710, H, H, Cl, H, Cl), (M-711, H, H, Cl, H, F), (M-712, H, H, Cl, H, CF₃), (M-713, H, H, Cl, H, Br), (M-714, H, H, Cl, H, CH₃), (M-715, H, H, Cl, F, H), (M-716, H, H, Cl, F, Cl), (M-717, H, H, Cl, F, F), (M-718, H, H, Cl, F, CF₃), (M-719, H, H, Cl, F, Br), (M-720, H, H, Cl, F, CH₃), (M-721, H, H, Cl, Cl, H), (M-722, H, H, Cl, Cl, Cl), (M-723, H, H, Cl, Cl, F), (M-724, H, H, Cl, Cl, CF₃), (M-725, H, H, Cl, Cl, Br), (M-726, H, H, Cl, Cl, CH₃), (M-727, H, H, Cl, CH₃, H), (M-728, H, H, Cl, CH₃, Cl), (M-729, H, H, Cl, CH₃, F), (M-730, H, H, Cl, CH₃, CF₃), (M-731, H, H, Cl, CH₃, Br), (M-732, H, H, Cl, CH₃, CH₃), (M-733, H, H, Cl, Et, H), (M-734, H, H, Cl, Et, Cl), (M-735, H, H, Cl, Et, F), (M-736, H, H, Cl, Et, CF₃), (M-737, H, H, Cl, Et, Br), (M-738, H, H, Cl, Et, CH₃), (M-739, H, H, Cl, n-Pr, H), (M-740, H, H, Cl, n-Pr, Cl), (M-741, H, H, Cl, n-Pr, F), (M-742, H, H, Cl, n-Pr, CF₃), (M-743, H, H, Cl, n-Pr, Br), (M-744, H, H, Cl, n-Pr, CH₃), (M-745, H, H, Cl, c-Pr, H), (M-746, H, H, Cl, c-Pr, Cl), (M-747, H, H, Cl, c-Pr, F), (M-748, H, H, Cl, c-Pr, CF₃), (M-749, H, H, Cl, c-Pr, Br), (M-750, H, H, Cl, c-Pr, CH₃), (M-751, H, H, Cl, i-Pr, H), (M-752, H, H, Cl, i-Pr, Cl), (M-753, H, H, Cl, i-Pr, F), (M-754, H, H, Cl, i-Pr, CF₃), (M-755, H, H, Cl, i-Pr, Br), (M-756, H, H, Cl, i-Pr, CH₃), (M-757, H, H, Cl, n-Bu, H), (M-758, H, H, Cl, n-Bu, Cl), (M-759, H, H, Cl, n-Bu, F), (M-760, H, H, Cl, n-Bu, CF₃), (M-761, H, H, Cl, n-Bu, Br), (M-762, H, H, Cl, n-Bu, CH₃), (M-763, H, H, Cl, i-Bu, H), (M-764, H, H, Cl, i-Bu, Cl), (M-765, H, H, Cl, i-Bu, F), (M-766, H, H, Cl, i-Bu, CF₃), (M-767, H, H, Cl, i-Bu, Br), (M-768, H, H, Cl, i-Bu, CH₃), (M-769, H, H, Cl, sec-Bu, H), (M-770, H, H, Cl, sec-Bu, Cl), (M-771, H, H, Cl, sec-Bu, F), (M-772, H, H, Cl, sec-Bu, CF₃), (M-773, H, H, Cl, sec-Bu, Br), (M-774, H, H, Cl, sec-Bu, CH₃), (M-775, H, H, Cl, n-Pen, H), (M-776, H, H, Cl, n-Pen, Cl), (M-777, H, H, Cl, n-Pen, F), (M-778, H, H, Cl, n-Pen, CF₃), (M-779, H, H, Cl, n-Pen, Br), (M-780, H, H, Cl, n-Pen, CH₃), (M-781, H, H, Cl, c-Pen, H), (M-782, H, H, Cl, c-Pen, Cl), (M-783, H, H, Cl, c-Pen, F), (M-784, H, H, Cl, c-Pen, CF₃), (M-785, H, H, Cl, c-Pen, Br), (M-786, H, H, Cl, c-Pen, CH₃), (M-787, H, H, Cl, n-Hex, H), (M-788, H, H, Cl, n-Hex, Cl), (M-789, H, H, Cl, n-Hex, F), (M-790, H, H, Cl, n-Hex, CF₃), (M-791, H, H, Cl, n-Hex, Br), (M-792, H, H, Cl, n-Hex, CH₃), (M-793, H, H, Cl, c-Hex, H), (M-794, H, H, Cl, c-Hex, Cl), (M-795, H, H, Cl, c-Hex, F), (M-796, H, H, Cl, c-Hex, CF₃), (M-797, H, H, Cl, c-Hex, Br), (M-798, H, H, Cl, c-Hex, CH₃), (M-799, H, H, Cl, OH, H), (M-800, H, H, Cl, OH, Cl), (M-801, H, H, Cl, OH, F), (M-802, H, H, Cl, OH, CF₃), (M-803, H, H, Cl, OH, Br), (M-804, H, H, Cl, OH, CH₃), (M-805, H, H, Cl, EtO, H), (M-806, H, H, Cl, EtO, Cl), (M-807, H, H, Cl, EtO, F), (M-808, H, H, Cl, EtO, CF₃), (M-809, H, H, Cl, EtO, Br), (M-810, H, H, Cl, EtO, CH₃), (M-811, H, H, Cl, n-PrO, H), (M-812, H, H, Cl, n-PrO, Cl), (M-813, H, H, Cl, n-PrO, F), (M-814, H, H, Cl, n-PrO, CF₃), (M-815, H, H, Cl, n-PrO, Br), (M-816, H, H, Cl, n-PrO, CH₃), (M-817, H, H, Cl, PhO, H), (M-818, H, H, Cl, PhO, Cl), (M-819, H, H, Cl, PhO, F), (M-820, H, H, Cl, PhO, CF₃), (M-821, H, H, Cl, PhO, Br), (M-822, H, H, Cl, PhO, CH₃), (M-823, H, H, Cl, BnO, H), (M-824, H, H, Cl, BnO, Cl), (M-825, H, H, Cl, BnO, F), (M-826, H, H, Cl, BnO, CF₃), (M-827, H, H, Cl, BnO, Br), (M-828, H, H, Cl, BnO, CH₃), (M-829, H, H, Cl PhCH₂CH₂O, H), (M-830, H, H, Cl, PhCH₂CH₂O, Cl), (M-831, H, H, Cl, PhCH₂CH₂O, F), (M-832, H, H, Cl, PhCH₂CH₂O, CF₃), (M-833, H, H, Cl, PhCH₂CH₂O, Br), (M-834, H, H, Cl, PhCH₂CH₂O, CH₃), (M-835, H, H, Cl, CF₃O, H), (M-836, H, H, Cl, CF₃O, Cl), (M-837, H, H, Cl, CF₃O, F), (M-838, H, H, Cl, CF₃O, CF₃), (M-839, H, H, Cl, CF₃O, Br), (M-840, H, H, Cl, CF₃O, CH₃), (M-841, H, H, Cl, Ph, H), (M-842, H, H, Cl, Ph, Cl), (M-843, H, H, Cl, Ph, F), (M-844, H, H, Cl, Ph, CF₃), (M-845, H, H, Cl, Ph, Br), (M-846, H, H, Cl, Ph, CH₃), (M-847, H, H, Cl, 4-F-Ph, H), (M-848, H, H, Cl, 4-F-Ph, Cl), (M-849, H, H, Cl, 4-F-Ph, F), (M-850, H, H, Cl, 4-F-Ph, CF₃), (M-851, H, H, Cl, 4-F-Ph, Br), (M-852, H, H, Cl, 4-F-Ph, CH₃), (M-853, H, H, Cl, 4-CF₃-Ph, H), (M-854, H, H, Cl, 4-CF₃-Ph, Cl), (M-855, H, H, Cl, 4-CF₃-Ph, F), (M-856, H, H, Cl, 4-CF₃-Ph, CF₃), (M-857, H, H, Cl, 4-CF₃-Ph, Br), (M-858, H, H, Cl, 4-CF₃-Ph, CH₃), (M-859, H, H, Cl, 4-(Me)₂N-Ph, H), (M-860, H, H, Cl, 4-(Me)₂N-Ph, Cl), (M-861, H, H, Cl, 4-(Me)₂N-Ph, F), (M-862, H, H, Cl, 4-(Me)₂N-Ph, CF₃), (M-863, H, H, Cl, 4-(Me)₂N-Ph, Br), (M-864, H, H, Cl, 4-(Me)₂N-Ph, CH₃), (M-865, H, H, Cl, 4-OH-Ph, H), (M-866, H, H, Cl, 4-OH-Ph, Cl), (M-867, H, H, Cl, 4-OH-Ph, F), (M-868, H, H, Cl, 4-OH-Ph, CF₃), (M-869, H, H, Cl, 4-OH-Ph, Br), (M-870, H, H, Cl, 4-OH-Ph, CH₃), (M-871, H, H, Cl, 3,4-di-F-Ph, H), (M-872, H, H, Cl, 3,4-di-F-Ph, Cl), (M-873, H, H, Cl, 3,4-di-F-Ph, F), (M-874, H, H, Cl, 3,4-di-F-Ph, CF₃), (M-875, H, H, Cl, 3,4-di-F-Ph, Br), (M-876, H, H, Cl, 3,4-di-F-Ph, CH₃), (M-877, H, H, Cl, 4-COOH-Ph, H), (M-878, H, H, Cl, 4-COOH-Ph, Cl), (M-879, H, H, Cl, 4-COOH-Ph, F), (M-880, H, H, Cl, 4-COOH-Ph, CF₃), (M-881, H, H, Cl, 4-COOH-Ph, Br), (M-882, H, H, Cl, 4-COOH-Ph, CH₃), (M-883, H, H, Cl, Bn, H), (M-884, H, H, Cl, Bn, Cl), (M-885, H, H, Cl, Bn, F), (M-886, H, H, Cl, Bn, CF₃), (M-887, H, H, Cl, Bn, Br), (M-888, H, H, Cl, Bn, CH₃), (M889, H, H, Cl, 4-F-Bn, H), (M-890, H, H, Cl, 4-F-Bn, Cl), (M-891, H, H, Cl, 4-F-Bn, F), (M-892, H, H, Cl, 4-F-Bn, CF₃), (M-893, H, H, Cl, 4-F-Bn, Br), (M-894, H, H, Cl, 4-F-Bn, CH₃), (M-895, H, H, Cl, 2-Py, H), (M-896, H, H, Cl, 2-Py, Cl), (M-897, H, H, Cl, 2-Py, F), (M-898, H, H, Cl, 2-Py, CF₃), (M-899, H, H, Cl, 2-Py, Br), (M-900, H, H, Cl, 2-Py, CH₃), (M-901, H, H, Cl, 3-Py, H), (M-902, H, H, Cl, 3-Py, Cl), (M-903, H, H, Cl, 3-Py, F), (M-904, H, H, Cl, 3-Py, CF₃), (M-905, H, H, Cl, 3-Py, Br), (M-906, H, H, Cl, 3-Py, CH₃), (M-907, H, H, Cl, 4-Py, H), (M-908, H, H, Cl, 4-Py, Cl), (M-909, H, H, Cl, 4-Py, F), (M-910, H, H, Cl, 4-Py, CF₃), (M-911, H, H, Cl, 4-Py, Br), (M-912, H, H, Cl, 4-Py, CH₃), (M-913, H, H, Cl, 2-Th, H), (M-914, H, H, Cl, 2-Th, Cl), (M-915, H, H, Cl, 2-Th, F), (M-916, H, H, Cl, 2-Th, CF₃), (M-917, H, H, Cl, 2-Th, Br), (M-918, H, H, Cl, 2-Th, CH₃), (M-919, H, H, Cl, 3-Th, H), (M-920, H, H, Cl, 3-Th, Cl), (M-921, H, H, Cl, 3-Th, F), (M-922, H, H, Cl, 3-Th, CF₃), (M-923, H, H, Cl, 3-Th, Br), (M-924, H, H, Cl, 3-Th, CH₃), (M-925, H, H, Cl, pyrrazol-2-yl, H), (M-926, H, H, Cl, pyrrazol-2-yl, Cl), (M-927, H, H, Cl, pyrrazol-2-yl, F), (M-928, H, H, Cl, pyrrazol-2-yl, CF₃), (M-929, H, H, Cl, pyrrazol-2-yl, Br), (M-930, H, H, Cl, pyrrazol-2-yl, CH₃), (M-931, H, H, Cl, pyrrazol-3-yl, H), (M-932, H, H, Cl, pyrrazol-3-yl, Cl), (M-933, H, H, Cl, pyrrazol-3-yl, F), (M-934, H, H, Cl, pyrrazol-3-yl, CF₃), (M-935, H, H, Cl, pyrrazol-3-yl, Br), (M-936, H, H, Cl, pyrrazol-3-yl, CH₃), (M-937, H, H, Cl, pyrimidin-2-yl, H), (M-938, H, H, Cl, pyrimidin-2-yl, Cl), (M-939, H, H, Cl, pyrimidin-2-yl, F), (M-940, H, H, Cl, pyrimidin-2-yl, CF₃), (M-941, H, H, Cl, pyrimidin-2-yl, Br), (M-942, H, H, Cl, pyrimidin-2-yl, CH₃), (M-943, H, H, Cl, pyrimidin-4-yl, H), (M-944, H, H, Cl, pyrimidin-4-yl, Cl), (M-945, H, H, Cl, pyrimidin-4-yl, F), (M-946, H, H, Cl, pyrimidin-4-yl, CF₃), (M-947, H, H, Cl, pyrimidin-4-yl, Br), (M-948, H, H, Cl, pyrimidin-4-yl, CH₃), (M-949, H, H, Cl, pyrimidin-5-yl, H), (M-950, H, H, Cl, pyrimidin-5-yl, Cl), (M-951, H, H, Cl, pyrimidin-5-yl, F), (M-952, H, H, Cl, pyrimidin-5-yl, CF₃), (M-953, H, H, Cl, pyrimidin-5-yl, Br), (M-954, H, H, Cl, pyrimidin-5-yl, CH₃), (M-955, H, H, Cl, HOOCCH₂CH₂CH₂, H), (M-956, H, H, Cl, HOOCCH₂CH₂CH₂, Cl), (M-957, H, H, Cl, HOOCCH₂CH₂CH₂, F), (M-958, H, H, Cl, HOOCCH₂CH₂CH₂, CF₃), (M-959, H, H, Cl, HOOCCH₂CH₂CH₂, Br), (M-960, H, H, Cl, HOOCCH₂CH₂CH₂, CH₃), (M-961, H, H, Cl, HOOCCH₂CH₂CH₂CH₂, H), (M-962, H, H, Cl, HOOCCH₂CH₂CH₂CH₂, Cl), (M-963, H, H, Cl, HOOCCH₂CH₂CH₂CH₂, F), (M-964, H, H, Cl, HOOCCH₂CH₂CH₂CH₂, CF₃), (M-965, H, H, Cl, HOOCCH₂CH₂CH₂CH₂, Br), (M-966, H, H, Cl, HOOCCH₂CH₂CH₂CH₂, CH₃), (M-967, H, H, Cl, (Me)₂NCOCH₂CH₂CH₂CH₂, H), (M-968, H, H, Cl, (Me)₂NCOCH₂CH₂CH₂CH₂, Cl), (M-969, H, H, Cl, (Me)₂NCOCH₂CH₂CH₂CH₂, F), (M-970, H, H, Cl, (Me)₂NCOCH₂CH₂CH₂CH₂, CF₃), (M-971, H, H, Cl, (Me)₂NCOCH₂CH₂CH₂CH₂, Br), (M-972, H, H, Cl, (Me)₂NCOCH₂CH₂CH₂CH₂, CH₃), (M-973, H, H, Cl, (Me)₂NCOCH₂CH₂CH₂CH₂CH₂, H), (M-974, H, H, Cl, (Me)₂NCOCH₂CH₂CH₂CH₂CH₂, Cl), (M-975, H, H, Cl, (Me)₂NCOCH₂CH₂CH₂CH₂CH₂, F), (M-976, H, H, Cl, (Me)₂NCOCH₂CH₂CH₂CH₂CH₂, CF₃), (M-977, H, H, Cl, (Me)₂NCOCH₂CH₂CH₂CH₂CH₂, Br), (M-978, H, H, Cl, (Me)₂NCOCH₂CH₂CH₂CH₂CH₂, CH₃), (M-979, H, H, Cl, MeOCH₂, H), (M-980, H, H, Cl, MeOCH₂, Cl), (M-981, H, H, Cl, MeOCH₂, F), (M-982, H, H, Cl, MeOCH₂, CF₃), (M-983, H, H, Cl, MeOCH₂, Br), (M-984, H, H, Cl, MeOCH₂, CH₃), (M-985, H, H, Cl, EtOCH₂, H), (M-986, H, H, Cl, EtOCH₂, Cl), (M-987, H, H, Cl, EtOCH₂, F), (M-988, H, H, Cl, EtOCH₂, CF₃), (M-989, H, H, Cl, EtOCH₂, Br), (M-990, H, H, Cl, EtOCH₂, CH₃), (M-991, H, H, Cl, EtOCH₂CH₂, H), (M-992, H, H, Cl, EtOCH₂CH₂, Cl), (M-993, H, H, Cl, EtOCH₂CH₂, F), (M-994, H, H, Cl, EtOCH₂CH₂, CF₃), (M-995, H, H, Cl, EtOCH₂CH₂, Br), (M-996, H, H, Cl, EtOCH₂CH₂, CH₃), (M-997, H, H, Cl, MeOCH₂CH₂OCH₂CH₂, H), (M-998, H, H, Cl, MeOCH₂CH₂OCH₂CH₂, Cl), (M-999, H, H, Cl, MeOCH₂CH₂OCH₂CH₂, F), (M-1000, H, H, Cl, MeOCH₂CH₂OCH₂CH₂, CF₃), (M-1001, H, H, Cl, MeOCH₂CH₂OCH₂CH₂, Br), (M-1002, H, H, Cl, MeOCH₂CH₂OCH₂CH₂, CH₃), (M-1003, H, H, Cl, MeOCH₂CH₂, H), (M-1004, H, H, Cl, MeOCH₂CH₂, Cl), (M-1005, H, H, Cl, MeOCH₂CH₂, F), (M-1006, H, H, Cl, MeOCH₂CH₂, CF₃), (M-1007, H, H, Cl, MeOCH₂CH₂, Br), (M-1008, H, H, Cl, MeOCH₂Cl₂, CH₃), (M-1009, H, H, Cl, HOCH₂, H), (M-1010, H, H, Cl, HOCH₂, Cl), (M-1011, H, H, Cl, HOCH₂, F), (M-1012, H, H, Cl, HOCH₂, CF₃), (M-1013, H, H, Cl, HOCH₂, Br), (M-1014, H, H, Cl, HOCH₂, CH₃), (M-1015, H, H, Cl, HOCH₂CH₂, H), (M-1016, H, H, Cl, HOCH₂CH₂, Cl), (M-1017, H, H, Cl, HOCH₂CH₂, F), (M-1018, H, H, Cl, HOCH₂CH₂, CF₃), (M-1019, H, H, Cl, HOCH₂CH₂, Br), (M-1020, H, H, Cl, HOCH₂CH₂, CH₃), (M-1021, H, H, Cl, HOCH₂CH₂CH₂, H), (M-1022, H, H, Cl, HOCH₂CH₂CH₂, Cl), (M-1023, H, H, Cl, HOCH₂CH₂CH₂, F), (M-1024, H, H, Cl, HOCH₂CH₂CH₂, CF₃), (M-1025, H, H, Cl, HOCH₂CH₂CH₂, Br), (M-1026, H, H, Cl, HOCH₂CH₂CH₂, CH₃), (M-1027, H, H, Cl, HOCH₂CH₂CH₂CH₂, H), (M-1028, H, H, Cl, HOCH₂CH₂CH₂CH₂, Cl), (M-1029, H, H, Cl, HOCH₂CH₂CH₂CH₂, F), (M-1030, H, H, Cl, HOCH₂CH₂CH₂CH₂, CF₃), (M-1031, H, H, Cl, HOCH₂CH₂CH₂CH₂, Br), (M-1032, H, H, Cl, HOCH₂CH₂CH₂CH₂, CH₃), (M-1033, H, H, Cl, HOCH₂CH₂CH₂CH₂CH₂, H), (M-1034, H, H, Cl, HOCH₂CH₂CH₂CH₂CH₂, Cl), (M-1035, H, H, Cl, HOCH₂CH₂CH₂CH₂CH₂, F), (M-1036, H, H, Cl, HOCH₂CH₂CH₂CH₂CH₂, CF₃), (M-1037, H, H, Cl, HOCH₂CH₂CH₂CH₂CH₂, Br), (M-1038, H, H, Cl, HOCH₂CH₂CH₂CH₂CH₂, CH₃), (M-1039, H, H, Cl, HOCH₂CH₂OCH₂CH₂, H), (M-1040, H, H, Cl, HOCH₂CH₂OCH₂CH₂, Cl), (M-1041, H, H, Cl, HOCH₂CH₂OCH₂CH₂, F), (M-1042, H, H, Cl, HOCH₂CH₂OCH₂CH₂, CF₃), (M-1043, H, H, Cl, HOCH₂CH₂OCH₂CH₂, Br), (M-1044, H, H, Cl, HOCH₂CH₂OCH₂CH₂, CH₃), (M-1045, H, H, Cl, (Me)₂N, H), (M-1046, H, H, Cl, (Me)₂N, Cl), (M-1047, H, H, Cl, (Me)₂N, F), (M-1048, H, H, Cl, (Me)₂N, CF₃), (M-1049, H, H, Cl, (Me)₂N, Br), (M-1050, H, H, Cl, (Me)₂N, CH₃), (M-1051, H, H, Cl, piperidin-4-yl-methyl, H), (M-1052, H, H, Cl, piperidin-4-yl-methyl, Cl), (M-1053, H, H, Cl, piperidin-4-yl-methyl, F), (M-1054, H, H, Cl, piperidin-4-yl-methyl, CF₃), (M-1055, H, H, Cl, piperidin-4-yl-methyl, Br), (M-1056, H, H, Cl, piperidin-4-yl-methyl, CH₃), (M-1057, H, H, Cl, cyclohexylmethyl, H), (M-1058, H, H, Cl, cyclohexylmethyl, Cl), (M-1059, H, H, Cl, cyclohexylmethyl, F), (M-1060, H, H, Cl, cyclohexylmethyl, CF₃), (M-1061, H, H, Cl, cyclohexylmethyl, Br), (M-1062, H, H, Cl, cyclohexylmethyl, CH₃), (M-1063, H, F, H, H, H), (M-1064, H, F, H, H, Cl), (M-1065, H, F, H, H, F), (M-1066, H, F, H, H, CF₃), (M-1067, H, F, H, H, Br), (M-1068, H, F, H, H, CH₃), (M-1069, H, F, H, F, H), (M-1070, H, F, H, F, Cl), (M-1071, H, F, H, F, F), (M-1072, H, F, H, F, CF₃), (M-1073, H, F, H, F, Br), (M-1074, H, F, H, F, CH₃), (M-1075, H, F, H, Cl, H), (M-1076, H, F, H, Cl, Cl), (M-1077, H, F, H, Cl, F), (M-1078, H, F, H, Cl, CF₃), (M-1079, H, F, H, Cl, Br), (M-1080, H, F, H, Cl, CH₃), (M-1081, H, F, H, CH₃, H), (M-1082, H, F, H, CH₃, Cl), (M-1083, H, F, H, CH₃, F), (M-1084, H, F, H, CH₃, CF₃), (M-1085, H, F, H, CH₃, Br), (M-1086, H, F, H, CH₃, CH₃), (M-1087, H, F, H, Et, H), (M-1088, H, F, H, Et, Cl), (M-1089, H, F, H, Et, F), (M-1090, H, F, H, Et, CF₃), (M-1091, H, F, H, Et, Br), (M-1092, H, F, H, Et, CH₃), (M-1093, H, F, H, n-Pr, H), (M-1094, H, F, H, n-Pr, Cl), (M-1095, H, F, H, n-Pr, F), (M-1096, H, F, H, n-Pr, CF₃), (M-1097, H, F, H, n-Pr, Br), (M-1098, H, F, H, n-Pr, CH₃), (M-1099, H, F, H, c-Pr, H), (M-1100, H, F, H, c-Pr, Cl), (M-1101, H, F, H, c-Pr, F), (M-1102, H, F, H, c-Pr, CF₃), (M-1103, H, F, H, c-Pr, Br), (M-1104, H, F, H, c-Pr, CH₃), (M-1105, H, F, H, i-Pr, H), (M-1106, H, F, H, i-Pr, Cl), (M-1107, H, F, H, i-Pr, F), (M-1108, H, F, H, i-Pr, CF₃), (M-1109, H, F, H, i-Pr, Br), (M-1110, H, F, H, i-Pr, CH₃), (M-1111, H, F, H, n-Bu, H), (M-1112, H, F, H, n-Bu, Cl), (M-1113, H, F, H, n-Bu, F), (M-1114, H, F, H, n-Bu, CF₃), (M-1115, H, F, H, n-Bu, Br), (M-1116, H, F, H, n-Bu, CH₃), (M-1117, H, F, H, i-Bu, H), (M-1118, H, F, H, i-Bu, Cl), (M-1119, H, F, H, i-Bu, F), (M-1120, H, F, H, i-Bu, CF₃), (M-1121, H, F, H, i-Bu, Br), (M-1122, H, F, H, i-Bu, CH₃), (M-1123, H, F, H, sec-Bu, H), (M-1124, H, F, H, sec-Bu, Cl), (M-1125, H, F, H, sec-Bu, F), (M-1126, H, F, H, sec-Bu, CF₃), (M-1127, H, F, H, sec-Bu, Br), (M-1128, H, F, H, sec-Bu, CH₃), (M-1129, H, F, H, n-Pen, H), (M-1130, H, F, H, n-Pen, Cl), (M-1131, H, F, H, n-Pen, F), (M-1132, H, F, H, n-Pen, CF₃), (M-1133, H, F, H, n-Pen, Br), (M-1134, H, F, H, n-Pen, CH₃), (M-1135, H, F, H, c-Pen, H), (M-1136, H, F, H, c-Pen, Cl), (M-1137, H, F, H, c-Pen, F), (M-1138, H, F, H, c-Pen, CF₃), (M-1139, H, F, H, c-Pen, Br), (M-1140, H, F, H, c-Pen, CH₃), (M-1141, H, F, H, n-Hex, H), (M-1142, H, F, H, n-Hex, Cl), (M-1143, H, F, H, n-Hex, F), (M-1144, H, F, H, n-Hex, CF₃), (M-1145, H, F, H, n-Hex, Br), (M-1146, H, F, H, n-Hex, CH₃), (M-1147, H, F, H, c-Hex, H), (M-1148, H, F, H, c-Hex, Cl), (M-1149, H, F, H, c-Hex, F), (M-1150, H, F, H, c-Hex, CF₃), (M-1151, H, F, H, c-Hex, Br), (M-1152, H, F, H, c-Hex, CH₃), (M-1153, H, F, H, OH, H), (M-1154, H, F, H, OH, Cl), (M-1155, H, F, H, OH, F), (M-1156, H, F, H, OH, CF₃), (M-1157, H, F, H, OH, Br), (M-1158, H, F, H, OH, CH₃), (M-1159, H, F, H, EtO, H), (M-1160, H, F, H, EtO, Cl), (M-1161, H, F, H, EtO, F), (M-1162, H, F, H, EtO, CF₃), (M-1163, H, F, H, EtO, Br), (M-1164, H, F, H, EtO, CH₃), (M-1165, H, F, H, n-PrO, H), (M-1166, H, F, H, n-PrO, Cl), (M-1167, H, F, H, n-PrO, F), (M-1168, H, F, H, n-PrO, CF₃), (M-1169, H, F, H, n-PrO, Br), (M-1170, H, F, H, n-PrO, CH₃), (M-1171, H, F, H, PhO, H), (M-1172, H, F, H, PhO, Cl), (M-1173, H, F, H, PhO, F), (M-1174, H, F, H, PhO, CF₃), (M-1175, H, F, H, PhO, Br), (M-1176, H, F, H, PhO, CH₃), (M-1177, H, F, H, BnO, H), (M-1178, H, F, H, BnO, Cl), (M-1179, H, F, H, BnO, F), (M-1180, H, F, H, BnO, CF₃), (M-1181, H, F, H, BnO, Br), (M-1182, H, F, H, BnO, CH₃), (M-1183, H, F, H, PhCH₂CH₂O, H), (M-1184, H, F, H, PhCH₂CH₂O, Cl), (M-1185, H, F, H, PhCH₂CH₂O, F), (M-1186, H, F, H, PhCH₂CH₂O, CF₃), (M-1187, H, F, H, PhCH₂CH₂O, Br), (M-1188, H, F, H, PhCH₂CH₂O, CH₃), (M-1189, H, F, H, CF₃O, H), (M-1190, H, F, H, CF₃O, Cl), (M-1191, H, F, H, CF₃O, F), (M-1192, H, F, H, CF₃O, CF₃), (M-1193, H, F, H, CF₃O, Br), (M-1194, H, F, H, CF₃O, CH₃), (M-1195, H, F, H, Ph, H), (M-1196, H, F, H, Ph, Cl), (M-1197, H, F, H, Ph, F), (M-1198, H, F, H, Ph, CF₃), (M-1199, H, F, H, Ph, Br), (M-1200, H, F, H, Ph, CH₃), (M-1201, H, F, H, 4-F-Ph, H), (M-1202, H, F, H, 4-F-Ph, Cl), (M-1203, H, F, H, 4-F-Ph, F), (M-1204, H, F, H, 4-F-Ph, CF₃), (M-1205, H, F, H, 4-F-Ph, Br), (M-1206, H, F, H, 4-F-Ph, CH₃), (M-1207, H, F, H, 4-CF₃-Ph, H), (M-1208, H, F, H, 4-CF₃-Ph, Cl), (M-1209, H, F, H, 4-CF₃-Ph, F), (M-1210, H, F, H, 4-CF₃-Ph, CF₃), (M-1211, H, F, H, 4-CF₃-Ph, Br), (M-1212, H, F, H, 4-CF₃-Ph, CH₃), (M-1213, H, F, H, 4-(Me)₂N-Ph, H), (M-1214, H, F, H, 4-(Me)₂N-Ph, Cl), (M-1215, H, F, H, 4-(Me)₂N-Ph, F), (M-1216, H, F, H, 4-(Me)₂N-Ph, CF₃), (M-1217, H, F, H, 4-(Me)₂N-Ph, Br), (M-1218, H, F, H, 4-(Me)₂N-Ph, CH₃), (M-1219, H, F, H, 4-OH-Ph, H), (M-1220, H, F, H, 4-OH-Ph, Cl), (M-1221, H, F, H, 4-OH-Ph, F), (M-1222, H, F, H, 4-OH-Ph, CF₃), (M-1223, H, F, H, 4-OH-Ph, Br), (M-1224, H, F, H, 4-OH-Ph, CH₃), (M-1225, H, F, H, 3,4-di-F-Ph, H), (M-1226, H, F, H, 3,4-di-F-Ph, Cl), (M-1227, H, F, H, 3,4-di-F-Ph, F), (M-1228, H, F, H, 3,4-di-F-Ph, CF₃), (M-1229, H, F, H, 3,4-di-F-Ph, Br), (M-1230, H, F, H, 3,4-di-F-Ph, CH₃), (M-1231, H, F, H, 4-COOH-Ph, H), (M-1232, H, F, H, 4-COOH-Ph, Cl), (M-1233, H, F, H, 4-COOH-Ph, F), (M-1234, H, F, H, 4-COOH-Ph, CF₃), (M-1235, H, F, H, 4-COOH-Ph, Br), (M-1236, H, F, H, 4-COOH-Ph, CH₃), (M-1237, H, F, H, Bn, H), (M-1238, H, F, H, Bn, Cl), (M-1239, H, F, H, Bn, F), (M-1240, H, F, H, Bn, CF₃), (M-1241, H, F, H, Bn, Br), (M-1242, H, F, H, Bn, CH₃), (M-1243, H, F, H, 4-F-Bn, H), (M-1244, H, F, H, 4-F-Bn, Cl), (M-1245, H, F, H, 4-F-Bn, F), (M-1246, H, F, H, 4-F-Bn, CF₃), (M-1247, H, F, H, 4-F-Bn, Br), (M-1248, H, F, H, 4-F-Bn, CH₃), (M-1249, H, F, H, 2-Py, H), (M-1250, H, F, H, 2-Py, Cl), (M-1251, H, F, H, 2-Py, F), (M-1252, H, F, H, 2-Py, CF₃), (M-1253, H, F, H, 2-Py, Br), (M-1254, H, F, H, 2-Py, CH₃), (M-1255, H, F, H, 3-Py, H), (M-1256, H, F, H, 3-Py, Cl), (M-1257, H, F, H, 3-Py, F), (M-1258, H, F, H, 3-Py, CF₃), (M-1259, H, F, H, 3-Py, Br), (M-1260, H, F, H, 3-Py, CH₃), (M-1261, H, F, H, 4-Py, H), (M-1262, H, F, H, 4-Py, Cl), (M-1263, H, F, H, 4-Py, F), (M-1264, H, F, H, 4-Py, CF₃), (M-1265, H, F, H, 4-Py, Br), (M-1266, H, F, H, 4-Py, CH₃), (M-1267, H, F, H, 2-Th, H), (M-1268, H, F, H, 2-Th, Cl), (M-1269, H, F, H, 2-Th, F), (M-1270, H, F, H, 2-Th, CF₃), (M-1271, H, F, H, 2-Th, Br), (M-1272, H, F, H, 2-Th, CH₃), (M-1273, H, F, H, 3-Th, H), (M-1274, H, F, H, 3-Th, Cl), (M-1275, H, F, H, 3-Th, F), (M-1276, H, F, H, 3-Th, CF₃), (M-1277, H, F, H, 3-Th, Br), (M-1278, H, F, H, 3-Th, CH₃), (M-1279, H, F, H, pyrrazol-2-yl, H), (M-1280, H, F, H, pyrrazol-2-yl, Cl), (M-1281, H, F, H, pyrrazol-2-yl, F), (M-1282, H, F, H, pyrrazol-2-yl, CF₃), (M-1283, H, F, H, pyrrazol-2-yl, Br), (M-1284, H, F, H, pyrrazol-2-yl, CH₃), (M-1285, H, F, H, pyrrazol-3-yl, H), (M-1286, H, F, H, pyrrazol-3-yl, Cl), (M-1287, H, F, H, pyrrazol-3-yl, F), (M-1288, H, F, H, pyrrazol-3-yl, CF₃), (M-1289, H, F, H, pyrrazol-3-yl, Br), (M-1290, H, F, H, pyrrazol-3-yl, CH₃), (M-1291, H, F, H, pyrimidin-2-yl, H), (M-1292, H, F, H, pyrimidin-2-yl, Cl), (M-1293, H, F, H, pyrimidin-2-yl, F), (M-1294, H, F, H, pyrimidin-2-yl, CF₃), (M-1295, H, F, H, pyrimidin-2-yl, Br), (M-1296, H, F, H, pyrimidin-2-yl, CH₃), (M-1297, H, F, H, pyrimidin-4-yl, H), (M-1298, H, F, H, pyrimidin-4-yl, Cl), (M-1299, H, F, H, pyrimidin-4-yl, F), (M-1300, H, F, H, pyrimidin-4-yl, CF₃), (M-1301, H, F, H, pyrimidin-4-yl, Br), (M-1302, H, F, H, pyrimidin-4-yl, CH₃), (M-1303, H, F, H, pyrimidin-5-yl, H), (M-1304, H, F, H, pyrimidin-5-yl, Cl), (M-1305, H, F, H, pyrimidin-5-yl, F), (M-1306, H, F, H, pyrimidin-5-yl, CF₃), (M-1307, H, F, H, pyrimidin-5-yl, Br), (M-1308, H, F, H, pyrimidin-5-yl, CH₃), (M-1309, H, F, H, HOOCCH₂CH₂, H), (M-1310, H, F, H, HOOCCH₂CH₂, Cl), (M-1311, H, F, H, HOOCCH₂CH₂, F), (M-1312, H, F, H, HOOCCH₂CH₂, CF₃), (M-1313, H, F, H, HOOCCH₂CH₂, Br), (M-1314, H, F, H, HOOCCH₂CH₂, CH₃), (M-1315, H, F, H, HOOCCH₂CH₂CH₂, H), (M-1316, H, F, H, HOOCCH₂CH₂CH₂, Cl), (M-1317, H, F, H, HOOCCH₂CH₂CH₂, F), (M-1318, H, F, H, HOOCCH₂CH₂CH₂, CF₃), (M-1319, H, F, H, HOOCCH₂CH₂CH₂, Br), (M-1320, H, F, H, HOOCCH₂CH₂CH₂, CH₃), (M-1321, H, F, H, (Me)₂NCOCH₂CH₂CH₂, H), (M-1322, H, F, H, (Me)₂NCOCH₂CH₂CH₂, Cl), (M-1323, H, F, H, (Me)₂NCOCH₂CH₂CH₂, F), (M-1324, H, F, H, (Me)₂NCOCH₂CH₂CH₂, CF₃), (M-1325, H, F, H, (Me)₂NCOCH₂CH₂CH₂, Br), (M-1326, H, F, H, (Me)₂NCOCH₂CH₂CH₂, CH₃), (M-1327, H, F, H, (Me)₂NCOCH₂CH₂CH₂CH₂, H), (M-1328, H, F, H, (Me)₂NCOCH₂CH₂CH₂CH₂, Cl), (M-1329, H, F, H, (Me)₂NCOCH₂CH₂CH₂CH₂, F), (M-1330, H, F, H, (Me)₂

NCOCH₂CH₂CH₂CH₂CH₂, CF₃), (M-1331, H, F, H, (Me)₂NCOCH₂CH₂CH₂CH₂CH₂, Br), (M-1332, H, F, H, (Me)₂NCOCH₂CH₂CH₂CH₂CH₂, CH₃), (M-1333, H, F, H, MeOCH₂, H), (M-1334, H, F, H, MeOCH₂, Cl), (M-1335, H, F, H, MeOCH₂, F), (M-1336, H, F, H, MeOCH₂, CF₃), (M-1337, H, F, H, MeOCH₂, Br), (M-1338, H, F, H, MeOCH₂, CH₃), (M-1339, H, F, H, EtOCH₂, H), (M-1340, H, F, H, EtOCH₂, Cl), (M-1341, H, F, H, EtOCH₂, F), (M-1342, H, F, H, EtOCH₂, CF₃), (M-1343, H, F, H, EtOCH₂, Br), (M-1344, H, F, H, EtOCH₂, CH₃), (M-1345, H, F, H, EtOCH₂CH₂, H), (M-1346, H, F, H, EtOCH₂CH₂, Cl), (M-1347, H, F, H, EtOCH₂CH₂, F), (M-1348, H, F, H, EtOCH₂CH₂, CF₃), (M-1349, H, F, H, EtOCH₂CH₂, Br), (M-1350, H, F, H, EtOCH₂CH₂, CH₃), (M-1351, H, F, H, MeOCH₂CH₂OCH₂CH₂, H), (M-1352, H, F, H, MeOCH₂CH₂OCH₂CH₂, Cl), (M-1353, H, F, H, MeOCH₂CH₂OCH₂CH₂, F), (M-1354, H, F, H, MeOCH₂CH₂OCH₂CH₂, CF₃), (M-1355, H, F, H, MeOCH₂CH₂OCH₂CH₂, Br), (M-1356, H, F, H, MeOCH₂CH₂OCH₂CH₂, CH₃), (M-1357, H, F, H, MeOCH₂CH₂, H), (M-1358, H, F, H, MeOCH₂CH₂, Cl), (M-1359, H, F, H, MeOCH₂CH₂, F), (M-1360, H, F, H, MeOCH₂CH₂, CF₃), (M-1361, H, F, H, MeOCH₂CH₂, Br), (M-1362, H, F, H, MeOCH₂CH₂, CH₃), (M-1363, H, F, H, HOCH₂, H), (M-1364, H, F, H, HOCH₂, Cl), (M-1365, H, F, H, HOCH₂, F), (M-1366, H, F, H, HOCH₂, CF₃), (M-1367, H, F, H, HOCH₂, Br), (M-1368, H, F, H, HOCH₂, CH₃), (M-1369, H, F, H, HOCH₂CH₂, H), (M-1370, H, F, H, HOCH₂CH₂, Cl), (M-1371, H, F, H, HOCH₂CH₂, F), (M-1372, H, F, H, HOCH₂CH₂, CF₃), (M-1373, H, F, H, HOCH₂CH₂, Br), (M-1374, H, F, H, HOCH₂CH₂, C₃), (M-1375, H, F, H, HOCH₂CH₂CH₂, H), (M-1376, H, F, H, HOCH₂CH₂CH₂, Cl), (M-1377, H, F, H, HOCH₂CH₂CH₂, F), (M-1378, H, F, H, HOCH₂CH₂CH₂, CF₃), (M-1379, H, F, H, HOCH₂CH₂CH₂, Br), (M-1380, H, F, H, HOCH₂CH₂CH₂, CH₃), (M-1381, H, F, H, HOCH₂CH₂CH₂CH₂, H), (M-1382, H, F, H, HOCH₂CH₂CH₂CH₂, Cl), (M-1383, H, F, H, HOCH₂CH₂CH₂CH₂, F), (M-1384, H, F, H, HOCH₂CH₂CH₂CH₂, CF₃), (M-1385, H, F, H, HOCH₂CH₂CH₂CH₂, Br), (M-1386, H, F, H, HOCH₂CH₂CH₂CH₂, CH₃), (M-1387, H, F, H, HOCH₂CH₂CH₂CH₂CH₂, H), (M-1388, H, F, H, HOCH₂CH₂CH₂CH₂CH₂, Cl), (M-1389, H, F, H, HOCH₂CH₂CH₂CH₂CH₂, F), (M-1390, H, F, H, HOCH₂CH₂CH₂CH₂CH₂, CF₃), (M-1391, H, F, H, HOCH₂CH₂CH₂CH₂CH₂, Br), (M-1392, H, F, H, HOCH₂CH₂CH₂CH₂CH₂, CH₃), (M-1393, H, F, H, HOCH₂CH₂OCH₂CH₂, H), (M-1394, H, F, H, HOCH₂CH₂OCH₂CH₂, Cl), (M-1395, H, F, H, HOCH₂CH₂OCH₂CH₂, F), (M-1396, H, F, H, HOCH₂CH₂OCH₂CH₂, CF₃), (M-1397, H, F, H, HOCH₂CH₂OCH₂CH₂, Br), (M-1398, H, F, H, HOCH₂CH₂OCH₂CH₂, CH₃), (M-1399, H, F, H, (Me)₂N, H), (M-1400, H, F, H, (Me)₂N, Cl), (M-1401, H, F, H, (Me)₂N, F), (M-1402, H, F, H, (Me)₂N, CF₃), (M-1403, H, F, H, (Me)₂N, Br), (M-1404, H, F, H, (Me)₂N, CH₃), (M-1405, H, F, H, piperidin-4-yl-methyl, H), (M-1406, H, F, H, piperidin-4-yl-methyl, Cl), (M-1407, H, F, H, piperidin-4-yl-methyl, F), (M-1408, H, F, H, piperidin-4-yl-methyl, CF₃), (M-1409, H, F, H, piperidin-4-yl-methyl, Br), (M-1410, H, F, H, piperidin-4-yl-methyl, CH₃), (M-1411, H, F, H, cyclohexylmethyl, H), (M-1412, H, F, H, cyclohexylmethyl, Cl), (M-1413, H, F, H, cyclohexylmethyl, F), (M-1414, H, F, H, cyclohexylmethyl, CF₃), (M-1415, H, F, H, cyclohexylmethyl, Br), (M-1416, H, F, H, cyclohexylmethyl, CH₃), (M-1417, H, F, F, H, H), (M-1418, H, F, F, H, Cl), (M-1419, H, F, F, H, F), (M-1420, H, F, F, H, CF₃), (M-1421, H, F, F, H, Br), (M-1422, H, F, F, H, CH₃), (M-1423, H, F, F, F, H), (M-1424, H, F, F, F, Cl), (M-1425, H, F, F, F, F), (M-1426, H, F, F, F, CF₃), (M-1427, H, F, F, F, Br), (M-1428, H, F, F, F, CH₃), (M-1429, H, F, F, Cl, H), (M-1430, H, F, F, Cl, Cl), (M-1431, H, F, F, Cl, F), (M-1432, H, F, F, Cl, CF₃), (M-1433, H, F, F, Cl, Br), (M-1434, H, F, F, Cl, CH₃), (M-1435, H, F, F, CH₃, H), (M-1436, H, F, F, CH₃, Cl), (M-1437, H, F, F, CH₃, F), (M-1438, H, F, F, CH₃, CF₃), (M-1439, H, F, F, CH₃, Br), (M-1440, H, F, F, CH₃, CH₃), (M-1441, H, F, F, Et, H), (M-1442, H, F, F, Et, Cl), (M-1443, H, F, F, Et, F), (M-1444, H, F, F, Et, CF₃), (M-1445, H, F, F, Et, Br), (M-1446, H, F, F, Et, CH₃), (M-1447, H, F, F, n-Pr, H), (M-1448, H, F, F, n-Pr, Cl), (M-1449, H, F, F, n-Pr, F), (M-1450, H, F, F, n-Pr, CF₃), (M-1451, H, F, F, n-Pr, Br), (M-1452, H, F, F, n-Pr, CH₃), (M-1453, H, F, F, c-Pr, H), (M-1454, H, F, F, c-Pr, Cl), (M-1455, H, F, F, c-Pr, F), (M-1456, H, F, F, c-Pr, CF₃), (M-1457, H, F, F, c-Pr, Br), (M-1458, H, F, F, c-Pr, CH₃), (M-1459, H, F, F, i-Pr, H), (M-1460, H, F, F, i-Pr, Cl), (M-1461, H, F, F, i-Pr, F), (M-1462, H, F, F, i-Pr, CF₃), (M-1463, H, F, F, i-Pr, Br), (M-1464, H, F, F, i-Pr, CH₃), (M-1465, H, F, F, n-Bu, H), (M-1466, H, F, F, n-Bu, Cl), (M-1467, H, F, F, n-Bu, F), (M-1468, H, F, F, n-Bu, CF₃), (M-1469, H, F, F, n-Bu, Br), (M-1470, H, F, F, n-Bu, CH₃), (M-1471, H, F, F, i-Bu, H), (M-1472, H, F, F, i-Bu, Cl), (M-1473, H, F, F, i-Bu, F), (M-1474, H, F, F, i-Bu, CF₃), (M-1475, H, F, F, i-Bu, Br), (M-1476, H, F, F, i-Bu, CH₃), (M-1477, H, F, F, sec-Bu, H), (M-1478, H, F, F, sec-Bu, Cl), (M-1479, H, F, F, sec-Bu, F), (M-1480, H, F, F, sec-Bu, CF₃), (M-1481, H, F, F, sec-Bu, Br), (M-1482, H, F, F, sec-Bu, CH₃), (M-1483, H, F, F, n-Pen, H), (M-1484, H, F, F, n-Pen, Cl), (M-1485, H, F, F, n-Pen, F), (M-1486, H, F, F, n-Pen, CF₃), (M-1487, H, F, F, n-Pen, Br), (M-1488, H, F, F, n-Pen, CH₃), (M-1489, H, F, F, c-Pen, H), (M-1490, H, F, F, c-Pen, Cl), (M-1491, H, F, F, c-Pen, F), (M-1492, H, F, F, c-Pen, CF₃), (M-1493, H, F, F, c-Pen, Br), (M-1494, H, F, F, c-Pen, CH₃), (M-1495, H, F, F, n-Hex, H), (M-1496, H, F, F, n-Hex, Cl), (M-1497, H, F, F, n-Hex, F), (M-1498, H, F, F, n-Hex, CF₃), (M-1499, H, F, F, n-Hex, Br), (M-1500, H, F, F, n-Hex, CH₃), (M-1501, H, F, F, c-Hex, H), (M-1502, H, F, F, c-Hex, Cl), (M-1503, H, F, F, c-Hex, F), (M-1504, H, F, F, c-Hex, CF₃), (M-1505, H, F, F, c-Hex, Br), (M-1506, H, F, F, c-Hex, CH₃), (M-1507, H, F, F, OH, H), (M-1508, H, F, F, OH, Cl), (M-1509, H, F, F, OH, F), (M-1510, H, F, F, OH, CF₃), (M-1511, H, F, F, OH, Br), (M-1512, H, F, F, OH, CH₃), (M-1513, H, F, F, EtO, H), (M-1514, H, F, F, EtO, Cl), (M-1515, H, F, F, EtO, F), (M-1516, H, F, F, EtO, CF₃), (M-1517, H, F, F, EtO, Br), (M-1518, H, F, F, EtO, CH₃), (M-1519, H, F, F, n-PrO, H), (M-1520, H, F, F, n-PrO, Cl), (M-1521, H, F, F, n-PrO, F), (M-1522, H, F, F, n-PrO, CF₃), (M-1523, H, F, F, n-PrO, Br), (M-1524, H, F, F, n-PrO, CH₃), (M-1525, H, F, F, PhO, H), (M-1526, H, F, F, PhO, Cl), (M-1527, H, F, F, PhO, F), (M-1528, H, F, F, PhO, CF₃), (M-1529, H, F, F, PhO, Br), (M-1530, H, F, F, PhO, CH₃), (M-1531, H, F, F, BnO, H), (M-1532, H, F, F, BnO, Cl), (M-1533, H, F, F, BnO, F), (M-1534, H, F, F, BnO, CF₃), (M-1535, H, F, F, BnO, Br), (M-1536, H, F, F, BnO, CH₃), (M-1537, H, F, F, PhCH₂CH₂O, H), (M-1538, H, F, F, PhCH₂CH₂O, Cl), (M-1539, H, F, F, PhCH₂CH₂O, F), (M-1540, H, F, F, PhCH₂CH₂O, CF₃), (M-1541, H, F, F, PhCH₂CH₂O, Br), (M-1542, H, F, F, PhCH₂CH₂O, CH₃), (M-1543, H, F, F, CF₃O, H), (M-1544, H, F, F, CF₃O, Cl), (M-1545, H, F, F, CF₃O, F), (M-1546, H, F, F, CF₃O, CF₃), (M-1547, H, F, F, CF₃O, Br), (M-1548, H, F, F, CF₃O, CH₃), (M-1549, H, F, F, Ph, H), (M-1550, H, F, F, Ph, Cl), (M-1551, H, F, F, Ph, F), (M-1552, H, F, F, Ph, CF₃), (M-1553, H, F, F, Ph, Br), (M-1554, H, F, F, Ph, CH₃), (M-1555, H, F, F, 4-F-Ph, H), (M-1556, H, F, F, 4-F-Ph, Cl), (M-1557, H, F, F, 4-F-Ph, F), (M-1558, H, F, F, 4-F-Ph, CF₃), (M-1559, H, F, F, 4-F-Ph, Br), (M-1560, H, F, F, 4-F-Ph, CH₃), (M-1561, H, F, F, 4-CF₃-Ph, H), (M-1562, H, F, F, 4-CF₃-Ph, Cl), (M-1563, H, F, F, 4-CF₃-Ph, F), (M-1564, H, F, F, 4-CF₃-Ph, CF₃), (M-1565, H, F, F, 4-CF₃-Ph, Br), (M-1566, H, F, F, 4-CF₃-Ph, CH₃), (M-1567, H, F, F, 4-(Me)₂N-Ph, H), (M-1568, H, F, F, 4-(Me)₂N-Ph, Cl), (M-1569, H, F, F, 4-(Me)₂N-Ph, F), (M-1570, H, F, F, 4-(Me)₂N-Ph, CF₃), (M-1571, H, F, F, 4-(Me)₂N-Ph, Br), (M-1572, H, F, F, 4-(Me)₂N-Ph, CH₃), (M-1573, H, F, F, 4-OH-Ph, H), (M-1574, H, F, F, 4-OH-Ph, Cl), (M-1575, H, F, F, 4-OH-Ph, F), (M-1576, H, F, F, 4-OH-Ph, CF₃), (M-1577, H, F, F, 4-OH-Ph, Br), (M-1578, H, F, F, 4-OH-Ph, CH₃), (M-1579, H, F, F, 3,4-di-F-Ph, H), (M-1580, H, F, F, 3,4-di-F-Ph, Cl), (M-1581, H, F, F, 3,4-di-F-Ph, F), (M-1582, H, F, F, 3,4-di-F-Ph, CF₃), (M-1583, H, F, F, 3,4-di-F-Ph, Br), (M-1584, H, F, F, 3,4-di-F-Ph, CH₃), (M-1585, H, F, F, 4-COOH-Ph, H), (M-1586, H, F, F, 4-COOH-Ph, Cl), (M-1587, H, F, F, 4-COOH-Ph, F), (M-1588, H, F, F, 4-COOH-Ph, CF₃), (M-1589, H, F, F, 4-COOH-Ph, Br), (M-1590, H, F, F, 4-COOH-Ph, CH₃), (M-1591, H, F, F, Bn, H), (M-1592, H, F, F, Bn, Cl), (M-1593, H, F, F, Bn, F), (M-1594, H, F, F, Bn, CF₃), (M-1595, H, F, F, Bn, Br), (M-1596, H, F, F, Bn, CH₃), (M-1597, H, F, F, 4-F-Bn, H), (M-1598, H, F, F, 4-F-Bn, Cl), (M-1599, H, F, F, 4-F-Bn, F), (M-1600, H, F, F, 4-F-Bn, CF₃), (M-1601, H, F, F, 4-F-Bn, Br), (M-1602, H, F, F, 4-F-Bn, CH₃), (M-1603, H, F, F, 2-Py, H), (M-1604, H, F, F, 2-Py, Cl), (M-1605, H, F, F, 2-Py, F), (M-1606, H, F, F, 2-Py, CF₃), (M-1607, H, F, F, 2-Py, Br), (M-1608, H, F, F, 2-Py, CH₃), (M-1609, H, F, F, 3-Py, H), (M-1610, H, F, F, 3-Py, Cl), (M-1611, H, F, F, 3-Py, F), (M-1612, H, F, F, 3-Py, CF₃), (M-1613, H, F, F, 3-Py, Br), (M-1614, H, F, F, 3-Py, CH₃), (M-1615, H, F, F, 4-Py, H), (M-1616, H, F, F, 4-Py, Cl), (M-1617, H, F, F, 4-Py, F), (M-1618, H, F, F, 4-Py, CF₃), (M-1619, H, F, F, 4-Py, Br), (M-1620, H, F, F, 4-Py, CH₃), (M-1621, H, F, F, 2-Th, H), (M-1622, H, F, F, 2-Th, Cl), (M-1623, H, F, F, 2-Th, F), (M-1624, H, F, F, 2-Th, CF₃), (M-1625, H, F, F, 2-Th, Br), (M-1626, H, F, F, 2-Th, CH₃), (M-1627, H, F, F, 3-Th, H), (M-1628, H, F, F, 3-Th, Cl), (M-1629, H, F, F, 3-Th, F), (M-1630, H, F, F, 3-Th, CF₃), (M-1631, H, F, F, 3-Th, Br), (M-1632, H, F, F, 3-Th, CH₃), (M-1633, H, F, F, pyrrazol-2-yl, H), (M-1634, H, F, F, pyrrazol-2-yl, Cl), (M-1635, H, F, F, pyrrazol-2-yl, F), (M-1636, H, F, F, pyrrazol-2-yl, CH₃), (M-1637, H, F, F, pyrrazol-2-yl, Br), (M-1638, H, F, F, pyrrazol-2-yl, CH₃), (M-1639, H, F, F, pyrrazol-3-yl, H), (M-1640, H, F, F, pyrrazol-3-yl, Cl), (M-1641, H, F, F, pyrrazol-3-yl, F), (M-1642, H, F, F, pyrrazol-3-yl, CF₃), (M-1643, H, F, F, pyrrazol-3-yl, Br), (M-1644, H, F, F, pyrrazol-3-yl, CH₃), (M-1645, H, F, F, pyrimidin-2-yl, H), (M-1646, H, F, F, pyrimidin-2-yl, Cl), (M-1647, H, F, F, pyrimidin-2-yl, F), (M-1648, H, F, F, pyrimidin-2-yl, CF₃), (M-1649, H, F, F, pyrimidin-2-yl, Br), (M-1650, H, F, F, pyrimidin-2-yl, C₃), (M-1651, H, F, F, pyrimidin-4-yl, H), (M-1652, H, F, F, pyrimidin-4-yl, Cl), (M-1653, H, F, F, pyrimidin-4-yl, F), (M-1654, H, F, F, pyrimidin-4-yl, CF₃), (M-1655, H, F, F, pyrimidin-4-yl, Br), (M-1656, H, F, F, pyrimidin-4-yl, CH₃), (M-1657, H, F, F, pyrimidin-5-yl, H), (M-1658, H, F, F, pyrimidin-5-yl, Cl), (M-1659, H, F, F, pyrimidin-5-yl, F), (M-1660, H, F, F, pyrimidin-5-yl, CF₃), (M-1661, H, F, F, pyrimidin-5-yl, Br), (M-1662, H, F, F, pyrimidin-5-yl, CH₃), (M-1663, H, F, F, HOOCCH₂CH₂CH₂, H), (M-1664, H, F, F, HOOCCH₂CH₂CH₂, Cl), (M-1665, H, F, F, HOOCCH₂CH₂CH₂, F), (M-1666, H, F, F, HOOCCH₂CH₂CH₂, CF₃), (M-1667, H, F, F, HOOCCH₂CH₂CH₂, Br), (M-1668, H, F, F, HOOCCH₂CH₂CH₂, CH₃), (M-1669, H, F, F, HOOCCH₂CH₂CH₂CH₂, H), (M-1670, H, F, F, HOOCCH₂CH₂CH₂CH₂, Cl), (M-1671, H, F, F, HOOCCH₂CH₂CH₂CH₂, F), (M-1672, H, F, F, HOOCCH₂CH₂CH₂CH₂, CF₃), (M-1673, H, F, F, HOOCCH₂CH₂CH₂CH₂, Br), (M-1674, H, F, F, HOOCCH₂CH₂CH₂CH₂, CH₃), (M-1675, H, F, F, (Me)₂NCOCH₂CH₂CH₂, H), (M-1676, H, F, F, (Me)₂NCOCH₂CH₂CH₂, Cl), (M-1677, H, F, F, (Me)₂NCOCH₂CH₂CH₂, F), (M-1678, H, F, F, (Me)₂NCOCH₂CH₂CH₂, CF₃), (M-1679, H, F, F, (Me)₂NCOCH₂CH₂CH₂, Br), (M-1680, H, F, F, (Me)₂NCOCH₂CH₂CH₂, CH₃), (M-1681, H, F, F, (Me)₂NCOCH₂CH₂CH₂CH₂, H), (M-1682, H, F, F, (Me)₂NCOCH₂CH₂CH₂CH₂, Cl), (M-1683, H, F, F, (Me)₂NCOCH₂CH₂CH₂CH₂, F), (M-1684, H, F, F, (Me)₂NCOCH₂CH₂CH₂CH₂, CF₃), (M-1685, H, F, F, (Me)₂NCOCH₂CH₂CH₂CH₂, Br), (M-1686, H, F, F, (Me)₂NCOCH₂CH₂CH₂CH₂, CH₃), (M-1687, H, F, F, MeOCH₂, H), (M-1688, H, F, F, MeOCH₂, Cl), (M-1689, H, F, F, MeOCH₂, F), (M-1690, H, F, F, MeOCH₂, CF₃), (M-1691, H, F, F, MeOCH₂, Br), (M-1692, H, F, F, MeOCH₂, CH₃), (M-1693, H, F, F, EtOCH₂, H), (M-1694, H, F, F, EtOCH₂, Cl), (M-1695, H, F, F, EtOCH₂, F), (M-1696, H, F, F, EtOCH₂, CF₃), (M-1697, H, F, F, EtOCH₂, Br), (M-1698, H, F, F, EtOCH₂, CH₃), (M-1699, H, F, F, EtOCH₂CH₂, H), (M-1700, H, F, F, EtOCH₂CH₂, Cl), (M-1701, H, F, F, EtOCH₂CH₂, F), (M-1702, H, F, F, EtOCH₂CH₂, CF₃), (M-1703, H, F, F, EtOCH₂CH₂, Br), (M-1704, H, F, F, EtOCH₂CH₂, CH₃), (M-1705, H, F, F, MeOCH₂CH₂OCH₂CH₂, H), (M-1706, H, F, F, MeOCH₂CH₂OCH₂CH₂, Cl), (M-1707, H, F, F, MeOCH₂CH₂OCH₂CH₂, F), (M-1708, H, F, F, MeOCH₂CH₂OCH₂CH₂, CF₃), (M-1709, H, F, F, MeOCH₂CH₂OCH₂CH₂, Br), (M-1710, H, F, F, MeOCH₂CH₂OCH₂CH₂, CH₃), (M-1711, H, F, F, MeOCH₂CH₂, H), (M-1712, H, F, F, MeOCH₂CH₂, Cl), (M-1713, H, F, F, MeOCH₂CH₂, F), (M-1714, H, F, F, MeOCH₂CH₂, CF₃), (M-1715, H, F, F, MeOCH₂CH₂, Br), (M-1716, H, F, F, MeOCH₂CH₂, CH₃), (M-1717, H, F, F, HOCH₂, H), (M-1718, H, F, F, HOCH₂, Cl), (M-1719, H, F, F, HOCH₂, F), (M-1720, H, F, F, HOCH₂, CF₃), (M-1721, H, F, F, HOCH₂, Br), (M-1722, H, F, F, HOCH₂, CH₃), (M-1723, H, F, F, HOCH₂CH₂, H), (M-1724, H, F, F, HOCH₂CH₂, Cl), (M-1725, H, F, F, HOCH₂CH₂, F), (M-1726, H, F, F, HOCH₂CH₂, CF₃), (M-1727, H, F, F, HOCH₂CH₂, Br), (M-1728, H, F, F, HOCH₂CH₂, CH₃), (M-1729, H, F, F, HOCH₂CH₂CH₂, H), (M-1730, H, F, F, HOCH₂CH₂CH₂, Cl), (M-1731, H, F, F, HOCH₂CH₂CH₂, F), (M-1732, H, F, F, HOCH₂CH₂CH₂, CF₃), (M-1733, H, F, F, HOCH₂CH₂CH₂, Br), (M-1734, H, F, F, HOCH₂CH₂CH₂, CH₃), (M-1735, H, F, F, HOCH₂CH₂CH₂CH₂, H), (M-1736, H, F, F, HOCH₂CH₂CH₂CH₂, Cl), (M-1737, H, F, F, HOCH₂CH₂CH₂CH₂, F), (M-1738, H, F, F, HOCH₂CH₂CH₂CH₂, CF₃), (M-1739, H, F, F, HOCH₂CH₂CH₂CH₂, Br), (M-1740, H, F, F, HOCH₂CH₂CH₂CH₂, CH₃), (M-1741, H, F, F, HOCH₂CH₂CH₂CH₂CH₂, H), (M-1742, H, F, F, HOCH₂CH₂CH₂CH₂CH₂, Cl), (M-1743, H, F, F, HOCH₂CH₂CH₂CH₂CH₂, F), (M-1744, H, F, F, HOCH₂CH₂CH₂CH₂CH₂, CF₃), (M-1745, H, F, F, HOCH₂CH₂CH₂CH₂CH₂, Br), (M-1746, H, F, F, HOCH₂CH₂CH₂CH₂CH₂, CH₃), (M-1747, H, F, F, HOCH₂CH₂OCH₂CH₂, H), (M-1748, H, F, F, HOCH₂CH₂OCH₂CH₂, Cl), (M-1749, H, F, F, HOCH₂CH₂OCH₂CH₂, F), (M-1750, H, F, F, HOCH₂CH₂OCH₂CH₂, CF₃), (M-1751, H, F, F, HOCH₂CH₂OCH₂CH₂, Br), (M-1752, H, F, F, HOCH₂CH₂OCH₂CH₂, CH₃), (M-1753, H, F, F, (Me)₂N, H), (M-1754, H, F, F, (Me)₂N, Cl), (M-1755, H, F, F, (Me)₂N, F), (M-1756, H, F, F, (Me)₂N, CF₃), (M-1757, H, F, F, (Me)₂N, Br), (M-1758, H, F, F, (Me)₂N, CH₃), (M-1759, H, F, F, piperidin-4-yl-methyl, H), (M-1760, H, F, F, piperidin-4-yl-methyl, Cl), (M-1761, H, F, F, piperidin-4-yl-methyl, F), (M-1762, H, F, F, piperidin-4-yl-methyl, CF₃), (M-1763, H, F, F, piperidin-4-yl-methyl, Br), (M-1764, H, F, F, piperidin-4-yl-methyl, CH₃), (M-1765, H, F, F, cyclohexylmethyl, H), (M-1766, H, F, F, cyclohexylmethyl, Cl), (M-1767, H, F, F, cyclohexylmethyl, F), (M-1768, H, F, F, cyclohexylmethyl, CF₃), (M-1769, H, F, F, cyclohexylmethyl, Br), (M-1770, H, F, F, cyclohexylmethyl, CH₃), (M-1771, H, F, Cl, H, H), (M-1772, H, F, Cl, H, Cl), (M-1773, H, F, Cl, H, F), (M-1774, H, F, Cl, H, CF₃), (M-1775, H, F, Cl, H, Br), (M-1776, H, F, Cl, H, CH₃), (M-1777, H, F, Cl, F, H), (M-1778, H, F, Cl, F, Cl), (M-1779, H, F, Cl, F, F), (M-1780, H, F, Cl, F, CF₃), (M-1781, H, F, Cl, F, Br), (M-1782, H, F, Cl, F, CH₃), (M-1783, H, F, Cl, Cl, H), (M-1784, H, F, Cl, Cl, Cl), (M-1785, H, F, Cl, Cl, F), (M-1786, H, F, Cl, Cl, CF₃), (M-1787, H, F, Cl, Cl, Br), (M-1788, H, F, Cl, Cl, CH₃), (M-1789, H, F, Cl, CH₃, H), (M-1790, H, F, Cl, CH₃, Cl), (M-1791, H, F, Cl, CH₃, F), (M-1792, H, F, Cl, CH₃, CF₃), (M-1793, H, F, Cl, CH₃, Br), (M-1794, H, F, Cl, CH₃, CH₃), (M-1795, H, F, Cl, Et, H), (M-1796, H, F, Cl, Et, Cl), (M-1797, H, F, Cl, Et, F), (M-1798, H, F, Cl, Et, CF₃), (M-1799, H, F, Cl, Et, Br), (M-1800, H, F, Cl, Et, CH₃), (M-1801, H, F, Cl, n-Pr, H), (M-1802, H, F, Cl, n-Pr, Cl), (M-1803, H, F, Cl, n-Pr, F), (M-1804, H, F, Cl, n-Pr, CF₃), (M-1805, H, F, Cl, n-Pr, Br), (M-1806, H, F, Cl, n-Pr, CH₃), (M-1807, H, F, Cl, c-Pr, H), (M-1808, H, F, Cl, c-Pr, Cl), (M-1809, H, F, Cl, c-Pr, F), (M-1810, H, F, Cl, c-Pr, CF₃), (M-1811, H, F, Cl, c-Pr, Br), (M-1812, H, F, Cl, c-Pr, CH₃), (M-1813, H, F, Cl, i-Pr, H), (M-1814, H, F, Cl, i-Pr, Cl), (M-1815, H, F, Cl, i-Pr, F), (M-1816, H, F, Cl, i-Pr, CF₃), (M-1817, H, F, Cl, i-Pr, Br), (M-1818, H, F, Cl, i-Pr, CH₃), (M-1819, H, F, Cl, n-Bu, H), (M-1820, H, F, Cl, n-Bu, Cl), (M-1821, H, F, Cl, n-Bu, F), (M-1822, H, F, Cl, n-Bu, CF₃), (M-1823, H, F, Cl, n-Bu, Br), (M-1824, H, F, Cl, n-Bu, CH₃), (M-1825, H, F, Cl, i-Bu, H), (M-1826, H, F, Cl, i-Bu, Cl), (M-1827, H, F, Cl, i-Bu, F), (M-1828, H, F, Cl, i-Bu, CF₃), (M-1829, H, F, Cl, i-Bu, Br), (M-1830, H, F, Cl, i-Bu, CH₃), (M-1831, H, F, Cl, sec-Bu, H), (M-1832, H, F, Cl, sec-Bu, Cl), (M-1833, H, F, Cl, sec-Bu, F), (M-1834, H, F, Cl, sec-Bu, CF₃), (M-1835, H, F, Cl, sec-Bu, Br), (M-1836, H, F, Cl, sec-Bu, CH₃), (M-1837, H, F, Cl, n-Pen, H), (M-1838, H, F, Cl, n-Pen, Cl), (M-1839, H, F, Cl, n-Pen, F), (M-1840, H, F, Cl, n-Pen, CF₃), (M-1841, H, F, Cl, n-Pen, Br), (M-1842, H, F, Cl, n-Pen, CH₃), (M-1843, H, F, Cl, c-Pen, H), (M-1844, H, F, Cl, c-Pen, Cl), (M-1845, H, F, Cl, c-Pen, F), (M-1846, H, F, Cl, c-Pen, CF₃), (M-1847, H, F, Cl, c-Pen, Br), (M-1848, H, F, Cl, c-Pen, CH₃), (M-1849, H, F, Cl, n-Hex, H), (M-1850, H, F, Cl, n-Hex, Cl), (M-1851, H, F, Cl, n-Hex, F), (M-1852, H, F, Cl, n-Hex, CF₃), (M-1853, H, F, Cl, n-Hex, Br), (M-1854, H, F, Cl, n-Hex, CH₃), (M-1855, H, F, Cl, c-Hex, H), (M-1856, H, F, Cl, c-Hex, Cl), (M-1857, H, F, Cl, c-Hex, F), (M-1858, H, F, Cl, c-Hex, CF₃), (M-1859, H, F, Cl, c-Hex, Br), (M-1860, H, F, Cl, c-Hex, CH₃), (M-1861, H, F, Cl, OH, H), (M-1862, H, F, Cl, OH, Cl), (M-1863, H, F, Cl, OH, F), (M-1864, H, F, Cl, OH, CF₃), (M-1865, H, F, Cl, OH, Br), (M-1866, H, F, Cl, OH, CH₃), (M-1867, H, F, Cl, EtO, H), (M-1868, H, F, Cl, EtO, Cl), (M-1869, H, F, Cl, EtO, F), (M-1870, H, F, Cl, EtO, CF₃), (M-1871, H, F, Cl, EtO, Br), (M-1872, H, F, Cl, EtO, CH₃), (M-1873, H, F, Cl, n-PrO, H), (M-1874, H, F, Cl, n-PrO, Cl), (M-1875, H, F, Cl, n-PrO, F), (M-1876, H, F, Cl, n-PrO, CF₃), (M-1877, H, F, Cl, n-PrO, Br), (M-1878, H, F, Cl, n-PrO, CH₃), (M-1879, H, F, Cl, PhO, H), (M-1880, H, F, Cl, PhO, Cl), (M-1881, H, F, Cl, PhO, F), (M-1882, H, F, Cl, PhO, CF₃), (M-1883, H, F, Cl, PhO, Br), (M-1884, H, F, Cl, PhO, CH₃), (M-1885, H, F, Cl, BnO, H), (M-1886, H, F, Cl, BnO, Cl), (M-1887, H, F, Cl, BnO, F), (M-1888, H, F, Cl, BnO, CF₃), (M-1889, H, F, Cl, BnO, Br), (M-1890, H, F, Cl, BnO, CH₃), (M-1891, H, F, Cl, PhCH₂CH₂O, H), (M-1892, H, F, Cl, PhCH₂CH₂O, Cl), (M-1893, H, F, Cl, PhCH₂CH₂O, F), (M-1894, H, F, Cl, PhCH₂CH₂O, CF₃), (M-1895, H, F, Cl, PhCH₂CH₂O, Br), (M-1896, H, F, Cl, PhCH₂CH₂O, CH₃), (M-1897, H, F, Cl, CF₃O, H), (M-1898, H, F, Cl, CF₃O, Cl), (M-1899, H, F, Cl, CF₃O, F), (M-1900, H, F, Cl, CF₃O, CF₃), (M-1901, H, F, Cl, CF₃O, Br), (M-1902, H, F, Cl, CF₃O, CH₃), (M-1903, H, F, Cl, Ph, H), (M-1904, H, F, Cl, Ph, Cl), (M-1905, H, F, Cl, Ph, F), (M-1906, H, F, Cl, Ph, CF₃), (M-1907, H, F, Cl, Ph, Br), (M-1908, H, F, Cl, Ph, CH₃), (M-1909, H, F, Cl, 4-F-Ph, H), (M-1910, H, F, Cl, 4-F-Ph, Cl), (M-1911, H, F, Cl, 4-F-Ph, F), (M-1912, H, F, Cl, 4-F-Ph, CF₃), (M-1913, H, F, Cl, 4-F-Ph, Br), (M-1914, H, F, Cl, 4-F-Ph, CH₃), (M-1915, H, F, Cl, 4-CF₃-Ph, H), (M-1916, H, F, Cl, 4-CF₃-Ph, Cl), (M-1917, H, F, Cl, 4-CF₃-Ph, F), (M-1918, H, F, Cl, 4-CF₃-Ph, CF₃), (M-1919, H, F, Cl, 4-CF₃-Ph, Br), (M-1920, H, F, Cl, 4-CF₃-Ph, CH₃), (M-1921, H, F, Cl, 4-(Me)₂N-Ph, H), (M-1922, H, F, Cl, 4-(Me)₂N-Ph, Cl), (M-1923, H, F, Cl, 4-(Me)₂N-Ph, F), (M-1924, H, F, Cl, 4-(Me)₂N-Ph, CF₃), (M-1925, H, F, Cl, 4-(Me)₂N-Ph, Br), (M-1926, H, F, Cl, 4-(Me)₂N-Ph, CH₃), (M-1927, H, F, Cl, 4-OH-Ph, H), (M-1928, H, F, Cl, 4-OH-Ph, Cl), (M-1929, H, F, Cl, 4-OH-Ph, F), (M-1930, H, F, Cl, 4-OH-Ph, CF₃), (M-1931, H, F, Cl, 4-OH-Ph, Br), (M-1932, H, F, Cl, 4-OH-Ph, CH₃), (M-1933, H, F, Cl, 3,4-di-F-Ph, H), (M-1934, H, F, Cl, 3,4-di-F-Ph, Cl), (M-1935, H, F, Cl, 3,4-di-F-Ph, F), (M-1936, H, F, Cl, 3,4-di-F-Ph, CF₃), (M-1937, H, F, Cl, 3,4-di-F-Ph, Br), (M-1938, H, F, Cl, 3,4-di-F-Ph, CH₃), (M-1939, H, F, Cl, 4-COOH-Ph, H), (M-1940, H, F, Cl, 4-COOH-Ph, Cl), (M-1941, H, F, Cl, 4-COOH-Ph, F), (M-1942, H, F, Cl, 4-COOH-Ph, CF₃), (M-1943, H, F, Cl, 4-COOH-Ph, Br), (M-1944, H, F, Cl, 4-COOH-Ph, CH₃), (M-1945, H, F, Cl, Bn, H), (M-1946, H, F, Cl, Bn, Cl), (M-1947, H, F, Cl, Bn, F), (M-1948, H, F, Cl, Bn, CF₃), (M-1949, H, F, Cl, Bn, Br), (M-1950, H, F, Cl, Bn, CH₃), (M-1951, H, F, Cl, 4-F-Bn, H), (M-1952, H, F, Cl, 4-F-Bn, Cl), (M-1953, H, F, Cl, 4-F-Bn, F), (M-1954, H, F, Cl, 4-F-Bn, CF₃), (M-1955, H, F, Cl, 4-F-Bn, Br), (M-1956, H, F, Cl, 4-F-Bn, CH₃), (M-1957, H, F, Cl, 2-Py, H), (M-1958, H, F, Cl, 2-Py, Cl), (M-1959, H, F, Cl, 2-Py, F), (M-1960, H, F, Cl, 2-Py, CF₃), (M-1961, H, F, Cl, 2-Py, Br), (M-1962, H, F, Cl, 2-Py, CH₃), (M-1963, H, F, Cl, 3-Py, H), (M-1964, H, F, Cl, 3-Py, Cl), (M-1965, H, F, Cl, 3-Py, F), (M-1966, H, F, Cl, 3-Py, CF₃), (M-1967, H, F, Cl, 3-Py, Br), (M-1968, H, F, Cl, 3-Py, CH₃), (M-1969, H, F, Cl, 4-Py, H), (M-1970, H, F, Cl, 4-Py, Cl), (M-1971, H, F, Cl, 4-Py, F), (M-1972, H, F, Cl, 4-Py, CF₃), (M-1973, H, F, Cl, 4-Py, Br), (M-1974, H, F, Cl, 4-Py, CH₃), (M-1975, H, F, Cl, 2-Th, H), (M-1976, H, F, Cl, 2-Th, Cl), (M-1977, H, F, Cl, 2-Th, F), (M-1978, H, F, Cl, 2-Th, CF₃), (M-1979, H, F, Cl, 2-Th, Br), (M-1980, H, F, Cl, 2-Th, CH₃), (M-1981, H, F, Cl, 3-Th, H), (M-1982, H, F, Cl, 3-Th, Cl), (M-1983, H, F, Cl, 3-Th, F), (M-1984, H, F, Cl, 3-Th, CF₃), (M-1985, H, F, Cl, 3-Th, Br), (M-1986, H, F, Cl, 3-Th, CH₃), (M-1987, H, F, Cl, pyrrazol-2-yl, H), (M-1988, H, F, Cl, pyrrazol-2-yl, Cl), (M-1989, H, F, Cl, pyrrazol-2-yl, F), (M-1990, H, F, Cl, pyrrazol-2-yl, CF₃), (M-1991, H, F, Cl, pyrrazol-2-yl, Br), (M-1992, H, F, Cl, pyrrazol-2-yl, CH₃), (M-1993, H, F, Cl, pyrrazol-3-yl, H), (M-1994, H, F, Cl, pyrrazol-3-yl, Cl), (M-1995, H, F, Cl, pyrrazol-3-yl, F), (M-1996, H, F, Cl, pyrrazol-3-yl, CF₃), (M-1997, H, F, Cl, pyrrazol-3-yl, Br), (M-1998, H, F, Cl, pyrrazol-3-yl, CH₃), (M-1999, H, F, Cl, pyrimidin-2-yl, H), (M-2000, H, F, Cl, pyrimidin-2-yl, Cl), (M-2001, H, F, Cl, pyrimidin-2-yl, F), (M-2002, H, F, Cl, pyrimidin-2yl, $CF_3$), (M-2003, H, F, Cl, pyrimidin-2-yl, Br), (M-2004, H, F, Cl, pyrimidin-2-yl, $CH_3$), (M-2005, H, F, Cl, pyrimidin-4-yl, H), (M-2006, H, F, Cl, pyrimidin-4-yl, Cl), (M-2007, H, F, Cl, pyrimidin-4-yl, F), (M-2008, H, F, Cl, pyrimidin-4-yl, $CF_3$), (M-2009, H, F, Cl, pyrimidin-4-yl, Br), (M-2010, H, F, Cl, pyrimidin-4-yl, $CH_3$), (M-2011, H, F, Cl, pyrimidin-5-yl, H), (M-2012, H, F, Cl, pyrimidin-5-yl, Cl), (M-2013, H, F, Cl, pyrimidin-5-yl, F), (M-2014, H, F, Cl, pyrimidin-5-yl, $CF_3$), (M-2015, H, F, Cl, pyrimidin-5-yl, Br), (M-2016, H, F, Cl, pyrimidin-5-yl, $CH_3$), (M-2017, H, F, Cl, $HOOCCH_2CH_2$, H), (M-2018, H, F, Cl, $HOOCCH_2CH_2$, Cl), (M-2019, H, F, Cl, $HOOCCH_2CH_2$, F), (M-2020, H, F, Cl, $HOOCCH_2CH_2$, $CF_3$), (M-2021, H, F, Cl, $HOOCCH_2CH_2$, Br), (M-2022, H, F, Cl, $HOOCCH_2CH_2$, $CH_3$), (M-2023, H, F, Cl, $HOOCCH_2CH_2CH_2$, H), (M-2024, H, F, Cl, $HOOCCH_2CH_2CH_2$, Cl), (M-2025, H, F, Cl, $HOOCCH_2CH_2CH_2$, F), (M-2026, H, F, Cl, $HOOCCH_2CH_2CH_2$, $CF_3$), (M-2027, H, F, Cl, $HOOCCH_2CH_2CH_2$, Br), (M-2028, H, F, Cl, $HOOCCH_2CH_2CH_2CH_2$, $CH_3$), (M-2029, H, F, Cl, $(Me)_2NCOCH_2CH_2CH_2$, H), (M-2030, H, F, Cl, $(Me)_2NCOCH_2CH_2CH_2$, Cl), (M-2031, H, F, Cl, $(Me)_2NCOCH_2CH_2CH_2$, F), (M-2032, H, F, Cl, $(Me)_2NCOCH_2CH_2CH_2$, $CF_3$), (M-2033, H, F, Cl, $(Me)_2NCOCH_2CH_2CH_2$, Br), (M-2034, H, F, Cl, $(Me)_2NCOCH_2CH_2CH_2$, $CH_3$), (M-2035, H, F, Cl, $(Me)_2NCOCH_2CH_2CH_2CH_2$, H), (M-2036, H, F, Cl, $(Me)_2NCOCH_2CH_2CH_2CH_2$, Cl), (M-2037, H, F, Cl, $(Me)_2NCOCH_2CH_2CH_2CH_2$, F), (M-2038, H, F, Cl, $(Me)_2NCOCH_2CH_2CH_2CH_2$, $CF_3$), (M-2039, H, F, Cl, $(Me)_2NCOCH_2CH_2CH_2CH_2$, Br), (M-2040, H, F, Cl, $(Me)_2NCOCH_2CH_2CH_2CH_2$, $CH_3$), (M-2041, H, F, Cl, $MeOCH_2$, H), (M-2042, H, F, Cl, $MeOCH_2$, Cl), (M-2043, H, F, Cl, $MeOCH_2$, F), (M-2044, H, F, Cl, $MeOCH_2$, $CF_3$), (M-2045, H, F, Cl, $MeOCH_2$, Br), (M-2046, H, F, Cl, $MeOCH_2$, $CH_3$), (M-2047, H, F, Cl, $EtOCH_2$, H), (M-2048, H, F, Cl, $EtOCH_2$, Cl), (M-2049, H, F, Cl, $EtOCH_2$, F), (M-2050, H, F, Cl, $EtOCH_2$, $CF_3$), (M-2051, H, F, Cl, $EtOCH_2$, Br), (M-2052, H, F, Cl, $EtOCH_2$, $CH_3$), (M-2053, H, F, Cl, $EtOCH_2CH_2$, H), (M-2054, H, F, Cl, $EtOCH_2CH_2$, Cl), (M-2055, H, F, Cl, $EtOCH_2CH_2$, F), (M-2056, H, F, Cl, $EtOCH_2CH_2$, $CF_3$), (M-2057, H, F, Cl, $EtOCH_2CH_2$, Br), (M-2058, H, F, Cl, $EtOCH_2CH_2$, $CH_3$), (M-2059, H, F, Cl, $MeOCH_2CH_2OCH_2CH_2$, H), (M-2060, H, F, Cl, $MeOCH_2CH_2OCH_2CH_2$, Cl), (M-2061, H, F, Cl, $MeOCH_2CH_2OCH_2CH_2$, F), (M-2062, H, F, Cl, $MeOCH_2CH_2OCH_2CH_2$, $CF_3$), (M-2063, H, F, Cl, $MeOCH_2CH_2OCH_2CH_2$, Br), (M-2064, H, F, Cl, $MeOCH_2CH_2OCH_2CH_2$, $CH_3$), (M-2065, H, F, Cl, $MeOCH_2CH_2$, H), (M-2066, H, F, Cl, $MeOCH_2CH_2$, Cl), (M-2067, H, F, Cl, $MeOCH_2CH_2$, F), (M-2068, H, F, Cl, $MeOCH_2CH_2$, $CF_3$), (M-2069, H, F, Cl, $MeOCH_2CH_2$, Br), (M-2070, H, F, Cl, $MeOCH_2CH_2$, $CH_3$), (M-2071, H, F, Cl, $HOCH_2$, H), (M-2072, H, F, Cl, $HOCH_2$, Cl), (M-2073, H, F, Cl, $HOCH_2$, F), (M-2074, H, F, Cl, $HOCH_2$, $CF_3$), (M-2075, H, F, Cl, $HOCH_2$, Br), (M-2076, H, F, Cl, $HOCH_2$, $CH_3$), (M-2077, H, F, Cl, $HOCH_2CH_2$, H), (M-2078, H, F, Cl, $HOCH_2CH_2$, Cl), (M-2079, H, F, Cl, $HOCH_2CH_2$, F), (M-2080, H, F, Cl, $HOCH_2CH_2$, $CF_3$), (M-2081, H, F, Cl, $HOCH_2CH_2$, Br), (M-2082, H, F, Cl, $HOCH_2CH_2$, $CH_3$), (M-2083, H, F, Cl, $HOCH_2CH_2CH_2$, H), (M-2084, H, F, Cl, $HOCH_2CH_2CH_2$, Cl), (M-2085, H, F, Cl, $HOCH_2CH_2CH_2$, F), (M-2086, H, F, Cl, $HOCH_2CH_2CH_2$, $CF_3$), (M-2087, H, F, Cl, $HOCH_2CH_2CH_2$, Br), (M-2088, H, F, Cl, $HOCH_2CH_2CH_2$, $CH_3$), (M-2089, H, F, Cl, $HOCH_2CH_2CH_2CH_2$, H), (M-2090, H, F, Cl, $HOCH_2CH_2CH_2CH_2$, Cl), (M-2091, H, F, Cl, $HOCH_2CH_2CH_2CH_2$, F), (M-2092, H, F, Cl, $HOCH_2CH_2CH_2CH_2$, $CF_3$), (M-2093, H, F, Cl, $HOCH_2CH_2CH_2CH_2$, Br), (M-2094, H, F, Cl, $HOCH_2CH_2CH_2CH_2$, $CH_3$), (M-2095, H, F, Cl, $HOCH_2CH_2CH_2CH_2CH_2$, H), (M-2096, H, F, Cl, $HOCH_2CH_2CH_2CH_2CH_2$, Cl), (M-2097, H, F, Cl, $HOCH_2CH_2CH_2CH_2CH_2$, F), (M-2098, H, F, Cl, $HOCH_2CH_2CH_2CH_2CH_2$, $CF_3$), (M-2099, H, F, Cl, $HOCH_2CH_2CH_2CH_2CH_2$, Br), (M-2100, H, F, Cl, $HOCH_2CH_2CH_2CH_2CH_2$, $CH_3$) (M-2101, H, F, Cl, $HOCH_2CH_2OCH_2CH_2$, H), (M-2102, H, F, Cl, $HOCH_2CH_2OCH_2CH_2$, Cl), (M-2103, H, F, Cl, $HOCH_2CH_2OCH_2CH_2$, F), (M-2104, H, F, Cl, $HOCH_2CH_2OCH_2CH_2$, $CF_3$), (M-2105, H, F, Cl, $HOCH_2CH_2OCH_2CH_2$, Br), (M-2106, H, F, Cl, $HOCH_2CH_2OCH_2CH_2$, $CH_3$), (M-2107, H, F, Cl, $(Me)_2N$, H), (M-2108, H, F, Cl, $(Me)_2N$, Cl), (M-2109, H, F, Cl, $(Me)_2N$, F), (M-2110, H, F, Cl, $(Me)_2N$, $CF_3$), (M-2111, H, F, Cl, $(Me)_2N$, Br), (M-2112, H, F, Cl, $(Me)_2N$, $CH_3$), (M-2113, H, F, Cl, piperidin-4-yl-methyl, H), (M-2114, H, F, Cl, piperidin-4-yl-methyl, Cl), (M-2115, H, F, Cl, piperidin-4-yl-methyl, F), (M-2116, H, F, Cl, piperidin-4-yl-methyl, $CF_3$), (M-2117, H, F, Cl, piperidin-4-yl-methyl, Br), (M-2118, H, F, Cl, piperidin-4-yl-methyl, $CH_3$), (M-2119, H, F, Cl, cyclohexylmethyl, H), (M-2120, H, F, Cl, cyclohexylmethyl, Cl), (M-2121, H, F, Cl, cyclohexylmethyl, F), (M-2122, H, F, Cl, cyclohexylmethyl, $CF_3$), (M-2123, H, F, Cl, cyclohexylmethyl, Br), (M-2124, H, F, Cl, cyclohexylmethyl, $CH_3$), (M-2125, H, $CH_3$, H, H, H), (M-2126, H, $CH_3$, H, H, Cl), (M-2127, H, $CH_3$, H, H, F), (M-2128, H, $CH_3$, H, H, $CF_3$), (M-2129, H, $CH_3$, H, H, Br), (M-2130, H, $CH_3$, H, H, $CH_3$), (M-2131, H, $CH_3$, H, F, H), (M-2132, H, $CH_3$, H, F, Cl), (M-2133, H, $CH_3$, H, F, F), (M-2134, H, $CH_3$, H, F, $CF_3$), (M-2135, H, $CH_3$, H, F, Br), (M-2136, H, $CH_3$, H, F, $CH_3$), (M-2137, H, $CH_3$, H, Cl, H), (M-2138, H, $CH_3$, H, Cl, Cl), (M-2139, H, $CH_3$, H, Cl, F), (M-2140, H, $CH_3$, H, Cl, $CF_3$), (M-2141, H, $CH_3$, H, Cl, Br), (M-2142, H, $CH_3$, H, Cl, $CH_3$), (M-2143, H, $CH_3$, H, $CH_3$, H), (M-2144, H, $CH_3$, H, $CH_3$, Cl), (M-2145, H, $CH_3$, H, $CH_3$, F), (M-2146, H, $CH_3$, H, $CH_3$, $CF_3$), (M-2147, H, $CH_3$, H, $CH_3$, Br), (M-2148, H, $CH_3$, H, $CH_3$, $CH_3$), (M-2149, H, $CH_3$, H, Et, H), (M-2150, H, $CH_3$, H, Et, Cl), (M-2151, H, $CH_3$, H, Et, F), (M-2152, H, $CH_3$, H, Et, $CF_3$), (M-2153, H, $CH_3$, H, Et, Br), (M-2154, H, $CH_3$, H, Et, $CH_3$), (M-2155, H, $CH_3$, H, n-Pr, H), (M-2156, H, $CH_3$, H, n-Pr, Cl), (M-2157, H, $CH_3$, H, n-Pr, F), (M-2158, H, $CH_3$, H, n-Pr, $CF_3$), (M-2159, H, $CH_3$, H, n-Pr, Br), (M-2160, H, $CH_3$, H, n-Pr, $CH_3$), (M-2161, H, $CH_3$, H, c-Pr, H), (M-2162, H, $CH_3$, H, c-Pr, Cl), (M-2163, H, $CH_3$, H, c-Pr, F), (M-2164, H, $CH_3$, H, c-Pr, $CF_3$), (M-2165, H, $CH_3$, H, c-Pr, Br), (M-2166, H, $CH_3$, H, c-Pr, $CH_3$), (M-2167, H, $CH_3$, H, i-Pr, H), (M-2168, H, $CH_3$, H, i-Pr, Cl), (M-2169, H, $CH_3$, H, i-Pr, F), (M-2170, H, $CH_3$, H, i-Pr, $CF_3$), (M-2171, H, $CH_3$, H, i-Pr, Br), (M-2172, H, $CH_3$, H, i-Pr, $CH_3$), (M-2173, H, $CH_3$, H, n-Bu, H), (M-2174, H, $CH_3$, H, n-Bu, Cl), (M-2175, H, $CH_3$, H, n-Bu, F), (M-2176, H, $CH_3$, H, n-Bu, $CF_3$), (M-2177, H, $CH_3$, H, n-Bu, Br), (M-2178, H, $CH_3$, H, n-Bu, $CH_3$), (M-2179, H, $CH_3$, H, i-Bu, H), (M-2180, H, $CH_3$, H, i-Bu, Cl), (M-2181, H, $CH_3$, H, i-Bu, F), (M-2182, H, $CH_3$, H, i-Bu, $CF_3$), (M-2183, H, $CH_3$, H, i-Bu, Br), (M-2184, H, $CH_3$, H, i-Bu, $CH_3$), (M-2185, H, $CH_3$, H, sec-Bu, H), (M-2186, H, $CH_3$, H, sec-Bu, Cl), (M-2187, H, $CH_3$, H, sec-Bu, F), (M-2188, H, $CH_3$, H, sec-Bu, $CF_3$), (M-2189, H, $CH_3$, H, sec-Bu, Br), (M-2190, H, $CH_3$, H, sec-Bu, $CH_3$), (M-2191, H, CH₃, H, n-Pen, H), (M-2192, H, CH₃, H, n-Pen, Cl), (M-2193, H, CH₃, H, n-Pen, F), (M-2194, H, CH₃, H, n-Pen, CF₃), (M-2195, H, CH₃, H, n-Pen, Br), (M-2196, H, CH₃, H, n-Pen, CH₃), (M-2197, H, CH₃, H, c-Pen, H), (M-2198, H, CH₃, H, c-Pen, Cl), (M-2199, H, CH₃, H, c-Pen, F), (M-2200, H, CH₃, H, c-Pen, CF₃), (M-2201, H, CH₃, H, c-Pen, Br), (M-2202, H, CH₃, H, c-Pen, CH₃), (M-2203, H, CH₃, H, n-Hex, H), (M-2204, H, CH₃, H, n-Hex, Cl), (M-2205, H, CH₃, H, n-Hex, F), (M-2206, H, CH₃, H, n-Hex, CF₃), (M-2207, H, CH₃, H, n-Hex, Br), (M-2208, H, CH₃, H, n-Hex, CH₃), (M-2209, H, CH₃, H, c-Hex, H), (M-2210, H, CH₃, H, c-Hex, Cl), (M-2211, H, CH₃, H, c-Hex, F), (M-2212, H, CH₃, H, c-Hex, CF₃), (M-2213, H, CH₃, H, c-Hex, Br), (M-2214, H, CH₃, H, c-Hex, CH₃), (M-2215, H, CH₃, H, OH, H), (M-2216, H, CH₃, H, OH, Cl), (M-2217, H, CH₃, H, OH, F), (M-2218, H, CH₃, H, OH, CF₃), (M-2219, H, CH₃, H, OH, Br), (M-2220, H, CH₃, H, OH, CH₃), (M-2221, H, CH₃, H, EtO, H), (M-2222, H, CH₃, H, EtO, Cl), (M-2223, H, CH₃, H, EtO, F), (M-2224, H, CH₃, H, EtO, CF₃), (M-2225, H, CH₃, H, EtO, Br), (M-2226, H, CH₃, H, EtO, CH₃), (M-2227, H, CH₃, H, n-PrO, H), (M-2228, H, CH₃, H, n-PrO, Cl), (M-2229, H, CH₃, H, n-PrO, F), (M-2230, H, CH₃, H, n-PrO, CF₃), (M-2231, H, CH₃, H, n-PrO, Br), (M-2232, H, CH₃, H, n-PrO, CH₃), (M-2233, H, CH₃, H, PhO, H), (M-2234, H, CH₃, H, PhO, Cl), (M-2235, H, CH₃, H, PhO, F), (M-2236, H, CH₃, H, PhO, CF₃), (M-2237, H, CH₃, H, PhO, Br), (M-2238, H, CH₃, H, PhO, CH₃), (M-2239, H, CH₃, H, BnO, H), (M-2240, H, CH₃, H, BnO, Cl), (M-2241, H, CH₃, H, BnO, F), (M-2242, H, CH₃, H, BnO, CF₃), (M-2243, H, CH₃, H, BnO, Br), (M-2244, H, CH₃, H, BnO, CH₃), (M-2245, H, CH₃, H, PhCH₂CH₂O, H), (M-2246, H, CH₃, H, PhCH₂CH₂O, Cl), (M-2247, H, CH₃, H, PhCH₂CH₂O, F), (M-2248, H, CH₃, H, PhCH₂CH₂O, CF₃), (M-2249, H, CH₃, H, PhCH₂CH₂O, Br), (M-2250, H, CH₃, H, PhCH₂CH₂O, CH₃), (M-2251, H, CH₃, H, CF₃O, H), (M-2252, H, CH₃, H, CF₃O, Cl), (M-2253, H, CH₃, H, CF₃O, F), (M-2254, H, CH₃, H, CF₃O, CF₃), (M-2255, H, CH₃, H, CF₃O, Br), (M-2256, H, CH₃, H, CF₃O, CH₃), (M-2257, H, CH₃, H, Ph, H), (M-2258, H, CH₃, H, Ph, Cl), (M-2259, H, CH₃, H, Ph, F), (M-2260, H, CH₃, H, Ph, CF₃), (M-2261, H, CH₃, H, Ph, Br), (M-2262, H, CH₃, H, Ph, CH₃), (M-2263, H, CH₃, H, 4-F-Ph, H), (M-2264, H, CH₃, H, 4-F-Ph, Cl), (M-2265, H, CH₃, H, 4-F-Ph, F), (M-2266, H, CH₃, H, 4-F-Ph, CF₃), (M-2267, H, CH₃, H, 4-F-Ph, Br), (M-2268, H, CH₃, H, 4-F-Ph, CH₃), (M-2269, H, CH₃, H, 4-CF₃-Ph, H), (M-2270, H, CH₃, H, 4-CF₃-Ph, Cl), (M-2271, H, CH₃, H, 4-CF₃-Ph, F), (M-2272, H, CH₃, H, 4-CF₃-Ph, CF₃), (M-2273, H, CH₃, H, 4-CF₃-Ph, Br), (M-2274, H, CH₃, H, 4-CF₃-Ph, CH₃), (M-2275, H, CH₃, H, 4-(Me)₂N-Ph, H), (M-2276, H, CH₃, H, 4-(Me)₂N-Ph, Cl), (M-2277, H, CH₃, H, 4-(Me)₂N-Ph, F), (M-2278, H, CH₃, H, 4-(Me)₂N-Ph, CF₃), (M-2279, H, CH₃, H, 4-(Me)₂N-Ph, Br), (M-2280, H, CH₃, H, 4-(Me)₂N-Ph, CH₃), (M-2281, H, CH₃, H, 4-OH-Ph, H), (M-2282, H, CH₃, H, 4-OH-Ph, Cl), (M-2283, H, CH₃, H, 4-OH-Ph, F), (M-2284, H, CH₃, H, 4-OH-Ph, CF₃), (M-2285, H, CH₃, H, 4-OH-Ph, Br), (M-2286, H, CH₃, H, 4-OH-Ph, CH₃), (M-2287, H, CH₃, H, 3,4-di-F-Ph, H), (M-2288, H, CH₃, H, 3,4-di-F-Ph, Cl), (M-2289, H, CH₃, H, 3,4-di-F-Ph, F), (M-2290, H, CH₃, H, 3,4-di-F-Ph, CF₃), (M-2291, H, CH₃, H, 3,4-di-F-Ph, Br), (M-2292, H, CH₃, H, 3,4-di-F-Ph, CH₃), (M-2293, H, CH₃, H, 4-COOH-Ph, H), (M-2294, H, CH₃, H, 4-COOH-Ph, Cl), (M-2295, H, CH₃, H, 4-COOH-Ph, F), (M-2296, H, CH₃, H, 4-COOH-Ph, CF₃), (M-2297, H, CH₃, H, 4-COOH-Ph, Br), (M-2298, H, CH₃, H, 4-COOH-Ph, CH₃), (M-2299, H, CH₃, H, Bn, H), (M-2300, H, CH₃, H, Bn, Cl), (M-2301, H, CH₃, H, Bn, F), (M-2302, H, CH₃, H, Bn, CF₃), (M-2303, H, CH₃, H, Bn, Br), (M-2304, H, CH₃, H, Bn, CH₃), (M-2305, H, CH₃, H, 4-F-Bn, H), (M-2306, H, CH₃, H, 4-F-Bn, Cl), (M-2307, H, CH₃, H, 4-F-Bn, F), (M-2308, H, CH₃, H, 4-F-Bn, CF₃), (M-2309, H, CH₃, H, 4-F-Bn, Br), (M-2310, H, CH₃, H, 4-F-Bn, CH₃), (M-2311, H, CH₃, H, 2-Py, H), (M-2312, H, CH₃, H, 2-Py, Cl), (M-2313, H, CH₃, H, 2-Py, F), (M-2314, H, CH₃, H, 2-Py, CF₃), (M-2315, H, CH₃, H, 2-Py, Br), (M-2316, H, CH₃, H, 2-Py, CH₃), (M-2317, H, CH₃, H, 3-Py, H), (M-2318, H, CH₃, H, 3-Py, Cl), (M-2319, H, CH₃, H, 3-Py, F), (M-2320, H, CH₃, H, 3-Py, CF₃), (M-2321, H, CH₃, H, 3-Py, Br), (M-2322, H, CH₃, H, 3-Py, CH₃), (M-2323, H, CH₃, H, 4-Py, H), (M-2324, H, CH₃, H, 4-Py, Cl), (M-2325, H, CH₃, H, 4-Py, F), (M-2326, H, CH₃, H, 4-Py, CF₃), (M-2327, H, CH₃, H, 4-Py, Br), (M-2328, H, CH₃, H, 4-Py, CH₃), (M-2329, H, CH₃, H, 2-Th, H), (M-2330, H, CH₃, H, 2-Th, Cl), (M-2331, H, CH₃, H, 2-Th, F), (M-2332, H, CH₃, H, 2-Th, CF₃), (M-2333, H, CH₃, H, 2-Th, Br), (M-2334, H, CH₃, H, 2-Th, CH₃), (M-2335, H, CH₃, H, 3-Th, H), (M-2336, H, CH₃, H, 3-Th, Cl), (M-2337, H, CH₃, H, 3-Th, F), (M-2338, H, CH₃, H, 3-Th, CF₃), (M-2339, H, CH₃, H, 3-Th, Br), (M-2340, H, CH₃, H, 3-Th, CH₃), (M-2341, H, CH₃, H, pyrrazol-2-yl, H), (M-2342, H, CH₃, H, pyrrazol-2-yl, Cl), (M-2343, H, CH₃, H, pyrrazol-2-yl, F), (M-2344, H, CH₃, H, pyrrazol-2-yl, CF₃), (M-2345, H, CH₃, H, pyrrazol-2-yl, Br), (M-2346, H, CH₃, H, pyrrazol-2-yl, CH₃), (M-2347, H, CH₃, H, pyrrazol-3-yl, H), (M-2348, H, CH₃, H, pyrrazol-3-yl, Cl), (M-2349, H, CH₃, H, pyrrazol-3-yl, F), (M-2350, H, CH₃, H, pyrrazol-3-yl, CF₃), (M-2351, H, C₃, H, pyrrazol-3-yl, Br), (M-2352, H, CH₃, H, pyrrazol-3-yl, CH₃), (M-2353, H, CH₃, H, pyrimidin-2-yl, H), (M-2354, H, CH₃, H, pyrimidin-2-yl, Cl), (M-2355, H, CH₃, H, pyrimidin-2-yl, F), (M-2356, H, CH₃, H, pyrimidin-2-yl, CF₃), (M-2357, H, CH₃, H, pyrimidin-2-yl, Br), (M-2358, H, CH₃, H, pyrimidin-2-yl, CH₃), (M-2359, H, CH₃, H, pyrimidin-4-yl, H), (M-2360, H, CH₃, H, pyrimidin-4-yl, Cl), (M-2361, H, CH₃, H, pyrimidin-4-yl, F), (M-2362, H, CH₃, H, pyrimidin-4-yl, CF₃), (M-2363, H, CH₃, H, pyrimidin-4-yl, Br), (M-2364, H, CH₃, H, pyrimidin-4-yl, CH₃), (M-2365, H, CH, H, pyrimidin-5-yl, H), (M-2366, H, CH₃, H, pyrimidin-5-yl, Cl), (M-2367, H, CH₃, H, pyrimidin-5-yl, F), (M-2368, H, CH₃, H, pyrimidin-5-yl, CH₃), (M-2369, H, CH₃, H, pyrimidin-5-yl, Br), (M-2370, H, CH₃, H, pyrimidin-5-yl, CH₃), (M-2371, H, CH₃, H, HOOCCH₂CH₂CH₂, H), (M-2372, H, CH₃, H, HOOCCH₂CH₂CH₂, Cl), (M-2373, H, CH₃, H, HOOCCH₂CH₂CH₂, F), (M-2374, H, CH₃, H, HOOCCH₂CH₂CH₂, CF₃), (M-2375, H, CH₃, H, HOOCCH₂CH₂CH₂, Br), (M-2376, H, CH₃, H, HOOCCH₂CH₂CH₂, CH₃), (M-2377, H, CH₃, H, HOOCCH₂CH₂CH₂CH₂, H), (M-2378, H, CH₃, H, HOOCCH₂CH₂CH₂CH₂, Cl), (M-2379, H, CH₃, H, HOOCCH₂CH₂CH₂CH₂, F), (M-2380, H, CH₃, H, HOOCCH₂CH₂CH₂CH₂, CF₃), (M-2381, H, CH₃, H, HOOCCH₂CH₂CH₂CH₂, Br), (M-2382, H, CH₃, H, HOOCCH₂CH₂CH₂CH₂, CH₃), (M-2383, H, CH₃, H, (Me)₂NCOCH₂CH₂CH₂CH₂, H), (M-2384, H, CH₃, H, (Me)₂NCOCH₂CH₂CH₂CH₂, Cl), (M-2385, H, CH₃, H, (Me)₂NCOCH₂CH₂CH₂CH₂, F), (M-2386, H, CH₃, H, (Me)₂NCOCH₂CH₂CH₂CH₂, CF₃), (M-2387, H, CH₃, H, (Me)₂NCOCH₂CH₂CH₂CH₂, Br), (M-2388, H, CH₃, H, (Me)₂NCOCH₂CH₂CH₂CH₂, CH₃), (M-2389, H, CH₃, H, (Me)₂NCOCH₂CH₂CH₂CH₂CH₂, H), (M-2390, H, CH₃, H, (Me)₂NCOCH₂CH₂CH₂CH₂CH₂, Cl), (M-2391, H, CH₃, H, (Me)₂NCOCH₂CH₂CH₂CH₂CH₂, F), (M-2392, H, CH₃, H, (Me)₂NCOCH₂CH₂CH₂CH₂CH₂, CF₃), (M-2393, H, CH₃, H, (Me)₂NCOCH₂CH₂CH₂CH₂CH₂, Br), (M-2394, H, CH₃, H, (Me)₂NCOCH₂CH₂CH₂CH₂CH₂, CH₃), (M-2395, H, CH₃, H, MeOCH₂, H), (M-2396, H, CH₃, H, MeOCH₂, Cl), (M-2397, H, CH₃, H, MeOCH₂, F), (M-2398, H, CH₃, H, MeOCH₂, CF₃), (M-2399, H, CH₃, H, MeOCH₂, Br), (M-2400, H, CH₃, H, MeOCH₂, CH₃), (M-2401, H, CH₃, H, EtOCH₂, H), (M-2402, H, CH₃, H, EtOCH₂, Cl), (M-2403, H, CH₃, H, EtOCH₂, F), (M-2404, H, CH₃, H, EtOCH₂, CF₃), (M-2405, H, CH₃, H, EtOCH₂, Br), (M-2406, H, CH₃, H, EtOCH₂, CH₃), (M-2407, H, CH₃, H, EtOCH₂CH₂, H), (M-2408, H, CH₃, H, EtOCH₂CH₂, Cl), (M-2409, H, CH₃, H, EtOCH₂CH₂, F), (M-2410, H, CH₃, H, EtOCH₂CH₂, CF₃), (M-2411, H, CH₃, H, EtOCH₂CH₂, Br), (M-2412, H, CH₃, H, EtOCH₂CH₂, CH₃), (M-2413, H, CH₃, H, MeOCH₂CH₂OCH₂CH₂, H), (M-2414, H, CH₃, H, MeOCH₂CH₂OCH₂CH₂, Cl), (M-2415, H, CH₃, H, MeOCH₂CH₂OCH₂CH₂, F), (M-2416, H, CH₃, H, MeOCH₂CH₂OCH₂CH₂, CF₃), (M-2417, H, CH₃, H, MeOCH₂CH₂OCH₂CH₂, Br), (M-2418, H, CH₃, H, MeOCH₂CH₂OCH₂CH₂, CH₃), (M-2419, H, CH₃, H, MeOCH₂CH₂, H), (M-2420, H, CH₃, H, MeOCH₂CH₂, Cl), (M-2421, H, CH₃, H, MeOCH₂CH₂, F), (M2422, H, CH₃, H, MeOCH₂CH₂, CF₃), (M-2423, H, CH₃, H, MeOCH₂CH₂, Br), (M-2424, H, CH₃, H, MeOCH₂CH₂, CH₃), (M-2425, H, CH₃, H, HOCH₂, H), (M-2426, H, CH₃, H, HOCH₂, Cl), (M-2427, H, CH₃, H, HOCH₂, F), (M-2428, H, CH₃, H, HOCH₂, CF₃), (M-2429, H, CH₃, H, HOCH₂, Br), (M-2430, H, CH₃, H, HOCH₂, CH₃), (M-2431, H, CH₃, H, HOCH₂CH₂, H), (M-2432, H, CH₃, H, HOCH₂CH₂, Cl), (M-2433, H, CH₃, H, HOCH₂CH₂, F), (M-2434, H, CH₃, H, HOCH₂CH₂, CF₃), (M-2435, H, CH₃, H, HOCH₂CH₂, Br), (M-2436, H, CH₃, H, HOCH₂CH₂, CH₃), (M-2437, H, CH₃, H, HOCH₂CH₂CH₂, H), (M-2438, H, CH₃, H, HOCH₂CH₂CH₂, C), (M-2439, H, CH₃, H, HOCH₂CH₂CH₂, F), (M-2440, H, CH₃, H, HOCH₂CH₂CH₂, CF₃), (M-2441, H, CH₃, H, HOCH₂CH₂CH₂, Br), (M-2442, H, CH₃, H, HOCH₂CH₂CH₂, CH₃), (M-2443, H, CH₃, H, HOCH₂CH₂CH₂CH₂, H), (M-2444, H, CH₃, H, HOCH₂CH₂CH₂CH₂, C), (M-2445, H, CH₃, H, HOCH₂CH₂CH₂CH₂, F), (M-2446, H, CH₃, H, HOCH₂CH₂CH₂CH₂, CF₃), (M-2447, H, CH₃, H, HOCH₂CH₂CH₂CH₂, Br), (M-2448, H, CH₃, H, HOCH₂CH₂CH₂CH₂, CH₃), (M-2449, H, CH₃, H, HOCH₂CH₂CH₂CH₂CH₂, H), (M-2450, H, CH₃, H, HOCH₂CH₂CH₂CH₂CH₂, Cl), (M-2451, H, CH₃, H, HOCH₂CH₂CH₂CH₂CH₂, F), (M-2452, H, CH₃, H, HOCH₂CH₂CH₂CH₂CH₂, CF₃), (M-2453, H, CH₃, H, HOCH₂CH₂CH₂CH₂CH₂, Br), (M-2454, H, CH₃, H, HOCH₂CH₂CH₂CH₂CH₂, CH₃), (M-2455, H, CH₃, H, HOCH₂CH₂OCH₂CH₂, H), (M-2456, H, CH₃, H, HOCH₂CH₂OCH₂CH₂, Cl), (M-2457, H, CH₃, H, HOCH₂CH₂OCH₂CH₂, F), (M-2458, H, CH₃, H, HOCH₂CH₂OCH₂CH₂, CF₃), (M-2459, H, CH₃, H, HOCH₂CH₂OCH₂CH₂, Br), (M-2460, H, CH₃, H, HOCH₂CH₂OCH₂CH₂, CH₃), (M-2461, H, CH₃, H, (Me)₂N, H), (M-2462, H, CH₃, H, (Me)₂N, Cl), (M-2463, H, CH₃, H, (Me)₂N, F), (M-2464, H, CH₃, H, (Me)₂N, CF₃), (M-2465, H, CH₃, H, (Me)₂N, Br), (M-2466, H, CH₃, H, (Me)₂N, CH₃), (M-2467, H, CH₃, H, piperidin-4-yl-methyl, H), (M-2468, H, CH₃, H, piperidin-4-yl-methyl, Cl), (M-2469, H, CH₃, H, piperidin-4-yl-methyl, F), (M-2470, H, CH₃, H, piperidin-4-yl-methyl, CF₃), (M-2471, H, CH₃, H, piperidin-4-yl-methyl, Br), (M-2472, H, CH₃, H, piperidin-4-yl-methyl, CH₃), (M-2473, H, CH₃, H, cyclohexylmethyl, H), (M-2474, H, CH₃, H, cyclohexylmethyl, Cl), (M-2475, H, CH₃, H, cyclohexylmethyl, F), (M-2476, H, CH₃, H, cyclohexylmethyl, CF₃), (M-2477, H, CH₃, H, cyclohexylmethyl, Br), (M-2478, H, CH₃, H, cyclohexylmethyl, CH₃), (M-2479, H, CH₃, F, H, H), (M-2480, H, CH₃, F, H, Cl), (M-2481, H, CH₃, F, H, F), (M-2482, H, CH₃, F, H, CF₃), (M-2483, H, CH₃, F, H, Br), (M-2484, H, CH₃, F, H, CH₃), (M-2485, H, CH₃, F, F, H), (M-2486, H, CH₃, F, F, Cl), (M-2487, H, CH₃, F, F, F), (M-2488, H, CH₃, F, F, CF₃), (M-2489, H, CH₃, F, F, Br), (M-2490, H, CH₃, F, F, CH₃), (M-2491, H, CH₃, F, Cl, H), (M-2492, H, CH₃, F, Cl, Cl), (M-2493, H, CH₃, F, Cl, F), (M-2494, H, CH₃, F, Cl, CF₃), (M-2495, H, CH₃, F, Cl, Br), (M-2496, H, CH₃, F, Cl, CH₃), (M-2497, H, CH₃, F, CH₃, H), (M-2498, H, CH₃, F, CH₃, Cl), (M-2499, H, CH₃, F, CH₃, F), (M-2500, H, CH₃, F, CH₃, CF₃), (M-2501, H, CH₃, F, CH₃, Br), (M-2502, H, CH₃, F, CH₃, CH₃), (M-2503, H, CH₃, F, Et, H), (M-2504, H, CH₃, F, Et, Cl), (M-2505, H, CH₃, F, Et, F), (M-2506, H, CH₃, F, Et, CF₃), (M-2507, H, CH₃, F, Et, Br), (M-2508, H, CH₃, F, Et, CH₃), (M-2509, H, CH₃, F, n-Pr, H), (M-2510, H, CH₃, F, n-Pr, Cl), (M-2511, H, CH₃, F, n-Pr, F), (M-2512, H, CH₃, F, n-Pr, CF₃), (M-2513, H, CH₃, F, n-Pr, Br), (M-2514, H, CH₃, F, n-Pr, CH₃), (M-2515, H, CH₃, F, c-Pr, H), (M-2516, H, CH₃, F, c-Pr, Cl), (M-2517, H, CH₃, F, c-Pr, F), (M-2518, H, CH₃, F, c-Pr, CF₃), (M-2519, H, CH₃, F, c-Pr, Br), (M-2520, H, CH₃, F, c-Pr, CH₃), (M-2521, H, CH₃, F, i-Pr, H), (M-2522, H, CH₃, F, i-Pr, Cl), (M-2523, H, CH₃, F, i-Pr, F), (M-2524, H, CH₃, F, i-Pr, CF₃), (M-2525, H, CH₃, F, i-Pr, Br), (M-2526, H, CH₃, F, i-Pr, CH₃), (M-2527, H, CH₃, F, n-Bu, H), (M-2528, H, CH₃, F, n-Bu, Cl), (M-2529, H, CH₃, F, n-Bu, F), (M-2530, H, CH₃, F, n-Bu, CF₃), (M-2531, H, CH₃, F, n-Bu, Br), (M-2532, H, CH₃, F, n-Bu, CH₃), (M-2533, H, CH₃, F, i-Bu, H), (M-2534, H, CH₃, F, i-Bu, Cl), (M-2535, H, CH₃, F, i-Bu, F), (M-2536, H, CH₃, F, i-Bu, CF₃), (M-2537, H, CH₃, F, i-Bu, Br), (M-2538, H, CH₃, F, i-Bu, CH₃), (M-2539, H, CH₃, F, sec-Bu, H), (M-2540, H, CH₃, F, sec-Bu, Cl), (M-2541, H, CH₃, F, sec-Bu, F), (M-2542, H, CH₃, F, sec-Bu, CF₃), (M-2543, H, CH₃, F, sec-Bu, Br), (M-2544, H, CH₃, F, sec-Bu, CH₃), (M-2545, H, CH₃, F, n-Pen, H), (M-2546, H, CH₃, F, n-Pen, Cl), (M-2547, H, CH₃, F, n-Pen, F), (M-2548, H, CH₃, F, n-Pen, CF₃), (M-2549, H, CH₃, F, n-Pen, Br), (M-2550, H, CH₃, F, n-Pen, CH₃), (M-2551, H, CH₃, F, c-Pen, H), (M-2552, H, CH₃, F, c-Pen, Cl), (M-2553, H, CH₃, F, c-Pen, F), (M-2554, H, CH₃, F, c-Pen, CF₃), (M-2555, H, CH₃, F, c-Pen, Br), (M-2556, H, CH₃, F, c-Pen, CH₃), (M-2557, H, CH₃, F, n-Hex, H), (M-2558, H, CH₃, F, n-Hex, Cl), (M-2559, H, CH₃, F, n-Hex, F), (M-2560, H, CH₃, F, n-Hex, CF₃), (M-2561, H, CH₃, F, n-Hex, Br), (M-2562, H, CH₃, F, n-Hex, CH₃), (M-2563, H, CH₃, F, c-Hex, H), (M-2564, H, CH₃, F, c-Hex, Cl), (M-2565, H, CH₃, F, c-Hex, F), (M-2566, H, CH₃, F, c-Hex, CF₃), (M-2567, H, CH₃, F, c-Hex, Br), (M-2568, H, CH₃, F, c-Hex, CH₃), (M-2569, H, CH₃, F, OH, H), (M-2570, H, CH₃, F, OH, Cl), (M-2571, H, CH₃, F, OH, F), (M-2572, H, CH₃, F, OH, CF₃), (M-2573, H, CH₃, F, OH, Br), (M-2574, H, CH₃, F, OH, CH₃), (M-2575, H, CH₃, F, EtO, H), (M-2576, H, CH₃, F, EtO, Cl), (M-2577, H, CH₃, F, EtO, F), (M-2578, H, CH₃, F, EtO, CF₃), (M-2579, H, CH₃, F, EtO, Br), (M-2580, H, CH₃, F, EtO, CH₃), (M-2581, H, CH₃, F, n-PrO, H), (M-2582, H, CH₃, F, n-PrO, Cl), (M-2583, H, CH₃, F, n-PrO, F), (M-2584, H, CH₃, F, n-PrO, CF₃), (M-2585, H, CH₃, F, n-PrO, Br), (M-2586, H, CH₃, F, n-PrO, CH₃), (M-2587, H, C₃, F, PhO, H), (M-2588, H, CH₃, F, PhO, Cl), (M-2589, H, CH₃, F, PhO, F), (M-2590, H, CH₃, F, PhO, CF₃), (M-2591, H, CH₃, F, PhO, Br), (M-2592, H, CH₃, F, PhO, CH₃), (M-2593, H, CH₃, F, BnO, H), (M-2594, H, CH₃, F, BnO, Cl), (M-2595, H, CH₃, F, BnO, F), (M-2596, H, CH₃, F, BnO, CF₃), (M-2597, H, CH₃, F, BnO, Br), (M-2598, H, CH₃, F, BnO, CH₃), (M-2599, H, CH₃, F, PhCH₂CH₂O, H), (M-2600, H, CH₃, F, PhCH₂CH₂O, Cl), (M-2601, H, CH₃, F, PhCH₂CH₂O, F), (M-2602, H, CH₃, F, PhCH₂CH₂O, CF₃), (M-2603, H, CH₃, F, PhCH₂CH₂O, Br), (M-2604, H, CH₃, F, PhCH₂CH₂O, CH₃), (M-2605, H, CH₃, F, CF₃O, H), (M-2606, H, CH₃, F, CF₃O, Cl), (M-2607, H, CH₃, F, CF₃O, F), (M-2608, H, CH₃, F, CF₃O, CF₃), (M-2609, H, CH₃, F, CF₃O, Br), (M-2610, H, CH₃, F, CF₃O, CH₃), (M-2611, H, CH₃, F, Ph, H), (M-2612, H, CH₃, F, Ph, Cl), (M-2613, H, CH₃, F, Ph, F), (M-2614, H, CH₃, F, Ph, CF₃), (M-2615, H, CH₃, F, Ph, Br), (M-2616, H, CH₃, F, Ph, CH₃), (M-2617, H, CH₃, F, 4-F-Ph, H), (M-2618, H, CH₃, F, 4-F-Ph, Cl), (M-2619, H, CH₃, F, 4-F-Ph, F), (M-2620, H, CH₃, F, 4-F-Ph, CF₃), (M-2621, H, CH₃, F, 4-F-Ph, Br), (M-2622, H, CH₃, F, 4-F-Ph, CH₃), (M-2623, H, CH₃, F, 4-CF₃-Ph, H), (M-2624, H, CH₃, F, 4-CF₃-Ph, Cl), (M-2625, H, CH₃, F, 4-CF₃-Ph, F), (M-2626, H, CH₃, F, 4-CF₃-Ph, CF₃), (M-2627, H, CH₃, F, 4-CF₃-Ph, Br), (M-2628, H, CH₃, F, 4-CF₃-Ph, CH₃), (M-2629, H, CH₃, F, 4-(Me)₂N-Ph, H), (M-2630, H, CH₃, F, 4-(Me)₂N-Ph, Cl), (M-2631, H, CH₃, F, 4-(Me)₂N-Ph, F), (M-2632, H, CH₃, F, 4-(Me)₂N-Ph, CF₃), (M-2633, H, CH₃, F, 4-(Me)₂N-Ph, Br), (M-2634, H, CH₃, F, 4-(Me)₂N-Ph, CH₃), (M-2635, H, CH₃, F, 4-OH-Ph, H), (M-2636, H, CH₃, F, 4-OH-Ph, Cl), (M-2637, H, CH₃, F, 4-OH-Ph, F), (M-2638, H, CH₃, F, 4-OH-Ph, CF₃), (M-2639, H, CH₃, F, 4-OH-Ph, Br), (M-2640, H, CH₃, F, 4-OH-Ph, CH₃), (M-2641, H, CH₃, F, 3,4-di-F-Ph, H), (M-2642, H, CH₃, F, 3,4-di-F-Ph, Cl), (M-2643, H, CH₃, F, 3,4-di-F-Ph, F), (M-2644, H, CH₃, F, 3,4-di-F-Ph, CF₃), (M-2645, H, CH₃, F, 3,4-di-F-Ph, Br), (M-2646, H, CH₃, F, 3,4-di-F-Ph, CH₃), (M-2647, H, CH₃, F, 4-COOH-Ph, H), (M-2648, H, CH₃, F, 4-COOH-Ph, Cl), (M-2649, H, CH₃, F, 4-COOH-Ph, F), (M-2650, H, CH₃, F, 4-COOH-Ph, CF₃), (M-2651, H, CH₃, F, 4-COOH-Ph, Br), (M-2652, H, CH₃, F, 4-COOH-Ph, CH₃), (M-2653, H, CH₃, F, Bn, H), (M-2654, H, CH₃, F, Bn, Cl), (M-2655, H, CH₃, F, Bn, F), (M-2656, H, CH₃, F, Bn, CF₃), (M-2657, H, CH₃, F, Bn, Br), (M-2658, H, CH₃, F, Bn, CH₃), (M-2659, H, CH₃, F, 4-F-Bn, H), (M-2660, H, CH₃, F, 4-F-Bn, Cl), (M-2661, H, CH₃, F, 4-F-Bn, F), (M-2662, H, CH₃, F, 4-F-Bn, CF₃), (M-2663, H, CH₃, F, 4-F-Bn, Br), (M-2664, H, CH₃, F, 4-F-Bn, CH₃), (M-2665, H, CH₃, F, 2-Py, H), (M-2666, H, CH₃, F, 2-Py, Cl), (M-2667, H, CH₃, F, 2-Py, F), (M-2668, H, CH₃, F, 2-Py, CF₃), (M-2669, H, CH₃, F, 2-Py, Br), (M-2670, H, CH₃, F, 2-Py, CH₃), (M-2671, H, CH₃, F, 3-Py, H), (M-2672, H, CH₃, F, 3-Py, Cl), (M-2673, H, CH₃, F, 3-Py, F), (M-2674, H, CH₃, F, 3-Py, CF₃), (M-2675, H, CH₃, F, 3-Py, Br), (M-2676, H, CH₃, F, 3-Py, CH₃), (M-2677, H, CH₃, F, 4-Py, H), (M-2678, H, CH₃, F, 4-Py, Cl), (M-2679, H, CH₃, F, 4-Py, F), (M-2680, H, CH₃, F, 4-Py, CF₃), (M-2681, H, CH₃, F, 4-Py, Br), (M-2682, H, CH₃, F, 4-Py, CH₃), (M-2683, H, CH₃, F, 2-Th, H), (M-2684, H, CH₃, F, 2-Th, Cl), (M-2685, H, CH₃, F, 2-Th, F), (M-2686, H, CH₃, F, 2-Th, CF₃), (M-2687, H, CH₃, F, 2-Th, Br), (M-2688, H, CH₃, F, 2-Th, CH₃), (M-2689, H, CH₃, F, 3-Th, H), (M-2690, H, CH₃, F, 3-Th, Cl), (M-2691, H, CH₃, F, 3-Th, F), (M-2692, H, CH₃, F, 3-Th, CF₃), (M-2693, H, CH₃, F, 3-Th, Br), (M-2694, H, CH₃, F, 3-Th, CH₃), (M-2695, H, CH₃, F, pyrrazol-2-yl, H), (M-2696, H, CH₃, F, pyrrazol-2-yl, Cl), (M-2697, H, CH₃, F, pyrrazol-2-yl, F), (M-2698, H, CH₃, F, pyrrazol-2-yl, CF₃), (M-2699, H, CH₃, F, pyrrazol-2-yl, Br), (M-2700, H, CH₃, F, pyrrazol-2-yl, CH₃), (M-2701, H, CH₃, F, pyrrazol-3-yl, H), (M-2702, H, CH₃, F, pyrrazol-3-yl, Cl), (M-2703, H, CH₃, F, pyrrazol-3-yl, F), (M-2704, H, CH₃, F, pyrrazol-3-yl, CF₃), (M-2705, H, CH₃, F, pyrrazol-3-yl, Br), (M-2706, H, CH₃, F, pyrrazol-3-yl, CH₃), (M-2707, H, CH₃, F, pyrimidin-2-yl, H), (M-2708, H, CH₃, F, pyrimidin-2-yl, Cl), (M-2709, H, CH₃, F, pyrimidin-2-yl, F), (M-2710, H, CH₃, F, pyrimidin-2-yl, CF₃), (M-2711, H, CH₃, F, pyrimidin-2-yl, Br), (M-2712, H, CH₃, F, pyrimidin-2-yl, CH₃), (M-2713, H, CH₃, F, pyrimidin-4-yl, H), (M-2714, H, CH₃, F, pyrimidin-4-yl, Cl), (M-2715, H, CH₃, F, pyrimidin-4-yl, F), (M-2716, H, CH₃, F, pyrimidin-4-yl, CF₃), (M-2717, H, CH₃, F, pyrimidin-4-yl, Br), (M-2718, H, CH₃, F, pyrimidin-4-yl, CH₃), (M-2719, H, CH₃, F, pyrimidin-5-yl, H), (M-2720, H, CH₃, F, pyrimidin-5-yl, Cl), (M-2721, H, CH₃, F, pyrimidin-5-yl, F), (M-2722, H, CH₃, F, pyrimidin-5-yl, CF₃), (M-2723, H, CH₃, F, pyrimidin-5-yl, Br), (M-2724, H, CH₃, F, pyrimidin-5-yl, CH₃), (M-2725, H, CH₃, F, HOOCCH₂CH₂CH₂, H), (M-2726, H, CH₃, F, HOOCCH₂CH₂CH₂, Cl), (M-2727, H, CH₃, F, HOOCCH₂CH₂CH₂, F), (M-2728, H, CH₃, F, HOOCCH₂CH₂CH₂, CF₃), (M-2729, H, CH₃, F, HOOCCH₂CH₂CH₂, Br), (M-2730, H, CH₃, F, HOOCCH₂CH₂CH₂, CH₃), (M-2731, H, CH₃, F, HOOCCH₂CH₂CH₂CH₂, H), (M-2732, H, CH₃, F, HOOCCH₂CH₂CH₂CH₂, Cl), (M-2733, H, CH₃, F, HOOCCH₂CH₂CH₂CH₂, F), (M-2734, H, CH₃, F, HOOCCH₂CH₂CH₂CH₂, CF₃), (M-2735, H, CH₃, F, HOOCCH₂CH₂CH₂CH₂, Br), (M-2736, H, CH₃, F, HOOCCH₂CH₂CH₂CH₂, CH₃), (M-2737, H, CH₃, F, (Me)₂NCOCH₂CH₂CH₂CH₂, H), (M-2738, H, CH₃, F, (Me)₂NCOCH₂CH₂CH₂CH₂, Cl), (M-2739, H, CH₃, F, (Me)₂NCOCH₂CH₂CH₂CH₂, F), (M-2740, H, CH₃, F, (Me)₂NCOCH₂CH₂CH₂CH₂, CF₃), (M-2741, H, CH₃, F, (Me)₂NCOCH₂CH₂CH₂CH₂, Br), (M-2742, H, CH₃, F, (Me)₂NCOCH₂CH₂CH₂CH₂, CH₃), (M-2743, H, CH₃, F, (Me)₂NCOCH₂CH₂CH₂CH₂CH₂, H), (M-2744, H, CH₃, F, (Me)₂NCOCH₂CH₂CH₂CH₂CH₂, Cl), (M-2745, H, CH₃, F, (Me)₂NCOCH₂CH₂CH₂CH₂CH₂, F), (M-2746, H, CH₃, F, (Me)₂NCOCH₂CH₂CH₂CH₂CH₂, CF₃), (M-2747, H, CH₃, F, (Me)₂NCOCH₂CH₂CH₂CH₂CH₂, Br), (M-2748, H, CH₃, F, (Me)₂NCOCH₂CH₂CH₂CH₂CH₂, CH₃), (M-2749, H, CH₃, F, MeOCH₂, H), (M-2750, H, CH₃, F, MeOCH₂, Cl), (M-2751, H, CH₃, F, MeOCH₂, F), (M-2752, H, CH₃, F, MeOCH₂, CF₃), (M-2753, H, CH₃, F, MeOCH₂, Br), (M-2754, H, CH₃, F, MeOCH₂, CH₃), (M-2755, H, CH₃, F, EtOCH₂, H), (M-2756, H, CH₃, F, EtOCH₂, Cl), (M-2757, H, CH₃, F, EtOCH₂, F), (M-2758, H, CH₃, F, EtOCH₂, CF₃), (M-2759, H, CH₃, F, EtOCH₂, Br), (M-2760, H, CH₃, F, EtOCH₂, CH₃), (M-2761, H, CH₃, F, EtOCH₂CH₂, H), (M-2762, H, CH₃, F, EtOCH₂CH₂, Cl), (M-2763, H, CH₃, F, EtOCH₂CH₂, F), (M-2764, H, CH₃, F, EtOCH₂CH₂, CF₃), (M-2765, H, CH₃, F, EtOCH₂CH₂, Br), (M-2766, H, CH₃, F, EtOCH₂CH₂, CH₃), (M-2767, H, CH₃, F, MeOCH₂CH₂OCH₂CH₂, H), (M-2768, H, CH₃, F, MeOCH₂CH₂OCH₂CH₂, Cl), (M-2769, H, CH₃, F, MeOCH₂CH₂OCH₂CH₂, F), (M-2770, H, CH₃, F, MeOCH₂CH₂OCH₂CH₂, CF₃), (M-2771, H, CH₃, F, MeOCH₂CH₂OCH₂CH₂, Br), (M-2772, H, CH₃, F, MeOCH₂CH₂OCH₂CH₂, CH₃), (M-2773, H, CH₃, F, MeOCH₂CH₂, H), (M-2774, H, CH₃, F, MeOCH₂CH₂, Cl), (M-2775, H, CH₃, F, MeOCH₂CH₂, F), (M-2776, H, CH₃, F, MeOCH₂CH₂, CF₃), (M-2777, H, CH₃, F, MeOCH₂CH₂, Br), (M-2778, H, CH₃, F, MeOCH₂CH₂, CH₃), (M-2779, H, CH₃, F, HOCH₂, H), (M-2780, H, CH₃, F, HOCH₂, Cl), (M-2781, H, CH₃, F, HOCH₂, F), (M-2782, H, CH₃, F, HOCH₂, CF₃), (M-2783, H, CH₃, F, HOCH₂, Br), (M-2784, H, CH₃, F, HOCH₂, CH₃), (M-2785, H, CH₃, F, HOCH₂CH₂, H), (M-2786, H, CH₃, F, HOCH₂CH₂, Cl), (M-2787, H, CH₃, F, HOCH₂CH₂, F), (M-2788, H, CH₃, F, HOCH₂CH₂, CF₃), (M-2789, H, CH₃, F, HOCH₂CH₂, Br), (M-2790, H, CH₃, F, HOCH₂CH₂, CH₃), (M-2791, H, CH₃, F, HOCH₂CH₂CH₂, H), (M-2792, H, CH₃, F, HOCH₂CH₂CH₂, Cl), (M-2793, H, CH₃, F, HOCH₂CH₂CH₂, F), (M-2794, H, CH₃, F, HOCH₂CH₂CH₂, CF₃), (M-2795, H, CH₃, F, HOCH₂CH₂CH₂, Br), (M-2796, H, CH₃, F, HOCH₂CH₂CH₂, CH₃), (M-2797, H, CH₃, F, HOCH₂CH₂CH₂CH₂, H), (M-2798, H, CH₃, F, HOCH₂CH₂CH₂CH₂, Cl), (M-2799, H, CH₃, F, HOCH₂CH₂CH₂CH₂, F), (M-2800, H, CH₃, F, HOCH₂CH₂CH₂CH₂, CF₃), (M-2801, H, CH₃, F, HOCH₂CH₂CH₂CH₂, Br), (M-2802, H, CH₃, F, HOCH₂CH₂CH₂CH₂, CH₃), (M-2803, H, CH₃, F, HOCH₂CH₂CH₂CH₂CH₂, H), (M-2804, H, CH₃, F, HOCH₂CH₂CH₂CH₂CH₂, Cl), (M-2805, H, CH₃, F, HOCH₂CH₂CH₂CH₂CH₂, F), (M-2806, H, CH₃, F, HOCH₂CH₂CH₂CH₂CH₂, CF₃), (M-2807, H, CH₃, F, HOCH₂CH₂CH₂CH₂CH₂, Br), (M-2808, H, CH₃, F, HOCH₂CH₂CH₂CH₂CH₂, CH₃), (M-2809, H, CH₃, F, HOCH₂CH₂OCH₂CH₂, H), (M-2810, H, CH₃, F, HOCH₂CH₂OCH₂CH₂, Cl), (M-2811, H, CH₃, F, HOCH₂CH₂OCH₂CH₂, F), (M-2812, H, CH₃, F, HOCH₂CH₂OCH₂CH₂, CF₃), (M-2813, H, CH₃, F, HOCH₂CH₂OCH₂CH₂, Br), (M-2814, H, CH₃, F, HOCH₂CH₂OCH₂CH₂, CH₃), (M-2815, H, CH₃, F, (Me)₂N, H), (M-2816, H, CH₃, F, (Me)₂N, Cl), (M-2817, H, CH₃, F, (Me)₂N, F), (M-2818, H, CH₃, F, (Me)₂N, CF₃), (M-2819, H, CH₃, F, (Me)₂N, Br), (M-2820, H, CH₃, F, (Me)₂N, CH₃), (M-2821, H, CH₃, F, piperidin-4-yl-methyl, H), (M-2822, H, CH₃, F, piperidin-4-yl-methyl, Cl), (M-2823, H, CH₃, F, piperidin-4-yl-methyl, F), (M-2824, H, CH₃, F, piperidin-4-yl-methyl, CF₃), (M-2825, H, CH₃, F, piperidin-4-yl-methyl, Br), (M-2826, H, CH₃, F, piperidin-4-yl-methyl, CH₃), (M-2827, H, CH₃, F, cyclohexylmethyl, H), (M-2828, H, CH₃, F, cyclohexylmethyl, Cl), (M-2829, H, CH₃, F, cyclohexylmethyl, F), (M-2830, F, cyclohexylmethyl, CF₃), (M-2831, H, CH₃, F, cyclohexylmethyl, Br), (M-2832, H, CH₃, F, cyclohexylmethyl, CH₃), (M-2833, H, CH₃, Cl, H, H), (M-2834, H, CH₃, Cl, H, Cl), (M-2835, H, CH₃, Cl, H, F), (M-2836, H, CH₃, Cl, H, CF₃), (M-2837, H, CH₃, Cl, H, Br), (M-2838, H, CH₃, Cl, H, CH₃), (M-2839, H, CH₃, Cl, F, H), (M-2840, H, CH₃, Cl, F, Cl), (M-2841, H, CH₃, Cl, F, F), (M-2842, H, CH₃, Cl, F, CF₃), (M-2843, H, CH₃, Cl, F, Br), (M-2844, H, CH₃, Cl, F, CH₃), (M-2845, H, CH₃, Cl, Cl, H), (M-2846, H, CH₃, Cl, Cl, Cl), (M-2847, H, CH₃, Cl, Cl, F), (M-2848, H, CH₃, Cl, Cl, CF₃), (M-2849, H, CH₃, Cl, Cl, Br), (M-2850, H, CH₃, Cl, Cl, CH₃), (M-2851, H, CH₃, Cl, CH₃, H), (M-2852, H, CH₃, Cl, CH₃, Cl), (M-2853, H, CH₃, Cl, CH₃, F), (M-2854, H, CH₃, Cl, CH₃, CF₃), (M-2855, H, CH₃, Cl, CH₃, Br), (M-2856, H, CH₃, Cl, CH₃, CH₃), (M-2857, H, CH₃, Cl, Et, H), (M-2858, H, CH₃, Cl, Et, Cl), (M-2859, H, CH₃, Cl, Et, F), (M-2860, H, CH₃, Cl, Et, CF₃), (M-2861, H, CH₃, Cl, Et, Br), (M-2862, H, CH₃, Cl, Et, CH₃), (M-2863, H, CH₃, Cl, n-Pr, H), (M-2864, H, CH₃, Cl, n-Pr, Cl), (M-2865, H, CH₃, Cl, n-Pr, F), (M-2866, H, CH₃, Cl, n-Pr, CF₃), (M-2867, H, CH₃, Cl, n-Pr, Br), (M-2868, H, CH₃, Cl, n-Pr, CH₃), (M-2869, H, CH₃, Cl, c-Pr, H), (M-2870, H, CH₃, Cl, c-Pr, Cl), (M-2871, H, CH₃, Cl, c-Pr, F), (M-2872, H, CH₃, Cl, c-Pr, CF₃), (M-2873, H, CH₃, Cl, c-Pr, Br), (M-2874, H, CH₃, Cl, c-Pr, CH₃), (M-2875, H, CH₃, Cl, i-Pr, H), (M-2876, H, CH₃, Cl, i-Pr, Cl), (M-2877, H, CH₃, Cl, i-Pr, F), (M-2878, H, CH₃, Cl, i-Pr, CF₃), (M-2879, H, CH₃, Cl, i-Pr, Br), (M-2880, H, CH₃, Cl, i-Pr, CH₃), (M-2881, H, CH₃, Cl, n-Bu, H), (M-2882, H, CH₃, Cl, n-Bu, Cl), (M-2883, H, CH₃, Cl, n-Bu, F), (M-2884, H, CH₃, Cl, n-Bu, CF₃), (M-2885, H, CH₃, Cl, n-Bu, Br), (M-2886, H, CH₃, Cl, n-Bu, CH₃), (M-2887, H, CH₃, Cl, i-Bu, H), (M-2888, H, CH₃, Cl, i-Bu, Cl), (M-2889, H, CH₃, Cl, i-Bu, F), (M-2890, H, CH₃, Cl, i-Bu, CF₃), (M-2891, H, CH₃, Cl, i-Bu, Br), (M-2892, H, CH₃, Cl, i-Bu, CH₃), (M-2893, H, CH₃, Cl, sec-Bu, H), (M-2894, H, CH₃, Cl, sec-Bu, Cl), (M-2895, H, CH₃, Cl, sec-Bu, F), (M-2896, H, CH₃, Cl, sec-Bu, CF₃), (M-2897, H, CH₃, Cl, sec-Bu, Br), (M-2898, H, CH₃, Cl, sec-Bu, CH₃), (M-2899, H, CH₃, Cl, n-Pen, H), (M-2900, H, CH₃, Cl, n-Pen, Cl), (M-2901, H, CH₃, Cl, n-Pen, F), (M-2902, H, CH₃, Cl, n-Pen, CF₃), (M-2903, H, CH₃, Cl, n-Pen, Br), (M-2904, H, CH₃, Cl, n-Pen, CH₃), (M-2905, H, CH₃, Cl, c-Pen, H), (M-2906, H, CH₃, Cl, c-Pen, Cl), (M-2907, H, CH₃, Cl, c-Pen, F), (M-2908, H, CH₃, Cl, c-Pen, CF₃), (M-2909, H, CH₃, Cl, c-Pen, Br), (M-2910, H, CH₃, Cl, c-Pen, CH₃), (M-2911, H, CH₃, Cl, n-Hex, H), (M-2912, H, CH₃, Cl, n-Hex, Cl), (M-2913, H, CH₃, Cl, n-Hex, F), (M-2914, H, CH₃, Cl, n-Hex, CF₃), (M-2915, H, CH₃, Cl, n-Hex, Br), (M-2916, H, CH₃, Cl, n-Hex, CH₃), (M-2917, H, CH₃, Cl, c-Hex, H), (M-2918, H, CH₃, Cl, c-Hex, Cl), (M-2919, H, CH₃, Cl, c-Hex, F), (M-2920, H, CH₃, Cl, c-Hex, CF₃), (M-2921, H, CH₃, Cl, c-Hex, Br), (M-2922, H, CH₃, Cl, c-Hex, CH₃), (M-2923, H, CH₃, Cl, OH, H), (M-2924, H, CH₃, Cl, OH, Cl), (M-2925, H, CH₃, Cl, OH, F), (M-2926, H, CH₃, Cl, OH, CF₃), (M-2927, H, CH₃, Cl, OH, Br), (M-2928, H, CH₃, Cl, OH, CH₃), (M-2929, H, CH₃, Cl, EtO, H), (M-2930, H, CH₃, Cl, EtO, Cl), (M-2931, H, CH₃, Cl, EtO, F), (M-2932, H, CH₃, Cl, EtO, CF₃), (M-2933, H, CH₃, Cl, EtO, Br), (M-2934, H, CH₃, Cl, EtO, CH₃), (M-2935, H, CH₃, Cl, n-PrO, H), (M-2936, H, CH₃, Cl, n-PrO, Cl), (M-2937, H, CH₃, Cl, n-PrO, F), (M-2938, H, CH₃, Cl, n-PrO, CF₃), (M-2939, H, CH₃, Cl, n-PrO, Br), (M-2940, H, CH₃, Cl, n-PrO, CH₃), (M-2941, H, CH₃, Cl, PhO, H), (M-2942, H, CH₃, Cl, PhO, Cl), (M-2943, H, CH₃, Cl, PhO, F), (M-2944, H, CH₃, Cl, PhO, CF₃), (M-2945, H, CH₃, Cl, PhO, Br), (M-2946, H, CH₃, Cl, PhO, CH₃), (M-2947, H, CH₃, Cl, BnO, H), (M-2948, H, CH₃, Cl, BnO, Cl), (M-2949, H, CH₃, Cl, BnO, F), (M-2950, H, CH₃, Cl, BnO, CF₃), (M-2951, H, CH₃, Cl, BnO, Br), (M-2952, H, CH₃, Cl, BnO, CH₃), (M-2953, H, CH₃, Cl, PhCH₂CH₂O, H), (M-2954, H, CH₃, Cl, PhCH₂CH₂O, Cl), (M-2955, H, CH₃, Cl, PhCH₂CH₂O, F), (M-2956, H, CH₃, Cl, PhCH₂CH₂O, CF₃), (M-2957, H, CH₃, Cl, PhCH₂CH₂O, Br), (M-2958, H, CH₃, Cl, PhCH₂CH₂O, CH₃), (M-2959, H, CH₃, Cl, CF₃O, H), (M-2960, H, CH₃, Cl, CF₃O, Cl), (M-2961, H, CH₃, Cl, CF₃O, F), (M-2962, H, CH₃, Cl, CF₃O, CF₃), (M-2963, H, CH₃, Cl, CF₃O, Br), (M-2964, H, CH₃, Cl, CF₃O, CH₃), (M-2965, H, CH₃, Cl, Ph, H), (M-2966, H, CH₃, Cl, Ph, Cl), (M-2967, H, CH₃, Cl, Ph, F), (M-2968, H, CH₃, Cl, Ph, CF₃), (M-2969, H, CH₃, Cl, Ph, Br), (M-2970, H, CH₃, Cl, Ph, CH₃), (M-2971, H, CH₃, Cl, 4-F-Ph, H), (M-2972, H, CH₃, Cl, 4-F-Ph, Cl), (M-2973, H, CH₃, Cl, 4-F-Ph, F), (M-2974, H, CH₃, Cl, 4-F-Ph, CF₃), (M-2975, H, CH₃, Cl, 4-F-Ph, Br), (M-2976, H, CH₃, Cl, 4-F-Ph, CH₃), (M-2977, H, CH₃, Cl, 4-CF₃-Ph, H), (M-2978, H, CH₃, Cl, 4-CF₃-Ph, Cl), (M-2979, H, CH₃, Cl, 4-CF₃-Ph, F), (M-2980, H, CH₃, Cl, 4-CF₃-Ph, CF₃), (M-2981, H, CH₃, Cl, 4-CF₃-Ph, Br), (M-2982, H, CH₃, Cl, 4-CF₃-Ph, CH₃), (M-2983, H, CH₃, Cl, 4-(Me)₂N-Ph, H), (M-2984, H, CH₃, Cl, 4-(Me)₂N-Ph, Cl), (M-2985, H, CH₃, Cl, 4-(Me)₂N-Ph, F), (M-2986, H, CH₃, Cl, 4-(Me)₂N-Ph, CF₃), (M-2987, H, CH₃, Cl, 4-(Me)₂N-Ph, Br), (M-2988, H, CH₃, Cl, 4-(Me)₂N-Ph, CH₃), (M-2989, H, CH₃, Cl, 4-OH-Ph, H), (M-2990, H, CH₃, Cl, 4-OH-Ph, Cl), (M-2991, H, CH₃, Cl, 4-OH-Ph, F), (M-2992, H, CH₃, Cl, 4-OH-Ph, CF₃), (M-2993, H, CH₃, Cl, 4-OH-Ph, Br), (M-2994, H, CH₃, Cl, 4-OH-Ph, CH₃), (M-2995, H, CH₃, Cl, 3,4-di-F-Ph, H), (M-2996, H, CH₃, Cl, 3,4-di-F-Ph, Cl), (M-2997, H, CH₃, Cl, 3,4-di-F-Ph, F), (M-2998, H, CH₃, Cl, 3,4-di-F-Ph, CF₃), (M-2999, H, CH₃, Cl, 3,4-di-F-Ph, Br), (M-3000, H, CH₃, Cl, 3,4-di-F-Ph, CH₃), (M-3001, H, CH₃, Cl, 4-COOH-Ph, H), (M-3002, H, CH₃, Cl, 4-COOH-Ph, Cl), (M-3003, H, CH₃, Cl, 4-COOH-Ph, F), (M-3004, H, CH₃, Cl, 4-COOH-Ph, CF₃), (M-3005, H, CH₃, Cl, 4-COOH-Ph, Br), (M-3006, H, CH₃, Cl, 4-COOH-Ph, CH₃), (M-3007, H, CH₃, Cl, Bn, H), (M-3008, H, CH₃, Cl, Bn, Cl), (M-3009, H, CH₃, Cl, Bn, F), (M-3010, H, CH₃, Cl, Bn, CF₃), (M-3011, H, CH₃, Cl, Bn, Br), (M-3012, H, CH₃, Cl, Bn, CH₃), (M-3013, H, CH₃, Cl, 4-F-Bn, H), (M-3014, H, CH₃, Cl, 4-F-Bn, Cl), (M-3015, H, CH₃, Cl, 4-F-Bn, F), (M-3016, H, CH₃, Cl, 4-F-Bn, CF₃), (M-3017, H, CH₃, Cl, 4-F-Bn, Br), (M-3018, H, CH₃, Cl, 4-F-Bn, CH₃), (M-3019, H, CH₃, Cl, 2-Py, H), (M-3020, H, CH₃, Cl, 2-Py, Cl), (M-3021, H, CH₃, Cl, 2-Py, F), (M-3022, H, CH₃, Cl, 2-Py, CF₃), (M-3023, H, CH₃, Cl, 2-Py, Br), (M-3024, H, CH₃, Cl, 2-Py, CH₃), (M-3025, H, CH₃, Cl, 3-Py, H), (M-3026, H, CH₃, Cl, 3-Py, Cl), (M-3027, H, CH₃, Cl, 3-Py, F), (M-3028, H, CH₃, Cl, 3-Py, CF₃), (M-3029, H, CH₃, Cl, 3-Py, Br), (M-3030, H, CH₃, Cl, 3-Py, CH₃), (M-3031, H, CH₃, Cl, 4-Py, H), (M-3032, H, CH₃, Cl, 4-Py, Cl), (M-3033, H, CH₃, Cl, 4-Py, F), (M-3034, H, CH₃, Cl, 4-Py, CF₃), (M-3035, H, CH₃, Cl, 4-Py, Br), (M-3036, H, CH₃, Cl, 4-Py, CH₃), (M-3037, H, CH₃, Cl, 2-Th, H), (M-3038, H, CH₃, Cl, 2-Th, Cl), (M-3039, H, CH₃, Cl, 2-Th, F), (M-3040, H, CH₃, Cl, 2-Th, CF₃), (M-3041, H, CH₃, Cl, 2-Th, Br), (M-3042, H, CH₃, Cl, 2-Th, CH₃), (M-3043, H, CH₃, Cl, 3-Th, H), (M-3044, H, CH₃, Cl, 3-Th, Cl), (M-3045, H, CH₃, Cl, 3-Th, F), (M-3046, H, CH₃, Cl, 3-Th, CF₃), (M-3047, H, CH₃, Cl, 3-Th, Br), (M-3048, H, CH₃, Cl, 3-Th, CH₃), (M-3049, H, CH₃, Cl, pyrrazol-2-yl, H), (M-3050, H, CH₃, Cl, pyrrazol-2-yl, Cl), (M-3051, H, CH₃, Cl, pyrrazol-2-yl, F), (M-3052, H, CH₃, Cl, pyrrazol-2-yl, CF₃), (M-3053, H, CH₃, Cl, pyrrazol-2-yl, Br), (M-3054, H, CH₃, Cl, pyrrazol-2-yl, CH₃), (M-3055, H, CH₃, Cl, pyrrazol-3-yl, H), (M-3056, H, CH₃, Cl, pyrrazol-3-yl, Cl), (M-3057, H, CH₃, Cl, pyrrazol-3-yl, F), (M-3058, H, CH₃, Cl, pyrrazol-3-yl, CF₃), (M-3059, H, CH₃, Cl, pyrrazol-3-yl, Br), (M-3060, H, CH₃, Cl, pyrrazol-3-yl, CH₃), (M-3061, H, CH₃, Cl, pyrimidin-2-yl, H), (M-3062, H, CH₃, Cl, pyrimidin-2-yl, Cl), (M-3063, H, CH₃, Cl, pyrimidin-2-yl, F), (M-3064, H, CH₃, Cl, pyrimidin-2-yl, CF₃), (M-3065, H, CH₃, Cl, pyrimidin-2-yl, Br), (M-3066, H, CH₃, Cl, pyrimidin-2-yl, CH₃), (M-3067, H, CH₃, Cl, pyrimidin-4-yl, H), (M-3068, H, CH₃, Cl, pyrimidin-4-yl, Cl), (M-3069, H, CH₃, Cl, pyrimidin-4-yl, F), (M-3070, H, CH₃, Cl, pyrimidin-4-yl, CF₃), (M-3071, H, CH₃, Cl, pyrimidin-4-yl, Br), (M-3072, H, CH₃, Cl, pyrimidin-4-yl, CH₃), (M-3073, H, CH₃, Cl, pyrimidin-5-yl, H), M-3074, H, CH₃, Cl, pyrimidin-5-yl, Cl), (M-3075, H, CH₃, Cl, pyrimidin-5-yl, F), (M-3076, H, CH₃, Cl, pyrimidin-5-yl, CF₃), (M-3077, H, CH₃, Cl, pyrimidin-5-yl, Br), (M-3078, H, CH₃, Cl, pyrimidin-5-yl, CH₃), (M-3079, H, CH₃, Cl, HOOCCH₂CH₂CH₂, H), (M-3080, H, CH₃, Cl, HOOCCH₂CH₂CH₂, Cl), (M-3081, H, CH₃, Cl, HOOCCH₂CH₂CH₂, F), (M-3082, H, CH₃, Cl, HOOCCH₂CH₂CH₂, CF₃), (M-3083, H, CH₃, Cl, HOOCCH₂CH₂CH₂, Br), (M-3084, H, CH₃, Cl, HOOCCH₂CH₂CH₂, CH₃), (M-3085, H, CH₃, Cl, HOOCCH₂CH₂CH₂CH₂, H), (M-3086, H, CH₃, Cl, HOOCCH₂CH₂CH₂CH₂, Cl), (M-3087, H, CH₃, Cl, HOOCCH₂CH₂CH₂CH₂, F), (M-3088, H, CH₃, Cl, HOOCCH₂CH₂CH₂CH₂, CF₃), (M-3089, H, CH₃, Cl, HOOCCH₂CH₂CH₂CH₂, Br), (M-3090, H, CH₃, Cl, HOOCCH₂CH₂CH₂CH₂, CH₃), (M-3091, H, CH₃, Cl, (Me)₂NCOCH₂CH₂CH₂, H), (M-3092, H, CH₃, Cl, (Me)₂NCOCH₂CH₂CH₂, Cl), (M-3093, H, CH₃, Cl, (Me)₂NCOCH₂CH₂CH₂, F), (M-3094, H, CH₃, Cl, (Me)₂NCOCH₂CH₂CH₂, CF₃), (M-3095, H, CH₃, Cl, (Me)₂NCOCH₂CH₂CH₂, Br), (M-3096, H, CH₃, Cl, (Me)₂NCOCH₂CH₂CH₂, CH₃), (M-3097, H, CH₃, Cl, (Me)₂NCOCH₂CH₂CH₂CH₂, H), (M-3098, H, CH₃, Cl, (Me)₂NCOCH₂CH₂CH₂CH₂, Cl), (M-3099, H, CH₃, Cl, (Me)₂NCOCH₂CH₂CH₂CH₂, F), (M-3100, H, CH₃, Cl, (Me)₂NCOCH₂CH₂CH₂CH₂, CF₃), (M-3101, H, CH₃, Cl, (Me)₂NCOCH₂CH₂CH₂CH₂, Br), (M-3102, H, CH₃, Cl, (Me)₂NCOCH₂CH₂CH₂CH₂, CH₃), (M-3103, H, CH₃, Cl, MeOCH₂, H), (M-3104, H, CH₃, Cl, MeOCH₂, Cl), (M-3105, H, CH₃, Cl, MeOCH₂, F), (M-3106, H, CH₃, Cl, MeOCH₂, CF₃), (M-3107, H, CH₃, Cl, MeOCH₂, Br), (M-3108, H, CH₃, Cl, MeOCH₂, CH₃), (M-3109, H, CH₃, Cl, EtOCH₂, H), (M-3110, H, CH₃, Cl, EtOCH₂, Cl), (M-3111, H, CH₃, Cl, EtOCH₂, F), (M-3112, H, CH₃, Cl, EtOCH₂, CF₃), (M-3113, H, CH₃, Cl, EtOCH₂, Br), (M-3114, H, CH₃, Cl, EtOCH₂, CH₃), (M-3115, H, CH₃, Cl, EtOCH₂CH₂, H), (M-3116, H, CH₃, Cl, EtOCH₂CH₂, Cl), (M-3117, H, CH₃, Cl, EtOCH₂CH₂, F), (M-3118, H, CH₃, Cl, EtOCH₂CH₂, CF₃), (M-3119, H, CH₃, Cl, EtOCH₂CH₂, Br), (M-3120, H, CH₃, Cl, EtOCH₂CH₂, CH₃), (M-3121, H, CH₃, Cl, MeOCH₂CH₂OCH₂CH₂, H), (M-3122, H, CH₃, Cl, MeOCH₂CH₂OCH₂CH₂, Cl), (M-3123, H, CH₃, Cl, MeOCH₂CH₂OCH₂CH₂, F), (M-3124, H, CH₃, Cl, MeOCH₂CH₂OCH₂CH₂, CF₃), (M-3125, H, CH₃, Cl, MeOCH₂CH₂OCH₂CH₂, Br), (M-3126, H, CH₃, Cl, MeOCH₂CH₂OCH₂CH₂, CH₃), (M-3127, H, CH₃, Cl, MeOCH₂CH₂, H), (M-3128, H, CH₃, Cl, MeOCH₂CH₂, Cl), (M-3129, H, CH₃, Cl, MeOCH₂CH₂, F), (M-3130, H, CH₃, Cl, MeOCH₂CH₂, CF₃), (M-3131, H, CH₃, Cl, MeOCH₂CH₂, Br), (M-3132, H, CH₃, Cl, MeOCH₂CH₂, CH₃), (M-3133, H, CH₃, Cl, HOCH₂, H), (M-3134, H, CH₃, Cl, HOCH₂, Cl), (M-3135, H, CH₃, Cl, HOCH₂, F), (M-3136, H, CH₃, Cl, HOCH₂, CF₃), (M-3137, H, CH₃, Cl, HOCH₂, Br), (M-3138, H, CH₃, Cl, HOCH₂, CH₃), (M-3139, H, CH₃, Cl, HOCH₂CH₂, H), (M-3140, H, CH₃, Cl, HOCH₂CH₂, Cl), (M-3141, H, CH₃, Cl, HOCH₂CH₂, F), (M-3142, H, CH₃, Cl, HOCH₂CH₂, CF₃), (M-3143, H, CH₃, Cl, HOCH₂CH₂, Br), (M-3144, H, CH₃, Cl, HOCH₂CH₂, CH₃), (M-3145, H, CH₃, Cl, HOCH₂CH₂CH₂, H), (M-3146, H, CH₃, Cl, HOCH₂CH₂CH₂, Cl), (M-3147, H, CH₃, Cl, HOCH₂CH₂CH₂, F), (M-3148, H, CH₃, Cl, HOCH₂CH₂CH₂, CF₃), (M-3149, H, CH₃, Cl, HOCH₂CH₂CH₂, Br), (M-3150, H, CH₃, Cl, HOCH₂CH₂CH₂, CH₃), (M-3151, H, CH₃, Cl, HOCH₂CH₂CH₂CH₂, H), (M-3152, H, CH₃, Cl, HOCH₂CH₂CH₂CH₂, Cl), (M-3153, H, CH₃, Cl, HOCH₂CH₂CH₂CH₂, F), (M-3154, H, CH₃, Cl, HOCH₂CH₂CH₂CH₂, CF₃), (M-3155, H, CH₃, Cl, HOCH₂CH₂CH₂CH₂, Br), (M-3156, H, CH₃, Cl, HOCH₂CH₂CH₂CH₂, CH₃), (M-3157, H, CH₃, Cl, HOCH₂CH₂CH₂CH₂CH₂, H), (M-3158, H, CH₃, Cl, HOCH₂CH₂CH₂CH₂CH₂, Cl), (M-3159, H, CH₃, Cl, HOCH₂CH₂CH₂CH₂CH₂, F), (M-3160, H, CH₃, Cl, HOCH₂CH₂CH₂CH₂CH₂, CF₃), (M-3161, H, CH₃, Cl, HOCH₂CH₂CH₂CH₂CH₂, Br), (M-3162, H, CH₃, Cl, HOCH₂CH₂CH₂CH₂CH₂, CH₃), (M-3163, H, CH₃, Cl, HOCH₂CH₂OCH₂CH₂, H), (M-3164, H, CH₃, Cl, HOCH₂CH₂OCH₂CH₂, Cl), (M-3165, H, CH₃, Cl, HOCH₂CH₂OCH₂CH₂, F), (M-3166, H, CH₃, Cl, HOCH₂CH₂OCH₂CH₂, CF₃), (M-3167, H, CH₃, Cl, HOCH₂CH₂OCH₂CH₂, Br), (M-3168, H, CH₃, Cl, HOCH₂CH₂OCH₂CH₂, CH₃) (M-3169, H, CH₃, Cl, (Me)₂N, H), (M-3170, H, CH₃, Cl, (Me)₂N, Cl), (M-3171, H, CH₃, Cl, (Me)₂N, F), (M-3172, H, CH₃, Cl, (Me)₂N, CF₃), (M-3173, H, CH₃, Cl, (Me)₂N, Br), (M-3174, H, CH₃, Cl, (Me)₂N, CH₃), (M-3175, H, CH₃, Cl, piperidin-4-yl-methyl, H), (M-3176, H, CH₃, Cl, piperidin-4-yl-methyl, Cl), (M-3177, H, CH₃, Cl, piperidin-4-yl-methyl, F), (M-3178, H, CH₃, Cl, piperidin-4-yl-methyl, CF₃), (M-3179, H, CH₃, Cl, piperidin-4-yl-methyl, Br), (M-3180, H, CH₃, Cl, piperidin-4-yl-methyl, CH₃), (M-3181, H, CH₃, Cl, cyclohexylmethyl, H), (M-3182, H, CH₃, Cl, cyclohexylmethyl, Cl), (M-3183, H, CH₃, Cl, cyclohexylmethyl, F), (M-3184, H, CH₃, Cl, cyclohexylmethyl, CF₃), (M-3185, H, CH₃, Cl, cyclohexylmethyl, Br), (M-3186, H, CH₃, Cl, cyclohexylmethyl, CH₃), (M-3187, F, H, H, H, H), (M-3188, F, H, H, H, Cl), (M-3189, MeO, F, H, H, H), (M-3190, MeO, F, H, H, CF₃), (M-3191, F, H, H, H, Br), (M-3192, F, H, H, H, CH₃), (M-3193, F, H, H, F, H), (M-3194, F, H, H, F, Cl), (M-3195, F, H, H, F, F), (M-3196, F, H, H, F, CF₃), (M-3197, F, H, H, F, Br), (M-3198, F, H, H, F, CH₃), (M-3199, F, H, H, Cl, H), (M-3200, MeO, F, H, H, n-Pr), (M-3201, F, H, H, Cl, F), (M-3202, F, H, H, Cl, CF₃), (M-3203, F, H, H, Cl, Br), (M-3204, F, H, H, Cl, CH₃), (M-3205, F, H, H, CH₃, H), (M-3206, F, H, H, CH₃, Cl), (M-3207, F, H, H, CH₃, F), (M-3208, F, H, H, CH₃, CF₃), (M-3209, F, H, H, CH₃, Br), (M-3210, F, H, H, CH₃, CH₃), (M-3211, F, H, H, Et, H), (M-3212, F, H, H, Et, Cl), (M-3213, F, H, H, Et, F), (M-3214, F, H, H, Et, CF₃), (M-3215, F, H, H, Et, Br), (M-3216, F, H, H, Et, CH₃), (M-3217, F, H, H, n-Pr, H), (M-3218, F, H, H, n-Pr, Cl), (M-3219, F, H, H, n-Pr, F), (M-3220, F, H, H, n-Pr, CF₃), (M-3221, F, H, H, n-Pr, Br), (M-3222, F, H, H, n-Pr, CH₃), (M-3223, F, H, H, c-Pr, H), (M-3224, F, H, H, c-Pr, Cl), (M-3225, F, H, H, c-Pr, F), (M-3226, F, H, H, c-Pr, CF₃), (M-3227, F, H, H, c-Pr, Br), (M-3228, F, H, H, c-Pr, CH₃), (M-3229, F, H, H, i-Pr, H), (M-3230, F, H, H, i-Pr, Cl), (M-3231, F, H, H, i-Pr, F), (M-3232, F, H, H, i-Pr, CF₃), (M-3233, F, H, H, i-Pr, Br), (M-3234, F, H, H, i-Pr, CH₃), (M-3235, F, H, H, n-Bu, H), (M-3236, F, H, H, n-Bu, Cl), (M-3237, F, H, H, n-Bu, F), (M-3238, F, H, H, n-Bu, CF₃), (M-3239, F, H, H, n-Bu, Br), (M-3240, F, H, H, n-Bu, CH₃), (M-3241, F, H, H, i-Bu, H), (M-3242, F, H, H, i-Bu, Cl), (M-3243, F, H, H, i-Bu, F), (M-3244, F, H, H, i-Bu, CF₃), (M-3245, F, H, H, i-Bu, Br), (M-3246, F, H, H, i-Bu, CH₃), (M-3247, F, H, H, sec-Bu, H), (M-3248, F, H, H, sec-Bu, Cl), (M-3249, F, H, H, sec-Bu, F), (M-3250, F, H, H, sec-Bu, CF₃), (M-3251, F, H, H, sec-Bu, Br), (M-3252, F, H, H, sec-Bu, CH₃), (M-3253, F, H, H, n-Pen, H), (M-3254, F, H, H, n-Pen, Cl), (M-3255, F, H, H, n-Pen, F), (M-3256, F, H, H, n-Pen, CF₃), (M-3257, F, H, H, n-Pen, Br), (M-3258, F, H, H, n-Pen, CH₃), (M-3259, F, H, H, c-Pen, H), (M-3260, F, H, H, c-Pen, Cl), (M-3261, F, H, H, c-Pen, F), (M-3262, F, H, H, c-Pen, CF₃), (M-3263, F, H, H, c-Pen, Br), (M-3264, F, H, H, c-Pen, CH₃), (M-3265, F, H, H, n-Hex, H), (M-3266, F, H, H, n-Hex, Cl), (M-3267, F, H, H, n-Hex, F), (M-3268, F, H, H, n-Hex, CF₃), (M-3269, F, H, H, n-Hex, Br), (M-3270, F, H, H, n-Hex, CH₃), (M-3271, F, H, H, c-Hex, H), (M-3272, F, H, H, c-Hex, Cl), (M-3273, F, H, H, c-Hex, F), (M-3274, F, H, H, c-Hex, CF₃), (M-3275, F, El, H, c-Hex, Br), (M-3276, F, H, H, c-Hex, CH₃), (M-3277, F, H, H, OH, H), (M-3278, F, H, H, OH, Cl), (M-3279, F, H, H, OH, F), (M-3280, F, H, H, OH, CF₃), (M-3281, F, H, H, OH, Br), (M-3282, F, H, H, OH, CH₃), (M-3283, F, H, H, EtO, H), (M-3284, F, H, H, EtO, Cl), (M-3285, F, H, H, EtO, F), (M-3286, F, H, H, EtO, CF₃), (M-3287, F, H, H, EtO, Br), (M-3288, F, H, H, EtO, CH₃), (M-3289, F, H, H, n-PrO, H), (M-3290, F, H, H, n-PrO, Cl), (M-3291, F, H, H, n-PrO, F), (M-3292, F, H, H, n-PrO, CF₃), (M-3293, F, H, H, n-PrO, Br), (M-3294, F, H, H, n-PrO, CH₃), (M-3295, F, H, H, PhO, H), (M-3296, F, H, H, PhO, Cl), (M-3297, F, H, H, PhO, F), (M-3298, F, H, H, PhO, CF₃), (M-3299, F, H, H, PhO, Br), (M-3300, F, H, H, PhO, CH₃), (M-3301, F, H, H, BnO, H), (M-3302, F, H, H, BnO, Cl), (M-3303, F, H, H, BnO, F), (M-3304, F, H, H, BnO, CF₃), (M-3305, F, H, H, BnO, Br), (M-3306, F, H, H, BnO, CH₃), (M-3307, F, H, H, PhCH₂CH₂O, H), (M-3308, F, H, H, PhCH₂CH₂O, Cl), (M-3309, F, H, H, PhCH₂CH₂O, F), (M-3310, F, H, H, PhCH₂CH₂O, CF₃), (M-3311, F, H, H, PhCH₂CH₂O, Br), (M-3312, F, H, H, PhCH₂CH₂O, CH₃), (M-3313, MeO, H, H, CF₃O, CH₃), (M-3314, F, H, H, CF₃O, Cl), (M-3315, F, H, H, CF₃O, F), (M-3316, F, H, H, CF₃O, CF₃), (M-3317, F, H, H, CF₃O, Br), (M-3318, F, H, H, CF₃O, CH₃), (M-3319, F, H, H, Ph, H), (M-3320, F, H, H, Ph, Cl), (M-3321, F, H, H, Ph, F), (M-3322, F, H, H, Ph, CF₃), (M-3323, F, H, H, Ph, Br), (M-3324, F, H, H, Ph, CH₃), (M-3325, F, H, H, 4-F-Ph, H), (M-3326, F, H, H, 4-F-Ph, Cl), (M-3327, F, H, H, 4-F-Ph, F), (M-3328, F, H, H, 4-F-Ph, CF₃), (M-3329, F, H, H, 4-F-Ph, Br), (M-3330, F, H, H, 4-F-Ph, CH₃), (M-3331, F, H, H, 4-CF₃-Ph, H), (M-3332, F, H, H, 4-CF₃-Ph, Cl), (M-3333, F, H, H, 4-CF₃-Ph, F), (M-3334, F, H, H, 4-CF₃-Ph, CF₃), (M-3335, F, H, H, 4-CF₃-Ph, Br), (M-3336, F, H, H, 4-CF₃-Ph, CH₃), (M-3337, F, H, H, 4-(Me)₂N-Ph, H), (M-3338, F, H, H, 4-(Me)₂N-Ph, Cl), (M-3339, F, H, H, 4-(Me)₂N-Ph, F), (M-3340, F, H, H, 4-(Me)₂N-Ph, CF₃), (M-3341, F, H, H, 4-(Me)₂N-Ph, Br), (M-3342, F, H, H, 4-(Me)₂N-Ph, CH₃), (M-3343, F, H, H, 4-OH-Ph, H), (M-3344, F, H, H, 4-OH-Ph, Cl), (M-3345, F, H, H, 4-OH-Ph, F), (M-3346, F, H, H, 4-OH-Ph, CF₃), (M-3347, F, H, H, 4-OH-Ph, Br), (M-3348, F, H, H, 4-OH-Ph, CH₃), (M-3349, F, H, H, 3,4-di-F-Ph, H), (M-3350, F, H, H, 3,4-di-F-Ph, Cl), (M-3351, F, H, H, 3,4-di-F-Ph, F), (M-3352, F, H, H, 3,4-di-F-Ph, CF₃), (M-3353, F, H, H, 3,4-di-F-Ph, Br), (M-3354, F, H, H, 3,4-di-F-Ph, CH₃), (M-3355, F, H, H, 4-COOH-Ph, H), (M-3356, F, H, H, 4-COOH-Ph, Cl), (M-3357, F, H, H, 4-COOH-Ph, F), (M-3358, F, H, H, 4-COOH-Ph, CF₃), (M-3359, F, H, H, 4-COOH-Ph, Br), (M-3360, F, H, H, 4-COOH-Ph, CH₃), (M-3361, F, H, H, Bn, H), (M-3362, F, H, H, Bn, Cl), (M-3363, F, H, H, Bn, F), (M-3364, F, H, H, Bn, CF₃), (M-3365, F, H, H, Bn, Br), (M-3366, F, H, H, Bn, CH₃), (M-3367, F, H, H, 4-F-Bn, H), (M-3368, F, H, H, 4-F-Bn, Cl), (M-3369, F, H, H, 4-F-Bn, F), (M-3370, F, H, H, 4-F-Bn, CF₃), (M-3371, F, H, H, 4-F-Bn, Br), (M-3372, F, H, H, 4-F-Bn, CH₃), (M-3373, F, H, H, 2-Py, H), (M-3374, F, H, H, 2-Py, Cl), (M-3375, F, H, H, 2-Py, F), (M-3376, F, H, H, 2-Py, CF₃), (M-3377, F, H, H, 2-Py, Br), (M-3378, F, H, H, 2-Py, CH₃), (M-3379, F, H, H, 3-Py, H), (M-3380, F, H, H, 3-Py, Cl), (M-3381, F, H, H, 3-Py, F), (M-3382, F, H, H, 3-Py, CF₃), (M-3383, F, H, H, 3-Py, Br), (M-3384, F, H, H, 3-Py, CH₃), (M-3385, F, H, H, 4-Py, H), (M-3386, F, H, H, 4-Py, Cl), (M-3387, F, H, H, 4-Py, F), (M-3388, F, H, H, 4-Py, CF₃), (M-3389, F, H, H, 4-Py, Br), (M-3390, F, H, H, 4-Py, CH₃), (M-3391, F, H, H, 2-Th, H), (M-3392, F, H, H, 2-Th, Cl), (M-3393, F, H, H, 2-Th, F), (M-3394, F, H, H, 2-Th, CF₃), (M-3395, F, H, H, 2-Th, Br), (M-3396, F, H, H, 2-Th, CH₃), (M-3397, F, H, H, 3-Th, H), (M-3398, F, H, H, 3-Th, Cl), (M-3399, F, H, H, 3-Th, F), (M-3400, F, H, H, 3-Th, CF₃), (M-3401, F, H, H, 3-Th, Br), (M-3402, F, H, H, 3-Th, CH₃), (M-3403, F, H, H, pyrrazol-2-yl, H), (M-3404, F, H, H, pyrrazol-2-yl, Cl), (M-3405, F, H, H, pyrrazol-2-yl, F), (M-3406, F, H, H, pyrrazol-2-yl, CF₃), (M-3407, F, H, H, pyrrazol-2-yl, Br), (M-3408, F, H, H, pyrrazol-2-yl, CH₃), (M-3409, F, H, H, pyrrazol-3-yl, H), (M-3410, F, H, H, pyrrazol-3-yl, Cl), (M-3411, F, H, H, pyrrazol-3-yl, F), (M-3412, F, H, H, pyrrazol-3-yl, CF₃), (M-3413, F, H, H, pyrrazol-3-yl, Br), (M-3414, F, H, H, pyrrazol-3-yl, CH₃), (M-3415, F, H, H, pyrimidin-2-yl, H), (M-3416, F, H, H, pyrimidin-2-yl, Cl), (M-3417, F, H, H, pyrimidin-2-yl, F), (M-3418, F, H, H, pyrimidin-2-yl, CF₃), (M-3419, F, H, H, pyrimidin-2-yl, Br), (M-3420, F, H, H, pyrimidin-2-yl, CH₃), (M-3421, F, H, H, pyrimidin-4-yl, H), (M-3422, F, H, H, pyrimidin-4-yl, Cl), (M-3423, F, H, H, pyrimidin-4-yl, F), (M-3424, F, H, H, pyrimidin-4-yl, CF₃), (M-3425, F, H, H, pyrimidin-4-yl, Br), (M-3426, F, H, H, pyrimidin-4-yl, CH₃), (M-3427, F, H, H, pyrimidin-5-yl, H), (M-3428, F, H, H, pyrimidin-5-yl, Cl), (M-3429, F, H, H, pyrimidin-5-yl, F), (M-3430, F, H, H, pyrimidin-5-yl, CF₃), (M-3431, F, H, H, pyrimidin-5-yl, Br), (M-3432, F, H, H, pyrimidin-5-yl, CH₃), (M-3433, F, H, H, HOOCCH₂CH₂CH₂, H), (M-3434, F, H, H, HOOCCH₂CH₂CH₂, Cl), (M-3435, F, H, H, HOOCCH₂CH₂CH₂, F), (M-3436, F, H, H, HOOCCH₂CH₂CH₂, CF₃), (M-3437, F, H, H, HOOCCH₂CH₂CH₂, Br), (M-3438, F, H, H, HOOCCH₂CH₂CH₂, CH₃), (M-3439, F, H, H, HOOCCH₂CH₂CH₂CH₂, H), (M-3440, F, H, H, HOOCCH₂CH₂CH₂CH₂, Cl), (M-3441, F, H, H, HOOCCH$_2$CH$_2$CH$_2$CH$_2$, F), (M-3442, F, H, H, HOOCCH$_2$CH$_2$CH$_2$CH$_2$, CF$_3$), (M-3443, F, H, H, HOOCCH$_2$CH$_2$CH$_2$CH$_2$, Br), (M-3444, F, H, H, HOOCCH$_2$CH$_2$CH$_2$CH$_2$, CH$_3$), (M-3445, F, H, H, (Me)$_2$NCOCH$_2$CH$_2$CH$_2$CH$_2$, H), (M-3446, F, H, H, (Me)$_2$NCOCH$_2$CH$_2$CH$_2$CH$_2$, Cl), (M-3447, F, H, H, (Me)$_2$NCOCH$_2$CH$_2$CH$_2$CH$_2$, F), (M-3448, F, H, H, (Me)$_2$NCOCH$_2$CH$_2$CH$_2$CH$_2$, CF$_3$), (M-3449, F, H, H, (Me)$_2$NCOCH$_2$CH$_2$CH$_2$CH$_2$, Br), (M-3450, F, H, H, (Me)$_2$NCOCH$_2$CH$_2$CH$_2$CH$_2$, CH$_3$), (M-3451, F, H, H, (Me)$_2$NCOCH$_2$CH$_2$CH$_2$CH$_2$CH$_2$, H), (M-3452, F, H, H, (Me)$_2$NCOCH$_2$CH$_2$CH$_2$CH$_2$CH$_2$, Cl), (M-3453, F, H, H, (Me)$_2$NCOCH$_2$CH$_2$CH$_2$CH$_2$CH$_2$, F), (M-3454, F, H, H, (Me)$_2$NCOCH$_2$CH$_2$CH$_2$CH$_2$CH$_2$, CF$_3$), (M-3455, F, H, H, (Me)$_2$NCOCH$_2$CH$_2$CH$_2$CH$_2$CH$_2$, Br), (M-3456, F, H, H, (Me)$_2$NCOCH$_2$CH$_2$CH$_2$CH$_2$CH$_2$, CH$_3$), (M-3457, F, H, H, MeOCH$_2$, H), (M-3458, F, H, H, MeOCH$_2$, Cl), (M-3459, F, H, H, MeOCH$_2$, F), (M-3460, F, H, H, MeOCH$_2$, CF$_3$), (M-3461, F, H, H, MeOCH$_2$, Br), (M-3462, F, H, H, MeOCH$_2$, CH$_3$), (M-3463, F, H, H, EtOCH$_2$, H), (M-3464, F, H, H, EtOCH$_2$, Cl), (M-3465, F, H, H, EtOCH$_2$, F), (M-3466, F, H, H, EtOCH$_2$, CF$_3$), (M-3467, F, H, H, EtOCH$_2$, Br), (M-3468, F, H, H, EtOCH$_2$, CH$_3$), (M-3469, F, H, H, EtOCH$_2$CH$_2$, H), (M-3470, F, H, H, EtOCH$_2$CH$_2$, Cl), (M-3471, F, H, H, EtOCH$_2$CH$_2$, F), (M-3472, F, H, H, EtOCH$_2$CH$_2$, CF$_3$), (M-3473, F, H, H, EtOCH$_2$CH$_2$, Br), (M-3474, F, H, H, EtOCH$_2$CH$_2$, CH$_3$), (M-3475, F, H, H, MeOCH$_2$CH$_2$OCH$_2$CH$_2$, H), (M-3476, F, H, H, MeOCH$_2$CH$_2$OCH$_2$CH$_2$, Cl), (M-3477, F, H, H, MeOCH$_2$CH$_2$OCH$_2$CH$_2$, F), (M-3478, F, H, H, MeOCH$_2$CH$_2$OCH$_2$CH$_2$, CF$_3$), (M-3479, F, H, H, MeOCH$_2$CH$_2$OCH$_2$CH$_2$, Br), (M-3480, F, H, H, MeOCH$_2$CH$_2$OCH$_2$CH$_2$, CH$_3$), (M-3481, F, H, H, MeOCH$_2$CH$_2$, H), (M-3482, F, H, H, MeOCH$_2$CH$_2$, Cl), (M-3483, F, H, H, MeOCH$_2$CH$_2$, F), (M-3484, F, H, H, MeOCH$_2$CH$_2$, CF$_3$), (M-3485, F, H, H, MeOCH$_2$CH$_2$, Br), (M-3486, F, H, H, MeOCH$_2$CH$_2$, CH$_3$), (M-3487, F, H, H, HOCH$_2$, H), (M-3488, F, H, H, HOCH$_2$, Cl), (M-3489, F, H, H, HOCH$_2$, F), (M-3490, F, H, H, HOCH$_2$, CF$_3$), (M-3491, F, H, H, HOCH$_2$, Br), (M-3492, F, H, H, HOCH$_2$, CH$_3$), (M-3493, F, H, H, HOCH$_2$CH$_2$, H), (M-3494, F, H, H, HOCH$_2$CH$_2$, Cl), (M-3495, F, H, H, HOCH$_2$CH$_2$, F), (M-3496, F, H, H, HOCH$_2$CH$_2$, CF$_3$), (M-3497, F, H, H, HOCH$_2$CH$_2$, Br), (M-3498, F, H, H, HOCH$_2$CH$_2$, CH$_3$), (M-3499, F, H, H, HOCH$_2$CH$_2$CH$_2$, H), (M-3500, F, H, H, HOCH$_2$CH$_2$CH$_2$, Cl), (M-3501, F, H, H, HOCH$_2$CH$_2$CH$_2$, F), (M-3502, F, H, H, HOCH$_2$CH$_2$CH$_2$, CF$_3$), (M-3503, F, H, H, HOCH$_2$CH$_2$CH$_2$, Br), (M-3504, F, H, H, HOCH$_2$CH$_2$CH$_2$, CH$_3$), (M-3505, F, H, H, HOCH$_2$CH$_2$CH$_2$CH$_2$, H), (M-3506, F, H, H, HOCH$_2$CH$_2$CH$_2$CH$_2$, Cl), (M-3507, F, H, H, HOCH$_2$CH$_2$CH$_2$CH$_2$, F), (M-3508, F, H, H, HOCH$_2$CH$_2$CH$_2$CH$_2$, CF$_3$), (M-3509, F, H, H, HOCH$_2$CH$_2$CH$_2$CH$_2$, Br), (M-3510, F, H, H, HOCH$_2$CH$_2$CH$_2$CH$_2$, CH$_3$), (M-3511, F, H, H, HOCH$_2$CH$_2$CH$_2$CH$_2$CH$_2$, H), (M-3512, F, H, H, HOCH$_2$CH$_2$CH$_2$CH$_2$CH$_2$, Cl), (M-3513, F, H, H, HOCH$_2$CH$_2$CH$_2$CH$_2$CH$_2$, F), (M-3514, F, H, H, HOCH$_2$CH$_2$CH$_2$CH$_2$CH$_2$, CF$_3$), (M-3515, F, H, H, HOCH$_2$CH$_2$CH$_2$CH$_2$CH$_2$, Br), (M-3516, F, H, H, HOCH$_2$CH$_2$CH$_2$CH$_2$CH$_2$, CH$_3$), (M-3517, F, H, H, HOCH$_2$CH$_2$OCH$_2$CH$_2$, H), (M-3518, F, H, H, HOCH$_2$CH$_2$OCH$_2$CH$_2$, Cl), (M-3519, F, H, H, HOCH$_2$CH$_2$OCH$_2$CH$_2$, F), (M3520, F, H, H, HOCH$_2$CH$_2$OCH$_2$CH$_2$, CF$_3$), (M-3521, F, H, H, HOCH$_2$CH$_2$OCH$_2$CH$_2$, Br), (M-3522, F, H, H, HOCH$_2$CH$_2$OCH$_2$CH$_2$, CH$_3$), (M-3523, F, H, H, (Me)$_2$N, H), (M-3524, F, H, H, (Me)$_2$N, Cl), (M-3525, F, H, H, (Me)$_2$N, F), (M-3526, F, H, H, (Me)$_2$N, CF$_3$), (M-3527, F, H, H, (Me)$_2$N, Br), (M-3528, F, H, H, (Me)$_2$N, CH$_3$), (M-3529, F, H, H, piperidin-4-yl-methyl, H), (M-3530, F, H, H, piperidin-4-yl-methyl, Cl), (M-3531, F, H, H, piperidin-4-yl-methyl, F), (M-3532, F, H, H, piperidin-4-yl-methyl, CF$_3$), (M-3533, F, H, H, piperidin-4-yl-methyl, Br), (M-3534, F, H, H, piperidin-4-yl-methyl, CH$_3$), (M-3535, F, H, H, cyclohexylmethyl, H), (M-3536, F, H, H, cyclohexylmethyl, Cl), (M-3537, F, H, H, cyclohexylmethyl, F), (M-3538, F, H, H, cyclohexylmethyl, CF$_3$), (M-3539, F, H, H, cyclohexylmethyl, Br), (M-3540, F, H, H, cyclohexylmethyl, CH$_3$), (M-3541, F, H, F, H, H), (M-3542, F, H, F, H, Cl), (M-3543, F, H, F, H, F), (M-3544, F, H, F, H, CF$_3$), (M-3545, F, H, F, H, Br), (M-3546, F, H, F, H, CH$_3$), (M-3547, F, H, F, F, H), (M-3548, F, H, F, F, Cl), (M-3549, F, H, F, F, F), (M-3550, F, H, F, F, CF$_3$), (M-3551, F, H, F, F, Br), (M-3552, F, H, F, F, CH$_3$), (M-3553, F, H, F, Cl, H), (M-3554, F, H, F, Cl, Cl), (M-3555, F, H, F, Cl, F), (M-3556, F, H, F, Cl, CF$_3$), (M-3557, F, H, F, Cl, Br), (M-3558, F, H, F, Cl, CH$_3$), (M-3559, F, H, F, CH$_3$, H), (M-3560, F, H, F, CH$_3$, Cl), (M-3561, F, H, F, CH$_3$, F), (M-3562, F, H, F, CH$_3$, CF$_3$), (M-3563, F, H, F, CH$_3$, Br), (M-3564, F, H, F, CH$_3$, CH$_3$), (M-3565, F, H, F, Et, H), (M-3566, F, H, F, Et, Cl), (M-3567, F, H, F, Et, F), (M-3568, F, H, F, Et, CF$_3$), (M-3569, F, H, F, Et, Br), (M-3570, F, H, F, Et, CH$_3$), (M-3571, F, H, F, n-Pr, H), (M-3572, F, H, F, n-Pr, Cl), (M-3573, F, H, F, n-Pr, F), (M-3574, F, H, F, n-Pr, CF$_3$), (M-3575, F, H, F, n-Pr, Br), (M-3576, F, H, F, n-Pr, CH$_3$), (M-3577, F, H, F, c-Pr, H), (M-3578, F, H, F, c-Pr, Cl), (M-3579, F, H, F, c-Pr, F), (M-3580, F, H, F, c-Pr, CF$_3$), (M-3581, F, H, F, c-Pr, Br), (M-3582, F, H, F, c-Pr, CH$_3$), (M-3583, F, H, F, i-Pr, H), (M-3584, F, H, F, i-Pr, Cl), (M-3585, F, H, F, i-Pr, F), (M-3586, F, H, F, i-Pr, CF$_3$), (M-3587, F, H, F, i-Pr, Br), (M-3588, F, H, F, i-Pr, CH$_3$), (M-3589, F, H, F, n-Bu, H), (M-3590, F, H, F, n-Bu, Cl), (M-3591, F, H, F, n-Bu, F), (M-3592, F, H, F, n-Bu, CF$_3$), (M-3593, F, H, F, n-Bu, Br), (M-3594, F, H, F, n-Bu, CH$_3$), (M-3595, F, H, F, i-Bu, H), (M-3596, F, H, F, i-Bu, Cl), (M-3597, F, H, F, i-Bu, F), (M-3598, F, H, F, i-Bu, CF$_3$), (M-3599, F, H, F, i-Bu, Br), (M-3600, F, H, F, i-Bu, CH$_3$), (M-3601, F, H, F, sec-Bu, H), (M-3602, F, H, F, sec-Bu, Cl), (M-3603, F, H, F, sec-Bu, F), (M-3604, F, H, F, sec-Bu, CF$_3$), (M-3605, F, H, F, sec-Bu, Br), (M-3606, F, H, F, sec-Bu, CH$_3$), (M-3607, F, H, F, n-Pen, H), (M-3608, F, H, F, n-Pen, Cl), (M-3609, F, H, F, n-Pen, F), (M-3610, F, H, F, n-Pen, CF$_3$), (M-3611, F, H, F, n-Pen, Br), (M-3612, F, H, F, n-Pen, CH$_3$), (M-3613, F, H, F, c-Pen, H), (M-3614, F, H, F, c-Pen, Cl), (M-3615, F, H, F, c-Pen, F), (M-3616, F, H, F, c-Pen, CF$_3$), (M-3617, F, H, F, c-Pen, Br), (M-3618, F, H, F, c-Pen, CH$_3$), (M-3619, F, H, F, n-Hex, H), (M-3620, F, H, F, n-Hex, Cl), (M-3621, F, H, F, n-Hex, F), (M-3622, F, H, F, n-Hex, CF$_3$), (M-3623, F, H, F, n-Hex, Br), (M-3624, F, H, F, n-Hex, CH$_3$), (M-3625, F, H, F, c-Hex, H), (M-3626, F, H, F, c-Hex, Cl), (M-3627, F, H, F, c-Hex, F), (M-3628, F, H, F, c-Hex, CF$_3$), (M-3629, F, H, F, c-Hex, Br), (M-3630, F, H, F, c-Hex, CH$_3$), (M-3631, F, H, F, OH, H), (M-3632, F, H, F, OH, Cl), (M-3633, F, H, F, OH, F), (M-3634, F, H, F, OH, CF$_3$), (M-3635, F, H, F, OH, Br), (M-3636, F, H, F, OH, CH$_3$), (M-3637, F, H, F, EtO, H), (M-3638, F, H, F, EtO, Cl), (M-3639, F, H, F, EtO, F), (M-3640, F, H, F, EtO, CF$_3$), (M-3641, F, H, F, EtO, Br), (M-3642, F, H, F, EtO, CH$_3$), (M-3643, F, H, F, n-PrO, H), (M-3644, F, H, F, n-PrO, Cl), (M-3645, F, H, F, n-PrO, F), (M-3646, F, H, F, n-PrO, CF$_3$), (M-3647, F, H, F, n-PrO, Br), (M-3648, F, H, F, n-PrO, CH$_3$), (M-3649, F, H, F, PhO, H), (M-3650, F, H, F, PhO, Cl), (M-3651, F, H, F, PhO, F), (M-3652, F, H, F, PhO, CF$_3$), (M-3653, F, H, F, PhO, Br), (M-3654, F, H, F, PhO, CH$_3$), (M-3655, F, H, F, BnO, H), (M-3656, F, H, F, BnO, Cl), (M-3657, F, H, F, BnO, F), (M-3658, F, H, F, BnO, CF₃), (M-3659, F, H, F, BnO, Br), (M-3660, F, H, F, BnO, CH₃), (M-3661, F, H, F, PhCH₂CH₂O, H), (M-3662, F, H, F, PhCH₂CH₂O, Cl), (M-3663, F, H, F, PhCH₂CH₂O, F), (M-3664, F, H, F, PhCH₂CH₂O, CF₃), (M-3665, F, H, F, PhCH₂CH₂O, Br), (M-3666, F, H, F, PhCH₂CH₂O, CH₃), (M-3667, F, H, F, CF₃O, H), (M-3668, F, H, F, CF₃O, Cl), (M-3669, F, H, F, CF₃O, F), (M-3670, F, H, F, CF₃O, CF₃), (M-3671, F, H, F, CF₃O, Br), (M-3672, F, H, F, CF₃O, CH₃), (M-3673, F, H, F, Ph, H), (M-3674, F, H, F, Ph, Cl), (M-3675, F, H, F, Ph, F), (M-3676, F, H, F, Ph, CF₃), (M-3677, F, H, F, Ph, Br), (M-3678, F, H, F, Ph, CH₃), (M-3679, F, H, F, 4-F-Ph, H), (M-3680, F, H, F, 4-F-Ph, Cl), (M-3681, F, H, F, 4-F-Ph, F), (M-3682, F, H, F, 4-F-Ph, CF₃), (M-3683, F, H, F, 4-F-Ph, Br), (M-3684, F, H, F, 4-F-Ph, CH₃), (M-3685, F, H, F, 4-CF₃-Ph, H), (M-3686, F, H, F, 4-CF₃-Ph, Cl), (M-3687, F, H, F, 4-CF₃-Ph, F), (M-3688, F, H, F, 4-CF₃-Ph, CF₃), (M-3689, F, H, F, 4-CF₃-Ph, Br), (M-3690, F, H, F, 4-CF₃-Ph, CH₃), (M-3691, F, H, F, 4-(Me)₂N-Ph, H), (M-3692, F, H, F, 4-(Me)₂N-Ph, Cl), (M-3693, F, H, F, 4-(Me)₂N-Ph, F), (M-3694, F, H, F, 4-(Me)₂N-Ph, CF₃), (M-3695, F, H, F, 4-(Me)₂N-Ph, Br), (M-3696, F, H, F, 4-(Me)₂N-Ph, CH₃), (M-3697, F, H, F, 4-OH-Ph, H), (M-3698, F, H, F, 4-OH-Ph, Cl), (M-3699, F, H, F, 4-OH-Ph, F), (M-3700, F, H, F, 4-OH-Ph, CF₃), (M-3701, F, H, F, 4-OH-Ph, Br), (M-3702, F, H, F, 4-OH-Ph, CH₃), (M-3703, F, H, F, 3,4-di-F-Ph, H), (M-3704, F, H, F, 3,4-di-F-Ph, Cl), (M-3705, F, H, F, 3,4-di-F-Ph, F), (M-3706, F, H, F, 3,4-di-F-Ph, CF₃), (M-3707, F, H, F, 3,4-di-F-Ph, Br), (M-3708, F, H, F, 3,4-di-F-Ph, CH₃), (M-3709, F, H, F, 4-COOH-Ph, H), (M-3710, F, H, F, 4-COOH-Ph, Cl), (M-3711, F, H, F, 4-COOH-Ph, F), (M-3712, F, H, F, 4-COOH-Ph, CF₃), (M-3713, F, H, F, 4-COOH-Ph, Br), (M-3714, F, H, F, 4-COOH-Ph, CH₃), (M-3715, F, H, F, Bn, H), (M-3716, F, H, F, Bn, Cl), (M-3717, F, H, F, Bn, F), (M-3718, F, H, F, Bn, CF₃), (M-3719, F, H, F, Bn, Br), (M-3720, F, H, F, Bn, CH₃), (M-3721, F, H, F, 4-F-Bn, H), (M-3722, F, H, F, 4-F-Bn, Cl), (M-3723, F, H, F, 4-F-Bn, F), (M-3724, F, H, F, 4-F-Bn, CF₃), (M-3725, F, H, F, 4-F-Bn, Br), (M-3726, F, H, F, 4-F-Bn, CH₃), (M-3727, F, H, F, 2-Py, H), (M-3728, F, H, F, 2-Py, Cl), (M-3729, F, H, F, 2-Py, F), (M-3730, F, H, F, 2-Py, CF₃), (M-3731, F, H, F, 2-Py, Br), (M-3732, F, H, F, 2-Py, CH₃), (M-3733, F, H, F, 3-Py, H), (M-3734, F, H, F, 3-Py, Cl), (M-3735, F, H, F, 3-Py, F), (M-3736, F, H, F, 3-Py, CF₃), (M-3737, F, H, F, 3-Py, Br), (M-3738, F, H, F, 3-Py, CH₃), (M-3739, F, H, F, 4-Py, H), (M-3740, F, H, F, 4-Py, Cl), (M-3741, F, H, F, 4-Py, F), (M-3742, F, H, F, 4-Py, CF₃), (M-3743, F, H, F, 4-Py, Br), (M-3744, F, H, F, 4-Py, CH₃), (M-3745, F, H, F, 2-Th, H), (M-3746, F, H, F, 2-Th, Cl), (M-3747, F, H, F, 2-Th, F), (M-3748, F, H, F, 2-Th, CF₃), (M-3749, F, H, F, 2-Th, Br), (M-3750, F, H, F, 2-Th, CH₃), (M-3751, F, H, F, 3-Th, H), (M-3752, F, H, F, 3-Th, Cl), (M-3753, F, H, F, 3-Th, F), (M-3754, F, H, F, 3-Th, CF₃), (M-3755, F, H, F, 3-Th, Br), (M-3756, F, H, F, 3-Th, CH₃), (M-3757, F, H, F, pyrrazol-2-yl, H), (M-3758, F, H, F, pyrrazol-2-yl, Cl), (M-3759, F, H, F, pyrrazol-2-yl, F), (M-3760, F, H, F, pyrrazol-2-yl, CF₃), (M-3761, F, H, F, pyrrazol-2-yl, Br), (M-3762, F, H, F, pyrrazol-2-yl, CH₃), (M-3763, F, H, F, pyrrazol-3-yl, H), (M-3764, F, H, F, pyrrazol-3-yl, Cl), (M-3765, F, H, F, pyrrazol-3-yl, F), (M-3766, F, H, F, pyrrazol-3-yl, CF₃), (M-3767, F, H, F, pyrrazol-3-yl, Br), (M-3768, F, H, F, pyrrazol-3-yl, CH₃), (M-3769, F, H, F, pyrimidin-2-yl, H), (M-3770, F, H, F, pyrimidin-2-yl, Cl), (M-3771, F, H, F, pyrimidin-2-yl, F), (M-3772, F, H, F, pyrimidin-2-yl, CF₃), (M-3773, F, H, F, pyrimidin-2-yl, Br), (M-3774, F, H, F, pyrimidin-2-yl, CH₃), (M-3775, F, H, F, pyrimidin-4-yl, H), (M-3776, F, H, F, pyrimidin-4-yl, Cl), (M-3777, F, H, F, pyrimidin-4-yl, F), (M-3778, F, H, F, pyrimidin-4-yl, CF₃), (M-3779, F, H, F, pyrimidin-4-yl, Br), (M-3780, F, H, F, pyrimidin-4-yl, CH₃), (M-3781, F, H, F, pyrimidin-5-yl, H), (M-3782, F, H, F, pyrimidin-5-yl, Cl), (M-3783, F, H, F, pyrimidin-5-yl, F), (M-3784, F, H, F, pyrimidin-5-yl, CF₃), (M-3785, F, H, F, pyrimidin-5-yl, Br), (M-3786, F, H, F, pyrimidin-5-yl, CH₃), (M-3787, F, H, F, HOOCCH₂CH₂CH₂, H), (M-3788, F, H, F, HOOCCH₂CH₂CH₂, Cl), (M-3789, F, H, F, HOOCCH₂CH₂CH₂, F), (M-3790, F, H, F, HOOCCH₂CH₂CH₂, CF₃), (M-3791, F, H, F, HOOCCH₂CH₂CH₂, Br), (M-3792, F, H, F, HOOCCH₂CH₂CH₂, CH₃), (M-3793, F, H, F, HOOCCH₂CH₂CH₂CH₂, H), (M-3794, F, H, F, HOOCCH₂CH₂CH₂CH₂, Cl), (M-3795, F, H, F, HOOCCH₂CH₂CH₂CH₂, F), (M-3796, F, H, F, HOOCCH₂CH₂CH₂CH₂, CF₃), (M-3797, F, H, F, HOOCCH₂CH₂CH₂CH₂, Br), (M-3798, F, H, F, HOOCCH₂CH₂CH₂CH₂, CH₃), (M-3799, F, H, F, (Me)₂NCOCH₂CH₂CH₂, H), (M-3800, F, H, F, (Me)₂NCOCH₂CH₂CH₂, Cl), (M-3801, F, H, F, (Me)₂NCOCH₂CH₂CH₂, F), (M-3802, F, H, F, (Me)₂NCOCH₂CH₂CH₂, CF₃), (M-3803, F, H, F, (Me)₂NCOCH₂CH₂CH₂, Br), (M-3804, F, H, F, (Me)₂NCOCH₂CH₂CH₂, CH₃), (M-3805, F, H, F, (Me)₂NCOCH₂CH₂CH₂CH₂, H), (M-3806, F, H, F, (Me)₂NCOCH₂CH₂CH₂CH₂, Cl), (M-3807, F, H, F, (Me)₂NCOCH₂CH₂CH₂CH₂, F), (M-3808, F, H, F, (Me)₂NCOCH₂CH₂CH₂CH₂, CF₃), (M-3809, F, H, F, (Me)₂NCOCH₂CH₂CH₂CH₂, Br), (M-3810, F, H, F, (Me)₂NCOCH₂CH₂CH₂CH₂, CH₃), (M-3811, F, H, F, MeOCH₂, H), (M-3812, F, H, F, MeOCH₂, Cl), (M-3813, F, H, F, MeOCH₂, F), (M-3814, F, H, F, MeOCH₂, CF₃), (M-3815, F, H, F, MeOCH₂, Br), (M-3816, F, H, F, MeOCH₂, CH₃), (M-3817, F, H, F, EtOCH₂, H), (M-3818, F, H, F, EtOCH₂, Cl), (M-3819, F, H, F, EtOCH₂, F), (M-3820, F, H, F, EtOCH₂, CF₃), (M-3821, F, H, F, EtOCH₂, Br), (M-3822, F, H, F, EtOCH₂, CH₃), (M-3823, F, H, F, EtOCH₂CH₂, H), (M-3824, F, H, F, EtOCH₂CH₂, Cl), (M-3825, F, H, F, EtOCH₂CH₂, F), (M-3826, F, H, F, EtOCH₂CH₂, CF₃), (M-3827, F, H, F, EtOCH₂CH₂, Br), (M-3828, F, H, F, EtOCH₂CH₂, CH₃), (M-3829, F, H, F, MeOCH₂CH₂OCH₂CH₂, H), (M-3830, F, H, F, MeOCH₂CH₂OCH₂CH₂, Cl), (M-3831, F, H, F, MeOCH₂CH₂OCH₂CH₂, F), (M-3832, F, H, F, MeOCH₂CH₂OCH₂CH₂, CF₃), (M-3833, F, H, F, MeOCH₂CH₂OCH₂CH₂, Br), (M-3834, F, H, F, MeOCH₂CH₂OCH₂CH₂, CH₃), (M-3835, F, H, F, MeOCH₂CH₂, H), (M-3836, F, H, F, MeOCH₂CH₂, Cl), (M-3837, F, H, F, MeOCH₂CH₂, F), (M-3838, F, H, F, MeOCH₂CH₂, CF₃), (M-3839, F, H, F, MeOCH₂CH₂, Br), (M-3840, F, H, F, MeOCH₂CH₂, CH₃), (M-3841, F, H, F, HOCH₂, H), (M-3842, F, H, F, HOCH₂, Cl), (M-3843, F, H, F, HOCH₂, F), (M-3844, F, H, F, HOCH₂, CF₃), (M-3845, F, H, F, HOCH₂, Br), (M-3846, F, H, F, HOCH₂, CH₃), (M-3847, F, H, F, HOCH₂CH₂, H), (M-3848, F, H, F, HOCH₂CH₂, Cl), (M-3849, F, H, F, HOCH₂CH₂, F), (M-3850, F, H, F, HOCH₂CH₂, CF₃), (M-3851, F, H, F, HOCH₂CH₂, Br), (M-3852, F, H, F, HOCH₂CH₂, CH₃), (M-3853, F, H, F, HOCH₂CH₂CH₂, H), (M-3854, F, H, F, HOCH₂CH₂CH₂, Cl), (M-3855, F, H, F, HOCH₂CH₂CH₂, F), (M-3856, F, H, F, HOCH₂CH₂CH₂, CF₃), (M-3857, F, H, F, HOCH₂CH₂CH₂, Br), (M-3858, F, H, F, HOCH₂CH₂CH₂, CH₃), (M-3859, F, H, F, HOCH₂CH₂CH₂CH₂, H), (M-3860, F, H, F, HOCH₂CH₂CH₂CH₂, Cl), (M-3861, F, H, F, HOCH₂CH₂CH₂CH₂, F), (M-3862, F, H, F, HOCH₂CH₂CH₂CH₂, CF₃), (M-3863, F, H, F, HOCH₂CH₂CH₂CH₂, Br), (M-3864, F, H, F, HOCH₂CH₂CH₂CH₂, CH₃), (M-3865, F, H, F, HOCH₂CH₂CH₂CH₂CH₂, H), (M-3866, F, H, F, HOCH₂CH₂CH₂CH₂CH₂, Cl), (M-3867, F, H, F, HOCH₂CH₂CH₂CH₂CH₂, F), (M-3868, F, H, F, HOCH₂CH₂CH₂CH₂CH₂, CF₃), (M-3869, F, H, F, HOCH₂CH₂CH₂CH₂CH₂, Br), (M-3870, F, H, F, HOCH₂CH₂CH₂CH₂CH₂, CH₃), (M-3871, F, H, F, HOCH₂CH₂OCH₂CH₂, H), (M-3872, F, H, F, HOCH₂CH₂OCH₂CH₂, Cl), (M-3873, F, H, F, HOCH₂CH₂OCH₂CH₂, F), (M-3874, F, H, F, HOCH₂CH₂OCH₂CH₂, CF₃), (M-3875, F, H, F, HOCH₂CH₂OCH₂CH₂, Br), (M-3876, F, H, F, HOCH₂CH₂OCH₂CH₂, CH₃), (M-3877, F, H, F, (Me)₂N, H), (M-3878, F, H, F, (Me)₂N, Cl), (M-3879, F, H, F, (Me)₂N, F), (M-3880, F, H, F, (Me)₂N, CF₃), (M-3881, F, H, F, (Me)₂N, Br), (M-3882, F, H, F, (Me)₂N, CH₃), (M-3883, F, H, F, piperidin-4-yl-methyl, H), (M-3884, F, H, F, piperidin-4-yl-methyl, Cl), (M-3885, F, H, F, piperidin-4-yl-methyl, F), (M-3886, F, H, F, piperidin-4-yl-methyl, CF₃), (M-3887, F, H, F, piperidin-4-yl-methyl, Br), (M-3888, F, H, F, piperidin-4-yl-methyl, CH₃), (M-3889, F, H, F, cyclohexylmethyl, H), (M-3890, F, H, F, cyclohexylmethyl, Cl), (M-3891, F, H, F, cyclohexylmethyl, F), (M-3892, F, H, F, cyclohexylmethyl, CF₃), (M-3893, F, H, F, cyclohexylmethyl, Br), (M-3894, F, H, F, cyclohexylmethyl, CH₃), (M-3895, F, H, Cl, H, H), (M-3896, F, H, Cl, H, Cl), (M-3897, F, H, Cl, H, F), (M-3898, F, H, Cl, H, CF₃), (M-3899, F, H, Cl, H, Br), (M-3900, F, H, Cl, H, CH₃), (M-3901, F, H, Cl, F, H), (M-3902, F, H, Cl, F, Cl), (M-3903, F, H, Cl, F, F), (M-3904, F, H, Cl, F, CF₃), (M-3905, F, H, Cl, F, Br), (M-3906, F, H, Cl, F, CH₃), (M-3907, F, H, Cl, Cl, H), (M-3908, F, H, Cl, Cl, Cl), (M-3909, F, H, Cl, Cl, F), (M-3910, F, H, Cl, Cl, CF₃), (M-3911, F, H, Cl, Cl, Br), (M-3912, F, H, Cl, Cl, CH₃), (M-3913, F, H, Cl, CH₃, H), (M-3914, F, H, Cl, CH₃, Cl), (M-3915, F, H, Cl, CH₃, F), (M-3916, F, H, Cl, CH₃, CF₃), (M-3917, F, H, Cl, CH₃, Br), (M-3918, F, H, Cl, CH₃, CH₃), (M-3919, F, H, Cl, Et, H), (M-3920, F, H, Cl, Et, Cl), (M-3921, F, H, Cl, Et, F), (M-3922, F, H, Cl, Et, CF₃), (M-3923, F, H, Cl, Et, Br), (M-3924, F, H, Cl, Et, CH₃), (M-3925, F, H, Cl, n-Pr, H), (M-3926, F, H, Cl, n-Pr, Cl), (M-3927, F, H, Cl, n-Pr, F), (M-3928, F, H, Cl, n-Pr, CF₃), (M-3929, F, H, Cl, n-Pr, Br), (M-3930, F, H, Cl, n-Pr, CH₃), (M-3931, F, H, Cl, c-Pr, H), (M-3932, F, H, Cl, c-Pr, Cl), (M-3933, F, H, Cl, c-Pr, F), (M-3934, F, H, Cl, c-Pr, CF₃), (M-3935, F, H, Cl, c-Pr, Br), (M-3936, F, H, Cl, c-Pr, CH₃), (M-3937, F, H, Cl, i-Pr, H), (M-3938, F, H, Cl, i-Pr, Cl), (M-3939, F, H, Cl, i-Pr, F), (M-3940, F, H, Cl, i-Pr, CF₃), (M-3941, F, H, Cl, i-Pr, Br), (M-3942, F, H, Cl, i-Pr, CH₃), (M-3943, F, H, Cl, n-Bu, H), (M-3944, F, H, Cl, n-Bu, Cl), (M-3945, F, H, Cl, n-Bu, F), (M-3946, F, H, Cl, n-Bu, CF₃), (M-3947, F, H, Cl, n-Bu, Br), (M-3948, F, H, Cl, n-Bu, CH₃), (M-3949, F, H, Cl, i-Bu, H), (M-3950, F, H, Cl, i-Bu, Cl), (M-3951, F, H, Cl, i-Bu, F), (M-3952, F, H, Cl, i-Bu, CF₃), (M-3953, F, H, Cl, i-Bu, Br), (M-3954, F, H, Cl, i-Bu, CH₃), (M-3955, F, H, Cl, sec-Bu, H), (M-3956, F, H, Cl, sec-Bu, Cl), (M-3957, F, H, Cl, sec-Bu, F), (M-3958, F, H, Cl, sec-Bu, CF₃), (M-3959, F, H, Cl, sec-Bu, Br), (M-3960, F, H, Cl, sec-Bu, CH₃), (M-3961, F, H, Cl, n-Pen, H), (M-3962, F, H, Cl, n-Pen, Cl), (M-3963, F, H, Cl, n-Pen, F), (M-3964, F, H, Cl, n-Pen, CF₃), (M-3965, F, H, Cl, n-Pen, Br), (M-3966, F, H, Cl, n-Pen, CH₃), (M-3967, F, H, Cl, c-Pen, H), (M-3968, F, H, Cl, c-Pen, Cl), (M-3969, F, H, Cl, c-Pen, F), (M-3970, F, H, Cl, c-Pen, CF₃), (M-3971, F, H, Cl, c-Pen, Br), (M-3972, F, H, Cl, c-Pen, CH₃), (M-3973, F, H, Cl, n-Hex, H), (M-3974, F, H, Cl, n-Hex, Cl), (M-3975, F, H, Cl, n-Hex, F), (M-3976, F, H, Cl, n-Hex, CF₃), (M-3977, F, H, Cl, n-Hex, Br), (M-3978, F, H, Cl, n-Hex, CH₃), (M-3979, F, H, Cl, c-Hex, H), (M-3980, F, H, Cl, c-Hex, Cl), (M-3981, F, H, Cl, c-Hex, F), (M-3982, F, H, Cl, c-Hex, CF₃), (M-3983, F, H, Cl, c-Hex, Br), (M-3984, F, H, Cl, c-Hex, CH₃), (M-3985, F, H, Cl, OH, H), (M-3986, F, H, Cl, OH, Cl), (M-3987, F, H, Cl, OH, F), (M-3988, F, H, Cl, OH, CF₃), (M-3989, F, H, Cl, OH, Br), (M-3990, F, H, Cl, OH, CH₃), (M-3991, F, H, Cl, EtO, H), (M-3992, F, H, Cl, EtO, Cl), (M-3993, F, H, Cl, EtO, F), (M-3994, F, H, Cl, EtO, CF₃), (M-3995, F, H, Cl, EtO, Br), (M-3996, F, H, Cl, EtO, CH₃), (M-3997, F, H, Cl, n-PrO, H), (M-3998, F, H, Cl, n-PrO, Cl), (M-3999, F, H, Cl, n-PrO, F), (M-4000, F, H, Cl, n-PrO, CF₃), (M-4001, F, H, Cl, n-PrO, Br), (M-4002, F, H, Cl, n-PrO, CH₃), (M-4003, F, H, Cl, PhO, H), (M-4004, F, H, Cl, PhO, Cl), (M-4005, F, H, Cl, PhO, F), (M-4006, F, H, Cl, PhO, CF₃), (M-4007, F, H, Cl, PhO, Br), (M-4008, F, H, Cl, PhO, CH₃), (M-4009, F, H, Cl, BnO, H), (M-4010, F, H, Cl, BnO, Cl), (M-4011, F, H, Cl, BnO, F), (M-4012, F, H, Cl, BnO, CF₃), (M-4013, F, H, Cl, BnO, Br), (M-4014, F, H, Cl, BnO, CH₃), (M-4015, F, H, Cl, PhCH₂CH₂O, H), (M-4016, F, H, Cl, PhCH₂CH₂O, Cl), (M-4017, F, H, Cl, PhCH₂CH₂O, F), (M-4018, F, H, Cl, PhCH₂CH₂O, CF₃), (M-4019, F, H, Cl, PhCH₂CH₂O, Br), (M-4020, F, H, Cl, PhCH₂CH₂O, CH₃), (M-4021, F, H, Cl, CF₃O, H), (M-4022, F, H, Cl, CF₃O, Cl), (M-4023, F, H, Cl, CF₃O, F), (M-4024, F, H, Cl, CF₃O, CF₃), (M-4025, F, H, Cl, CF₃O, Br), (M-4026, F, H, Cl, CF₃O, CH₃), (M-4027, F, H, Cl, Ph, H), (M-4028, F, H, Cl, Ph, Cl), (M-4029, F, H, Cl, Ph, F), (M-4030, F, H, Cl, Ph, CF₃), (M-4031, F, H, Cl, Ph, Br), (M-4032, F, H, Cl, Ph, CH₃), (M-4033, F, H, Cl, 4-F-Ph, H), (M-4034, F, H, Cl, 4-F-Ph, Cl), (M-4035, F, H, Cl, 4-F-Ph, F), (M-4036, F, H, Cl, 4-F-Ph, CF₃), (M-4037, F, H, Cl, 4-F-Ph, Br), (M-4038, F, H, Cl, 4-F-Ph, CH₃), (M-4039, F, H, Cl, 4-CF₃-Ph, H), (M-4040, F, H, Cl, 4-CF₃-Ph, Cl), (M-4041, F, H, Cl, 4-CF₃-Ph, F), (M-4042, F, H, Cl, 4-CF₃-Ph, CF₃), (M-4043, F, H, Cl, 4-CF₃-Ph, Br), (M-4044, F, H, Cl, 4-CF₃-Ph, CH₃), (M-4045, F, H, Cl, 4-(Me)₂N-Ph, H), (M-4046, F, H, Cl, 4-(Me)₂N-Ph, Cl), (M-4047, F, H, Cl, 4-(Me)₂N-Ph, F), (M-4048, F, H, Cl, 4-(Me)₂N-Ph, CF₃), (M-4049, F, H, Cl, 4-(Me)₂N-Ph, Br), (M-4050, F, H, Cl, 4-(Me)₂N-Ph, CH₃), (M-4051, F, H, Cl, 4-OH-Ph, H), (M-4052, F, H, Cl, 4-OH-Ph, Cl), (M-4053, F, H, Cl, 4-OH-Ph, F), (M-4054, F, H, Cl, 4-OH-Ph, CF₃), (M-4055, F, H, Cl, 4-OH-Ph, Br), (M-4056, F, H, Cl, 4-OH-Ph, CH₃), (M-4057, F, H, Cl, 3,4-di-F-Ph, H), (M-4058, F, H, Cl, 3,4-di-F-Ph, Cl), (M-4059, F, H, Cl, 3,4-di-F-Ph, F), (M-4060, F, H, Cl, 3,4-di-F-Ph, CF₃), (M-4061, F, H, Cl, 3,4-di-F-Ph, Br), (M-4062, F, H, Cl, 3,4-di-F-Ph, CH₃), (M-4063, F, H, Cl, 4-COOH-Ph, H), (M-4064, F, H, Cl, 4-COOH-Ph, Cl), (M-4065, F, H, Cl, 4-COOH-Ph, F), (M-4066, F, H, Cl, 4-COOH-Ph, CF₃), (M-4067, F, H, Cl, 4-COOH-Ph, Br), (M-4068, F, H, Cl, 4-COOH-Ph, CH₃), (M-4069, F, H, Cl, Bn, H), (M-4070, F, H, Cl, Bn, Cl), (M-4071, F, H, Cl, Bn, F), (M-4072, F, H, Cl, Bn, CF₃), (M-4073, F, H, Cl, Bn, Br), (M-4074, F, H, Cl, Bn, CH₃), (M-4075, F, H, Cl, 4-F-Bn, H), (M-4076, F, H, Cl, 4-F-Bn, Cl), (M-4077, F, H, Cl, 4-F-Bn, F), (M-4078, F, H, Cl, 4-F-Bn, CF₃), (M-4079, F, H, Cl, 4-F-Bn, Br), (M-4080, F, H, Cl, 4-F-Bn, CH₃), (M-4081, F, H, Cl, 2-Py, H), (M-4082, F, H, Cl, 2-Py, Cl), (M-4083, F, H, Cl, 2-Py, F), (M-4084, F, H, Cl, 2-Py, CF₃), (M-4085, F, H, Cl, 2-Py, Br), (M-4086, F, H, Cl, 2-Py, CH₃), (M-4087, F, H, Cl, 3-Py, H), (M-4088, F, H, Cl, 3-Py, Cl), (M-4089, F, H, Cl, 3-Py, F), (M-4090, F, H, Cl, 3-Py, CF₃), (M-4091, F, H, Cl, 3-Py, Br), (M-4092, F, H, Cl, 3-Py, CH₃), (M-4093, F, H, Cl, 4-Py, H), (M-4094, F, H, Cl, 4-Py, Cl), (M-4095, F, H, Cl, 4-Py, F), (M-4096, F, H, Cl, 4-Py, CF₃), (M-4097, F, H, Cl, 4-Py, Br), (M-4098, F, H, Cl, 4-Py, CH₃), (M-4099, F, H, Cl, 2-Th, H), (M-4100, F, H, Cl, 2-Th, Cl), (M-4101, F, H, Cl, 2-Th, F), (M-4102, F, H, Cl, 2-Th, CF₃), (M-4103, F, H, Cl, 2-Th, Br), (M-4104, F, H, Cl, 2-Th, CH₃), (M-4105, F, H, Cl, 3-Th, H), (M-4106, F, H, Cl, 3-Th, Cl), (M-4107, F, H, Cl, 3-Th, F), (M-4108, F, H, Cl, 3-Th, CF₃), (M-4109, F, H, Cl, 3-Th, Br), (M-4110, F, H, Cl, 3-Th, CH₃), (M-4111, F, H, Cl, pyrrazol-2-yl, H), (M-4112, F, H, Cl, pyrrazol-2-yl, Cl), (M-4113, F, H, Cl, pyrrazol-2-yl, F), (M-4114, F, H, Cl, pyrrazol-2-yl, CF₃), (M-4115, F, H, Cl, pyrrazol-2-yl, Br), (M-4116, F, H, Cl, pyrrazol-2-yl, CH₃), (M-4117, F, H, Cl, pyrrazol-3-yl, H), (M-4118, F, H, Cl, pyrrazol-3-yl, Cl), (M-4119, F, H, Cl, pyrrazol-3-yl, F), (M-4120, F, H, Cl, pyrrazol-3-yl, CF₃), (M-4121, F, H, Cl, pyrrazol-3-yl, Br), (M-4122, F, H, Cl, pyrrazol-3-yl, CH₃), (M-4123, F, H, Cl, pyrimidin-2-yl, H), (M-4124, F, H, Cl, pyrimidin-2-yl, Cl), (M-4125, F, H, Cl, pyrimidin-2-yl, F), (M-4126, F, H, Cl, pyrimidin-2-yl, CF₃), (M-4127, F, H, Cl, pyrimidin-2-yl, Br), (M-4128, F, H, Cl, pyrimidin-2-yl, CH₃), (M-4129, F, H, Cl, pyrimidin-4-yl, H), (M-4130, F, H, Cl, pyrimidin-4-yl, Cl), (M-4131, F, H, Cl, pyrimidin-4-yl, F), (M-4132, F, H, Cl, pyrimidin-4-yl, CF₃), (M-4133, F, H, Cl, pyrimidin-4-yl, Br), (M-4134, F, H, Cl, pyrimidin-4-yl, CH₃), (M-4135, F, H, Cl, pyrimidin-5-yl, H), (M-4136, F, H, Cl, pyrimidin-5-yl, Cl), (M-4137, F, H, Cl, pyrimidin-5-yl, F), (M-4138, F, H, Cl, pyrimidin-5-yl, CF₃), (M-4139, F, H, Cl, pyrimidin-5-yl, Br), (M-4140, F, H, Cl, pyrimidin-5-yl, CH₃), (M-4141, F, H, Cl, HOOCCH₂CH₂CH₂, H), (M-4142, F, H, Cl, HOOCCH₂CH₂CH₂, Cl), (M-4143, F, H, Cl, HOOCCH₂CH₂CH₂, F), (M-4144, F, H, Cl, HOOCCH₂CH₂CH₂, CF₃), (M-4145, F, H, Cl, HOOCCH₂CH₂CH₂, Br), (M-4146, F, H, Cl, HOOCCH₂CH₂CH₂, CH₃), (M-4147, F, H, Cl, HOOCCH₂CH₂CH₂CH₂, H), (M-4148, F, H, Cl, HOOCCH₂CH₂CH₂CH₂, Cl), (M-4149, F, H, Cl, HOOCCH₂CH₂CH₂CH₂, F), (M-4150, F, H, Cl, HOOCCH₂CH₂CH₂CH₂, CF₃), (M-4151, F, H, Cl, HOOCCH₂CH₂CH₂CH₂, Br), (M-4152, F, H, Cl, HOOCCH₂CH₂CH₂CH₂, CH₃), (M-4153, F, H, Cl, (Me)₂NCOCH₂CH₂CH₂CH₂, H), (M-4154, F, H, Cl, (Me)₂NCOCH₂CH₂CH₂CH₂, Cl), (M-4155, F, H, Cl, (Me)₂NCOCH₂CH₂CH₂CH₂, F), (M-4156, F, H, Cl, (Me)₂NCOCH₂CH₂CH₂CH₂, CF₃), (M-4157, F, H, Cl, (Me)₂NCOCH₂CH₂CH₂CH₂, Br), (M-4158, F, H, Cl, (Me)₂NCOCH₂CH₂CH₂CH₂, CH₃), (M-4159, F, H, Cl, (Me)₂NCOCH₂CH₂CH₂CH₂CH₂, H), (M-4160, F, H, Cl, (Me)₂NCOCH₂CH₂CH₂CH₂CH₂, Cl), (M-4161, F, H, Cl, (Me)₂NCOCH₂CH₂CH₂CH₂CH₂, F), (M-4162, F, H, Cl, (Me)₂NCOCH₂ CH₂CH₂CH₂CH₂, CF₃), (M-4163, F, H, Cl, (Me)₂NCOCH₂CH₂CH₂CH₂CH₂, Br), (M-4164, F, H, Cl, (Me)₂NCOCH₂CH₂CH₂CH₂CH₂, CH₃), (M-4165, F, H, Cl, MeOCH₂, H), (M-4166, F, H, Cl, MeOCH₂, Cl), (M-4167, F, H, Cl, MeOCH₂, F), (M-4168, F, H, Cl, MeOCH₂, CF₃), (M-4169, F, H, Cl, MeOCH₂, Br), (M-4170, F, H, Cl, MeOCH₂, CH₃), (M-4171, F, H, Cl, EtOCH₂, H), (M-4172, F, H, Cl, EtOCH₂, Cl), (M-4173, F, H, Cl, EtOCH₂, F), (M-4174, F, H, Cl, EtOCH₂, CF₃), (M-4175, F, H, Cl, EtOCH₂, Br), (M-4176, F, H, Cl, EtOCH₂, CH₃), (M-4177, F, H, Cl, EtOCH₂CH₂, H), (M-4178, F, H, Cl, EtOCH₂CH₂, Cl), (M-4179, F, H, Cl, EtOCH₂CH₂, F), (M-4180, F, H, Cl, EtOCH₂CH₂, CF₃), (M-4181, F, H, Cl, EtOCH₂CH₂, Br), (M-4182, F, H, Cl, EtOCH₂CH₂, CH₃), (M-4183, F, H, Cl, MeOCH₂CH₂OCH₂CH₂, H), (M-4184, F, H, Cl, MeOCH₂CH₂OCH₂CH₂, Cl), (M-4185, F, H, Cl, MeOCH₂CH₂OCH₂CH₂, F), (M-4186, F, H, Cl, MeOCH₂CH₂OCH₂CH₂, CF₃), (M-4187, F, H, Cl, MeOCH₂CH₂OCH₂CH₂, Br), (M-4188, F, H, Cl, MeOCH₂CH₂OCH₂CH₂, CH₃), (M-4189, F, H, Cl, MeOCH₂CH₂, H), (M-4190, F, H, Cl, MeOCH₂CH₂, Cl), (M-4191, F, H, Cl, MeOCH₂CH₂, F), (M-4192, F, H, Cl, MeOCH₂CH₂, CF₃), (M-4193, F, H, Cl, MeOCH₂CH₂, Br), (M-4194, F, H, Cl, MeOCH₂CH₂, CH₃), (M-4195, F, H, Cl, HOCH₂, H), (M-4196, F, H, Cl, HOCH₂, Cl), (M-4197, F, H, Cl, HOCH₂, F), (M-4198, F, H, Cl, HOCH₂, CF₃), (M-4199, F, H, Cl, HOCH₂, Br), (M-4200, F, H, Cl, HOCH₂, CH₃), (M-4201, F, H, Cl, HOCH₂CH₂, H), (M-4202, F, H, Cl, HOCH₂CH₂, Cl), (M-4203, F, H, Cl, HOCH₂CH₂, F), (M-4204, F, H, Cl, HOCH₂CH₂, CF₃), (M-4205, F, H, Cl, HOCH₂CH₂, Br), (M-4206, F, H, Cl, HOCH₂CH₂, CH₃), (M-4207, F, H, Cl, HOCH₂CH₂CH₂, H), (M-4208, F, H, Cl, HOCH₂CH₂CH₂, Cl), (M-4209, F, H, Cl, HOCH₂CH₂CH₂, F), (M-4210, F, H, Cl, HOCH₂CH₂CH₂, CF₃), (M-4211, F, H, Cl, HOCH₂CH₂CH₂, Br), (M-4212, F, H, Cl, HOCH₂CH₂CH₂, CH₃), (M-4213, F, H, Cl, HOCH₂CH₂CH₂CH₂, H), (M-4214, F, H, Cl, HOCH₂CH₂CH₂CH₂, Cl), (M-4215, F, H, Cl, HOCH₂CH₂CH₂CH₂, F), (M-4216, F, H, Cl, HOCH₂CH₂CH₂CH₂, CF₃), (M-4217, F, H, Cl, HOCH₂CH₂CH₂CH₂, Br), (M-4218, F, H, Cl, HOCH₂CH₂CH₂CH₂, CH₃), (M-4219, F, H, Cl, HOCH₂CH₂CH₂CH₂CH₂, H), (M-4220, F, H, Cl, HOCH₂CH₂CH₂CH₂CH₂, Cl), (M-4221, F, H, Cl, HOCH₂CH₂CH₂CH₂CH₂, F), (M-4222, F, H, Cl, HOCH₂CH₂CH₂CH₂CH₂, CF₃), (M-4223, F, H, Cl, HOCH₂CH₂CH₂CH₂CH₂, Br), (M-4224, F, H, Cl, HOCH₂CH₂CH₂CH₂CH₂, CH₃), (M-4225, F, H, Cl, HOCH₂CH₂OCH₂CH₂, H), (M-4226, F, H, Cl, HOCH₂CH₂OCH₂CH₂, Cl), (M-4227, F, H, Cl, HOCH₂CH₂OCH₂CH₂, F), (M-4228, F, H, Cl, HOCH₂CH₂OCH₂CH₂, CF₃), (M-4229, F, H, Cl, HOCH₂CH₂OCH₂CH₂, Br), (M-4230, F, H, Cl, HOCH₂CH₂OCH₂CH₂, CH₃), (M-4231, F, H, Cl, (Me)₂N, H), (M-4232, F, H, Cl, (Me)₂N, Cl), (M-4233, F, H, Cl, (Me)₂N, F), (M-4234, F, H, Cl, (Me)₂N, CF₃), (M-4235, F, H, Cl, (Me)₂N, Br), (M-4236, F, H, Cl, (Me)₂N, CH₃), (M-4237, F, H, Cl, piperidin-4-yl-methyl, H), (M-4238, F, H, Cl, piperidin-4-yl-methyl, Cl), (M-4239, F, H, Cl, piperidin-4-yl-methyl, F), (M-4240, F, H, Cl, piperidin-4-yl-methyl, CF₃), (M-4241, F, H, Cl, piperidin-4-yl-methyl, Br), (M-4242, F, H, Cl, piperidin-4-yl-methyl, CH₃), (M-4243, F, H, Cl, cyclohexylmethyl, H), (M-4244, F, H, Cl, cyclohexylmethyl, Cl), (M-4245, F, H, Cl, cyclohexylmethyl, F), (M-4246, F, H, Cl, cyclohexylmethyl, CF₃), (M-4247, F, H, Cl, cyclohexylmethyl, Br), (M-4248, F, H, Cl, cyclohexylmethyl, CH₃), (M-4249, F, F, H, H, H), (M-4250, F, F, H, H, Cl), (M-4251, F, F, H, H, F), (M-4252, F, F, H, H, CF₃), (M-4253, F, F, H, H, Br), (M-4254, F, F, H, H, CH₃), (M-4255, F, F, H, F, H), (M-4256, F, F, H, F, Cl), (M-4257, F, F, H, F, F), (M-4258, F, F, H, F, CF₃), (M-4259, F, F, H, F, Br), (M-4260, F, F, H, F, CH₃), (M-4261, F, F, H, Cl, H), (M-4262, F, F, H, Cl, Cl), (M-4263, F, F, H, Cl, F), (M-4264, F, F, H, Cl, CF₃), (M-4265, F, F, H, Cl, Br), (M-4266, F, F, H, Cl, CH₃), (M-4267, F, F, H, CH₃, H), (M-4268, F, F, H, CH₃, Cl), (M-4269, F, F, H, CH₃, F), (M-4270, F, F, H, CH₃, CF₃), (M-4271, F, F, H, CH₃, Br), (M-4272, F, F, H, CH₃, CH₃), (M-4273, F, F, H, Et, H), (M-4274, F, F, H, Et, Cl), (M-4275, F, F, H, Et, F), (M-4276, F, F, H, Et, CF₃), (M-4277, F, F, H, Et, Br), (M-4278, F, F, H, Et, CH₃), (M-4279, F, F, H, n-Pr, H), (M-4280, F, F, H, n-Pr, Cl), (M-4281, F, F, H, n-Pr, F), (M-4282, F, F, H, n-Pr, CF₃), (M-4283, F, F, H, n-Pr, Br), (M-4284, F, F, H, n-Pr, CH₃), (M-4285, F, F, H, c-Pr, H), (M-4286, F, F, H, c-Pr, Cl), (M-4287, F, F, H, c-Pr, F), (M-4288, F, F, H, c-Pr, CF₃), (M-4289, F, F, H, c-Pr, Br), (M-4290, F, F, H, c-Pr, CH₃), (M-4291, F, F, H, i-Pr, H), (M-4292, F, F, H, i-Pr, Cl), (M-4293, F, F, H, i-Pr, F), (M-4294, F, F, H, i-Pr, CF₃), (M-4295, F, F, H, i-Pr, Br), (M-4296, F, F, H, i-Pr, CH₃), (M-4297, F, F, H, n-Bu, H), (M-4298, F, F, H, n-Bu, Cl), (M-4299, F, F, H, n-Bu, F), (M-4300, F, F, H, n-Bu, CF₃), (M-4301, F, F, H, n-Bu, Br), (M-4302, F, F, H, n-Bu, CH₃), (M-4303, F, F, H, i-Bu, H), (M-4304, F, F, H, i-Bu, Cl), (M-4305, F, F, H, i-Bu, F), (M-4306, F, F, H, i-Bu, CF₃), (M-4307, F, F, H, i-Bu, Br), (M-4308, F, F, H, i-Bu, CH₃), (M-4309, F, F, H, sec-Bu, H), (M-4310, F, F, H, sec-Bu, Cl), (M-4311, F, F, H, sec-Bu, F), (M-4312, F, F, H, sec-Bu, CF₃), (M-4313, F, F, H, sec-Bu, Br), (M-4314, F, F, H, sec-Bu, CH₃), (M-4315, F, F, H, n-Pen, H), (M-4316, F, F, H, n-Pen, Cl), (M-4317, F, F, H, n-Pen, F), (M-4318, F, F, H, n-Pen, CF₃), (M-4319, F, F, H, n-Pen, Br), (M-4320, F, F, H, n-Pen, CH₃), (M-4321, F, F, H, c-Pen, H), (M-4322, F, F, H, c-Pen, Cl), (M-4323, F, F, H, c-Pen, F), (M-4324, F, F, H, c-Pen, CF₃), (M-4325, F, F, H, c-Pen, Br), (M-4326, F, F, H, c-Pen, CH₃), (M-4327, F, F, H, n-Hex, H), (M-4328, F, F, H, n-Hex, Cl), (M-4329, F, F, H, n-Hex, F), (M-4330, F, F, H, n-Hex, CF₃), (M-4331, F, F, H, n-Hex, Br), (M-4332, F, F, H, n-Hex, CH₃), (M-4333, F, F, H, c-Hex, H), (M-4334, F, F, H, c-Hex, Cl), (M-4335, F, F, H, c-Hex, F), (M-4336, F, F, H, c-Hex, CF₃), (M-4337, F, F, H, c-Hex, Br), (M-4338, F, F, H, c-Hex, CH₃), (M-4339, F, F, H, OH, H), (M-4340, F, F, H, OH, Cl), (M-4341, F, F, H, OH, F), (M-4342, F, F, H, OH, CF₃), (M-4343, F, F, H, OH, Br), (M-4344, F, F, H, OH, CH₃), (M-4345, F, F, H, EtO, H), (M-4346, F, F, H, EtO, Cl), (M-4347, F, F, H, EtO, F), (M-4348, F, F, H, EtO, CF₃), (M-4349, F, F, H, EtO, Br), (M-4350, F, F, H, EtO, CH₃), (M-4351, F, F, H, n-PrO, H), (M-4352, F, F, H, n-PrO, Cl), (M-4353, F, F, H, n-PrO, F), (M-4354, F, F, H, n-PrO, CF₃), (M-4355, F, F, H, n-PrO, Br), (M-4356, F, F, H, n-PrO, CH₃), (M-4357, F, F, H, PhO, H), (M-4358, F, F, H, PhO, Cl), (M-4359, F, F, H, PhO, F), (M-4360, F, F, H, PhO, CF₃), (M-4361, F, F, H, PhO, Br), (M-4362, F, F, H, PhO, CH₃), (M-4363, F, F, H, BnO, H), (M-4364, F, F, H, BnO, Cl), (M-4365, F, F, H, BnO, F), (M-4366, F, F, H, BnO, CF₃), (M-4367, F, F, H, BnO, Br), (M-4368, F, F, H, BnO, CH₃), (M-4369, F, F, H, PhCH₂CH₂O, H), (M-4370, F, F, H, PhCH₂CH₂O, Cl), (M-4371, F, F, H, PhCH₂CH₂O, F), (M-4372, F, F, H, PhCH₂CH₂O, CF₃), (M-4373, F, F, H, PhCH₂CH₂O, Br), (M-4374, F, F, H, PhCH₂CH₂O, CH₃), (M-4375, F, F, H, CF₃O, H), (M-4376, F, F, H, CF₃O, Cl), (M-4377, F, F, H, CF₃O, F), (M-4378, F, F, H, CF₃O, CF₃), (M-4379, F, F, H, CF₃O, Br), (M-4380, F, F, H, CF₃O, CH₃), (M-4381, F, F, H, Ph, H), (M-4382, F, F, H, Ph, Cl), (M-4383, F, F, H, Ph, F), (M-4384, F, F, H, Ph, CF₃), (M-4385, F, F, H, Ph, Br), (M-4386, F, F, H, Ph, CH₃), (M-4387, F, F, H, 4-F-Ph, H), (M-4388, F, F, H, 4-F-Ph, Cl), (M-4389, F, F, H, 4-F-Ph, F), (M-4390, F, F, H, 4-F-Ph, CF₃), (M-4391, F, F, H, 4-F-Ph, Br), (M-4392, F, F, H, 4-F-Ph, CH₃), (M-4393, F, F, H, 4-CF₃-Ph, H), (M-4394, F, F, H, 4-CF₃-Ph, Cl), (M-4395, F, F, H, 4-CF₃-Ph, F), (M-4396, F, F, H, 4-CF₃-Ph, CF₃), (M-4397, F, F, H, 4-CF₃-Ph, Br), (M-4398, F, F, H, 4-CF₃-Ph, CH₃), (M-4399, F, F, H, 4-(Me)₂N-Ph, H), (M-4400, F, F, H, 4-(Me)₂N-Ph, Cl), (M-4401, F, F, H, 4-(Me)₂N-Ph, F), (M-4402, F, F, H, 4-(Me)₂N-Ph, CF₃), (M-4403, F, F, H, 4-(Me)₂N-Ph, Br), (M-4404, F, F, H, 4-(Me)₂N-Ph, CH₃), (M-4405, F, F, H, 4-OH-Ph, H), (M-4406, F, F, H, 4-OH-Ph, Cl), (M-4407, F, F, H, 4-OH-Ph, F), (M-4408, F, F, H, 4-OH-Ph, CF₃), (M-4409, F, F, H, 4-OH-Ph, Br), (M-4410, F, F, H, 4-OH-Ph, CH₃), (M-4411, F, F, H, 3,4-di-F-Ph, H), (M-4412, F, F, H, 3,4-di-F-Ph, Cl), (M-4413, F, F, H, 3,4-di-F-Ph, F), (M-4414, F, F, H, 3,4-di-F-Ph, CF₃), (M-4415, F, F, H, 3,4-di-F-Ph, Br), (M-4416, F, F, H, 3,4-di-F-Ph, CH₃), (M-4417, F, F, H, 4-COOH-Ph, H), (M-4418, F, F, H, 4-COOH-Ph, Cl), (M-4419, F, F, H, 4-COOH-Ph, F), (M-4420, F, F, H, 4-COOH-Ph, CF₃), (M-4421, F, F, H, 4-COOH-Ph, Br), (M-4422, F, F, H, 4-COOH-Ph, CH₃), (M-4423, F, F, H, Bn, H), (M-4424, F, F, H, Bn, Cl), (M-4425, F, F, H, Bn, F), (M-4426, F, F, H, Bn, CF₃), (M-4427, F, F, H, Bn, Br), (M-4428, F, F, H, Bn, CH₃), (M-4429, F, F, H, 4-F-Bn, H), (M-4430, F, F, H, 4-F-Bn, Cl), (M-4431, F, F, H, 4-F-Bn, F), (M-4432, F, F, H, 4-F-Bn, CF₃), (M-4433, F, F, H, 4-F-Bn, Br), (M-4434, F, F, H, 4-F-Bn, CH₃), (M-4435, F, F, H, 2-Py, H), (M-4436, F, F, H, 2-Py, Cl), (M-4437, F, F, H, 2-Py, F), (M-4438, F, F, H, 2-Py, CF₃), (M-4439, F, F, H, 2-Py, Br), (M-4440, F, F, H, 2-Py, CH₃), (M-4441, F, F, H, 3-Py, H), (M-4442, F, F, H, 3-Py, Cl), (M-4443, F, F, H, 3-Py, F), (M-4444, F, F, H, 3-Py, CF₃), (M-4445, F, F, H, 3-Py, Br), (M-4446, F, F, H, 3-Py, CH₃), (M-4447, F, F, H, 4-Py, H), (M-4448, F, F, H, 4-Py, Cl), (M-4449, F, F, H, 4-Py, F), (M-4450, F, F, H, 4-Py, CF₃), (M-4451, F, F, H, 4-Py, Br), (M-4452, F, F, H, 4-Py, CH₃), (M-4453, F, F, H, 2-Th, H), (M-4454, F, F, H, 2-Th, Cl), (M-4455, F, F, H, 2-Th, F), (M-4456, F, F, H, 2-Th, CF₃), (M-4457, F, F, H, 2-Th, Br), (M-4458, F, F, H, 2-Th, CH₃), (M-4459, F, F, H, 3-Th, H), (M-4460, F, F, H, 3-Th, Cl), (M-4461, F, F, H, 3-Th, F), (M-4462, F, F, H, 3-Th, CF₃), (M-4463, F, F, H, 3-Th, Br), (M-4464, F, F, H, 3-Th, CH₃), (M-4465, F, F, H, pyrrazol-2-yl, H), (M-4466, F, F, H, pyrrazol-2-yl, Cl), (M-4467, F, F, H, pyrrazol-2-yl, F), (M-4468, F, F, H, pyrrazol-2-yl, CF₃), (M-4469, F, F, H, pyrrazol-2-yl, Br), (M-4470, F, F, H, pyrrazol-2-yl, CH₃), (M-4471, F, F, H, pyrrazol-3-yl, H), (M-4472, F, F, H, pyrrazol-3-yl, Cl), (M-4473, F, F, H, pyrrazol-3-yl, F), (M-4474, F, F, H, pyrrazol-3-yl, CF₃), (M-4475, F, F, H, pyrrazol-3-yl, Br), (M-4476, F, F, H, pyrrazol-3-yl, CH₃), (M-4477, F, F, H, pyrimidin-2-yl, H), (M-4478, F, F, H, pyrimidin-2-yl, Cl), (M-4479, F, F, H, pyrimidin-2-yl, F), (M-4480, F, F, H, pyrimidin-2-yl, CF₃), (M-4481, F, F, H, pyrimidin-2-yl, Br), (M-4482, F, F, H, pyrimidin-2-yl, CH₃), (M-4483, F, F, H, pyrimidin-4-yl, H), (M-4484, F, F, H, pyrimidin-4-yl, Cl), (M-4485, F, F, H, pyrimidin-4-yl, F), (M-4486, F, F, H, pyrimidin-4-yl, CF₃), (M-4487, F, F, H, pyrimidin-4-yl, Br), (M-4488, F, F, H, pyrimidin-4-yl, CH₃), (M-4489, F, F, H, pyrimidin-5-yl, H), (M-4490, F, F, H, pyrimidin-5-yl, Cl), (M-4491, F, F, H, pyrimidin-5-yl, F), (M-4492, F, F, H, pyrimidin-5-yl, CF₃), (M-4493, F, F, H, pyrimidin-5-yl, Br), (M-4494, F, F, H, pyrimidin-5-yl, CH₃), (M-4495, F, F, H, HOOCCH₂CH₂CH₂, H), (M-4496, F, F, H, HOOCCH₂CH₂CH₂, Cl), (M-4497, F, F, H, HOOCCH₂CH₂CH₂, F), (M-4498, F, F, H, HOOCCH₂CH₂CH₂, CF₃), (M-4499, F, F, H, HOOCCH₂CH₂CH₂, Br), (M-4500, F, F, H, HOOCCH₂CH₂CH₂, CH₃), (M-4501, F, F, H, HOOCCH₂CH₂CH₂CH₂, H), (M-4502, F, F, H, HOOCCH₂CH₂CH₂CH₂, Cl), (M-4503, F, F, H, HOOCCH₂CH₂CH₂CH₂, F), (M-4504, F, F, H, HOOCCH₂CH₂CH₂CH₂, CF₃), (M-4505, F, F, H, HOOCCH₂CH₂CH₂CH₂, Br), (M-4506, F, F, H, HOOCCH₂CH₂CH₂CH₂, CH₃), (M-4507, F, F, H, (Me)₂NCOCH₂CH₂CH₂, H), (M-4508, F, F, H, (Me)₂NCOCH₂CH₂CH₂, Cl), (M-4509, F, F, H, (Me)₂NCOCH₂CH₂CH₂, F), (M-4510, F, F, H, (Me)₂NCOCH₂CH₂CH₂, CF₃), (M-4511, F, F, H, (Me)₂NCOCH₂CH₂CH₂Br), (M-4512, F, F, H, (Me)₂NCOCH₂CH₂CH₂, CH₃), (M-4513, F, F, H, (Me)₂NCOCH₂CH₂CH₂CH₂, H), (M-4514, F, F, H, (Me)₂NCOCH₂CH₂CH₂CH₂, Cl), (M-4515, F, F, H, (Me)₂NCOCH₂CH₂CH₂CH₂, F), (M-4516, F, F, H, (Me)₂NCOCH₂CH₂CH₂CH₂, CF₃), (M-4517, F, F, H, (Me)₂NCOCH₂CH₂CH₂CH₂, Br), (M-4518, F, F, H, (Me)₂NCOCH₂CH₂CH₂CH₂, CH₃), (M-4519, F, F, H, MeOCH₂, H), (M-4520, F, F, H, MeOCH₂, Cl), (M-4521, F, F, H, MeOCH₂, F), (M-4522, F, F, H, MeOCH₂, CF₃), (M-4523, F, F, H, MeOCH₂, Br), (M-4524, F, F, H, MeOCH₂, CH₃), (M-4525, F, F, H, EtOCH₂, H), (M-4526, F, F, H, EtOCH₂, Cl), (M-4527, F, F, H, EtOCH₂, F), (M-4528, F, F, H, EtOCH₂, CF₃), (M-4529, F, F, H, EtOCH₂, Br), (M-4530, F, F, H, EtOCH₂, CH₃), (M-4531, F, F, H, EtOCH₂CH₂, H), (M-4532, F, F, H, EtOCH₂CH₂, Cl), (M-4533, F, F, H, EtOCH₂CH₂, F), (M-4534, F, F, H, EtOCH₂CH₂, CF₃), (M-4535, F, F, H, EtOCH₂CH₂, Br), (M-4536, F, F, H, EtOCH₂CH₂, CH₃), (M-4537, F, F, H, MeOCH₂CH₂OCH₂CH₂, H), (M-4538, F, F, H, MeOCH₂CH₂OCH₂CH₂, Cl), (M-4539, F, F, H, MeOCH₂CH₂OCH₂CH₂, F), (M-4540, F, F, H, MeOCH₂CH₂OCH₂CH₂, CF₃), (M-4541, F, F, H, MeOCH₂CH₂OCH₂CH₂, Br), (M-4542, F, F, H, MeOCH₂CH₂OCH₂CH₂, CH₃), (M-4543, F, F, H, MeOCH₂CH₂, H), (M-4544, F, F, H, MeOCH₂CH₂, Cl), (M-4545, F, F, H, MeOCH₂CH₂, F), (M-4546, F, F, H, MeOCH₂CH₂, CF₃), (M-4547, F, F, H, MeOCH₂CH₂, Br), (M-4548, F, F, H, MeOCH₂CH₂, CH₃), (M-4549, F, F, H, HOCH₂, H), (M-4550, F, F, H, HOCH₂, Cl), (M-4551, F, F, H, HOCH₂, F), (M-4552, F, F, H, HOCH₂, CF₃), (M-4553, F, F, H, HOCH₂, Br), (M-4554, F, F, H, HOCH₂, CH₃), (M-4555, F, F, H, HOCH₂CH₂, H), (M-4556, F, F, H, HOCH₂CH₂, Cl), (M-4557, F, F, H, HOCH₂CH₂, F), (M-4558, F, F, H, HOCH₂CH₂, CF₃), (M-4559, F, F, H, HOCH₂CH₂, Br), (M-4560, F, F, H, HOCH₂CH₂, CH₃), (M-4561, F, F, H, HOCH₂CH₂CH₂, H), (M-4562, F, F, H, HOCH₂CH₂CH₂, Cl), (M-4563, F, F, H, HOCH₂CH₂CH₂, F), (M-4564, F, F, H, HOCH₂CH₂CH₂, CF₃), (M-4565, F, F, H, HOCH₂CH₂CH₂, Br), (M-4566, F, F, H, HOCH₂CH₂CH₂, CH₃), (M-4567, F, F, H, HOCH₂CH₂CH₂CH₂, H), (M-4568, F, F, H, HOCH₂CH₂CH₂CH₂, Cl), (M-4569, F, F, H, HOCH₂CH₂CH₂CH₂, F), (M-4570, F, F, H, HOCH₂CH₂CH₂CH₂, CF₃), (M-4571, F, F, H, HOCH₂CH₂CH₂CH₂, Br), (M-4572, F, F, H, HOCH₂CH₂CH₂CH₂, CH₃), (M-4573, F, F, H, HOCH₂CH₂CH₂CH₂CH₂, H), (M-4574, F, F, H, HOCH₂CH₂CH₂CH₂CH₂, Cl), (M-4575, F, F, H, HOCH₂CH₂CH₂CH₂CH₂, F), (M-4576, F, F, H, HOCH₂CH₂CH₂CH₂CH₂, CF₃), (M-4577, F, F, H, HOCH₂CH₂CH₂CH₂CH₂, Br) (M-4578, F, F, H, HOCH₂CH₂CH₂CH₂CH₂, CH₃), (M-4579, F, F, H, HOCH₂CH₂OCH₂CH₂, H), (M-4580, F, F, H, HOCH₂CH₂OCH₂CH₂, Cl), (M-4581, F, F, H, HOCH₂CH₂OCH₂CH₂, F), (M-4582, F, F, H, HOCH₂CH₂OCH₂CH₂, CF₃), (M-4583, F, F, H, HOCH₂CH₂OCH₂CH₂, Br), (M-4584, F, F, H, HOCH₂CH₂OCH₂CH₂, CH₃), (M-4585, F, F, H, (Me)₂N, H), (M-4586, F, F, H, (Me)₂N, Cl), (M-4587, F, F, H, (Me)₂N, F), (M-4588, F, F, H, (Me)₂N, CF₃), (M-4589, F, F, H, (Me)₂N, Br), (M-4590, F, F, H, (Me)₂N, CH₃), (M-4591, F, F, H, piperidin-4-yl-methyl, H), (M-4592, F, F, H, piperidin-4-yl-methyl, Cl), (M-4593, F, F, H, piperidin-4-yl-methyl, F), (M-4594, F, F, H, piperidin-4-yl-methyl, CF₃), (M-4595, F, F, H, piperidin-4-yl-methyl, Br), (M-4596, F, F, H, piperidin-4-yl-methyl, CH₃), (M-4597, F, F, H, cyclohexylmethyl, H), (M-4598, F, F, H, cyclohexylmethyl, Cl), (M-4599, F, F, H, cyclohexylmethyl, F), (M-4600, F, F, H, cyclohexylmethyl, CF₃), (M-4601, F, F, H, cyclohexylmethyl, Br), (M-4602, F, F, H, cyclohexylmethyl, CH₃), (M-4603, F, F, F, H, H), (M-4604, F, F, F, H, Cl), (M-4605, F, F, F, H, F), (M-4606, F, F, H, CF₃), (M-4607, F, F, F, H, Br), (M-4608, F, F, F, H, CH₃), (M-4609, F, F, F, F, H), (M-4610, F, F, F, F, Cl), (M-4611, F, F, F, F, F), (M-4612, F, F, F, F, CF₃), (M-4613, F, F, F, F, Br), (M-4614, F, F, F, F, CH₃), (M-4615, F, F, F, Cl, H), (M-4616, F, F, F, Cl, Cl), (M-4617, F, F, F, Cl, F), (M-4618, F, F, F, Cl, CF₃), (M-4619, F, F, F, Cl, Br), (M-4620, F, F, F, Cl, CH₃), (M-4621, F, F, F, CH₃, H), (M-4622, F, F, F, CH₃, Cl), (M-4623, F, F, F, CH₃, F), (M-4624, F, F, F, CH₃, CF₃), (M-4625, F, F, F, CH₃, Br), (M-4626, F, F, F, CH₃, CH₃), (M-4627, F, F, F, Et, H), (M-4628, F, F, F, Et, Cl), (M-4629, F, F, F, Et, F), (M-4630, F, F, F, Et, CF₃), (M-4631, F, F, F, Et, Br), (M-4632, F, F, F, Et, CH₃), (M-4633, F, F, F, n-Pr, H), (M-4634, F, F, F, n-Pr, Cl), (M-4635, F, F, F, n-Pr, F), (M-4636, F, F, F, n-Pr, CF₃), (M-4637, F, F, F, n-Pr, Br), (M-4638, F, F, F, n-Pr, CH₃), (M-4639, F, F, F, c-Pr, H), (M-4640, F, F, F, c-Pr, Cl), (M-4641, F, F, F, c-Pr, F), (M-4642, F, F, F, c-Pr, CF₃), (M-4643, F, F, F, c-Pr, Br), (M-4644, F, F, F, c-Pr, CH₃), (M-4645, F, F, F, i-Pr, H), (M-4646, F, F, F, i-Pr, Cl), (M-4647, F, F, F, i-Pr, F), (M-4648, F, F, F, i-Pr, CF₃), (M-4649, F, F, F, i-Pr, Br), (M-4650, F, F, F, i-Pr, CH₃), (M-4651, F, F, F, n-Bu, H), (M-4652, F, F, F, n-Bu, Cl), (M-4653, F, F, F, n-Bu, F), (M-4654, F, F, F, n-Bu, CF₃), (M-4655, F, F, F, n-Bu, Br), (M-4656, F, F, F, n-Bu, CH₃), (M-4657, F, F, F, i-Bu, H), (M-4658, F, F, F, i-Bu, Cl), (M-4659, F, F, F, i-Bu, F), (M-4660, F, F, F, i-Bu, CF₃), (M-4661, F, F, F, i-Bu, Br), (M-4662, F, F, F, i-Bu, CH₃), (M-4663, F, F, F, sec-Bu, H), (M-4664, F, F, F, sec-Bu, Cl), (M-4665, F, F, F, sec-Bu, F), (M-4666, F, F, F, sec-Bu, CF₃), (M-4667, F, F, F, sec-Bu, Br), (M-4668, F, F, F, sec-Bu, CH₃), (M-4669, F, F, F, n-Pen, H), (M-4670, F, F, F, n-Pen, Cl), (M-4671, F, F, F, n-Pen, F), (M-4672, F, F, F, n-Pen, CF₃), (M-4673, F, F, F, n-Pen, Br), (M-4674, F, F, F, n-Pen, CH₃), (M-4675, F, F, F, c-Pen, H), (M-4676, F, F, F, c-Pen, Cl), (M-4677, F, F, F, c-Pen, F), (M-4678, F, F, F, c-Pen, CF₃), (M-4679, F, F, F, c-Pen, Br), (M-4680, F, F, F, c-Pen, CH₃), (M-4681, F, F, F, n-Hex, H), (M-4682, F, F, F, n-Hex, Cl), (M-4683, F, F, F, n-Hex, F), (M-4684, F, F, F, n-Hex, CF₃), (M-4685, F, F, F, n-Hex, Br), (M-4686, F, F, F, n-Hex, CH₃), (M-4687, F, F, F, c-Hex, H), (M-4688, F, F, F, c-Hex, Cl), (M-4689, F, F, F, c-Hex, F), (M-4690, F, F, F, c-Hex, CF₃), (M-4691, F, F, F, c-Hex, Br), (M-4692, F, F, F, c-Hex, CH₃), (M-4693, F, F, F, OH, H), (M-4694, F, F, F, OH, Cl), (M-4695, F, F, F, OH, F), (M-4696, F, F, F, OH, CF₃), (M-4697, F, F, F, OH, Br), (M-4698, F, F, F, OH, CH₃), (M-4699, F, F, F, EtO, H), (M-4700, F, F, F, EtO, Cl), (M-4701, F, F, F, EtO, F), (M-4702, F, F, F, EtO, CF₃), (M-4703, F, F, F, EtO, Br), (M-4704, F, F, F, EtO, CH₃), (M-4705, F, F, F, n-PrO, H), (M-4706, F, F, F, n-PrO, Cl), (M-4707, F, F, F, n-PrO, F), (M-4708, F, F, F, n-PrO, CF₃), (M-4709, F, F, F, n-PrO, Br), (M-4710, F, F, F, n-PrO, CH₃), (M-4711, F, F, F, PhO, H), (M-4712, F, F, F, PhO, Cl), (M-4713, F, F, F, PhO, F), (M-4714, F, F, F, PhO, CF₃), (M-4715, F, F, F, PhO, Br), (M-4716, F, F, F, PhO, CH₃), (M-4717, F, F, F, BnO, H), (M-4718, F, F, F, BnO, Cl), (M-4719, F, F, F, BnO, F), (M-4720, F, F, F, BnO, CF₃), (M-4721, F, F, F, BnO, Br), (M-4722, F, F, F, BnO, CH₃), (M-4723, F, F, F, PhCH₂CH₂O, H), (M-4724, F, F, F, PhCH₂CH₂O, Cl), (M-4725, F, F, F, PhCH₂CH₂O, F), (M-4726, F, F, F, PhCH₂CH₂O, CF₃), (M-4727, F, F, F, PhCH₂CH₂O, Br), (M-4728, F, F, F, PhCH₂CH₂O, CH₃), (M-4729, F, F, F, CF₃O, H), (M-4730, F, F, F, CF₃O, Cl), (M-4731, F, F, F, CF₃O, F), (M-4732, F, F, F, CF₃O, CF₃), (M-4733, F, F, F, CF₃O, Br), (M-4734, F, F, F, CF₃O, CH₃), (M-4735, F, F, F, Ph, H), (M-4736, F, F, F, Ph, Cl), (M-4737, F, F, F, Ph, F), (M-4738, F, F, F, Ph, CF₃), (M-4739, F, F, F, Ph, Br), (M-4740, F, F, F, Ph, CH₃), (M-4741, F, F, F, 4-F-Ph, H), (M-4742, F, F, F, 4-F-Ph, Cl), (M-4743, F, F, F, 4-F-Ph, F), (M-4744, F, F, F, 4-F-Ph, CF₃), (M-4745, F, F, F, 4-F-Ph, Br), (M-4746, F, F, F, 4-F-Ph, CH₃), (M-4747, F, F, F, 4-CF₃-Ph, H), (M-4748, F, F, F, 4-CF₃-Ph, Cl), (M-4749, F, F, F, 4-CF₃-Ph, F), (M-4750, F, F, F, 4-CF₃-Ph, CF₃), (M-4751, F, F, F, 4-CF₃-Ph, Br), (M-4752, F, F, F, 4-CF₃-Ph, CH₃), (M-4753, F, F, F, 4-(Me)₂N-Ph, H), (M-4754, F, F, F, 4-(Me)₂N-Ph, Cl), (M-4755, F, F, F, 4-(Me)₂

N-Ph, F), (M-4756, F, F, F, 4-(Me)₂N-Ph, CF₃), (M-4757, F, F, F, 4-(Me)₂N-Ph, Br), (M-4758, F, F, F, 4-(Me)₂N-Ph, CH₃), (M-4759, F, F, F, 4-OH-Ph, H), (M-4760, F, F, F, 4-OH-Ph, Cl), (M-4761, F, F, F, 4-OH-Ph, F), (M-4762, F, F, F, 4-OH-Ph, CF₃), (M-4763, F, F, F, 4-OH-Ph, Br), (M-4764, F, F, F, 4-OH-Ph, CH₃), (M-4765, F, F, F, 3,4-di-F-Ph, H), (M-4766, F, F, F, 3,4-di-F-Ph, Cl), (M-4767, F, F, F, 3,4-di-F-Ph, F), (M-4768, F, F, F, 3,4-di-F-Ph, CF₃), (M-4769, F, F, F, 3,4-di-F-Ph, Br), (M-4770, F, F, F, 3,4-di-F-Ph, CH₃), (M-4771, F, F, F, 4-COOH-Ph, H), (M-4772, F, F, F, 4-COOH-Ph, Cl), (M-4773, F, F, F, 4-COOH-Ph, F), (M-4774, F, F, F, 4-COOH-Ph, CF₃), (M-4775, F, F, F, 4-COOH-Ph, Br), (M-4776, F, F, F, 4-COOH-Ph, CH₃), (M-4777, F, F, F, Bn, H), (M-4778, F, F, F, Bn, Cl), (M-4779, F, F, F, Bn, F), (M-4780, F, F, F, Bn, CF₃), (M-4781, F, F, F, Bn, Br), (M-4782, F, F, F, Bn, CH₃), (M-4783, F, F, F, 4-F-Bn, H), (M-4784, F, F, F, 4-F-Bn, Cl), (M-4785, F, F, F, 4-F-Bn, F), (M-4786, F, F, F, 4-F-Bn, CF₃), (M-4787, F, F, F, 4-F-Bn, Br), (M-4788, F, F, F, 4-F-Bn, CH₃), (M-4789, F, F, F, 2-Py, H), (M-4790, F, F, F, 2-Py, Cl), (M-4791, F, F, F, 2-Py, F), (M-4792, F, F, F, 2-Py, CF₃), (M-4793, F, F, F, 2-Py, Br), (M-4794, F, F, F, 2-Py, CH₃), (M-4795, F, F, F, 3-Py, H), (M-4796, F, F, F, 3-Py, Cl), (M-4797, F, F, F, 3-Py, F), (M-4798, F, F, F, 3-Py, CF₃), (M-4799, F, F, F, 3-Py, Br), (M-4800, F, F, F, 3-Py, CH₃), (M-4801, F, F, F, 4-Py, H), (M-4802, F, F, F, 4-Py, Cl), (M-4803, F, F, F, 4-Py, F), (M-4804, F, F, F, 4-Py, CF₃), (M-4805, F, F, F, 4-Py, Br), (M-4806, F, F, F, 4-Py, CH₃), (M-4807, F, F, F, 2-Th, H), (M-4808, F, F, F, 2-Th, Cl), (M-4809, F, F, F, 2-Th, F), (M-4810, F, F, F, 2-Th, CF₃), (M-4811, F, F, F, 2-Th, Br), (M-4812, F, F, F, 2-Th, CH₃), (M-4813, F, F, F, 3-Th, H), (M-4814, F, F, F, 3-Th, Cl), (M-4815, F, F, F, 3-Th, F), (M-4816, F, F, F, 3-Th, CF₃), (M-4817, F, F, F, 3-Th, Br), (M-4818, F, F, F, 3-Th, CH₃), (M-4819, F, F, F, pyrrazol-2-yl, H), (M-4820, F, F, F, pyrrazol-2-yl, Cl), (M-4821, F, F, F, pyrrazol-2-yl, F), (M-4822, F, F, F, pyrrazol-2-yl, CF₃), (M-4823, F, F, F, pyrrazol-2-yl, Br), (M-4824, F, F, F, pyrrazol-2-yl, CH₃), (M-4825, F, F, F, pyrrazol-3-yl, H), (M-4826, F, F, F, pyrrazol-3-yl, Cl), (M-4827, F, F, F, pyrrazol-3-yl, F), (M-4828, F, F, F, pyrrazol-3-yl, CF₃), (M-4829, F, F, F, pyrrazol-3-yl, Br), (M-4830, F, F, F, pyrrazol-3-yl, CH₃), (M-4831, F, F, F, pyrimidin-2-yl, H), (M-4832, F, F, F, pyrimidin-2-yl, Cl), (M-4833, F, F, F, pyrimidin-2-yl, F), (M-4834, F, F, F, pyrimidin-2-yl, CF₃), (M-4835, F, F, F, pyrimidin-2-yl, Br), (M-4836, F, F, F, pyrimidin-2-yl, CH₃), (M-4837, F, F, F, pyrimidin-4-yl, H), (M-4838, F, F, F, pyrimidin-4-yl, Cl), (M-4839, F, F, F, pyrimidin-4-yl, F), (M-4840, F, F, F, pyrimidin-4-yl, CF₃), (M-4841, F, F, F, pyrimidin-4-yl, Br), (M-4842, F, F, F, pyrimidin-4-yl, CH₃), (M-4843, F, F, F, pyrimidin-5-yl, H), (M-4844, F, F, F, pyrimidin-5-yl, Cl), (M-4845, F, F, F, pyrimidin-5-yl, F), (M-4846, F, F, F, pyrimidin-5-yl, CF₃), (M-4847, F, F, F, pyrimidin-5-yl, Br), (M-4848, F, F, F, pyrimidin-5-yl, CH₃), (M-4849, F, F, F, HOOCCH₂CH₂CH₂, H), (M-4850, F, F, F, HOOCCH₂CH₂CH₂, Cl), (M-4851, F, F, F, HOOCCH₂CH₂CH₂, F), (M-4852, F, F, F, HOOCCH₂CH₂CH₂, CF₃), (M-4853, F, F, F, HOOCCH₂CH₂CH₂, Br), (M-4854, F, F, F, HOOCCH₂CH₂CH₂, CH₃), (M-4855, F, F, F, HOOCCH₂CH₂CH₂CH₂, H), (M-4856, F, F, F, HOOCCH₂CH₂CH₂CH₂, Cl), (M-4857, F, F, F, HOOCCH₂CH₂CH₂CH₂, F), (M-4858, F, F, F, HOOCCH₂CH₂CH₂CH₂, CF₃), (M-4859, F, F, F, HOOCCH₂CH₂CH₂CH₂, Br), (M-4860, F, F, F, HOOCCH₂CH₂CH₂CH₂, CH₃), (M-4861, F, F, F, (Me)₂NCOCH₂CH₂CH₂, H), (M-4862, F, F, F, (Me)₂NCOCH₂CH₂CH₂, Cl), (M-4863, F, F, F, (Me)₂NCOCH₂CH₂CH₂, F), (M-4864, F, F, F, (Me)₂NCOCH₂CH₂CH₂, CF₃), (M-4865, F, F, F, (Me)₂NCOCH₂CH₂CH₂, Br), (M-4866, F, F, F, (Me)₂NCOCH₂CH₂CH₂, CH₃), (M-4867, F, F, F, (Me)₂NCOCH₂CH₂CH₂CH₂, H), (M-4868, F, F, F, (Me)₂NCOCH₂CH₂CH₂CH₂, Cl), (M-4869, F, F, F, (Me)₂NCOCH₂CH₂CH₂CH₂, F), (M-4870, F, F, F, (Me)₂NCOCH₂CH₂CH₂CH₂, CF₃), (M-4871, F, F, F, (Me)₂NCOCH₂CH₂CH₂CH₂, Br), (M-4872, F, F, F, (Me)₂NCOCH₂CH₂CH₂CH₂, CH₃), (M-4873, F, F, F, MeOCH₂, H), (M-4874, F, F, F, MeOCH₂, Cl), (M-4875, F, F, F, MeOCH₂, F), (M-4876, F, F, F, MeOCH₂, CF₃), (M-4877, F, F, F, MeOCH₂, Br), (M-4878, F, F, F, MeOCH₂, CH₃), (M-4879, F, F, F, EtOCH₂, H), (M-4880, F, F, F, EtOCH₂, Cl), (M-4881, F, F, F, EtOCH₂, F), (M-4882, F, F, F, EtOCH₂, CF₃), (M-4883, F, F, F, EtOCH₂, Br), (M-4884, F, F, F, EtOCH₂, CH₃), (M-4885, F, F, F, EtOCH₂CH₂, H), (M-4886, F, F, F, EtOCH₂CH₂, Cl), (M-4887, F, F, F, EtOCH₂CH₂, F), (M-4888, F, F, F, EtOCH₂CH₂, CF₃), (M-4889, F, F, F, EtOCH₂CH₂, Br), (M-4890, F, F, F, EtOCH₂CH₂, CH₃), (M-4891, F, F, F, MeOCH₂CH₂OCH₂CH₂, H), (M-4892, F, F, F, MeOCH₂CH₂OCH₂CH₂, Cl), (M-4893, F, F, F, MeOCH₂CH₂OCH₂CH₂, F), (M-4894, F, F, F, MeOCH₂CH₂OCH₂CH₂, CF₃), (M-4895, F, F, F, MeOCH₂CH₂OCH₂CH₂, Br), (M-4896, F, F, F, MeOCH₂CH₂OCH₂CH₂, CH₃), (M-4897, F, F, F, MeOCH₂CH₂, H), (M-4898, F, F, F, MeOCH₂CH₂, Cl), (M-4899, F, F, F, MeOCH₂CH₂, F), (M-4900, F, F, F, MeOCH₂CH₂, CF₃), (M-4901, F, F, F, MeOCH₂CH₂, Br), (M-4902, F, F, F, MeOCH₂CH₂, CH₃), (M-4903, F, F, F, HOCH₂, H), (M-4904, F, F, F, HOCH₂, Cl), (M-4905, F, F, F, HOCH₂, F), (M-4906, F, F, F, HOCH₂, CF₃), (M-4907, F, F, F, HOCH₂, Br), (M-4908, F, F, F, HOCH₂, CH₃), (M-4909, F, F, F, HOCH₂CH₂, H), (M-4910, F, F, F, HOCH₂CH₂, Cl), (M-4911, F, F, F, HOCH₂CH₂, F), (M-4912, F, F, F, HOCH₂CH₂, CF₃), (M-4913, F, F, F, HOCH₂CH₂, Br), (M-4914, F, F, F, HOCH₂CH₂, CH₃), (M-4915, F, F, F, HOCH₂CH₂CH₂, H), (M-4916, F, F, F, HOCH₂CH₂CH₂, Cl), (M-4917, F, F, F, HOCH₂CH₂CH₂, F), (M-4918, F, F, F, HOCH₂CH₂CH₂, CF₃), (M-4919, F, F, F, HOCH₂CH₂CH₂, Br), (M-4920, F, F, F, HOCH₂CH₂CH₂, CH₃), (M-4921, F, F, F, HOCH₂CH₂CH₂CH₂, H), (M-4922, F, F, F, HOCH₂CH₂CH₂CH₂, Cl), (M-4923, F, F, F, HOCH₂CH₂CH₂CH₂, F), (M-4924, F, F, F, HOCH₂CH₂CH₂CH₂, CF₃), (M-4925, F, F, F, HOCH₂CH₂CH₂CH₂, Br), (M-4926, F, F, F, HOCH₂CH₂CH₂CH₂, CH₃), (M-4927, F, F, F, HOCH₂CH₂CH₂CH₂CH₂, H), (M-4928, F, F, F, HOCH₂CH₂CH₂CH₂CH₂, Cl), (M-4929, F, F, F, HOCH₂CH₂CH₂CH₂CH₂, F), (M-4930, F, F, F, HOCH₂CH₂CH₂CH₂CH₂, CF₃), (M-4931, F, F, F, HOCH₂CH₂CH₂CH₂CH₂, Br), (M-4932, F, F, F, HOCH₂CH₂CH₂CH₂CH₂, CH₃), (M-4933, F, F, F, HOCH₂CH₂OCH₂CH₂, H), (M-4934, F, F, F, HOCH₂CH₂OCH₂CH₂, Cl), (M-4935, F, F, F, HOCH₂CH₂OCH₂CH₂, F), (M-4936, F, F, F, HOCH₂CH₂OCH₂CH₂, CF₃), (M-4937, F, F, F, HOCH₂CH₂OCH₂CH₂, Br), (M-4938, F, F, F, HOCH₂CH₂OCH₂CH₂, CH₃), (M-4939, F, F, F, (Me)₂N, H), (M-4940, F, F, F, (Me)₂N, Cl), (M-4941, F, F, F, (Me)₂N, F), (M-4942, F, F, F, (Me)₂N, CF₃), (M-4943, F, F, F, (Me)₂N, Br), (M-4944, F, F, F, (Me)₂N, CH₃), (M-4945, F, F, F, piperidin-4-yl-methyl, H), (M-4946, F, F, F, piperidin-4-yl-methyl, Cl), (M-4947, F, F, F, piperidin-4-yl-methyl, F), (M-4948, F, F, F, piperidin-4-yl-methyl, CF₃), (M-4949, F, F, F, piperidin-4-yl-methyl, Br), (M-4950, F, F, F, piperidin-4-yl-methyl, CH₃), (M-4951, F, F, F, cyclohexylmethyl, H), (M-4952, F, F, F, cyclohexylmethyl, Cl), (M-4953, F, F, F, cyclohexylmethyl, F), (M-4954, F, F, F, cyclohexylmethyl, CF₃), (M-4955, F, F, F, cyclohexylmethyl, Br), (M-4956, F, F, F, cyclohexylmethyl, CH₃), (M-4957, F, F, Cl, H, H), (M-4958, F, F, Cl, H, Cl), (M-4959, F, F, Cl, H, F), (M-4960, F, F, Cl, H, Br), (M-4961, F, F, Cl, H, Br), (M-4962, F, F, Cl, H, CH₃), (M-4963, F, F, Cl, F, H), (M-4964, F, F, Cl, F, Cl), (M-4965, F, F, Cl, F, F), (M-4966, F, F, Cl, F, CF₃), (M-4967, F, F, Cl, F, Br), (M-4968, F, F, Cl, F, CH₃), (M-4969, F, F, Cl, Cl, H), (M-4970, F, F, Cl, Cl, Cl), (M-4971, F, F, Cl, Cl, F), (M-4972, F, F, Cl, Cl, CF₃), (M-4973, F, F, Cl, Cl, Br), (M-4974, F, F, Cl, Cl, CH₃), (M-4975, F, F, Cl, CH₃, H), (M-4976, F, F, Cl, CH₃, Cl), (M-4977, F, F, Cl, CH₃, F), (M-4978, F, F, Cl, CH₃, CF₃), (M-4979, F, F, Cl, CH₃, Br), (M-4980, F, F, Cl, CH₃, CH₃), (M-4981, F, F, Cl, Et, H), (M-4982, F, F, Cl, Et, Cl), (M-4983, F, F, Cl, Et, F), (M-4984, F, F, Cl, Et, CF₃), (M-4985, F, F, Cl, Et, Br), (M-4986, F, F, Cl, Et, CH₃), (M-4987, F, F, Cl, n-Pr, H), (M-4988, F, F, Cl, n-Pr, Cl), (M-4989, F, F, Cl, n-Pr, F), (M-4990, F, F, Cl, n-Pr, CF₃), (M-4991, F, F, Cl, n-Pr, Br), (M-4992, F, F, Cl, n-Pr, CH₃), (M-4993, F, F, Cl, c-Pr, H), (M-4994, F, F, Cl, c-Pr, Cl), (M-4995, F, F, Cl, c-Pr, F), (M-4996, F, F, Cl, c-Pr, CF₃), (M-4997, F, F, Cl, c-Pr, Br), (M-4998, F, F, Cl, c-Pr, CH₃), (M-4999, F, F, Cl, i-Pr, H), (M-5000, F, F, Cl, i-Pr, Cl), (M-5001, F, F, Cl, i-Pr, F), (M-5002, F, F, Cl, i-Pr, CF₃), (M-5003, F, F, Cl, i-Pr, Br), (M-5004, F, F, Cl, i-Pr, CH₃), (M-5005, F, F, Cl, n-Bu, H), (M-5006, F, F, Cl, n-Bu, Cl), (M-5007, F, F, Cl, n-Bu, F), (M-5008, F, F, Cl, n-Bu, CF₃), (M-5009, F, F, Cl, n-Bu, Br), (M-5010, F, F, Cl, n-Bu, CH₃), (M-5011, F, F, Cl, i-Bu, H), (M-5012, F, F, Cl, i-Bu, Cl), (M-5013, F, F, Cl, i-Bu, F), (M-5014, F, F, Cl, i-Bu, CF₃), (M-5015, F, F, Cl, i-Bu, Br), (M-5016, F, F, Cl, i-Bu, CH₃), (M-5017, F, F, Cl, sec-Bu, H), (M-5018, F, F, Cl, sec-Bu, Cl), (M-5019, F, F, Cl, sec-Bu, F), (M-5020, F, F, Cl, sec-Bu, CF₃), (M-5021, F, F, Cl, sec-Bu, Br), (M-5022, F, F, Cl, sec-Bu, CH₃), (M-5023, F, F, Cl, n-Pen, H), (M-5024, F, F, Cl, n-Pen, Cl), (M-5025, F, F, Cl, n-Pen, F), (M-5026, F, F, Cl, n-Pen, CF₃), (M-5027, F, F, Cl, n-Pen, Br), (M-5028, F, F, Cl, n-Pen, CH₃), (M-5029, F, F, Cl, c-Pen, H), (M-5030, F, F, Cl, c-Pen, Cl), (M-5031, F, F, Cl, c-Pen, F), (M-5032, F, F, Cl, c-Pen, CF₃), (M-5033, F, F, Cl, c-Pen, Br), (M-5034, F, F, Cl, c-Pen, CH₃), (M-5035, F, F, Cl, n-Hex, H), (M-5036, F, F, Cl, n-Hex, Cl), (M-5037, F, F, Cl, n-Hex, F), (M-5038, F, F, Cl, n-Hex, CF₃), (M-5039, F, F, Cl, n-Hex, Br), (M-5040, F, F, Cl, n-Hex, CH₃), (M-5041, F, F, Cl, c-Hex, H), (M-5042, F, F, Cl, c-Hex, Cl), (M-5043, F, F, Cl, c-Hex, F), (M-5044, F, F, Cl, c-Hex, CF₃), (M-5045, F, F, Cl, c-Hex, Br), (M-5046, F, F, Cl, c-Hex, CH₃), (M-5047, F, F, Cl, OH, H), (M-5048, F, F, Cl, OH, Cl), (M-5049, F, F, Cl, OH, F), (M-5050, F, F, Cl, OH, CF₃), (M-5051, F, F, Cl, OH, Br), (M-5052, F, F, Cl, OH, CH₃), (M-5053, F, F, Cl, EtO, H), (M-5054, F, F, Cl, EtO, Cl), (M-5055, F, F, Cl, EtO, F), (M-5056, F, F, Cl, EtO, CF₃), (M-5057, F, F, Cl, EtO, Br), (M-5058, F, F, Cl, EtO, CH₃), (M-5059, F, F, Cl, n-PrO, H), (M-5060, F, F, Cl, n-PrO, Cl), (M-5061, F, F, Cl, n-PrO, F), (M-5062, F, F, Cl, n-PrO, CF₃), (M-5063, F, F, Cl, n-PrO, Br), (M-5064, F, F, Cl, n-PrO, CH₃), (M-5065, F, F, Cl, PhO, H), (M-5066, F, F, Cl, PhO, Cl), (M-5067, F, F, Cl, PhO, F), (M-5068, F, F, Cl, PhO, CF₃), (M-5069, F, F, Cl, PhO, Br), (M-5070, F, F, Cl, PhO, CH₃), (M-5071, F, F, Cl, BnO, H), (M-5072, F, F, Cl, BnO, Cl), (M-5073, F, F, Cl, BnO, F), (M-5074, F, F, Cl, BnO, CF₃), (M-5075, F, F, Cl, BnO, Br), (M-5076, F, F, Cl, BnO, CH₃), (M-5077, F, F, Cl, PhCH₂CH₂O, H), (M-5078, F, F, Cl, PhCH₂CH₂O, Cl), (M-5079, F, F, Cl, PhCH₂CH₂O, F), (M-5080, F, F, Cl, PhCH₂CH₂O, CF₃), (M-5081, F, F, Cl, PhCH₂CH₂O, Br), (M-5082, F, F, Cl, PhCH₂CH₂O, CH₃), (M-5083, F, F, Cl, CF₃O, H), (M-5084, F, F, Cl, CF₃O, Cl), (M-5085, F, F, Cl, CF₃O, F), (M-5086, F, F, Cl, CF₃O, CF₃), (M-5087, F, F, Cl, CF₃O, Br), (M-5088, F, F, Cl, CF₃O, CH₃), (M-5089, F, F, Cl, Ph, H), (M-5090, F, F, Cl, Ph, Cl), (M-5091, F, F, Cl, Ph, F), (M-5092, F, F, Cl, Ph, CF₃), (M-5093, F, F, Cl, Ph, Br), (M-5094, F, F, Cl, Ph, CH₃), (M-5095, F, F, Cl, 4-F-Ph, H), (M-5096, F, F, Cl, 4-F-Ph, Cl), (M-5097, F, F, Cl, 4-F-Ph, F), (M-5098, F, F, Cl, 4-F-Ph, CF₃), (M-5099, F, F, Cl, 4-F-Ph, Br), (M-5100, F, F, Cl, 4-F-Ph, CH₃), (M-5101, F, F, Cl, 4-CF₃-Ph, H), (M-5102, F, F, Cl, 4-CF₃-Ph, Cl), (M-5103, F, F, Cl, 4-CF₃-Ph, F), (M-5104, F, F, Cl, 4-CF₃-Ph, CF₃), (M-5105, F, F, Cl, 4-CF₃-Ph, Br), (M-5106, F, F, Cl, 4-CF₃-Ph, CH₃), (M-5107, F, F, Cl, 4-(Me)₂N-Ph, H), (M-5108, F, F, Cl, 4-(Me)₂N-Ph, Cl), (M-5109, F, F, Cl, 4-(Me)₂N-Ph, F), (M-5110, F, F, Cl, 4-(Me)₂N-Ph, CF₃), (M-5111, F, F, Cl, 4-(Me)₂N-Ph, Br), (M-5112, F, F, Cl, 4-(Me)₂N-Ph, CH₃), (M-5113, F, F, Cl, 4-OH-Ph, H), (M-5114, F, F, Cl, 4-OH-Ph, Cl), (M-5115, F, F, Cl, 4-OH-Ph, F), (M-5116, F, F, Cl, 4-OH-Ph, CF₃), (M-5117, F, F, Cl, 4-OH-Ph, Br), (M-5118, F, F, Cl, 4-OH-Ph, CH₃), (M-5119, F, F, Cl, 3,4-di-F-Ph, H), (M-5120, F, F, Cl, 3,4-di-F-Ph, Cl), (M-5121, F, F, Cl, 3,4-di-F-Ph, F), (M-5122, F, F, Cl, 3,4-di-F-Ph, CF₃), (M-5123, F, F, Cl, 3,4-di-F-Ph, Br), (M-5124, F, F, Cl, 3,4-di-F-Ph, CH₃), (M-5125, F, F, Cl, 4-COOH-Ph, H), (M-5126, F, F, Cl, 4-COOH-Ph, Cl), (M-5127, F, F, Cl, 4-COOH-Ph, F), (M-5128, F, F, Cl, 4-COOH-Ph, CF₃), (M-5129, F, F, Cl, 4-COOH-Ph, Br), (M-5130, F, F, Cl, 4-COOH-Ph, CH₃), (M-5131, F, F, Cl, Bn, H), (M-5132, F, F, Cl, Bn, Cl), (M-5133, F, F, Cl, Bn, F), (M-5134, F, F, Cl, Bn, CF₃), (M-5135, F, F, Cl, Bn, Br), (M-5136, F, F, Cl, Bn, CH₃), (M-5137, F, F, Cl, 4-F-Bn, H), (M-5138, F, F, Cl, 4-F-Bn, Cl), (M-5139, F, F, Cl, 4-F-Bn, F), (M-5140, F, F, Cl, 4-F-Bn, CF₃), (M-5141, F, F, Cl, 4-F-Bn, Br), (M-5142, F, F, Cl, 4-F-Bn, CH₃), (M-5143, F, F, Cl, 2-Py, H), (M-5144, F, F, Cl, 2-Py, Cl), (M-5145, F, F, Cl, 2-Py, F), (M-5146, F, F, Cl, 2-Py, CF₃), (M-5147, F, F, Cl, 2-Py, Br), (M-5148, F, F, Cl, 2-Py, CH₃), (M-5149, F, F, Cl, 3-Py, H), (M-5150, F, F, Cl, 3-Py, Cl), (M-5151, F, F, Cl, 3-Py, F), (M-5152, F, F, Cl, 3-Py, CF₃), (M-5153, F, F, Cl, 3-Py, Br), (M-5154, F, F, Cl, 3-Py, CH₃), (M-5155, F, F, Cl, 4-Py, H), (M-5156, F, F, Cl, 4-Py, Cl), (M-5157, F, F, Cl, 4-Py, F), (M-5158, F, F, Cl, 4-Py, CF₃), (M-5159, F, F, Cl, 4-Py, Br), (M-5160, F, F, Cl, 4-Py, CH₃), (M-5161, F, F, Cl, 2-Th, H), (M-5162, F, F, Cl, 2-Th, Cl), (M-5163, F, F, Cl, 2-Th, F), (M-5164, F, F, Cl, 2-Th, CF₃), (M-5165, F, F, Cl, 2-Th, Br), (M-5166, F, F, Cl, 2-Th, CH₃), (M-5167, F, F, Cl, 3-Th, H), (M-5168, F, F, Cl, 3-Th, Cl), (M-5169, F, F, Cl, 3-Th, F), (M-5170, F, F, Cl, 3-Th, CF₃), (M-5171, F, F, Cl, 3-Th, Br), (M-5172, F, F, Cl, 3-Th, CH₃), (M-5173, F, F, Cl, pyrrazol-2-yl, H), (M-5174, F, F, Cl, pyrrazol-2-yl, Cl), (M-5175, F, F, Cl, pyrrazol-2-yl, F), (M-5176, F, F, Cl, pyrrazol-2-yl, CF₃), (M-5177, F, F, Cl, pyrrazol-2-yl, Br), (M-5178, F, F, Cl, pyrrazol-2-yl, CH₃), (M-5179, F, F, Cl, pyrrazol-3-yl, H), (M-5180, F, F, Cl, pyrrazol-3-yl, Cl), (M-5181, F, F, Cl, pyrrazol-3-yl, F), (M-5182, F, F, Cl, pyrrazol-3-yl, CF₃), (M-5183, F, F, Cl, pyrrazol-3-yl, Br), (M-5184, F, F, Cl, pyrrazol-3-yl, CH₃), (M-5185, F, F, Cl, pyrimidin-2-yl, H), (M-5186, F, F, Cl, pyrimidin-2-yl, Cl), (M-5187, F, F, Cl, pyrimidin-2-yl, F), (M-5188, F, F, Cl, pyrimidin-2-yl, CF₃), (M-5189, F, F, Cl, pyrimidin-2-yl, Br), (M-5190, F, F, Cl, pyrimidin-2-yl, CH₃), (M-5191, F, F, Cl, pyrimidin-4-yl, H), (M-5192, F, F, Cl, pyrimidin-4-yl, Cl), (M-5193, F, F, Cl, pyrimidin-4-yl, F), (M-5194, F, F, Cl, pyrimidin-4-yl, CF₃), (M-5195, F, F, Cl, pyrimidin-4-yl, Br), (M-5196, F, F, Cl, pyrimidin-4-yl, CH₃), (M-5197, F, F, Cl, pyrimidin-5-yl, H), (M-5198, F, F, Cl, pyrimidin-5-yl, Cl), (M-5199, F, F, Cl, pyrimidin-5-yl, F), (M-5200, F, F, Cl, pyrimidin-5-yl, CF₃), (M-5201, F, F, Cl, pyrimidin-5-yl, Br), (M-5202, F, F, Cl, pyrimidin-5-yl, CH₃), (M-5203, F, F, Cl, HOOCCH₂CH₂CH₂, H), (M-5204, F, F, Cl, HOOCCH$_2$CH$_2$CH$_2$, Cl), (M-5205, F, F, Cl, HOOCCH$_2$CH$_2$CH$_2$, F), (M-5206, F, F, Cl, HOOCCH$_2$CH$_2$CH$_2$, CF$_3$), (M-5207, F, F, Cl, HOOCCH$_2$CH$_2$CH$_2$, Br), (M-5208, F, F, Cl, HOOCCH$_2$CH$_2$CH$_2$, CH$_3$), (M-5209, F, F, Cl, HOOCCH$_2$CH$_2$CH$_2$CH$_2$, H), (M-5210, F, F, Cl, HOOCCH$_2$CH$_2$CH$_2$CH$_2$, Cl), (M-5211, F, F, Cl, HOOCCH$_2$CH$_2$CH$_2$CH$_2$, F), (M-5212, F, F, Cl, HOOCCH$_2$CH$_2$CH$_2$CH$_2$, CF$_3$), (M-5213, F, F, Cl, HOOCCH$_2$CH$_2$CH$_2$CH$_2$, Br), (M-5214, F, F, Cl, HOOCCH$_2$CH$_2$CH$_2$CH$_2$, CH$_3$), (M-5215, F, F, Cl, (Me)$_2$NCOCH$_2$CH$_2$CH$_2$CH$_2$, H), (M-5216, F, F, Cl, (Me)$_2$NCOCH$_2$CH$_2$CH$_2$CH$_2$, Cl), (M-5217, F, F, Cl, (Me)$_2$NCOCH$_2$CH$_2$CH$_2$CH$_2$, F), (M-5218, F, F, Cl, (Me)$_2$NCOCH$_2$CH$_2$CH$_2$CH$_2$, CF$_3$), (M-5219, F, F, Cl, (Me)$_2$NCOCH$_2$CH$_2$CH$_2$CH$_2$, Br), (M-5220, F, F, Cl, (Me)$_2$NCOCH$_2$CH$_2$CH$_2$CH$_2$, CH$_3$), (M-5221, F, F, Cl, (Me)$_2$NCOCH$_2$CH$_2$CH$_2$CH$_2$CH$_2$, H), (M-5222, F, F, Cl, (Me)$_2$NCOCH$_2$CH$_2$CH$_2$CH$_2$CH$_2$, Cl), (M-5223, F, F, Cl, (Me)$_2$NCOCH$_2$CH$_2$CH$_2$CH$_2$CH$_2$, F), (M-5224, F, F, Cl, (Me)$_2$NCOCH$_2$CH$_2$CH$_2$CH$_2$CH$_2$, CF$_3$), (M-5225, F, F, Cl, (Me)$_2$NCOCH$_2$CH$_2$CH$_2$CH$_2$CH$_2$, Br), (M-5226, F, F, Cl, (Me)$_2$NCOCH$_2$CH$_2$CH$_2$CH$_2$CH$_2$, CH$_3$), (M-5227, F, F, Cl, MeOCH$_2$, H), (M-5228, F, F, Cl, MeOCH$_2$, Cl), (M-5229, F, F, Cl, MeOCH$_2$, F), (M-5230, F, F, Cl, MeOCH$_2$, CF$_3$), (M-5231, F, F, Cl, MeOCH$_2$, Br), (M-5232, F, F, Cl, MeOCH$_2$, CH$_3$), (M-5233, F, F, Cl, EtOCH$_2$, H), (M-5234, F, F, Cl, EtOCH$_2$, Cl), (M-5235, F, F, Cl, EtOCH$_2$, F), (M-5236, F, F, Cl, EtOCH$_2$, CF$_3$), (M-5237, F, F, Cl, EtOCH$_2$, Br), (M-5238, F, F, Cl, EtOCH$_2$, CH$_3$), (M-5239, F, F, Cl, EtOCH$_2$CH$_2$, H), (M-5240, F, F, Cl, EtOCH$_2$CH$_2$, Cl), (M-5241, F, F, Cl, EtOCH$_2$CH$_2$, F), (M-5242, F, F, Cl, EtOCH$_2$CH$_2$, CF$_3$), (M-5243, F, F, Cl, EtOCH$_2$CH$_2$, Br), (M-5244, F, F, Cl, EtOCH$_2$CH$_2$, CH$_3$), (M-5245, F, F, Cl, MeOCH$_2$CH$_2$OCH$_2$CH$_2$, H), (M-5246, F, F, Cl, MeOCH$_2$CH$_2$OCH$_2$CH$_2$, Cl), (M-5247, F, F, Cl, MeOCH$_2$CH$_2$OCH$_2$CH$_2$, F), (M-5248, F, F, Cl, MeOCH$_2$CH$_2$OCH$_2$CH$_2$, CF$_3$), (M-5249, F, F, Cl, MeOCH$_2$CH$_2$OCH$_2$CH$_2$, Br), (M-5250, F, F, Cl, MeOCH$_2$CH$_2$OCH$_2$CH$_2$, CH$_3$), (M-5251, F, F, Cl, MeOCH$_2$CH$_2$, H), (M-5252, F, F, Cl, MeOCH$_2$CH$_2$, Cl), (M-5253, F, F, Cl, MeOCH$_2$CH$_2$, F), (M-5254, F, F, Cl, MeOCH$_2$CH$_2$, CF$_3$), (M-5255, F, F, Cl, MeOCH$_2$CH$_2$, Br), (M-5256, F, F, Cl, MeOCH$_2$CH$_2$, CH$_3$), (M-5257, F, F, Cl, HOCH$_2$, H), (M-5258, F, F, Cl, HOCH$_2$, Cl), (M-5259, F, F, Cl, HOCH$_2$, F), (M-5260, F, F, Cl, HOCH$_2$, CF$_3$), (M-5261, F, F, Cl, HOCH$_2$, Br), (M-5262, F, F, Cl, HOCH$_2$, CH$_3$), (M-5263, F, F, Cl, HOCH$_2$CH$_2$, H), (M-5264, F, F, Cl, HOCH$_2$CH$_2$, Cl), (M-5265, F, F, Cl, HOCH$_2$CH$_2$, F), (M-5266, F, F, Cl, HOCH$_2$CH$_2$, CF$_3$), (M-5267, F, F, Cl, HOCH$_2$CH$_2$, Br), (M-5268, F, F, Cl, HOCH$_2$CH$_2$, CH$_3$), (M-5269, F, F, Cl, HOCH$_2$CH$_2$CH$_2$, H), (M-5270, F, F, Cl, HOCH$_2$CH$_2$CH$_2$, Cl), (M-5271, F, F, Cl, HOCH$_2$CH$_2$CH$_2$, F), (M-5272, F, F, Cl, HOCH$_2$CH$_2$CH$_2$, CF$_3$), (M-5273, F, F, Cl, HOCH$_2$CH$_2$CH$_2$, Br), (M-5274, F, F, Cl, HOCH$_2$CH$_2$CU$_2$, CH$_3$), (M5275, F, F, Cl, HOCH$_2$CH$_2$CH$_2$CH$_2$, H), (M-5276, F, F, Cl, HOCH$_2$CH$_2$CH$_2$CH$_2$, Cl), (M-5277, F, F, Cl, HOCH$_2$CH$_2$CH$_2$CH$_2$, F), (M-5278, F, F, Cl, HOCH$_2$CH$_2$CH$_2$CH$_2$, CF$_3$), (M-5279, F, F, Cl, HOCH$_2$CH$_2$CH$_2$CH$_2$, Br), (M-5280, F, F, Cl, HOCH$_2$CH$_2$CH$_2$CH$_2$, CH$_3$), (M-5281, F, F, Cl, HOCH$_2$CH$_2$CH$_2$CH$_2$CH$_2$, H), (M-5282, F, F, Cl, HOCH$_2$CH$_2$CH$_2$CH$_2$CH$_2$, Cl), (M-5283, F, F, Cl, HOCH$_2$CH$_2$CH$_2$CH$_2$CH$_2$, F), (M-5284, F, F, Cl, HOCH$_2$CH$_2$CH$_2$CH$_2$CH$_2$, CF$_3$), (M-5285, F, F, Cl, HOCH$_2$CH$_2$CH$_2$CH$_2$CH$_2$, Br), (M-5286, F, F, Cl, HOCH$_2$CH$_2$CH$_2$CH$_2$CH$_2$, CH$_3$), (M-5287, F, F, Cl, HOCH$_2$CH$_2$O CH$_2$CH$_2$, H), (M-5288, F, F, Cl, HOCH$_2$CH$_2$OCH$_2$CH$_2$, Cl), (M-5289, F, F, Cl, HOCH$_2$CH$_2$OCH$_2$CH$_2$, F), (M-5290, F, F, Cl, HOCH$_2$CH$_2$OCH$_2$CH$_2$, CF$_3$), (M-5291, F, F, Cl, HOCH$_2$CH$_2$CH$_2$CH$_2$, Br), (M-5292, F, F, Cl, HOCH$_2$CH$_2$OCH$_2$CH$_2$, CH$_3$), (M-5293, F, F, Cl, (Me)$_2$N, H), (M-5294, F, F, Cl, (Me)$_2$N, Cl), (M-5295, F, F, Cl, (Me)$_2$N, F), (M-5296, F, F, Cl, (Me)$_2$N, CF$_3$), (M-5297, F, F, Cl, (Me)$_2$N, Br), (M-5298, F, F, Cl, (Me)$_2$N, CH$_3$), (M-5299, F, F, Cl, piperidin-4-yl-methyl, H), (M-5300, F, F, Cl, piperidin-4-yl-methyl, Cl), (M-5301, F, F, Cl, piperidin-4-yl-methyl, F), (M-5302, F, F, Cl, piperidin-4-yl-methyl, CF$_3$), (M-5303, F, F, Cl, piperidin-4-yl-methyl, Br), (M-5304, F, F, Cl, piperidin-4-yl-methyl, CH$_3$), (M-5305, F, F, Cl, cyclohexylmethyl, H), (M-5306, F, F, Cl, cyclohexylmethyl, Cl), (M-5307, F, F, Cl, cyclohexylmethyl, F), (M-5308, F, F, Cl, cyclohexylmethyl, CF$_3$), (M-5309, F, F, Cl, cyclohexylmethyl, Br), (M-5310, F, F, Cl, cyclohexylmethyl, CH$_3$), (M-5311, F, CH$_3$, H, H, H), (M-5312, F, CH$_3$, H, H, Cl), (M-5313, F, CH$_3$, H, H, F), (M-5314, F, CH$_3$, H, H, CF$_3$), (M-5315, F, CH$_3$, H, H, Br), (M-5316, F, CH$_3$, H, H, CH$_3$), (M-5317, F, CH$_3$, H, F, H), (M-5318, F, CH$_3$, H, F, Cl), (M-5319, F, CH$_3$, H, F, F), (M-5320, F, CH$_3$, H, F, CF$_3$), (M-5321, F, CH$_3$, H, F, Br), (M-5322, F, CH$_3$, H, F, CH$_3$), (M-5323, F, CH$_3$, H, Cl, H), (M-5324, F, CH$_3$, H, Cl, Cl), (M-5325, F, CH$_3$, H, Cl, F), (M-5326, F, CH$_3$, H, Cl, CF$_3$), (M-5327, F, CH$_3$, H, Cl, Br), (M-5328, F, CH$_3$, H, Cl, CH$_3$), (M-5329, F, CH$_3$, H, CH$_3$, H), (M-5330, F, CH$_3$, H, CH$_3$, Cl), (M-5331, F, CH$_3$, H, CH$_3$, F), (M-5332, F, CH$_3$, H, CH$_3$, CF$_3$), (M-5333, F, CH$_3$, H, CH$_3$, Br), (M-5334, F, CH$_3$, H, CH$_3$, CH$_3$), (M-5335, F, CH$_3$, H, Et, H), (M-5336, F, CH$_3$, H, Et, Cl), (M-5337, F, CH$_3$, H, Et, F), (M-5338, F, CH$_3$, H, Et, CF$_3$), (M-5339, F, CH$_3$, H, Et, Br), (M-5340, F, CH$_3$, H, Et, CH$_3$), (M-5341, F, CH$_3$, H, n-Pr, H), (M-5342, F, CH$_3$, H, n-Pr, Cl), (M-5343, F, CH$_3$, H, n-Pr, F), (M-5344, F, CH$_3$, H, n-Pr, CF$_3$), (M-5345, F, CH$_3$, H, n-Pr, Br), (M-5346, F, CH$_3$, H, n-Pr, CH$_3$), (M-5347, F, CH$_3$, H, c-Pr, H), (M-5348, F, CH$_3$, H, c-Pr, Cl), (M-5349, F, CH$_3$, H, c-Pr, F), (M-5350, F, CH$_3$, H, c-Pr, CF$_3$), (M-5351, F, CH$_3$, H, c-Pr, Br), (M-5352, F, CH$_3$, H, c-Pr, CH$_3$), (M-5353, F, CH$_3$, H, i-Pr, H), (M-5354, F, CH$_3$, H, i-Pr, Cl), (M-5355, F, CH$_3$, H, i-Pr, F), (M-5356, F, CH$_3$, H, i-Pr, CF$_3$), (M-5357, F, CH$_3$, H, i-Pr, Br), (M-5358, F, CH$_3$, H, i-Pr, CH$_3$), (M-5359, F, CH$_3$, H, n-Bu, H), (M-5360, F, CH$_3$, H, n-Bu, Cl), (M-5361, F, CH$_3$, H, n-Bu, F), (M-5362, F, CH$_3$, H, n-Bu, CF$_3$), (M-5363, F, CH$_3$, H, n-Bu, Br), (M-5364, F, CH$_3$, H, n-Bu, CH$_3$), (M-5365, F, CH$_3$, H, i-Bu, H), (M-5366, F, CH$_3$, H, i-Bu, Cl), (M-5367, F, CH$_3$, H, i-Bu, F), (M-5368, F, CH$_3$, H, i-Bu, CF$_3$), (M-5369, F, CH$_3$, H, i-Bu, Br), (M-5370, F, CH$_3$, H, i-Bu, CH$_3$), (M-5371, F, CH$_3$, H, sec-Bu, H), (M-5372, F, CH$_3$, H, sec-Bu, Cl), (M-5373, F, CH$_3$, H, sec-Bu, F), (M-5374, F, CH$_3$, H, sec-Bu, CF$_3$), (M-5375, F, CH$_3$, H, sec-Bu, Br), (M-5376, F, CH$_3$, H, sec-Bu, CH$_3$), (M-5377, F, CH$_3$, H, n-Pen, H), (M-5378, F, CH$_3$, H, n-Pen, Cl), (M-5379, F, CH$_3$, H, n-Pen, F), (M-5380, F, CH$_3$, H, n-Pen, CF$_3$), (M-5381, F, CH$_3$, H, n-Pen, Br), (M-5382, F, CH$_3$, H, n-Pen, CH$_3$), (M-5383, F, CH$_3$, H, c-Pen, H), (M-5384, F, CH$_3$, H, c-Pen, Cl), (M-5385, F, CH$_3$, H, c-Pen, F), (M-5386, F, CH$_3$, H, c-Pen, CF$_3$), (M-5387, F, CH$_3$, H, c-Pen, Br), (M-5388, F, CH$_3$, H, c-Pen, CH$_3$), (M-5389, F, CH$_3$, H, n-Hex, H), (M-5390, F, CH$_3$, H, n-Hex, Cl), (M-5391, F, CH$_3$, H, n-Hex, F), (M-5392, F, CH$_3$, H, n-Hex, CF$_3$), (M-5393, F, CH$_3$, H, n-Hex, Br), (M-5394, F, CH$_3$, H, n-Hex, CH$_3$), (M-5395, F, CH$_3$, H, c-Hex, H), (M-5396, F, CH$_3$, H, c-Hex, Cl), (M-5397, F, CH$_3$, H, c-Hex, F), (M-5398, F, CH$_3$, H, c-Hex, CF$_3$), (M-5399, F, CH$_3$, H, c-Hex, Br), (M-5400, F, CH$_3$, H, c-Hex, CH$_3$), (M-5401, F, CH₃, H, OH, H), (M-5402, F, CH₃, H, OH, Cl), (M-5403, F, CH₃, H, OH, F), (M-5404, F, CH₃, H, OH, CF₃), (M-5405, F, CH₃, H, OH, Br), (M-5406, F, CH₃, H, OH, CH₃), (M-5407, F, CH₃, H, EtO, H), (M-5408, F, CH₃, H, EtO, Cl), (M-5409, F, CH₃, H, EtO, F), (M-5410, F, CH₃, H, EtO, CF₃), (M-5411, F, CH₃, H, EtO, Br), (M-5412, F, CH₃, H, EtO, CH₃), (M-5413, F, CH₃, H, n-PrO, H), (M-5414, F, CH₃, H, n-PrO, Cl), (M-5415, F, CH₃, H, n-PrO, F), (M-5416, F, CH₃, H, n-PrO, CF₃), (M-5417, F, CH₃, H, n-PrO, Br), (M-5418, F, CH₃, H, n-PrO, CH₃), (M-5419, F, CH₃, H, PhO, H), (M-5420, F, CH₃, H, PhO, Cl), (M-5421, F, CH₃, H, PhO, F), (M-5422, F, CH₃, H, PhO, CF₃), (M-5423, F, CH₃, H, PhO, Br), (M-5424, F, CH₃, H, PhO, CH₃), (M-5425, F, CH₃, H, BnO, H), (M-5426, F, CH₃, H, BnO, Cl), (M-5427, F, CH₃, H, BnO, F), (M-5428, F, CH₃, H, BnO, CF₃), (M-5429, F, CH₃, H, BnO, Br), (M-5430, F, CH₃, H, BnO, CH₃), (M-5431, F, CH₃, H, PhCH₂CH₂O, H), (M-5432, F, CH₃, H, PhCH₂CH₂O, Cl), (M-5433, F, CH₃, H, PhCH₂CH₂O, F), (M-5434, F, CH₃, H, PhCH₂CH₂O, CF₃), (M-5435, F, CH₃, H, PhCH₂CH₂O, Br), (M-5436, F, CH₃, H, PhCH₂CH₂O, CH₃), (M-5437, F, CH₃, H, CF₃O, H), (M-5438, F, CH₃, H, CF₃O, Cl), (M-5439, F, CH₃, H, CF₃O, F), (M-5440, F, CH₃, H, CF₃O, CF₃), (M-5441, F, CH₃, H, CF₃O, Br), (M-5442, F, CH₃, H, CF₃O, CH₃), (M-5443, F, CH₃, H, Ph, H), (M-5444, F, CH₃, H, Ph, Cl), (M-5445, F, CH₃, H, Ph, F), (M-5446, F, CH₃, H, Ph, CF₃), (M-5447, F, CH₃, H, Ph, Br), (M-5448, F, CH₃, H, Ph, CH₃), (M-5449, F, CH₃, H, 4-F-Ph, H), (M-5450, F, CH₃, H, 4-F-Ph, Cl), (M-5451, F, CH₃, H, 4-F-Ph, F), (M-5452, F, CH₃, H, 4-F-Ph, CF₃), (M-5453, F, CH₃, H, 4-F-Ph, Br), (M-5454, F, CH₃, H, 4-F-Ph, CH₃), (M-5455, F, CH₃, H, 4-CF₃-Ph, H), (M-5456, F, CH₃, H, 4-CF₃-Ph, Cl), (M-5457, F, CH₃, H, 4-CF₃-Ph, F), (M-5458, F, CH₃, H, 4-CF₃-Ph, CF₃), (M-5459, F, CH₃, H, 4-CF₃-Ph, Br), (M-5460, F, CH₃, H, 4-CF₃-Ph, CH₃), (M-5461, F, CH₃, H, 4-(Me)₂N-Ph, H), (M-5462, F, CH₃, H, 4-(Me)₂N-Ph, Cl), (M-5463, F, CH₃, H, 4-(Me)₂N-Ph, F), (M-5464, F, CH₃, H, 4-(Me)₂N-Ph, CF₃), (M-5465, F, CH₃, H, 4-(Me)₂N-Ph, Br), (M-5466, F, CH₃, H, 4-(Me)₂N-Ph, CH₃), (M-5467, F, CH₃, H, 4-OH-Ph, H), (M-5468, F, CH₃, H, 4-OH-Ph, Cl), (M-5469, F, CH₃, H, 4-OH-Ph, F), (M-5470, F, CH₃, H, 4-OH-Ph, CF₃), (M-5471, F, CH₃, H, 4-OH-Ph, Br), (M-5472, F, CH₃, H, 4-OH-Ph, CH₃), (M-5473, F, CH₃, H, 3,4-di-F-Ph, H), (M-5474, F, CH₃, H, 3,4-di-F-Ph, Cl), (M-5475, F, CH₃, H, 3,4-di-F-Ph, F), (M-5476, F, CH₃, H, 3,4-di-F-Ph, CF₃), (M-5477, F, CH₃, H, 3,4-di-F-Ph, Br), (M-5478, F, CH₃, H, 3,4-di-F-Ph, CH₃), (M-5479, F, CH₃, H, 4-COOH-Ph, H), (M-5480, F, CH₃, H, 4-COOH-Ph, Cl), (M-5481, F, CH₃, H, 4-COOH-Ph, F), (M-5482, F, CH₃, H, 4-COOH-Ph, CF₃), (M-5483, F, CH₃, H, 4-COOH-Ph, Br), (M-5484, F, CH₃, H, 4-COOH-Ph, CH₃), (M-5485, F, CH₃, H, Bn, H), (M-5486, F, CH₃, H, Bn, Cl), (M-5487, F, CH₃, H, Bn, F), (M-5488, F, CH₃, H, Bn, CF₃), (M-5489, F, CH₃, H, Bn, Br), (M-5490, F, CH₃, H, Bn, CH₃), (M-5491, F, CH₃, H, 4-F-Bn, H), (M-5492, F, CH₃, H, 4-F-Bn, Cl), (M-5493, F, CH₃, H, 4-F-Bn, F), (M-5494, F, CH₃, H, 4-F-Bn, CF₃), (M-5495, F, CH₃, H, 4-F-Bn, Br), (M-5496, F, CH₃, H, 4-F-Bn, CH₃), (M-5497, F, CH₃, H, 2-Py, H), (M-5498, F, CH₃, H, 2-Py, Cl), (M-5499, F, CH₃, H, 2-Py, F), (M-5500, F, CH₃, H, 2-Py, CF₃), (M-5501, F, CH₃, H, 2-Py, Br), (M-5502, F, CH₃, H, 2-Py, CH₃), (M-5503, F, CH₃, H, 3-Py, H), (M-5504, F, CH₃, H, 3-Py, Cl), (M-5505, F, CH₃, H, 3-Py, F), (M-5506, F, CH₃, H, 3-Py, CF₃), (M-5507, F, CH₃, H, 3-Py, Br), (M-5508, F, CH₃, H, 3-Py, CH₃), (M-5509, F, CH₃, H, 4-Py, H), (M-5510, F, CH₃, H, 4-Py, Cl), (M-5511, F, CH₃, H, 4-Py, F), (M-5512, F, CH₃, H, 4-Py, CF₃), (M-5513, F, CH₃, H, 4-Py, Br), (M-5514, F, CH₃, H, 4-Py, CH₃), (M-5515, F, CH₃, H, 2-Th, H), (M-5516, F, CH₃, H, 2-Th, Cl), (M-5517, F, CH₃, H, 2-Th, F), (M-5518, F, CH₃, H, 2-Th, CF₃), (M-5519, F, CH₃, H, 2-Th, Br), (M-5520, F, CH₃, H, 2-Th, CH₃), (M-5521, F, CH₃, H, 3-Th, H), (M-5522, F, CH₃, H, 3-Th, Cl), (M-5523, F, CH₃, H, 3-Th, F), (M-5524, F, CH₃, H, 3-Th, CF₃), (M-5525, F, CH₃, H, 3-Th, Br), (M-5526, F, CH₃, H, 3-Th, CH₃), (M-5527, F, CH₃, H, pyrrazol-2-yl, H), (M-5528, F, CH₃, H, pyrrazol-2-yl, Cl), (M-5529, F, CH₃, H, pyrrazol-2-yl, F), (M-5530, F, CH₃, H, pyrrazol-2-yl, CF₃), (M-5531, F, CH₃, H, pyrrazol-2-yl, Br), (M-5532, F, CH₃, H, pyrrazol-2-yl, CH₃), (M-5533, F, CH₃, H, pyrrazol-3-yl, H), (M-5534, F, CH₃, H, pyrrazol-3-yl, Cl), (M-5535, F, CH₃, H, pyrrazol-3-yl, F), (M-5536, F, CH₃, H, pyrrazol-3-yl, CF₃), (M-5537, F, CH₃, H, pyrrazol-3-yl, Br), (M-5538, F, CH₃, H, pyrrazol-3-yl, CH₃), (M-5539, F, CH₃, H, pyrimidin-2-yl, H), (M-5540, F, CH₃, H, pyrimidin-2-yl, Cl), (M-5541, F, CH₃, H, pyrimidin-2-yl, F), (M-5542, F, CH₃, H, pyrimidin-2-yl, CF₃), (M-5543, F, CH₃, H, pyrimidin-2-yl, Br), (M-5544, F, CH₃, H, pyrimidin-2-yl, CH₃), (M-5545, F, CH₃, H, pyrimidin-4-yl, H), (M-5546, F, CH₃, H, pyrimidin-4-yl, Cl), (M-5547, F, CH₃, H, pyrimidin-4-yl, F), (M-5548, F, CH₃, H, pyrimidin-4-yl, CF₃), (M-5549, F, CH₃, H, pyrimidin-4-yl, Br), (M-5550, F, CH₃, H, pyrimidin-4-yl, CH₃), (M-5551, F, CH₃, H, pyrimidin-5-yl, H), (M-5552, F, CH₃, H, pyrimidin-5-yl, Cl), (M-5553, F, CH₃, H, pyrimidin-5-yl, F), (M-5554, F, CH₃, H, pyrimidin-5-yl, CF₃), (M-5555, F, CH₃, H, pyrimidin-5-yl, Br), (M-5556, F, CH₃, H, pyrimidin-5-yl, CH₃), (M-5557, F, CH₃, H, HOOCCH₂CH₂CH₂, H), (M-5558, F, CH₃, H, HOOCCH₂CH₂CH₂, Cl), (M-5559, F, CH₃, H, HOOCCH₂CH₂CH₂, F), (M-5560, F, CH₃, H, HOOCCH₂CH₂CH₂, CF₃), (M-5561, F, CH₃, H, HOOCCH₂CH₂CH₂, Br), (M-5562, F, CH₃, H, HOOCCH₂CH₂CH₂, CH₃), (M-5563, F, CH₃, H, HOOCCH₂CH₂CH₂CH₂, H), (M-5564, F, CH₃, H, HOOCCH₂CH₂CH₂CH₂, Cl), (M-5565, F, CH₃, H, HOOCCH₂CH₂CH₂CH₂, F), (M-5566, F, CH₃, H, HOOCCH₂CH₂CH₂CH₂, CF₃), (M-5567, F, CH₃, H, HOOCCH₂CH₂CH₂CH₂, Br), (M-5568, F, CH₃, H, HOOCCH₂CH₂CH₂CH₂, CH₃), (M-5569, F, CH₃, H, (Me)₂NCOCH₂CH₂CH₂, H), (M-5570, F, CH₃, H, (Me)₂NCOCH₂CH₂CH₂, Cl), (M-5571, F, CH₃, H, (Me)₂NCOCH₂CH₂CH₂, F), (M-5572, F, CH₃, H, (Me)₂NCOCH₂CH₂CH₂CF₃), (M-5573, F, CH₃, H, (Me)₂NCOCH₂CH₂CH₂, Br), (M-5574, F, CH₃, H, (Me)₂NCOCH₂CH₂CH₂, CH₃), (M-5575, F, CH₃, H, (Me)₂NCOCH₂CH₂CH₂CH₂, H), (M-5576, F, CH₃, H, (Me)₂NCOCH₂CH₂CH₂CH₂, Cl), (M-5577, F, CH₃, H, (Me)₂NCOCH₂CH₂CH₂CH₂, F), (M-5578, F, CH₃, H, (Me)₂NCOCH₂CH₂CH₂CH₂, CF₃), (M-5579, F, CH₃, H, (Me)₂NCOCH₂CH₂CH₂CH₂, Br), (M-5580, F, CH₃, H, (Me)₂NCOCH₂CH₂CH₂CH₂, CH₃), (M-5581, F, CH₃, H, MeOCH₂, H), (M-5582, F, CH₃, H, MeOCH₂, Cl), (M-5583, F, CH₃, H, MeOCH₂, F), (M-5584, F, CH₃, H, MeOCH₂, CF₃), (M-5585, F, CH₃, H, MeOCH₂, Br), (M-5586, F, CH₃, H, MeOCH₂, CH₃), (M-5587, F, CH₃, H, EtOCH₂, H), (M-5588, F, CH₃, H, EtOCH₂, Cl), (M-5589, F, CH₃, H, EtOCH₂, F), (M-5590, F, CH₃, H, EtOCH₂, CF₃), (M-5591, F, CH₃, H, EtOCH₂, Br), (M-5592, F, CH₃, H, EtOCH₂, CH₃), (M-5593, F, CH₃, H, EtOCH₂CH₂, H), (M-5594, F, CH₃, H, EtOCH₂CH₂, Cl), (M-5595, F, CH₃, H, EtOCH₂CH₂, F), (M-5596, F, CH₃, H, EtOCH₂CH₂, CF₃), (M-5597, F, CH₃, H, EtOCH₂CH₂, Br), (M-5598, F, CH₃, H, EtOCH₂CH₂, CH₃), (M-5599, F, CH₃, H, MeOCH₂CH₂OCH₂CH₂, H), (M-5600, F, CH₃, H, MeOCH₂CH₂OCH₂CH₂, Cl), (M-5601, F, CH₃, H, MeOCH₂CH₂OCH₂CH₂, F), (M-5602, F, CH₃, H, MeOCH₂CH₂OCH₂CH₂, CF₃), (M-5603, F, CH₃, H, MeOCH₂CH₂OCH₂CH₂, Br), (M-5604, F, CH₃, H, MeOCH$_2$CH$_2$OCH$_2$CH$_2$, CH$_3$), (M-5605, F, CH$_3$, H, MeOCH$_2$CH$_2$, H), (M-5606, F, CH$_3$, H, MeOCH$_2$CH$_2$, Cl), (M-5607, F, CH$_3$, H, MeOCH$_2$CH$_2$, F), (M-5608, F, CH$_3$, H, MeOCH$_2$CH$_2$, CF$_3$), (M-5609, F, CH$_3$, H, MeOCH$_2$CH$_2$, Br), (M-5610, F, CH$_3$, H, MeOCH$_2$CH$_2$, CH$_3$), (M-5611, F, CH$_3$, H, HOCH$_2$, H), (M-5612, F, CH$_3$, H, HOCH$_2$, Cl), (M-5613, F, CH$_3$, H, HOCH$_2$, F), (M-5614, F, CH$_3$, H, HOCH$_2$, CF$_3$), (M-5615, F, CH$_3$, H, HOCH$_2$, Br), (M-5616, F, CH$_3$, H, HOCH$_2$, CH$_3$), (M-5617, F, CH$_3$, H, HOCH$_2$CH$_2$, H), (M-5618, F, CH$_3$, H, HOCH$_2$CH$_2$, Cl), (M-5619, F, CH$_3$, H, HOCH$_2$CH$_2$, F), (M-5620, F, CH$_3$, H, HOCH$_2$CH$_2$, CF$_3$), (M-5621, F, CH$_3$, H, HOCH$_2$CH$_2$, Br), (M-5622, F, CH$_3$, H, HOCH$_2$CH$_2$, CH$_3$), (M-5623, F, CH$_3$, H, HOCH$_2$CH$_2$CH$_2$, H), (M-5624, F, CH$_3$, H, HOCH$_2$CH$_2$CH$_2$, Cl), (M-5625, F, CH$_3$, H, HOCH$_2$CH$_2$CH$_2$, F), (M-5626, F, CH$_3$, H, HOCH$_2$CH$_2$CH$_2$, CF$_3$), (M-5627, F, CH$_3$, H, HOCH$_2$CH$_2$CH$_2$, Br), (M-5628, F, CH$_3$, H, HOCH$_2$CH$_2$CH$_2$, CH$_3$), (M-5629, F, CH$_3$, H, HOCH$_2$CH$_2$CH$_2$CH$_2$, H), (M-5630, F, CH$_3$, H, HOCH$_2$CH$_2$CH$_2$CH$_2$, Cl), (M-5631, F, CH$_3$, H, HOCH$_2$CH$_2$CH$_2$CH$_2$, F), (M-5632, F, CH$_3$, H, HOCH$_2$CH$_2$CH$_2$CH$_2$, CF$_3$), (M-5633, F, CH$_3$, H, HOCH$_2$CH$_2$CH$_2$CH$_2$, Br), (M-5634, F, CH$_3$, H, HOCH$_2$CH$_2$CH$_2$CH$_2$, CH$_3$), (M-5635, F, CH$_3$, H, HOCH$_2$CH$_2$CH$_2$CH$_2$CH$_2$, H), (M-5636, F, CH$_3$, H, HOCH$_2$CH$_2$CH$_2$CH$_2$CH$_2$, Cl), (M-5637, F, CH$_3$, H, HOCH$_2$CH$_2$CH$_2$CH$_2$CH$_2$, F), (M-5638, F, CH$_3$, H, HOCH$_2$CH$_2$CH$_2$CH$_2$CH$_2$, CF$_3$), (M-5639, F, CH$_3$, H, HOCH$_2$CH$_2$CH$_2$CH$_2$CH$_2$, Br), (M-5640, F, CH$_3$, H, HOCH$_2$CH$_2$CH$_2$CH$_2$CH$_2$, CH$_3$), (M-5641, F, CH$_3$, H, HOCH$_2$CH$_2$OCH$_2$CH$_2$, H), (M-5642, F, CH$_3$, H, HOCH$_2$CH$_2$OCH$_2$CH$_2$, Cl), (M-5643, F, CH$_3$, H, HOCH$_2$CH$_2$OCH$_2$CH$_2$, F), (M-5644, F, CH$_3$, H, HOCH$_2$CH$_2$OCH$_2$CH$_2$, CF$_3$), (M-5645, F, CH$_3$, H, HOCH$_2$CH$_2$OCH$_2$CH$_2$, Br) (M-5646, F, CH$_3$, H, HOCH$_2$CH$_2$OCH$_2$CH$_2$, CH$_3$), (M-5647, F, CH$_3$, H, (Me)$_2$N, H), (M-5648, F, CH$_3$, H, (Me)$_2$N, Cl), (M-5649, F, CH$_3$, H, (Me)$_2$N, F), (M-5650, F, CH$_3$, H, (Me)$_2$N, CF$_3$), (M-5651, F, CH$_3$, H, (Me)$_2$N, Br), (M-5652, F, CH$_3$, H, (Me)$_2$N, CH$_3$), (M-5653, F, CH$_3$, H, piperidin-4-yl-methyl, H), (M-5654, F, CH$_3$, H, piperidin-4-yl-methyl, Cl), (M-5655, F, CH$_3$, H, piperidin-4-yl-methyl, F), (M-5656, F, CH$_3$, H, piperidin-4-yl-methyl, CF$_3$), (M-5657, F, CH$_3$, H, piperidin-4-yl-methyl, Br), (M-5658, F, CH$_3$, H, piperidin-4-yl-methyl, CH$_3$), (M-5659, F, CH$_3$, H, cyclohexylmethyl, H), (M-5660, F, CH$_3$, H, cyclohexylmethyl, Cl), (M-5661, F, CH$_3$, H, cyclohexylmethyl, F), (M-5662, F, CH$_3$, H, cyclohexylmethyl, CF$_3$), (M-5663, F, CH$_3$, H, cyclohexylmethyl, Br), (M-5664, F, CH$_3$, H, cyclohexylmethyl, CH$_3$), (M-5665, F, CH$_3$, F, H, H), (M-5666, F, CH$_3$, F, H, Cl), (M-5667, F, CH$_3$, F, H, F), (M-5668, F, CH$_3$, F, H, CF$_3$), (M-5669, F, CH$_3$, F, H, Br), (M-5670, F, CH$_3$, F, H, CH$_3$), (M-5671, F, CH$_3$, F, F, H), (M-5672, F, CH$_3$, F, F, Cl), (M-5673, F, CH$_3$, F, F, F), (M-5674, F, CH$_3$, F, F, CF$_3$), (M-5675, F, CH$_3$, F, F, Br), (M-5676, F, CH$_3$, F, F, CH$_3$), (M-5677, F, CH$_3$, F, Cl, H), (M-5678, F, CH$_3$, F, Cl, Cl), (M-5679, F, CH$_3$, F, Cl, F), (M-5680, F, CH$_3$, F, Cl, CF$_3$), (M-5681, F, CH$_3$, F, Cl, Br), (M-5682, F, CH$_3$, F, Cl, CH$_3$), (M-5683, F, CH$_3$, F, CH$_3$, H), (M-5684, F, CH$_3$, F, CH$_3$, Cl), (M-5685, F, CH$_3$, F, CH$_3$, F), (M-5686, F, CH$_3$, F, CH$_3$, CF$_3$), (M-5687, F, CH$_3$, F, CH$_3$, Br), (M-5688, F, CH$_3$, F, CH$_3$, CH$_3$), (M-5689, F, CH$_3$, F, Et, H), (M-5690, F, CH$_3$, F, Et, Cl), (M-5691, F, CH$_3$, F, Et, F), (M-5692, F, CH$_3$, F, Et, CF$_3$), (M-5693, F, CH$_3$, F, Et, Br), (M-5694, F, CH$_3$, F, Et, CH$_3$), (M-5695, F, CH$_3$, F, n-Pr, H), (M-5696, F, CH$_3$, F, n-Pr, Cl), (M-5697, F, CH$_3$, F, n-Pr, F), (M-5698, F, CH$_3$, F, n-Pr, CF$_3$), (M-5699, F, CH$_3$, F, n-Pr, Br), (M-5700, F, CH$_3$, F, n-Pr, CH$_3$), (M-5701, F, CH$_3$, F, c-Pr, H), (M-5702, F, CH$_3$, F, c-Pr, Cl), (M-5703, F, CH$_3$, F, c-Pr, F), (M-5704, F, CH$_3$, F, c-Pr, CF$_3$), (M-5705, F, CH$_3$, F, c-Pr, Br), (M-5706, F, CH$_3$, F, c-Pr, CH$_3$), (M-5707, F, CH$_3$, F, i-Pr, H), (M-5708, F, CH$_3$, F, i-Pr, Cl), (M-5709, F, CH$_3$, F, i-Pr, F), (M-5710, F, CH$_3$, F, i-Pr, CF$_3$), (M-5711, F, CH$_3$, F, i-Pr, Br), (M-5712, F, CH$_3$, F, i-Pr, CH$_3$), (M-5713, F, CH$_3$, F, n-Bu, H), (M-5714, F, CH$_3$, F, n-Bu, Cl), (M-5715, F, CH$_3$, F, n-Bu, F), (M-5716, F, CH$_3$, F, n-Bu, CF$_3$), (M-5717, F, CH$_3$, F, n-Bu, Br), (M-5718, F, CH$_3$, F, n-Bu, CH$_3$), (M-5719, F, CH$_3$, F, i-Bu, H), (M-5720, F, CH$_3$, F, i-Bu, Cl), (M-5721, F, CH$_3$, F, i-Bu, F), (M-5722, F, CH$_3$, F, i-Bu, CF$_3$), (M-5723, F, CH$_3$, F, i-Bu, Br), (M-5724, F, CH$_3$, F, i-Bu, CH$_3$), (M-5725, F, CH$_3$, F, sec-Bu, H), (M-5726, F, CH$_3$, F, sec-Bu, Cl), (M-5727, F, CH$_3$, F, sec-Bu, F), (M-5728, F, CH$_3$, F, sec-Bu, CF$_3$), (M-5729, F, CH$_3$, F, sec-Bu, Br), (M-5730, F, CH$_3$, F, sec-Bu, CH$_3$), (M-5731, F, CH$_3$, F, n-Pen, H), (M-5732, F, CH$_3$, F, n-Pen, Cl), (M-5733, F, CH$_3$, F, n-Pen, F), (M-5734, F, CH$_3$, F, n-Pen, CF$_3$), (M-5735, F, CH$_3$, F, n-Pen, Br), (M-5736, F, CH$_3$, F, n-Pen, CH$_3$), (M-5737, F, CH$_3$, F, c-Pen, H), (M-5738, F, CH$_3$, F, c-Pen, Cl), (M-5739, F, CH$_3$, F, c-Pen, F), (M-5740, F, CH$_3$, F, c-Pen, CF$_3$), (M-5741, F, CH$_3$, F, c-Pen, Br), (M-5742, F, CH$_3$, F, c-Pen, CH$_3$), (M-5743, F, CH$_3$, F, n-Hex, H), (M-5744, F, CH$_3$, F, n-Hex, Cl), (M-5745, F, CH$_3$, F, n-Hex, F), (M-5746, F, CH$_3$, F, n-Hex, CF$_3$), (M-5747, F, CH$_3$, F, n-Hex, Br), (M-5748, F, CH$_3$, F, n-Hex, CH$_3$), (M-5749, F, CH$_3$, F, c-Hex, H), (M-5750, F, CH$_3$, F, c-Hex, Cl), (M-5751, F, CH$_3$, F, c-Hex, F), (M-5752, F, CH$_3$, F, c-Hex, CF$_3$), (M-5753, F, CH$_3$, F, c-Hex, Br), (M-5754, F, CH$_3$, F, c-Hex, CH$_3$), (M-5755, F, CH$_3$, F, OH, H), (M-5756, F, CH$_3$, F, OH, Cl), (M-5757, F, CH$_3$, F, OH, F), (M-5758, F, CH$_3$, F, OH, CF$_3$), (M-5759, F, CH$_3$, F, OH, Br), (M-5760, F, CH$_3$, F, OH, CH$_3$), (M-5761, F, CH$_3$, F, EtO, H), (M-5762, F, CH$_3$, F, EtO, Cl), (M-5763, F, CH$_3$, F, EtO, F), (M-5764, F, CH$_3$, F, EtO, CF$_3$), (M-5765, F, CH$_3$, F, EtO, Br), (M-5766, F, CH$_3$, F, EtO, CH$_3$), (M-5767, F, CH$_3$, F, n-PrO, H), (M-5768, F, CH$_3$, F, n-PrO, Cl), (M-5769, F, CH$_3$, F, n-PrO, F), (M-5770, F, CH$_3$, F, n-PrO, CF$_3$), (M-5771, F, CH$_3$, F, n-PrO, Br), (M-5772, F, CH$_3$, F, n-PrO, CH$_3$), (M-5773, F, CH$_3$, F, PhO, H), (M-5774, F, CH$_3$, F, PhO, Cl), (M-5775, F, CH$_3$, F, PhO, F), (M-5776, F, CH$_3$, F, PhO, CF$_3$), (M-5777, F, CH$_3$, F, PhO, Br), (M-5778, F, CH$_3$, F, PhO, CH$_3$), (M-5779, F, CH$_3$, F, BnO, H), (M-5780, F, CH$_3$, F, BnO, Cl), (M-5781, F, CH$_3$, F, BnO, F), (M-5782, F, CH$_3$, F, BnO, CF$_3$), (M-5783, F, CH$_3$, F, BnO, Br), (M-5784, F, CH$_3$, F, BnO, CH$_3$), (M-5785, F, CH$_3$, F, PhCH$_2$CH$_2$O, H), (M-5786, F, CH$_3$, F, PhCH$_2$CH$_2$O, Cl), (M-5787, F, CH$_3$, F, PhCH$_2$CH$_2$O, F), (M-5788, F, CH$_3$, F, PhCH$_2$CH$_2$O, CF$_3$), (M-5789, F, CH$_3$, F, PhCH$_2$CH$_2$O, Br), (M-5790, F, CH$_3$, F, PhCH$_2$CH$_2$O, CH$_3$), (M-5791, F, CH$_3$, F, CF$_3$O, H), (M-5792, F, CH$_3$, F, CF$_3$O, Cl), (M-5793, F, CH$_3$, F, CF$_3$O, F), (M-5794, F, CH$_3$, F, CF$_3$O, CF$_3$), (M-5795, F, CH$_3$, F, CF$_3$O, Br), (M-5796, F, CH$_3$, F, CF$_3$O, CH$_3$), (M-5797, F, CH$_3$, F, Ph, H), (M-5798, F, CH$_3$, F, Ph, Cl), (M-5799, F, CH$_3$, F, Ph, F), (M-5800, F, CH$_3$, F, Ph, CF$_3$), (M-5801, F, CH$_3$, F, Ph, Br), (M-5802, F, CH$_3$, F, Ph, CH$_3$), (M-5803, F, CH$_3$, F, 4-F-Ph, H), (M-5804, F, CH$_3$, F, 4-F-Ph, Cl), (M-5805, F, CH$_3$, F, 4-F-Ph, F), (M-5806, F, CH$_3$, F, 4-F-Ph, CF$_3$), (M-5807, F, CH$_3$, F, 4-F-Ph, Br), (M-5808, F, CH$_3$, F, 4-F-Ph, CH$_3$), (M-5809, F, CH$_3$, F, 4-CF$_3$-Ph, H), (M-5810, F, CH$_3$, F, 4-CF$_3$-Ph, Cl), (M-5811, F, CH$_3$, F, 4-CF$_3$-Ph, F), (M-5812, F, CH$_3$, F, 4-CF$_3$-Ph, CF$_3$), (M-5813, F, CH$_3$, F, 4-CF$_3$-Ph, Br), (M-5814, F, CH$_3$, F, 4-CF$_3$-Ph, CH$_3$), (M-5815, F, CH$_3$, F, 4-(Me)$_2$N-Ph, H), (M-5816, F, CH$_3$, F, 4-(Me)$_2$N-Ph, Cl), (M-5817, F, CH$_3$, F, 4-(Me)$_2$N-Ph, F), (M-5818, F, CH$_3$, F, 4-(Me)$_2$N-Ph, CF$_3$), (M-5819, F, CH$_3$, F, 4-(Me)$_2$N-Ph, Br), (M-5820, F, CH$_3$, F, 4-(Me)$_2$N-Ph, CH$_3$), (M-5821, F, CH$_3$, F, 4-OH-Ph, H), (M-5822, F, CH$_3$, F, 4-OH-Ph, Cl), (M-5823, F, CH$_3$, F, 4-OH-Ph, F), (M-5824, F, CH₃, F, 4-OH-Ph, CF₃), (M-5825, F, CH₃, F, 4-OH-Ph, Br), (M-5826, F, CH₃, F, 4-OH-Ph, CH₃), (M-5827, F, CH₃, F, 3,4-di-F-Ph, H), (M-5828, F, CH₃, F, 3,4-di-F-Ph, Cl), (M-5829, F, CH₃, F, 3,4-di-F-Ph, F), (M-5830, F, CH₃, F, 3,4-di-F-Ph, CF₃), (M-5831, F, CH₃, F, 3,4-di-F-Ph, Br), (M-5832, F, CH₃, F, 3,4-di-F-Ph, CH₃), (M-5833, F, CH₃, F, 4-COOH-Ph, H), (M-5834, F, CH₃, F, 4-COOH-Ph, Cl), (M-5835, F, CH₃, F, 4-COOH-Ph, F), (M-5836, F, CH₃, F, 4-COOH-Ph, CF₃), (M-5837, F, CH₃, F, 4-COOH-Ph, Br), (M-5838, F, CH₃, F, 4-COOH-Ph, CH₃), (M-5839, F, CH₃, F, Bn, H), (M-5840, F, CH₃, F, Bn, Cl), (M-5841, F, CH₃, F, Bn, F), (M-5842, F, CH₃, F, Bn, CF₃), (M-5843, F, CH₃, F, Bn, Br), (M-5844, F, CH₃, F, Bn, CH₃), (M-5845, F, CH₃, F, 4-F-Bn, H), (M-5846, F, CH₃, F, 4-F-Bn, Cl), (M-5847, F, CH₃, F, 4-F-Bn, F), (M-5848, F, CH₃, F, 4-F-Bn, CF₃), (M-5849, F, CH₃, F, 4-F-Bn, Br), (M-5850, F, CH₃, F, 4-F-Bn, CH₃), (M-5851, F, CH₃, F, 2-Py, H), (M-5852, F, CH,3, F, 2-Py, Cl), (M-5853, F, CH₃, F, 2-Py, F), (M-5854, F, CH₃, F, 2-Py, CF₃), (M-5855, F, CH₃, F, 2-Py, Br), (M-5856, F, CH₃, F, 2-Py, CH₃), (M-5857, F, CH₃, F, 3-Py, H), (M-5858, F, CH₃, F, 3-Py, Cl), (M-5859, F, CH₃, F, 3-Py, F), (M-5860, F, CH₃, F, 3-Py, CF₃), (M-5861, F, CH₃, F, 3-Py, Br), (M-5862, F, CH₃, F, 3-Py, CH₃), (M-5863, F, CH₃, F, 4-Py, H), (M-5864, F, CH₃, F, 4-Py, Cl), (M-5865, F, CH₃, F, 4-Py, F), (M-5866, F, CH₃, F, 4-Py, CF₃), (M-5867, F, CH₃, F, 4-Py, Br), (M-5868, F, CH₃, F, 4-Py, CH₃), (M-5869, F, CH₃, F, 2-Th, H), (M-5870, F, CH₃, F, 2-Th, Cl), (M-5871, F, CH₃, F, 2-Th, F), (M-5872, F, CH₃, F, 2-Th, CF₃), (M-5873, F, CH₃, F, 2-Th, Br), (M-5874, F, CH₃, F, 2-Th, CH₃), (M-5875, F, CH₃, F, 3-Th, H), (M-5876, F, CH₃, F, 3-Th, Cl), (M-5877, F, CH₃, F, 3-Th, F), (M-5878, F, CH₃, F, 3-Th, CF₃), (M-5879, F, CH₃, F, 3-Th, Br), (M-5880, F, CH₃, F, 3-Th, CH₃), (M-5881, F, CH₃, F, pyrrazol-2-yl, H), (M-5882, F, CH₃, F, pyrrazol-2-yl, Cl), (M-5883, F, CH₃, F, pyrrazol-2-yl, F), (M-5884, F, CH₃, F, pyrrazol-2-yl, CF₃), (M-5885, F, CH₃, F, pyrrazol-2-yl, Br), (M-5886, F, CH₃, F, pyrrazol-2-yl, CH₃), (M-5887, F, CH₃, F, pyrrazol-3-yl, H), (M-5888, F, CH₃, F, pyrrazol-3-yl, Cl), (M-5889, F, CH₃, F, pyrrazol-3-yl, F), (M-5890, F, CH₃, F, pyrrazol-3-yl, CF₃), (M-5891, F, CH₃, F, pyrrazol-3-yl, Br), (M-5892, F, CH₃, F, pyrrazol-3-yl, CH₃), (M-5893, F, CH₃, F, pyrimidin-2-yl, H), (M-5894, F, CH₃, F, pyrimidin-2-yl, Cl), (M-5895, F, CH₃, F, pyrimidin-2-yl, F), (M-5896, F, CH₃, F, pyrimidin-2-yl, CF₃), (M-5897, F, CH₃, F, pyrimidin-2-yl, Br), (M-5898, F, CH₃, F, pyrimidin-2-yl, CH₃), (M-5899, F, CH₃, F, pyrimidin-4-yl, H), (M-5900, F, CH₃, F, pyrimidin-4-yl, Cl), (M-5901, F, CH₃, F, pyrimidin-4-yl, F), (M-5902, F, CH₃, F, pyrimidin-4-yl, CF₃), (M-5903, F, CU₃, F, pyrimidin-4-yl, Br), (M-5904, F, CH₃, F, pyrimidin-4-yl, CH₃), (M-5905, F, CH₃, F, pyrimidin-5-yl, H), (M-5906, F, CH₃, F, pyrimidin-5-yl, Cl), (M-5907, F, CH₃, F, pyrimidin-5-yl, F), (M-5908, F, CH₃, F, pyrimidin-5-yl, CF₃), (M-5909, F, CH₃, F, pyrimidin-5-yl, Br), (M-5910, F, CH₃, F, pyrimidin-5-yl, CH₃), (M-5911, F, CH₃, F, HOOCCH₂CH₂CH₂, H), (M-5912, F, CH₃, F, HOOCCH₂CH₂CH₂, Cl), (M-5913, F, CH₃, F, HOOCCH₂CH₂CH₂, F), (M-5914, F, CH₃, F, HOOCCH₂CH₂CH₂, CF₃), (M-5915, F, CH₃, F, HOOCCH₂CH₂CH₂, Br), (M-5916, F, CH₃, F, HOOCCH₂CH₂CH₂, CH₃), (M-5917, F, CH₃, F, HOOCCH₂CH₂CH₂CH₂, H), (M-5918, F, CH₃, F, HOOCCH₂CH₂CH₂CH₂, Cl), (M-5919, F, CH₃, F, HOOCCH₂CH₂CH₂CH₂, F), (M-5920, F, CH₃, F, HOOCCH₂CH₂CH₂CH₂, CF₃), (M-5921, F, CH₃, F, HOOCCH₂CH₂CH₂CH₂, Br), (M-5922, F, CH₃, F, HOOCCH₂CH₂CH₂CH₂, CH₃), (M-5923, F, CH₃, F, (Me)₂NCOCH₂CH₂CH₂CH₂, H), (M-5924, F, CH₃, F, (Me)₂NCOCH₂CH₂CH₂CH₂, Cl), (M-5925, F, CH₃, F, (Me)₂NCOCH₂CH₂CH₂CH₂, F), (M-5926, F, CH₃, F, (Me)₂NCOCH₂CH₂CH₂CH₂, CF₃), (M-5927, F, CH₃, F, (Me)₂NCOCH₂CH₂CH₂CH₂, Br), (M-5928, F, CH₃, F, (Me)₂NCOCH₂CH₂CH₂CH₂, CH₃), (M-5929, F, CH₃, F, (Me)₂NCOCH₂CH₂CH₂CH₂CH₂, H), (M-5930, F, CH₃, F, (Me)₂NCOCH₂CH₂CH₂CH₂CH₂, Cl), (M-5931, F, CH₃, F, (Me)₂NCOCH₂CH₂CH₂CH₂CH₂, F), (M-5932, F, CH₃, F, (Me)₂NCOCH₂CH₂CH₂CH₂CH₂, CF₃), (M-5933, F, CH₃, F, (Me)₂NCOCH₂CH₂CH₂CH₂CH₂, Br), (M-5934, F, CH₃, F, (Me)₂NCOCH₂CH₂CH₂CH₂CH₂, CH₃), (M-5935, F, CH₃, F, MeOCH₂, H), (M-5936, F, CH₃, F, MeOCH₂, Cl), (M-5937, F, CH₃, F, MeOCH₂, F), (M-5938, F, CH₃, F, MeOCH₂, CF₃), (M-5939, F, CH₃, F, MeOCH₂, Br), (M-5940, F, CH₃, F, MeOCH₂, CH₃), (M-5941, F, CH₃, F, EtOCH₂, H), (M-5942, F, CH₃, F, EtOCH₂, Cl), (M-5943, F, CH₃, F, EtOCH₂, F), (M-5944, F, CH₃ F, EtOCH₂, CF₃), (M-5945, F, CH₃, F, EtOCH₂, Br), (M-5946, F, CH₃, F, EtOCH₂, CH₃), (M-5947, F, CH₃, F, EtOCH₂CH₂, H), (M-5948, F, CH₃, F, EtOCH₂CH₂, Cl), (M-5949, F, CH₃, F, EtOCH₂CH₂, F), (M-5950, F, CH₃, F, EtOCH₂CH₂, CF₃), (M-5951, F, CH₃, F, EtOCH₂CH₂, Br), (M-5952, F, CH₃, F, EtOCH₂CH₂, CH₃), (M-5953, F, CH₃, F, MeOCH₂CH₂OCH₂CH₂, H), (M-5954, F, CH₃, F, MeOCH₂CH₂OCH₂CH₂, Cl), (M-5955, F, CH₃, F, MeOCH₂CH₂OCH₂CH₂, F), (M-5956, F, CH₃, F, MeOCH₂CH₂OCH₂CH₂, CF₃), (M-5957, F, CH₃, F, MeOCH₂CH₂OCH₂CH₂, Br), (M-5958, F, CH₃, F, MeOCH₂CH₂OCH₂CH₂, CH₃), (M-5959, F, CH₃, F, MeOCH₂CH₂, H), (M-5960, F, CH₃, F, MeOCH₂CH₂, C), (M-5961, F, CH₃, F, MeOCH₂CH₂, F), (M-5962, F, CH₃, F, MeOCH₂CH₂, CF₃), (M-5963, F, CH₃, F, MeOCH₂CH₂, Br), (M-5964, F, CH₃, F, MeOCH₂CH₂, CH₃), (M-5965, F, CH₃, F, HOCH₂, H), (M-5966, F, CH₃, F, HOCH₂, Cl), (M-5967, F, CH₃, F, HOCH₂, F), (M-5968, F, CH₃, F, HOCH₂, CF₃), (M-5969, F, CH₃, F, HOCH₂, Br), (M-5970, F, CH₃, F, HOCH₂, CH₃), (M-5971, F, CH₃, F, HOCH₂CH₂, H), (M-5972, F, CH₃, F, HOCH₂CH₂, Cl), (M-5973, F, CH₃, F, HOCH₂CH₂, F), (M-5974, F, CH₃, F, HOCH₂CH₂, CF₃), (M-5975, F, CH₃, F, HOCH₂CH₂, Br), (M-5976, F, CH₃, F, HOCH₂CH₂, CH₃), (M-5977, F, CH₃, F, HOCH₂CH₂CH₂, H), (M-5978, F, CH₃, F, HOCH₂CH₂CH₂, Cl), (M-5979, F, CH₃, F, HOCH₂CH₂CH₂, F), (M-5980, F, CH₃, F, HOCH₂CH₂CH₂, CF₃), (M-5981, F, CH₃, F, HOCH₂CH₂CH₂, Br), (M-5982, F, CH₃, F, HOCH₂CH₂CH₂, CH₃), (M-5983, F, CH₃, F, HOCH₂CH₂CH₂CH₂, H), (M-5984, F, CH₃, F, HOCH₂CH₂CH₂CH₂, Cl), (M-5985, F, CH₃, F, HOCH₂CH₂CH₂CH₂, F), (M-5986, F, CH₃, F, HOCH₂CH₂CH₂CH₂, CF₃), (M-5987, F, CH₃, F, HOCH₂CH₂CH₂CH₂, Br), (M-5988, F, CH₃, F, HOCH₂CH₂CH₂CH₂, CH₃), (M-5989, F, CH₃, F, HOCH₂CH₂CH₂CH₂CH₂, H), (M-5990, F, CH₃, F, HOCH₂CH₂CH₂CH₂CH₂, Cl), (M-5991, F, CH₃, F, HOCH₂CH₂CH₂CH₂CH₂, F), (M-5992, F, CH₃, F, HOCH₂CH₂CH₂CH₂CH₂, CF₃), (M-5993, F, CH₃, F, HOCH₂CH₂CH₂CH₂CH₂, Br), (M-5994, F, CH₃, F, HOCH₂CH₂CH₂CH₂CH₂, CH₃), (M-5995, F, CH₃, F, HOCH₂CH₂OCH₂CH₂, (M-5996, F, CH₃, F, HOCH₂CH₂OCH₂CH₂, Cl), (M-5997, F, CH₃, F, HOCH₂CH₂OCH₂CH₂, F), (M-5998, F, CH₃, F, HOCH₂CH₂OCH₂CH₂, CF₃), (M-5999, F, CH₃, F, HOCH₂CH₂OCH₂CH₂, Br), (M-6000, F, CH₃, F, HOCH₂CH₂OCH₂CH₂, CH₃), (M-6001, F, CH₃, F, (Me)₂N, H), (M-6002, F, CH₃, F, (Me)₂N, Cl), (M-6003, F, CH₃, F, (Me)₂N, F), (M-6004, F, CH₃, F, (Me)₂N, CF₃), (M-6005, F, CH₃, F, (Me)₂N, Br), (M-6006, F, CH₃, F, (Me)₂N, CH₃), (M-6007, F, CH₃, F, piperidin-4-yl-methyl, H), (M-6008, F, CH₃, F, piperidin-4-yl-methyl, Cl), (M-6009, F, CH₃, F, piperidin-4-yl-methyl, F), (M-6010, F, CH₃, F, piperidin-4-yl-methyl, CF₃), (M-6011, F, CH₃, F, piperidin-4-yl-methyl, Br), (M-6012, F, CH₃, F, piperidin-4-yl-methyl, CH₃), (M-6013, F, CH₃, F, cyclohexylmethyl, H), (M-6014, F, CH₃, F, cyclohexylmethyl, Cl), (M-6015, F, CH₃, F, cyclohexylmethyl, F), (M-6016, F, CH₃, F, cyclohexylmethyl, CF₃), (M-6017, F, CH₃, F, cyclohexylmethyl, Br), (M-6018, F, CH₃, F, cyclohexylmethyl, CH₃), (M-6019, F, CH₃, Cl, H, H), (M-6020, F, CH₃, Cl, H, Cl), (M-6021, F, CH₃, Cl, H, F), (M-6022, F, CH₃, Cl, H, CF₃), (M-6023, F, CH₃, Cl, H, Br), (M-6024, F, CH₃, Cl, H, CH₃), (M-6025, F, CH₃, Cl, F, H), (M-6026, F, CH₃, Cl, F, Cl), (M-6027, F, CH₃, Cl, F, F), (M-6028, F, CH₃, Cl, F, CF₃), (M-6029, F, CH₃, Cl, F, Br), (M-6030, F, CH₃, Cl, F, CH₃), (M-6031, F, CH₃, Cl, Cl, H), (M-6032, F, CH₃, Cl, Cl, Cl), (M-6033, F, CH₃, Cl, Cl, F), (M-6034, F, CH₃, Cl, Cl, CF₃), (M-6035, F, CH₃, Cl, Cl, Br), (M-6036, F, CH₃, Cl, Cl, CH₃), (M-6037, F, CH₃, Cl, CH₃, H), (M-6038, F, CH₃, Cl, CH₃, Cl), (M-6039, F, CH₃, Cl, CH₃, F), (M-6040, F, CH₃, Cl, CH₃, CF₃), (M-6041, F, CH₃, Cl, CH₃, Br), (M-6042, F, CH₃, Cl, CH₃, CH₃), (M-6043, F, CH₃, Cl, Et, H), (M-6044, F, CH₃, Cl, Et, Cl), (M-6045, F, CH₃, Cl, Et, F), (M-6046, F, CH₃, Cl, Et, CF₃), (M-6047, F, CH₃, Cl, Et, Br), (M-6048, F, CH₃, Cl, Et, CH₃), (M-6049, F, CH₃, Cl, n-Pr, H), (M-6050, F, CH₃, Cl, n-Pr, Cl), (M-6051, F, CH₃, Cl, n-Pr, F), (M-6052, F, CH₃, Cl, n-Pr, CF₃), (M-6053, F, CH₃, Cl, n-Pr, Br), (M-6054, F, CH₃, Cl, n-Pr, CH₃), (M-6055, F, CH₃, Cl, c-Pr, H), (M-6056, F, CH₃, Cl, c-Pr, Cl), (M-6057, F, CH₃, Cl, c-Pr, F), (M-6058, F, CH₃, Cl, c-Pr, CF₃), (M-6059, F, CH₃, Cl, c-Pr, Br), (M-6060, F, CH₃, Cl, c-Pr, CH₃), (M-6061, F, CH₃, Cl, i-Pr, H), (M-6062, F, CH₃, Cl, i-Pr, Cl), (M-6063, F, CH₃, Cl, i-Pr, F), (M-6064, F, CH₃, Cl, i-Pr, CF₃), (M-6065, F, CH₃, Cl, i-Pr, Br), (M-6066, F, CH₃, Cl, i-Pr, CH₃), (M-6067, F, CH₃, Cl, n-Bu, H), (M-6068, F, CH₃, Cl, n-Bu, Cl), (M-6069, F, CH₃, Cl, n-Bu, F), (M-6070, F, CH₃, Cl, n-Bu, CF₃), (M-6071, F, CH₃, Cl, n-Bu, Br), (M-6072, F, CH₃, Cl, n-Bu, CH₃), (M-6073, F, CH₃, Cl, i-Bu, H), (M-6074, F, CH₃, Cl, i-Bu, Cl), (M-6075, F, CH₃, Cl, i-Bu, F), (M-6076, F, CH₃, Cl, i-Bu, CF₃), (M-6077, F, CH₃, Cl, i-Bu, Br), (M-6078, F, CH₃, Cl, i-Bu, CH₃), (M-6079, F, CH₃, Cl, Sec-Bu, H), (M-6080, F, CH₃, Cl, sec-Bu, Cl), (M-6081, F, CH₃, Cl, sec-Bu, F), (M-6082, F, CH₃, Cl, sec-Bu, CF₃), (M-6083, F, CH₃, Cl, sec-Bu, Br), (M-6084, F, CH₃, Cl, sec-Bu, CH₃), (M-6085, F, CH₃, Cl, n-Pen, H), (M-6086, F, CH₃, Cl, n-Pen, Cl), (M-6087, F, CH₃, Cl, n-Pen, F), (M-6088, F, CH₃, Cl, n-Pen, CF₃), (M-6089, F, CH₃, Cl, n-Pen, Br), (M-6090, F, CH₃, Cl, n-Pen, CH₃), (M-6091, F, CH₃, Cl, c-Pen, H), (M-6092, F, CH₃, Cl, c-Pen, Cl), (M-6093, F, CH₃, Cl, c-Pen, F), (M-6094, F, CH₃, Cl, c-Pen, CF₃), (M-6095, F, CH₃, Cl, c-Pen, Br), (M-6096, F, CH₃, Cl, c-Pen, CH₃), (M-6097, F, CH₃, Cl, n-Hex, H), (M-6098, F, CH₃, Cl, n-Hex, Cl), (M-6099, F, CH₃, Cl, n-Hex, F), (M-6100, F, CH₃, Cl, n-Hex, CF₃), (M-6101, F, CH₃, Cl, n-Hex, Br), (M-6102, F, CH₃, Cl, n-Hex, CH₃), (M-6103, F, CH₃, Cl, c-Hex, H), (M-6104, F, CH₃, Cl, c-Hex, Cl), (M-6105, F, CH₃, Cl, c-Hex, F), (M-6106, F, CH₃, Cl, c-Hex, CF₃), (M-6107, F, CH₃, Cl, c-Hex, Br), (M-6108, F, CH₃, Cl, c-Hex, CH₃), (M-6109, F, CH₃, Cl, OH, H), (M-6110, F, CH₃, Cl, OH, Cl), (M-6111, F, CH₃, Cl, OH, F), (M-6112, F, CH₃, Cl, OH, CF₃), (M-6113, F, CH₃, Cl, OH, Br), (M-6114, F, CH₃, Cl, OH, CH₃), (M-6115, F, CH₃, Cl, EtO, H), (M-6116, F, CH₃, Cl, EtO, Cl), (M-6117, F, CH₃, Cl, EtO, F), (M-6118, F, CH₃, Cl, EtO, CF₃), (M-6119, F, CH₃, Cl, EtO, Br), (M-6120, F, CH₃, Cl, EtO, CH₃), (M-6121, F, CH₃, Cl, n-PrO, H), (M-6122, F, CH₃, Cl, n-PrO, Cl), (M-6123, F, CH₃, Cl, n-PrO, F), (M-6124, F, CH₃, Cl, n-PrO, CF₃), (M-6125, F, CH₃, Cl, n-PrO, Br), (M-6126, F, CH₃, Cl, n-PrO, CH₃), (M-6127, F, CH₃, Cl, PhO, H), (M-6128, F, CH₃, Cl, PhO, Cl), (M-6129, F, CH₃, Cl, PhO, F), (M-6130, F, CH₃, Cl, PhO, CF₃), (M-6131, F, CH₃, Cl, PhO, Br), (M-6132, F, CH₃, Cl, PhO, CH₃), (M-6133, F, CH₃, Cl, BnO, H), (M-6134, F, CH₃, Cl, BnO, Cl), (M-6135, F, CH₃, Cl, BnO, F), (M-6136, F, CH₃, Cl, BnO, CF₃), (M-6137, F, CH₃, Cl, BnO, Br), (M-6138, F, CH₃, Cl, BnO, CH₃), (M-6139, F, CH₃, Cl, PhCH₂CH₂O, H), (M-6140, F, CH₃, Cl, PhCH₂CH₂O, Cl), (M-6141, F, CH₃, Cl, PhCH₂CH₂O, F), (M-6142, F, CH₃, Cl, PhCH₂CH₂O, CF₃), (M-6143, F, CH₃, Cl, PhCH₂CH₂O, Br), (M-6144, F, CH₃, Cl, PhCH₂CH₂O, CH₃), (M-6145, F, CH₃, Cl, CF₃O, H), (M-6146, F, CH₃, Cl, CF₃O, Cl), (M-6147, F, CH₃, Cl, CF₃O, F), (M-6148, F, CH₃, Cl, CF₃O, CF₃), (M-6149, F, CH₃, Cl, CF₃O, Br), (M-6150, F, CH₃, Cl, CF₃O, CH₃), (M-6151, F, CH₃, Cl, Ph, H), (M-6152, F, CH₃, Cl, Ph, Cl), (M-6153, F, CH₃, Cl, Ph, F), (M-6154, F, CH₃, Cl, Ph, CF₃), (M-6155, F, CH₃, Cl, Ph, Br), (M-6156, F, CH₃, Cl, Ph, CH₃), (M-6157, F, CH₃, Cl, 4-F-Ph, H), (M-6158, F, CH₃, Cl, 4-F-Ph, Cl), (M-6159, F, CH₃, Cl, 4-F-Ph, F), (M-6160, F, CH₃, Cl, 4-F-Ph, CF₃), (M-6161, F, CH₃, Cl, 4-F-Ph, Br), (M-6162, F, CH₃, Cl, 4-F-Ph, CH₃), (M-6163, F, CH₃, Cl, 4-CF₃-Ph, H), (M-6164, F, CH₃, Cl, 4-CF₃-Ph, Cl), (M-6165, F, CH₃, Cl, 4-CF₃-Ph, F), (M-6166, F, CH₃, Cl, 4-CF₃-Ph, CF₃), (M-6167, F, CH₃, Cl, 4-CF₃-Ph, Br), (M-6168, F, CH₃, Cl, 4-CF₃-Ph, CH₃), (M-6169, F, CH₃, Cl, 4-(Me)₂N-Ph, H), (M-6170, F, CH₃, Cl, 4-(Me)₂N-Ph, Cl), (M-6171, F, CH₃, Cl, 4-(Me)₂N-Ph, F), (M-6172, F, CH₃, Cl, 4-(Me)₂N-Ph, CF₃), (M-6173, F, CH₃, Cl, 4-(Me)₂N-Ph, Br), (M-6174, F, CH₃, Cl, 4-(Me)₂N-Ph, CH₃), (M-6175, F, CH₃, Cl, 4-OH-Ph, H), (M-6176, F, CH₃, Cl, 4-OH-Ph, Cl), (M-6177, F, CH₃, Cl, 4-OH-Ph, F), (M-6178, F, CH₃, Cl, 4-OH-Ph, CF₃), (M-6179, F, CH₃, Cl, 4-OH-Ph, Br), (M-6180, F, CH₃, Cl, 4-OH-Ph, CH₃), (M-6181, F, CH₃, Cl, 3,4-di-F-Ph, H), (M-6182, F, CH₃, Cl, 3,4-di-F-Ph, Cl), (M-6183, F, CH₃, Cl, 3,4-di-F-Ph, F), (M-6184, F, CH₃, Cl, 3,4-di-F-Ph, CF₃), (M-6185, F, CH₃, Cl, 3,4-di-F-Ph, Br), (M-6186, F, CH₃, Cl, 3,4-di-F-Ph, CH₃), (M-6187, F, CH₃, Cl, 4-COOH-Ph, H), (M-6188, F, CH₃, Cl, 4-COOH-Ph, Cl), (M-6189, F, CH₃, Cl, 4-COOH-Ph, F), (M-6190, F, CH₃, Cl, 4-COOH-Ph, CF₃), (M-6191, F, CH₃, Cl, 4-COOH-Ph, Br), (M-6192, F, CH₃, Cl, 4-COOH-Ph, CH₃), (M-6193, F, CH₃, Cl, Bn, H), (M-6194, F, CH₃, Cl, Bn, Cl), (M-6195, F, CH₃, Cl, Bn, F), (M-6196, F, CH₃, Cl, Bn, CF₃), (M-6197, F, CH₃, Cl, Bn, Br), (M-6198, F, CH₃, Cl, Bn, CH₃), (M-6199, F, CH₃, Cl, 4-F-Bn, H), (M-6200, F, CH₃, Cl, 4-F-Bn, Cl), (M-6201, F, CH₃, Cl, 4-F-Bn, F), (M-6202, F, CH₃, Cl, 4-F-Bn, CF₃), (M-6203, F, CH₃, Cl, 4-F-Bn, Br), (M-6204, F, CH₃, Cl, 4-F-Bn, CH₃), (M-6205, F, CH₃, Cl, 2-Py, H), (M-6206, F, CH₃, Cl, 2-Py, Cl), (M-6207, F, CH₃, Cl, 2-Py, F), (M-6208, F, CH₃, Cl, 2-Py, CF₃), (M-6209, F, CH₃, Cl, 2-Py, Br), (M-6210, F, CH₃, Cl, 2-Py, CH₃), (M-6211, F, CH₃, Cl, 3-Py, H), (M-6212, F, CH₃, Cl, 3-Py, Cl), (M-6213, F, CH₃, Cl, 3-Py, F), (M-6214, F, CH₃, Cl, 3-Py, CF₃), (M-6215, F, CH₃, Cl, 3-Py, Br), (M-6216, F, CH₃, Cl, 3-Py, CH₃), (M-6217, F, CH₃, Cl, 4-Py, H), (M-6218, F, CH₃, Cl, 4-Py, Cl), (M-6219, F, CH₃, Cl, 4-Py, F), (M-6220, F, CH₃, Cl, 4-Py, CF₃), (M-6221, F, CH₃, Cl, 4-Py, Br), (M-6222, F, CH₃, Cl, 4-Py, CH₃), (M-6223, F, CH₃, Cl, 2-Th, H), (M-6224, F, CH₃, Cl, 2-Th, Cl), (M-6225, F, CH₃, Cl, 2-Th, F), (M-6226, F, CH₃, Cl, 2-Th, CF₃), (M-6227, F, CH₃, Cl, 2-Th, Br), (M-6228, F, CH₃, Cl, 2-Th, CH₃), (M-6229, F, CH₃, Cl, 3-Th, H), (M-6230, F, CH₃, Cl, 3-Th, Cl), (M-6231, F, CH₃, Cl, 3-Th, F), (M-6232, F, CH₃, Cl, 3-Th, CF₃), (M-6233, F, CH₃, Cl, 3-Th, Br), (M-6234, F, CH₃, Cl, 3-Th, CH₃), (M-6235, F, CH₃, Cl, pyrrazol-2-yl, H), (M-6236, F, CH₃, Cl, pyrrazol-2-yl, Cl), (M-6237, F, CH₃, Cl, pyrrazol-2-yl, F), (M-6238, F, CH₃, Cl, pyrrazol-2-yl, CF₃),-(M-6239, F, CH₃, Cl, pyrrazol-2-yl, Br), (M-6240, F, CH₃, Cl, pyrrazol-2-yl, CH₃), (M-6241, F, CH₃, Cl, pyrrazol-3-yl, H), (M-6242, F, CH₃, Cl, pyrrazol-3-yl, Cl), (M-6243, F, CH₃, Cl, pyrrazol-3-yl, F), (M-6244, F, CH₃, Cl, pyrrazol-3-yl, CF₃), (M-6245, F, CH₃, Cl, pyrrazol-3-yl, Br), (M-6246, F, CH₃, Cl, pyrrazol-3-yl, CH₃), (M-6247, F, CH₃, Cl, pyrimidin-2-yl, H), (M-6248, F, CH₃, Cl, pyrimidin-2-yl, Cl), (M-6249, F, CH₃, Cl, pyrimidin-2-yl, F), (M-6250, F, CH₃, Cl, pyrimidin-2-yl, CF₃), (M-6251, F, CH₃, Cl, pyrimidin-2-yl, Br), (M-6252, F, CH₃, Cl, pyrimidin-2-yl, CH₃), (M-6253, F, CH₃, Cl, pyrimidin-4-yl, H), (M-6254, F, CH₃, Cl, pyrimidin-4-yl, Cl), (M-6255, F, CH₃, Cl, pyrimidin-4-yl, F), (M-6256, F, CH₃, Cl, pyrimidin-4-yl, CF₃), (M-6257, F, CH₃, Cl, pyrimidin-4-yl, Br), (M-6258, F, CH₃, Cl, pyrimidin-4-yl, CH₃), (M-6259, F, CH₃, Cl, pyrimidin-5-yl, E), (M-6260, F, CH₃, Cl, pyrimidin-5-yl, Cl), (M-6261, F, CH₃, Cl, pyrimidin-5-yl, F), (M-6262, F, CH₃, Cl, pyrimidin-5-yl, CF₃), (M-6263, F, CH₃, Cl, pyrimidin-5-yl, Br), (M-6264, F, CH₃, Cl, pyrimidin-5-yl, CH₃), (M-6265, F, CH₃, Cl, HOOCCH₂CH₂CH₂, H), (M-6266, F, CH₃, Cl, HOOCCH₂CH₂CH₂, Cl), (M-6267, F, CH₃, Cl, HOOCCH₂CH₂CH₂, F), (M-6268, F, CH₃, Cl, HOOCCH₂CH₂CH₂, CF₃), (M-6269, F, CH₃, Cl, HOOCCH₂CH₂CH₂, Br), (M-6270, F, CH₃, Cl, HOOCCH₂CH₂CH₂, CH₃), (M-6271, F, CH₃, Cl, HOOCCH₂CH₂CH₂CH₂, H), (M-6272, F, CH₃, Cl, HOOCCH₂CH₂CH₂CH₂, Cl), (M-6273, F, CH₃, Cl, HOOCCH₂CH₂CH₂CH₂, F), (M-6274, F, CH₃, Cl, HOOCCH₂CH₂CU₂CH₂, CF₃), (M-6275, F, CH₃, Cl, HOOCCH₂CH₂CH₂CH₂, Br), (M-6276, F, CH₃, Cl, HOOCCH₂CH₂CH₂CH₂, CH₃), (M-6277, F, CH₃, Cl, (Me)₂NCOCH₂CH₂CH₂CH₂H), (M-6278, F, CH₃, Cl, (Me)₂NCOCH₂CH₂CH₂CH₂, Cl), (M-6279, F, CH₃, Cl, (Me)₂NCOCH₂CH₂CH₂CH₂, F), (M-6280, F, CH₃, Cl, (Me)₂NCOCH₂CH₂CH₂CH₂, CF₃), (M-6281, F, CH₃, Cl, (Me)₂NCOCH₂CH₂CH₂CH₂, Br), (M-6282, F, CH₃, Cl, (Me)₂NCOCH₂CH₂CH₂CH₂, CH₃), (M-6283, F, CH₃, Cl, (Me)₂NCOCH₂CH₂CH₂CH₂CH₂, H), (M-6284, F, CH₃, Cl, (Me)₂NCOCH₂CH₂CH₂CH₂CH₂, Cl), (M-6285, F, CH₃, Cl, (Me)₂NCOCH₂CH₂CH₂CH₂CH₂, F), (M-6286, F, CH₃, Cl, (Me)₂NCOCH₂CH₂CH₂CH₂CH₂, CF₃), (M-6287, F, CH₃, Cl, (Me)₂NCOCH₂CH₂CH₂CH₂CH₂, Br), (M-6288, F, CH₃, Cl, (Me)₂NCOCH₂CH₂CH₂CH₂CH₂, CH₃), (M-6289, F, CH₃, Cl, MeOCH₂, H), (M-6290, F, CH₃, Cl, MeOCH₂, Cl), (M-6291, F, CH₃, Cl, MeOCH₂, F), (M-6292, F, CH₃, Cl, MeOCH₂, CF₃), (M-6293, F, CH₃, Cl, MeOCH₂, Br), (M-6294, F, CH₃, Cl, MeOCH₂, CH₃), (M-6295, F, CH₃, Cl, EtOCH₂, H), (M-6296, F, CH₃, Cl, EtOCH₂, Cl), (M-6297, F, CH₃, Cl, EtOCH₂, F), (M-6298, F, CH₃, Cl, EtOCH₂, CF₃), (M-6299, F, CH₃, Cl, EtOCH₂, Br), (M-6300, F, CH₃, Cl, EtOCH₂, CH₃), (M-6301, F, CH₃, Cl, EtOCH₂CH₂, H), (M-6302, F, CH₃, Cl, EtOCH₂CH₂, Cl), (M-6303, F, CH₃, Cl, EtOCH₂CH₂, F), (M-6304, F, CH₃, Cl, EtOCH₂CH₂, CF₃), (M-6305, F, CH₃, Cl, EtOCH₂CH₂, Br), (M-6306, F, CH₃, Cl, EtOCH₂CH₂, CH₃), (M-6307, F, CH₃, Cl, MeOCH₂CH₂OCH₂CH₂, H), (M-6308, F, CH₃, Cl, MeOCH₂CH₂OCH₂CH₂, Cl), (M-6309, F, CH₃, Cl, MeOCH₂CH₂OCH₂CH₂, F), (M-6310, F, CH₃, Cl, MeOCH₂CH₂OCH₂CH₂, CF₃), (M-6311, F, CH₃, Cl, MeOCH₂CH₂OCH₂CH₂, Br), (M-6312, F, CH₃, Cl, MeOCH₂CH₂OCH₂CH₂, CH₃), (M-6313, F, CH₃, Cl, MeOCH₂CH₂, H), (M-6314, F, CH₃, Cl, MeOCH₂CH₂, Cl), (M-6315, F, CH₃, Cl, MeOCH₂CH₂, F), (M-6316, F, CH₃, Cl, MeOCH₂CH₂, CF₃), (M-6317, F, CH₃, Cl, MeOCH₂CH₂, Br), (M-6318, F, CH₃, Cl, MeOCH₂CH₂, CH₃), (M-6319, F, CH₃, Cl, HOCH₂, H), (M-6320, F, CH₃, Cl, HOCH₂, Cl), (M-6321, F, CH₃, Cl, HOCH₂, F), (M-6322, F, CH₃, Cl, HOCH₂, CF₃), (M-6323, F, CH₃, Cl, HOCH₂, Br), (M-6324, F, CH₃, Cl, HOCH₂, CH₃), (M-6325, F, CH₃, Cl, HOCH₂CH₂, H), (M-6326, F, CH₃, Cl, HOCH₂CH₂, Cl), (M-6327, F, CH₃, Cl, HOCH₂CH₂, F), (M-6328, F, CH₃, Cl, HOCH₂CH₂, CF₃), (M-6329, F, CH₃, Cl, HOCH₂CH₂, Br), (M-6330, F, CH₃, Cl, HOCH₂CH₂, CH₃), (M-6331, F, CH₃, Cl, HOCH₂CH₂CH₂, H), (M-6332, F, CH₃, Cl, HOCH₂CH₂CH₂, Cl), (M-6333, F, CH₃, Cl, HOCH₂CH₂CH₂, F), (M-6334, F, CH₃, Cl, HOCH₂CH₂CH₂, CF₃), (M-6335, F, CH₃, Cl, HOCH₂CH₂CH₂, Br), (M-6336, F, CH₃, Cl, HOCH₂CH₂CH₂, CH₃), (M-6337, F, CH₃, Cl, HOCH₂CH₂CH₂CH₂, H), (M-6338, F, CH₃, Cl, HOCH₂CH₂CH₂CH₂, Cl), (M-6339, F, CH₃, Cl, HOCH₂CH₂CH₂CH₂, F), (M-6340, F, CH₃, Cl, HOCH₂CH₂CH₂CH₂, CF₃), (M-6341, F, CH₃, Cl, HOCH₂CH₂CH₂CH₂, Br), (M-6342, F, CH₃, Cl, HOCH₂CH₂CH₂CH₂, CH₃), (M-6343, F, CH₃, Cl, HOCH₂CH₂CH₂CH₂CH₂, H), (M-6344, F, CH₃, Cl, HOCH₂CH₂CH₂CH₂CH₂, Cl), (M-6345, F, CH₃, Cl, HOCH₂CH₂CH₂CH₂CH₂, F), (M-6346, F, CH₃, Cl, HOCH₂CH₂CH₂CH₂CH₂, CF₃), (M-6347, F, CH₃, Cl, HOCH₂CH₂CH₂CH₂CH₂, Br), (M-6348, F, CH₃, Cl, HOCH₂CH₂CH₂CH₂CH₂, CH₃), (M-6349, F, CH₃, Cl, HOCH₂CH₂OCH₂CH₂, H), (M-6350, F, CH₃, Cl, HOCH₂CH₂OCH₂CH₂, Cl), (M-6351, F, CH₃, Cl, HOCH₂CH₂OCH₂CH₂, F), (M-6352, F, CH₃, Cl, HOCH₂CH₂OCH₂CH₂, CF₃), (M-6353, F, CH₃, Cl, HOCH₂CH₂OCH₂CH₂, Br), (M-6354, F, CH₃, Cl, HOCH₂CH₂OCH₂CH₂, CH₃), (M-6355, F, CH₃, Cl, (Me)₂N, H), (M-6356, F, CH₃, Cl, (Me)₂N, Cl), (M-6357, F, CH₃, Cl, (Me)₂N, F), (M-6358, F, CH₃, Cl, (Me)₂N, CF₃), (M-6359, F, CH₃, Cl, (Me)₂N, Br), (M-6360, F, CH₃, Cl, (Me)₂N, CH₃), (M-6361, F, CH₃, Cl, piperidin-4-yl-methyl, H), (M-6362, F, CH₃, Cl, piperidin-4-yl-methyl, Cl), (M-6363, F, CH₃, Cl, piperidin-4-yl-methyl, F), (M-6364, F, CH₃, Cl, piperidin-4-yl-methyl, CF₃), (M-6365, F, CH₃, Cl, piperidin-4-yl-methyl, Br), (M-6366, F, CH₃, Cl, piperidin-4-yl-methyl, CH₃), (M-6367, F, CH₃, Cl, cyclohexylmethyl, H), (M-6368, F, CH₃, Cl, cyclohexylmethyl, Cl), (M-6369, F, CH₃, Cl, cyclohexylmethyl, F), (M-6370, F, CH₃, Cl, cyclohexylmethyl, CF₃), (M-6371, F, CH₃, Cl, cyclohexylmethyl, Br), (M-6372, F, CH₃, Cl, cyclohexylmethyl, CH₃), (M-6373, Cl, H, H, H, H), (M-6374, Cl, H, H, H, Cl), (M-6375, MeO, F, H, H, F), (M-6376, MeO, F, H, H, c-Pr), (M-6377, Cl, H, H, H, Br), (M-6378, Cl, H, H, H, CH₃), (M-6379, MeO, H, H, F, c-Pr), (M-6380, Cl, H, H, F, Cl), (M-6381, MeO, H, H, F, F), (M-6382, Cl, H, H, F, CF₃), (M-6383, Cl, H, H, F, Br), (M-6384, Cl, H, H, F, CH₃), (M-6385, Cl, H, H, Cl, H), (M-6386, MeO, F, H, H, Et), (M-6387, MeO, H, H, Cl, F), (M-6388, Cl, H, H, Cl, CF₃), (M-6389, Cl, H, H, Cl, Br), (M-6390, Cl, H, H, Cl, CH₃), (M-6391, Cl, H, H, CH₃, H), (M-6392, Cl, H, H, CH₃, Cl), (M-6393, Cl, H, H, CH₃, F), (M-6394, Cl, H, H, CH₃, CF₃), (M-6395, Cl, H, H, CH₃, Br), (M-6396, Cl, H, H, CH₃, CH₃), (M-6397, Cl, H, H, Et, H), (M-6398, Cl, H, H, Et, Cl), (M-6399, Cl, H, H, Et, F), (M-6400, Cl, H, H, Et, CF₃), (M-6401, Cl, H, H, Et, Br), (M-6402, Cl, H, H, Et, CH₃), (M-6403, Cl, H, H, n-Pr, H), (M-6404, Cl, H, H, n-Pr, Cl), (M-6405, Cl, H, H, n-Pr, F), (M-6406, Cl, H, H, n-Pr, CF₃), (M-6407, Cl, H, H, n-Pr, Br), (M-6408, Cl, H, H, n-Pr, CH₃), (M-6409, Cl, H, H, c-Pr, H), (M-6410, Cl, H, H, c-Pr, Cl), (M-6411, Cl, H, H, c-Pr, F), (M-6412, Cl, H, H, c-Pr, CF₃), (M-6413, Cl, H, H, c-Pr, Br), (M-6414, Cl, H, H, c-Pr, CH₃), (M-6415, Cl, H, H, i-Pr, H), (M-6416, Cl, H, H, i-Pr, Cl), (M-6417, Cl, H, H, i-Pr, F), (M-6418, Cl, H, H, i-Pr, CF₃), (M-6419, Cl, H, H, i-Pr, Br), (M-6420, Cl, H, H, i-Pr, CH₃), (M-6421, MeO, H, H, n-Bu, H), (M-6422, Cl, H, H, n-Bu, Cl), (M-6423, Cl, H, H, n-Bu, F), (M-6424, Cl, H, H, n-Bu, CF₃), (M-6425, Cl, H, H, n-Bu, Br), (M-6426, Cl, H, H, n-Bu, CH₃), (M-6427, Cl, H, H, i-Bu, H), (M-6428, Cl, H, H, i-Bu, Cl), (M-6429, Cl, H, H, i-Bu, F), (M-6430, Cl, H, H, i-Bu, CF₃), (M-6431, Cl, H, H, i-Bu, Br), (M-6432, Cl, H, H, i-Bu, CH₃), (M-6433, Cl, H, H, sec-Bu, H), (M-6434, Cl, H, H, sec-Bu, Cl), (M-6435, Cl, H, H, sec-Bu, F), (M-6436, Cl, H, H, sec-Bu, CF₃), (M-6437, Cl, H, H, sec-Bu, Br), (M-6438, Cl, H, H, sec-Bu, CH₃), (M-6439, Cl, H, H, n-Pen, H), (M-6440, Cl, H, H, n-Pen, Cl), (M-6441, MeO, H, H, n-Pen, F), (M-6442, Cl, H, H, n-Pen, CF₃), (M-6443, Cl, H, H, n-Pen, Br), (M-6444, Cl, H, H, n-Pen, CH₃), (M-6445, Cl, H, H, c-Pen, H), (M-6446, Cl, H, H, c-Pen, Cl), (M-6447, Cl, H, H, c-Pen, F), (M-6448, Cl, H, H, c-Pen, CF₃), (M-6449, Cl, H, H, c-Pen, Br), (M-6450, Cl, H, H, c-Pen, CH₃), (M-6451, Cl, H, H, n-Hex, H), (M-6452, Cl, H, H, n-Hex, Cl), (M-6453, Cl, H, H, n-Hex, F), (M-6454, Cl, H, H, n-Hex, CF₃), (M-6455, Cl, H, H, n-Hex, Br), (M-6456, Cl, H, H, n-Hex, CH₃), (M-6457, Cl, H, H, c-Hex, H), (M-6458, Cl, H, H, c-Hex, Cl), (M-6459, Cl, H, H, c-Hex, F), (M-6460, Cl, H, H, c-Hex, CF₃), (M-6461, Cl, H, H, c-Hex, Br), (M-6462, Cl, H, H, c-Hex, CH₃), (M-6463, Cl, H, H, OH, H), (M-6464, Cl, H, H, OH, Cl), (M-6465, Cl, H, H, OH, F), (M-6466, Cl, H, H, OH, CF₃), (M-6467, Cl, H, H, OH, Br), (M-6468, Cl, H, H, OH, CH₃), (M-6469, Cl, H, H, EtO, H), (M-6470, Cl, H, H, EtO, Cl), (M-6471, Cl, H, H, EtO, F), (M-6472, Cl, H, H, EtO, CF₃), (M-6473, Cl, H, H, EtO, Br), (M-6474, Cl, H, H, EtO, CH₃), (M-6475, Cl, H, H, n-PrO, H), (M-6476, Cl, H, H, n-PrO, Cl), (M-6477, Cl, H, H, n-PrO, F), (M-6478, Cl, H, H, n-PrO, CF₃), (M-6479, Cl, H, H, n-PrO, Br), (M-6480, Cl, H, H, n-PrO, CH₃), (M-6481, Cl, H, H, PhO, H), (M-6482, Cl, H, H, PhO, Cl), (M-6483, Cl, H, H, PhO, F), (M-6484, Cl, H, H, PhO, CF₃), (M-6485, Cl, H, H, PhO, Br), (M-6486, Cl, H, H, PhO, CH₃), (M-6487, Cl, H, H, BnO, H), (M-6488, Cl, H, H, BnO, Cl), (M-6489, Cl, H, H, BnO, F), (M-6490, Cl, H, H, BnO, CF₃), (M-6491, Cl, H, H, BnO, Br), (M-6492, Cl, H, H, BnO, CH₃), (M-6493, Cl, H, H, PhCH₂CH₂O, H), (M-6494, Cl, H, H, PhCH₂CH₂O, Cl), (M-6495, Cl, H, H, PhCH₂CH₂O, F), (M-6496, Cl, H, H, PhCH₂CH₂O, CF₃), (M-6497, Cl, H, H, PhCH₂CH₂O, Br), (M-6498, Cl, H, H, PhCH₂CH₂O, CH₃), (M-6499, MeO, H, H, CF₃O, CF₃), (M-6500, Cl, H, H, CF₃O, Cl), (M-6501, Cl, H, H, CF₃O, F), (M-6502, Cl, H, H, CF₃O, CF₃), (M-6503, Cl, H, H, CF₃O, Br), (M-6504, Cl, H, H, CF₃O, CH₃), (M-6505, MeO, H, H, Ph, H), (M-6506, Cl, H, H, Ph, Cl), (M-6507, Cl, H, H, Ph, F), (M-6508, Cl, H, H, Ph, CF₃), (M-6509, Cl, H, H, Ph, Br), (M-6510, Cl, H, H, Ph, CH₃), (M-6511, Cl, H, H, 4-F-Ph, H), (M-6512, Cl, H, H, 4-F-Ph, Cl), (M-6513, Cl, H, H, 4-F-Ph, F), (M-6514, Cl, H, H, 4-F-Ph, CF₃), (M-6515, Cl, H, H, 4-F-Ph, Br), (M-6516, Cl, H, H, 4-F-Ph, CH₃), (M-6517, Cl, H, H, 4-CF₃-Ph, H), (M-6518, Cl, H, H, 4-CF₃-Ph, Cl), (M-6519, Cl, H, H, 4-CF₃-Ph, F), (M-6520, Cl, H, H, 4-CF₃-Ph, CF₃), (M-6521, Cl, H, H, 4-CF₃-Ph, Br), (M-6522, Cl, H, H, 4-CF₃-Ph, CH₃), (M-6523, Cl, H, H, 4-(Me)₂N-Ph, H), (M-6524, Cl, H, H, 4-(Me)₂N-Ph, Cl), (M-6525, Cl, H, H, 4-(Me)₂N-Ph, F), (M-6526, Cl, H, H, 4-(Me)₂N-Ph, CF₃), (M-6527, Cl, H, H, 4-(Me)₂N-Ph, Br), (M-6528, Cl, H, H, 4-(Me)₂N-Ph, CH₃), (M-6529, Cl, H, H, 4-OH-Ph, H), (M-6530, Cl, H, H, 4-OH-Ph, Cl), (M-6531, Cl, H, H, 4-OH-Ph, F), (M-6532, Cl, H, H, 4-OH-Ph, CF₃), (M-6533, Cl, H, H, 4-OH-Ph, Br), (M-6534, Cl, H, H, 4-OH-Ph, CH₃), (M-6535, Cl, H, H, 3,4-di-F-Ph, H), (M-6536, Cl, H, H, 3,4-di-F-Ph, Cl), (M-6537, Cl, H, H, 3,4-di-F-Ph, F), (M-6538, Cl, H, H, 3,4-di-F-Ph, CF₃), (M-6539, Cl, H, H, 3,4-di-F-Ph, Br), (M-6540, Cl, H, H, 3,4-di-F-Ph, CH₃), (M-6541, Cl, H, H, 4-COOH-Ph, H), (M-6542, Cl, H, H, 4-COOH-Ph, Cl), (M-6543, Cl, H, H, 4-COOH-Ph, F), (M-6544, Cl, H, H, 4-COOH-Ph, CF₃), (M-6545, Cl, H, H, 4-COOH-Ph, Br), (M-6546, Cl, H, H, 4-COOH-Ph, CH₃), (M-6547, Cl, H, H, Bn, H), (M-6548, Cl, H, H, Bn, Cl), (M-6549, Cl, H, H, Bn, F), (M-6550, Cl, H, H, Bn, CF₃), (M-6551, Cl, H, H, Bn, Br), (M-6552, Cl, H, H, Bn, CH₃), (M-6553, Cl, H, H, 4-F-Bn, H), (M-6554, Cl, H, H, 4-F-Bn, Cl), (M-6555, Cl, H, H, 4-F-Bn, F), (M-6556, Cl, H, H, 4-F-Bn, CF₃), (M-6557, Cl, H, H, 4-F-Bn, Br), (M-6558, Cl, H, H, 4-F-Bn, CH₃), (M-6559, Cl, H, H, 2-Py, H), (M-6560, Cl, H, H, 2-Py, Cl), (M-6561, Cl, H, H, 2-Py, F), (M-6562, Cl, H, H, 2-Py, CF₃), (M-6563, Cl, H, H, 2-Py, Br), (M-6564, Cl, H, H, 2-Py, CH₃), (M-6565, Cl, H, H, 3-Py, H), (M-6566, Cl, H, H, 3-Py, Cl), (M-6567, Cl, H, H, 3-Py, F), (M-6568, Cl, H, H, 3-Py, CF₃), (M-6569, Cl, H, H, 3-Py, Br), (M-6570, Cl, H, H, 3-Py, CH₃), (M-6571, Cl, H, H, 4-Py, H), (M-6572, Cl, H, H, 4-Py, Cl), (M-6573, Cl, H, H, 4-Py, F), (M-6574, Cl, H, H, 4-Py, CF₃), (M-6575, Cl, H, H, 4-Py, Br), (M-6576, Cl, H, H, 4-Py, CH₃), (M-6577, Cl, H, H, 2-Th, H), (M-6578, Cl, H, H, 2-Th, Cl), (M-6579, Cl, H, H, 2-Th, F), (M-6580, Cl, H, H, 2-Th, CF₃), (M-6581, Cl, H, H, 2-Th, Br), (M-6582, Cl, H, H, 2-Th, CH₃), (M-6583, Cl, H, H, 3-Th, H), (M-6584, Cl, H, H, 3-Th, Cl), (M-6585, Cl, H, H, 3-Th, F), (M-6586, Cl, H, H, 3-Th, CF₃), (M-6587, Cl, H, H, 3-Th, Br), (M-6588, Cl, H, H, 3-Th, CH₃), (M-6589, Cl, H, H, pyrrazol-2-yl, H), (M-6590, Cl, H, H, pyrrazol-2-yl, Cl), (M-6591, Cl, H, H, pyrrazol-2-yl, F), (M-6592, Cl, H, H, pyrrazol-2-yl, CF₃), (M-6593, Cl, H, H, pyrrazol-2-yl, Br), (M-6594, Cl, H, H, pyrrazol-2-yl, CH₃), (M-6595, Cl, H, H, pyrrazol-3-yl, H), (M-6596, Cl, H, H, pyrrazol-3-yl, Cl), (M-6597, Cl, H, H, pyrrazol-3-yl, F), (M-6598, Cl, H, H, pyrrazol-3-yl, CF₃), (M-6599, Cl, H, H, pyrrazol-3-yl, Br), (M-6600, Cl, H, H, pyrrazol-3-yl, CH₃), (M-6601, Cl, H, H, pyrimidin-2-yl, H), (M-6602, Cl, H, H, pyrimidin-2-yl, Cl), (M-6603, Cl, H, H, pyrimidin-2-yl, F), (M-6604, Cl, H, H, pyrimidin-2-yl, CF₃), (M-6605, Cl, H, H, pyrimidin-2-yl, Br), (M-6606, Cl, H, H, pyrimidin-2-yl, CH₃), (M-6607, Cl, H, H, pyrimidin-4-yl, H), (M-6608, Cl, H, H, pyrimidin-4-yl, Cl), (M-6609, Cl, H, H, pyrimidin-4-yl, F), (M-6610, Cl, H, H, pyrimidin-4-yl, CF₃), (M-6611, Cl, H, H, pyrimidin-4-yl, Br), (M-6612, Cl, H, H, pyrimidin-4-yl, CH₃), (M-6613, Cl, H, H, pyrimidin-5-yl, H), (M-6614, Cl, H, H, pyrimidin-5-yl, Cl), (M-6615, Cl, H, H, pyrimidin-5-yl, F), (M-6616, Cl, H, H, pyrimidin-5-yl, CF₃), (M-6617, Cl, H, H, pyrimidin-5-yl, Br), (M-6618, Cl, H, H, pyrimidin-5-yl, CH₃), (M-6619, Cl, H, H, HOOCCH₂CH₂CH₂, H), (M-6620, Cl, H, H, HOOCCH₂CH₂CH₂, Cl), (M-6621, Cl, H, H, HOOCCH₂CH₂CH₂, F), (M-6622, Cl, H, H, HOOCCH₂CH₂CH₂, CF₃), (M-6623, Cl, H, H, HOOCCH₂CH₂CH₂, Br), (M-6624, Cl, H, H, HOOCCH₂CH₂CH₂, CH₃), (M-6625, Cl, H, H, HOOCCH₂CH₂CH₂CH₂, H), (M-6626, Cl, H, H, HOOCCH₂CH₂CH₂CH₂, Cl), (M-6627, Cl, H, H, HOOCCH₂CH₂CH₂CH₂, F), (M-6628, Cl, H, H, HOOCCH₂CH₂CH₂CH₂, CF₃), (M-6629, Cl, H, H, HOOCCH₂CH₂CH₂CH₂, Br), (M-6630, Cl, H, H, HOOCCH₂CH₂CH₂CH₂, CH₃), (M-6631, Cl, H, H, (Me)₂NCOCH₂CH₂CH₂, H), (M-6632, Cl, H, H, (Me)₂NCOCH₂CH₂CH₂, Cl), (M-6633, Cl, H, H, (Me)₂NCOCH₂CH₂CH₂, F), (M-6634, Cl, H, H, (Me)₂NCOCH₂CH₂CH₂, CF₃), (M-6635, Cl, H, H, (Me)₂NCOCH₂CH₂CH₂, Br), (M-6636, Cl, H, H, (Me)₂NCOCH₂CH₂CH₂, CH₃), (M-6637, Cl, H, H, (Me)₂NCOCH₂CH₂CH₂CH₂, H), (M-6638, Cl, H, H, (Me)₂NCOCH₂CH₂CH₂CH₂, Cl), (M-6639, Cl, H, H, (Me)₂NCOCH₂CH₂CH₂CH₂, F), (M-6640, Cl, H, H, (Me)₂NCOCH₂CH₂CH₂CH₂, CF₃), (M-6641, Cl, H, H, (Me)₂NCOCH₂CH₂CH₂CH₂, Br), (M-6642, Cl, H, H, (Me)₂NCOCH₂CH₂CH₂CH₂, CH₃), (M-6643, Cl, H, H, MeOCH₂, H), (M-6644, Cl, H, H, MeOCH₂, Cl), (M-6645, Cl, H, H, MeOCH₂, F), (M-6646, Cl, H, H, MeOCH₂, CF₃), (M-6647, Cl, H, H, MeOCH₂, Br), (M-6648, Cl, H, H, MeOCH$_2$, CH$_3$), (M-6649, Cl, H, H, EtOCH$_2$, H), (M-6650, Cl, H, H, EtOCH$_2$, Cl), (M-6651, Cl, H, H, EtOCH$_2$, F), (M-6652, Cl, H, H, EtOCH$_2$, CF$_3$), (M-6653, Cl, H, H, EtOCH$_2$, Br), (M-6654, Cl, H, H, EtOCH$_2$, CH$_3$), (M-6655, Cl, H, H, EtOCH$_2$CH$_2$, H), (M-6656, Cl, H, H, EtOCH$_2$CH$_2$, Cl), (M-6657, Cl, H, H, EtOCH$_2$CH$_2$, F), (M-6658, Cl, H, H, EtOCH$_2$CH$_2$, CF$_3$), (M-6659, Cl, H, H, EtOCH$_2$CH$_2$, Br), (M-6660, Cl, H, H, EtOCH$_2$CH$_2$, CH$_3$), (M-6661, Cl, H, H, MeOCH$_2$CH$_2$OCH$_2$CH$_2$, H), (M-6662, Cl, H, H, MeOCH$_2$CH$_2$OCH$_2$CH$_2$, Cl), (M-6663, Cl, H, H, MeOCH$_2$CH$_2$OCH$_2$CH$_2$, F), (M-6664, Cl, H, H, MeOCH$_2$CH$_2$OCH$_2$CH$_2$, CF$_3$), (M-6665, Cl, H, H, MeOCH$_2$CH$_2$OCH$_2$CH$_2$, Br), (M-6666, Cl, H, H, MeOCH$_2$CH$_2$OCH$_2$CH$_2$, CH$_3$), (M-6667, Cl, H, H, MeOCH$_2$CH$_2$, H), (M-6668, Cl, H, H, MeOCH$_2$CH$_2$, Cl), (M-6669, Cl, H, H, MeOCH$_2$CH$_2$, F), (M-6670, Cl, H, H, MeOCH$_2$CH$_2$, CF$_3$), (M-6671, Cl, H, H, MeOCH$_2$CH$_2$, Br), (M-6672, Cl, H, H, MeOCH$_2$CH$_2$, CH$_3$), (M-6673, Cl, H, H, HOCH$_2$, H), (M-6674, Cl, H, H, HOCH$_2$, Cl), (M-6675, Cl, H, H, HOCH$_2$, F), (M-6676, Cl, H, H, HOCH$_2$, CF$_3$), (M-6677, Cl, H, H, HOCH$_2$, Br), (M-6678, Cl, H, H, HOCH$_2$, CH$_3$), (M-6679, Cl, H, H, HOCH$_2$CH$_2$, H), (M-6680, Cl, H, H, HOCH$_2$CH$_2$, Cl), (M-6681, Cl, H, H, HOCH$_2$CH$_2$, F), (M-6682, Cl, H, H, HOCH$_2$CH$_2$, CF$_3$), (M-6683, Cl, H, H, HOCH$_2$CH$_2$, Br), (M-6684, Cl, H, H, HOCH$_2$CH$_2$, CH$_3$), (M-6685, Cl, H, H, HOCH$_2$CH$_2$CH$_2$, H), (M-6686, Cl, H, H, HOCH$_2$CH$_2$CH$_2$, Cl), (M-6687, Cl, H, H, HOCH$_2$CH$_2$CH$_2$, F), (M-6688, Cl, H, H, HOCH$_2$CH$_2$CH$_2$, CF$_3$), (M-6689, Cl, H, H, HOCH$_2$CH$_2$CH$_2$, Br), (M-6690, Cl, H, H, HOCH$_2$CH$_2$CH$_2$, CH$_3$), (M-6691, Cl, H, H, HOCH$_2$CH$_2$CH$_2$CH$_2$, H), (M-6692, Cl, H, H, HOCH$_2$CH$_2$CH$_2$CH$_2$, Cl), (M-6693, Cl, H, H, HOCH$_2$CH$_2$CH$_2$CH$_2$, F), (M-6694, Cl, H, H, HOCH$_2$CH$_2$CH$_2$CH$_2$, CF$_3$), (M-6695, Cl, H, H, HOCH$_2$CH$_2$CH$_2$CH$_2$, Br), (M-6696, Cl, H, H, HOCH$_2$CH$_2$CH$_2$CH$_2$, CH$_3$), (M-6697, Cl, H, H, HOCH$_2$CH$_2$CH$_2$CH$_2$CH$_2$, H), (M-6698, Cl, H, H, HOCH$_2$CH$_2$CH$_2$CH$_2$CH$_2$, Cl), (M-6699, Cl, H, H, HOCH$_2$CH$_2$CH$_2$CH$_2$CH$_2$, F), (M-6700, Cl, H, H, HOCH$_2$CH$_2$CH$_2$CH$_2$CH$_2$, CF$_3$), (M-6701, Cl, H, H, HOCH$_2$CH$_2$CH$_2$CH$_2$CH$_2$Br), (M-6702, Cl, H, H, HOCH$_2$CH$_2$CH$_2$CH$_2$CH$_2$, CH$_3$), (M-6703, Cl, H, H, HOCH$_2$CH$_2$OCH$_2$CH$_2$, H), (M-6704, Cl, H, H, HOCH$_2$CH$_2$OCH$_2$CH$_2$, Cl), (M-6705, Cl, H, H, HOCH$_2$CH$_2$OCH$_2$CH$_2$, F), (M-6706, Cl, H, H, HOCH$_2$CH$_2$OCH$_2$CH$_2$, CF$_3$), (M-6707, Cl, H, H, HOCH$_2$CH$_2$OCH$_2$CH$_2$, Br), (M-6708, Cl, H, H, HOCH$_2$CH$_2$OCH$_2$CH$_2$, CH$_3$), (M-6709, Cl, H, H, (Me)$_2$N, H), (M-6710, Cl, H, H, (Me)$_2$N, Cl), (M-6711, Cl, H, H, (Me)$_2$N, F), (M-6712, Cl, H, H, (Me)$_2$N, CF$_3$), (M-6713, Cl, H, H, (Me)$_2$N, Br), (M-6714, Cl, H, H, (Me)$_2$N, CH$_3$), (M-6715, Cl, H, H, piperidin-4-yl-methyl, H), (M-6716, Cl, H, H, piperidin-4-yl-methyl, Cl), (M-6717, Cl, H, H, piperidin-4-yl-methyl, F), (M-6718, Cl, H, H, piperidin-4-yl-methyl, CF$_3$), (M-6719, Cl, H, H, piperidin-4-yl-methyl, Br), (M-6720, Cl, H, H, piperidin-4-yl-methyl, CH$_3$), (M-6721, Cl, H, H, cyclohexylmethyl, H), (M-6722, Cl, H, H, cyclohexylmethyl, Cl), (M-6723, Cl, H, H, cyclohexylmethyl, F), (M-6724, Cl, H, H, cyclohexylmethyl, CF$_3$), (M-6725, Cl, H, H, cyclohexylmethyl, Br), (M-6726, Cl, H, H, cyclohexylmethyl, CH$_3$), (M-6727, MeO, H, F, H, H), (M-6728, Cl, H, F, H, Cl), (M-6729, MeO, H, F, H, F), (M-6730, MeO, H, F, H, CF$_3$), (M-6731, MeO, H, F, H, Br), (M-6732, MeO, H, F, H, CH$_3$), (M-6733, MeO, H, F, F, H), (M-6734, Cl, H, F, F, Cl), (M-6735, Cl, H, F, F, F), (M-6736, Cl, H, F, F, CF$_3$), (M-6737, Cl, H, F, F, Br), (M-6738, Cl, H, F, F, CH$_3$), (M-6739, Cl, H, F, Cl, H), (M-6740, Cl, H, F, Cl, Cl), (M-6741, Cl, H, F, Cl, F), (M-6742, Cl, H, F, Cl, CF$_3$), (M-6743, Cl, H, F, Cl, Br), (M-6744, Cl, H, F, Cl, CH$_3$), (M-6745, MeO, H, F, CH$_3$, H), (M-6746, Cl, H, F, CH$_3$, Cl), (M-6747, Cl, H, F, CH$_3$, F), (M-6748, Cl, H, F, CH$_3$, CF$_3$), (M-6749, Cl, H, F, CH$_3$, Br), (M-6750, Cl, H, F, CH$_3$, CH$_3$), (M-6751, MeO, H, F, Et, H), (M-6752, Cl, H, F, Et, Cl), (M-6753, Cl, H, F, Et, F), (M-6754, Cl, H, F, Et, CF$_3$), (M-6755, Cl, H, F, Et, Br), (M-6756, Cl, H, F, Et, CH$_3$), (M-6757, MeO, H, F, n-Pr, H), (M-6758, Cl, H, F, n-Pr, Cl), (M-6759, Cl, H, F, n-Pr, F), (M-6760, Cl, H, F, n-Pr, CF$_3$), (M-6761, MeO, H, F, n-Pr, Br), (M-6762, Cl, H, F, n-Pr, CH$_3$), (M-6763, Cl, H, F, c-Pr, H), (M-6764, Cl, H, F, c-Pr, Cl), (M-6765, Cl, H, F, c-Pr, F), (M-6766, Cl, H, F, c-Pr, CF$_3$), (M-6767, Cl, H, F, c-Pr, Br), (M-6768, Cl, H, F, c-Pr, CH$_3$), (M-6769, Cl, H, F, i-Pr, H), (M-6770, Cl, H, F, i-Pr, Cl), (M-6771, Cl, H, F, i-Pr, F), (M-6772, Cl, H, F, i-Pr, CF$_3$), (M-6773, Cl, H, F, i-Pr, Br), (M-6774, Cl, H, F, i-Pr, CH$_3$), (M-6775, MeO, H, F, n-Bu, H), (M-6776, Cl, H, F, n-Bu, Cl), (M-6777, Cl, H, F, n-Bu, F), (M-6778, Cl, H, F, n-Bu, CF$_3$), (M-6779, Cl, H, F, n-Bu, Br), (M-6780, Cl, H, F, n-Bu, CH$_3$), (M-6781, Cl, H, F, i-Bu, H), (M-6782, Cl, H, F, i-Bu, Cl), (M-6783, Cl, H, F, i-Bu, F), (M-6784, Cl, H, F, i-Bu, CF$_3$), (M-6785, Cl, H, F, i-Bu, Br), (M-6786, Cl, H, F, i-Bu, CH$_3$), (M-6787, Cl, H, F, sec-Bu, H), (M-6788, Cl, H, F, sec-Bu, Cl), (M-6789, Cl, H, F, sec-Bu, F), (M-6790, Cl, H, F, sec-Bu, CF$_3$), (M-6791, Cl, H, F, sec-Bu, Br), (M-6792, Cl, H, F, sec-Bu, CH$_3$), (M-6793, MeO, H, F, n-Pen, H), (M-6794, Cl, H, F, n-Pen, Cl), (M-6795, MeO, H, F, n-Pen, F), (M-6796, Cl, H, F, n-Pen, CF$_3$), (M-6797, Cl, H, F, n-Pen, Br), (M-6798, Cl, H, F, n-Pen, CH$_3$), (M-6799, Cl, H, F, c-Pen, H), (M-6800, Cl, H, F, c-Pen, Cl), (M-6801, Cl, H, F, c-Pen, F), (M-6802, Cl, H, F, c-Pen, CF$_3$), (M-6803, Cl, H, F, c-Pen, Br), (M-6804, Cl, H, F, c-Pen, CH$_3$), (M-6805, MeO, H, F, n-Hex, H), (M-6806, Cl, H, F, n-Hex, Cl), (M-6807, Cl, H, F, n-Hex, F), (M-6808, Cl, H, F, n-Hex, CF$_3$), (M-6809, Cl, H, F, n-Hex, Br), (M-6810, Cl, H, F, n-Hex, CH$_3$), (M-6811, MeO, H, F, c-Hex, H), (M-6812, Cl, H, F, c-Hex, Cl), (M-6813, Cl, H, F, c-Hex, F), (M-6814, Cl, H, F, c-Hex, CF$_3$), (M-6815, Cl, H, F, c-Hex, Br), (M-6816, Cl, H, F, c-Hex, CH$_3$), (M-6817, Cl, H, F, OH, H), (M-6818, Cl, H, F, OH, Cl), (M-6819, Cl, H, F, OH, F), (M-6820, Cl, H, F, OH, CF$_3$), (M-6821, Cl, H, F, OH, Br), (M-6822, Cl, H, F, OH, CH$_3$), (M-6823, MeO, H, F, EtO, H), (M-6824, Cl, H, F, EtO, Cl), (M-6825, Cl, H, F, EtO, F), (M-6826, Cl, H, F, EtO, CF$_3$), (M-6827, Cl, H, F, EtO, Br), (M-6828, Cl, H, F, EtO, CH$_3$), (M-6829, Cl, H, F, n-PrO, H), (M-6830, Cl, H, F, n-PrO, Cl), (M-6831, Cl, H, F, n-PrO, F), (M-6832, Cl, H, F, n-PrO, CF$_3$), (M-6833, Cl, H, F, n-PrO, Br), (M-6834, Cl, H, F, n-PrO, CH$_3$), (M-6835, Cl, H, F, PhO, H), (M-6836, Cl, H, F, PhO, Cl), (M-6837, Cl, H, F, PhO, F), (M-6838, Cl, H, F, PhO, CF$_3$), (M-6839, Cl, H, F, PhO, Br), (M-6840, Cl, H, F, PhO, CH$_3$), (M-6841, Cl, H, F, BnO, H), (M-6842, Cl, H, F, BnO, Cl), (M-6843, Cl, H, F, BnO, F), (M-6844, Cl, H, F, BnO, CF$_3$), (M-6845, Cl, H, F, BnO, Br), (M-6846, Cl, H, F, BnO, CH$_3$), (M-6847, Cl, H, F, PhCH$_2$CH$_2$O, H), (M-6848, Cl, H, F, PhCH$_2$CH$_2$O, Cl), (M-6849, Cl, H, F, PhCH$_2$CH$_2$O, F), (M-6850, Cl, H, F, PhCH$_2$CH$_2$O, CF$_3$), (M-6851, Cl, H, F, PhCH$_2$CH$_2$O, Br), (M-6852, Cl, H, F, PhCH$_2$CH$_2$O, CH$_3$), (M-6853, Cl, H, F, CF$_3$O, H), (M-6854, Cl, H, F, CF$_3$O, Cl), (M-6855, Cl, H, F, CF$_3$O, F), (M-6856, Cl, H, F, CF$_3$O, CF$_3$), (M-6857, Cl, H, F, CF$_3$O, Br), (M-6858, Cl, H, F, CF$_3$O, CH$_3$), (M-6859, MeO, H, F, Ph, H), (M-6860, Cl, H, F, Ph, Cl), (M-6861, MeO, H, F, Ph, F), (M-6862, Cl, H, F, Ph, CF$_3$), (M-6863, Cl, H, F, Ph, Br), (M-6864, Cl, H, F, Ph, CH$_3$), (M-6865, MeO, H, F, 4-F-Ph, H), (M-6866, Cl, H, F, 4-F-Ph, Cl), (M-6867, Cl, H, F, 4-F-Ph, F), (M-6868, Cl, H, F, 4-F-Ph, CF$_3$), (M-6869, Cl, H, F, 4-F-Ph, Br), (M-6870, Cl, H, F, 4-F-Ph, CH$_3$), (M-6871, Cl, H, F, 4-CF$_3$-Ph, H), (M-6872, Cl, H, F, 4-CF$_3$-Ph, Cl), (M-6873, Cl, H, F, 4-CF₃-Ph, F), (M-6874, Cl, H, F, 4-CF₃-Ph, CF₃), (M-6875, Cl, H, F, 4-CF₃-Ph, Br), (M-6876, Cl, H, F, 4-CF₃-Ph, CH₃), (M-6877, Cl, H, F, 4-(Me)₂N-Ph, H), (M-6878, Cl, H, F, 4-(Me)₂N-Ph, Cl), (M-6879, Cl, H, F, 4-(Me)₂N-Ph, F), (M-6880, Cl, H, F, 4-(Me)₂N-Ph, CF₃), (M-6881, Cl, H, F, 4-(Me)₂N-Ph, Br), (M-6882, Cl, H, F, 4-(Me)₂N-Ph, CH₃), (M-6883, Cl, H, F, 4-OH-Ph, H), (M-6884, Cl, H, F, 4-OH-Ph, Cl), (M-6885, Cl, H, F, 4-OH-Ph, F), (M-6886, Cl, H, F, 4-OH-Ph, CF₃), (M-6887, Cl, H, F, 4-OH-Ph, Br), (M-6888, Cl, H, F, 4-OH-Ph, CH₃), (M-6889, Cl, H, F, 3,4-di-F-Ph, H), (M-6890, Cl, H, F, 3,4-di-F-Ph, Cl), (M-6891, Cl, H, F, 3,4-di-F-Ph, F), (M-6892, Cl, H, F, 3,4-di-F-Ph, CF₃), (M-6893, Cl, H, F, 3,4-di-F-Ph, Br), (M-6894, Cl, H, F, 3,4-di-F-Ph, CH₃), (M-6895, Cl, H, F, 4-COOH-Ph, H), (M-6896, Cl, H, F, 4-COOH-Ph, Cl), (M-6897, Cl, H, F, 4-COOH-Ph, F), (M-6898, Cl, H, F, 4-COOH-Ph, CF₃), (M-6899, Cl, H, F, 4-COOH-Ph, Br), (M-6900, Cl, H, F, 4-COOH-Ph, CH₃), (M-6901, MeO, H, F, Bn, H), (M-6902, Cl, H, F, Bn, Cl), (M-6903, Cl, H, F, Bn, F), (M-6904, Cl, H, F, Bn, CF₃), (M-6905, Cl, H, F, Bn, Br), (M-6906, Cl, H, F, Bn, CH₃), (M-6907, Cl, H, F, 4-F-Bn, H), (M-6908, Cl, H, F, 4-F-Bn, Cl), (M-6909, Cl, H, F, 4-F-Bn, F), (M-6910, Cl, H, F, 4-F-Bn, CF₃), (M-6911, Cl, H, F, 4-F-Bn, Br), (M-6912, Cl, H, F, 4-F-Bn, CH₃), (M-6913, Cl, H, F, 2-Py, H), (M-6914, Cl, H, F, 2-Py, Cl), (M-6915, Cl, H, F, 2-Py, F), (M-6916, Cl, H, F, 2-Py, CF₃), (M-6917, Cl, H, F, 2-Py, Br), (M-6918, Cl, H, F, 2-Py, CH₃), (M-6919, MeO, H, F, 3-Py, H), (M-6920, Cl, H, F, 3-Py, Cl), (M-6921, Cl, H, F, 3-Py, F), (M-6922, Cl, H, F, 3-Py, CF₃), (M-6923, Cl, H, F, 3-Py, Br), (M-6924, Cl, H, F, 3-Py, CH₃), (M-6925, Cl, H, F, 4-Py, H), (M-6926, Cl, H, F, 4-Py, Cl), (M-6927, Cl, H, F, 4-Py, F), (M-6928, Cl, H, F, 4-Py, CF₃), (M-6929, Cl, H, F, 4-Py, Br), (M-6930, Cl, H, F, 4-Py, CH₃), (M-6931, Cl, H, F, 2-Th, H), (M-6932, Cl, H, F, 2-Th, Cl), (M-6933, Cl, H, F, 2-Th, F), (M-6934, Cl, H, F, 2-Th, CF₃), (M-6935, Cl, H, F, 2-Th, Br), (M-6936, Cl, H, F, 2-Th, CH₃), (M-6937, Cl, H, F, 3-Th, H), (M-6938, Cl, H, F, 3-Th, Cl), (M-6939, Cl, H, F, 3-Th, F), (M-6940, Cl, H, F, 3-Th, CF₃), (M-6941, Cl, H, F, 3-Th, Br), (M-6942, Cl, H, F, 3-Th, CH₃), (M-6943, Cl, H, F, pyrrazol-2-yl, H), (M-6944, Cl, H, F, pyrrazol-2-yl, Cl), (M-6945, Cl, H, F, pyrrazol-2-yl, F), (M-6946, Cl, H, F, pyrrazol-2-yl, CF₃), (M-6947, Cl, H, F, pyrrazol-2-yl, Br), (M-6948, Cl, H, F, pyrrazol-2-yl, CH₃), (M-6949, Cl, H, F, pyrrazol-3-yl, H), (M-6950, Cl, H, F, pyrrazol-3-yl, Cl), (M-6951, Cl, H, F, pyrrazol-3-yl, F), (M-6952, Cl, H, F, pyrrazol-3-yl, CF₃), (M-6953, Cl, H, F, pyrrazol-3-yl, Br), (M-6954, Cl, H, F, pyrrazol-3-yl, CH₃), (M-6955, Cl, H, F, pyrimidin-2-yl, H), (M-6956, Cl, H, F, pyrimidin-2-yl, Cl), (M-6957, Cl, H, F, pyrimidin-2-yl, F), (M-6958, Cl, H, F, pyrimidin-2-yl, CF₃), (M-6959, Cl, H, F, pyrimidin-2-yl, Br), (M-6960, Cl, H, F, pyrimidin-2-yl, CH₃), (M-6961, Cl, H, F, pyrimidin-4-yl, H), (M-6962, Cl, H, F, pyrimidin-4-yl, Cl), (M-6963, Cl, H, F, pyrimidin-4-yl, F), (M-6964, Cl, H, F, pyrimidin-4-yl, CF₃), (M-6965, Cl, H, F, pyrimidin-4-yl, Br), (M-6966, Cl, H, F, pyrimidin-4yl, CH₃), (M-6967, Cl, H, F, pyrimidin-5-yl, H), (M-6968, Cl, H, F, pyrimidin-5-yl, Cl), (M-6969, Cl, H, F, pyrimidin-5-yl, F), (M-6970, Cl, H, F, pyrimidin-5-yl, CF₃), (M-6971, Cl, H, F, pyrimidin-5-yl, Br), (M-6972, Cl, H, F, pyrimidin-5-yl, CH₃), (M-6973, Cl, H, F, HOOCCH₂CH₂CH₂, H), (M-6974, Cl, H, F, HOOCCH₂CH₂CH₂, Cl), (M-6975, Cl, H, F, HOOCCH₂CH₂CH₂, F), (M-6976, Cl, H, F, HOOCCH₂CH₂CH₂, CF₃), (M-6977, Cl, H, F, HOOCCH₂CH₂CH₂, Br), (M-6978, Cl, H, F, HOOCCH₂CH₂CH₂, CH₃), (M-6979, Cl, H, F, HOOCCH₂CH₂CH₂CH₂, H), (M-6980, Cl, H, F, HOOCCH₂CH₂CH₂CH₂, Cl), (M-6981, Cl, H, F, HOOCCH₂CH₂CH₂CH₂, F), (M-6982, Cl, H, F, HOOCCH₂CH₂CH₂CH₂, CF₃), (M-6983, Cl, H, F, HOOCCH₂CH₂CH₂CH₂, Br), (M-6984, Cl, H, F, HOOCCH₂CH₂CH₂CH₂, CH₃), (M-6985, Cl, H, F, (Me)₂NCOCH₂CH₂CH₂CH₂, H), (M-6986, Cl, H, F, (Me)₂NCOCH₂CH₂CH₂CH₂, Cl), (M-6987, Cl, H, F, (Me)₂NCOCH₂CH₂CH₂CH₂, F), (M-6988, Cl, H, F, (Me)₂NCOCH₂CH₂CH₂CH₂, CF₃), (M-6989, Cl, H, F, (Me)₂NCOCH₂CH₂CH₂CH₂, Br), (M-6990, Cl, H, F, (Me)₂NCOCH₂CH₂CH₂CH₂, CH₃), (M-6991, Cl, H, F, (Me)₂NCOCH₂CH₂CH₂CH₂CH₂, H), (M-6992, Cl, H, F, (Me)₂NCOCH₂CH₂CH₂CH₂CH₂, Cl), (M-6993, Cl, H, F, (Me)₂NCOCH₂CH₂CH₂CH₂CH₂, F), (M-6994, Cl, H, F, (Me)₂NCOCH₂CH₂CH₂CH₂CH₂, CF₃), (M-6995, Cl, H, F, (Me)₂NCOCH₂CH₂CH₂CH₂CH₂, Br), (M-6996, Cl, H, F, (Me)₂NCOCH₂CH₂CH₂CH₂CH₂, CH₃), (M-6997, Cl, H, F, MeOCH₂, H), (M-6998, Cl, H, F, MeOCH₂, Cl), (M-6999, Cl, H, F, MeOCH₂, F), (M-7000, Cl, H, F, MeOCH₂, CF₃), (M-7001, Cl, H, F, MeOCH₂, Br), (M-7002, Cl, H, F, MeOCH₂, CH₃), (M-7003, Cl, H, F, EtOCH₂, H), (M-7004, Cl, H, F, EtOCH₂, Cl), (M-7005, Cl, H, F, EtOCH₂, F), (M-7006, Cl, H, F, EtOCH₂, CF₃), (M-7007, Cl, H, F, EtOCH₂, Br), (M-7008, Cl, H, F, EtOCH₂, CH₃), (M-7009, MeO, H, F, EtOCH₂CH₂, H), (M-7010, Cl, H, F, EtOCH₂CH₂, Cl), (M-7011, Cl, H, F, EtOCH₂CH₂, F), (M-7012, Cl, H, F, EtOCH₂CH₂, CF₃), (M-7013, Cl, H, F, EtOCH₂CH₂, Br), (M-7014, Cl, H, F, EtOCH₂CH₂, CH₃), (M-7015, Cl, H, F, MeOCH₂CH₂OCH₂CH₂, H), (M-7016, Cl, H, F, MeOCH₂CH₂OCH₂CH₂, Cl), (M-7017, Cl, H, F, MeOCH₂CH₂OCH₂CH₂, F), (M-7018, Cl, H, F, MeOCH₂CH₂OCH₂CH₂, CF₃), (M-7019, Cl, H, F, MeOCH₂CH₂OCH₂CH₂, Br), (M-7020, Cl, H, F, MeOCH₂CH₂OCH₂CH₂, CH₃), (M-7021, Cl, H, F, MeOCH₂CH₂, H), (M-7022, Cl, H, F, MeOCH₂CH₂, Cl), (M-7023, Cl, H, F, MeOCH₂CH₂, F), (M-7024, Cl, H, F, MeOCH₂CH₂, CF₃), (M-7025, Cl, H, F, MeOCH₂CH₂, Br), (M-7026, Cl, H, F, MeOCH₂CH₂, CH₃), (M-7027, Cl, H, F, HOCH₂, H), (M-7028, Cl, H, F, HOCH₂, Cl), (M-7029, Cl, H, F, HOCH₂, F), (M-7030, Cl, H, F, HOCH₂, CF₃), (M-7031, Cl, H, F, HOCH₂, Br), (M-7032, Cl, H, F, HOCH₂, CH₃), (M-7033, Cl, H, F, HOCH₂CH₂, H), (M-7034, Cl, H, F, HOCH₂CH₂, Cl), (M-7035, Cl, H, F, HOCH₂CH₂, F), (M-7036, Cl, H, F, HOCH₂CH₂, CF₃), (M-7037, Cl, H, F, HOCH₂CH₂, Br), (M-7038, Cl, H, F, HOCH₂CH₂, CH₃), (M-7039, Cl, H, F, HOCH₂CH₂CH₂, H), (M-7040, Cl, H, F, HOCH₂CH₂CH₂, Cl), (M-7041, Cl, H, F, HOCH₂CH₂CH₂, F), (M-7042, Cl, H, F, HOCH₂CH₂CH₂, CF₃), (M-7043, Cl, H, F, HOCH₂CH₂CH₂, Br), (M-7044, Cl, H, F, HOCH₂CH₂CH₂, CH₃), (M-7045, Cl, H, F, HOCH₂CH₂CH₂CH₂, H), (M-7046, Cl, H, F, HOCH₂CH₂CH₂CH₂, Cl), (M-7047, Cl, H, F, HOCH₂CH₂CH₂CH₂, F), (M-7048, Cl, H, F, HOCH₂CH₂CH₂CH₂, CF₃), (M-7049, Cl, H, F, HOCH₂CH₂CH₂CH₂, Br), (M-7050, Cl, H, F, HOCH₂CH₂CH₂CH₂, CH₃), (M-7051, Cl, H, F, HOCH₂CH₂CH₂CH₂CH₂, H), (M-7052, Cl, H, F, HOCH₂CH₂CH₂CH₂CH₂, Cl), (M-7053, Cl, H, F, HOCH₂CH₂CH₂CH₂CH₂, F), (M-7054, Cl, H, F, HOCH₂CH₂CH₂CH₂CH₂, CF₃), (M-7055, Cl, H, F, HOCH₂CH₂CH₂CH₂CH₂Br), (M-7056, Cl, H, F, HOCH₂CH₂CH₂CH₂CH₂, CH₃), (M-7057, Cl, H, F, HOCH₂CH₂OCH₂CH₂, H), (M-7058, Cl, H, F, HOCH₂CH₂OCH₂CH₂, Cl), (M-7059, Cl, H, F, HOCH₂CH₂OCH₂CH₂, F), (M-7060, Cl, H, F, HOCH₂CH₂OCH₂CH₂, CF₃), (M-7061, Cl, H, F, HOCH₂CH₂OCH₂CH₂, Br), (M-7062, Cl, H, F, HOCH₂CH₂OCH₂CH₂, CH₃), (M-7063, Cl, H, F, (Me)₂N, H), (M-7064, Cl, H, F, (Me)₂N, Cl), (M-7065, Cl, H, F, (Me)₂N, F), (M-7066, Cl, H, F, (Me)₂N, CF₃), (M-7067, Cl, H, F, (Me)₂N, Br), (M-7068, Cl, H, F, (Me)₂N, CH₃), (M-7069, Cl, H, F, piperidin-4-yl-methyl, H), (M-7070, Cl, H, F, piperidin-4-yl-methyl, Cl), (M-7071, Cl, H, F, piperidin-4-yl-methyl, F), (M-7072, Cl, H, F, piperidin-4-yl-methyl, CF₃), (M-7073, Cl, H, F, piperidin-4-yl-methyl, Br), (M-7074, Cl, H, F, piperidin-4-yl-methyl, CH₃), (M-7075, Cl, H, F, cyclohexylmethyl, H), (M-7076, Cl, H, F, cyclohexylmethyl, Cl), (M-7077, Cl, H, F, cyclohexylmethyl, F), (M-7078, Cl, H, F, cyclohexylmethyl, CF₃), (M-7079, Cl, H, F, cyclohexylmethyl, Br), (M-7080, Cl, H, F, cyclohexylmethyl, CH₃), (M-7081, Cl, H, Cl, H, H), (M-7082, Cl, H, Cl, H, Cl), (M-7083, Cl, H, Cl, H, F), (M-7084, Cl, H, Cl, H, CF₃), (M-7085, Cl, H, Cl, H, Br), (M-7086, Cl, H, Cl, H, CH₃), (M-7087, Cl, H, Cl, F, H), (M-7088, Cl, H, Cl, F, Cl), (M-7089, Cl, H, Cl, F, F), (M-7090, Cl, H, Cl, F, CF₃), (M-7091, Cl, H, Cl, F, Br), (M-7092, Cl, H, Cl, F, CH₃), (M-7093, MeO, H, Cl, Cl, H), (M-7094, Cl, H, Cl, Cl, Cl), (M-7095, Cl, H, Cl, Cl, F), (M-7096, Cl, H, Cl, Cl, CF₃), (M-7097, Cl, H, Cl, Cl, Br), (M-7098, Cl, H, Cl, Cl, CH₃), (M-7099, Cl, H, Cl, CH₃, H), (M-7100, Cl, H, Cl, CH₃, Cl), (M-7101, Cl, H, Cl, CH₃, F), (M-7102, Cl, H, Cl, CH₃, CF₃), (M-7103, Cl, H, Cl, CH₃, Br), (M-7104, Cl, H, Cl, CH₃, CH₃), (M-7105, Cl, H, Cl, Et, H), (M-7106, Cl, H, Cl, Et, Cl), (M-7107, Cl, H, Cl, Et, F), (M-7108, Cl, H, Cl, Et, CF₃), (M-7109, Cl, H, Cl, Et, Br), (M-7110, Cl, H, Cl, Et, CH₃), (M-7111, Cl, H, Cl, n-Pr, H), (M-7112, Cl, H, Cl, n-Pr, Cl), (M-7113, Cl, H, Cl, n-Pr, F), (M-7114, Cl, H, Cl, n-Pr, CF₃), (M-7115, Cl, H, Cl, n-Pr, Br), (M-7116, Cl, H, Cl, n-Pr, CH₃), (M-7117, Cl, H, Cl, c-Pr, H), (M-7118, Cl, H, Cl, c-Pr, Cl), (M-7119, Cl, H, Cl, c-Pr, F), (M-7120, Cl, H, Cl, c-Pr, CF₃), (M-7121, Cl, H, Cl, c-Pr, Br), (M-7122, Cl, H, Cl, c-Pr, CH₃), (M-7123, Cl, H, Cl, i-Pr, H), (M-7124, Cl, H, Cl, i-Pr, Cl), (M-7125, Cl, H, Cl, i-Pr, F), (M-7126, Cl, H, Cl, i-Pr, CF₃), (M-7127, Cl, H, Cl, i-Pr, Br), (M-7128, Cl, H, Cl, i-Pr, CH₃), (M-7129, Cl, H, Cl, n-Bu, H), (M-7130, Cl, H, Cl, n-Bu, Cl), (M-7131, Cl, H, Cl, n-Bu, F), (M-7132, Cl, H, Cl, n-Bu, CF₃), (M-7133, Cl, H, Cl, n-Bu, Br), (M-7134, Cl, H, Cl, n-Bu, CH₃), (M-7135, Cl, H, Cl, i-Bu, H), (M-7136, Cl, H, Cl, i-Bu, Cl), (M-7137, Cl, H, Cl, i-Bu, F), (M-7138, Cl, H, Cl, i-Bu, CF₃), (M-7139, Cl, H, Cl, i-Bu, Br), (M-7140, Cl, H, Cl, i-Bu, CH₃), (M-7141, Cl, H, Cl, sec-Bu, H), (M-7142, Cl, H, Cl, sec-Bu, Cl), (M-7143, Cl, H, Cl, sec-Bu, F), (M-7144, Cl, H, Cl, sec-Bu, CF₃), (M-7145, Cl, H, Cl, sec-Bu, Br), (M-7146, Cl, H, Cl, sec-Bu, CH₃), (M-7147, Cl, H, Cl, n-Pen, H), (M-7148, Cl, H, Cl, n-Pen, Cl), (M-7149, Cl, H, Cl, n-Pen, F), (M-7150, Cl, H, Cl, n-Pen, CF₃), (M-7151, Cl, H, Cl, n-Pen, Br), (M-7152, Cl, H, Cl, n-Pen, CH₃), (M-7153, Cl, H, Cl, c-Pen, H), (M-7154, Cl, H, Cl, c-Pen, Cl), (M-7155, Cl, H, Cl, c-Pen, F), (M-7156, Cl, H, Cl, c-Pen, CF₃), (M-7157, Cl, H, Cl, c-Pen, Br), (M-7158, Cl, H, Cl, c-Pen, CH₃), (M-7159, Cl, H, Cl, n-Hex, H), (M-7160, Cl, H, Cl, n-Hex, Cl), (M-7161, Cl, H, Cl, n-Hex, F), (M-7162, Cl, H, Cl, n-Hex, CF₃), (M-7163, Cl, H, Cl, n-Hex, Br), (M-7164, Cl, H, Cl, n-Hex, CH₃), (M-7165, Cl, H, Cl, c-Hex, H), (M-7166, Cl, H, Cl, c-Hex, Cl), (M-7167, Cl, H, Cl, c-Hex, F), (M-7168, Cl, H, Cl, c-Hex, CF₃), (M-7169, Cl, H, Cl, c-Hex, Br), (M-7170, Cl, H, Cl, c-Hex, CH₃), (M-7171, Cl, H, Cl, OH, H), (M-7172, Cl, H, Cl, OH, Cl), (M-7173, Cl, H, Cl, OH, F), (M-7174, Cl, H, Cl, OH, CF₃), (M-7175, Cl, H, Cl, OH, Br), (M-7176, Cl, H, Cl, OH, CH₃), (M-7177, Cl, H, Cl, EtO, H), (M-7178, Cl, H, Cl, EtO, Cl), (M-7179, Cl, H, Cl, EtO, F), (M-7180, Cl, H, Cl, EtO, CF₃), (M-7181, Cl, H, Cl, EtO, Br), (M-7182, Cl, H, Cl, EtO, CH₃), (M-7183, Cl, H, Cl, n-PrO, H), (M-7184, Cl, H, Cl, n-PrO, Cl), (M-7185, Cl, H, Cl, n-PrO, F), (M-7186, Cl, H, Cl, n-PrO, CF₃), (M-7187, Cl, H, Cl, n-PrO, Br), (M-7188, Cl, H, Cl, n-PrO, CH₃), (M-7189, Cl, H, Cl, PhO, H), (M-7190, Cl, H, Cl, PhO, Cl), (M-7191, Cl, H, Cl, PhO, F), (M-7192, Cl, H, Cl, PhO, CF₃), (M-7193, Cl, H, Cl, PhO, Br), (M-7194, Cl, H, Cl, PhO, CH₃), (M-7195, Cl, H, Cl, BnO, H), (M-7196, Cl, H, Cl, BnO, Cl), (M-7197, Cl, H, Cl, BnO, F), (M-7198, Cl, H, Cl, BnO, CF₃), (M-7199, Cl, H, Cl, BnO, Br), (M-7200, Cl, H, Cl, BnO, CH₃), (M-7201, Cl, H, Cl, PhCH₂CH₂O, H), (M-7202, Cl, H, Cl, PhCH₂CH₂O, Cl), (M-7203, Cl, H, Cl, PhCH₂CH₂O, F), (M-7204, Cl, H, Cl, PhCH₂CH₂O, CF₃), (M-7205, Cl, H, Cl, PhCH₂CH₂O, Br), (M-7206, Cl, H, Cl, PhCH₂CH₂O, CH₃), (M-7207, Cl, H, Cl, CF₃O, H), (M-7208, Cl, H, Cl, CF₃O, Cl), (M-7209, Cl, H, Cl, CF₃O, F), (M-7210, Cl, H, Cl, CF₃O, CF₃), (M-7211, Cl, H, Cl, CF₃O, Br), (M-7212, Cl, H, Cl, CF₃O, CH₃), (M-7213, Cl, H, Cl, Ph, H), (M-7214, Cl, H, Cl, Ph, Cl), (M-7215, Cl, H, Cl, Ph, F), (M-7216, Cl, H, Cl, Ph, CF₃), (M-7217, Cl, H, Cl, Ph, Br), (M-7218, Cl, H, Cl, Ph, CH₃), (M-7219, Cl, H, Cl, 4-F-Ph, H), (M-7220, Cl, H, Cl, 4-F-Ph, Cl), (M-7221, Cl, H, Cl, 4-F-Ph, F), (M-7222, Cl, H, Cl, 4-F-Ph, CF₃), (M-7223, Cl, H, Cl, 4-F-Ph, Br), (M-7224, Cl, H, Cl, 4-F-Ph, CH₃), (M-7225, Cl, H, Cl, 4-CF₃-Ph, H), (M-7226, Cl, H, Cl, 4-CF₃-Ph, Cl), (M-7227, Cl, H, Cl, 4-CF₃-Ph, F), (M-7228, Cl, H, Cl, 4-CF₃-Ph, CF₃), (M-7229, Cl, H, Cl, 4-CF₃-Ph, Br), (M-7230, Cl, H, Cl, 4-CF₃-Ph, CH₃), (M-7231, Cl, H, Cl, 4-(Me)₂N-Ph, H), (M-7232, Cl, H, Cl, 4-(Me)₂N-Ph, Cl), (M-7233, Cl, H, Cl, 4-(Me)₂N-Ph, F), (M-7234, Cl, H, Cl, 4-(Me)₂N-Ph, CF₃), (M-7235, Cl, H, Cl, 4-(Me)₂N-Ph, Br), (M-7236, Cl, H, Cl, 4-(Me)₂N-Ph, CH₃), (M-7237, Cl, H, Cl, 4-OH-Ph, H), (M-7238, Cl, H, Cl, 4-OH-Ph, Cl), (M-7239, Cl, H, Cl, 4-OH-Ph, F), (M-7240, Cl, H, Cl, 4-OH-Ph, CF₃), (M-7241, Cl, H, Cl, 4-OH-Ph, Br), (M-7242, Cl, H, Cl, 4-OH-Ph, CH₃), (M-7243, Cl, H, Cl, 3,4-di-F-Ph, H), (M-7244, Cl, H, Cl, 3,4-di-F-Ph, Cl), (M-7245, Cl, H, Cl, 3,4-di-F-Ph, F), (M-7246, Cl, H, Cl, 3,4-di-F-Ph, CF₃), (M-7247, Cl, H, Cl, 3,4-di-F-Ph, Br), (M-7248, Cl, H, Cl, 3,4-di-F-Ph, CH₃), (M-7249, Cl, H, Cl, 4-COOH-Ph, H), (M-7250, Cl, H, Cl, 4-COOH-Ph, Cl), (M-7251, Cl, H, Cl, 4-COOH-Ph, F), (M-7252, Cl, H, Cl, 4-COOH-Ph, CF₃), (M-7253, Cl, H, Cl, 4-COOH-Ph, Br), (M-7254, Cl, H, Cl, 4-COOH-Ph, CH₃), (M-7255, Cl, H, Cl, Bn, H), (M-7256, Cl, H, Cl, Bn, Cl), (M-7257, Cl, H, Cl, Bn, F), (M-7258, Cl, H, Cl, Bn, CF₃), (M-7259, Cl, H, Cl, Bn, Br), (M-7260, Cl, H, Cl, Bn, CH₃), (M-7261, Cl, H, Cl, 4-F-Bn, H), (M-7262, Cl, H, Cl, 4-F-Bn, Cl), (M-7263, Cl, H, Cl, 4-F-Bn, F), (M-7264, Cl, H, Cl, 4-F-Bn, CF₃), (M-7265, Cl, H, Cl, 4-F-Bn, Br), (M-7266, Cl, H, Cl, 4-F-Bn, CH₃), (M-7267, Cl, H, Cl, 2-Py, H), (M-7268, Cl, H, Cl, 2-Py, Cl), (M-7269, Cl, H, Cl, 2-Py, F), (M-7270, Cl, H, Cl, 2-Py, CF₃), (M-7271, Cl, H, Cl, 2-Py, Br), (M-7272, Cl, H, Cl, 2-Py, CH₃), (M-7273, Cl, H, Cl, 3-Py, H), (M-7274, Cl, H, Cl, 3-Py, Cl), (M-7275, Cl, H, Cl, 3-Py, F), (M-7276, Cl, H, Cl, 3-Py, CF₃), (M-7277, Cl, H, Cl, 3-Py, Br), (M-7278, Cl, H, Cl, 3-Py, CH₃), (M-7279, Cl, H, Cl, 4-Py, H), (M-7280, Cl, H, Cl, 4-Py, Cl), (M-7281, Cl, H, Cl, 4-Py, F), (M-7282, Cl, H, Cl, 4-Py, CF₃), (M-7283, Cl, H, Cl, 4-Py, Br), (M-7284, Cl, H, Cl, 4-Py, CH₃), (M-7285, Cl, H, Cl, 2-Th, H), (M-7286, Cl, H, Cl, 2-Th, Cl), (M-7287, Cl, H, Cl, 2-Th, F), (M-7288, Cl, H, Cl, 2-Th, CF₃), (M-7289, Cl, H, Cl, 2-Th, Br), (M-7290, Cl, H, Cl, 2-Th, CH₃), (M-7291, Cl, H, Cl, 3-Th, H), (M-7292, Cl, H, Cl, 3-Th, Cl), (M-7293, Cl, H, Cl, 3-Th, F), (M-7294, Cl, H, Cl, 3-Th, CF₃), (M-7295, Cl, H, Cl, 3-Th, Br), (M-7296, Cl, H, Cl, 3-Th, CH₃), (M-7297, Cl, H, Cl, pyrrazol-2-yl, H), (M-7298, Cl, H, Cl, pyrrazol-2-yl, Cl), (M-7299, Cl, H, Cl, pyrrazol-2-yl, F), (M-7300, Cl, H, Cl, pyrrazol-2-yl, CF₃), (M-7301, Cl, H, Cl, pyrrazol-2-yl, Br), (M-7302, Cl, H, Cl, pyrrazol-2-yl, CH₃), (M-7303, Cl, H, Cl, pyrrazol-3-yl, H), (M-7304, Cl, H, Cl, pyrrazol-3-yl, Cl), (M-7305, Cl, H, Cl, pyrrazol-3-yl, F), (M-7306, Cl, H, Cl, pyrrazol-3-yl, CF₃), (M-7307, Cl, H, Cl, pyrrazol-3-yl, Br), (M-7308, Cl, H, Cl, pyrrazol-3-yl, CH₃), (M-7309, Cl, H, Cl, pyrimidin-2-yl, H), (M-7310, Cl, H, Cl, pyrimidin-2-yl, Cl), (M-7311, Cl, H, Cl, pyrimidin-2-yl, F), (M-7312, Cl, H, Cl, pyrimidin-2-yl, CF₃), (M-7313, Cl, H, Cl, pyrimidin-2-yl, Br), (M-7314, Cl, H, Cl, pyrimidin-2-yl, CH₃), (M-7315, Cl, H, Cl, pyrimidin-4-yl, H), (M-7316, Cl, H, Cl, pyrimidin-4-yl, Cl), (M-7317, Cl, H, Cl, pyrimidin-4-yl, F), (M-7318, Cl, H, Cl, pyrimidin-4-yl, CF₃), (M-7319, Cl, H, Cl, pyrimidin-4-yl, Br), (M-7320, Cl, H, Cl, pyrimidin-4-yl, CH₃), (M-7321, Cl, H, Cl, pyrimidin-5-yl, H), (M-7322, Cl, H, Cl, pyrimidin-5-yl, Cl), (M-7323, Cl, H, Cl, pyrimidin-5-yl, F), (M-7324, Cl, H, Cl, pyrimidin-5-yl, CF₃), (M-7325, Cl, H, Cl, pyrimidin-5-yl, Br), (M-7326, Cl, H, Cl, pyrimidin-5-yl, CH₃), (M-7327, Cl, H, Cl, HOOCCH₂CH₂CH₂, H), (M-7328, Cl, H, Cl, HOOCCH₂CH₂CH₂, Cl), (M-7329, Cl, H, Cl, HOOCCH₂CH₂CH₂, F), (M-7330, Cl, H, Cl, HOOCCH₂CH₂CH₂, CF₃), (M-7331, Cl, H, Cl, HOOCCH₂CH₂CH₂, Br), (M-7332, Cl, H, Cl, HOOCCH₂CH₂CH₂, CH₃), (M-7333, Cl, H, Cl, HOOCCH₂CH₂CH₂CH₂, H), (M-7334, Cl, H, Cl, HOOCCH₂CH₂CH₂CH₂, Cl), (M-7335, Cl, H, Cl, HOOCCH₂CH₂CH₂CH₂, F), (M-7336, Cl, H, Cl, HOOCCH₂CH₂CH₂CH₂, CF₃), (M-7337, Cl, H, Cl, HOOCCH₂CH₂CH₂CH₂, Br), (M-7338, Cl, H, Cl, HOOCCH₂CH₂CH₂CH₂, CH₃), (M-7339, Cl, H, Cl, (Me)₂NCOCH₂CH₂CH₂, H), (M-7340, Cl, H, Cl, (Me)₂NCOCH₂CH₂CH₂, Cl), (M-7341, Cl, H, Cl, (Me)₂NCOCH₂CH₂CH₂, F), (M-7342, Cl, H, Cl, (Me)₂NCOCH₂CH₂CH₂, CF₃), (M-7343, Cl, H, Cl, (Me)₂NCOCH₂CH₂CH₂, Br), (M-7344, Cl, H, Cl, (Me)₂NCOCH₂CH₂CH₂, CH₃), (M-7345, Cl, H, Cl, (Me)₂NCOCH₂CH₂CH₂CH₂, H), (M-7346, Cl, H, Cl, (Me)₂NCOCH₂CH₂CH₂CH₂, Cl), (M-7347, Cl, H, Cl, (Me)₂NCOCH₂CH₂CH₂CH₂, F), (M-7348, Cl, H, Cl, (Me)₂NCOCH₂CH₂CH₂CH₂, CF₃), (M-7349, Cl, H, Cl, (Me)₂NCOCH₂CH₂CH₂CH₂, Br), (M-7350, Cl, H, Cl, (Me)₂NCOCH₂CH₂CH₂CH₂, CH₃), (M-7351, Cl, H, Cl, MeOCH₂, H), (M-7352, Cl, H, Cl, MeOCH₂, Cl), (M-7353, Cl, H, Cl, MeOCH₂, F), (M-7354, Cl, H, Cl, MeOCH₂, CF₃), (M-7355, Cl, H, Cl, MeOCH₂, Br), (M-7356, Cl, H, Cl, MeOCH₂, CH₃), (M-7357, Cl, H, Cl, EtOCH₂, H), (M-7358, Cl, H, Cl, EtOCH₂, Cl), (M-7359, Cl, H, Cl, EtOCH₂, F), (M-7360, Cl, H, Cl, EtOCH₂, CF₃), (M-7361, Cl, H, Cl, EtOCH₂, Br), (M-7362, Cl, H, Cl, EtOCH₂, CH₃), (M-7363, Cl, H, Cl, EtOCH₂CH₂, H), (M-7364, Cl, H, Cl, EtOCH₂CH₂, Cl), (M-7365, Cl, H, Cl, EtOCH₂CH₂, F), (M-7366, Cl, H, Cl, EtOCH₂CH₂, CF₃), (M-7367, Cl, H, Cl, EtOCH₂CH₂, Br), (M-7368, Cl, H, Cl, EtOCH₂CH₂, CH₃), (M-7369, Cl, H, Cl, MeOCH₂CH₂OCH₂CH₂, H), (M-7370, Cl, H, Cl, MeOCH₂CH₂OCH₂CH₂, Cl), (M-7371, Cl, H, Cl, MeOCH₂CH₂OCH₂CH₂, F), (M-7372, Cl, H, Cl, MeOCH₂CH₂OCH₂CH₂, CF₃), (M-7373, Cl, H, Cl, MeOCH₂CH₂OCH₂CH₂, Br), (M-7374, Cl, H, Cl, MeOCH₂CH₂OCH₂CH₂, CH₃), (M-7375, Cl, H, Cl, MeOCH₂CH₂, H), (M-7376, Cl, H, Cl, MeOCH₂CH₂, Cl), (M-7377, Cl, H, Cl, MeOCH₂CH₂, F), (M-7378, Cl, H, Cl, MeOCH₂CH₂, CF₃), (M-7379, Cl, H, Cl, MeOCH₂CH₂, Br), (M-7380, Cl, H, Cl, MeOCH₂CH₂, CH₃), (M-7381, Cl, H, Cl, HOCH₂, H), (M-7382, Cl, H, Cl, HOCH₂, Cl), (M-7383, Cl, H, Cl, HOCH₂, F), (M-7384, Cl, H, Cl, HOCH₂, CF₃), (M-7385, Cl, H, Cl, HOCH₂, Br), (M-7386, Cl, H, Cl, HOCH₂, CH₃), (M-7387, Cl, H, Cl, HOCH₂CH₂, H), (M-7388, Cl, H, Cl, HOCH₂CH₂, Cl), (M-7389, Cl, H, Cl, HOCH₂CH₂, F), (M-7390, Cl, H, Cl, HOCH₂CH₂, CF₃), (M-7391, Cl, H, Cl, HOCH₂CH₂, Br), (M-7392, Cl, H, Cl, HOCH₂CH₂, CH₃), (M-7393, Cl, H, Cl, HOCH₂CH₂CH₂, H), (M-7394, Cl, H, Cl, HOCH₂CH₂CH₂, Cl), (M-7395, Cl, H, Cl, HOCH₂CH₂CH₂, F), (M-7396, Cl, H, Cl, HOCH₂CH₂CH₂, CF₃), (M-7397, Cl, H, Cl, HOCH₂CH₂CH₂, Br), (M-7398, Cl, H, Cl, HOCH₂CH₂CH₂, CH₃), (M-7399, Cl, H, Cl, HOCH₂CH₂CH₂CH₂, H), (M-7400, Cl, H, Cl, HOCH₂CH₂CH₂CH₂, Cl), (M-7401, Cl, H, Cl, HOCH₂CH₂CH₂CH₂, F), (M-7402, Cl, H, Cl, HOCH₂CH₂CH₂CH₂CF₃), (M-7403, Cl, H, Cl, HOCH₂CH₂CH₂CH₂, Br), (M-7404, Cl, H, Cl, HOCH₂CH₂CH₂CH₂, CH₃), (M-7405, Cl, H, Cl, HOCH₂CH₂CH₂CH₂CH₂, H), (M-7406, Cl, H, Cl, HOCH₂CH₂CH₂CH₂CH₂, Cl), (M-7407, Cl, H, Cl, HOCH₂CH₂CH₂CH₂CH₂, F), (M-7408, Cl, H, Cl, HOCH₂CH₂CH₂CH₂CH₂, CF₃), (M-7409, Cl, H, Cl, HOCH₂CH₂CH₂CH₂CH₂, Br), (M-7410, Cl, H, Cl, HOCH₂CH₂CH₂CH₂CH₂, CH₃), (M-7411, Cl, H, Cl, HOCH₂CH₂OCH₂CH₂, H), (M-7412, Cl, H, Cl, HOCH₂CH₂OCH₂CH₂, Cl), (M-7413, Cl, H, Cl, HOCH₂CH₂OCH₂CH₂, F), (M-7414, Cl, H, Cl, HOCH₂CH₂OCH₂CH₂, CF₃), (M-7415, Cl, H, Cl, HOCH₂CH₂OCH₂CH₂, Br), (M-7416, Cl, H, Cl, HOCH₂CH₂OCH₂CH₂, CH₃), (M-7417, Cl, H, Cl, (Me)₂N, H), (M-7418, Cl, H, Cl, (Me)₂N, Cl), (M-7419, Cl, H, Cl, (Me)₂N, F), (M-7420, Cl, H, Cl, (Me)₂N, CF₃), (M-7421, Cl, H, Cl, (Me)₂N, Br), (M-7422, Cl, H, Cl, (Me)₂N, CH₃), (M-7423, Cl, H, Cl, piperidin-4-yl-methyl, H), (M-7424, Cl, H, Cl, piperidin-4-yl-methyl, Cl), (M-7425, Cl, H, Cl, piperidin-4-yl-methyl, F), (M-7426, Cl, H, Cl, piperidin-4-yl-methyl, CF₃), (M-7427, Cl, H, Cl, piperidin-4-yl-methyl, Br), (M-7428, Cl, H, Cl, piperidin-4-yl-methyl, CH₃), (M-7429, Cl, H, Cl, cyclohexylmethyl, H), (M-7430, Cl, H, Cl, cyclohexylmethyl, Cl), (M-7431, Cl, H, Cl, cyclohexylmethyl, F), (M-7432, Cl, H, Cl, cyclohexylmethyl, CF₃), (M-7433, Cl, H, Cl, cyclohexylmethyl, Br), (M-7434, Cl, H, Cl, cyclohexylmethyl, CH₃), (M-7435, Cl, F, H, H, H), (M-7436, Cl, F, H, H, Cl), (M-7437, Cl, F, H, H, F), (M-7438, Cl, F, H, H, CF₃), (M-7439, Cl, F, H, H, Br), (M-7440, Cl, F, H, H, CH₃), (M-7441, Cl, F, H, F, H), (M-7442, Cl, F, H, F, Cl), (M-7443, Cl, F, H, F, F), (M-7444, Cl, F, H, F, CF₃), (M-7445, Cl, F, H, F, Br), (M-7446, Cl, F, H, F, CH₃), (M-7447, Cl, F, H, Cl, H), (M-7448, Cl, F, H, Cl, Cl), (M-7449, Cl, F, H, Cl, F), (M-7450, Cl, F, H, Cl, CF₃), (M-7451, Cl, F, H, Cl, Br), (M-7452, Cl, F, H, Cl, CH₃), (M-7453, Cl, F, H, CH₃, H), (M-7454, Cl, F, H, CH₃, Cl), (M-7455, Cl, F, H, CH₃, F), (M-7456, Cl, F, H, CH₃, CF₃), (M-7457, Cl, F, H, CH₃, Br), (M-7458, Cl, F, H, CH₃, CH₃), (M-7459, Cl, F, H, Et, H), (M-7460, Cl, F, H, Et, Cl), (M-7461, Cl, F, H, Et, F), (M-7462, Cl, F, H, Et, CF₃), (M-7463, Cl, F, H, Et, Br), (M-7464, Cl, F, H, Et, CH₃), (M-7465, Cl, F, H, n-Pr, H), (M-7466, Cl, F, H, n-Pr, Cl), (M-7467, Cl, F, H, n-Pr, F), (M-7468, Cl, F, H, n-Pr, CF₃), (M-7469, Cl, F, H, n-Pr, Br), (M-7470, Cl, F, H, n-Pr, CH₃), (M-7471, Cl, F, H, c-Pr, H), (M-7472, Cl, F, H, c-Pr, Cl), (M-7473, Cl, F, H, c-Pr, F), (M-7474, Cl, F, H, c-Pr, CF₃), (M-7475, Cl, F, H, c-Pr, Br), (M-7476, Cl, F, H, c-Pr, CH₃), (M-7477, Cl, F, H, i-Pr, H), (M-7478, Cl, F, H, i-Pr, Cl), (M-7479, Cl, F, H, i-Pr, F), (M-7480, Cl, F, H, i-Pr, CF₃), (M-7481, Cl, F, H, i-Pr, Br), (M-7482, Cl, F, H, i-Pr, CH₃), (M-7483, MeO, F, H, n-Bu, H), (M-7484, Cl, F, H, n-Bu, Cl), (M-7485, Cl, F, H, n-Bu, F), (M-7486, Cl, F, H, n-Bu, CF₃), (M-7487, Cl, F, H, n-Bu, Br), (M-7488, Cl, F, H, n-Bu, CH₃), (M-7489, Cl, F, H, i-Bu, H), (M-7490, Cl, F, H, i-Bu, Cl), (M-7491, Cl, F, H, i-Bu, F), (M-7492, Cl, F, H, i-Bu, CF₃), (M-7493, Cl, F, H, i-Bu, Br), (M-7494, Cl, F, H, i-Bu, CH₃), (M-7495, Cl, F, H, sec-Bu, H), (M-7496, Cl, F, H, sec-Bu, Cl), (M-7497, Cl, F, H, sec-Bu, F), (M-7498, Cl, F, H, sec-Bu, CF₃), (M-7499, Cl, F, H, sec-Bu, Br), (M-7500, Cl, F, H, sec-Bu, CH₃), (M-7501, Cl, F, H, n-Pen, H), (M-7502, Cl, F, H, n-Pen, Cl), (M-7503, Cl, F, H, n-Pen, F), (M-7504, Cl, F, H, n-Pen, CF₃), (M-7505, Cl, F, H, n-Pen, Br), (M-7506, Cl, F, H, n-Pen, CH₃), (M-7507, Cl, F, H, c-Pen, H), (M-7508, Cl, F, H, c-Pen, Cl), (M-7509, Cl, F, H, c-Pen, F), (M-7510, Cl, F, H, c-Pen, CF₃), (M-7511, Cl, F, H, c-Pen, Br), (M-7512, Cl, F, H, c-Pen, CH₃), (M-7513, Cl, F, H, n-Hex, H), (M-7514, Cl, F, H, n-Hex, Cl), (M-7515, Cl, F, H, n-Hex, F), (M-7516, Cl, F, H, n-Hex, CF₃), (M-7517, Cl, F, H, n-Hex, Br), (M-7518, Cl, F, H, n-Hex, CH₃), (M-7519, Cl, F, H, c-Hex, H), (M-7520, Cl, F, H, c-Hex, Cl), (M-7521, Cl, F, H, c-Hex, F), (M-7522, Cl, F, H, c-Hex, CF₃), (M-7523, Cl, F, H, c-Hex, Br), (M-7524, Cl, F, H, c-Hex, CH₃), (M-7525, Cl, F, H, OH, H), (M-7526, Cl, F, H, OH, Cl), (M-7527, Cl, F, H, OH, F), (M-7528, Cl, F, H, OH, CF₃), (M-7529, Cl, F, H, OH, Br), (M-7530, Cl, F, H, OH, CH₃), (M-7531, Cl, F, H, EtO, H), (M-7532, Cl, F, H, EtO, Cl), (M-7533, Cl, F, H, EtO, F), (M-7534, Cl, F, H, EtO, CF₃), (M-7535, Cl, F, H, EtO, Br), (M-7536, Cl, F, H, EtO, CH₃), (M-7537, Cl, F, H, n-PrO, H), (M-7538, Cl, F, H, n-PrO, Cl), (M-7539, Cl, F, H, n-PrO, F), (M-7540, Cl, F, H, n-PrO, CF₃), (M-7541, Cl, F, H, n-PrO, Br), (M-7542, Cl, F, H, n-PrO, CH₃), (M-7543, Cl, F, H, PhO, H), (M-7544, Cl, F, H, PhO, Cl), (M-7545, Cl, F, H, PhO, F), (M-7546, Cl, F, H, PhO, CF₃), (M-7547, Cl, F, H, PhO, Br), (M-7548, Cl, F, H, PhO, CH₃), (M-7549, Cl, F, H, BnO, H), (M-7550, Cl, F, H, BnO, Cl), (M-7551, Cl, F, H, BnO, F), (M-7552, Cl, F, H, BnO, CF₃), (M-7553, Cl, F, H, BnO, Br), (M-7554, Cl, F, H, BnO, CH₃), (M-7555, Cl, F, H, PhCH₂CH₂O, H), (M-7556, Cl, F, H, PhCH₂CH₂O, Cl), (M-7557, Cl, F, H, PhCH₂CH₂O, F), (M-7558, Cl, F, H, PhCH₂CH₂O, CF₃), (M-7559, Cl, F, H, PhCH₂CH₂O, Br), (M-7560, Cl, F, H, PhCH₂CH₂O, CH₃), (M-7561, Cl, F, H, CF₃O, H), (M-7562, Cl, F, H, CF₃O, Cl), (M-7563, Cl, F, H, CF₃O, F), (M-7564, Cl, F, H, CF₃O, CF₃), (M-7565, Cl, F, H, CF₃O, Br), (M-7566, Cl, F, H, CF₃O, CH₃), (M-7567, Cl, F, H, Ph, H), (M-7568, Cl, F, H, Ph, Cl), (M-7569, Cl, F, H, Ph, F), (M-7570, Cl, F, H, Ph, CF₃), (M-7571, Cl, F, H, Ph, Br), (M-7572, Cl, F, H, Ph, CH₃), (M-7573, Cl, F, H, 4-F-Ph, H), (M-7574, Cl, F, H, 4-F-Ph, Cl), (M-7575, Cl, F, H, 4-F-Ph, F), (M-7576, Cl, F, H, 4-F-Ph, CF₃), (M-7577, Cl, F, H, 4-F-Ph, Br), (M-7578, Cl, F, H, 4-F-Ph, CH₃), (M-7579, Cl, F, H, 4-CF₃-Ph, H), (M-7580, Cl, F, H, 4-CF₃-Ph, Cl), (M-7581, Cl, F, H, 4-CF₃-Ph, F), (M-7582, Cl, F, H, 4-CF₃-Ph, CF₃), (M-7583, Cl, F, H, 4-CF₃-Ph, Br), (M-7584, Cl, F, H, 4-CF₃-Ph, CH₃), (M-7585, Cl, F, H, 4-(Me)₂N-Ph, H), (M-7586, Cl, F, H, 4-(Me)₂N-Ph, Cl), (M-7587, Cl, F, H, 4-(Me)₂N-Ph, F), (M-7588, Cl, F, H, 4-(Me)₂N-Ph, CF₃), (M-7589, Cl, F, H, 4-(Me)₂N-Ph, Br), (M-7590, Cl, F, H, 4-(Me)₂N-Ph, CH₃), (M-7591, Cl, F, H, 4-OH-Ph, H), (M-7592, Cl, F, H, 4-OH-Ph, Cl), (M-7593, Cl, F, H, 4-OH-Ph, F), (M-7594, Cl, F, H, 4-OH-Ph, CF₃), (M-7595, Cl, F, H, 4-OH-Ph, Br), (M-7596, Cl, F, H, 4-OH-Ph, CH₃), (M-7597, Cl, F, H, 3,4-di-F-Ph, H), (M-7598, Cl, F, H, 3,4-di-F-Ph, Cl), (M-7599, Cl, F, H, 3,4-di-F-Ph, F), (M-7600, Cl, F, H, 3,4-di-F-Ph, CF₃), (M-7601, Cl, F, H, 3,4-di-F-Ph, Br), (M-7602, Cl, F, H, 3,4-di-F-Ph, CH₃), (M-7603, Cl, F, H, 4-COOH-Ph, H), (M-7604, Cl, F, H, 4-COOH-Ph, Cl), (M-7605, Cl, F, H, 4-COOH-Ph, F), (M-7606, Cl, F, H, 4-COOH-Ph, CF₃), (M-7607, Cl, F, H, 4-COOH-Ph, Br), (M-7608, Cl, F, H, 4-COOH-Ph, CH₃), (M-7609, Cl, F, H, Bn, H), (M-7610, Cl, F, H, Bn, Cl), (M-7611, Cl, F, H, Bn, F), (M-7612, Cl, F, H, Bn, CF₃), (M-7613, Cl, F, H, Bn, Br), (M-7614, Cl, F, H, Bn, CH₃), (M-7615, Cl, F, H, 4-F-Bn, H), (M-7616, Cl, F, H, 4-F-Bn, Cl), (M-7617, Cl, F, H, 4-F-Bn, F), (M-7618, Cl, F, H, 4-F-Bn, CF₃), (M-7619, Cl, F, H, 4-F-Bn, Br), (M-7620, Cl, F, H, 4-F-Bn, CH₃), (M-7621, Cl, F, H, 2-Py, H), (M-7622, Cl, F, H, 2-Py, Cl), (M-7623, Cl, F, H, 2-Py, F), (M-7624, Cl, F, H, 2-Py, CF₃), (M-7625, Cl, F, H, 2-Py, Br), (M-7626, Cl, F, H, 2-Py, CH₃), (M-7627, Cl, F, H, 3-Py, H), (M-7628, Cl, F, H, 3-Py, Cl), (M-7629, Cl, F, H, 3-Py, F), (M-7630, Cl, F, H, 3-Py, CF₃), (M-7631, Cl, F, H, 3-Py, Br), (M-7632, Cl, F, H, 3-Py, CH₃), (M-7633, Cl, F, H, 4-Py, H), (M-7634, Cl, F, H, 4-Py, Cl), (M-7635, Cl, F, H, 4-Py, F), (M-7636, Cl, F, H, 4-Py, CF₃), (M-7637, Cl, F, H, 4-Py, Br), (M-7638, Cl, F, H, 4-Py, CH₃), (M-7639, Cl, F, H, 2-Th, H), (M-7640, Cl, F, H, 2-Th, Cl), (M-7641, Cl, F, H, 2-Th, F), (M-7642, Cl, F, H, 2-Th, CF₃), (M-7643, Cl, F, H, 2-Th, Br), (M-7644, Cl, F, H, 2-Th, CH₃), (M-7645, Cl, F, H, 3-Th, H), (M-7646, Cl, F, H, 3-Th, Cl), (M-7647, Cl, F, H, 3-Th, F), (M-7648, Cl, F, H, 3-Th, CF₃), (M-7649, Cl, F, H, 3-Th, Br), (M-7650, Cl, F, H, 3-Th, CH₃), (M-7651, Cl, F, H, pyrrazol-2-yl, H), (M-7652, Cl, F, H, pyrrazol-2-yl, Cl), (M-7653, Cl, F, H, pyrrazol-2-yl, F), (M-7654, Cl, F, H, pyrrazol-2-yl, CF₃), (M-7655, Cl, F, H, pyrrazol-2-yl, Br), (M-7656, Cl, F, H, pyrrazol-2-yl, CH₃), (M-7657, Cl, F, H, pyrrazol-3-yl, H), (M-7658, Cl, F, H, pyrrazol-3-yl, Cl), (M-7659, Cl, F, H, pyrrazol-3-yl, F), (M-7660, Cl, F, H, pyrrazol-3-yl, CF₃), (M-7661, Cl, F, H, pyrrazol-3-yl, Br), (M-7662, Cl, F, H, pyrrazol-3-yl, CH₃), (M-7663, Cl, F, H, pyrimidin-2-yl, H), (M-7664, Cl, F, H, pyrimidin-2-yl, Cl), (M-7665, Cl, F, H, pyrimidin-2-yl, F), (M-7666, Cl, F, H, pyrimidin-2-yl, CF₃), (M-7667, Cl, F, H, pyrimidin-2-yl, Br), (M-7668, Cl, F, H, pyrimidin-2-yl, CH₃), (M-7669, Cl, F, H, pyrimidin-4-yl, H), (M-7670, Cl, F, H, pyrimidin-4-yl, Cl), (M-7671, Cl, F, H, pyrimidin-4-yl, F), (M-7672, Cl, F, H, pyrimidin-4-yl, CF₃), (M-7673, Cl, F, H, pyrimidin-4-yl, Br), (M-7674, Cl, F, H, pyrimidin-4-yl, CH₃), (M-7675, Cl, F, H, pyrimidin-5-yl, H), (M-7676, Cl, F, H, pyrimidin-5-yl, Cl), (M-7677, Cl, F, H, pyrimidin-5-yl, F), (M-7678, Cl, F, H, pyrimidin-5-yl, CF₃), (M-7679, Cl, F, H, pyrimidin-5-yl, Br), (M-7680, Cl, F, H, pyrimidin-5-yl, CH₃), (M-7681, Cl, F, H, HOOCCH₂CH₂CH₂, H), (M-7682, Cl, F, H, HOOCCH₂CH₂CH₂, Cl), (M-7683, Cl, F, H, HOOCCH₂CH₂CH₂, F), (M-7684, Cl, F, H, HOOCCH₂CH₂CH₂, CF₃), (M-7685, Cl, F, H, HOOCCH₂CH₂CH₂, Br), (M-7686, Cl, F, H, HOOCCH₂CH₂CH₂, CH₃), (M-7687, Cl, F, H, HOOCCH₂CH₂CH₂CH₂, H), (M-7688, Cl, F, H, HOOCCH₂CH₂CH₂CH₂, Cl), (M-7689, Cl, F, H, HOOCCH₂CH₂CH₂CH₂, F), (M-7690, Cl, F, H, HOOCCH₂CH₂CH₂CH₂, CF₃), (M-7691, Cl, F, H, HOOCCH₂CH₂CH₂CH₂, Br), (M-7692, Cl, F, H, HOOCCH₂CH₂CH₂CH₂, CH₃), (M-7693, Cl, F, H, (Me)₂NCOCH₂CH₂CH₂, H), (M-7694, Cl, F, H, (Me)₂NCOCH₂CH₂CH₂, Cl), (M-7695, Cl, F, H, (Me)₂NCOCH₂CH₂CH₂, F), (M-7696, Cl, F, H, (Me)₂NCOCH₂CH₂CH₂, CF₃), (M-7697, Cl, F, H, (Me)₂NCOCH₂CH₂CH₂, Br), (M-7698, Cl, F, H, (Me)₂NCOCH₂CH₂CH₂, CH₃), (M-7699, Cl, F, H, (Me)₂NCOCH₂CH₂CH₂CH₂, H), (M-7700, Cl, F, H, (Me)₂NCOCH₂CH₂CH₂CH₂, Cl), (M-7701, Cl, F, H, (Me)₂NCOCH₂CH₂CH₂CH₂, F), (M-7702, Cl, F, H, (Me)₂NCOCH₂CH₂CH₂CH₂, CF₃), (M-7703, Cl, F, H, (Me)₂NCOCH₂CH₂CH₂CH₂, Br), (M-7704, Cl, F, H, (Me)₂NCOCH₂CH₂CH₂CH₂, CH₃), (M-7705, Cl, F, H, MeOCH₂, H), (M-7706, Cl, F, H, MeOCH₂, Cl), (M-7707, Cl, F, H, MeOCH₂, F), (M-7708, Cl, F, H, MeOCH₂, CF₃), (M-7709, Cl, F, H, MeOCH₂, Br), (M-7710, Cl, F, H, MeOCH₂, CH₃), (M-7711, Cl, F, H, EtOCH₂, H), (M-7712, Cl, F, H, EtOCH₂, Cl), (M-7713, Cl, F, H, EtOCH₂, F), (M-7714, Cl, F, H, EtOCH₂, CF₃), (M-7716, Cl, F, H, EtOCH₂, Br), (M-7716, Cl, F, H, EtOCH₂, CH₃), (M-7717, Cl, F, H, EtOCH₂CH₂, H), (M-7718, Cl, F, H, EtOCH₂CH₂, Cl), (M-7719, Cl, F, H, EtOCH₂CH₂, F), (M-7720, Cl, F, H, EtOCH₂CH₂, CF₃), (M-7721, Cl, F, H, EtOCH₂CH₂, Br), (M-7722, Cl, F, H, EtOCH₂CH₂, CH₃), (M-7723, Cl, F, H, MeOCH₂CH₂OCH₂CH₂, H), (M-7724, Cl, F, H, MeOCH₂CH₂OCH₂CH₂, Cl), (M-7725, Cl, F, H, MeOCH₂CH₂OCH₂CH₂, F), (M-7726, Cl, F, H, MeOCH₂CH₂OCH₂CH₂, CF₃), (M-7727, Cl, F, H, MeOCH₂CH₂OCH₂CH₂, Br), (M-7728, Cl, F, H, MeOCH₂CH₂OCH₂CH₂, CH₃), (M-7729, Cl, F, H, MeOCH₂CH₂, H), (M-7730, Cl, F, H, MeOCH₂CH₂, Cl), (M-7731, Cl, F, H, MeOCH₂CH₂, F), (M-7732, Cl, F, H, MeOCH₂CH₂, CF₃), (M-7733, Cl, F, H, MeOCH₂CH₂, Br), (M-7734, Cl, F, H, MeOCH₂CH₂, CH₃), (M-7735, Cl, F, H, HOCH₂, H), (M-7736, Cl, F, H, HOCH₂, Cl), (M-7737, Cl, F, H, HOCH₂, F), (M-7738, Cl, F, H, HOCH₂, CF₃), (M-7739, Cl, F, H, HOCH₂, Br), (M-7740, Cl, F, H, HOCH₂, CH₃), (M-7741, Cl, F, H, HOCH₂CH₂, H), (M-7742, Cl, F, H, HOCH₂CH₂, Cl), (M-7743, Cl, F, H, HOCH₂CH₂, F), (M-7744, Cl, F, H, HOCH₂CH₂, CF₃), (M-7745, Cl, F, H, HOCH₂CH₂, Br), (M-7746, Cl, F, H, HOCH₂CH₂, CH₃), (M-7747, Cl, F, H, HOCH₂CH₂CH₂, H), (M-7748, Cl, F, H, HOCH₂CH₂CH₂, Cl), (M-7749, Cl, F, H, HOCH₂CH₂CH₂, F), (M-7750, Cl, F, H, HOCH₂CH₂CH₂, CF₃), (M-7751, Cl, F, H, HOCH₂CH₂CH₂, Br), (M-7752, Cl, F, H, HOCH₂CH₂CH₂, CH₃), (M-7753, Cl, F, H, HOCH₂CH₂CH₂CH₂, H), (M-7754, Cl, F, H, HOCH₂CH₂CH₂CH₂, Cl), (M-7755, Cl, F, H, HOCH₂CH₂CH₂CH₂, F), (M-7756, Cl, F, H, HOCH₂CH₂CH₂CH₂, CF₃), (M-7757, Cl, F, H, HOCH₂CH₂CH₂CH₂, Br), (M-7758, Cl, F, H, HOCH₂CH₂CH₂CH₂, CH₃), (M-7759, Cl, F, H, HOCH₂CH₂CH₂CH₂CH₂, H), (M-7760, Cl, F, H, HOCH₂CH₂CH₂CH₂CH₂, Cl), (M-7761, Cl, F, H, HOCH₂CH₂CH₂CH₂CH₂, F), (M-7762, Cl, F, H, HOCH₂CH₂CH₂CH₂CH₂, CF₃), (M-7763, Cl, F, H, HOCH₂CH₂CH₂CH₂CH₂Br), (M-7764, Cl, F, H, HOCH₂CH₂CH₂CH₂CH₂, CH₃), (M-7765, Cl, F, H, HOCH₂CH₂OCH₂CH₂, H), (M-7766, Cl, F, H, HOCH₂CH₂OCH₂CH₂, Cl), (M-7767, Cl, F, H, HOCH₂CH₂OCH₂CH₂, F), (M-7768, Cl, F, H, HOCH₂CH₂OCH₂CH₂, CF₃), (M-7769, Cl, F, H, HOCH₂CH₂OCH₂CH₂, Br), (M-7770, Cl, F, H, HOCH₂CH₂OCH₂CH₂, CH₃), (M-7771, Cl, F, H, (Me)₂N, H), (M-7772, Cl, F, H, (Me)₂N, Cl), (M-7773, Cl, F, H, (Me)₂N, F), (M-7774, Cl, F, H, (Me)₂N, CF₃), (M-7775, Cl, F, H, (Me)₂N, Br), (M-7776, Cl, F, H, (Me)₂N, CH₃), (M-7777, Cl, F, H, piperidin-4-yl-methyl, H), (M-7778, Cl, F, H, piperidin-4-yl-methyl, Cl), (M-7779, Cl, F, H, piperidin-4-yl-methyl, F), (M-7780, Cl, F, H, piperidin-4-yl-methyl, CF₃), (M-7781, Cl, F, H, piperidin-4-yl-methyl, Br), (M-7782, Cl, F, H, piperidin-4-yl-methyl, CH₃), (M-7783, Cl, F, H, cyclohexylmethyl, H), (M-7784, Cl, F, H, cyclohexylmethyl, Cl), (M-7785, Cl, F, H, cyclohexylmethyl, F), (M-7786, Cl, F, H, cyclohexylmethyl, CF₃), (M-7787, Cl, F, H, cyclohexylmethyl, Br), (M-7788, Cl, F, H, cyclohexylmethyl, CH₃), (M-7789, Cl, F, F, H, H), (M-7790, Cl, F, F, H, Cl), (M-7791, Cl, F, F, H, F), (M-7792, Cl, F, F, H, CF₃), (M-7793, Cl, F, F, H, Br), (M-7794, Cl, F, F, H, CH₃), (M-7795, Cl, F, F, F, H), (M-7796, Cl, F, F, F, Cl), (M-7797, Cl, F, F, F, F), (M-7798, Cl, F, F, F, CF₃), (M-7799, Cl, F, F, F, Br), (M-7800, Cl, F, F, F, CH₃), (M-7801, Cl, F, F, Cl, H), (M-7802, Cl, F, F, Cl, Cl), (M-7803, Cl, F, F, Cl, F), (M-7804, Cl, F, F, Cl, CF₃), (M-7805, Cl, F, F, Cl, Br), (M-7806, Cl, F, F, Cl, CH₃), (M-7807, Cl, F, F, CH₃, H), (M-7808, Cl, F, F, CH₃, Cl), (M-7809, Cl, F, F, CH₃, F), (M-7810, Cl, F, F, CH₃, CF₃), (M-7811, Cl, F, F, CH₃, Br), (M-7812, Cl, F, F, CH₃, CH₃), (M-7813, Cl, F, F, Et, H), (M-7814, Cl, F, F, Et, Cl), (M-7815, Cl, F, F, Et, F), (M-7816, Cl, F, F, Et, CF₃), (M-7817, Cl, F, F, Et, Br), (M-7818, Cl, F, F, Et, CH₃), (M-7819, Cl, F, F, n-Pr, H), (M-7820, Cl, F, F, n-Py, Cl), (M-7821, Cl, F, F, n-Pr, F), (M-7822, Cl, F, F, n-Pr, CF₃), (M-7823, Cl, F, F, n-Pr, Br), (M-7824, Cl, F, F, n-Pr, CH₃), (M-7825, Cl, F, F, c-Pr, H), (M-7826, Cl, F, F, c-Pr, Cl), (M-7827, Cl, F, F, c-Pr, F), (M-7828, Cl, F, F, c-Pr, CF₃), (M-7829, Cl, F, F, c-Pr, Br), (M-7830, Cl, F, F, c-Pr, CH₃), (M-7831, Cl, F, F, i-Pr, H), (M-7832, Cl, F, F, i-Pr, Cl), (M-7833, Cl, F, F, i-Pr, F), (M-7834, Cl, F, F, i-Pr, CF₃), (M-7835, Cl, F, F, i-Pr, Br), (M-7836, Cl, F, F,i Pr, CH,3), (M-7837, Cl, F, F, n-Bu, H), (M-7838, Cl, F, F, n-Bu, Cl), (M-7839, Cl, F, F, n-Bu, F), (M-7840, Cl, F, F, n-Bu, CF₃), (M-7841, Cl, F, F, n-Bu, Br), (M-7842, Cl, F, F, n-Bu, CH₃), (M-7843, Cl, F, F, i-Bu, H), (M-7844, Cl, F, F, i-Bu, Cl), (M-7845, Cl, F, F, i-Bu, F), (M-7846, Cl, F, F, i-Bu, CF₃), (M-7847, Cl, F, F, i-Bu, Br), (M-7848, Cl, F, F, i-Bu, CH₃), (M-7849, Cl, F, F, sec-Bu, H), (M-7850, Cl, F, F, sec-Bu, Cl), (M-7851, Cl, F, F, sec-Bu, F), (M-7852, Cl, F, F, sec-Bu, CF₃), (M-7853, Cl, F, F, sec-Bu, Br), (M-7854, Cl, F, F, sec-Bn, CH₃), (M-7855, Cl, F, F, n-Pen, H), (M-7856, Cl, F, F, n-Pen, Cl), (M-7857, Cl, F, F, n-Pen, F), (M-7858, Cl, F, F, n-Pen, CF₃), (M-7859, Cl, F, F, n-Pen, Br), (M-7860, Cl, F, F, n-Pen, CH₃), (M-7861, Cl, F, F, c-Pen, HI), (M-7862, Cl, F, F, c-Pen, Cl), (M-7863, Cl, F, F, c-Pen, F), (M-7864, Cl, F, F, c-Pen, CF₃), (M-7865, Cl, F, F, c-Pen, Br), (M-7866, Cl, F, F, c-Pen, CH₃), (M-7867, Cl, F, F, n-Hex, H), (M-7868, Cl, F, F, n-Hex, Cl), (M-7869, Cl, F, F, n-Hex, F), (M-7870, Cl, F, F, n-Hex, CF₃), (M-7871, Cl, F, F, n-Hex, Br), (M-7872, Cl, F, F, n-Hex, CH₃), (M-7873, Cl, F, F, c-Hex, H), (M-7874, Cl, F, F, c-Hex, Cl), (M-7875, Cl, F, F, c-Hex, F), (M-7876, Cl, F, F, c-Hex, CF₃), (M-7877, Cl, F, F, c-Hex, Br), (M-7878, Cl, F, F, c-Hex, CH₃), (M-7879, Cl, F, F, OH, H), (M-7880, Cl, F, F, OH, Cl), (M-7881, Cl, F, F, OH, F), (M-7882, Cl, F, F, OH, CF₃), (M-7883, Cl, F, F, OH, Br), (M-7884, Cl, F, F, OH, CH₃), (M-7885, Cl, F, F, EtO, H), (M-7886, Cl, F, F, EtO, Cl), (M-7887, Cl, F, F, EtO, F), (M-7888, Cl, F, F, EtO, CF₃), (M-7889, Cl, F, F, EtO, Br), (M-7890, Cl, F, F, EtO, CH₃), (M-7891, Cl, F, F, n-PrO, H), (M-7892, Cl, F, F, n-PrO, Cl), (M-7893, Cl, F, F, n-PrO, F), (M-7894, Cl, F, F, n-PrO, CF₃), (M-7895, Cl, F, F, n-PrO, Br), (M-7896, Cl, F, F, n-PrO, CH₃), (M-7897, Cl, F, F, PhO, H), (M-7898, Cl, F, F, PhO, Cl), (M-7899, Cl, F, F, PhO, F), (M-7900, Cl, F, F, PhO, CF₃), (M-7901, Cl, F, F, PhO, Br), (M-7902, Cl, F, F, PhO, CH₃), (M-7903, Cl, F, F, BnO, H), (M-7904, Cl, F, F, BnO, Cl), (M-7905, Cl, F, F, BnO, F), (M-7906, Cl, F, F, BnO, CF₃), (M-7907, Cl, F, F, BnO, Br), (M-7908, Cl, F, F, BnO, CH₃), (M-7909, Cl, F, F, PhCH₂CH₂O, H), (M-7910, Cl, F, F, PhCH₂CH₂O, Cl), (M-7911, Cl, F, F, PhCH₂CH₂O, F), (M-7912, Cl, F, F, PhCH₂CH₂O, CF₃), (M-7913, Cl, F, F, PhCH₂CH₂O, Br), (M-7914, Cl, F, F, PhCH₂CH₂O, CH₃), (M-7915, Cl, F, F, CF₃O, H), (M-7916, Cl, F, F, CF₃O, Cl), (M-7917, Cl, F, F, CF₃O, F), (M-7918, Cl, F, F, CF₃O, CF₃), (M-7919, Cl, F, F, CF₃O, Br), (M-7920, Cl, F, F, CF₃O, CH₃), (M-7921, Cl, F, F, Ph, H), (M-7922, Cl, F, F, Ph, Cl), (M-7923, Cl, F, F, Ph, F), (M-7924, Cl, F, F, Ph, CF₃), (M-7925, Cl, F, F, Ph, Br), (M-7926, Cl, F, F, Ph, CH₃), (M-7927, Cl, F, F, 4-F-Ph, H), (M-7928, Cl, F, F, 4-F-Ph, Cl), (M-7929, Cl, F, F, 4-F-Ph, F), (M-7930, Cl, F, F, 4-F-Ph, CF₃), (M-7931, Cl, F, F, 4-F-Ph, Br), (M-7932, Cl, F, F, 4-F-Ph, CH₃), (M-7933, Cl, F, F, 4-CF₃-Ph, H), (M-7934, Cl, F, F, 4-CF₃-Ph, Cl), (M-7935, Cl, F, F, 4-CF₃-Ph, F), (M-7936, Cl, F, F, 4-CF₃-Ph, CF₃), (M-7937, Cl, F, F, 4-CF₃-Ph, Br), (M-7938, Cl, F, F, 4-CF₃-Ph, CH₃), (M-7939, Cl, F, F, 4-(Me)₂N-Ph, H), (M-7940, Cl, F, F, 4-(Me)₂N-Ph, Cl), (M-7941, Cl, F, F, 4-(Me)₂N-Ph, F), (M-7942, Cl, F, F, 4-(Me)₂N-Ph, CF₃), (M-7943, Cl, F, F, 4-(Me)₂N-Ph, Br), (M-7944, Cl, F, F, 4-(Me)₂N-Ph, CH₃), (M-7945, Cl, F, F, 4-OH-Ph, H), (M-7946, Cl, F, F, 4-OH-Ph, Cl), (M-7947, Cl, F, F, 4-OH-Ph, F), (M-7948, Cl, F, F, 4-OH-Ph, CF₃), (M-7949, Cl, F, F, 4-OH-Ph, Br), (M-7950, Cl, F, F, 4-OH-Ph, CH₃), (M-7951, Cl, F, F, 3,4-di-F-Ph, H), (M-7952, Cl, F, F, 3,4-di-F-Ph, Cl), (M-7953, Cl, F, F, 3,4-di-F-Ph, F), (M-7954, Cl, F, F, 3,4-di-F-Ph, CF$_3$), (M-7955, Cl, F, F, 3,4-di-F-Ph, Br), (M-7956, Cl, F, F, 3,4-di-F-Ph, CH$_3$), (M-7957, Cl, F, F, 4-COOH-Ph, H), (M-7958, Cl, F, F, 4-COOH-Ph, Cl), (M-7959, Cl, F, F, 4-COOH-Ph, F), (M-7960, Cl, F, F, 4-COOH-Ph, CF$_3$), (M-7961, Cl, F, F, 4-COOH-Ph, Br), (M-7962, Cl, F, F, 4-COOH-Ph, CH$_3$), (M-7963, Cl, F, F, Bn, H), (M-7964, Cl, F, F, Bn, Cl), (M-7965, Cl, F, F, Bn, F), (M-7966, Cl, F, F, Bn, CF$_3$), (M-7967, Cl, F, F, Bn, Br), (M-7968, Cl, F, F, Bn, CH$_3$), (M-7969, Cl, F, F, 4-F-Bn, H), (M-7970, Cl, F, F, 4-F-Bn, Cl), (M-7971, Cl, F, F, 4-F-Bn, F), (M-7972, Cl, F, F, 4-F-Bn, CF$_3$), (M-7973, Cl, F, F, 4-F-Bn, Br), (M-7974, Cl, F, F, 4-F-Bn, CH$_3$), (M-7975, Cl, F, F, 2-Py, H), (M-7976, Cl, F, F, 2-Py, Cl), (M-7977, Cl, F, F, 2-Py, F), (M-7978, Cl, F, F, 2-Py, CF$_3$), (M-7979, Cl, F, F, 2-Py, Br), (M-7980, Cl, F, F, 2-Py, CH$_3$), (M-7981, Cl, F, F, 3-Py, H), (M-7982, Cl, F, F, 3-Py, Cl), (M-7983, Cl, F, F, 3-Py, F), (M-7984, Cl, F, F, 3-Py, CF$_3$), (M-7985, Cl, F, F, 3-Py, Br), (M-7986, Cl, F, F, 3-Py, CH$_3$), (M-7987, Cl, F, F, 4-Py, H), (M-7988, Cl, F, F, 4-Py, Cl), (M-7989, Cl, F, F, 4-Py, F), (M-7990, Cl, F, F, 4-Py, CF$_3$), (M-7991, Cl, F, F, 4-Py, Br), (M-7992, Cl, F, F, 4-Py, CH$_3$), (M-7993, Cl, F, F, 2-Th, H), (M-7994, Cl, F, F, 2-Th, Cl), (M-7995, Cl, F, F, 2-Th, F), (M-7996, Cl, F, F, 2-Th, CF$_3$), (M-7997, Cl, F, F, 2-Th, Br), (M-7998, Cl, F, F, 2-Th, CH$_3$), (M-7999, Cl, F, F, 3-Th, H), (M-8000, Cl, F, F, 3-Th, Cl), (M-8001, Cl, F, F, 3-Th, F), (M-8002, Cl, F, F, 3-Th, CF$_3$), (M-8003, Cl, F, F, 3-Th, Br), (M-8004, Cl, F, F, 3-Th, CH$_3$), (M-8005, Cl, F, F, pyrrazol-2-yl, H), (M-8006, Cl, F, F, pyrrazol-2-yl, Cl), (M-8007, Cl, F, F, pyrrazol-2-yl, F), (M-8008, Cl, F, F, pyrrazol-2-yl, CF$_3$), (M-8009, Cl, F, F, pyrrazol-2-yl, Br), (M-8010, Cl, F, F, pyrrazol-2-yl, CH$_3$), (M-8011, Cl, F, F, pyrrazol-3-yl, H), (M-8012, Cl, F, F, pyrrazol-3-yl, Cl), (M-8013, Cl, F, F, pyrrazol-3-yl, F), (M-8014, Cl, F, F, pyrrazol-3-yl, CF$_3$), (M-8015, Cl, F, F, pyrrazol-3-yl, Br), (M-8016, Cl, F, F, pyrrazol-3-yl, CH$_3$), (M-8017, Cl, F, F, pyrimidin-2-yl, H), (M-8018, Cl, F, F, pyrimidin-2-yl, Cl), (M-8019, Cl, F, F, pyrimidin-2-yl, F), (M-8020, Cl, F, F, pyrimidin-2-yl, CF$_3$), (M-8021, Cl, F, F, pyrimidin-2-yl, Br), (M-8022, Cl, F, F, pyrimidin-2-yl, CH$_3$), (M-8023, Cl, F, F, pyrimidin-4-yl, H), (M-8024, Cl, F, F, pyrimidin-4-yl, Cl), (M-8025, Cl, F, F, pyrimidin-4-yl, F), (M-8026, Cl, F, F, pyrimidin-4-yl, CF$_3$), (M-8027, Cl, F, F, pyrimidin-4-yl, Br), (M-8028, Cl, F, F, pyrimidin-4-yl, CH$_3$), (M-8029, Cl, F, F, pyrimidin-5-yl, H), (M-8030, Cl, F, F, pyrimidin-5-yl, Cl), (M-8031, Cl, F, F, pyrimidin-5-yl, F), (M-8032, Cl, F, F, pyrimidin-5-yl, CF$_3$), (M-8033, Cl, F, F, pyrimidin-5-yl, Br), (M-8034, Cl, F, F, pyrimidin-5-yl, CH$_3$), (M-8035, Cl, F, F, HOOCCH$_2$CH$_2$CH$_2$, H), (M-8036, Cl, F, F, HOOCCH$_2$CH$_2$CH$_2$, Cl), (M-8037, Cl, F, F, HOOCCH$_2$CH$_2$CH$_2$, F), (M-8038, Cl, F, F, HOOCCH$_2$CH$_2$CH$_2$, CF$_3$), (M-8039, Cl, F, F, HOOCCH$_2$CH$_2$CH$_2$, Br), (M-8040, Cl, F, F, HOOCCH$_2$CH$_2$CH$_2$, CH$_3$), (M-8041, Cl, F, F, HOOCCH$_2$CH$_2$CH$_2$CH$_2$, H), (M-8042, Cl, F, F, HOOCCH$_2$CH$_2$CH$_2$CH$_2$, Cl), (M-8043, Cl, F, F, HOOCCH$_2$CH$_2$CH$_2$CH$_2$, F), (M-8044, Cl, F, F, HOOCCH$_2$CH$_2$CH$_2$CH$_2$, CF$_3$), (M-8045, Cl, F, F, HOOCCH$_2$CH$_2$CH$_2$CH$_2$, Br), (M-8046, Cl, F, F, HOOCCH$_2$CH$_2$CH$_2$CH$_2$, CH$_3$), (M-8047, Cl, F, F, (Me)$_2$NCOCH$_2$CH$_2$CH$_2$, H), (M-8048, Cl, F, F, (Me)$_2$NCOCH$_2$CH$_2$CH$_2$, Cl), (M-8049, Cl, F, F, (Me)$_2$NCOCH$_2$CH$_2$CH$_2$, F), (M-8050, Cl, F, F, (Me)$_2$NCOCH$_2$CH$_2$CH$_2$CF$_3$), (M-8051, Cl, F, F, (Me)$_2$NCOCH$_2$CH$_2$CH$_2$, Br), (M-8052, Cl, F, F, (Me)$_2$NCOCH$_2$CH$_2$CH$_2$, CH$_3$), (M-8053, Cl, F, F, (Me)$_2$NCOCH$_2$CH$_2$CH$_2$CH$_2$, H), (M-8054, Cl, F, F, (Me)$_2$NCOCH$_2$CH$_2$CH$_2$CH$_2$, Cl), (M-8055, Cl, F, F, (Me)$_2$NCOCH$_2$CH$_2$CH$_2$CH$_2$, F), (M-8056, Cl, F, F, (Me)$_2$NCOCH$_2$CH$_2$CH$_2$CH$_2$, CF$_3$), (M-8057, Cl, F, F, (Me)$_2$NCOCH$_2$CH$_2$CH$_2$CH$_2$, Br), (M-8058, Cl, F, F, (Me)$_2$NCOCH$_2$CH$_2$CH$_2$CH$_2$, CH$_3$), (M-8059, Cl, F, F, MeOCH$_2$, H), (M-8060, Cl, F, F, MeOCH$_2$, Cl), (M-8061, Cl, F, F, MeOCH$_2$, F), (M-8062, Cl, F, F, MeOCH$_2$, CF$_3$), (M-8063, Cl, F, F, MeOCH$_2$, Br), (M-8064, Cl, F, F, MeOCH$_2$, CH$_3$), (M-8065, Cl, F, F, EtOCH$_2$, H), (M-8066, Cl, F, F, EtOCH$_2$, Cl), (M-8067, Cl, F, F, EtOCH$_2$, F), (M-8068, Cl, F, F, EtOCH$_2$, CF$_3$), (M-8069, Cl, F, F, EtOCH$_2$, Br), (M-8070, Cl, F, F, EtOCH$_2$, CH$_3$), (M-8071, Cl, F, F, EtOCH$_2$CH$_2$, H), (M-8072, Cl, F, F, EtOCH$_2$CH$_2$, Cl), (M-8073, Cl, F, F, EtOCH$_2$CH$_2$, F), (M-8074, Cl, F, F, EtOCH$_2$CH$_2$, CF$_3$), (M-8075, Cl, F, F, EtOCH$_2$CH$_2$, Br), (M-8076, Cl, F, F, EtOCH$_2$CH$_2$, CH$_3$), (M-8077, Cl, F, F, MeOCH$_2$CH$_2$OCH$_2$CH$_2$, H), (M-8078, Cl, F, F, MeOCH$_2$CH$_2$OCH$_2$CH$_2$, Cl), (M-8079, Cl, F, F, MeOCH$_2$CH$_2$OCH$_2$CH$_2$, F), (M-8080, Cl, F, F, MeOCH$_2$CH$_2$OCH$_2$CH$_2$, CF$_3$), (M-8081, Cl, F, F, MeOCH$_2$CH$_2$OCH$_2$CH$_2$, Br), (M-8082, Cl, F, F, MeOCH$_2$CH$_2$OCH$_2$CH$_2$, CH$_3$), (M-8083, Cl, F, F, MeOCH$_2$CH$_2$, H), (M-8084, Cl, F, F, MeOCH$_2$CH$_2$, Cl), (M-8085, Cl, F, F, MeOCH$_2$CH$_2$, F), (M-8086, Cl, F, F, MeOCH$_2$CH$_2$, CF$_3$), (M-8087, Cl, F, F, MeOCH$_2$CH$_2$, Br), (M-8088, Cl, F, F, MeOCH$_2$CH$_2$, CH$_3$), (M-8089, Cl, F, F, HOCH$_2$, H), (M-8090, Cl, F, F, HOCH$_2$, Cl), (M-8091, Cl, F, F, HOCH$_2$, F), (M-8092, Cl, F, F, HOCH$_2$, CF$_3$), (M-8093, Cl, F, F, HOCH$_2$, Br), (M-8094, Cl, F, F, HOCH$_2$, CH$_3$), (M-8095, Cl, F, F, HOCH$_2$CH$_2$, H), (M-8096, Cl, F, F, HOCH$_2$CH$_2$, Cl), (M-8097, Cl, F, F, HOCH$_2$CH$_2$, F), (M-8098, Cl, F, F, HOCH$_2$CH$_2$, CF$_3$), (M-8099, Cl, F, F, HOCH$_2$CH$_2$, Br), (M-8100, Cl, F, F, HOCH$_2$CH$_2$, CH$_3$), (M-8101, Cl, F, F, HOCH$_2$CH$_2$CH$_2$, H), (M-8102, Cl, F, F, HOCH$_2$CH$_2$CH$_2$, Cl), (M-8103, Cl, F, F, HOCH$_2$CH$_2$CH$_2$, F), (M-8104, Cl, F, F, HOCH$_2$CH$_2$CH$_2$, CF$_3$), (M-8105, Cl, F, F, HOCH$_2$CH$_2$CH$_2$, Br), (M-8106, Cl, F, F, HOCH$_2$CH$_2$CH$_2$, CH$_3$), (M-8107, Cl, F, F, HOCH$_2$CH$_2$CH$_2$CH$_2$, H), (M-8108, Cl, F, F, HOCH$_2$CH$_2$CH$_2$CH$_2$, Cl), (M-8109, Cl, F, F, HOCH$_2$CH$_2$CH$_2$CH$_2$, F), (M-8110, Cl, F, F, HOCH$_2$CH$_2$CH$_2$CH$_2$, CF$_3$), (M-8111, Cl, F, F, HOCH$_2$CH$_2$CH$_2$CH$_2$, Br), (M-8112, Cl, F, F, HOCH$_2$CH$_2$CH$_2$CH$_2$CH$_3$), (M-8113, Cl, F, F, HOCH$_2$CH$_2$CH$_2$CH$_2$CH$_2$, H), (M-8114, Cl, F, F, HOCH$_2$CH$_2$CH$_2$CH$_2$CH$_2$, Cl), (M-8115, Cl, F, F, HOCH$_2$CH$_2$CH$_2$CH$_2$CH$_2$, F), (M-8116, Cl, F, F, HOCH$_2$CH$_2$CH$_2$CH$_2$CH$_2$, CF$_3$), (M-8117, Cl, F, F, HOCH$_2$CH$_2$CH$_2$CH$_2$CH$_2$, Br), (M-8118, Cl, F, F, HOCH$_2$CH$_2$CH$_2$CH$_2$CH$_2$, CH$_3$), (M-8119, Cl, F, F, HOCH$_2$CH$_2$OCH$_2$CH$_2$, H), (M-8120, Cl, F, F, HOCH$_2$CH$_2$OCH$_2$CH$_2$, Cl), (M-8121, Cl, F, F, HOCH$_2$CH$_2$OCH$_2$CH$_2$, F), (M-8122, Cl, F, F, HOCH$_2$CH$_2$OCH$_2$CH$_2$, CF$_3$), (M-8123, Cl, F, F, HOCH$_2$CH$_2$OCH$_2$CH$_2$, Br), (M-8124, Cl, F, F, HOCH$_2$CH$_2$OCH$_2$CH$_2$, CH$_3$), (M-8125, Cl, F, F, (Me)$_2$N, H), (M-8126, Cl, F, F, (Me)$_2$N, Cl), (M-8127, Cl, F, F, (Me)$_2$N, F), (M-8128, Cl, F, F, (Me)$_2$N, CF$_3$), (M-8129, Cl, F, F, (Me)$_2$N, Br), (M-8130, Cl, F, F, (Me)$_2$N, CH$_3$), (M-8131, Cl, F, F, piperidin-4-yl-methyl, H), (M-8132, Cl, F, F, piperidin-4-yl-methyl, Cl), (M-8133, Cl, F, F, piperidin-4-yl-methyl, F), (M-8134, Cl, F, F, piperidin-4-yl-methyl, CF$_3$), (M-8135, Cl, F, F, piperidin-4-yl-methyl, Br), (M-8136, Cl, F, F, piperidin-4-yl-methyl, CH$_3$), (M-8137, Cl, F, F, cyclohexylmethyl, H), (M-8138, Cl, F, F, cyclohexylmethyl, Cl), (M-8139, Cl, F, F, cyclohexylmethyl, F), (M-8140, Cl, F, F, cyclohexylmethyl, CF$_3$), (M-8141, Cl, F, F, cyclohexylmethyl, Br), (M-8142, Cl, F, F, cyclohexylmethyl, CH$_3$), (M-8143, Cl, F, Cl, H, H), (M-8144, Cl, F, Cl, H, Cl), (M-8145, Cl, F, Cl, H, F), (M-8146, Cl, F, Cl, H, CF$_3$), (M-8147, Cl, F, Cl, H, Br), (M-8148, Cl, F, Cl, H, CH$_3$), (M-8149, Cl, F, Cl, F, H), (M-8150, Cl, F, Cl, F, Cl), (M-8151, Cl, F, Cl, F, F), (M-8152, Cl, F, Cl, F, CF$_3$), (M-8153, Cl, F, Cl, F, Br), (M-8154, Cl, F, Cl, F, CH$_3$), (M-8155, Cl, F, Cl, Cl, H), (M-8156, Cl, F, Cl, Cl, Cl), (M-8157, Cl, F, Cl, Cl, F), (M-8158, Cl, F, Cl, Cl, CF$_3$), (M-8159, Cl, F, Cl, Cl, Br), (M-8160, Cl, F, Cl, Cl, CH$_3$), (M-8161, Cl, F, Cl, CH$_3$, H), (M-8162, Cl, F, Cl, CH$_3$, Cl), (M-8163, Cl, F, Cl, CH$_3$, F), (M-8164, Cl, F, Cl, CH$_3$, CF$_3$), (M-8165, Cl, F, Cl, CH$_3$, Br), (M-8166, Cl, F, Cl, CH$_3$, CH$_3$), (M-8167, Cl, F, Cl, Et, H), (M-8168, Cl, F, Cl, Et, Cl), (M-8169, Cl, F, Cl, Et, F), (M-8170, Cl, F, Cl, Et, CF$_3$), (M-8171, Cl, F, Cl, Et, Br), (M-8172, Cl, F, Cl, Et, CH$_3$), (M-8173, Cl, F, Cl, n-Pr, H), (M-8174, Cl, F, Cl, n-Pr, Cl), (M-8175, Cl, F, Cl, n-Pr, F), (M-8176, Cl, F, Cl, n-Pr, CF$_3$), (M-8177, Cl, F, Cl, n-Pr, Br), (M-8178, Cl, F, Cl, a-Pr, CH$_3$), (M-8179, Cl, F, Cl, c-Pr, H), (M-8180, Cl, F, Cl, c-Pr, Cl), (M-8181, Cl, F, Cl, c-Pr, F), (M-8182, Cl, F, Cl, c-Pr, CF$_3$), (M-8183, Cl, F, Cl, c-Pr, Br), (M-8184, Cl, F, Cl, c-Pr, CH$_3$), (M-8185, Cl, F, Cl, i-Pr, H), (M-8186, Cl, F, Cl, i-Pr, Cl), (M-8187, Cl, F, Cl, i-Pr, F), (M-8188, Cl, F, Cl, i-Pr, CF$_3$), (M-8189, Cl, F, Cl, i-Pr, Br), (M-8190, Cl, F, Cl, i-Pr, CH$_3$), (M-8191, Cl, F, Cl, n-Bu, H), (M-8192, Cl, F, Cl, n-Bu, Cl), (M-8193, Cl, F, Cl, n-Bu, F), (M-8194, Cl, F, Cl, n-Bu, CF$_3$), (M-8195, Cl, F, Cl, n-Bu, Br), (M-8196, Cl, F, Cl, n-Bu, CH$_3$), (M-8197, Cl, F, Cl, i-Bu, H), (M-8198, Cl, F, Cl, i-Bu, Cl), (M-8199, Cl, F, Cl, i-Bu, F), (M-8200, Cl, F, Cl, i-Bu, CF$_3$), (M-8201, Cl, F, Cl, i-Bu, Br), (M-8202, Cl, F, Cl, i-Bu, CH$_3$), (M-8203, Cl, F, Cl, sec-Bu, H), (M-8204, Cl, F, Cl, sec-Bu, Cl), (M-8205, Cl, F, Cl, sec-Bu, F), (M-8206, Cl, F, Cl, sec-Bu, CF$_3$), (M-8207, Cl, F, Cl, sec-Bu, Br), (M-8208, Cl, F, Cl, sec-Bu, CH$_3$), (M-8209, Cl, F, Cl, n-Pen, H), (M-8210, Cl, F, Cl, n-Pen, Cl), (M-8211, Cl, F, Cl, n-Pen, F), (M-8212, Cl, F, Cl, n-Pen, CF$_3$), (M-8213, Cl, F, Cl, n-Pen, Br), (M-8214, Cl, F, Cl, n-Pen, CH$_3$), (M-8215, Cl, F, Cl, c-Pen, H), (M-8216, Cl, F, Cl, c-Pen, Cl), (M-8217, Cl, F, Cl, c-Pen, F), (M-8218, Cl, F, Cl, c-Pen, CF$_3$), (M-8219, Cl, F, Cl, c-Pen, Br), (M-8220, Cl, F, Cl, c-Pen, CH$_3$), (M-8221, Cl, F, Cl, n-Hex, H), (M-8222, Cl, F, Cl, n-Hex, Cl), (M-8223, Cl, F, Cl, n-Hex, F), (M-8224, Cl, F, Cl, n-Hex, CF$_3$), (M-8225, Cl, F, Cl, n-Hex, Br), (M-8226, Cl, F, Cl, n-Hex, CH$_3$), (M-8227, Cl, F, Cl, c-Hex, H), (M-8228, Cl, F, Cl, c-Hex, Cl), (M-8229, Cl, F, Cl, c-Hex, F), (M-8230, Cl, F, Cl, c-Hex, CF$_3$), (M-8231, Cl, F, Cl, c-Hex, Br), (M-8232, Cl, F, Cl, c-Hex, CH$_3$), (M-8233, Cl, F, Cl, OH, H), (M-8234, Cl, F, Cl, OH, Cl), (M-8235, Cl, F, Cl, OH, F), (M-8236, Cl, F, Cl, OH, CF$_3$), (M-8237, Cl, F, Cl, OH, Br), (M-8238, Cl, F, Cl, OH, CH$_3$), (M-8239, Cl, F, Cl, EtO, H), (M-8240, Cl, F, Cl, EtO, Cl), (M-8241, Cl, F, Cl, EtO, F), (M-8242, Cl, F, Cl, EtO, CF$_3$), (M-8243, Cl, F, Cl, EtO, Br), (M-8244, Cl, F, Cl, EtO, CH$_3$), (M-8245, Cl, F, Cl, n-PrO, H), (M-8246, Cl, F, Cl, n-PrO, Cl), (M-8247, Cl, F, Cl, n-PrO, F), (M-8248, Cl, F, Cl, n-PrO, CF$_3$), (M-8249, Cl, F, Cl, n-PrO, Br), (M-8250, Cl, F, Cl, n-PrO, CH$_3$), (M-8251, Cl, F, Cl, PhO, H), (M-8252, Cl, F, Cl, PhO, Cl), (M-8253, Cl, F, Cl, PhO, F), (M-8254, Cl, F, Cl, PhO, CF$_3$), (M-8255, Cl, F, Cl, PhO, Br), (M-8256, Cl, F, Cl, PhO, CH$_3$), (M-8257, Cl, F, Cl, BnO, H), (M-8258, Cl, F, Cl, BnO, Cl), (M-8259, Cl, F, Cl, BnO, F), (M-8260, Cl, F, Cl, BnO, CF$_3$), (M-8261, Cl, F, Cl, BnO, Br), (M-8262, Cl, F, Cl, BnO, CH$_3$), (M-8263, Cl, F, Cl, PhCH$_2$CH$_2$O, H), (M-8264, Cl, F, Cl, PhCH$_2$CH$_2$O, Cl), (M-8265, Cl, F, Cl, PhCH$_2$CH$_2$O, F), (M-8266, Cl, F, Cl, PhCH$_2$CH$_2$O, CF$_3$), (M-8267, Cl, F, Cl, PhCH$_2$CH$_2$O, Br), (M-8268, Cl, F, Cl, PhCH$_2$CH$_2$O, CH$_3$), (M-8269, Cl, F, Cl, CF$_3$O, H), (M-8270, Cl, F, Cl, CF$_3$O, Cl), (M-8271, Cl, F, Cl, CF$_3$O, F), (M-8272, Cl, F, Cl, CF$_3$O, CF$_3$), (M-8273, Cl, F, Cl, CF$_3$O, Br), (M-8274, Cl, F, Cl, CF$_3$O, CH$_3$), (M-8275, Cl, F, Cl, Ph, H), (M-8276, Cl, F, Cl, Ph, Cl), (M-8277, Cl, F, Cl, Ph, F), (M-8278, Cl, F, Cl, Ph, CF$_3$), (M-8279, Cl, F, Cl, Ph, Br), (M-8280, Cl, F, Cl, Ph, CH$_3$), (M-8281, Cl, F, Cl, 4-F-Ph, H), (M-8282, Cl, F, Cl, 4-F-Ph, Cl), (M-8283, Cl, F, Cl, 4-F-Ph, F), (M-8284, Cl, F, Cl, 4-F-Ph, CF$_3$), (M-8285, Cl, F, Cl, 4-F-Ph, Br), (M-8286, Cl, F, Cl, 4-F-Ph, CH$_3$), (M-8287, Cl, F, Cl, 4-CF$_3$-Ph, H), (M-8288, Cl, F, Cl, 4-CF$_3$-Ph, Cl), (M-8289, Cl, F, Cl, 4-CF$_3$-Ph, F), (M-8290, Cl, F, Cl, 4-CF$_3$-Ph, CF$_3$), (M-8291, Cl, F, Cl, 4-CF$_3$-Ph, Br), (M-8292, Cl, F, Cl, 4-CF$_3$-Ph, CH$_3$), (M-8293, Cl, F, Cl, 4-(Me)$_2$N-Ph, H), (M-8294, Cl, F, Cl, 4-(Me)$_2$N-Ph, Cl), (M-8295, Cl, F, Cl, 4-(Me)$_2$N-Ph, F), (M-8296, Cl, F, Cl, 4-(Me)$_2$N-Ph, CF$_3$), (M-8297, Cl, F, Cl, 4-(Me)$_2$N-Ph, Br), (M-8298, Cl, F, Cl, 4-(Me)$_2$N-Ph, CH$_3$), (M-8299, Cl, F, Cl, 4-OH-Ph, H), (M-8300, Cl, F, Cl, 4-OH-Ph, Cl), (M-8301, Cl, F, Cl, 4-OH-Ph, F), (M-8302, Cl, F, Cl, 4-OH-Ph, CF$_3$), (M-8303, Cl, F, Cl, 4-OH-Ph, Br), (M-8304, Cl, F, Cl, 4-OH-Ph, CH$_3$), (M-8305, Cl, F, Cl, 3,4-di-F-Ph, H), (M-8306, Cl, F, Cl, 3,4-di-F-Ph, Cl), (M-8307, Cl, F, Cl, 3,4-di-F-Ph, F), (M-8308, Cl, F, Cl, 3,4-di-F-Ph, CF$_3$), (M-8309, Cl, F, Cl, 3,4-di-F-Ph, Br), (M-8310, Cl, F, Cl, 3,4-di-F-Ph, CH$_3$), (M-8311, Cl, F, Cl, 4-COOH-Ph, H), (M-8312, Cl, F, Cl, 4-COOH-Ph, Cl), (M-8313, Cl, F, Cl, 4-COOH-Ph, F), (M-8314, Cl, F, Cl, 4-COOH-Ph, CF$_3$), (M-8315, Cl, F, Cl, 4-COOH-Ph, Br), (M-8316, Cl, F, Cl, 4-COOH-Ph, CH$_3$), (M-8317, Cl, F, Cl, Bn, H), (M-8318, Cl, F, Cl, Bn, Cl), (M-8319, Cl, F, Cl, Bn, F), (M-8320, Cl, F, Cl, Bn, CF$_3$), (M-8321, Cl, F, Cl, Bn, Br), (M-8322, Cl, F, Cl, Bn, CH$_3$), (M-8323, Cl, F, Cl, 4-F-Bn, H), (M-8324, Cl, F, Cl, 4-F-Bn, Cl), (M-8325, Cl, F, Cl, 4-F-Bn, F), (M-8326, Cl, F, Cl, 4-F-Bn, CF$_3$), (M-8327, Cl, F, Cl, 4-F-Bn, Br), (M-8328, Cl, F, Cl, 4-F-Bn, CH$_3$), (M-8329, Cl, F, Cl, 2-Py, H), (M-8330, Cl, F, Cl, 2-Py, Cl), (M-8331, Cl, F, Cl, 2-Py, F), (M-8332, Cl, F, Cl, 2-Py, CF$_3$), (M-8333, Cl, F, Cl, 2-Py, Br), (M-8334, Cl, F, Cl, 2-Py, CH$_3$), (M-8335, Cl, F, Cl, 3-Py, H), (M-8336, Cl, F, Cl, 3-Py, Cl), (M-8337, Cl, F, Cl, 3-Py, F), (M-8338, Cl, F, Cl, 3-Py, CF$_3$), (M-8339, Cl, F, Cl, 3-Py, Br), (M-8340, Cl, F, Cl, 3-Py, CH$_3$), (M-8341, Cl, F, Cl, 4-Py, H), (M-8342, Cl, F, Cl, 4-Py, Cl), (M-8343, Cl, F, Cl, 4-Py, F), (M-8344, Cl, F, Cl, 4-Py, CF$_3$), (M-8345, Cl, F, Cl, 4-Py, Br), (M-8346, Cl, F, Cl, 4-Py, CH$_3$), (M-8347, Cl, F, Cl, 2-Th, H), (M-8348, Cl, F, Cl, 2-Th, Cl), (M-8349, Cl, F, Cl, 2-Th, F), (M-8350, Cl, F, Cl, 2-Th, CF$_3$), (M-8351, Cl, F, Cl, 2-Th, Br), (M-8352, Cl, F, Cl, 2-Th, CH$_3$), (M-8353, Cl, F, Cl, 3-Th, H), (M-8354, Cl, F, Cl, 3-Th, Cl), (M-8355, Cl, F, Cl, 3-Th, F), (M-8356, Cl, F, Cl, 3-Th, CF$_3$), (M-8357, Cl, F, Cl, 3-Th, Br), (M-8358, Cl, F, Cl, 3-Th, CH$_3$), (M-8359, Cl, F, Cl, pyrrazol-2-yl, H), (M-8360, Cl, F, Cl, pyrrazol-2-yl, Cl), (M-8361, Cl, F, Cl, pyrrazol-2-yl, F), (M-8362, Cl, F, Cl, pyrrazol-2-yl, CF$_3$), (M-8363, Cl, F, Cl, pyrrazol-2-yl, Br), (M-8364, Cl, F, Cl, pyrrazol-2-yl, CH$_3$), (M-8365, Cl, F, Cl, pyrrazol-3-yl, H), (M-8366, Cl, F, Cl, pyrrazol-3-yl, Cl), (M-8367, Cl, F, Cl, pyrrazol-3-yl, F), (M-8368, Cl, F, Cl, pyrrazol-3-yl, CF$_3$), (M-8369, Cl, F, Cl, pyrrazol-3-yl, Br), (M-8370, Cl, F, Cl, pyrrazol-3-yl, CH$_3$), (M-8371, Cl, F, Cl, pyrimidin-2-yl, H), (M-8372, Cl, F, Cl, pyrimidin-2-yl, Cl), (M-8373, Cl, F, Cl, pyrimidin-2-yl, F), (M-8374, Cl, F, Cl, pyrimidin-2-yl, CF$_3$), (M-8375, Cl, F, Cl, pyrimidin-2-yl, Br), (M-8376, Cl, F, Cl, pyrimidin-2-yl, CH$_3$), (M-8377, Cl, F, Cl, pyrimidin-4-yl, H), (M-8378, Cl, F, Cl, pyrimidin-4-yl, Cl), (M-8379, Cl, F, Cl, pyrimidin-4-yl, F), (M-8380, Cl, F, Cl, pyrimidin-4-yl, CF$_3$), (M-8381, Cl, F, Cl, pyrimidin-4-yl, Br), (M-8382, Cl, F, Cl, pyrimidin-4-yl, CH$_3$), (M-8383, Cl, F, Cl, pyrimidin-5-yl, H), (M-8384, Cl, F, Cl, pyrimidin-5-yl, Cl), (M-8385, Cl, F, Cl, pyrimidin-5-yl, F), (M-8386, Cl, F, Cl, pyrimidin-5-yl, CF$_3$), (M-8387, Cl, F, Cl, pyrimidin-5-yl, Br), (M-8388, Cl, F, Cl, pyrimidin-5-yl, CH₃), (M-8389, Cl, F, Cl, HOOCCH₂CH₂CH₂, H), (M-8390, Cl, F, Cl, HOOCCH₂CH₂CH₂, Cl), (M-8391, Cl, F, Cl, HOOCCH₂CH₂CH₂, F), (M-8392, Cl, F, Cl, HOOCCH₂CH₂CH₂, CF₃), (M-8393, Cl, F, Cl, HOOCCH₂CH₂CH₂, Br), (M-8394, Cl, F, Cl, HOOCCH₂CH₂CH₂, CH₃), (M-8395, Cl, F, Cl, HOOCCH₂CH₂CH₂CH₂, H), (M-8396, Cl, F, Cl, HOOCCH₂CH₂CH₂CH₂, Cl), (M-8397, Cl, F, Cl, HOOCCH₂CH₂CH₂CH₂, F), (M-8398, Cl, F, Cl, HOOCCH₂CH₂CH₂CH₂, CF₃), (M-8399, Cl, F, Cl, HOOCCH₂CH₂CH₂CH₂, Br), (M-8400, Cl, F, Cl, HOOCCH₂CH₂CH₂CH₂, CH₃), (M-8401, Cl, F, Cl, (Me)₂NCOCH₂CH₂CH₂CH₂, H), (M-8402, Cl, F, Cl, (Me)₂NCOCH₂CH₂CH₂CH₂, Cl), (M-8403, Cl, F, Cl, (Me)₂NCOCH₂CH₂CH₂CH₂, F), (M-8404, Cl, F, Cl, (MO)₂NCOCH₂CH₂CH₂CH₂, CF₃), (M-8405, Cl, F, Cl, (Me)₂NCOCH₂CH₂CH₂CH₂, Br), (M-8406, Cl, F, Cl, (Me)₂NCOCH₂CH₂CH₂CH₂, CH₃), (M-8407, Cl, F, Cl, (Me)₂NCOCH₂CH₂CH₂CH₂CH₂, H), (M-8408, Cl, F, Cl, (Me)₂NCOCH₂CH₂CH₂CH₂CH₂, Cl), (M-8409, Cl, F, Cl, (Me)₂NCOCH₂CH₂CH₂CH₂CH₂, F), (M-8410, Cl, F, Cl, (Me)₂NCOCH₂CH₂CH₂CH₂CH₂, CF₃), (M-8411, Cl, F, Cl, (Me)₂NCOCH₂CH₂CH₂CH₂CH₂, Br), (M-8412, Cl, F, Cl, (Me)₂NCOCH₂CH₂CH₂CH₂CH₂, CH₃), (M-8413, Cl, F, Cl, MeOCH₂, H), (M-8414, Cl, F, Cl, MeOCH₂, Cl), (M-8415, Cl, F, Cl, MeOCH₂, F), (M-8416, Cl, F, Cl, MeOCH₂, CF₃), (M-8417, Cl, F, Cl, MeOCH₂, Br), (M-8418, Cl, F, Cl, MeOCH₂, CH₃), (M-8419, Cl, F, Cl, EtOCH₂, H), (M-8420, Cl, F, Cl, EtOCH₂, Cl), (M-8421, Cl, F, Cl, EtOCH₂, F), (M-8422, Cl, F, Cl, EtOCH₂, CF₃), (M-8423, Cl, F, Cl, EtOCH₂, Br), (M-8424, Cl, F, Cl, EtOCH₂, CH₃), (M-8425, Cl, F, Cl, EtOCH₂CH₂, H), (M-8426, Cl, F, Cl, EtOCH₂CH₂, Cl), (M-8427, Cl, F, Cl, EtOCH₂CH₂, F), (M-8428, Cl, F, Cl, EtOCH₂CH₂, CF₃), (M-8429, Cl, F, Cl, EtOCH₂CH₂, Br), (M-8430, Cl, F, Cl, EtOCH₂CH₂, CH₃), (M-8431, Cl, F, Cl, MeOCH₂CH₂OCH₂CH₂, H), (M-8432, Cl, F, Cl, MeOCH₂CH₂OCH₂CH₂, Cl), (M-8433, Cl, F, Cl, MeOCH₂CH₂OCH₂CH₂, F), (M-8434, Cl, F, Cl, MeOCH₂CH₂OCH₂CH₂, CF₃), (M-8435, Cl, F, Cl, MeOCH₂CH₂OCH₂CH₂, Br), (M-8436, Cl, F, Cl, MeOCH₂CH₂OCH₂CH₂, CH₃), (M-8437, Cl, F, Cl, MeOCH₂CH₂, H), (M-8438, Cl, F, Cl, MeOCH₂CH₂, Cl), (M-8439, Cl, F, Cl, MeOCH₂CH₂, F), (M-8440, Cl, F, Cl, MeOCH₂CH₂, CF₃), (M-8441, Cl, F, Cl, MeOCH₂CH₂, Br), (M-8442, Cl, F, Cl, MeOCH₂CH₂, CH₃), (M-8443, Cl, F, Cl, HOCH₂, H), (M-8444, Cl, F, Cl, HOCH₂, Cl), (M-8445, Cl, F, Cl, HOCH₂, F), (M-8446, Cl, F, Cl, HOCH₂, CF₃), (M-8447, Cl, F, Cl, HOCH₂, Br), (M-8448, Cl, F, Cl, HOCH₂, CH₃), (M-8449, Cl, F, Cl, HOCH₂CH₂, H), (M-8450, Cl, F, Cl, HOCH₂CH₂, Cl), (M-8451, Cl, F, Cl, HOCH₂CH₂, F), (M-8452, Cl, F, Cl, HOCH₂CH₂, CF₃), (M-8453, Cl, F, Cl, HOCH₂CH₂, Br), (M-8454, Cl, F, Cl, HOCH₂CH₂, CH₃), (M-8455, Cl, F, Cl, HOCH₂CH₂CH₂, H), (M-8456, Cl, F, Cl, HOCH₂CH₂CH₂, Cl), (M-8457, Cl, F, Cl, HOCH₂CH₂CH₂, F), (M-8458, Cl, F, Cl, HOCH₂CH₂CH₂, CF₃), (M-8459, Cl, F, Cl, HOCH₂CH₂CH₂, Br), (M-8460, Cl, F, Cl, HOCH₂CH₂CH₂, CH₃), (M-8461, Cl, F, Cl, HOCH₂CH₂CH₂CH₂, H), (M-8462, Cl, F, Cl, HOCH₂CH₂CH₂CH₂, Cl), (M-8463, Cl, F, Cl, HOCH₂CH₂CH₂CH₂, F), (M-8464, Cl, F, Cl, HOCH₂CH₂CH₂CH₂, CF₃), (M-8465, Cl, F, Cl, HOCH₂CH₂CH₂CH₂, Br), (M-8466, Cl, F, Cl, HOCH₂CH₂CH₂CH₂, CH₃), (M-8467, Cl, F, Cl, HOCH₂CH₂CH₂CH₂CH₂, H), (M-8468, Cl, F, Cl, HOCH₂CH₂CH₂CH₂CH₂, Cl), (M-8469, Cl, F, Cl, HOCH₂CH₂CH₂CH₂CH₂, F), (M-8470, Cl, F, Cl, HOCH₂CH₂CH₂CH₂CH₂, CF₃), (M-8471, Cl, F, Cl, HOCH₂CH₂CH₂CH₂CH₂, Br), (M-8472, Cl, F, Cl, HOCH₂CH₂CH₂CH₂CH₂, CH₃), (M-8473, Cl, F, Cl, HOCH₂CH₂OCH₂CH₂, H), (M-8474, Cl, F, Cl, HOCH₂CH₂OCH₂CH₂, Cl), (M-8475, Cl, F, Cl, HOCH₂CH₂OCH₂CH₂, F), (M-8476, Cl, F, Cl, HOCH₂CH₂OCH₂CH₂, CF₃), (M-8477, Cl, F, Cl, HOCH₂CH₂OCH₂CH₂, Br), (M-8478, Cl, F, Cl, HOCH₂CH₂OCH₂CH₂, CH₃), (M-8479, Cl, F, Cl, (Me)₂N, H), (M-8480, Cl, F, Cl, (Me)₂N, Cl), (M-8481, Cl, F, Cl, (Me)₂N, F), (M-8482, Cl, F, Cl, (Me)₂N, CF₃), (M-8483, Cl, F, Cl, (Me)₂N, Br), (M-8484, Cl, F, Cl, (Me)₂N, CH₃), (M-8485, Cl, F, Cl, piperidin-4-yl-methyl, H), (M-8486, Cl, F, Cl, piperidin-4-yl-methyl, Cl), (M-8487, Cl, F, Cl, piperidin-4-yl-methyl, F), (M-8488, Cl, F, Cl, piperidin-4-yl-methyl, CF₃), (M-8489, Cl, F, Cl, piperidin-4-yl-methyl, Br), (M-8490, Cl, F, Cl, piperidin-4-yl-methyl, CH₃), (M-8491, Cl, F, Cl, cyclohexylmethyl, H), (M-8492, Cl, F, Cl, cyclohexylmethyl, Cl), (M-8493, Cl, F, Cl, cyclohexylmethyl, F), (M-8494, Cl, F, Cl, cyclohexylmethyl, CF₃), (M-8495, Cl, F, Cl, cyclohexylmethyl, Br), (M-8496, Cl, F, Cl, cyclohexylmethyl, CH₃), (M-8497, Cl, CH₃, H, H, H), (M-8498, Cl, CH₃, H, H, Cl), (M-8499, Cl, CH₃, H, H, F), (M-8500, Cl, CH₃, H, H, CF₃), (M-8501, Cl, CH₃, H, H, Br), (M-8502, Cl, CH₃, H, H, CH₃), (M-8503, Cl, CH₃, H, F, H), (M-8504, Cl, CH₃, H, F, Cl), (M-8505, Cl, CH₃, H, F, F), (M-8506, Cl, CH₃, H, F, CF₃), (M-8507, Cl, CH₃, H, F, Br), (M-8508, Cl, CH₃, H, F, CH₃), (M-8509, Cl, CH₃, H, Cl, H), (M-8510, Cl, CH₃, H, Cl, Cl), (M-8511, Cl, CH₃, H, Cl, F), (M-8512, Cl, CH₃, H, Cl, CF₃), (M-8513, Cl, CH₃, H, Cl, Br), (M-8514, Cl, CH₃, H, Cl, CH₃), (M-8515, Cl, CH₃, H, CH₃, H), (M-8516, Cl, CH₃, H, CH₃, Cl), (M-8517, Cl, CH₃, H, CH₃, F), (M-8518, Cl, CH₃, H, CH₃, CF₃), (M-8519, Cl, CH₃, H, CH₃, Br), (M-8520, Cl, CH₃, H, CH₃, CH₃), (M-8521, Cl, CH₃, H, Et, H), (M-8522, Cl, CH₃, H, Et, Cl), (M-8523, Cl, CH₃, H, Et, F), (M-8524, Cl, CH₃, H, Et, CF₃), (M-8525, Cl, CH₃, H, Et, Br), (M-8526, Cl, CH₃, H, Et, CH₃), (M-8527, Cl, CH₃, H, n-Pr, H), (M-8528, Cl, CH₃, H, n-Pr, Cl), (M-8529, Cl, CH₃, H, n-Pr, F), (M-8530, Cl, CH₃, H, n-Pr, CF₃), (M-8531, Cl, CH₃, H, n-Pr, Br), (M-8532, Cl, CH₃, H, n-Pr, CH₃), (M-8533, Cl, CH₃, H, c-Pr, H), (M-8534, Cl, CH₃, H, c-Pr, Cl), (M-8535, Cl, CH₃, H, c-Pr, F), (M-8536, Cl, CH₃, H, c-Pr, CF₃), (M-8537, Cl, CH₃, H, c-Pr, Br), (M-8538, Cl, CH₃, H, c-Pr, CH₃), (M-8539, Cl, CH₃, H, i-Pr, HI), (M-8540, Cl, CH₃, H, i-Pr, Cl), (M-8541, Cl, CH₃, H, i-Pr, F), (M-8542, Cl, CH₃, H, i-Pr, CF₃), (M-8543, Cl, CH₃, H, i-Pr, Br), (M-8544, Cl, CH₃, H, i-Pr, CH₃), (M-8545, Cl, CH₃, H, n-Bu, H), (M-8546, Cl, CH₃, H, n-Bu, Cl), (M-8547, Cl, CH₃, H, n-Bu, F), (M-8548, Cl, CH₃, H, n-Bu, CF₃), (M-8549, Cl, CH₃, H, n-Bu, Br), (M-8550, Cl, CH₃, H, n-Bu, CH₃), (M-8551, Cl, CH₃, H, i-Bu, H), (M-8552, Cl, CH₃, H, i-Bu, Cl), (M-8553, Cl, CH₃, H, i-Bu, F), (M-8554, Cl, CH₃, H, i-Bu, CF₃), (M-8555, Cl, CH₃, H, i-Bu, Br), (M-8556, Cl, CH₃, H, i-Bu, CH₃), (M-8557, Cl, CH₃, H, sec-Bu, H), (M-8558, Cl, CH₃, H, sec-Bu, Cl), (M-8559, Cl, CH₃, H, sec-Bu, F), (M-8560, Cl, CH₃, H, sec-Bu, CF₃), (M-8561, Cl, CH₃, H, sec-Bu, Br), (M-8562, Cl, CH₃, H, sec-Bu, CH₃), (M-8563, Cl, CH₃, H, n-Pen, H), (M-8564, Cl, CH₃, H, n-Pen, Cl), (M-8565, Cl, CH₃, H, n-Pen, F), (M-8566, Cl, CH₃, H, n-Pen, CF₃), (M-8567, Cl, CH₃, H, n-Pen, Br), (M-8568, Cl, CH₃, H, n-Pen, CH₃), (M-8569, Cl, CH₃, H, c-Pen, H), (M-8570, Cl, CH₃, H, c-Pen, Cl), (M-8571, Cl, CH₃, H, c-Pen, F), (M-8572, Cl, CH₃, H, c-Pen, CF₃), (M-8573, Cl, CH₃, H, c-Pen, Br), (M-8574, Cl, CH₃, H, c-Pen, CH₃), (M-8575, Cl, CH₃, H, n-Hex, H), (M-8576, Cl, CH₃, H, n-Hex, Cl), (M-8577, Cl, CH₃, H, n-Hex, F), (M-8578, Cl, CH₃, H, n-Hex, CF₃), (M-8579, Cl, CH₃, H, n-Hex, Br), (M-8580, Cl, CH₃, H, n-Hex, CH₃), (M-8581, Cl, CH₃, H, c-Hex, H), (M-8582, Cl, CH₃, H, c-Hex, Cl), (M-8583, Cl, CH₃, H, c-Hex, F), (M-8584, Cl, CH₃, H, c-Hex, CF₃), (M-8585, Cl, CH₃, H, c-Hex, Br), (M-8586, Cl, CH₃, H, c-Hex, CH₃), (M-8587, Cl, CH₃, H, OH, H), (M-8588, Cl, CH₃, H, OH, Cl), (M-8589, Cl, CH₃, H, OH, F), (M-8590, Cl, CH₃, H, OH, CF₃), (M-8591, Cl, CH₃, H, OH, Br), (M-8592, Cl, CH₃, H, OH, CH₃), (M-8593, Cl, CH₃, H, EtO, H), (M-8594, Cl, CH₃, H, EtO, Cl), (M-8595, Cl, CH₃, H, EtO, F), (M-8596, Cl, CH₃, H, EtO, CF₃), (M-8597, Cl, CH₃, H, EtO, Br), (M-8598, Cl, CH₃, H, EtO, CH₃), (M-8599, Cl, CH₃, H, n-PrO, H), (M-8600, Cl, CH₃, H, n-PrO, Cl), (M-8601, Cl, CH₃, H, n-PrO, F), (M-8602, Cl, CH₃, H, n-PrO, CF₃), (M-8603, Cl, CH₃, H, n-PrO, Br), (M-8604, Cl, CH₃, H, n-PrO, CH₃), (M-8605, Cl, CH₃, H, PhO, H), (M-8606, Cl, CH₃, H, PhO, Cl), (M-8607, Cl, CH₃, H, PhO, F), (M-8608, Cl, CH₃, H, PhO, CF₃), (M-8609, Cl, C₃, H, PhO, Br), (M-8610, Cl, CH₃, H, PhO, CH₃), (M-8611, Cl, CH₃, H, BnO, H), (M-8612, Cl, CH₃, H, BnO, Cl), (M-8613, Cl, CH₃, H, BnO, F), (M-8614, Cl, CH₃, H, BnO, CF₃), (M-8615, Cl, CH₃, H, BnO, Br), (M-8616, Cl, CH₃, H, BnO, CH₃), (M-8617, Cl, CH₃, H, PhCH₂CH₂O, H), (M-8618, Cl, CH₃, H, PhCH₂CH₂O, Cl), (M-8619, Cl, CH₃, H, PhCH₂CH₂O, F), (M-8620, Cl, CH₃, H, PhCH₂CH₂O, CF₃), (M-8621, Cl, CH₃, H, PhCH₂CH₂O, Br), (M-8622, Cl, CH₃, H, PhCH₂CH₂O, CH₃), (M-8623, Cl, CH₃, H, CF₃O, H), (M-8624, Cl, CH₃, H, CF₃O, Cl), (M-8625, Cl, CH₃, H, CF₃O, F), (M-8626, Cl, CH₃, H, CF₃O, CF₃), (M-8627, Cl, CH₃, H, CF₃O, Br), (M-8628, Cl, CH₃, H, CF₃O, CH₃), (M-8629, Cl, CH₃, H, Ph, H), (M-8630, Cl, CH₃, H, Ph, Cl), (M-8631, Cl, CH₃, H, Ph, F), (M-8632, Cl, CH₃, H, Ph, CF₃), (M-8633, Cl, CH₃, H, Ph, Br), (M-8634, Cl, CH₃, H, Ph, CH₃), (M-8635, Cl, CH₃, H, 4-F-Ph, H), (M-8636, Cl, CH₃, H, 4-F-Ph, Cl), (M-8637, Cl, CH₃, H, 4-F-Ph, F), (M-8638, Cl, CH₃, H, 4-F-Ph, CF₃), (M-8639, Cl, CH₃, H, 4-F-Ph, Br), (M-8640, Cl, CH₃, H, 4-F-Ph, CH₃), (M-8641, Cl, CH₃, H, 4-CF₃-Ph, H), (M-8642, Cl, CH₃, H, 4-CF₃-Ph, Cl), (M-8643, Cl, CH₃, H, 4-CF₃-Ph, F), (M-8644, Cl, CH₃, H, 4-CF₃-Ph, CF₃), (M-8645, Cl, CH₃, H, 4-CF₃-Ph, Br), (M-8646, Cl, CH₃, H, 4-CF₃-Ph, CH₃), (M-8647, Cl, CH₃, H, 4-(Me)₂N-Ph, H), (M-8648, Cl, CH₃, H, 4-(Me)₂N-Ph, Cl), (M-8649, Cl, CH₃, H, 4-(Me)₂N-Ph, F), (M-8650, Cl, CH₃, H, 4-(Me)₂N-Ph, CF₃), (M-8651, Cl, CH₃, H, 4-(Me)₂N-Ph, Br), (M-8652, Cl, CH₃, H, 4-(Me)₂N-Ph, CH₃), (M-8653, Cl, CH₃, H, 4-OH-Ph, H), (M-8654, Cl, CH₃, H, 4-OH-Ph, Cl), (M-8655, Cl, CH₃, H, 4-OH-Ph, F), (M-8656, Cl, CH₃, H, 4-OH-Ph, CF₃), (M-8657, Cl, CH₃, H, 4-OH-Ph, Br), (M-8658, Cl, CH₃, H, 4-OH-Ph, CH₃), (M-8659, Cl, CH₃, H, 3,4-di-F-Ph, H), (M-8660, Cl, CH₃, H, 3,4-di-F-Ph, Cl), (M-8661, Cl, CH₃, H, 3,4-di-F-Ph, F), (M-8662, Cl, CH₃, H, 3,4-di-F-Ph, CF₃), (M-8663, Cl, CH₃, H, 3,4-di-F-Ph, Br), (M-8664, Cl, CH₃, H, 3,4-di-F-Ph, CH₃), (M-8665, Cl, CH₃, H, 4-COOH-Ph, H), (M-8666, Cl, CH₃, H, 4-COOH-Ph, Cl), (M-8667, Cl, CH₃, H, 4-COOH-Ph, F), (M-8668, Cl, CH₃, H, 4-COOH-Ph, CF₃), (M-8669, Cl, CH₃, H, 4-COOH-Ph, Br), (M-8670, Cl, CH₃, H, 4-COOH-Ph, CH₃), (M-8671, Cl, CH₃, H, Bn, H), (M-8672, Cl, CH₃, H, Bn, Cl), (M-8673, Cl, CH₃, H, Bn, F), (M-8674, Cl, CH₃, H, Bn, CF₃), (M-8675, Cl, CH₃, H, Bn, Br), (M-8676, Cl, CH₃, H, Bn, CH₃), (M-8677, Cl, CH₃, H, 4-F-Bn, H), (M-8678, Cl, CH₃, H, 4-F-Bn, Cl), (M-8679, Cl, CH₃, H, 4-F-Bn, F), (M-8680, Cl, CH₃, H, 4-F-Bn, CF₃), (M-8681, Cl, CH₃, H, 4-F-Bn, Br), (M-8682, Cl, CH₃, H, 4-F-Bn, CH₃), (M-8683, Cl, CH₃, H, 2-Py, H), (M-8684, Cl, CH₃, H, 2-Py, Cl), (M-8685, Cl, CH₃, H, 2-Py, F), (M-8686, Cl, CH₃, H, 2-Py, CF₃), (M-8687, Cl, CH₃, H, 2-Py, Br), (M-8688, Cl, CH₃, H, 2-Py, CH₃), (M-8689, Cl, CH₃, H, 3-Py, H), (M-8690, Cl, CH₃, H, 3-Py, Cl), (M-8691, Cl, CH₃, H, 3-Py, F), (M-8692, Cl, CH₃, H, 3-Py, CF₃), (M-8693, Cl, CH₃, H, 3-Py, Br), (M-8694, Cl, CH₃, H, 3-Py, CH₃), (M-8695, Cl, CH₃, H, 4-Py, H), (M-8696, Cl, CH₃, H, 4-Py, Cl), (M-8697, Cl, CH₃, H, 4-Py, F), (M-8698, Cl, CH₃, H, 4-Py, CF₃), (M-8699, Cl, CH₃, H, 4-Py, Br), (M-8700, Cl, CH₃, H, 4-Py, CH₃), (M-8701, Cl, CH₃, H, 2-Th, H), (M-8702, Cl, CH₃, H, 2-Th, Cl), (M-8703, Cl, CH₃, H, 2-Th, F), (M-8704, Cl, CH₃, H, 2-Th, CF₃), (M-8705, Cl, CH₃, H, 2-Th, Br), (M-8706, Cl, CH₃, H, 2-Th, CH₃), (M-8707, Cl, CH₃, H, 3-Th, H), (M-8708, Cl, CH₃, H, 3-Th, Cl), (M-8709, Cl, CH₃, H, 3-Th, F), (M-8710, Cl, CH₃, H, 3-Th, CF₃), (M-8711, Cl, CH₃, H, 3-Th, Br), (M-8712, Cl, CH₃, H, 3-Th, CH₃), (M-8713, Cl, CH₃, H, pyrrazol-2-yl, H), (M-8714, Cl, CH₃, H, pyrrazol-2-yl, Cl), (M-8715, Cl, CH₃, H, pyrrazol-2-yl, F), (M-8716, Cl, CH₃, H, pyrrazol-2-yl, CF₃), (M-8717, Cl, CH₃, H, pyrrazol-2-yl, Br), (M-8718, Cl, CH₃, H, pyrrazol-2-yl, CH₃), (M-8719, Cl, CH₃, H, pyrrazol-3-yl, H), (M-8720, Cl, CH₃, H, pyrrazol-3-yl, Cl), (M-8721, Cl, CH₃, H, pyrrazol-3-yl, F), (M-8722, Cl, CH₃, H, pyrrazol-3-yl, CF₃), (M-8723, Cl, CH₃, H, pyrrazol-3-yl, Br), (M-8724, Cl, CH₃, H, pyrrazol-3-yl, CH₃), (M-8725, Cl, CH₃, H, pyrimidin-2-yl, H), (M-8726, Cl, CH₃, H, pyrimidin-2-yl, Cl), (M-8727, Cl, CH₃, H, pyrimidin-2-yl, F), (M-8728, Cl, CH₃, H, pyrimidin-2-yl, CF₃), (M-8729, Cl, CH₃, H, pyrimidin-2-yl, Br), (M-8730, Cl, CH₃, H, pyrimidin-2-yl, CH₃), (M-8731, Cl, CH₃, H, pyrimidin-4-yl, H), (M-8732, Cl, CH₃, H, pyrimidin-4-yl, Cl), (M-8733, Cl, CH₃, H, pyrimidin-4-yl, F), (M-8734, Cl, CH₃, H, pyrimidin-4-yl, CF₃), (M-8735, Cl, CH₃, H, pyrimidin-4-yl, Br), (M-8736, Cl, CH₃, H, pyrimidin-4-yl, CH₃), (M-8737, Cl, CH₃, H, pyrimidin-5-yl, H), (M-8738, Cl, CH₃, H, pyrimidin-5-yl, Cl), (M-8739, Cl, CH₃, H, pyrimidin-5-yl, F), (M-8740, Cl, CH₃, H, pyrimidin-5-yl, CF₃), (M-8741, Cl, CH₃, H, pyrimidin-5-yl, Br), (M-8742, Cl, CH₃, H, pyrimidin-5-yl, CH₃), (M-8743, Cl, CH₃, H, HOOCCH₂CH₂CH₂, H), (M-8744, Cl, CH₃, H, HOOCCH₂CH₂CH₂, Cl), (M-8745, Cl, CH₃, H, HOOCCH₂CH₂CH₂, F), (M-8746, Cl, CH₃, H, HOOCCH₂CH₂CH₂, CF₃), (M-8747, Cl, CH₃, H, HOOCCH₂CH₂CH₂, Br), (M-8748, Cl, CH₃, H, HOOCCH₂CH₂CH₂, CH₃), (M-8749, Cl, CH₃, H, HOOCCH₂CH₂CH₂CH₂, H), (M-8750, Cl, CH₃, H, HOOCCH₂CH₂CH₂CH₂, Cl), (M-8751, Cl, CH₃, H, HOOCCH₂CH₂CH₂CH₂, F), (M-8752, Cl, CH₃, H, HOOCCH₂CH₂CH₂CH₂, CF₃), (M-8753, Cl, CH₃, H, HOOCCH₂CH₂CH₂CH₂, Br), (M-8754, Cl, CH₃, H, HOOCCH₂CH₂CH₂CH₂, CH₃), (M-8755, Cl, CH₃, H, (Me)₂NCOCH₂CH₂CH₂CH₂, H), (M-8756, Cl, CH₃, H, (Me)₂NCOCH₂CH₂CH₂CH₂, Cl), (M-8757, Cl, CH₃, H, (Me)₂NCOCH₂CH₂CH₂CH₂, F), (M-8758, Cl, CH₃, H, (Me)₂NCOCH₂CH₂CH₂CH₂, CF₃), (M-8759, Cl, CH₃, H, (Me)₂NCOCH₂CH₂CH₂CH₂, Br), (M-8760, Cl, CH₃, H, (Me)₂NCOCH₂CH₂CH₂CH₂, CH₃), (M-8761, Cl, CH₃, H, (Me)₂NCOCH₂CH₂CH₂CH₂CH₂, H), (M-8762, Cl, CH₃, H, (Me)₂NCOCH₂CH₂CH₂CH₂CH₂, Cl), (M-8763, Cl, CH₃, H, (Me)₂NCOCH₂CH₂CH₂CH₂CH₂, F), (M-8764, Cl, CH₃, H, (Me)₂NCOCH₂CH₂CH₂CH₂CH₂, CF₃), (M-8765, Cl, CH₃, H, (Me)₂NCOCH₂CH₂CH₂CH₂CH₂, Br), (M-8766, Cl, CH₃, H, (Me)₂NCOCH₂CH₂CH₂CH₂CH₂, CH₃), (M-8767, Cl, CH₃, H, MeOCH₂, H), (M-8768, Cl, CH₃, H, MeOCH₂, Cl), (M-8769, Cl, CH₃, H, MeOCH₂, F), (M-8770, Cl, CH₃, H, MeOCH₂, CF₃), (M-8771, Cl, CH₃, H, MeOCH₂, Br), (M-8772, Cl, CH₃, H, MeOCH₂, CH₃), (M-8773, Cl, CH₃, H, EtOCH₂, H), (M-8774, Cl, CH₃, H, EtOCH₂, Cl), (M-8775, Cl, CH₃, H, EtOCH₂, F), (M-8776, Cl, CH₃, H, EtOCH₂, CF₃), (M-8777, Cl, CH₃, H, EtOCH₂, Br), (M-8778, Cl, CH₃, H, EtOCH₂, CH₃), (M-8779, Cl, CH₃, H, EtOCH₂CH₂, H), (M-8780, Cl, CH₃, H, EtOCH₂CH₂, Cl), (M-8781, Cl, CH₃, H, EtOCH₂CH₂, F), (M-8782, Cl, CH₃, H, EtOCH₂CH₂, CF₃), (M-8783, Cl, CH₃, H, EtOCH₂CH₂, Br), (M-8784, Cl, CH₃, H, EtOCH₂CH₂, CH₃), (M-8785, Cl, CH₃, H, MeOCH₂CH₂OCH₂CH₂, H), (M-8786, Cl, CH₃, H, MeOCH₂CH₂OCH₂CH₂, Cl), (M-8787, Cl, CH₃, H, MeOCH₂CH₂OCH₂CH₂, F), (M-8788, Cl, CH₃, H, MeOCH₂CH₂OCH₂CH₂, CF₃), (M-8789, Cl, CH₃, H, MeOCH₂CH₂OCH₂CH₂, Br), (M-8790, Cl, CH₃, H, MeOCH₂CH₂OCH₂CH₂, CH₃), (M-8791, Cl, CH₃, H, MeOCH₂CH₂, H), (M-8792, Cl, CH₃, H, MeOCH₂CH₂, Cl), (M-8793, Cl, CH₃, H, MeOCH₂CH₂, F), (M-8794, Cl, CH₃, H, MeOCH₂CH₂, CF₃), (M-8795, Cl, CH₃, H, MeOCH₂CH₂, Br), (M-8796, Cl, CH₃, H, MeOCH₂CH₂, CH₃), (M-8797, Cl, CH₃, H, HOCH₂, H), (M-8798, Cl, CH₃, H, HOCH₂, Cl), (M-8799, Cl, CH₃, H, HOCH₂, F), (M-8800, Cl, CH₃, H, HOCH₂, CF₃), (M-8801, Cl, CH₃, H, HOCH₂, Br), (M-8802, Cl, CH₃, H, HOCH₂, CH₃), (M-8803, Cl, CH₃, H, HOCH₂CH₂, H), (M-8804, Cl, CH₃, H, HOCH₂CH₂, Cl), (M-8805, Cl, CH₃, H, HOCH₂CH₂, F), (M-8806, Cl, CH₃, H, HOCH₂CH₂, CF₃), (M-8807, Cl, CH₃, H, HOCH₂CH₂, Br), (M-8808, Cl, CH₃, H, HOCH₂CH₂, CH₃), (M-8809, Cl, CH₃, H, HOCH₂CH₂CH₂, H), (M-8810, Cl, CH₃, H, HOCH₂CH₂CH₂, Cl), (M-8811, Cl, CH₃, H, HOCH₂CH₂CH₂, F), (M-8812, Cl, CH₃, H, HOCH₂CH₂CH₂, CF₃), (M-8813, Cl, CH₃, H, HOCH₂CH₂CH₂, Br), (M-8814, Cl, CH₃, H, HOCH₂CH₂CH₂, CH₃), (M-8815, Cl, CH₃, H, HOCH₂CH₂CH₂CH₂, H), (M-8816, Cl, CH₃, H, HOCH₂CH₂CH₂CH₂, Cl), (M-8817, Cl, CH₃, H, HOCH₂CH₂CH₂CH₂, F), (M-8818, Cl, CH₃, H, HOCH₂CH₂CH₂CH₂, CF₃), (M-8819, Cl, CH₃, H, HOCH₂CH₂CH₂CH₂, Br), (M-8820, Cl, CH₃, H, HOCH₂CH₂CH₂CH₂, CH₃), (M-8821, Cl, CH₃, H, HOCH₂CH₂CH₂CH₂CH₂, H), (M-8822, Cl, CH₃, H, HOCH₂CH₂CH₂CH₂CH₂Cl), (M-8823, Cl, CH₃H, HOCH₂CH₂CH₂CH₂CH₂, F), (M-8824, Cl, CH₃, H, HOCH₂CH₂CH₂CH₂CH₂, CF₃), (M-8825, Cl, CH₃, H, HOCH₂CH₂CH₂CH₂CH₂, Br), (M-8826, Cl, CH₃, H, HOCH₂CH₂CH₂CH₂CH₂, CH₃), (M-8827, Cl, CH₃, H, HOCH₂CH₂OCH₂CH₂, H), (M-8828, Cl, CH₃, H, HOCH₂CH₂OCH₂CH₂, Cl), (M-8829, Cl, CH₃, H, HOCH₂CH₂OCH₂CH₂, F), (M-8830, Cl, CH₃, H, HOCH₂CH₂OCH₂CH₂, CF₃), (M-8831, Cl, CH₃, H, HOCH₂CH₂OCH₂CH₂, Br), (M-8832, Cl, CH₃, H, HOCH₂CH₂OCH₂CH₂, CH₃), (M-8833, Cl, CH₃, H, (Me)₂N, H), (M-8834, Cl, CH₃, H, (Me)₂N, Cl), (M-8835, Cl, CH₃, H, (Me)₂N, F), (M-8836, Cl, CH₃, H, (Me)₂N, CF₃), (M-8837, Cl, CH₃, H, (Me)₂N, Br), (M-8838, Cl, CH₃, H, (Me)₂N, CH₃), (M-8839, Cl, CH₃, H, piperidin-4-yl-methyl, H), (M-8840, Cl, CH₃, H, piperidin-4-yl-methyl, Cl), (M-8841, Cl, CH₃, H, piperidin-4-yl-methyl, F), (M-8842, Cl, CH₃, H, piperidin-4-yl-methyl, CF₃), (M-8843, Cl, CH₃, H, piperidin-4-yl-methyl, Br), (M-8844, Cl, CH₃, H, piperidin-4-yl-methyl, CH₃), (M-8845, Cl, CH₃, H, cyclohexylmethyl, H), (M-8846, Cl, CH₃, H, cyclohexylmethyl, Cl), (M-8847, Cl, CH₃, H, cyclohexylmethyl, F), (M-8848, Cl, CH₃, H, cyclohexylmethyl, CF₃), (M-8849, Cl, CH₃, H, cyclohexylmethyl, Br), (M-8850, Cl, CH₃, H, cyclohexylmethyl, CH₃), (M-8851, Cl, CH₃, F, H, H), (M-8852, Cl, CH₃, F, H, Cl), (M-8853, MeO, CH₃, F, H, F), (M-8854, Cl, CH₃, F, H, CF₃), (M-8855, Cl, CH₃, F, H, Br), (M-8856, Cl, CH₃, F, H, CH₃), (M-8857, Cl, CH₃, F, F, H), (M-8858, Cl, CH₃, F, F, Cl), (M-8859, Cl, CH₃, F, F, F), (M-8860, Cl, CH₃, F, F, CF₃), (M-8861, Cl, CH₃, F, F, Br), (M-8862, Cl, CH₃, F, F, CH₃), (M-8863, Cl, CH₃, F, Cl, H), (M-8864, Cl, CH₃, F, Cl, Cl), (M-8865, Cl, CH₃, F, Cl, F), (M-8866, Cl, CH₃, F, Cl, CF₃), (M-8867, Cl, CH₃, F, Cl, Br), (M-8868, Cl, CH₃, F, Cl, CH₃), (M-8869, Cl, CH₃, F, CH₃, H), (M-8870, Cl, CH₃, F, CH₃, Cl), (M-8871, Cl, CH₃, F, CH₃, F), (M-8872, Cl, CH₃, F, CH₃, CF₃), (M-8873, Cl, CH₃, F, CH₃, Br), (M-8874, Cl, CH₃, F, CH₃, CH₃), (M-8875, Cl, CH₃, F, Et, H), (M-8876, Cl, CH₃, F, Et, Cl), (M-8877, Cl, CH₃, F, Et, F), (M-8878, Cl, CH₃, F, Et, CF₃), (M-8879, Cl, CH₃, F, Et, Br), (M-8880, Cl, CH₃, F, Et, CH₃), (M-8881, Cl, CH₃, F, n-Pr, H), (M-8882, Cl, CH₃, F, n-Pr, Cl), (M-8883, Cl, CH₃, F, n-Pr, F), (M-8884, Cl, CH₃, F, n-Pr, CF₃), (M-8885, Cl, CH₃, F, n-Pr, Br), (M-8886, Cl, CH₃, F, n-Pr, CH₃), (M-8887, Cl, CH₃, F, c-Pr, H), (M-8888, Cl, CH₃, F, c-Pr, Cl), (M-8889, Cl, CH₃, F, c-Pr, F), (M-8890, Cl, CH₃, F, c-Pr, CF₃), (M-8891, Cl, CH₃, F, c-Pr, Br), (M-8892, Cl, CH₃, F, c-Pr, CH₃), (M-8893, Cl, CH₃, F, i-Pr, H), (M-8894, Cl, C₃, F, i-Pr, Cl), (M-8895, Cl, CH₃, F, i-Pr, F), (M-8896, Cl, CH₃, F, i-Pr, CF₃), (M-8897, Cl, CH₃, F, i-Pr, Br), (M-8898, Cl, CH₃, F, i-Pr, CH₃), (M-8899, Cl, CH₃, F, n-Bu, H), (M-8900, Cl, CH₃, F, n-Bu, Cl), (M-8901, Cl, CH₃, F, n-Bu, F), (M-8902, Cl, CH₃, F, n-Bu, CF₃), (M-8903, Cl, CH₃, F, n-Bu, Br), (M-8904, Cl, CH₃, F, n-Bu, CH₃), (M-8905, Cl, CH₃, F, i-Bu, H), (M-8906, Cl, CH₃, F, i-Bu, Cl), (M-8907, Cl, CH₃, F, i-Bu, F), (M-8908, Cl, C₃, F, i-Bu, CF₃), (M-8909, Cl, CH₃, F, i-Bu, Br), (M-8910, Cl, CH₃, F, i-Bu, CH₃), (M-8911, Cl, CH₃, F, sec-Bu, H), (M-8912, Cl, CH₃, F, sec-Bu, Cl), (M-8913, Cl, CH₃, F, sec-Bu, F), (M-8914, Cl, CH₃, F, sec-Bu, CF₃), (M-8915, Cl, CH₃, F, sec-Bu, Br), (M-8916, Cl, CH₃, F, sec-Bu, CH₃), (M-8917, Cl, CH₃, F, n-Pen, H), (M-8918, Cl, CH₃, F, n-Pen, Cl), (M-8919, Cl, CH₃, F, n-Pen, F), (M-8920, Cl, CH₃, F, n-Pen, CF₃), (M-8921, Cl, CH₃, F, n-Pen, Br), (M-8922, Cl, CH₃, F, n-Pen, CH₃), (M-8923, Cl, CH₃, F, c-Pen, H), (M-8924, Cl, CH₃, F, c-Pen, Cl), (M-8925, Cl, CH₃, F, c-Pen, F), (M-8926, Cl, CH₃, F, c-Pen, CF₃), (M-8927, Cl, CH₃, F, c-Pen, Br), (M-8928, Cl, CH₃, F, c-Pen, CH₃), (M-8929, Cl, CH₃, F, n-Hex, H), (M-8930, Cl, CH₃, F, n-Hex, Cl), (M-8931, Cl, CH₃, F, n-Hex, F), (M-8932, Cl, CH₃, F, n-Hex, CF₃), (M-8933, Cl, CH₃, F, n-Hex, Br), (M-8934, Cl, CH₃, F, n-Hex, CH₃), (M-8935, Cl, CH₃, F, c-Hex, H), (M-893G, Cl, CH₃, F, c-Hex, Cl), (M-8937, Cl, CH₃, F, c-Hex, F), (M-8938, Cl, CH₃, F, c-Hex, CF₃), (M-8939, Cl, CH₃, F, c-Hex, Br), (M-8940, Cl, CH₃, F, c-Hex, CH₃), (M-8941, Cl, CH₃, F, OH, H), (M-8942, Cl, CH₃, F, OH, Cl), (M-8943, Cl, CH₃, F, OH, F), (M-8944, Cl, CH₃, F, OH, CF₃), (M-8945, Cl, CH₃, F, OH, Br), (M-8946, Cl, CH₃, F, OH, CH₃), (M-8947, Cl, CH₃, F, EtO, H), (M-8948, Cl, CH₃, F, EtO, Cl), (M-8949, Cl, CH₃, F, EtO, F), (M-8950, Cl, CH₃, F, EtO, CF₃), (M-8951, Cl, CH₃, F, EtO, Br), (M-8952, Cl, CH₃, F, EtO, CH₃), (M-8953, Cl, CH₃, F, n-PrO, H), (M-8954, Cl, CH₃, F, n-PrO, Cl), (M-8955, Cl, CH₃, F, n-PrO, F), (M-8956, Cl, CH₃, F, n-PrO, CF₃), (M-8957, Cl, CH₃, F, n-PrO, Br), (M-8958, Cl, CH₃, F, n-PrO, CH₃), (M-8959, Cl, CH₃, F, PhO, H), (M-8960, Cl, CH₃, F, PhO, Cl), (M-8961, Cl, CH₃, F, PhO, F), (M-8962, Cl, CH₃, F, PhO, CF₃), (M-8963, Cl, CH₃, F, PhO, Br), (M-8964, Cl, CH₃, F, PhO, CH₃), (M-8965, Cl, CH₃, F, BnO, H), (M-8966, Cl, CH₃, F, BnO, Cl), (M-8967, Cl, CH₃, F, BnO, F), (M-8968, Cl, CH₃, F, BnO, CF₃), (M-8969, Cl, CH₃, F, BnO, Br), (M-8970, Cl, CH₃, F, BnO, CH₃), (M-8971, Cl, CH₃, F, PhCH₂CH₂O, H), (M-8972, Cl, CH₃, F, PhCH₂CH₂O, Cl), (M-8973, Cl, CH₃, F, PhCH₂CH₂O, F) 8974, Cl, CH₃, F, PhCH₂CH₂O, CF₃), (M-8975, Cl, CH₃, F, PhCH₂CH₂O, Br), (M-8976, Cl, CH₃, F, PhCH₂CH₂O, CH₃), (M-8977, Cl, CH₃, F, CF₃O, H), (M-8978, Cl, CH₃, F, CF₃O, Cl), (M-8979, Cl, CH₃, F, CF₃O, F), (M-8980, Cl, CH₃, F, CF₃O, CF₃), (M-8981, Cl, CH₃, F, CF₃O, Br), (M-8982, Cl, CH₃, F, CF₃O, CH₃), (M-8983, Cl, CH₃, F, Ph, H), (M-8984, Cl, CH₃, F, Ph, Cl), (M-8985, Cl, CH₃, F, Ph, F), (M-8986, Cl, CH₃, F, Ph, CF₃), (M-8987, Cl, CH₃, F, Ph, Br), (M-8988, Cl, CH₃, F, Ph, CH₃), (M-8989, Cl, CH₃, F, 4-F-Ph, H), (M-8990, Cl, CH₃, F, 4-F-Ph, Cl), (M-8991, Cl, CH₃, F, 4-F-Ph, F), (M-8992, Cl, CH₃, F, 4-F-Ph, CF₃), (M-8993, Cl, CH₃, F, 4-F-Ph, Br), (M-8994, Cl, CH₃, F, 4-F-Ph, CH₃), (M-8995, Cl, CH₃, F, 4-CF₃-Ph, H), (M-8996, Cl, CH₃, F, 4-CF₃-Ph, Cl), (M-8997, Cl, CH₃, 4-CF₃-Ph, F), (M-8998, Cl, CH₃, F, 4-CF₃-Ph, CF₃), (M-8999, Cl, CH₃, F, 4-CF₃-Ph, Br), (M-9000, Cl, CH₃, F, 4-CF₃-Ph, CH₃), (M-9001, Cl, CH₃, F, 4-(Me)₂N-Ph, H), (M-9002, Cl, CH₃, F, 4-(Me)₂N-Ph, Cl), (M-9003, Cl, CH₃, F, 4-(Me)₂N-Ph, F), (M-9004, Cl, CH₃, F, 4-(Me)₂N-Ph, CF₃), (M-9005, Cl, CH₃, F, 4-(Me)₂N-Ph, Br), (M-9006, Cl, CH₃, F, 4-(Me)₂N-Ph, CH₃), (M-9007, Cl, CH₃, F, 4-OH-Ph, H), (M-9008, Cl, CH₃, F, 4-OH-Ph, Cl), (M-9009, Cl, CH₃, F, 4-OH-Ph, F), (M-9010, Cl, CH₃, F, 4-OH-Ph, CF₃), (M-9011, Cl, CH₃, F, 4-OH-Ph, Br), (M-9012, Cl, CH₃, F, 4-OH-Ph, CH₃), (M-9013, Cl, CH₃, F, 3,4-di-F-Ph, H), (M-9014, Cl, CH₃, F, 3,4-di-F-Ph, Cl), (M-9015, Cl, CH₃, F, 3,4-di-F-Ph, F), (M-9016, Cl, CH₃, F, 3,4-di-F-Ph, CF₃), (M-9017, Cl, CH₃, F, 3,4-di-F-Ph, Br), (M-9018, Cl, CH₃, F, 3,4-di-F-Ph, CH₃), (M-9019, Cl, CH₃, F, 4-COOH-Ph, H), (M-9020, Cl, CH₃, F, 4-COOH-Ph, Cl), (M-9021, Cl, CH₃, F, 4-COOH-Ph, F), (M-9022, Cl, CH₃, F, 4-COOH-Ph, CF₃), (M-9023, Cl, CH₃, F, 4-COOH-Ph, Br), (M-9024, Cl, CH₃, F, 4-COOH-Ph, CH₃), (M-9025, Cl, CH₃, F, Bn, H), (M-9026, Cl, CH₃, F, Bn, Cl), (M-9027, Cl, CH₃, F, Bn, F), (M-9028, Cl, CH₃, F, Bn, CF₃), (M-9029, Cl, CH₃, F, Bn, Br), (M-9030, Cl, CH₃, F, Bn, CH₃), (M-9031, Cl, CH₃, F, 4-F-Bn, H), (M-9032, Cl, CH₃, F, 4-F-Bn, Cl), (M-9033, Cl, CH₃, F, 4-F-Bn, F), (M-9034, Cl, CH₃, F, 4-F-Bn, CF₃), (M-9035, Cl, CH₃, F, 4-F-Bn, Br), (M-9036, Cl, CH₃, F, 4-F-Bn, CH₃), (M-9037, Cl, CH₃, F, 2-Py, H), (M-9038, Cl, CH₃, F, 2-Py, Cl), (M-9039, Cl, CH₃, F, 2-Py, F), (M-9040, Cl, CH₃, F, 2-Py, CF₃), (M-9041, Cl, CH₃, F, 2-Py, Br), (M-9042, Cl, CH₃, F, 2-Py, CH₃), (M-9043, Cl, CH₃, F, 3-Py, H), (M-9044, Cl, CH₃, F, 3-Py, Cl), (M-9045, Cl, CH₃, F, 3-Py, F), (M-9046, Cl, CH₃, F, 3-Py, CF₃), (M-9047, Cl, CH₃, F, 3-Py, Br), (M-9048, Cl, CH₃, F, 3-Py, CH₃), (M-9049, Cl, CH₃, F, 4-Py, H), (M-9050, Cl, CH₃, F, 4-Py, Cl), (M-9051, Cl, CH₃, F, 4-Py, F), (M-9052, Cl, CH₃, F, 4-Py, CF₃), (M-9053, Cl, CH₃, F, 4-Py, Br), (M-9054, Cl, CH₃, F, 4-Py, CH₃), (M-9055, Cl, CH, F, 2-Th, H), (M-9056, Cl, CH₃, F, 2-Th, Cl), (M-9057, Cl, CH₃, F, 2-Th, F), (M-9058, Cl, CH₃, F, 2-Th, CF₃), (M-9059, Cl, CH₃, F, 2-Th, Br), (M-9060, Cl, CH₃, F, 2-Th, CH₃), (M-9061, Cl, CH₃, F, 3-Th, H), (M-9062, Cl, CH₃, F, 3-Th, Cl), (M-9063, Cl, CH₃, F, 3-Th, F), (M-9064, Cl, CH₃, F, 3-Th, CF₃), (M-9065, Cl, CH₃, F, 3-Th, Br), (M-9066, Cl, CH₃, F, 3-Th, CH₃), (M-9067, Cl, CH₃, F, pyrrazol-2-yl, H), (M-9068, Cl, CH₃, F, pyrrazol-2-yl, Cl), (M-9069, Cl, CH₃, F, pyrrazol-2-yl, F), (M-9070, Cl, CH₃, F, pyrrazol-2-yl, CF₃), (M-9071, Cl, CH₃, F, pyrrazol-2-yl, Br), (M-9072, Cl, CH₃, F, pyrrazol-2-yl, CH₃), (M-9073, Cl, CH₃, F, pyrrazol-3-yl, H), (M-9074, Cl, CH₃, F, pyrrazol-3-yl, Cl), (M-9075, Cl, CH₃, F, pyrrazol-3-yl, F), (M-9076, Cl, CH₃, F, pyrrazol-3-yl, CF₃), (M-9077, Cl, CH₃, F, pyrrazol-3-yl, Br), (M-9078, Cl, CH₃, F, pyrrazol-3-yl, CH₃), (M-9079, Cl, CH₃, F, pyrimidin-2-yl, H), (M-9080, Cl, CH₃, F, pyrimidin-2-yl, Cl), (M-9081, Cl, CH₃, F, pyrimidin-2-yl, F), (M-9082, Cl, CH₃, F, pyrimidin-2-yl, CF₃), (M-9083, Cl, CH₃, F, pyrimidin-2-yl, Br), (M-9084, Cl, CH₃, F, pyrimidin-2-yl, CH₃), (M-9085, Cl, CH₃, F, pyrimidin-4-yl, H), (M-9086, Cl, CH₃, F, pyrimidin-4-yl, Cl), (M-9087, Cl, CH₃, F, pyrimidin-4-yl, F), (M-9088, Cl, CH₃, F, pyrimidin-4-yl, CF₃), (M-9089, Cl, CH₃, F, pyrimidin-4-yl, Br), (M-9090, Cl, CH₃, F, pyrimidin-4-yl, CH₃), (M-9091, Cl, CH₃, F, pyrimidin-5-yl, H), (M-9092, Cl, CH₃, F, pyrimidin-5-yl, Cl), (M-9093, Cl, CH₃, F, pyrimidin-5-yl, F), (M-9094, Cl, CH₃, F, pyrimidin-5-yl, CF₃), (M-9095, Cl, CH₃, F, pyrimidin-5-yl, Br), (M-9096, Cl, CH₃, F, pyrimidin-5-yl, CH₃), (M-9097, Cl, CH₃, F, HOOCCH₂CH₂, H), (M-9098, Cl, CH₃, F, HOOCCH₂CH₂, Cl), (M-9099, Cl, CH₃, F, HOOCCH₂CH₂, F), (M-9100, Cl, CH₃, F, HOOCCH₂CH₂, CF₃), (M-9101, Cl, CH₃, F, HOOCCH₂CH₂, Br), (M-9102, Cl, CH₃, F, HOOCCH₂CH₂, CH₃), (M-9103, Cl, CH₃, F, HOOCCH₂CH₂CH₂, H), (M-9104, Cl, CH₃, F, HOOCCH₂CH₂CH₂, Cl), (M-9105, Cl, CH₃, F, HOOCCH₂CH₂CH₂, F), (M-9106, Cl, CH₃, F, HOOCCH₂CH₂CH₂, CF₃), (M-9107, Cl, CH₃, F, HOOCCH₂CH₂CH₂, Br), (M-9108, Cl, CH₃, F, HOOCCH₂CH₂CH₂, CH₃), (M-9109, Cl, CH₃F, (Me)₂NCOCH₂CH₂CH₂, H), (M-9110, Cl, CH₃, F, (Me)₂NCOCH₂CH₂CH₂, Cl), (M-9111, Cl, CH₃, F, (Me)₂NCOCH₂CH₂CH₂, F), (M-9112, Cl, CH₃, F, (Me)₂NCOCH₂CH₂CH₂, CF₃), (M-9113, Cl, CH₃, F, (Me)₂NCOCH₂CH₂CH₂, Br), (M-9114, Cl, CH₃, F, (Me)₂NCOCH₂CH₂CH₂, CH₃), (M-9115, Cl, CH₃, F, (Me)₂NCOCH₂CH₂CH₂CH₂, H), (M-9116, Cl, CH₃, F, (Me)₂NCOCH₂CH₂CH₂CH₂, Cl), (M-9117, Cl, CH₃, F, (Me)₂NCOCH₂CH₂CH₂CH₂, F), (M-9118, Cl, CH₃, F, (Me)₂NCOCH₂CH₂CH₂CH₂, CF₃), (M-9119, Cl, CH₃, F, (Me)₂NCOCH₂CH₂CH₂CH₂, Br), (M-9120, Cl, CH₃, F, (Me)₂NCOCH₂CH₂CH₂CH₂, CH₃), (M-9121, Cl, CH₃, F, MeOCH₂, U), (M-9122, Cl, CH₃, F, MeOCH₂, Cl), (M-9123, Cl, CH₃, F, MeOCH₂, F), (M-9124, Cl, CH₃, F, MeOCH₂, CF₃), (M-9125, Cl, CH₃, F, MeOCH₂, Br), (M-9126, Cl, CH₃, F, MeOCH₂, CH₃), (M-9127, Cl, CH₃, F, EtOCH₂, H), (M-9128, Cl, CH₃, F, EtOCH₂, Cl), (M-9129, Cl, CH₃, F, EtOCH₂, F), (M-9130, Cl, CH₃, F, EtOCH₂, CF₃), (M-9131, Cl, CH₃, F, EtOCH₂, Br), (M-9132, Cl, CH₃, F, EtOCH₂, CH₃), (M-9133, Cl, CH₃, F, EtOCH₂CH₂, H), (M-9134, Cl, CH₃, F, EtOCH₂CH₂, Cl), (M-9135, Cl, CH₃, F, EtOCH₂CH₂, F); (M-9136, Cl, CH₃, F, EtOCH₂CH₂, CF₃), (M-9137, Cl, CH₃, F, EtOCH₂CH₂, Br), (M-9138, Cl, CH₃, F, EtOCH₂CH₂, CH₃), (M-9139, Cl, CH₃, F, MeOCH₂CH₂OCH₂CH₂, H), (M-9140, Cl, CH₃, F, MeOCH₂CH₂OCH₂CH₂, Cl), (M-9141, Cl, CH₃, F, MeOCH₂CH₂OCH₂CH₂, F), (M-9142, Cl, CH₃, F, MeOCH₂CH₂OCH₂CH₂, CF₃), (M-9143, Cl, CH₃, F, MeOCH₂CH₂OCH₂CH₂, Br), (M-9144, Cl, CH₃, F, MeOCH₂CH₂OCH₂CH₂, CH₃), (M-9145, Cl, CH₃, F, MeOCH₂CH₂, H), (M-9146, Cl, CH₃, F, MeOCH₂CH₂, Cl), (M-9147, Cl, CH₃, F, MeOCH₂CH₂, F), (M-9148, Cl, CH₃, F, MeOCH₂CH₂, CF₃), (M-9149, Cl, CH₃, F, MeOCH₂CH₂, Br), (M-9150, Cl, CH₃, F, MeOCH₂CH₂, CH₃), (M-9151, Cl, CH₃, F, HOCH₂, H), (M-9152, Cl, CH₃, F, HOCH₂, Cl), (M-9153, Cl, CH₃, F, HOCH₂, F), (M-9154, Cl, CH₃, F, HOCH₂, CF₃), (M-9155, Cl, CH₃, F, HOCH₂, Br), (M-9156, Cl, CH₃, F, HOCH₂, CH₃), (M-9157, Cl, CH₃, F, HOCH₂CH₂, H), (M-9158, Cl, CH₃, F, HOCH₂CH₂, Cl), (M-9159, Cl, CH₃, F, HOCH₂CH₂, F), (M-9160, Cl, CH₃, F, HOCH₂CH₂, CF₃), (M-9161, Cl, CH₃, F, HOCH₂CH₂, Br), (M-9162, Cl, CH₃, F, HOCH₂CH₂, CH₃), (M-9163, Cl, CH₃, F, HOCH₂CH₂CH₂, H), (M-9164, Cl, CH₃, F, HOCH₂CH₂CH₂, Cl), (M-9165, Cl, CH₃, F, HOCH₂CH₂CH₂, F), (M-9166, Cl, CH₃, F, HOCH₂CH₂CH₂, CF₃), (M-9167, Cl, CH₃, F, HOCH₂CH₂CH₂, Br), (M-9168, Cl, CH₃, F, HOCH₂CH₂CH₂, CH₃), (M-9169, Cl, CH₃, F, HOCH₂CH₂CH₂CH₂, H), (M-9170, Cl, CH₃, F, HOCH₂CH₂CH₂CH₂, Cl), (M-9171, Cl, CH₃, F, HOCH₂CH₂CH₂CH₂, F), (M-9172, Cl, CH₃F, HOCH₂CH₂CH₂CH₂CF₃), (M-9173, Cl, CH₃F, HOCH₂CH₂CH₂CH₂, Br), (M-9174, Cl, CH₃, F, HOCH₂CH₂CH₂CH₂, CH₃), (M-9175, Cl, CH₃, F, HOCH₂CH₂CH₂CH₂CH₂H), (M-9176, Cl, CH₃F, HOCH₂CH₂CH₂CH₂CH₂, Cl) (M-9177, Cl, CH₃, F, HOCH₂CH₂CH₂CH₂CH₂, F), (M-9178, Cl, CH₃, F, HOCH₂CH₂CH₂CH₂CH₂CF₃), (M-9179, Cl, CH₃F, HOCH₂CH₂CH₂CH₂CH₂, Br), (M-9180, Cl, CH₃, F, HOCH$_2$CH$_2$CH$_2$CH$_2$CH$_2$, CH$_3$), (M-9181, Cl, CH$_3$, F, HOCH$_2$CH$_2$OCH$_2$CH$_2$, H), (M-9182, Cl, CH$_3$, F, HOCH$_2$CH$_2$OCH$_2$CH$_2$Cl), (M-9183, Cl, CH$_3$, F, HOCH$_2$CH$_2$OCH$_2$CH$_2$, F), (M-9184, Cl, CH$_3$, F, HOCH$_2$CH$_2$OCH$_2$CH$_2$, CF$_3$), (M-9185, Cl, CH$_3$, F, HOCH$_2$CH$_2$OCH$_2$CH$_2$, Br), (M-9186, Cl, CH$_3$, F, HOCH$_2$CH$_2$OCH$_2$CH$_2$,CH$_3$), (M-9187, Cl, CH$_3$, F, (Me)$_2$N, H), (M-9188, Cl, CH$_3$, F, (Me)$_2$N, Cl), (M-9189, Cl, CH$_3$, F, (Me)$_2$N, F), (M-9190, Cl, CH$_3$, F, (Me)$_2$N, CF$_3$), (M-9191, Cl, CH$_3$, F, (Me)$_2$N, Br), (M-9192, Cl, CH$_3$, F, (Me)$_2$N, CH$_3$), (M-9193, Cl, CH$_3$, F, piperidin-4-yl-methyl, H), (M-9194, Cl, CH$_3$, F, piperidin-4-yl-methyl, Cl), (M-9195, Cl, CH$_3$, F, piperidin-4-yl-methyl, F), (M-9196, Cl, CH$_3$, F, piperidin-4-yl-methyl, CF$_3$), (M-9197, Cl, CH$_3$, F, piperidin-4-yl-methyl, Br), (M-9198, Cl, CH$_3$, F, piperidin-4-yl-methyl, CH$_3$), (M-9199, Cl, CH$_3$, F, cyclohexylmethyl, H), (M-9200, Cl, CH$_3$, F, cyclohexylmethyl, Cl), (M-9201, Cl, CH$_3$, F, cyclohexylmethyl, F), (M-9202, Cl, CH$_3$, F, cyclohexylmethyl, CF$_3$), (M-9203, Cl, CH$_3$, F, cyclohexylmethyl, Br), (M-9204, Cl, CH$_3$, F, cyclohexylmethyl, CH$_3$), (M-9205, Cl, CH$_3$, Cl, H, H), (M-9206, Cl, CH$_3$, Cl, H, Cl), (M-9207, Cl, CH$_3$, Cl, H, F), (M-9208, Cl, CH$_3$, Cl, H, CF$_3$), (M-9209, Cl, CH$_3$, Cl, H, Br), (M-9210, Cl, CH$_3$, Cl, H, CH$_3$), (M-9211, Cl, CH$_3$, Cl, F, H), (M-9212, Cl, CH$_3$, Cl, F, Cl), (M-9213, Cl, CH$_3$, Cl, F, F), (M-9214, Cl, CH$_3$, Cl, F, CF$_3$), (M-9215, Cl, CH$_3$, Cl, F, Br), (M-9216, Cl, CH$_3$, Cl, F, CH$_3$), (M-9217, Cl, CH$_3$, Cl, Cl, H), (M-9218, Cl, CH$_3$, Cl, Cl, Cl), (M-9219, Cl, CH$_3$, Cl, Cl, F), (M-9220, Cl, CH$_3$, Cl, Cl, CF$_3$), (M-9221, Cl, CH$_3$, Cl, Cl, Br), (M-9222, Cl, CH$_3$, Cl, Cl, CH$_3$), (M-9223, Cl, CH$_3$, Cl, CH$_3$, H), (M-9224, Cl, CH$_3$, Cl, CH$_3$, Cl), (M-9225, Cl, CH$_3$, Cl, CH$_3$, F), (M-9226, Cl, CH$_3$, Cl, CH$_3$, CF$_3$), (M-9227, Cl, CH$_3$, Cl, CH$_3$, Br), (M-9228, Cl, CH$_3$, Cl, CH$_3$, CH$_3$), (M-9229, Cl, CH$_3$, Cl, Et, H), (M-9230, Cl, CH$_3$, Cl, Et, Cl), (M-9231, Cl, CH$_3$, Cl, Et, F), (M-9232, Cl, CH$_3$, Cl, Et, CF$_3$), (M-9233, Cl, CH$_3$, Cl, Et, Br), (M-9234, Cl, CH$_3$, Cl, Et, CH$_3$), (M-9235, Cl, CH$_3$, Cl, n-Pr, H), (M-9236, Cl, CH$_3$, Cl, n-Pr, Cl), (M-9237, Cl, CH$_3$, Cl, n-Pr, F), (M-9238, Cl, CH$_3$, Cl, n-Pr, CF$_3$), (M-9239, Cl, CH$_3$, Cl, n-Pr, Br), (M-9240, Cl, CH$_3$, Cl, n-Pr, CH$_3$), (M-9241, Cl, CH$_3$, Cl, c-Pr, H), (M-9242, Cl, CH$_3$, Cl, c-Pr, Cl), (M-9243, Cl, CH$_3$, Cl, c-Pr, F), (M-9244, Cl, CH$_3$, Cl, c-Pr, CF$_3$), (M-9245, Cl, CH$_3$, Cl, c-Pr, Br), (M-9246, Cl, CH$_3$, Cl, c-Pr, CH$_3$), (M-9247, Cl, CH$_3$, Cl, i-Pr, H), (M-9248, Cl, CH$_3$, Cl, i-Pr, Cl), (M-9249, Cl, CH$_3$, Cl, i-Pr, F), (M-9250, Cl, CH$_3$, Cl, i-Pr, CF$_3$), (M-9251, Cl, CH$_3$, Cl, i-Pr, Br), (M-9252, Cl, CH$_3$, Cl, i-Pr, CH$_3$), (M-9253, Cl, CH$_3$, Cl, n-Bu, H), (M-9254, Cl, CH$_3$, Cl, n-Bu, Cl), (M-9255, Cl, CH$_3$, Cl, n-Bu, F), (M-9256, Cl, CH$_3$, Cl, n-Bu, CF$_3$), (M-9257, Cl, CH$_3$, Cl, n-Bu, Br), (M-9258, Cl, CH$_3$, Cl, n-Bu, CH$_3$), (M-9259, Cl, CH$_3$, Cl, i-Bu, H), (M-9260, Cl, CH$_3$, Cl, i-Bu, Cl), (M-9261, Cl, CH$_3$, Cl, i-Bu, F), (M-9262, Cl, CH$_3$, Cl, i-Bu, CF$_3$), (M-9263, Cl, CH$_3$, Cl, i-Bu, Br), (M-9264, Cl, CH$_3$, Cl, i-Bu, CH$_3$), (M-9265, Cl, CH$_3$, Cl, sec-Bu, H), (M-9266, Cl, CH$_3$, Cl, sec-Bu, Cl), (M-9267, Cl, CH$_3$, Cl, sec-Bu, F), (M-9268, Cl, CH$_3$, Cl, sec-Bu, CF$_3$), (M-9269, Cl, CH$_3$, Cl, sec-Bu, Br), (M-9270, Cl, CH$_3$, Cl, sec-Bu, CH$_3$), (M-9271, Cl, CH$_3$, Cl, n-Pen, H), (M-9272, Cl, CH$_3$, Cl, n-Pen, Cl), (M-9273, Cl, CH$_3$, Cl, n-Pen, F), (M-9274, Cl, CH$_3$, Cl, n-Pen, CF$_3$), (M-9275, Cl, CH$_3$, Cl, n-Pen, Br), (M-9276, Cl, CH$_3$, Cl, n-Pen, CH$_3$), (M-9277, Cl, CH$_3$, Cl, c-Pen, H), (M-9278, Cl, CH$_3$, Cl, c-Pen, Cl), (M-9279, Cl, CH$_3$, Cl, c-Pen, F), (M-9280, Cl, CH$_3$, Cl, c-Pen, CF$_3$), (M-9281, Cl, CH$_3$, Cl, c-Pen, Br), (M-9282, Cl, CH$_3$, Cl, c-Pen, CH$_3$), (M-9283, Cl, CH$_3$, Cl, n-Hex, H), (M-9284, Cl, CH$_3$, Cl, n-Hex, Cl), (M-9285, Cl, CH$_3$, Cl, n-Hex, F), (M-9286, Cl, CH$_3$, Cl, n-Hex, CF$_3$), (M-9287, Cl, CH$_3$, Cl, n-Hex, Br), (M-9288, Cl, CH$_3$, Cl, n-Hex, CH$_3$), (M-9289, Cl, CH$_3$, Cl, c-Hex, H), (M-9290, Cl, CH$_3$, Cl, c-Hex, Cl), (M-9291, Cl, CH$_3$, Cl, c-Hex, F), (M-9292, Cl, CH$_3$, Cl, c-Hex, CF$_3$), (M-9293, Cl, CH$_3$, Cl, c-Hex, Br), (M-9294, Cl, CH$_3$, Cl, c-Hex, CH$_3$), (M-9295, Cl, CH$_3$, Cl, OH, H), (M-9296, Cl, CH$_3$, Cl, OH, Cl), (M-9297, Cl, CH$_3$, Cl, OH, F), (M-9298, Cl, CH$_3$, Cl, OH, CF$_3$), (M-9299, Cl, CH$_3$, Cl, OH, Br), (M-9300, Cl, CH$_3$, Cl, OH, CH$_3$), (M-9301, Cl, CH$_3$, Cl, EtO, H), (M-9302, Cl, CH$_3$, Cl, EtO, Cl), (M-9303, Cl, CH$_3$, Cl, EtO, F), (M-9304, Cl, CH$_3$, Cl, EtO, CF$_3$), (M-9305, Cl, CH$_3$, Cl, EtO, Br), (M-9306, Cl, CH$_3$, Cl, EtO, CH$_3$), (M-9307, Cl, CH$_3$, Cl, n-PrO, H), (M-9308, Cl, CH$_3$, Cl, n-PrO, Cl), (M-9309, Cl, CH$_3$, Cl, n-PrO, F), (M-9310, Cl, CH$_3$, Cl, n-PrO, CF$_3$), (M-9311, Cl, CH$_3$, Cl, n-PrO, Br), (M-9312, Cl, CH$_3$, Cl, n-PrO, CH$_3$), (M-9313, Cl, CH$_3$, Cl, PhO, H), (M-9314, Cl, CH$_3$, Cl, PhO, Cl), (M-9315, Cl, CH$_3$, Cl, PhO, F), (M-9316, Cl, CH$_3$, Cl, PhO, CF$_3$), (M-9317, Cl, CH$_3$, Cl, PhO, Br), (M-9318, Cl, CH$_3$, Cl, PhO, CH$_3$), (M-9319, Cl, CH$_3$, Cl, BnO, H), (M-9320, Cl, CH$_3$, Cl, BnO, Cl), (M-9321, Cl, CH$_3$, Cl, BnO, F), (M-9322, Cl, CH$_3$, Cl, BnO, CF$_3$), (M-9323, Cl, CH$_3$, Cl, BnO, Br), (M-9324, Cl, CH$_3$, Cl, BnO, CH$_3$), (M-9325, Cl, CH$_3$, Cl, PhCH$_2$CH$_2$O, H), (M-9326, Cl, CH$_3$, Cl, PhCH$_2$CH$_2$O, Cl), (M-9327, Cl, CH$_3$, Cl, PhCH$_2$CH$_2$O, F), (M-9328, Cl, CH$_3$, Cl, PhCH$_2$CH$_2$O, CF$_3$), (M-9329, Cl, CH$_3$, Cl, PhCH$_2$CH$_2$O, Br), (M-9330, Cl, CH$_3$, Cl, PhCH$_2$CH$_2$O, CH$_3$), (M-9331, Cl, CH$_3$, Cl, CF$_3$O, H), (M-9332, Cl, CH$_3$, Cl, CF$_3$O, Cl), (M-9333, Cl, CH$_3$, Cl, CF$_3$O, F), (M-9334, Cl, CH$_3$, Cl, CF$_3$O, CF$_3$), (M-9335, Cl, CH$_3$, Cl, CF$_3$O, Br), (M-9336, Cl, CH$_3$, Cl, CF$_3$O, CH$_3$), (M-9337, Cl, CH$_3$, Cl, Ph, H), (M-9338, Cl, CH$_3$, Cl, Ph, Cl), (M-9339, Cl, CH$_3$, Cl, Ph, F), (M-9340, Cl, CH$_3$, Cl, Ph, CF$_3$), (M-9341, Cl, CH$_3$, Cl, Ph, Br), (M-9342, Cl, CH$_3$, Cl, Ph, CH$_3$), (M-9343, Cl, CH$_3$, Cl, 4-F-Ph, H), (M-9344, Cl, CH$_3$, Cl, 4-F-Ph, Cl), (M-9345, Cl, CH$_3$, Cl, 4-F-Ph, F), (M-9346, Cl, CH$_3$, Cl, 4-F-Ph, CF$_3$), (M-9347, Cl, CH$_3$, Cl, 4-F-Ph, Br), (M-9348, Cl, CH$_3$, Cl, 4-F-Ph, CH$_3$), (M-9349, Cl, CH$_3$, Cl, 4-CF$_3$-Ph, H), (M-9350, Cl, CH$_3$, Cl, 4-CF$_3$-Ph, Cl), (M-9351, Cl, CH$_3$, Cl, 4-CF$_3$-Ph, F), (M-9352, Cl, CH$_3$, Cl, 4-CF$_3$-Ph, CF$_3$), (M-9353, Cl, CH$_3$, Cl, 4-CF$_3$-Ph, Br), (M-9354, Cl, CH$_3$, Cl, 4-CF$_3$-Ph, CH$_3$), (M-9355, Cl, CH$_3$, Cl, 4-(Me)$_2$N-Ph, H), (M-9356, Cl, CH$_3$, Cl, 4-(Me)$_2$N-Ph, Cl), (M-9357, Cl, CH$_3$, Cl, 4-(Me)$_2$N-Ph, F), (M-9358, Cl, CH$_3$, Cl, 4-(Me)$_2$N-Ph, CF$_3$), (M-9359, Cl, CH$_3$, Cl, 4-(Me)$_2$N-Ph, Br), (M-9360, Cl, CH$_3$, Cl, 4-(Me)$_2$N-Ph, CH$_3$), (M-9361, Cl, CH$_3$, Cl, 4-OH-Ph, H), (M-9362, Cl, CH$_3$, Cl, 4-OH-Ph, Cl), (M-9363, Cl, CH$_3$, Cl, 4-OH-Ph, F), (M-9364, Cl, CH$_3$, Cl, 4-OH-Ph, CF$_3$), (M-9365, Cl, CH$_3$, Cl, 4-OH-Ph, Br), (M-9366, Cl, CH$_3$, Cl, 4-OH-Ph, CH$_3$), (M-9367, Cl, CH$_3$, Cl, 3,4-di-F-Ph, H), (M-9368, Cl, CH$_3$, Cl, 3,4-di-F-Ph, Cl), (M-9369, Cl, CH$_3$, Cl, 3,4-di-F-Ph, F), (M-9370, Cl, CH$_3$, Cl, 3,4-di-F-Ph, CF$_3$), (M-9371, Cl, CH$_3$, Cl, 3,4-di-F-Ph, Br), (M-9372, Cl, CH$_3$, Cl, 3,4-di-F-Ph, CH$_3$), (M-9373, Cl, CH$_3$, Cl, 4-COOH-Ph, H), (M-9374, Cl, CH$_3$, Cl, 4-COOH-Ph, Cl), (M-9375, Cl, CH$_3$, Cl, 4-COOH-Ph, F), (M-9376, Cl, CH$_3$, Cl, 4-COOH-Ph, CF$_3$), (M-9377, Cl, CH$_3$, Cl, 4-COOH-Ph, Br), (M-9378, Cl, CH$_3$, Cl, 4-COOH-Ph, CH$_3$), (M-9379, Cl, CH$_3$, Cl, Bn, H), (M-9380, Cl, CH$_3$, Cl, Bn, Cl), (M-9381, Cl, CH$_3$, Cl, Bn, F), (M-9382, Cl, CH$_3$, Cl, Bn, CF$_3$), (M-9383, Cl, CH$_3$, Cl, Bn, Br), (M-9384, Cl, CH$_3$, Cl, Bn, CH$_3$), (M-9385, Cl, CH$_3$, Cl, 4-F-Bn, H), (M-9386, Cl, CH$_3$, Cl, 4-F-Bn, Cl), (M-9387, Cl, CH$_3$, Cl, 4-F-Bn, F), (M-9388, Cl, CH$_3$, Cl, 4-F-Bn, CF$_3$), (M-9389, Cl, CH$_3$, Cl, 4-F-Bn, Br), (M-9390, Cl, CH$_3$, Cl, 4-F-Bn, CH$_3$), (M-9391, Cl, CH$_3$, Cl, 2-Py, H), (M-9392, Cl, CH$_3$, Cl, 2-Py, Cl), (M-9393, Cl, CH$_3$, Cl, 2-Py, F), (M-9394, Cl, CH$_3$, Cl, 2-Py, CF$_3$), (M-9395, Cl, CH$_3$, Cl, 2-Py, Br), (M-9396, Cl, CH$_3$, Cl, 2-Py, CH$_3$), (M-9397, Cl, CH$_3$, Cl, 3-Py, H), (M-9398, Cl, CH$_3$, Cl, 3-Py, Cl), (M-9399, Cl, CH$_3$, Cl, 3-Py, F), (M-9400, Cl, CH₃, Cl, 3-Py, CF₃), (M-9401, Cl, CH₃, Cl, 3-Py, Br), (M-9402, Cl, CH₃, Cl, 3-Py, CH₃), (M-9403, Cl, CH₃, Cl, 4-Py, H), (M-9404, Cl, CH₃, Cl, 4-Py, Cl), (M-9405, Cl, CH₃, Cl, 4-Py, F), (M-9406, Cl, CH₃, Cl, 4-Py, CF₃), (M-9407, Cl, CH₃, Cl, 4-Py, Br), (M-9408, Cl, CH₃, Cl, 4-Py, CH₃), (M-9409, Cl, CH₃, Cl, 2-Th, H), (M-9410, Cl, CH₃, Cl, 2-Th, Cl), (M-9411, Cl, CH₃, Cl, 2-Th, F), (M-9412, Cl, CH₃, Cl, 2-Th, CF₃), (M-9413, Cl, CH₃, Cl, 2-Th, Br), (M-9414, Cl, CH₃, Cl, 2-Th, CH₃), (M-9415, Cl, CH₃, Cl, 3-Th, H), (M-9416, Cl, CH₃, Cl, 3-Th, Cl), (M-9417, Cl, CH₃, Cl, 3-Th, F), (M-9418, Cl, CH₃, Cl, 3-Th, CF₃), (M-9419, Cl, CH₃, Cl, 3-Th, Br), (M-9420, Cl, CH₃, Cl, 3-Th, CH₃), (M-9421, Cl, CH₃, Cl, pyrrazol-2-yl, H), (M-9422, Cl, CH₃, Cl, pyrrazol-2-yl, Cl), (M-9423, Cl, CH₃, Cl, pyrrazol-2-yl, F), (M-9424, Cl, CH₃, Cl, pyrrazol-2-yl, CF₃), (M-9425, Cl, CH₃, Cl, pyrrazol-2-yl, Br), (M-9426, Cl, CH₃, Cl, pyrrazol-2-yl, CH₃), (M-9427, Cl, CH₃, Cl, pyrrazol-3-yl, H), (M-9428, Cl, CH₃, Cl, pyrrazol-3-yl, Cl), (M-9429, Cl, CH₃, Cl, pyrrazol-3-yl, F), (M-9430, Cl, CH₃, Cl, pyrrazol-3-yl, CF₃), (M-9431, Cl, CH₃, Cl, pyrrazol-3-yl, Br), (M-9432, Cl, CH₃, Cl, pyrrazol-3-yl, CH₃), (M-9433, Cl, CH₃, Cl, pyrimidin-2-yl, H), (M-9434, Cl, CH₃, Cl, pyrimidin-2-yl, Cl), (M-9435, Cl, CH₃, Cl, pyrimidin-2-yl, F), (M-9436, Cl, CH₃, Cl, pyrimidin-2-yl, CF₃), (M-9437, Cl, CH₃, Cl, pyrimidin-2-yl, Br), (M-9438, Cl, CH₃, Cl, pyrimidin-2-yl, CH₃), (M-9439, Cl, CH₃, Cl, pyrimidin-4-yl, H), (M-9440, Cl, CH₃, Cl, pyrimidin-4-yl, Cl), (M-9441, Cl, CH₃, Cl, pyrimidin-4-yl, F), (M-9442, Cl, CH₃, Cl, pyrimidin-4-yl, CF₃), (M-9443, Cl, CH₃, Cl, pyrimidin-4-yl, Br), (M-9444, Cl, CH₃, Cl, pyrimidin-4-yl, CH₃), (M-9445, Cl, CH₃, Cl, pyrimidin-5-yl, H), (M-9446, Cl, CH₃, Cl, pyrimidin-5-yl, Cl), (M-9447, Cl, CH₃, Cl, pyrimidin-5-yl, F), (M-9448, Cl, CH₃, Cl, pyrimidin-5-yl, CF₃), (M-9449, Cl, CH₃, Cl, pyrimidin-5-yl, Br), (M-9450, Cl, CH₃, Cl, pyrimidin-5-yl, CH₃), (M-9451, Cl, CH₃, Cl, HOOCCH₂CH₂CH₂, H), (M-9452, Cl, CH₃, Cl, HOOCCH₂CH₂CH₂, Cl), (M-9453, Cl, CH₃, Cl, HOOCCH₂CH₂CH₂, F), (M-9454, Cl, CH₃, Cl, HOOCCH₂CH₂CH₂, CF₃), (M-9455, Cl, CH₃, Cl, HOOCCH₂CH₂CH₂, Br), (M-9456, Cl, CH₃, Cl, HOOCCH₂CH₂CH₂, CH₃), (M-9457, Cl, CH₃, Cl, HOOCCH₂CH₂CH₂CH₂, H), (M-9458, Cl, CH₃, Cl, HOOCCH₂CH₂CH₂CH₂, Cl), (M-9459, Cl, CH₃, Cl, HOOCCH₂CH₂CH₂CH₂, F), (M-9460, Cl, CH₃, Cl, HOOCCH₂CH₂CH₂CH₂, CF₃), (M-9461, Cl, CH₃, Cl, HOOCCH₂CH₂CH₂CH₂, Br), (M-9462, Cl, CH₃, Cl, HOOCCH₂CH₂CH₂CH₂, CH₃), (M-9463, Cl, CH₃Cl, (Me)₂NCOCH₂CH₂CH₂CH₂, H), (M-9464, Cl, CH₃, Cl, (Me)₂NCOCH₂CH₂CH₂CH₂, Cl), (M-9465, Cl, CH₃, Cl, (Me)₂NCOCH₂CH₂CH₂CH₂, F), (M-9466, Cl, CH₃, Cl, (Me)₂NCOCH₂CH₂CH₂CH₂, CF₃), (M-9467, Cl, CH₃, Cl, (Me)₂NCOCH₂CH₂CH₂CH₂, Br), (M-9468, Cl, CH₃, Cl, (Me)₂NCOCH₂CH₂CH₂CH₂, CH₃), (M-9469, Cl, CH₃, Cl, (Me)₂NCOCH₂CH₂CH₂CH₂CH₂, H), (M-9470, Cl, CH₃, Cl, (Me)₂NCOCH₂CH₂CH₂CH₂CH₂, Cl), (M-9471, Cl, CH₃, Cl, (Me)₂NCOCH₂CH₂CH₂CH₂CH₂, F), (M-9472, Cl, CH₃, Cl, (Me)₂NCOCH₂CH₂CH₂CH₂CH₂, CF₃), (M-9473, Cl, CH₃, Cl, (Me)₂NCOCH₂CH₂CH₂CH₂CH₂, Br), (M-9474, Cl, CH₃, Cl, (Me)₂NCOCH₂CH₂CH₂CH₂CH₂, CH₃), (M-9475, Cl, CH₃, Cl, MeOCH₂, H), (M-9476, Cl, CH₃, Cl, MeOCH₂, Cl), (M-9477, Cl, CH₃, Cl, MeOCH₂, F), (M-9478, Cl, CH₃, Cl, MeOCH₂, CF₃), (M-9479, Cl, CH₃, Cl, MeOCH₂, Br), (M-9480, Cl, CH₃, Cl, MeOCH₂, CH₃), (M-9481, Cl, CH₃, Cl, EtOCH₂, H), (M-9482, Cl, CH₃, Cl, EtOCH₂, Cl), (M-9483, Cl, CH₃, Cl, EtOCH₂, F), (M-9484, Cl, CH₃, Cl, EtOCH₂, CF₃), (M-9485, Cl, CH₃, Cl, EtOCH₂, Br), (M-9486, Cl, CH₃, Cl, EtOCH₂, CH₃), (M-9487, Cl, CH₃, Cl, EtOCH₂CH₂, H), (M-9488, Cl, CH₃, Cl, EtOCH₂CH₂, Cl), (M-9489, Cl, CH₃, Cl, EtOCH₂CH₂, F), (M-9490, Cl, CH₃, Cl, EtOCH₂CH₂, CF₃), (M-9491, Cl, CH₃, Cl, EtOCH₂CH₂, Br), (M-9492, Cl, CH₃, Cl, EtOCH₂CH₂, CH₃), (M-9493, Cl, CH₃, Cl, MeOCH₂CH₂OCH₂CH₂, H), (M-9494, Cl, CH₃, Cl, MeOCH₂CH₂OCH₂CH₂, Cl), (M-9495, Cl, CH₃, Cl, MeOCH₂CH₂OCH₂CH₂, F), (M-9496, Cl, CH₃, Cl, MeOCH₂CH₂OCH₂CH₂, CF₃), (M-9497, Cl, CH₃, Cl, MeOCH₂CH₂OCH₂CH₂, Br), (M-9498, Cl, CH₃, Cl, MeOCH₂CH₂OCH₂CH₂, CH₃), (M-9499, Cl, CH₃, Cl, MeOCH₂CH₂, H), (M-9500, Cl, CH₃, Cl, MeOCH₂CH₂, Cl), (M-9501, Cl, CH₃, Cl, MeOCH₂CH₂, F), (M-9502, Cl, CH₃, Cl, MeOCH₂CH₂, CF₃), (M-9503, Cl, CH₃, Cl, MeOCH₂CH₂, Br), (M-9504, Cl, CH₃, Cl, MeOCH₂CH₂, CH₃), (M-9506, Cl, CH₃, Cl, HOCH₂, H), (M-9507, Cl, CH₃, Cl, HOCH₂, C), (M-9507, Cl, CH₃, Cl, HOCH₂, F), (M-9508, Cl, CH₃, Cl, HOCH₂, CF₃), (M-9509, Cl, CH₃, Cl, HOCH₂, Br), (M-9510, Cl, CH₃, Cl, HOCH₂, CH₃), (M-9511, Cl, CH₃, Cl, HOCH₂CH₂, H), (M-9512, Cl, CH₃, Cl, HOCH₂CH₂, Cl), (M-9513, Cl, CH₃, Cl, HOCH₂CH₂, F), (M-9514, Cl, CH₃, Cl, HOCH₂CH₂, CF₃), (M-9515, Cl, CH₃, Cl, HOCH₂CH₂, Br), (M-9516, Cl, CH₃, Cl, HOCH₂CH₂, CH₃), (M-9517, Cl, CH₃, Cl, HOCH₂CH₂CH₂, H), (M-9518, Cl, CH₃, Cl, HOCH₂CH₂CH₂, Cl), (M-9519, Cl, CH₃, Cl, HOCH₂CH₂CH₂, F), (M-9520, Cl, CH₃, Cl, HOCH₂CH₂CH₂, CF₃), (M-9521, Cl, CH₃, Cl, HOCH₂CH₂CH₂, Br), (M-9522, Cl, CH₃, Cl, HOCH₂CH₂CH₂, CH₃), (M-9523, Cl, CH₃, Cl, HOCH₂CH₂CH₂CH₂, H), (M-9524, Cl, CH₃, Cl, HOCH₂CH₂CH₂CH₂, Cl), (M-9525, Cl, CH₃, Cl, HOCH₂CH₂CH₂CH₂, F), (M-9526, Cl, CH₃, Cl, HOCH₂CH₂CH₂CH₂, CF₃), (M-9527, Cl, CH₃, Cl, HOCH₂CH₂CH₂CH₂, Br), (M-9528, Cl, CH₃, Cl, HOCH₂CH₂CH₂CH₂, CH₃), (M-9529, Cl, CH₃, Cl, HOCH₂CH₂CH₂CH₂CH₂, H), (M-9530, Cl, CH₃, Cl, HOCH₂CH₂CH₂CH₂CH₂, Cl (M-9531, Cl, CH₃, Cl, HOCH₂CH₂CH₂CH₂CH₂, F), (M-9532, Cl, CH₃, Cl, HOCH₂CH₂CH₂CH₂CH₂, CF₃), (M-9533, Cl, CH₃, Cl, HOCH₂CH₂CH₂CH₂CH₂, Br), (M-9534, Cl, CH₃, Cl, HOCH₂CH₂CH₂CH₂CH₂, CH₃), (M-9535, Cl, CH₃, Cl, HOCH₂CH₂O CH₂CH₂, H), (M-9536, Cl, CH₃, Cl, HOCH₂CH₂OCH₂CH₂, Cl), (M-9537, Cl, CH₃, Cl, HOCH₂CH₂O CH₂CH₂, F), (M-9538, Cl, CH₃, Cl, HOCH₂CH₂O CH₂CH₂, CF₃), (M-9539, Cl, CH₃Cl, HOCH₂CH₂O CH₂CH₂, Br), (M-9540, Cl, CH₃, Cl, HOCH₂CH₂O CH₂CH₂, CH₃), (M-9541, Cl, CH₃, Cl, (Me)₂N, H), (M-9542, Cl, CH, Cl, (Me)₂N, Cl), (M-9543, Cl, CH₃, Cl, (Me)₂N, F), (M-9544, Cl, CH₃, Cl, (Me)₂N, CF₃), (M-9545, Cl, CH₃, Cl, (Me)₂N, Br), (M-9546, Cl, CH₃, Cl, (Me)₂N, CH₃), (M-9547, Cl, CH₃, Cl, piperidin-4-yl-methyl, H), (M-9548, Cl, CH₃, Cl, piperidin-4-yl-methyl, Cl), (M-9549, Cl, CH₃, Cl, piperidin-4-yl-methyl, F), (M-9550, Cl, CH₃, Cl, piperidin-4-yl-methyl, CF₃), (M-9551, Cl, CH₃, Cl, piperidin-4-yl-methyl, Br), (M-9552, Cl, CH₃, Cl, piperidin-4-yl-methyl, CH₃), (M-9553, Cl, CH₃, Cl, cyclohexylmethyl, H), (M-9554, Cl, CH₃, Cl, cyclohexylmethyl, Cl), (M-9555, Cl, CH₃, Cl, cyclohexylmethyl, F), (M-9556, Cl, CH₃, Cl, cyclohexylmethyl, CF₃), (M-9557, Cl, CH₃, Cl, cyclohexylmethyl, Br), (M-9558, Cl, CH₃, Cl, cyclohexylmethyl, CH₃), (M-9559, CH₃, H, H, H, H), (M-9560, CH₃, H, H, H, Cl), (M-9561, MeO, H, H, H, F), (M-9562, MeO, H, H, H, CF₃), (M-9563, CH₃, H, H, H, Br), (M-9564, CH₃, H, H, H, CH₃), (M-9565, MeO, H, H, F, H), (M-9566, CH₃, H, H, F, Cl), (M-9567, MeO, F, H, F, F), (M-9568, CH₃, H, H, F, CF₃), (M-9569, CH₃, H, H, F, Br), (M-9570, CH₃, H, H, F, CH₃), (M-9571, CH₃, H, H, Cl, H), (M-9572, MeO, F, H, H, i-Pr), (M-9573, CH₃, H, H, Cl, F), (M-9574, CH₃, H, H, Cl, CF₃), (M-9575, CH₃, H, H, Cl, Br), (M-9576, CH₃, H, H, Cl, CH₃), (M-9577, CH₃, H, H, CH₃, H), (M-9578, CH₃, H, H, CH₃, Cl), (M-9579, CH₃, H, H, CH₃, F), (M-9580, CH₃, H, H, CH₃, CF₃), (M-9581, CH₃, H, H, CH₃, Br), (M-9582, CH₃, H, H, CH₃, CH₃), (M-9583, CH₃, H, H, Et, H), (M-9584, CH₃, H, H, Et, Cl), (M-9585, CH₃, H, H, Et, F), (M-9586, CH₃, H, H, Et, CF₃), (M-9587, CH₃, H, H, Et, Br), (M-9588, CH₃, H, H, Et, CH₃), (M-9589, CH₃, H, H, n-Pr, H), (M-9590, CH₃, H, H, n-Pr, Cl), (M-9591, CH₃, H, H, n-Pr, F), (M-9592, CH₃, H, H, n-Pr, CF₃), (M-9593, CH₃, H, H, n-Pr, Br), (M-9594, CH₃, H, H, n-Pr, CH₃), (M-9595, CH₃, H, H, c-Pr, H), (M-9596, CH₃, H, H, c-Pr, Cl), (M-9597, CH₃, H, H, c-Pr, F), (M-9598, CH₃, H, H, c-Pr, CF₃), (M-9599, CH₃, H, H, c-Pr, Br), (M-9600, CH₃, H, H, c-Pr, CH₃), (M-9601, CH₃, H, H, i-Pr, H), (M-9602, CH₃, H, H, i-Pr, Cl), (M-9603, CH₃, H, H, i-Pr, F), (M-9604, CH₃, H, H, i-Pr, CF₃), (M-9605, CH₃, H, H, i-Pr, Br), (M-9606, CH₃, H, H, i-Pr, CH₃), (M-9607, CH₃, H, H, n-Bu, H), (M-9608, CH₃, H, H, n-Bu, Cl), (M-9609, CH₃, H, H, n-Bu, F), (M-9610, CH₃, H, H, n-Bu, CF₃), (M-9611, CH₃, H, H, n-Bu, Br), (M-9612, CH₃, H, H, n-Bu, CH₃), (M-9613, CH₃, H, H, i-Bu, H), (M-9614, CH₃, H, H, i-Bu, Cl), (M-9615, CH₃, H, H, i-Bu, F), (M-9616, CH₃, H, H, i-Bu, CF₃), (M-9617, CH₃, H, H, i-Bu, Br), (M-9618, CH₃, H, H, i-Bu, CH₃), (M-9619, CH₃, H, H, sec-Bu, H), (M-9620, CH₃, H, H, sec-Bu, Cl), (M-9621, CH₃, H, H, sec-Bu, F), (M-9622, CH₃, H, H, sec-Bu, CF₃), (M-9623, CH₃, H, H, sec-Bu, Br), (M-9624, CH₃, H, H, sec-Bu, CH₃), (M-9625, CH₃, H, H, n-Pen, H), (M-9626, CH₃, H, H, n-Pen, Cl), (M-9627, CH₃, H, H, n-Pen, F), (M-9628, CH₃, H, H, n-Pen, CF₃), (M-9629, CH₃, H, H, n-Pen, Br), (M-9630, CH₃, H, H, n-Pen, CH₃), (M-9631, CH₃, H, H, c-Pen, H), (M-9632, CH₃, H, H, c-Pen, Cl), (M-9633, CH₃, H, H, c-Pen, F), (M-9634, CH₃, H, H, c-Pen, CF₃), (M-9635, CH₃, H, H, c-Pen, Br), (M-9636, CH₃, H, H, c-Pen, CH₃), (M-9637, CH₃, H, H, n-Hex, H), (M-9638, CH₃, H, H, n-Hex, Cl), (M-9639, CH₃, H, H, n-Hex, F), (M-9640, CH₃, H, H, n-Hex, CF₃), (M-9641, CH₃, H, H, n-Hex, Br), (M-9642, CH₃, H, H, n-Hex, CH₃), (M-9643, CH₃, H, H, c-Hex, H), (M-9644, CH₃, H, H, c-Hex, Cl), (M-9645, CH₃, H, H, c-Hex, F), (M-9646, CH₃, H, H, c-Hex, CF₃), (M-9647, CH₃, H, H, c-Hex, Br), (M-9648, CH₃, H, H, c-Hex, CH₃), (M-9649, CH₃, H, H, OH, H), (M-9650, CH₃, H, H, OH, Cl), (M-9651, CH₃, H, H, OH, F), (M-9652, CH₃, H, H, OH, CF₃), (M-9653, CH₃, H, H, OH, Br), (M-9654, CH₃, H, H, OH, CH₃), (M-9655, CH₃, H, H, EtO, H), (M-9656, CH₃, H, H, EtO, Cl), (M-9657, CH₃, H, H, EtO, F), (M-9658, CH₃, H, H, EtO, CF₃), (M-9659, CH₃, H, H, EtO, Br), (M-9660, CH₃, H, H, EtO, CH₃), (M-9661, CH₃, H, H, n-PrO, H), (M-9662, CH₃, H, H, n-PrO, Cl), (M-9663, CH₃, H, H, n-PrO, F), (M-9664, CH₃, H, H, n-PrO, CF₃), (M-9665, CH₃, H, H, n-PrO, Br), (M-9666, CH₃, H, H, n-PrO, CH₃), (M-9667, CH₃, H, H, PhO, H), (M-9668, CH₃, H, H, PhO, Cl), (M-9669, CH₃, H, H, PhO, F), (M-9670, CH₃, H, H, PhO, CF₃), (M-9671, CH₃, H, H, PhO, Br), (M-9672, CH₃, H, H, PhO, CH₃), (M-9673, CH₃, H, H, BnO, H), (M-9674, CH₃, H, H, BnO, Cl), (M-9675, CH₃, H, H, BnO, F), (M-9676, CH₃, H, H, BnO, CF₃), (M-9677, CH₃, H, H, BnO, Br), (M-9678, CH₃, H, H, BnO, CH₃), (M-9679, CH₃, H, H, PhCH₂CH₂O, H), (M-9680, CH₃, H, H, PhCH₂CH₂O, Cl), (M-9681, CH₃, H, H, PhCH₂CH₂O, F), (M-9682, CH₃, H, H, PhCH₂CH₂O, CF₃), (M-9683, CH₃, H, H, PhCH₂CH₂O, Br), (M-9684, CH₃, H, H, PhCH₂CH₂O, CH₃), (M-9685, MeO, H, H, CF₃O, H), (M-9686, CH₃, H, H, CF₃O, Cl), (M-9687, CH₃, H, H, CF₃O, F), (M-9688, CH₃, H, H, CF₃O, CF₃), (M-9689, CH₃, H, H, CF₃O, Br), (M-9690, CH₃, H, H, CF₃O, CH₃), (M-9691, CH₃, H, H, Ph, H), (M-9692, CH₃, H, H, Ph, Cl), (M-9693, CH₃, H, H, Ph, F), (M-9694, CH₃, H, H, Ph, CF₃), (M-9695, CH₃, H, H, Ph, Br), (M-9696, CH₃, H, H, Ph, CH₃), (M-9697, CH₃, H, H, 4-F-Ph, H), (M-9698, CH₃, H, H, 4-F-Ph, Cl), (M-9699, CH₃, H, H, 4-F-Ph, F), (M-9700, CH₃, H, H, 4-F-Ph, CF₃), (M-9701, CH₃, H, H, 4-F-Ph, Br), (M-9702, CH₃, H, H, 4-F-Ph, CH₃), (M-9703, CH₃, H, H, 4-CF₃-Ph, H), (M-9704, CH₃, H, H, 4-CF₃-Ph, Cl), (M-9705, CH₃, H, H, 4-CF₃-Ph, F), (M-9706, CH₃, H, H, 4-CF₃-Ph, CF₃), (M-9707, CH₃, H, H, 4-CF₃-Ph, Br), (M-9708, CH₃, H, H, 4-CF₃-Ph, CH₃), (M-9709, CH₃, H, H, 4-(Me)₂N-Ph, H), (M-9710, CH₃, H, H, 4-(Me)₂N-Ph, Cl), (M-9711, CH₃, H, H, 4-(Me)₂N-Ph, F), (M-9712, CH₃, H, H, 4-(Me)₂N-Ph, CF₃), (M-9713, CH₃, H, H, 4-(Me)₂N-Ph, Br), (M-9714, CH₃, H, H, 4-(Me)₂N-Ph, CH₃), (M-9715, CH₃, H, H, 4-OH-Ph, H), (M-9716, CH₃, H, H, 4-OH-Ph, Cl), (M-9717, CH₃, H, H, 4-OH-Ph, F), (M-9718, CH₃, H, H, 4-OH-Ph, CF₃), (M-9719, CH₃, H, H, 4-OH-Ph, Br), (M-9720, CH₃, H, H, 4-OH-Ph, CH₃), (M-9721, CH₃, H, H, 3,4-di-F-Ph, H), (M-9722, CH₃, H, H, 3,4-di-F-Ph, Cl), (M-9723, CH₃, H, H, 3,4-di-F-Ph, F), (M-9724, CH₃, H, H, 3,4-di-F-Ph, CF₃), (M-9725, CH₃, H, H, 3,4-di-F-Ph, Br), (M-9726, CH₃, H, H, 3,4-di-F-Ph, CH₃), (M-9727, CH₃, H, H, 4-COOH-Ph, H), (M-9728, CH₃, H, H, 4-COOH-Ph, Cl), (M-9729, CH₃, H, H, 4-COOH-Ph, F), (M-9730, CH₃, H, H, 4-COOH-Ph, CF₃), (M-9731, CH₃, H, H, 4-COOH-Ph, Br), (M-9732, CH₃, H, H, 4-COOH-Ph, CH₃), (M-9733, CH₃, H, H, Bn, H), (M-9734, CH₃, H, H, Bn, Cl), (M-9735, CH₃, H, H, Bn, F), (M-9736, CH₃, H, H, Bn, CF₃), (M-9737, CH₃, H, H, Bn, Br), (M-9738, CH₃, H, H, Bn, CH₃), (M-9739, CH₃, H, H, 4-F-Bn, H), (M-9740, CH₃, H, H, 4-F-Bn, Cl), (M-9741, CH₃, H, H, 4-F-Bn, F), (M-9742, CH₃, H, H, 4-F-Bn, CF₃), (M-9743, CH₃, H, H, 4-F-Bn, Br), (M-9744, CH₃, H, H, 4-F-Bn, CH₃), (M-9745, CH₃, H, H, 2-Py, H), (M-9746, CH₃, H, H, 2-Py, Cl), (M-9747, CH₃, H, H, 2-Py, F), (M-9748, CH₃, H, H, 2-Py, CF₃), (M-9749, CH₃, H, H, 2-Py, Br), (M-9750, CH₃, H, H, 2-Py, CH₃), (M-9751, CH₃, H, H, 3-Py, H), (M-9752, CH₃, H, H, 3-Py, Cl), (M-9753, CH₃, H, H, 3-Py, F), (M-9754, CH₃, H, H, 3-Py, CF₃), (M-9755, CH₃, H, H, 3-Py, Br), (M-9756, CH₃, H, H, 3-Py, CH₃), (M-9757, CH₃, H, H, 4-Py, H), (M-9758, CH₃, H, H, 4-Py, Cl), (M-9759, CH₃, H, H, 4-Py, F), (M-9760, CH₃, H, H, 4-Py, CF₃), (M-9761, CH₃, H, H, 4-Py, Br), (M-9762, CH₃, H, H, 4-Py, CH₃), (M-9763, CH₃, H, H, 2-Th, H), (M-9764, CH₃, H, H, 2-Th, Cl), (M-9765, CH₃, H, H, 2-Th, F), (M-9766, CH₃, H, H, 2-Th, CF₃), (M-9767, CH₃, H, H, 2-Th, Br), (M-9768, CH₃, H, H, 2-Th, CH₃), (M-9769, CH₃, H, H, 3-Th, H), (M-9770, CH₃, H, H, 3-Th, Cl), (M9771, CH₃, H, H, 3-Th, F), (M-9772, CH₃, H, H, 3-Th, CF₃), (M-9773, CH₃, H, H, 3-Th, Br), (M-9774, CH₃, H, H, 3-Th, CH₃), (M-9775, CH₃, H, H, pyrrazol-2-yl, H), (M-9776, CH₃, H, H, pyrrazol-2-yl, Cl), (M-9777, CH₃, H, H, pyrrazol-2-yl, F), (M-9778, CH₃, H, H, pyrrazol-2-yl, CF₃), (M-9779, CH₃, H, H, pyrrazol-2-yl, Br), (M-9780, CH₃, H, H, pyrrazol-2-yl, CH₃), (M-9781, CH₃, H, H, pyrrazol-3-yl, H), (M-9782, CH₃, H, H, pyrrazol-3-yl, Cl), (M-9783, CH₃, H, H, pyrrazol-3-yl, F), (M-9784, CH₃, H, H, pyrrazol-3-yl, CF₃), (M-9785, CH₃, H, H, pyrrazol-3-yl, Br), (M-9786, CH₃, H, H, pyrrazol-3-yl, CH₃), (M-9787, CH₃, H, H, pyrimidin-2-yl, H), (M-9788, CH₃, H, H, pyrimidin-2-yl, Cl), (M-9789, CH₃, H, H, pyrimidin-2-yl, F), (M-9790, CH₃, H, H, pyrimidin-2-yl, CF₃), (M-9791, CH₃, H, H, pyrimidin-2-yl, Br), (M-9792, CH₃, H, H, pyrimidin-2-yl, CH₃), (M-9793, CH₃, H, H, pyrimidin-4-yl, H), (M-9794, CH₃, H, H, pyrimidin-4-yl, Cl), (M-9795, CH₃, H, H, pyrimidin-4-yl, F), (M-9796, CH₃, H, H, pyrimidin-4-yl, CF₃), (M-9797, CH₃, H, H, pyrimidin-4-yl, Br), (M-9798, CH₃, H, H, pyrimidin-4-yl, CH₃), (M-9799, CH₃, H, H, pyrimidin-5-yl, H), (M-9800, CH₃, H, H, pyrimidin-5-yl, Cl), (M-9801, CH₃, H, H, pyrimidin-5-yl, F), (M-9802, CH₃, H, H, pyrimidin-5-yl, CF₃), (M-9803, CH₃, H, H, pyrimidin-5-yl, Br), (M-9804, CH₃, H, H, pyrimidin-5-yl, CH₃), (M-9805, CH₃, H, H, HOOCCH₂CH₂CH₂, H), (M-9806, CH₃, H, H, HOOCCH₂CH₂CH₂, Cl), (M-9807, CH₃, H, H, HOOCCH₂CH₂CH₂, F), (M-9808, CH₃, H, H, HOOCCH₂CH₂CH₂, CF₃), (M-9809, CH₃, H, H, HOOCCH₂CH₂CH₂, Br), (M-9810, CH₃, H, H, HOOCCH₂CH₂CH₂, CH₃), (M-9811, CH₃, H, H, HOOCCH₂CH₂CH₂CH₂, H), (M-9812, CH₃, H, H, HOOCCH₂CH₂CH₂CH₂, Cl), (M-9813, CH₃, H, H, HOOCCH₂CH₂CH₂CH₂, F), (M-9814, CH₃, H, H, HOOCCH₂CH₂CH₂CH₂, CF₃), (M-9815, CH₃, H, H, HOOCCH₂CH₂CH₂CH₂, Br), (M-9816, CH₃, H, H, HOOCCH₂CH₂CH₂CH₂, CH₃), (M-9817, CH₃H, H, (Me)₂NCOCH₂CH₂CH₂CH₂, H), (M-9818, CH₃, H, H, (Me)₂NCOCH₂CH₂CH₂CH₂, Cl), (M-9819, CH₃, H, H, (Me)₂NCOCH₂CH₂CH₂CH₂, F), (M-9820, CH₃, H, H, (Me)₂NCOCH₂CH₂CH₂CH₂, CF₃), (M-9821, CH₃, H, H, (Me)₂NCOCH₂CH₂CH₂CH₂, Br), (M-9822, CH₃, H, H, (Me)₂NCOCH₂CH₂CH₂CH₂, CH₃), (M-9823, CH₃, H, H, (Me)₂NCOCH₂CH₂CH₂CH₂CH₂, H), (M-9824, CH₃, H, H, (Me)₂NCOCH₂CH₂CH₂CH₂CH₂, Cl), (M-9825, CH₃, H, H, (Me)₂NCOCH₂CH₂CH₂CH₂CH₂, F), (M-9826, CH₃, H, H, (Me)₂NCOCH₂CH₂CH₂CH₂CH₂, CF₃), (M-9827, CH₃, H, H, (Me)₂NCOCH₂CH₂CH₂CH₂CH₂, Br), (M-9828, CH₃, H, H, (Me)₂NCOCH₂CH₂CH₂CH₂CH₂, CH₃), (M-9829, CH₃, H, H, MeOCH₂, H), (M-9830, CH₃, H, H, MeOCH₂, Cl), (M-9831, CH₃, H, H, MeOCH₂, F), (M-9832, CH₃, H, H, MeOCH₂, CF₃), (M-9833, CH₃, H, H, MeOCH₂, Br), (M-9834, CH₃, H, H, MeOCH₂, CH₃), (M-9835, CH₃, H, H, EtOCH₂, H), (M-9836, CH₃, H, H, EtOCH₂, Cl), (M-9837, CH₃, H, H, EtOCH₂, F), (M-9838, CH₃, H, H, EtOCH₂, CF₃), (M-9839, CH₃, H, H, EtOCH₂, Br), (M-9840, CH₃, H, H, EtOCH₂, CH₃), (M-9841, CH₃, H, H, EtOCH₂CH₂, H), (M-9842, CH₃, H, H, EtOCH₂CH₂, Cl), (M-9843, CH₃, H, H, EtOCH₂CH₂, F), (M-9844, CH₃, H, H, EtOCH₂CH₂, CF₃), (M-9845, CH₃, H, H, EtOCH₂CH₂, Br), (M-9846, CH₃, H, H, EtOCH₂CH₂, CH₃), (M-9847, CH₃, H, H, MeOCH₂CH₂OCH₂CH₂, H), (M-9848, CH₃, H, H, MeOCH₂CH₂OCH₂CH₂, Cl), (M-9849, CH₃, H, H, MeOCH₂CH₂OCH₂CH₂, F), (M-9850, CH₃, H, H, MeOCH₂CH₂OCH₂CH₂, CF₃), (M-9851, CH₃, H, H, MeOCH₂CH₂OCH₂CH₂, Br), (M-9852, CH₃, H, H, MeOCH₂CH₂OCH₂CH₂, CH₃), (M-9853, CH₃, H, H, MeOCH₂CH₂, H), (M-9854, CH₃, H, H, MeOCH₂CH₂, Cl), (M-9855, CH₃, H, H, MeOCH₂CH₂, F), (M-9856, CH₃, H, H, MeOCH₂CH₂, CF₃), (M-9857, CH₃, H, H, MeOCH₂CH₂, Br), (M-9858, CH₃, H, H, MeOCH₂CH₂, CH₃), (M-9859, CH₃, H, H, HOCH₂, H), (M-9860, CH₃, H, H, HOCH₂, Cl), (M-9861, CH₃, H, H, HOCH₂, F), (M-9862, CH₃, H, H, HOCH₂, CF₃), (M-9863, CH₃, H, H, HOCH₂, Br), (M-9864, CH₃, H, H, HOCH₂, CH₃), (M-9865, CH₃, H, H, HOCH₂CH₂, H), (M-9866, CH₃, H, H, HOCH₂CH₂, Cl), (M-9867, CH₃, H, H, HOCH₂CH₂, F), (M-9868, CH₃, H, H, HOCH₂CH₂, CF₃), (M-9869, CH₃, H, H, HOCH₂CH₂, Br), (M-9870, CH₃, H, H, HOCH₂CH₂, CH₃), (M-9871, CH₃, H, H, HOCH₂CH₂CH₂, H), (M-9872, CH₃, H, H, HOCH₂CH₂CH₂, Cl), (M-9873, CH₃, H, H, HOCH₂CH₂CH₂, F), (M-9874, CH₃, H, H, HOCH₂CH₂CH₂, CF₃), (M-9875, CH₃, H, H, HOCH₂CH₂CH₂, Br), (M-9876, CH₃, H, H, HOCH₂CH₂CH₂, CH₃), (M-9877, CH₃, H, H, HOCH₂CH₂CH₂CH₂, H), (M-9878, CH₃, H, H, HOCH₂CH₂CH₂CH₂, Cl), (M-9879, CH₃, H, H, HOCH₂CH₂CH₂CH₂, F), (M-9880, CH₃H, H, HOCH₂CH₂CH₂CH₂, CF₃), (M-9881, CH₃H, H, HOCH₂CH₂CH₂CH₂Br), (M-9882, CH₃, H, H, HOCH₂CH₂CH₂CH₂, CH₃), (M-9883, CH₃, H, H, HOCH₂CH₂CH₂CH₂CH₂, H), (M-9884, CH₃H, H, HOCH₂CH₂CH₂CH₂CH₂, Cl), (M-9885, CH₃, H, H, HOCH₂CH₂CH₂CH₂CH₂, F), (M-9886, CH₃, H, H, HOCH₂CH₂CH₂CH₂CH₂, CF₃), (M-9887, CH₃H, H, HOCH₂CH₂CH₂CH₂CH₂, Br), (M-9888, CH₃, H, H, HOCH₂CH₂CH₂CH₂CH₂CH₃), (M-9889, CH₃, H, H, HOCH₂CH₂O CH₂CH₂, H), (M-9890, CH₃, H, H, HOCH₂CH₂OCH₂CH₂, Cl), (M-9891, CH₃, H, H, HOCH₂CH₂OCH₂CH₂, F), (M-9892, CH₃, H, H, HOCH₂CH₂O CH₂CH₂, CF₃), (M-9893, CH₃, H, H, HOCH₂CH₂OCH₂CH₂, Br), (M-9894, CH₃, H, H, HOCH₂CH₂OCH₂CH₂, CH₃), (M-9895, CH₃, H, H, (Me)₂N, H), (M-9896, CH₃, H, H, (Me)₂N, Cl), (M-9897, CH₃, H, H, (Me)₂N, F), (M-9898, CH₃, H, H, (Me)₂N, CF₃), (M-9899, CH₃, H, H, (Me)₂N, Br), (M-9900, CH₃, H, H, (Me)₂N, CH₃), (M-9901, CH₃, H, H, piperidin-4-yl-methyl, H), (M-9902, CH₃, H, H, piperidin-4-yl-methyl, Cl), (M-9903, CH₃, H, H, piperidin-4-yl-methyl, F), (M-9904, CH₃, H, H, piperidin-4-yl-methyl, CF₃), (M-9905, CH₃, H, H, piperidin-4-yl-methyl, Br), (M-9906, CH₃, H, H, piperidin-4-yl-methyl, CH₃), (M-9907, CH₃, H, H, cyclohexylmethyl, H), (M-9908, CH₃, H, H, cyclohexylmethyl, Cl), (M-9909, CH₃, H, H, cyclohexylmethyl, F), (M-9910, CH₃, H, H, cyclohexylmethyl, CF₃), (M-9911, CH₃, H, H, cyclohexylmethyl, Br), (M-9912, CH₃, H, H, cyclohexylmethyl, CH₃), (M-9913, CH₃, H, F, H, H), (M-9914, CH₃, H, F, H, Cl), (M-9915, CH₃, H, F, H, F), (M-9916, CH₃, H, F, H, CF₃), (M-9917, CH₃, H, F, H, Br), (M-9918, CH₃, H, F, H, CH₃), (M-9919, CH₃, H, F, F, H), (M-9920, CH₃, H, F, F, Cl), (M-9921, CH₃, H, F, F, F), (M-9922, CH₃, H, F, F, CF₃), (M-9923, CH₃, H, F, F, Br), (M-9924, CH₃, H, F, F, CH₃), (M-9925, CH₃, H, F, Cl, H), (M-9926, CH₃, H, F, Cl, Cl), (M-9927, CH₃, H, F, Cl, F), (M-9928, CH₃, H, F, Cl, CF₃), (M-9929, CH₃, H, F, Cl, Br), (M-9930, CH₃, H, F, Cl, CH₃), (M-9931, CH₃, H, F, CH₃, H), (M-9932, CH₃, H, F, CH₃, Cl), (M-9933, CH₃, H, F, CH₃, F), (M-9934, CH₃, H, F, CH₃, CF₃), (M-9935, CH₃, H, F, CH₃, Br), (M-9936, CH₃, H, F, CH₃, CH₃), (M-9937, CH₃H, F, Et, H), (M-9938, CH₃, H, F, Et, Cl), (M-9939, CH₃, H, F, Et, F), (M-9940, CH₃, H, F, Et, CF₃), (M-9941, CH₃, H, F, Et, Br), (M-9942, CH₃, H, F, Et, CH₃), (M-9943, CH₃, H, F, n-Pr, H), (M-9944, CH₃, H, F, n-Pr, Cl), (M-9945, CH₃, H, F, n-Pr, F), (M-9946, CH₃, H, F, n-Pr, CF₃), (M-9947, CH₃, H, F, n-Pr, Br), (M-9948, CH₃, H, F, n-Pr, CH₃), (M-9949, CH₃, H, F, c-Pr, H), (M-9950, CH₃, H, F, c-Pr, Cl), (M-9951, CH₃, H, F, c-Pr, F), (M-9952, CH₃, H, F, c-Pr, CF₃), (M-9953, CH₃, H, F, c-Pr, Br), (M-9954, CH₃, H, F, c-Pr, CH₃), (M-9955, CH₃, H, F, i-Pr, H), (M-9956, CH₃, H, F, i-Pr, Cl), (M-9957, CH₃, H, F, i-Pr, F), (M-9958, CH₃, H, F, i-Pr, CF₃), (M-9959, CH₃, H, F, i-Pr, Br), (M-9960, CH₃, H, F, i-Pr, CH₃), (M-9961, CH₃, H, F, n-Bu, H), (M-9962, CH₃, H, F, n-Bu, Cl), (M-9963, CH₃, H, F, n-Bu, F), (M-9964, CH₃, H, F, n-Bu, CF₃), (M-9965, CH₃, H, F, n-Bu, Br), (M-9966, CH₃, H, F, n-Bu, CH₃), (M-9967, CH₃, H, F, i-Bu, H), (M-9968, CH₃, H, F, i-Bu, Cl), (M-9969, CH₃, H, F, i-Bu, F), (M-9970, CH₃, H, F, i-Bu, CF₃), (M-9971, CH₃, H, F, i-Bu, Br), (M-9972, CH₃, H, F, i-Bu, CH₃), (M-9973, CH₃, H, F, sec-Bu, H), (M-9974, CH₃, H, F, i-Bu, CH₃), (M-9973, CH₃H, F, sec-Bu, H), (M-9974, CH₃, H, F, sec-Bu, Cl), (M-9975, CH₃, H, F, sec-Bu, F), (M-9976, CH₃, H, F, sec-Bu, CF₃), (M-9977, CH₃, H, F, sec-Bu, Br), (M-9978, CH₃, H, F, sec-Bu, CH₃), (M-9979, CH₃, H, F, n-Pen, H), (M-9980, CH₃, H, F, n-Pen, Cl), (M-9981, CH₃, H, F, n-Pen, F), (M-9982, CH₃, H, F, n-Pen, CF₃), (M-9983, CH₃, H, F, n-Pen, Br), (M-9984, CH₃, H, F, n-Pen, CH₃), (M-9985, CH₃, H, F, c-Pen, H), (M-9986, CH₃, H, F, c-Pen, Cl), (M-9987, CH₃, H, F, c-Pen, F), (M-9988, CH₃, H, F, c-Pen, CF₃), (M-9989, CH₃, H, F, c-Pen, Br), (M-9990, CH₃, H, F, c-Pen, CH₃), (M-9991, CH₃, H, F, n-Hex, H), (M-9992, CH₃, H, F, n-Hex, Cl), (M-9993, CH₃, H, F, n-Hex, F), (M-9994, CH₃, H, F, n-Hex, CF₃), (M-9995, CH₃, H, F, n-Hex, Br), (M-9996, CH₃, H, F, n-Hex, CH₃), (M-9997, CH₃, H, F, c-Hex, H), (M-9998, CH₃, H, F, c-Hex, Cl), (M-9999, CH₃, H, F, c-Hex, F), (M-10000, CH₃, H, F, c-Hex, CF₃), (M-10001, CH₃, H, F, c-Hex, Br), (M-10002, CH₃, H, F, c-Hex, CH₃), (M-10003, CH₃, H, F, OH, H), (M-10004, CH₃, H, F, OH, Cl), (M-10005, CH₃, H, F, OH, F), (M-10006, CH₃, H, F, OH, CF₃), (M-10007, CH₃, H, F, OH, Br), (M-10008, CH₃, H, F, OH, CH₃), (M-10009, CH₃, H, F, EtO, H), (M-10010, CH₃, H, F, EtO, Cl), (M-10011, CH₃, H, F, EtO, F), (M-10012, CH₃, H, F, EtO, CF₃), (M-10013, CH₃, H, F, EtO, Br), (M-10014, CH₃, H, F, EtO, CH₃), (M-10015, CH₃, H, F, n-PrO, H), (M-10016, CH₃, H, F, n-PrO, Cl), (M-10017, CH₃, H, F, n-PrO, F), (M-10018, CH₃, H, F, n-PrO, CF₃), (M-10019, CH₃, H, F, n-PrO, Br), (M-10020, CH₃, H, F, n-PrO, CH₃), (M-10021, CH₃, H, F, PhO, H), (M-10022, CH₃, H, F, PhO, Cl), (M-10023, CH₃, H, F, PhO, F), (M-10024, CH₃, H, F, PhO, CF₃), (M-10025, CH₃, H, F, PhO, Br), (M-10026, CH₃, H, F, PhO, CH₃), (M-10027, CH₃, H, F, BnO, H), (M-10028, CH₃, H, F, BnO, Cl), (M-10029, CH₃, H, F, BnO, F), (M-10030, CH₃, H, F, BnO, CF₃), (M-10031, CH₃, H, F, BnO, Br), (M-10032, CH₃, H, F, BnO, CH₃), (M-10033, CH₃, H, F, PhCH₂CH₂O, H), (M-10034, CH₃, H, F, PhCH₂CH₂O, Cl), (M-10035, CH₃, H, F, PhCH₂CH₂O, F), (M-10036, CH₃, H, F, PhCH₂CH₂O, CF₃), (M-10037, CH₃, H, F, PhCH₂CH₂O, Br), (M-10038, CH₃, H, F, PhCH₂CH₂O, CH₃), (M-10039, CH₃, H, F, CF₃O, H), (M-10040, CH₃, H, F, CF₃O, Cl), (M-10041, CH₃, H, F, CF₃O, F), (M-10042, CH₃, H, F, CF₃O, CF₃), (M-10043, CH₃, H, F, CF₃O, Br), (M-10044, CH₃, H, F, CF₃O, CH₃), (M-10045, CH₃, H, F, Ph, H), (M-10046, CH₃, H, F, Ph, Cl), (M-10047, CH₃, H, F, Ph, F), (M-10048, CH₃, H, F, Ph, CF₃), (M-10049, CH₃, H, F, Ph, Br), (M-10050, CH₃, H, F, Ph, CH₃), (M-10051, CH₃, H, F, 4-F-Ph, H), (M-10052, CH₃, H, F, 4-F-Ph, Cl), (M-10053, CH₃, H, F, 4-F-Ph, F), (M-10054, CH₃, H, F, 4-F-Ph, CF₃), (M-10055, CH₃, H, F, 4-F-Ph, Br), (M-10056, CH₃, H, F, 4-F-Ph, CH₃), (M-10057, CH₃, H, F, 4-CF₃-Ph, H), (M-10058, CH₃, H, F, 4-CF₃-Ph, Cl), (M-10059, CH₃, H, F, 4-CF₃-Ph, F), (M-10060, CH₃, H, F, 4-CF₃-Ph, CF₃), (M-10061, CH₃, H, F, 4-CF₃-Ph, Br), (M-10062, CH₃, H, F, 4-CF₃-Ph, CH₃), (M-10063, CH₃, H, F, 4-(Me)₂N-Ph, H), (M-10064, CH₃, H, F, 4-(Me)₂N-Ph, Cl), (M-10065, CH₃, H, F, 4-(Me)₂N-Ph, F), (M-10066, CH₃, H, F, 4-(Me)₂N-Ph, CF₃), (M-10067, CH₃, H, F, 4-(Me)₂N-Ph, Br), (M-10068, CH₃, H, F, 4-(Me)₂N-Ph, CH₃), (M-10069, CH₃, H, F, 4-OH-Ph, H), (M-10070, CH₃, H, F, 4-OH-Ph, Cl), (M-10071, CH₃, H, F, 4-OH-Ph, F), (M-10072, CH₃, H, F, 4-OH-Ph, CF₃), (M-10073, CH₃, H, F, 4-OH-Ph, Br), (M-10074, CH₃, H, F, 4-OH-Ph, CH₃), (M-10075, CH₃, H, F, 3,4-di-F-Ph, H), (M-10076, CH₃, H, F, 3,4-di-F-Ph, Cl), (M-10077, CH₃, H, F, 3,4-di-F-Ph, F), (M-10078, CH₃, H, F, 3,4-di-F-Ph, CF₃), (M-10079, CH₃, H, F, 3,4-di-F-Ph, Br), (M-10080, CH₃, H, F, 3,4-di-F-Ph, CH₃), (M-10081, CH₃, H, F, 4-COOH-Ph, H), (M-10082, CH₃, H, F, 4-COOH-Ph, Cl), (M-10083, CH₃, H, F, 4-COOH-Ph, F), (M-10084, CH₃, H, F, 4-COOH-Ph, CF₃), (M-10085, CH₃, H, F, 4-COOH-Ph, Br), (M-10086, CH₃, H, F, 4-COOH-Ph, CH₃), (M-10087, CH₃, H, F, Bn, H), (M-10088, CH₃, H, F, Bn, Cl), (M-10089, CH₃, H, F, Bn, F), (M-10090, CH₃, H, F, Bn, CF₃), (M-10091, CH₃, H, F, Bn, Br), (M-10092, CH₃, H, F, Bn, CH₃), (M-10093, CH₃, H, F, 4-F-Bn, H), (M-10094, CH₃, H, F, 4-F-Bn, Cl), (M-10095, CH₃, H, F, 4-F-Bn, F), (M-10096, CH₃, H, F, 4-F-Bn, CF₃), (M-10097, CH₃, H, F, 4-F-Bn, Br), (M-10098, CH₃, H, F, 4-F-Bn, CH₃), (M-10099, CH₃, H, F, 2-Py, H), (M-10100, CH₃, H, F, 2-Py, Cl), (M-10101, CH₃, H, F, 2-Py, F), (M-10102, CH₃, H, F, 2-Py, CF₃), (M-10103, CH₃, H, F, 2-Py, Br), (M-10104, CH₃, H, F, 2-Py, CH₃), (M-10105, CH₃, H, F, 3-Py, H), (M-10106, CH₃, H, F, 3-Py, Cl), (M-10107, CH₃, H, F, 3-Py, F), (M-10108, CH₃, H, F, 3-Py, CF₃), (M-10109, CH₃, H, F, 3-Py, Br), (M-10110, CH₃, H, F, 3-Py, CH₃), (M-10111, CH₃, H, F, 4-Py, H), (M-10112, CH₃, H, F, 4-Py, Cl), (M-10113, CH₃, H, F, 4-Py, F), (M-10114, CH₃, H, F, 4-Py, CF₃), (M-10115, CH₃, H, F, 4-Py, Br), (M-10116, CH₃, H, F, 4-Py, CH₃), (M-10117, CH₃, H, F, 2-Th, H), (M-10118, CH₃, H, F, 2-Th, Cl), (M-10119, CH₃, H, F, 2-Th, F), (M-10120, CH₃, H, F, 2-Th, CF₃), (M-10121, CH₃, H, F, 2-Th, Br), (M-10122, CH₃, H, F, 2-Th, CH₃), (M-10123, CH₃, H, F, 3-Th, H), (M-10124, CH₃, H, F, 3-Th, Cl), (M-10125, CH₃, H, F, 3-Th, F), (M-10126, CH₃, H, F, 3-Th, CF₃), (M-10127, CH₃, H, F, 3-Th, Br), (M-10128, CH₃, H, F, 3-Th, CH₃), (M-10129, CH₃, H, F, pyrrazol-2-yl, H), (M-10130, CH₃, H, F, pyrrazol-2-yl, Cl), (M-10131, CH₃, H, F, pyrrazol-2-yl, F), (M-10132, CH₃, H, F, pyrrazol-2-yl, CF₃), (M-10133, CH₃, H, F, pyrrazol-2-yl, Br), (M-10134, CH₃, H, F, pyrrazol-2-yl, CH₃), (M-10135, CH₃, H, F, pyrrazol-3-yl, H), (M-10136, CH₃, H, F, pyrrazol-3-yl, Cl), (M-10137, CH₃, H, F, pyrrazol-3-yl, F), (M-10138, CH₃, H, F, pyrrazol-3-yl, CF₃), (M-10139, CH₃, H, F, pyrrazol-3-yl, Br), (M-10140, CH₃, H, F, pyrrazol-3-yl, CH₃), (M-10141, CH₃, H, F, pyrimidin-2-yl, H), (M-10142, CH₃, H, F, pyrimidin-2-yl, Cl), (M-10143, CH₃, H, F, pyrimidin-2-yl, F), (M-10144, CH₃, H, F, pyrimidin-2-yl, CF₃), (M-10145, CH₃, H, F, pyrimidin-2-yl, Br), (M-10146, CH₃, H, F, pyrimidin-2-yl, CH₃), (M-10147, CH₃, H, F, pyrimidin-4-yl, H), (M-10148, CH₃, H, F, pyrimidin-4-yl, Cl), (M-10149, CH₃, H, F, pyrimidin-4-yl, F), (M-10150, CH₃, H, F, pyrimidin-4-yl, CF₃), (M-10151, CH₃, H, F, pyrimidin-4-yl, Br), (M-10152, CH₃, H, F, pyrimidin-4-yl, CH₃), (M-10153, CH₃, H, F, pyrimidin-5-yl, H), (M-10154, CH₃, H, F, pyrimidin-5-yl, Cl), (M-10155, CH₃, H, F, pyrimidin-5-yl, F), (M-10156, CH₃, H, F, pyrimidin-5-yl, CF₃), (M-10157, CH₃, H, F, pyrimidin-5-yl, Br), (M-10158, CH₃, H, F, pyrimidin-5-yl, CH₃), (M-10159, CH₃, H, F, HOOCCH₂CH₂CH₂, H), (M-10160, CH₃, H, F, HOOCCH₂CH₂CH₂, Cl), (M-10161, CH₃, H, F, HOOCCH₂CH₂CH₂, F), (M-10162, CH₃, H, F, HOOCCH₂CH₂CH₂, CF₃), (M-10163, CH₃, H, F, HOOCCH₂CH₂CH₂, Br), (M-10164, CH₃, H, F, HOOCCH₂CH₂CH₂, CH₃), (M-10165, CH₃, H, F, HOOCCH₂CH₂CH₂CH₂, H), (M-10166, CH₃, H, F, HOOCCH₂CH₂CH₂CH₂, Cl), (M-10167, CH₃, H, F, HOOCCH₂CH₂CH₂CH₂, F), (M-10168, CH₃, H, F, HOOCCH₂CH₂CH₂CH₂, CF₃), (M-10169, CH₃, H, F, HOOCCH₂CH₂CH₂CH₂, Br), (M-10170, CH₃, H, F, HOOCCH₂CH₂CH₂CH₂, CH₃), (M-10171, CH₃, H, F, (Me)₂NCOCH₂CH₂CH₂CH₂, H), (M-10172, CH₃, H, F, (Me)₂NCOCH₂CH₂CH₂CH₂, Cl), (M-10173, CH₃, H, F, (Me)₂NCOCH₂CH₂CH₂CH₂, F), (M-10174, CH₃, H, F, (Me)₂NCOCH₂CH₂CH₂CH₂, CF₃), (M-10175, CH₃, H, F, (Me)₂NCOCH₂CH₂CH₂CH₂, Br), (M-10176, CH₃, H, F, (Me)₂NCOCH₂CH₂CH₂CH₂, CH₃), (M-10177, CH₃, H, F, (Me)₂NCOCH₂CH₂CH₂CH₂CH₂, H), (M-10178, CH₃, H, F, (Me)₂NCOCH₂CH₂CH₂CH₂CH₂, Cl), (M-10179, CH₃, H, F, (Me)₂NCOCH₂CH₂CH₂CH₂CH₂, F), (M-10180, CH₃, H, F, (Me)₂NCOCH₂CH₂CH₂CH₂CH₂, CF₃), (M-10181, CH₃, H, F, (Me)₂NCOCH₂CH₂CH₂CH₂CH₂, Br), (M-10182, CH₃, H, F, (Me)₂NCOCH₂CH₂CH₂CH₂CH₂, CH₃), (M-10183, CH₃, H, F, MeOCH₂, H), (M-10184, CH₃, H, F, MeOCH₂, Cl), (M-10185, CH₃, H, F, MeOCH₂, F), (M-10186, CH₃, H, F, MeOCH₂, CF₃), (M-10187, CH₃, H, F, MeOCH₂, Br), (M-10188, CH₃, H, F, MeOCH₂, CH₃), (M-10189, CH₃, H, F, EtOCH₂, H), (M-10190, CH₃, H, F, EtOCH₂, Cl), (M-10191, CH₃, H, F, EtOCH₂, F), (M-10192, CH₃, H, F, EtOCH₂, CF₃), (M-10193, CH₃, H, F, EtOCH₂, Br), (M-10194, CH₃, H, F, EtOCH₂, CH₃), (M-10195, CH₃, H, F, EtOCH₂CH₂, H), (M-10196, CH₃, H, F, EtOCH₂CH₂, Cl), (M-10197, CH₃, H, F, EtOCH₂CH₂, F), (M-10198, CH₃, H, F, EtOCH₂CH₂, CF₃), (M-10199, CH₃, H, F, EtOCH₂CH₂, Br), (M-10200, CH₃, H, F, EtOCH₂CH₂, CH₃), (M-10201, CH₃, H, F, MeOCH₂CH₂OCH₂CH₂, H), (M-10202, CH₃, H, F, MeOCH₂CH₂OCH₂CH₂, Cl), (M-10203, CH₃, H, F, MeOCH₂CH₂OCH₂CH₂, F), (M-10204, CH₃, H, F, MeOCH₂CH₂OCH₂CH₂, CF₃), (M-10205, CH₃, H, F, MeOCH₂CH₂OCH₂CH₂, Br), (M-10206, CH₃, H, F, MeOCH₂CH₂OCH₂CH₂, CH₃), (M-10207, CH₃, H, F, MeOCH₂CH₂, H), (M-10208, CH₃, H, F, MeOCH₂CH₂, Cl), (M-10209, CH₃, H, F, MeOCH₂CH₂, F), (M-10210, CH₃, H, F, MeOCH₂CH₂, CF₃), (M-10211, CH₃, H, F, MeOCH₂CH₂, Br), (M-10212, CH₃, H, F, MeOCH₂CH₂, CH₃), (M-10213, CH₃, H, F, HOCH₂, H), (M-10214, CH₃, H, F, HOCH₂, Cl), (M-10215, CH₃, H, F, HOCH₂, F), (M-10216, CH₃, H, F, HOCH₂, CF₃), (M-10217, CH₃, H, F, HOCH₂, Br), (M-10218, CH₃, H, F, HOCH₂, CH₃), (M-10219, CH₃, H, F, HOCH₂CH₂, H), (M-10220, CH₃, H, F, HOCH₂CH₂, Cl), (M-10221, CH₃, H, F, HOCH₂CH₂, F), (M-10222, CH₃, H, F, HOCH₂CH₂, CF₃), (M-10223, CH₃, H, F, HOCH₂CH₂, Br), (M-10224, CH₃, H, F, HOCH₂CH₂, CH₃), (M-10225, CH₃, H, F, HOCH₂CH₂CH₂, H), (M-10226, CH₃, H, F, HOCH₂CH₂CH₂, Cl), (M-10227, CH₃, H, F, HOCH₂CH₂CH₂, F), (M-10228, CH₃, H, F, HOCH₂CH₂CH₂, CF₃), (M-10229, CH₃, H, F, HOCH₂CH₂CH₂, Br), (M-10230, CH₃, H, F, HOCH₂CH₂CH₂, CH₃), (M-10231, CH₃, H, F, HOCH₂CH₂CH₂CH₂, H), (M-10232, CH₃, H, F, HOCH₂CH₂CH₂CH₂, Cl), (M-10233, CH₃, H, F, HOCH₂CH₂CH₂CH₂, F), (M-10234, CH₃, H, F, HOCH₂CH₂CH₂CH₂, CF₃), (M-10235, CH₃, H, F, HOCH₂CH₂CH₂CH₂, Br), (M-10236, CH₃, H, F, HOCH₂CH₂CH₂CH₂, CH₃), (M-10237, CH₃, H, F, HOCH₂CH₂CH₂CH₂CH₂, H), (M-10238, CH₃, H, F, HOCH₂CH₂CH₂CH₂CH₂, Cl), (M-10239, CH₃, H, F, HOCH₂CH₂CH₂CH₂CH₂, F), (M-10240, CH₃, H, F, HOCH₂CH₂CH₂CH₂CH₂, CF₃), (M-10241, CH₃H, F, HOCH₂CH₂CH₂CH₂CH₂, Br), (M-10242, CH₃, H, F, HOCH₂CH₂CH₂CH₂CH₂, CH₃), (M-10243, CH₃, H, F, HOCH₂CH₂OCH₂CH₂, H), (M-10244, CH₃, H, F, HOCH₂CH₂OCH₂CH₂, Cl), (M-10245, CH₃, H, F, HOCH₂CH₂OCH₂CH₂, F), (M-10246, CH₃, H, F, HOCH₂CH₂OCH₂CH₂, CF₃), (M-10247, CH₃, H, F, HOCH₂CH₂OCH₂CH₂, Br), (M-10248, CH₃, H, F, HOCH₂CH₂OCH₂CH₂, CH₃), (M-10249, CH₃, H, F, (Me)₂N, H), (M-10250, CH₃, H, F, (Me)₂N, Cl), (M-10251, CH₃, H, F, (Me)₂N, F), (M-10252, CH₃, H, F, (Me)₂N, CF₃), (M-10253, CH₃, H, F, (Me)₂N, Br), (M-10254, CH₃, H, F, (Me)₂N, CH₃), (M-10255, CH₃, H, F, piperidin-4-yl-methyl, H), (M-10256, CH₃, H, F, piperidin-4-yl-methyl, Cl), (M-10257, CH₃, H, F, piperidin-4-yl-methyl, F), (M-10258, CH₃, H, F, piperidin-4-yl-methyl, CF₃), (M-10259, CH₃, H, F, piperidin-4-yl-methyl, Br), (M-10260, CH₃, H, F, piperidin-4-yl-methyl, CH₃), (M-10261, CH₃, H, F, cyclohexylmethyl, H), (M-10262, CH₃, H, F, cyclohexylmethyl, Cl), (M-10263, CH₃, H, F, cyclohexylmethyl, F), (M-10264, CH₃, H, F, cyclohexylmethyl, CF₃), (M-10265, CH₃, H, F, cyclohexylmethyl, Br), (M-10266, CH₃, H, F, cyclohexylmethyl, CH₃), (M-10267, CH₃, H, Cl, H, H), (M-10268, CH₃, H, Cl, H, Cl), (M-10269, CH₃, H, Cl, H, F), (M-10270, CH₃, H, Cl, H, CF₃), (M-10271, CH₃, H, Cl, H, Br), (M-10272, CH₃, H, Cl, H, CH₃), (M-10273, CH₃, H, Cl, F, H), (M-10274, CH₃, H, Cl, F, CF₃), (M-10275, CH₃, H, Cl, F, F), (M-10276, CH₃, H, Cl, F, Br), (M-10277, CH₃, H, Cl, F, CH₃), (M-10278, CH₃, H, Cl, Cl, H), (M-10279, CH₃, H, Cl, Cl, H), (M-10280, CH₃, H, Cl, Cl, Cl), (M-10281, CH₃, H, Cl, Cl, F), (M-10282, CH₃, H, Cl, Cl, CF₃), (M-10283, CH₃, H, Cl, Cl, Br), (M-10284, CH₃, H, Cl, Cl, CH₃), (M-10285, CH₃, H, Cl, CH₃, H), (M-10286, CH₃, H, Cl, CH₃, Cl), (M-10287, CH₃, H, Cl, CH₃, F), (M-10288, CH₃, H, Cl, CH₃, CF₃), (M-10289, CH₃, H, Cl, CH₃, Br), (M-10290, CH₃, H, Cl, CH₃, CH₃), (M-10291, CH₃, H, Cl, Et, H), (M-10292, CH₃, H, Cl, Et, Cl), (M-10293, CH₃, H, Cl, Et, F), (M-10294, CH₃, H, Cl, Et, CF₃), (M-10295, CH₃, H, Cl, Et, Br), (M-10296, CH₃, H, Cl, Et, CH₃), (M-10297, CH₃, H, Cl, n-Pr, H), (M-10298, CH₃, H, Cl, n-Pr, Cl), (M-10299, CH₃, H, Cl, n-Pr, F), (M-10300, CH₃, H, Cl, n-Pr, CF₃), (M-10301, CH₃, H, Cl, n-Pr, Br), (M-10302, CH₃, H, Cl, n-Pr, CH₃), (M-10303, CH₃, H, Cl, c-Pr, H), (M-10304, CH₃, H, Cl, c-Pr, Cl), (M-10305, CH₃, H, Cl, c-Pr, F), (M-10306, CH₃, H, Cl, c-Pr, CF₃), (M-10307, CH₃, H, Cl, c-Pr, Br), (M-10308, CH₃, H, Cl, c-Pr, CH₃), (M-10309, CH₃, H, Cl, i-Pr, H), (M-10310, CH₃, H, Cl, i-Pr, Cl), (M-10311, CH₃, H, Cl, i-Pr, F), (M-10312, CH₃, H, Cl, i-Pr, CF₃), (M-10313, CH₃, H, Cl, i-Pr, Br), (M-10314, CH₃, H, Cl, i-Pr, CH₃), (M-10315, CH₃, H, Cl, n-Bu, H), (M-10316, CH₃, H, Cl, n-Bu, Cl), (M-10317, CH₃, H, Cl, n-Bu, F), (M-10318, CH₃, H, Cl, n-Bu, CF₃), (M-10319, CH₃, H, Cl, n-Bu, Br), (M-10320, CH₃, H, Cl, n-Bu, CH₃), (M-10321, CH₃, H, Cl, i-Bu, H), (M-10322, CH₃, H, Cl, i-Bu, Cl), (M-10323, CH₃, H, Cl, i-Bu, F), (M-10324, CH₃, H, Cl, i-Bu, CF₃), (M-10325, CH₃, H, Cl, i-Bu, Br), (M-10326, CH₃, H, Cl, i-Bu, CH₃), (M-10327, CH₃, H, Cl, sec-Bu, H), (M-10328, CH₃, H, Cl, sec-Bu, Cl), (M-10329, CH₃, H, Cl, sec-Bu, F), (M-10330, CH₃, H, Cl, sec-Bu, CF₃), (M-10331, CH₃, H, Cl, sec-Bu, Br), (M-10332, CH₃, H, Cl, sec-Bu, CH₃), (M-10333, CH₃, H, Cl, n-Pen, H), (M-10334, CH₃, H, Cl, n-Pen, Cl), (M-10335, CH₃, H, Cl, n-Pen, F), (M-10336, CH₃H, Cl, n-Pen, CF₃), (M-10337, CH₃, H, Cl, n-Pen, Br), (M-10338, CH₃, H, Cl, n-Pen, CH₃), (M-10339, CH₃, H, Cl, c-Pen, H), (M-10340, CH₃, H, Cl, c-Pen, Cl), (M-10341, CH₃, H, Cl, c-Pen, F), (M-10342, CH₃, H, Cl, c-Pen, CF₃), (M-10343, CH₃, H, Cl, c-Pen, Br), (M-10344, CH₃, H, Cl, c-Pen, CH₃), (M-10345, CH₃, H, Cl, n-Hex, H), (M-10346, CH₃, H, Cl, n-Hex, Cl), (M-10347, CH₃, H, Cl, n-Hex, F), (M-10348, CH₃, H, Cl, n-Hex, CF₃), (M-10349, CH₃, H, Cl, n-Hex, Br), (M-10350, CH₃, H, Cl, n-Hex, C₃), (M-10351, CH₃, H, Cl, c-Hex, H), (M-10352, CH₃, H, Cl, c-Hex, Cl), (M-10353, CH₃, H, Cl, c-Hex, F), (M-10354, CH₃, H, Cl, c-Hex, CF₃), (M-10355, CH₃, H, Cl, c-Hex, Br), (M-10356, CH₃, H, Cl, c-Hex, CH₃), (M-10357, CH₃, H, Cl, OH, H), (M-10358, CH₃, H, Cl, OH, Cl), (M-10359, CH₃, H, Cl, OH, F), (M-10360, CH₃, H, Cl, OH, CF₃), (M-10361, CH₃, H, Cl, OH, Br), (M-10362, CH₃, H, Cl, OH, CH₃), (M-10363, CH₃, H, Cl, EtO, H), (M-10364, CH₃, H, Cl, EtO, Cl), (M-10365, CH₃, H, Cl, EtO, F), (M-10366, CH₃, H, Cl, EtO, CF₃), (M-10367, CH₃, H, Cl, EtO, Br), (M-10368, CH₃, H, Cl, EtO, CH₃), (M-10369, CH₃, H, Cl, n-PrO, H), (M-10370, CH₃, H, Cl, n-PrO, Cl), (M-10371, CH₃, H, Cl, n-PrO, F), (M-10372, CH₃, H, Cl, n-PrO, CF₃), (M-10373, CH₃, H, Cl, n-PrO, Br), (M-10374, CH₃, H, Cl, n-PrO, CH₃), (M-10375, CH₃, H, Cl, PhO, H), (M-10376, CH₃, H, Cl, PhO, Cl), (M-10377, CH₃, H, Cl, PhO, F), (M-10378, CH₃, H, Cl, PhO, CF₃), (M-10379, CH₃, H, Cl, PhO, Br), (M-10380, CH₃, H, Cl, PhO, CH₃), (M-10381, CH₃, H, Cl, BnO, H), (M-10382, CH₃, H, Cl, BnO, Cl), (M-10383, CH₃, H, Cl, BnO, F), (H-10384, CH₃, H, Cl, BnO, CF₃), (M-10385, CH₃, H, Cl, BnO, Br), (M-10386, CH₃, H, Cl, BnO, CH₃), (M-10387, CH₃, H, Cl, PhCH₂CH₂O, H), (M-10388, CH₃, H, Cl, PhCH₂CH₂O, Cl), (M-10389, CH₃, H, Cl, PhCH₂CH₂O, F), (M-10390, CH₃, H, Cl, PhCH₂CH₂O, CF₃), (M-10391, CH₃, H, Cl, PhCH₂CH₂O, Br), (M-10392, CH₃, H, Cl, PhCH₂CH₂O, CH₃), (M-10393, CH₃, H, Cl, CF₃O, H), (M-10394, CH₃, H, Cl, CF₃O, Cl), (M-10395, CH₃, H, Cl, CF₃O, F), (M-10396, CH₃, H, Cl, CF₃O, CF₃), (M-10397, CH₃, H, Cl, CF₃O, Br), (M-10398, CH₃, H, Cl, CF₃O, CH₃), (M-10399, CH₃, H, Cl, Ph, H), (M-10400, CH₃, H, Cl, Ph, Cl), (M-10401, CH₃, H, Cl, Ph, F), (M-10402, CH₃, H, Cl, Ph, CF₃), (M-10403, CH₃, H, Cl, Ph, Br), (M-10404, CH₃, H, Cl, Ph, CH₃), (M-10405, CH₃, H, Cl, 4-F-Ph, H), (M-10406, CH₃, H, Cl, 4-F-Ph, Cl), (M-10407, CH₃, H, Cl, 4-F-Ph, F), (M-10408, CH₃, H, Cl, 4-F-Ph, CF₃), (M-10409, CH₃, H, Cl, 4-F-Ph, Br), (M-10410, CH₃, H, Cl, 4-F-Ph, CH₃), (M-10411, CH₃, H, Cl, 4-CF₃-Ph, H), (M-10412, CH₃, H, Cl, 4-CF₃-Ph, Cl), (M-10413, CH₃, H, Cl, 4-CF₃-Ph, F), (M-10414, CH₃, H, Cl, 4-CF₃-Ph, CF₃), (M-10415, CH₃, H, Cl, 4-CF₃-Ph, Br), (M-10416, CH₃, H, Cl, 4-CF₃-Ph, CH₃), (M-10417, CH₃, H, Cl, 4-(Me)₂N-Ph, H), (M-10418, CH₃, H, Cl, 4-(Me)₂N-Ph, Cl), (M-10419, CH₃, H, Cl, 4-(Me)₂N-Ph, F), (M-10420, CH₃, H, Cl, 4-(Me)₂N-Ph, CF₃), (M-10421, CH₃, H, Cl, 4-(Me)₂N-Ph, Br), (M-10422, CH₃, H, Cl, 4-(Me)₂N-Ph, CH₃), (M-10423, CH₃, H, Cl, 4-OH-Ph, H), (M-10424, CH₃, H, Cl, 4-OH-Ph, Cl), (M-10425, CH₃, H, Cl, 4-OH-Ph, F), (M-10426, CH₃, H, Cl, 4-OH-Ph, CF₃), (M-10427, CH₃, H, Cl, 4-OH-Ph, Br), (M-10428, CH₃, H, Cl, 4-OH-Ph, CH₃), (M-10429, CH₃, H, Cl, 3,4-di-F-Ph, H), (M-10430, CH₃, H, Cl, 3,4-di-F-Ph, Cl), (M-10431, CH₃, H, Cl, 3,4-di-F-Ph, F), (M-10432, CH₃, H, Cl, 3,4-di-F-Ph, CF₃), (M-10433, CH₃, H, Cl, 3,4-di-F-Ph, Br), (M-10434, CH₃, H, Cl, 3,4-di-F-Ph, CH₃), (M-10435, CH₃, H, Cl, 4-COOH-Ph, H), (M-10436, CH₃, H, Cl, 4-COOH-Ph, Cl), (M-10437, CH₃, H, Cl, 4-COOH-Ph, F), (M-10438, CH₃, H, Cl, 4-COOH-Ph, CF₃), (M-10439, CH₃, H, Cl, 4-COOH-Ph, Br), (M-10440, CH₃, H, Cl, 4-COOH-Ph, CH₃), (M-10441, CH₃, H, Cl, Bn, H), (M-10442, CH₃, H, Cl, Bn, Cl), (M-10443, CH₃, H, Cl, Bn, F), (M-10444, CH₃, H, Cl, Bn, CF₃), (M-10445, CH₃, H, Cl, Bn, Br), (M-10446, CH₃, H, Cl, Bn, CH₃), (M-10447, CH₃, H, Cl, 4-F-Bn, H), (M-10448, CH₃, H, Cl, 4-F-Bn, Cl), (M-10449, CH₃, H, Cl, 4-F-Bn, F), (M-10450, CH₃, H, Cl, 4-F-Bn, CF₃), (M-10451, CH₃, H, Cl, 4-F-Bn, Br), (M-10452, CH₃, H, Cl, 4-F-Bn, CH₃), (M-10453, CH₃, H, Cl, 2-Py, H), (M-10454, CH₃, H, Cl, 2-Py, Cl), (M-10455, CH₃, H, Cl, 2-Py, F), (M-10456, CH₃, H, Cl, 2-Py, CF₃), (M-10457, CH₃, H, Cl, 2-Py, Br), (M-10458, CH₃, H, Cl, 2-Py, CH₃), (M-10459, CH₃, H, Cl, 3-Py, H), (M-10460, CH₃, H, Cl, 3-Py, Cl), (M-10461, CH₃, H, Cl, 3-Py, F), (M-10462, CH₃, H, Cl, 3-Py, CF₃), (M-10463, CH₃, H, Cl, 3-Py, Br), (M-10464, CH₃, H, Cl, 3-Py, CH₃), (M-10465, CH₃, H, Cl, 4-Py, H), (M-10466, CH₃, H, Cl, 4-Py, Cl), (M-10467, CH₃, H, Cl, 4-Py, F), (M-10468, CH₃, H, Cl, 4-Py, CF₃), (M-10469, CH₃, H, Cl, 4-Py, Br), (M-10470, CH₃, H, Cl, 4-Py, CH₃), (M-10471, CH₃, H, Cl, 2-Th, H), (M-10472, CH₃, H, Cl, 2-Th, Cl), (M-10473, CH₃, H, Cl, 2-Th, F), (M-10474, CH₃, H, Cl, 2-Th, CF₃), (M-10475, CH₃, H, Cl, 2-Th, Br), (M-10476, CH₃, H, Cl, 2-Th, CH₃), (M-10477, CH₃, H, Cl, 3-Th, H), (M-10478, CH₃, H, Cl, 3-Th, Cl), (M-10479, CH₃, H, Cl, 3-Th, F), (M-10480, CH₃, H, Cl, 3-Th, CF₃), (M-10481, CH₃, H, Cl, 3-Th, Br), (M-10482, CH₃, H, Cl, 3-Th, CH₃), (M-10483, CH₃, H, Cl, pyrrazol-2-yl, H), (M-10484, CH₃, H, Cl, pyrrazol-2-yl, Cl), (M-10485, CH₃, H, Cl, pyrrazol-2-yl, F), (M-10486, CH₃, H, Cl, pyrrazol-2-yl, CF₃), (M-10487, CH₃, H, Cl, pyrrazol-2-yl, Br), (M-10488, CH₃, H, Cl, pyrrazol-2-yl, CH₃), (M-10489, CH₃, H, Cl, pyrrazol-3-yl, H), (M-10490, CH₃, H, Cl, pyrrazol-3-yl, Cl), (M-10491, CH₃, H, Cl, pyrrazol-3-yl, F), (M-10492, CH₃, H, Cl, pyrrazol-3-yl, CF₃), (M-10493, CH₃, H, Cl, pyrrazol-3-yl, Br), (M-10494, CH₃, H, Cl, pyrrazol-3-yl, CH₃), (M-10495, CH₃, H, Cl, pyrimidin-2-yl, H), (M-10496, CH₃, H, Cl, pyrimidin-2-yl, Cl), (M-10497, CH₃, H, Cl, pyrimidin-2-yl, F), (M-10498, CH₃, H, Cl, pyrimidin-2-yl, CF₃), (M-10499, CH₃, H, Cl, pyrimidin-2-yl, Br), (M-10500, CH₃, H, Cl, pyrimidin-2-yl, CH₃), (M-10501, CH₃, H, Cl, pyrimidin-4-yl, H), (M-10502, CH₃, H, Cl, pyrimidin-4-yl, Cl), (M-10503, CH₃, H, Cl, pyrimidin-4-yl, F), (M-10504, CH₃, H, Cl, pyrimidin-4-yl, CF₃), (M-10505, CH₃, H, Cl, pyrimidin-4-yl, Br), (M-10506, CH₃, H, Cl, pyrimidin-4-yl, CH₃), (M-10507, CH₃, H, Cl, pyrimidin-5-yl, H), (M-10508, CH₃, H, Cl, pyrimidin-5-yl, Cl), (M-10509, CH₃, H, Cl, pyrimidin-5-yl, F), (M-10510, CH₃, H, Cl, pyrimidin-5-yl, CF₃), (M-10511, CH₃, H, Cl, pyrimidin-5-yl, Br), (M-10512, CH₃, H, Cl, pyrimidin-5-yl, CH₃), (M-10513, CH₃, H, Cl, HOOCCH₂CH₂CH₂, H), (M-10514, CH₃, H, Cl, HOOCCH₂CH₂CH₂, Cl), (M-10515, CH₃, H, Cl, HOOCCH₂CH₂CH₂, F), (M-10516, CH₃, H, Cl, HOOCCH₂CH₂CH₂, CF₃), (M-10517, CH₃, H, Cl, HOOCCH₂CH₂CH₂, Br), (M-10518, CH₃, H, Cl, HOOCCH₂CH₂CH₂, CH₃), (M-10519, CH₃, H, Cl, HOOCCH₂CH₂CH₂CH₂, H), (M-10520, CH₃, H, Cl, HOOCCH₂CH₂CH₂CH₂, Cl), (M-10521, CH₃, H, Cl, HOOCCH₂CH₂CH₂CH₂, F), (M-10522, CH₃, H, Cl, HOOCCH₂CH₂CH₂CH₂, CF₃), (M-10523, CH₃, H, Cl, HOOCCH₂CH₂CH₂CH₂, Br), (M-10524, CH₃, H, Cl, HOOCCH₂CH₂CH₂CH₂, CH₃), (M-10525, CH₃, H, Cl, (Me)₂NCOCH₂CH₂CH₂CH₂, H), (M-10526, CH₃, H, Cl, (Me)₂NCOCH₂CH₂CH₂CH₂, Cl), (M-10527, CH₃, H, Cl, (Me)₂NCOCH₂CH₂CH₂CH₂, F), (M-10528, CH₃, H, Cl, (Me)₂NCOCH₂CH₂CH₂CH₂, CF₃), (M-10529, CH₃, H, Cl, (Me)₂NCOCH₂CH₂CH₂CH₂, Br), (M-10530, CH₃, H, Cl, (Me)₂NCOCH₂CH₂CH₂CH₂, CH₃), (M-10531, CH₃, H, Cl, (Me)₂NCOCH₂CH₂CH₂CH₂CH₂, H), (M-10532, CH₃, H, Cl, (Me)₂NCOCH₂CH₂CH₂CH₂CH₂, Cl), (M-10533, CH₃, H, Cl, (Me)₂NCOCH₂CH₂CH₂CH₂CH₂, F), (M-10534, CH₃, H, Cl, (Me)₂NCOCH₂CH₂CH₂CH₂CH₂, CF₃), (M-10535, CH₃, H, Cl, (Me)₂NCOCH₂CH₂CH₂CH₂CH₂, Br), (M-10536, CH₃, H, Cl, (Me)₂NCOCH₂CH₂CH₂CH₂CH₂, CH₃), (M-10537, CH₃, H, Cl, MeOCH₂, H), (M-10538, CH₃, H, Cl, MeOCH₂, Cl), (M-10539, CH₃, H, Cl, MeOCH₂, F), (M-10540, CH₃, H, Cl, MeOCH₂, CF₃), (M-10541, CH₃, H, Cl, MeOCH₂, Br), (M-10542, CH₃, H, Cl, MeOCH₂, CH₃), (M-10543, CH₃, H, Cl, EtOCH₂, H), (M-10544, CH₃, H, Cl, EtOCH₂, Cl), (M-10545, CH₃, H, Cl, EtOCH₂, F), (M-10546, CH₃, H, Cl, EtOCH₂, CF₃), (M-10547, CH₃, H, Cl, EtOCH₂, Br), (M-10548, CH₃, H, Cl, EtOCH₂, CH₃), (M-10549, CH₃, H, Cl, EtOCH₂CH₂, H), (M-10550, CH₃, H, Cl, EtOCH₂CH₂, Cl), (M-10551, CH₃, H, Cl, EtOCH₂CH₂, F), (M-10552, CH₃, H, Cl, EtOCH₂CH₂, CF₃), (M-10553, CH₃, H, Cl, EtOCH₂CH₂, Br), (M-10554, CH₃, H, Cl, EtOCH₂CH₂, CH₃), (M-10555, CH₃, H, Cl, MeOCH₂CH₂OCH₂CH₂, H), (M-10556, CH₃, H, Cl, MeOCH₂CH₂OCH₂CH₂, Cl), (M-10557, CH₃, H, Cl, MeOCH₂CH₂OCH₂CH₂, F), (M-10558, CH₃, H, Cl, MeOCH₂CH₂OCH₂CH₂, CF₃), (M-10559, CH₃, H, Cl, MeOCH₂CH₂OCH₂CH₂, Br), (M-10560, CH₃, H, Cl, MeOCH₂CH₂OCH₂CH₂, CH₃), (M-10561, CH₃, H, Cl, MeOCH₂CH₂, H), (M-10562, CH₃, H, Cl, MeOCH₂CH₂, Cl), (M-10563, CH₃, H, Cl, MeOCH₂CH₂, F), (M-10564, CH₃, H, Cl, MeOCH₂CH₂, CF₃), (M-10565, CH₃, H, Cl, MeOCH₂CH₂, Br), (M-10566, CH₃, H, Cl, MeOCH₂CH₂, CH₃), (M-10567, CH₃, H, Cl, HOCH₂, H), (M-10568, CH₃, H, Cl, HOCH₂, Cl), (M-10569, CH₃, H, Cl, HOCH₂, F), (M-10570, CH₃, H, Cl, HOCH₂, CF₃), (M-10571, CH₃, H, Cl, HOCH₂, Br), (M-10572, CH₃, H, Cl, HOCH₂, CH₃), (M-10573, CH₃, H, Cl, HOCH₂CH₂, H), (M-10574, CH₃, H, Cl, HOCH₂CH₂, Cl), (M10575, CH₃, H, Cl, HOCH₂CH₂, F), (M-10576, CH₃, H, Cl, HOCH₂CH₂, CF₃), (M-10577, CH₃, H, Cl, HOCH₂CH₂, Br), (M-10578, CH₃, H, Cl, HOCH₂CH₂, CH₃), (M-10579, CH₃, H, Cl, HOCH₂CH₂CH₂, H), (M-10580, CH₃, H, Cl, HOCH₂CH₂CH₂, Cl), (M-10581, CH₃, H, Cl, HOCH₂CH₂CH₂, F), (M-10582, CH₃, H, Cl, HOCH₂CH₂CH₂, CF₃), (M-10583, CH₃, H, Cl, HOCH₂CH₂CH₂, Br), (M-10584, CH₃, H, Cl, HOCH₂CH₂CH₂, CH₃), (M-10585, CH₃, H, Cl, HOCH₂CH₂CH₂CH₂, H), (M-10586, CH₃, H, Cl, HOCH₂CH₂CH₂CH₂, Cl), (M-10587, CH₃, H, Cl, HOCH₂CH₂CH₂CH₂, F), (M-10588, CH₃, H, Cl, HOCH₂CH₂CH₂CH₂, CF₃), (M-10589, CH₃, H, Cl, HOCH₂CH₂CH₂CH₂, Br), (M-10590, CH₃, H, Cl, HOCH₂CH₂CH₂CH₂, CH₃), (M-10591, CH₃, H, Cl, HOCH₂CH₂CH₂CH₂CH₂, H), (M-10592, CH₃, H, Cl, HOCH₂CH₂CH₂CH₂CH₂, Cl), (M-10593, CH₃, H, Cl, HOCH₂CH₂CH₂CH₂CH₂, F), (M-10594, CH₃, H, Cl, HOCH₂CH₂CH₂CH₂CH₂, CF₃), (M-10595, CH₃, H, Cl, HOCH₂CH₂CH₂CH₂CH₂, Br), (M-10596, CH₃, H, Cl, HOCH₂CH₂CH₂CH₂CH₂, CH₃), (M-10597, CH₃, H, Cl, HOCH₂CH₂OCH₂CH₂, H), (M-10598, CH₃, H, Cl, HOCH₂CH₂OCH₂CH₂, Cl), (M-10599, CH₃, H, Cl, HOCH₂CH₂OCH₂CH₂, F), (M-10600, CH₃, H, Cl, HOCH₂CH₂OCH₂CH₂, CF₃), (M-10601, CH₃, H, Cl, HOCH₂CH₂OCH₂CH₂, Br), (M-10602, CH₃, H, Cl, HOCH₂CH₂OCH₂CH₂, CH₃), (M-10603, CH₃, H, Cl, (Me)₂N, H), (M-10604, CH₃, H, Cl, (Me)₂N, Cl), (M-10605, CH₃, H, Cl, (Me)₂N, F), (M-10606, CH₃, H, Cl, (Me)₂N, CF₃), (M-10607, CH₃, H, Cl, (Me)₂N, Br), (M-10608, CH₃, H, Cl, (Me)₂N, CH₃), (M-10609, CH₃, H, Cl, piperidin-4-yl-methyl, H), (M-10610, CH₃, H, Cl, piperidin-4-yl-methyl, Cl), piperidin-4-yl-methyl, CF₃), (M-10613, CH₃, H, Cl, piperidin-4-yl-methyl, Br), (M-10614, CH₃, H, Cl, piperidin-4-yl-methyl, CH₃), (M-10615, CH₃, H, Cl, cyclohexylmethyl, H), (M-10616, CH₃, H, Cl, cyclohexylmethyl, Cl), (M-10617, CH₃, H, Cl, cyclohexylmethyl, F), (M-10618, CH₃, H, Cl, cyclohexylmethyl, CF₃), (M-10619, CH₃, H, Cl, cyclohexylmethyl, Br), (M-10620, CH₃, H, Cl, cyclohexylmethyl, CH₃), (M-10621, CH₃, F, H, H, H), (M-10622, CH₃, F, H, H, Cl), (M-10623, CH₃, F, H, H, F), (M-10624, CH₃, F, H, H, CF₃), (M-10625, CH₃, F, H, H, Br), (M-10626, CH₃, F, H, H, CH₃), (M-10627, CH₃, F, H, F, H), (M-10628, CH₃, F, H, F, Cl), (M-10629, CH₃, F, H, F, F), (M-10630, CH₃, F, H, F, CF₃), (M-10631, CH₃, F, H, F, Br), (M-10632, CH₃, F, H, F, CH₃), (M-10633, CH₃, F, H, Cl, H), (M-10634, CH₃, F, H, Cl, Cl), (M-10635, CH₃, F, H, Cl, F), (M-10636, CH₃, F, H, Cl, CF₃), (M-10637, CH₃, F, H, Cl, Br), (M-10638, CH₃, F, H, Cl, CH₃), (M-10639, CH₃, F, H, CH₃, H), (M-10640, CH₃, F, H, CH₃, Cl), (M-10641, CH₃, F, H, CH₃, F), (M-10642, CH₃, F, H, CH₃, CF₃), (M-10643, CH₃, F, H, CH₃, Br), (M-10644, CH₃, F, H, CH₃, CH₃), (M-10645, CH₃, F, H, Et, H), (M-10646, CH₃, F, H, Et, Cl), (M-10647, CH₃, F, H, Et, F), (M-10648, CH₃, F, H, Et, CF₃), (M-10649, CH₃, F, H, Et, Br), (M-10650, CH₃, F, H, Et, CH₃), (M-10651, CH₃, F, H, n-Pr, H), (M-10652, CH₃, F, H, n-Pr, Cl), (M-10653, CH₃, F, H, n-Pr, F), (M-10654, CH₃, F, H, n-Pr, CF₃), (M-10655, CH₃, F, H, n-Pr, Br), (M-10656, CH₃, F, H, n-Pr, CH₃), (M-10657, CH₃, F, H, c-Pr, H), (M-10658, CH₃, F, H, c-Pr, Cl), (M-10659, CH₃, F, H, c-Pr, F), (M-10660, CH₃, F, H, c-Pr, CF₃), (M-10661, CH₃, F, H, c-Pr, Br), (M-10662, CH₃, F, H, c-Pr, CH₃), (M-10663, CH₃, F, H, i-Pr, H), (M-10664, CH₃, F, H, i-Pr, Cl), (M-10665, CH₃, F, H, i-Pr, F), (M-10666, CH₃, F, H, i-Pr, CF₃), (M-10667, CH₃, F, H, i-Pr, Br), (M-10668, CH₃, F, H, i-Pr, CH₃), (M-10669, CH₃, F, H, n-Bu, H), (M-10670, CH₃, F, H, n-Bu, Cl), (M-10671, CH₃, F, H, n-Bu, F), (M-10672, CH₃, F, H, n-Bu, CF₃), (M-10673, CH₃, F, H, n-Bu, Br), (M-10674, CH₃, F, H, n-Bu, CH₃), (M-10675, CH₃, F, H, i-Bu, H), (M-10676, CH₃, F, H, i-Bu, Cl), (M-10677, CH₃, F, H, i-Bu, F), (M-10678, CH₃, F, H, i-Bu, CF₃), (M-10679, CH₃, F, H, i-Bu, Br), (M-10680, CH₃, F, H, i-Bu, CH₃), (M-10681, CH₃, F, H, sec-Bu, H), (M-10682, CH₃, F, H, sec-Bu, Cl), (M-10683, CH₃, F, H, sec-Bu, F), (M-10684, CH₃, F, H, sec-Bu, CF₃), (M-10685, CH₃, F, H, sec-Bu, Br), (M-10686, CH₃, F, H, sec-Bu, CH₃), (M-10687, CH₃, F, H, n-Pen, H), (M-10688, CH₃, F, H, n-Pen, Cl), (M-10689, CH₃, F, H, n-Pen, F), (M-10690, CH₃, F, H, n-Pen, CF₃), (M-10691, CH₃, F, H, n-Pen, Br), (M-10692, CH₃, F, H, n-Pen, CH₃), (M-10693, CH₃, F, H, c-Pen, H), (M-10694, CH₃, F, H, c-Pen, Cl), (M-10695, CH₃, F, H, c-Pen, F), (M-10696, CH₃, F, H, c-Pen, CF₃), (M-10697, CH₃, F, H, c-Pen, Br), (M-10698, CH₃, F, H, c-Pen, CH₃), (M-10699, CH₃, F, H, n-Hex, H), (M-10700, CH₃, F, H, n-Hex, Cl), (M-10701, CH₃, F, H, n-Hex, F), (M-10702, CH₃, F, H, n-Hex, CF₃), (M-10703, CH₃, F, H, n-Hex, Br), (M-10704, CH₃, F, H, n-Hex, CH₃), (M-10705, CH₃, F, H, c-Hex, H), (M-10706, CH₃, F, H, c-Hex, Cl), (M-10707, CH₃, F, H, c-Hex, F), (M-10708, CH₃, F, H, c-Hex, CF₃), (M-10709, CH₃, F, H, c-Hex, Br), (M-10710, CH₃, F, H, c-Hex, CH₃), (M-10711, CH₃, F, H, OH, H), (M-10712, CH₃, F, H, OH, Cl), (M-10713, CH₃, F, H, OH, F), (M-10714, CH₃, F, H, OH, CF₃), (M-10715, CH₃, F, H, OH, Br), (M-10716, CH₃, F, H, OH, CH₃), (M-10717, CH₃, F, H, EtO, H), (M-10718, CH₃, F, H, EtO, Cl), (M-10719, CH₃, F, H, EtO, F), (M-10720, CH₃, F, H, EtO, CF₃), (M-10721, CH₃, F, H, EtO, Br), (M-10722, CH₃, F, H, EtO, CH₃), (M-10723, CH₃, F, H, n-PrO, H), (M-10724, CH₃, F, H, n-PrO, Cl), (M-10725, CH₃, F, H, n-PrO, F), (M-10726, CH₃, F, H, n-PrO, CF₃), (M-10727, CH₃, F, H, n-PrO, Br), (M-10728, CH₃, F, H, n-PrO, CH₃), (M-10729, CH₃, F, H, PhO, H), (M-10730, CH₃, F, H, PhO, Cl), (M-10731, CH₃, F, H, PhO, F), (M-10732, CH₃, F, H, PhO, CF₃), (M-10733, CH₃, F, H, PhO, Br), (M-10734, CH₃, F, H, PhO, CH₃), (M-10735, CH₃, F, H, BnO, H), (M-10736, CH₃, F, H, BnO, Cl), (M-10737, CH₃, F, H, BnO, F), (M-10738, CH₃, F, H, BnO, CF₃), (M-10739, CH₃, F, H, BnO, Br), (M-10740, CH₃, F, H, BnO, CH₃), (M-10741, CH₃, F, H, PhCH₂CH₂O, H), (M-10742, CH₃, F, H, PhCH₂CH₂O, Cl), (M-10743, CH₃, F, H, PhCH₂CH₂O, F), (M-10744, CH₃, F, H, PhCH₂CH₂O, CF₃), (M-10745, CH₃, F, H, PhCH₂CH₂O, Br), (M-10746, CH₃, F, H, PhCH₂CH₂O, CH₃), (M-10747, CH₃, F, H, CF₃O, H), (M-10748, CH₃, F, H, CF₃O, Cl), (M-10749, CH₃, F, H, CF₃O, F), (M-10750, CH₃, F, H, CF₃O, CF₃), (M-10751, CH₃, F, H, CF₃, Br), (M-10752, CH₃, F, H, CF₃O, CH₃), (M-10753, CH₃, F, H, Ph, H), (M-10754, CH₃, F, H, Ph, Cl), (M-10755, CH₃, F, H, Ph, F), (M-10756, CH₃, F, H, Ph, CF₃), (M-10757, CH₃, F, H, Ph, Br), (M-10758, CH₃, F, H, Ph, CH₃), (M-10759, CH₃, F, H, 4-F-Ph, H), (M-10760, CH₃, F, H, 4-F-Ph, Cl), (M-10761, CH₃, F, H, 4-F-Ph, F), (M-10762, CH₃, F, H, 4-F-Ph, CF₃), (M-10763, CH₃, F, H, 4-F-Ph, Br), (M-10764, CH₃, F, H, 4-F-Ph, CH₃), (M-10765, CH₃, F, H, 4-CF₃-Ph, H), (M-10766, CH₃, F, H, 4-CF₃-Ph, Cl), (M-10767, CH₃, F, H, 4-CF₃-Ph, F), (M-10768, CH₃, F, H, 4-CF₃-Ph, CF₃), (M-10769, CH₃, F, H, 4-CF₃-Ph, Br), (M-10770, CH₃, F, H, 4-CF₃-Ph, CH₃), (M-10771, CH₃, F, H, 4-(Me)₂N-Ph, H), (M-10772, CH₃, F, H, 4-(Me)₂N-Ph, Cl), (M-10773, CH₃, F, H, 4-(Me)₂N-Ph, F), (M-10774, CH₃, F, H, 4-(Me)₂N-Ph, CF₃), (M-10775, CH₃, F, H, 4-(Me)₂N-Ph, Br), (M-10776, CH₃, F, H, 4-(Me)₂N-Ph, CH₃), (M-10777, CH₃, F, H, 4-OH-Ph, H), (M-10778, CH₃, F, H, 4-OH-Ph, Cl), (M-10779, CH₃, F, H, 4-OH-Ph, F), (M-10780, CH₃, F, H, 4-OH-Ph, CF₃), (M-10781, CH₃, F, H, 4-OH-Ph, Br), (M-10782, CH₃, F, H, 4-OH-Ph, CH₃), (M-10783, CH₃, F, H, 3,4-di-F-Ph, H), (M-10784, CH₃, F, H, 3,4-di-F-Ph, Cl), (M-10785, CH₃, F, H, 3,4-di-F-Ph, F), (M-10786, CH₃, F, H, 3,4-di-F-Ph, CF₃), (M-10787, CH₃, F, H, 3,4-di-F-Ph, Br), (M-10788, CH₃, F, H, 3,4-di-F-Ph, CH₃), (M-10789, CH₃, F, H, 4-COOH-Ph, H), (M-10790, CH₃, F, H, 4-COOH-Ph, Cl), (M-10791, CH₃, F, H, 4-COOH-Ph, F), (M-10792, CH₃, F, H, 4-COOH-Ph, CF₃), (M-10793, CH₃, F, H, 4-COOH-Ph, Br), (M-10794, CH₃, F, H, 4-COOH-Ph, CH₃), (M-10795, CH₃, F, H, Bn, H), (M-10796, CH₃, F, H, Bn, Cl), (M-10797, CH₃, F, H, Bn, F), (M-10798, CH₃, F, H, Bn, CF₃), (M-10799, CH₃, F, H, Bn, Br), (M-10800, CH₃, F, H, Bn, CH₃), (M-10801, CH₃, F, H, 4-F-Bn, H), (M-10802, CH₃, F, H, 4-F-Bn, Cl), (M-10803, CH₃, F, H, 4-F-Bn, F), (M-10804, CH₃, F, H, 4-F-Bn, CF₃), (M-10805, CH₃, F, H, 4-F-Bn, Br), (M-10806, CH₃, F, H, 4-F-Bn, CH₃), (M-10807, CH₃, F, H, 2-Py, H), (M-10808, CH₃, F, H, 2-Py, Cl), (M-10809, CH₃, F, H, 2-Py, F), (M-10810, CH₃, F, H, 2-Py, CF₃), (M-10811, CH₃, F, H, 2-Py, Br), (M-10812, CH₃, F, H, 2-Py, CH₃), (M-10813, CH₃, F, H, 3-Py, H), (M-10814, CH₃, F, H, 3-Py, Cl), (M-10815, CH₃, F, H, 3-Py, F), (M-10816, CH₃, F, H, 3-Py, CF₃), (M-10817, CH₃, F, H, 3-Py, Br), (M-10818, CH₃, F, H, 3-Py, CH₃), (M-10819, CH₃, F, H, 4-Py, H), (M-10820, CH₃, F, H, 4-Py, Cl), (M-10821, CH₃, F, H, 4-Py, F), (M-10822, CH₃, F, H, 4-Py, CF₃), (M-10823, CH₃, F, H, 4-Py, Br), (M-10824, CH₃, F, H, 4-Py, CH₃), (M-10825, ClT₃, F, H, 2-Th, H), (M-10826, CH₃, F, H, 2-Th, Cl), (M-10827, CH₃, F, H, 2-Th, F), (M-10828, CH₃, F, H, 2-Th, CF₃), (M-10829, CH₃, F, H, 2-Th, Br), (M-10830, CH₃; F, H, 2-Th, CH₃), (M-10831, CH₃, F, H, 3-Th, H), (M-10832, CH₃, F, H, 3-Th, Cl), (M-10833, CH₃, F, H, 3-Th, F), (M-10834, CH₃, F, H, 3-Th, CF₃), (M-10835, CH₃, F, H, 3-Th, Br), (M-10836, CH₃, F, H, 3-Th, CH₃), (M-10837, CH₃, F, H, pyrrazol-2-yl, H), (M-10838, CH₃, F, H, pyrrazol-2-yl, Cl), (M-10839, CH₃, F, H, pyrrazol-2-yl, F), (M-10840, CH₃, F, H, pyrrazol-2-yl, CF₃), (M-10841, CH₃, F, H, pyrrazol-2-yl, Br), (M-10842, CH₃, F, H, pyrrazol-2-yl, CH₃), (M-10843, CH₃, F, H, pyrrazol-3-yl, H), (M-10844, CH₃, F, H, pyrrazol-3-yl, Cl), (M-10845, CH₃, F, H, pyrrazol-3-yl, F), (M-10846, CH₃, F, H, pyrrazol-3-yl, CF₃), (M-10847, CH₃, F, H, pyrrazol-3-yl, Br), (M-10848, CH₃, F, H, pyrrazol-3-yl, CH₃), (M-10849, CH₃, F, H, pyrimidin-2-yl, H), (M-10850, CH₃, F, H, pyrimidin-2-yl, Cl), (M-10851, CH₃, F, H, pyrimidin-2-yl, F), (M-10852, CH₃, F, H, pyrimidin-2-yl, CF₃), (M-10853, CH₃, F, H, pyrimidin-2-yl, Br), (M-10854, CH₃, F, H, pyrimidin-2-yl, CH₃), (M-10855, CH₃, F, H, pyrimidin-4-yl, H), (M-10856, CH₃, F, H, pyrimidin-4-yl, Cl), (M-10857, CH₃, F, H, pyrimidin-4-yl, F), (M-10858, CH₃, F, H, pyrimidin-4-yl, CF₃), (M-10859, CH₃, F, H, pyrimidin-4-yl, Br), (M-10860, CH₃, F, H, pyrimidin-4-yl, CH₃), (M-10861, CH₃, F, H, pyrimidin-5-yl, H), (M-10862, CH₃, F, H, pyrimidin-5-yl, Cl), (M-10863, CH₃, F, H, pyrimidin-5-yl, F), (M-10864, CH₃, F, H, pyrimidin-5-yl, CF₃), (M-10865, CH₃, F, H, pyrimidin-5-yl, Br), (M-10866, CH₃, F, H, pyrimidin-5-yl, CH₃), (M-10867, CH₃, F, H, HOOCCH₂CH₂CH₂, H), (M-10868, CH₃, F, H, HOOCCH₂CH₂CH₂, Cl), (M-10869, CH₃, F, H, HOOCCH₂CH₂CH₂, F), (M-10870, CH₃, F, H, HOOCCH₂CH₂CH₂, CF₃), (M-10871, CH₃, F, H, HOOCCH₂CH₂CH₂, Br), (M-10872, CH₃, F, H, HOOCCH₂CH₂CH₂, CH₃), (M-10873, CH₃, F, H, HOOCCH₂CH₂CH₂CH₂, H), (M-10874, CH₃, F, H, HOOCCH₂CH₂CH₂CH₂, Cl), (M-10875, CH₃, F, H, HOOCCH₂CH₂CH₂CH₂, F), (M-10876, CH₃, F, H, HOOCCH₂CH₂CH₂CH₂, CF₃), (M-10877, CH₃, F, H, HOOCCH₂CH₂CH₂CH₂, Br), (M-10878, CH₃, F, H, HOOCCH₂CH₂CH₂CH₂, CH₃), (M-10879, CH₃, F, H, (Me)₂NCOCH₂CH₂CH₂, H), (M-10880, CH₃, F, H, (Me)₂NCOCH₂CH₂CH₂, Cl), (M-10881, CH₃, F, H, (Me)₂NCOCH₂CH₂CH₂, F), (M-10882, CH₃, F, H, (Me)₂NCOCH₂CH₂CH₂, CF₃), (M-10883, CH₃, F, H, (Me)₂NCOCH₂CH₂CH₂, Br), (M-10884, CH₃, F, H, (Me)₂NCOCH₂CH₂CH₂, CH₃), (M-10885, CH₃, F, H, (Me)₂NCOCH₂CH₂CH₂CH₂, H), (M-10886, CH₃, F, H, (Me)₂NCOCH₂CH₂CH₂CH₂, Cl), (M-10887, CH₃, F, H, (Me)₂NCOCH₂CH₂CH₂CH₂, F), (M-10888, CH₃, F, H, (Me)₂NCOCH₂CH₂CH₂CH₂, CF₃), (M-10889, CH₃, F, H, (Me)₂NCOCH₂CH₂CH₂CH₂, Br), (M-10890, CH₃, F, H, (Me)₂NCOCH₂CH₂CH₂CH₂, CH₃), (M-10891, CH₃, F, H, MeOCH₂, H), (M-10892, CH₃, F, H, MeOCH₂, Cl), (M-10893, CH₃, F, H, MeOCH₂, F), (M-10894, CH₃, F, H, MeOCH₂, CF₃), (M-10895, CH₃, F, H, MeOCH₂, Br), (M-10896, CH₃, F, H, MeOCH₂, CH₃), (M-10897, CH₃, F, H, EtOCH₂, H), (M-10898, CH₃, F, H, EtOCH₂, Cl), (M-10899, CH₃, F, H, EtOCH₂, F), (M-10900, CH₃, F, H, EtOCH₂, CF₃), (M-10901, CH₃, F, H, EtOCH₂, Br), (M-10902, CH₃, F, H, EtOCH₂, CH₃), (M-10903, CH₃, F, H, EtOCH₂CH₂, H), (M-10904, CH₃, F, H, EtOCH₂CH₂, Cl), (M-10905, CH₃, F, H, EtOCH₂CH₂, F), (M-10906, CH₃, F, H, EtOCH₂CH₂, CF₃), (M-10907, CH₃, F, H, EtOCH₂CH₂, Br), (M-10908, CH₃, F, H, EtOCH₂CH₂, CH₃), (M-10909, CH₃, F, H, MeOCH₂CH₂OCH₂CH₂, H), (M-10910, CH₃, F, H, MeOCH₂CH₂OCH₂CH₂, Cl), (M-10911, CH₃, F, H, MeOCH₂CH₂OCH₂CH₂, F), (M-10912, CH₃, F, H, MeOCH₂CH₂OCH₂CH₂, CF₃), (M-10913, CH₃, F, H, MeOCH₂CH₂OCH₂CH₂, Br), (M-10914, CH₃, F, H, MeOCH₂CH₂OCH₂CH₂, CH₃), (M-10915, CH₃, F, H, MeOCH₂CH₂, H), (M-10916, CH₃, F, H, MeOCH₂CH₂, Cl), (M-10917, CH₃, F, H, MeOCH₂CH₂, F), (M-10918, CH₃, F, H, MeOCH₂CH₂, CF₃), (M-10919, CH₃, F, H, MeOCH₂CH₂, Br), (M-10920, CH₃, F, H, MeOCH₂CH₂, CH₃), (M-10921, CH₃, F, H, HOCH₂, H), (M-10922, CH₃, F, H, HOCH₂, Cl), (M-10923, CH₃, F, H, HOCH₂, F), (M-10924, CH₃, F, H, HOCH₂, CF₃), (M-10925, CH₃, F, H, HOCH₂, Br), (M-10926, CH₃, F, H, HOCH₂, CH₃), (M-10927, CH₃, F, H, HOCH₂CH₂, H), (M-10928, CH₃, F, H, HOCH₂CH₂, Cl), (M-10929, CH₃, F, H, HOCH₂CH₂, F), (M-10930, CH₃, F, H, HOCH₂CH₂, CF₃), (M-10931, CH₃, F, H, HOCH₂CH₂, Br), (M-10932, CH₃, F, H, HOCH₂CH₂, CH₃), (M-10933, CH₃, F, H, HOCH₂CH₂CH₂, H), (M-10934, CH₃, F, H, HOCH₂CH₂CH₂, Cl), (M-10935, CH₃, F, H, HOCH₂CH₂CH₂, F), (M-10936, CH₃, F, H, HOCH₂CH₂CH₂, CF₃), (M-10937, CH₃, F, H, HOCH₂CH₂CH₂, Br), (M-10938, CH₃, F, H, HOCH₂CH₂CH₂, CH₃), (M-10939, CH₃, F, H, HOCH₂CH₂CH₂CH₂, H), (M-10940, CH₃, F, H, HOCH₂CH₂CH₂CH₂, Cl), (M-10941, CH₃, F, H, HOCH₂CH₂CH₂CH₂, F), (M-10942, CH₃, F, H, HOCH₂CH₂CH₂CH₂, CF₃), (M-10943, CH₃, F, H, HOCH₂CH₂CH₂CH₂, Br), (M-10944, CH₃, F, H, HOCH₂CH₂CH₂CH₂, CH₃), (M-10945, CH₃, F, H, HOCH₂CH₂CH₂CH₂CH₂, H), (M-10946, CH₃, F, H, HOCH₂CH₂CH₂CH₂CH₂, Cl), (M-10947, CH₃, F, H, HOCH₂CH₂CH₂CH₂CH₂, F), (M-10948, CH₃, F, H, HOCH₂CH₂CH₂CH₂CH₂, CF₃), (M-10949, CH₃, F, H, HOCH₂CH₂CH₂CH₂CH₂, Br), (M-10950, CH₃, F, H, HOCH₂CH₂CH₂CH₂CH₂, CH₃), (M-10951, CH₃, F, H, HOCH₂CH₂OCH₂CH₂, H), (M-10952, CH₃, F, H, HOCH₂CH₂OCH₂CH₂, Cl), (M-10953, CH₃, F, H, HOCH₂CH₂O CH₂CH₂, F), (M-10954, CH₃, F, H, HOCH₂CH₂OCH₂CH₂, CF₃), (M-10955, CH₃, F, H, HOCH₂CH₂OCH₂CH₂, Br), (M-10956, CH₃, F, H, HOCH₂CH₂OCH₂CH₂, CH₃), (M-10957, CH₃, F, H, (Me)₂N, H), (M-10958, CH₃, F, H, (Me)₂N, Cl), (M-10959, CH₃, F, H, (Me)₂N, F), (M-10960, CH₃, F, H, (Me)₂N, CF₃), (M-10961, CH₃, F, H, (Me)₂N, Br), (M-10962, CH₃, F, H, (Me)₂N, CH₃), (M-10963, CH₃, F, H, piperidin-4-yl-methyl, H), (M-10964, CH₃, F, H, piperidin-4-yl-methyl, Cl), (M-10965, CH₃, F, H, piperidin-4-yl-methyl, F), (M-10966, CH₃, F, H, piperidin-4-yl-methyl, CF₃), (M-10967, CH₃, F, H, piperidin-4-yl-methyl, Br), (M-10968, CH₃, F, H, piperidin-4-yl-methyl, CH₃), (M-10969, CH₃, F, H, cyclohexylmethyl, H), (M-10970, CH₃, F, H, cyclohexylmethyl, Cl), (M-10971, CH₃, F, H, cyclohexylmethyl, F), (M-10972, CH₃, F, H, cyclohexylmethyl, CF₃), (M-10973, CH₃, F, H, cyclohexylmethyl, Br), (M-10974, CH₃, F, H, cyclohexylmethyl, CH₃), (M-10975, CH₃, F, F, H, H), (M-10976, CH₃, F, F, H, Cl), (M-10977, CH₃, F, F, H, F), (M-10978, CH₃, F, F, H, CF₃), (M-10979, CH₃, F, F, H, Br), (M-10980, CH₃, F, F, H, CH₃), (M-10981, CH₃, F, F, F, H), (M-10982, CH₃, F, F, F, Cl), (M-10983, CH₃, F, F, F, F), (M-10984, CH₃, F, F, F, CF₃), (M-10985, CH₃, F, F, F, Br), (M-10986, CH₃, F, F, F, CH₃), (M-10987, CH₃, F, F, Cl, H), (M-10988, CH₃, F, F, Cl, Cl), (M-10989, CH₃, F, F, Cl, F), (M-10990, CH₃, F, F, Cl, CF₃), (M-10991, CH₃, F, F, Cl, Br), (M-10992, CH₃, F, F, Cl, CH₃), (M-10993, CH₃, F, F, CH₃, H), (M-10994, CH₃, F, F, CH₃, Cl), (M-10995, CH₃, F, F, CH₃, F), (M-10996, CH₃, F, F, CH₃, CF₃), (M-10997, CH₃, F, F, CH₃, Br), (M-10998, CH₃, F, F, CH₃, CH₃), (M-10999, CH₃, F, F, Et, H), (M-11000, CH₃, F, F, Et, Cl), (M-11001, CH₃, F, F, Et, F), (M-11002, CH₃, F, F, Et, CF₃), (M-11003, CH₃, F, F, Et, Br), (M-11004, CH₃, F, F, Et, CH₃), (M-11005, CH₃, F, F, n-Pr, H), (M-11006, CH₃, F, F, n-Pr, Cl), (M-11007, CH₃, F, F, n-Pr, F), (M-11008, CH₃, F, F, n-Pr, CF₃), (M-11009, CH₃, F, F, n-Pr, Br), (M-11010, CH₃, F, F, n-Pr, CH₃), (M-11011, CH₃, F, F, c-Pr, H), (M-11012, CH₃, F, F, c-Pr, Cl), (M-11013, CH₃, F, F, c-Pr, F), (M-11014, CH₃, F, F, c-Pr, CF₃), (M-11015, CH₃, F, F, c-Pr, Br), (M-11016, CH₃, F, F, c-Pr, CH₃), (M-11017, CH₃, F, F, i-Pr, H), (M-11018, CH₃, F, F, i-Pr, Cl), (M-11019, CH₃, F, F, i-Pr, F), (M-11020, CH₃, F, F, i-Pr, CF₃), (M-11021, CH₃, F, F, i-Pr, Br), (M-11022, CH₃, F, F, i-Pr, CH₃), (M-11023, CH₃, F, F, n-Bu, H), (M-11024, CH₃, F, F, n-Bu, Cl), (M-11025, CH₃, F, F, n-Bu, F), (M-11026, CH₃, F, F, n-Bu, CF₃), (M-11027, CH₃, F, F, n-Bu, Br), (M-11028, CH₃, F, F, n-Bu, CH₃), (M-11029, CH₃, F, F, i-Bu, H), (M-11030, CH₃, F, F, i-Bu, Cl), (M-11031, CH₃, F, F, i-Bu, F), (M-11032, CH₃, F, F, i-Bu, CF₃), (M-11033, CH₃, F, F, i-Bu, Br), (M-11034, CH₃, F, F, i-Bu, CH₃), (M-11035, CH₃, F, F, sec-Bu, H), (M-11036, CH₃, F, F, sec-Bu, Cl), (M-11037, CH₃, F, F, sec-Bu, F), (M-11038, CH₃, F, F, sec-Bu, CF₃), (M-11039, CH₃, F, F, sec-Bu, Br), (M-11040, CH₃, F, F, sec-Bu, CH₃), (M-11041, CH₃, F, F, n-Pen, H), (M-11042, CH₃, F, F, n-Pen, Cl), (M-11043, CH₃, F, F, n-Pen, F), (M-11044, CH₃, F, F, n-Pen, CF₃), (M-11045, CH₃, F, F, n-Pen, Br), (M-11046, CH₃, F, F, n-Pen, CH₃), (M-11047, CH₃, F, F, c-Pen, H), (M-11048, CH₃, F, F, c-Pen, Cl), (M-11049, CH₃, F, F, c-Pen, F), (M-11050, CH₃, F, F, c-Pen, CF₃), (M-11051, CH₃, F, F, c-Pen, Br), (M-11052, CH₃, F, F, c-Pen, CH₃), (M-11053, CH₃, F, F, n-Hex, H), (M-11054, CH₃, F, F, n-Hex, Cl), (M-11055, CH₃, F, F, n-Hex, F), (M-11056, CH₃, F, F, n-Hex, CF₃), (M-11057, CH₃, F, F, n-Hex, Br), (M-11058, CH₃, F, F, n-Hex, CH₃), (M-11059, CH₃, F, F, c-Hex, H), (M-11060, CH₃, F, F, c-Hex, Cl), (M-11061, CH₃, F, F, c-Hex, F), (M-11062, CH₃, F, F, c-Hex, CF₃), (M-11063, CH₃, F, F, c-Hex, Br), (M-11064, CH₃, F, F, c-Hex, CH₃), (M-11065, CH₃, F, F, OH, H), (M-11066, CH₃, F, F, OH, Cl), (M-11067, CH₃, F, F, OH, F), (M-11068, CH₃, F, F, OH, CF₃), (M-11069, CH₃, F, F, OH, Br), (M-11070, CH₃, F, F, OH, CH₃), (M-11071, CH₃, F, F, EtO, H), (M-11072, CH₃, F, F, EtO, Cl), (M-11073, CH₃, F, F, EtO, F), (M-11074, CH₃, F, F, EtO, CF₃), (M-11075, CH₃, F, F, EtO, Br), (M-11076, CH₃, F, F, EtO, CH₃), (M-11077, CH₃, F, F, n-PrO, H), (M-11078, CH₃, F, F, n-PrO, Cl), (M-11079, CH₃, F, F, n-PrO, F), (M-11080, CH₃, F, F, n-PrO, CF₃), (M-11081, CH₃, F, F, n-PrO, Br), (M-11082, CH₃, F, F, n-PrO, CH₃), (M-11083, CH₃, F, F, PhO, H), (M-11084, CH₃, F, F, PhO, Cl), (M-11085, CH₃, F, F, PhO, F), (M-11086, CH₃, F, F, PhO, CF₃), (M-11087, CH₃, F, F, PhO, Br), (M-11088, CH₃, F, F, PhO, CH₃), (M-11089, CH₃, F, F, BnO, H), (M-11090, CH₃, F, F, BnO, Cl), (M-11091, CH₃, F, F, BnO, F), (M-11092, CH₃, F, F, BnO, CF₃), (M-11093, CH₃, F, F, BnO, Br), (M-11094, CH₃, F, F, BnO, CH₃), (M-11095, CH₃, F, F, PhCH₂CH₂O, H), (M-11096, CH₃, F, F, PhCH₂CH₂O, Cl), (M-11097, CH₃, F, F, PhCH₂CH₂O, F), (M-11098, CH₃, F, F, PhCH₂CH₂O, CF₃), (M-11099, CH₃, F, F, PhCH₂CH₂O, Br), (M-11100, CH₃, F, F, PhCH₂CH₂O, CH₃), (M-11101, CH₃, F, F, CF₃O, H), (M-11102, CH₃, F, F, CF₃O, Cl), (M-11103, CH₃, F, F, CF₃O, F), (M-11104, CH₁₃, F, F, CF₃O, CF₃), (M-11105, CH₃, F, F, CF₃O, Br), (M-11106, CH₃, F, F, CF₃O, CH₃), (M-11107, CH₃, F, F, Ph, H), (M-11108, CH₃, F, F, Ph, Cl), (M-11109, CH₃, F, F, Ph, F), (M-11110, CH₃, F, F, Ph, CF₃), (M-11111, CH₃, F, F, Ph, Br), (M-11112, CH₃, F, F, Ph, CH₃), (M-11113, CH₃, F, F, 4-F-Ph, H), (M-11114, CH₃, F, F, 4-F-Ph, Cl), (M-11115, CH₃, F, F, 4-F-Ph, F), (M-11116, CH₃, F, F, 4-F-Ph, CF₃), (M-11117, CH₃, F, F, 4-F-Ph, Br), (M-11118, CH₃, F, F, 4-F-Ph, CH₃), (M-11119, CH₃, F, F, 4-CF₃-Ph, H), (M-11120, CH₃, F, F, 4-CF₃-Ph, Cl), (M-11121, CH₃, F, F, 4-CF₃-Ph, F), (M-11122, CH₃, F, F, 4-CF₃-Ph, CF₃), (M-11123, CH₃, F, F, 4-CF₃-Ph, Br), (M-11124, CH₃, F, F, 4-CF₃-Ph, CH₃), (M-11125, CH₃, F, F, 4-(Me)₂N-Ph, H), (M-11126, CH₃, F, F, 4-(Me)₂N-Ph, Cl), (M-11127, CH₃, F, F, 4-(Me)₂N-Ph, F), (M-11128, CH₃, F, F, 4-(Me)₂N-Ph, CF₃), (M-11129, CH₃, F, F, 4-(Me)₂N-Ph, Br), (M-11130, CH₃, F, F, 4-(Me)₂N-Ph, CH₃), (M-11131, CH₃, F, F, 4-OH-Ph, H), (M-11132, CH₃, F, F, 4-OH-Ph, Cl), (M-11133, CH₃, F, F, 4-OH-Ph, F), (M-11134, CH₃, F, F, 4-OH-Ph, CF₃), (M-11135, CH₃, F, F, 4-OH-Ph, Br), (M-11136, CH₃, F, F, 4-OH-Ph, CH₃), (M-11137, CH₃, F, F, 3,4-di-F-Ph, H), (M-11138, CH₃, F, F, 3,4-di-F-Ph, Cl), (M-11139, CH₃, F, F, 3,4-di-F-Ph, F), (M-11140, CH₃, F, F, 3,4-di-F-Ph, CF₃), (M-11141, CH₃, F, F, 3,4-di-F-Ph, Br), (M-11142, CH₃, F, F, 3,4-di-F-Ph, CH₃), (M-11143, CH₃, F, F, 4-COOH-Ph, H), (M-11144, CH₃, F, F, 4-COOH-Ph, Cl), (M-11145, CH₃, F, F, 4-COOH-Ph, F), (M-11146, CH₃, F, F, 4-COOH-Ph, CF₃), (M-11147, CH₃, F, F, 4-COOH-Ph, Br), (M-11148, CH₃, F, F, 4-COOH-Ph, CH₃), (M-11149, CH₃, F, F, Bn, H), (M-11150, CH₃, F, F, Bn, Cl), (M-11151, CH₃, F, F, Bn, F), (M-11152, CH₃, F, F, Bn, CF₃), (M-11153, CH₃, F, F, Bn, Br), (M-11154, CH₃, F, F, Bn, CH₃), (M-11155, CH₃, F, F, 4-F-Bn, H), (M-11156, CH₃, F, F, 4-F-Bn, Cl), (M-11157, CH₃, F, F, 4-F-Bn, F), (M-11158, CH₃, F, F, 4-F-Bn, CF₃), (M-11159, CH₃, F, F, 4-F-Bn, Br), (M-11160, CH₃, F, F, 4-F-Bn, CH₃), (M-11161, CH₃, F, F, 2-Py, H), (M-11162, CH₃, F, F, 2-Py, Cl), (M-11163, CH₃, F, F, 2-Py, F), (M-11164, CH₃, F, F, 2-Py, CF₃), (M-11165, CH₃, F, F, 2-Py, Br), (M-11166, CH₃, F, F, 2-Py, CH₃), (M-11167, CH₃, F, F, 3-Py, H), (M-11168, CH₃, F, F, 3-Py, Cl), (M-11169, CH₃, F, F, 3-Py, F), (M-11170, CH₃, F, F, 3-Py, CF₃), (M-11171, CH₃, F, F, 3-Py, Br), (M-11172, CH₃, F, F, 3-Py, CH₃), (M-11173, CH₃, F, F, 4-Py, H), (M-11174, CH₃, F, F, 4-Py, Cl), (M-11175, CH₃, F, F, 4-Py, F), (M-11176, CH₃, F, F, 4-Py, CF₃), (M-11177, CH₃, F, F, 4-Py, Br), (M-11178, CH₃, F, F, 4-Py, CH₃), (M-11179, CH₃, F, F, 2-Th, H), (M-11180, CH₃, F, F, 2-Th, Cl), (M-11181, CH₃, F, F, 2-Th, F), (M-11182, CH₃, F, F, 2-Th, CF₃), (M-11183, CH₃, F, F, 2-Th, Br), (M-11184, CH₃, F, F, 2-Th, CH₃), (M-11185, CH₃, F, F, 3-Th, H), (M-11186, CH₃, F, F, 3-Th, Cl), (M-11187, CH₃, F, F, 3-Th, F), (M-11188, CH₃, F, F, 3-Th, CF₃), (M-11189, CH₃, F, F, 3-Th, Br), (M-11190, CH₃, F, F, 3-Th, CH₃), (M-11191, CH₃, F, F, pyrrazol-2-yl, H), (M-11192, CH₃, F, F, pyrrazol-2-yl, Cl), (M-11193, CH₃, F, F, pyrrazol-2-yl, F), (M-11194, CH₃, F, F, pyrrazol-2-yl, CF₃), (M-11195, CH₃, F, F, pyrrazol-2-yl, Br), (M-11196, CH₃, F, F, pyrrazol-2-yl, CH₃), (M-11197, CH₃, F, F, pyrrazol-3-yl, H), (M-11198, CH₃, F, F, pyrrazol-3-yl, Cl), (M-11199, CH₃, F, F, pyrrazol-3-yl, F), (M-11200, CH₃, F, F, pyrrazol-3-yl, CF₃), (M-11201, CH₃, F, F, pyrrazol-3-yl, Br), (M-11202, CH₃, F, F, pyrrazol-3-yl, CH₃), (M-11203, CH₃, F, F, pyrimidin-2-yl, H), (M-11204, CH₃, F, F, pyrimidin-2-yl, Cl), (M-11205, CH₃, F, F, pyrimidin-2-yl, F), (M-11206, CH₃, F, F, pyrimidin-2-yl, CF₃), (M-11207, CH₃, F, F, pyrimidin-2-yl, Br), (M-11208, CH₃, F, F, pyrimidin-2-yl, CH₃), (M-11209, CH₃, F, F, pyrimidin-4-yl, H), (M-11210, CH₃, F, F, pyrimidin-4-yl, Cl), (M-11211, CH₃, F, F, pyrimidin-4-yl, F), (M-11212, CH₃, F, F, pyrimidin-4-yl, CF₃), (M-11213, CH₃, F, F, pyrimidin-4-yl, Br), (M-11214, CH₃, F, F, pyrimidin-4-yl, CH₃), (M-11215, CH₃, F, F, pyrimidin-5-yl, H), (M-11216, CH₃, F, F, pyrimidin-5-yl, Cl), (M-11217, CH₃, F, F, pyrimidin-5-yl, F), (M-11218, CH₃, F, F, pyrimidin-5-yl, CF₃), (M-11219, CH₃, F, F, pyrimidin-5-yl, Br), (M-11220, CH₃, F, F, pyrimidin-5-yl, CH₃), (M-11221, CH₃, F, F, HOOCCH₂CH₂CH₂, H), (M-11222, CH₃, F, F, HOOCCH₂CH₂CH₂, Cl), (M-11223, CH₃, F, F, HOOCCH₂CH₂CH₂, F), (M-11224, CH₃, F, F, HOOCCH₂CH₂CH₂, CF₃), (M-11225, CH₃, F, F, HOOCCH₂CH₂CH₂, Br), (M-11226, CH₃, F, F, HOOCCH₂CH₂CH₂, CH₃), (M-11227, CH₃, F, F, HOOCCH₂CH₂CH₂CH₂, H), (M-11228, CH₃, F, F, HOOCCH₂CH₂CH₂CH₂, Cl), (M-11229, CH₃, F, F, HOOCCH₂CH₂CH₂CH₂, F), (M-11230, CH₃, F, F, HOOCCH₂CH₂CH₂CH₂, CF₃), (M-11231, CH₃, F, F, HOOCCH₂CH₂CH₂CH₂, Br), (M-11232, CH₃, F, F, HOOCCH₂CH₂CH₂CH₂, CH₃), (M-11233, CH₃, F, F, (Me)₂NCOCH₂CH₂CH₂, H), (M-11234, CH₃, F, F, (Me)₂NCOCH₂CH₂CH₂, Cl), (M-11235, CH₃, F, F, (Me)₂NCOCH₂CH₂CH₂, F), (M-11236, CH₃, F, F, (Me)₂NCOCH₂CH₂CH₂, CF₃), (M-11237, CH₃, F, F, (Me)₂NCOCH₂CH₂CH₂, Br), (M-11238, CH₃, F, F, (Me)₂NCOCH₂CH₂CH₂, CH₃), (M-11239, CH₃, F, F, (Me)₂NCOCH₂CH₂CH₂CH₂, H), (M-11240, CH₃, F, F, (Me)₂NCOCH₂CH₂CH₂CH₂, Cl), (M-11241, CH₃, F, F, (Me)₂NCOCH₂CH₂CH₂CH₂, F), (M-11242, CH₃, F, F, (Me)₂NCOCH₂CH₂CH₂CH₂, CF₃), (M-11243, CH₃, F, F, (Me)₂NCOCH₂CH₂CH₂CH₂, Br), (M-11244, CH₃, F, F, (Me)₂NCOCH₂CH₂CH₂CH₂, CH₃), (M-11245, CH₃, F, F, MeOCH₂, H), (M-11246, CH₃, F, F, MeOCH₂, Cl), (M-11247, CH₃, F, F, MeOCH₂, F), (M-11248, CH₃, F, F, MeOCH₂, CF₃), (M-11249, CH₃, F, F, MeOCH₂, Br), (M-11250, CH₃, F, F, MeOCH₂, CH₃), (M-11251, CH₃, F, F, EtOCH₂, H), (M-11252, CH₃, F, F, EtOCH₂, Cl), (M-11253, CH₃, F, F, EtOCH₂, F), (M-11254, CH₃, F, F, EtOCH₂, CF₃), (M-11255, CH₃, F, F, EtOCH₂, Br), (M-11256, CH₃, F, F, EtOCH₂, CH₃), (M-11257, CH₃, F, F, EtOCH₂CH₂, H), (M-11258, CH₃, F, F, EtOCH₂CH₂, Cl), (M-11259, CH₃, F, F, EtOCH₂CH₂, F), (M-11260, CH₃, F, F, EtOCH₂CH₂, CF₃), (M-11261, CH₃, F, F, EtOCH₂CH₂, Br), (M-11262, CH₃, F, F, EtOCH₂CH₂, CH₃), (M-11263, CH₃, F, F, MeOCH₂CH₂OCH₂CH₂, H), (M-11264, CH₃, F, F, MeOCH₂CH₂OCH₂CH₂, Cl), (M-11265, CH₃, F, F, MeOCH₂CH₂OCH₂CH₂, F), (M-11266, CH₃, F, F, MeOCH₂CH₂OCH₂CH₂, CF₃), (M-11267, CH₃, F, F, MeOCH₂CH₂OCH₂CH₂, Br), (M-11268, CH₃, F, F, MeOCH₂CH₂OCH₂CH₂, CH₃), (M-11269, CH₃, F, F, MeOCH₂CH₂, H), (M-11270, CH₃, F, F, MeOCH₂CH₂, Cl), (M-11271, CH₃, F, F, MeOCH₂CH₂, F), (M-11272, CH₃, F, F, MeOCH₂CH₂, CF₃), (M-11273, CH₃, F, F, MeOCH₂CH₂, Br), (M-11274, CH₃, F, F, MeOCH₂CH₂, CH₃), (M-11275, CH₃, F, F, HOCH₂, H), (M-11276, CH₃, F, F, HOCH₂, Cl), (M-11277, CH₃, F, F, HOCH₂, F), (M-11278, CH₃, F, F, HOCH₂, CF₃), (M-11279, CH₃, F, F, HOCH₂, Br), (M-11280, CH₃, F, F, HOCH₂, CH₃), (M-11281, CH₃, F, F, HOCH₂CH₂, H), (M-11282, CH₃, F, F, HOCH₂CH₂, Cl), (M-11283, CH₃, F, F, HOCH₂CH₂, F), (M-11284, CH₃, F, F, HOCH₂CH₂, CF₃), (M-11285, CH₃, F, F, HOCH₂CH₂, Br), (M-11286, CH₃, F, F, HOCH₂CH₂, CH₃), (M-11287, CH₃, F, F, HOCH₂CH₂CH₂, H), (M-11288, CH₃, F, F, HOCH₂CH₂CH₂, Cl), (M-11289, CH₃, F, F, HOCH₂CH₂CH₂, F), (M-11290, CH₃, F, F, HOCH₂CH₂CH₂, CF₃), (M-11291, CH₃, F, F, HOCH₂CH₂CH₂, Br), (M-11292, CH₃, F, F, HOCH₂CH₂CH₂, CH₃), (M-11293, CH₃, F, F, HOCH₂CH₂CH₂CH₂, H), (M-11294, CH₃, F, F, HOCH₂CH₂CH₂CH₂, Cl), (M-11295, CH₃, F, F, HOCH₂CH₂CH₂CH₂, F), (M-11296, CH₃, F, F, HOCH₂CH₂CH₂CH₂, CF₃), (M-11297, CH₃, F, F, HOCH₂CH₂CH₂CH₂, Br), (M-11298, CH₃, F, F, HOCH₂CH₂CH₂CH₂, CH₃), (M-11299, CH₃, F, F, HOCH₂CH₂CH₂CH₂CH₂, H), (M-11300, CH₃, F, F, HOCH₂CH₂CH₂CH₂CH₂, Cl), (M-11301, CH₃, F, F, HOCH₂CH₂CH₂CH₂CH₂, F), (M-11302, CH₃, F, F, HOCH₂CH₂CH₂CH₂CH₂, CF₃), (M-11303, CH₃, F, F, HOCH₂CH₂CH₂CH₂CH₂, Br), (M-11304, CH₃, F, F, HOCH₂CH₂CH₂CH₂CH₂, CH₃), (M-11305, CH₃, F, F, HOCH₂CH₂OCH₂CH₂, H), (M-11306, CH₃, F, F, HOCH₂CH₂OCH₂CH₂, Cl), (M-11307, CH₃, F, F, HOCH₂CH₂O CH₂CH₂, F), (M-11308, CH₃, F, F, HOCH₂CH₂O CH₂CH₂, CF₃), (M-11309, CH₃, F, F, HOCH₂CH₂O CH₂CH₂, Br), (M-11310, CH₃, F, F, HOCH₂CH₂OCH₂CH₂, CH₃), (M-11311, CH₃, F, F, (Me)₂N, H), (M-11312, CH₃, F, F, (Me)₂N, Cl), (M-11313, CH₃, F, F, (Me)₂N, F), (M-11314, CH₃, F, F, (Me)₂N, CF₃), (M-11315, CH₃, F, F, (Me)₂N, Br), (M-11316, CH₃, F, F, (Me)₂N, CH₃), (M-11317, CH₃, F, F, piperidin-4-yl-methyl, H), (M-11318, CH₃, F, F, piperidin-4-yl-methyl, Cl), (M-11319, CH₃, F, F, piperidin-4-yl-methyl, F), (M-11320, CH₃, F, F, piperidin-4-yl-methyl, CF₃), (M-11321, CH₃, F, F, piperidin-4-yl-methyl, Br), (M-11322, CH₃, F, F, piperidin-4-yl-methyl, CH₃), (M-11323, CH₃, F, F, cyclohexylmethyl, H), (M-11324, CH₃, F, F, cyclohexylmethyl, Cl), (M-11325, CH₃, F, F, cyclohexylmethyl, F), (M-11326, CH₃, F, F, cyclohexylmethyl, CF₃), (M-11327, CH₃, F, F, cyclohexylmethyl, Br), (M-11328, CH₃, F, F, cyclohexylmethyl, CH₃), (M-11329, CH₃, F, Cl, H, H), (M-11330, CH₃, F, Cl, H, Cl), (M-11331, CH₃, F, Cl, H, F), (M-11332, CH₃, F, Cl, H, CF₃), (M-11333, CH₃, F, Cl, H, Br), (M-11334, CH₃, F, Cl, H, CH₃), (M-11335, CH₃, F, Cl, F, H), (M-11336, CH₃, F, Cl, F, Cl), (M-11337, CH₃, F, Cl, F, F), (M-11338, CH₃, F, Cl, F, CF₃), (M-11339, CH₃, F, Cl, F, Br), (M-11340, CH₃, F, Cl, F, CH₃), (M-11341, CH₃, F, Cl, Cl, H), (M-11342, CH₃, F, Cl, Cl, Cl), (M-11343, CH₃, F, Cl, Cl, F), (M-11344, CH₃, F, Cl, Cl, CF₃), (M-11345, CH₃, F, Cl, Cl, Br), (M-11346, CH₃, F, Cl, Cl, CH₃), (M-11347, CH₃, F, Cl, CH₃, H), (M-11348, CH₃, F, Cl, CH₃, Cl), (M-11349, CH₃, F, Cl, CH₃, F), (M-11350, CH₃, F, Cl, CH₃, CF₃), (M-11351, CH₃, F, Cl, CH₃, Br), (M-11352, CH₃, F, Cl, CH₃, CH₃), (M-11353, CH₃, F, Cl, Et, H), (M-11354, CH₃, F, Cl, Et, Cl), (M-11355, CH₃, F, Cl, Et, F), (M-11356, CH₃, F, Cl, Et, CF₃), (M-11357, CH₃, F, Cl, Et, Br), (M-11358, CH₃, F, Cl, Et, CH₃), (M-11359, CH₃, F, Cl, n-Pr, H), (M-11360, CH₃, F, Cl, n-Pr, Cl), (M-11361, CH₃, F, Cl, n-Pr, F), (M-11362, CH₃, F, Cl, n-Pr, CF₃), (M-11363, CH₃, F, Cl, n-Pr, Br), (M-11364, CH₃, F, Cl, n-Pr, CH₃), (M-11365, CH₃, F, Cl, c-Pr, H), (M-11366, CH₃, F, Cl, c-Pr, Cl), (M-11367, CH₃, F, Cl, c-Pr, F), (M-11368, CH₃, F, Cl, c-Pr, CF₃), (M-11369, CH₃, F, Cl, c-Pr, Br), (M-11370, CH₃, F, Cl, c-Pr, CH₃), (M-11371, CH₃, F, Cl, i-Pr, H), (M-11372, CH₃, F, Cl, i-Pr, Cl), (M-11373, CH₃, F, Cl, i-Pr, F), (M-11374, CH₃, F, Cl, i-Pr, CF₃), (M-11375, CH₃, F, Cl, i-Pr, Br), (M-11376, CH₃, F, Cl, i-Pr, CH₃), (M-11377, CH₃, F, Cl, n-Bu, H), (M-11378, CH₃, F, Cl, n-Bu, Cl), (M-11379, CH₃, F, Cl, n-Bu, F), (M-11380, CH₃, F, Cl, n-Bu, CF₃), (M-11381, CH₃, F, Cl, n-Bu, Br), (M-11382, CH₃, F, Cl, n-Bu, CH₃), (M-11383, CH₃, F, Cl, i-Bu, H), (M-11384, CH₃, F, Cl, i-Bu, Cl), (M-11385, CH₃, F, Cl, i-Bu, F), (M-11386, CH₃, F, Cl, i-Bu, CF₃), (M-11387, CH₃, F, Cl, i-Bu, Br), (M-11388, CH₃, F, Cl, i-Bu, CH₃), (M-11389, CH₃, F, Cl, sec-Bu, H), (M-11390, CH₃, F, Cl, sec-Bu, Cl), (M-11391, CH₃, F, Cl, sec-Bu, F), (M-11392, CH₃, F, Cl, sec-Bu, CF₃), (M-11393, CH₃, F, Cl, sec-Bu, Br), (M-11394, CH₃, F, Cl, sec-Bu, CH₃), (M-11395, CH₃, F, Cl, n-Pen, H), (M-11396, CH₃, F, Cl, n-Pen, Cl), (M-11397, CH₃, F, Cl, n-Pen, F), (M-11398, CH₃, F, Cl, n-Pen, CF₃), (M-11399, CH₃, F, Cl, n-Pen, Br), (M-11400, CH₃, F, Cl, n-Pen, CH₃), (M-11401, CH₃, F, Cl, c-Pen, H), (M-11402, CH₃, F, Cl, c-Pen, Cl), (M-11403, CH₃, F, Cl, c-Pen, F), (M-11404, CH₃, F, Cl, c-Pen, CF₃), (M-11405, CH₃, F, Cl, c-Pen, Br), (M-11406, CH₃, F, Cl, c-Pen, CH₃), (M-11407, CH₃, F, Cl, n-Hex, H), (M-11408, CH₃, F, Cl, n-Hex, Cl), (M-11409, CH₃, F, Cl, n-Hex, F), (M-11410, CH₃, F, Cl, n-Hex, CF₃), (M-11411, CH₃, F, Cl, n-Hex, Br), (M-11412, CH₃, F, Cl, n-Hex, CH₃), (M-11413, CH₃, F, Cl, c-Hex, H), (M-11414, CH₃, F, Cl, c-Hex, Cl), (M-11415, CH₃, F, Cl, c-Hex, F), (M-11416, CH₃, F, Cl, c-Hex, CF₃), (M-11417, CH₃, F, Cl, c-Hex, Br), (M-11418, CH₃, F, Cl, c-Hex, CH₃), (M-11419, CH₃, F, Cl, OH, H), (M-11420, CH₃, F, Cl, OH, Cl), (M-11421, CH₃, F, Cl, OH, F), (M-11422, CH₃, F, Cl, OH, CF₃), (M-11423, CH₃, F, Cl, OH, Br), (M-11424, CH₃, F, Cl, OH, CH₃), (M-11425, CH₃, F, Cl, EtO, H), (M-11426, CH₃, F, Cl, EtO, Cl), (M-11427, CH₃, F, Cl, EtO, F), (M-11428, CH₃, F, Cl, EtO, CF₃), (M-11429, CH₃, F, Cl, EtO, Br), (M-11430, CH₃, F, Cl, EtO, CH₃), (M-11431, CH₃, F, Cl, n-PrO, H), (M-11432, CH₃, F, Cl, n-PrO, Cl), (M-11433, CH₃, F, Cl, n-PrO, F), (M-11434, CH₃, F, Cl, n-PrO, CF₃), (M-11435, CH₃, F, Cl, n-PrO, Br), (M-11436, CH₃, F, Cl, n-PrO, CH₃), (M-11437, CH₃, F, Cl, PhO, H), (M-11438, CH₃, F, Cl, PhO, Cl), (M-11439, CH₃, F, Cl, PhO, F), (M-11440, CH₃, F, Cl, PhO, CF₃), (M-11441, CH₃, F, Cl, PhO, Br), (M-11442, CH₃, F, Cl, PhO, CH₃), (M-11443, CH₃, F, Cl, BnO, H), (M-11444, CH₃, F, Cl, BnO, Cl), (M-11445, CH₃, F, Cl, BnO, F), (M-11446, CH₃, F, Cl, BnO, CF₃), (M-11447, CH₃, F, Cl, BnO, Br), (M-11448, CH₃, F, Cl, BnO, CH₃), (M-11449, CH₃, F, Cl, PhCH₂CH₂O, H), (M-11450, CH₃, F, Cl, PhCH₂CH₂O, Cl), (M-11451, CH₃, F, Cl, PhCH₂CH₂O, F), (M-11452, CH₃, F, Cl, PhCH₂CH₂O, CF₃), (M-11453, CH₃, F, Cl, PhCH₂CH₂O, Br), (M-11454, CH₃, F, Cl, PhCH₂CH₂O, CH₃), (M-11455, CH₃, F, Cl, CF₃O, H), (M-11456, CH₃, F, Cl, CF₃O, Cl), (M-11457, CH₃, F, Cl, CF₃O, F), (M-11458, CH₃, F, Cl, CF₃O, CF₃), (M-11459, CH₃, F, Cl, CF₃O, Br), (M-11460, CH₃, F, Cl, CF₃O, CH₃), (M-11461, CH₃, F, Cl, Ph, H), (M-11462, CH₃, F, Cl, Ph, Cl), (M-11463, CH₃, F, Cl, Ph, F), (M-11464, CH₃, F, Cl, Ph, CF₃), (M-11465, CH₃, F, Cl, Ph, Br), (M-11466, CH₃, F, Cl, Ph, CH₃), (M-11467, CH₃, F, Cl, 4-F-Ph, H), (M-11468, CH₃, F, Cl, 4-F-Ph, Cl), (M-11469, CH₃, F, Cl, 4-F-Ph, F), (M-11470, CH₃, F, Cl, 4-F-Ph, CF₃), (M-11471, CH₃, F, Cl, 4-F-Ph, Br), (M-11472, CH₃, F, Cl, 4-F-Ph, CH₃), (M-11473, CH₃, F, Cl, 4-CF₃-Ph, H), (M-11474, CH₃, F, Cl, 4-CF₃-Ph, Cl), (M-11475, CH₃, F, Cl, 4-CF₃-Ph, F), (M-11476, CH₃, F, Cl, 4-CF₃-Ph, CF₃), (M-11477, CH₃, F, Cl, 4-CF₃-Ph, Br), (M-11478, CH₃, F, Cl, 4-CF₃-Ph, CH₃), (M-11479, CH₃, F, Cl, 4-(Me)₂N-Ph, H), (M-11480, CH₃, F, Cl, 4-(Me)₂N-Ph, Cl), (M-11481, CH₃, F, Cl, 4-(Me)₂N-Ph, F), (M-11482, CH₃, F, Cl, 4-(Me)₂N-Ph, CF₃), (M-11483, CH₃, F, Cl, 4-(Me)₂N-Ph, Br), (M-11484, CH₃, F, Cl, 4-(Me)₂N-Ph, CH₃), (M-11485, CH₃, F, Cl, 4-OH-Ph, H), (M-11486, CH₃, F, Cl, 4-OH-Ph, Cl), (M-11487, CH₃, F, Cl, 4-OH-Ph, F), (M-11488, CH₃, F, Cl, 4-OH-Ph, CF₃), (M-11489, CH₃, F, Cl, 4-OH-Ph, Br), (M-11490, CH₃, F, Cl, 4-OH-Ph, CH₃), (M-11491, CH₃, F, Cl, 3,4-di-F-Ph, H), (M-11492, CH₃, F, Cl, 3,4-di-F-Ph, Cl), (M-11493, CH₃, F, Cl, 3,4-di-F-Ph, F), (M-11494, CH₃, F, Cl, 3,4-di-F-Ph, CF₃), (M-11495, CH₃, F, Cl, 3,4-di-F-Ph, Br), (M-11496, CH₃, F, Cl, 3,4-di-F-Ph, CH₃), (M-11497, CH₃, F, Cl, 4-COOH-Ph, H), (M-11498, CH₃, F, Cl, 4-COOH-Ph, Cl), (M-11499, CH₃, F, Cl, 4-COOH-Ph, F), (M-11500, CH₃, F, Cl, 4-COOH-Ph, CF₃), (M-11501, CH₃, F, Cl, 4-COOH-Ph, Br), (M-11502, CH₃, F, Cl, 4-COOH-Ph, CH₃), (M-11503, CH₃, F, Cl, Bn, H), (M-11504, CH₃, F, Cl, Bn, Cl), (M-11505, CH₃, F, Cl, Bn, F), (M-11506, CH₃, F, Cl, Bn, CF₃), (M-11507, CH₃, F, Cl, Bn, Br), (M-11508, CH₃, F, Cl, Bn, CH₃), (M-11509, CH₃, F, Cl, 4-F-Bn, H), (M-11510, CH₃, F, Cl, 4-F-Bn, Cl), (M-11511, CH₃, F, Cl, 4-F-Bn, F), (M-11512, CH₃, F, Cl, 4-F-Bn, CF₃), (M-11513, CH₃, F, Cl, 4-F-Bn, Br), (M-11514, CH₃, F, Cl, 4-F-Bn, CH₃), (M-11515, CH₃, F, Cl, 2-Py, H), (M-11516, CH₃, F, Cl, 2-Py, Cl), (M-11517, CH₃, F, Cl, 2-Py, F), (M-11518, CH₃, F, Cl, 2-Py, CF₃), (M-11519, CH₃, F, Cl, 2-Py, Br), (M-11520, CH₃, F, Cl, 2-Py, CH₃), (M-11521, CH₃, F, Cl, 3-Py, H), (M-11522, CH₃, F, Cl, 3-Py, Cl), (M-11523, CH₃, F, Cl, 3-Py, F), (M-11524, CH₃, F, Cl, 3-Py, CF₃), (M-11525, CH₃, F, Cl, 3-Py, Br), (M-11526, CH₃, F, Cl, 3-Py, CH₃), (M-11527, CH₃, F, Cl, 4-Py, H), (M-11528, CH₃, F, Cl, 4-Py, Cl), (M-11529, CH₃, F, Cl, 4-Py, F), (M-11530, CH₃, F, Cl, 4-Py, CF₃), (M-11531, CH₃, F, Cl, 4-Py, Br), (M-11532, CH₃, F, Cl, 4-Py, CH₃), (M-11533, CH₃, F, Cl, 2-Th, H), (M-11534, CH₃, F, Cl, 2-Th, Cl), (M-11535, CH₃, F, Cl, 2-Th, F), (M-11536, CH₃, F, Cl, 2-Th, CF₃), (M-11537, CH₃, F, Cl, 2-Th, Br), (M-11538, CH₃, F, Cl, 2-Th, CH₃), (M-11539, CH₃, F, Cl, 3-Th, H), (M-11540, CH₃, F, Cl, 3-Th, Cl), (M-11541, CH₃, F, Cl, 3-Th, F), (M-11542, CH₃, F, Cl, 3-Th, CF₃), (M-11543, CH₃, F, Cl, 3-Th, Br), (M-11544, CH₃, F, Cl, 3-Th, CH₃), (M-11545, CH₃, F, Cl, pyrrazol-2-yl, H), (M-11546, CH₃, F, Cl, pyrrazol-2-yl, Cl), (M-11547, CH₃, F, Cl, pyrrazol-2-yl, F), (M-11548, CH₃, F, Cl, pyrrazol-2-yl, CF₃), (M-11549, CH₃, F, Cl, pyrrazol-2-yl, Br), (M-11550, CH₃, F, Cl, pyrrazol-2-yl, CH₃), (M-11551, CH₃, F, Cl, pyrrazol-3-yl, H), (M-11552, CH₃, F, Cl, pyrrazol-3-yl, Cl), (M-11553, CH₃, F, Cl, pyrrazol-3-yl, F), (M-11554, CH₃, F, Cl, pyrrazol-3-yl, CF₃), (M-11555, CH₃, F, Cl, pyrrazol-3-yl, Br), (M-11556, CH₃, F, Cl, pyrrazol-3-yl, CH₃), (M-11557, CH₃, F, Cl, pyrimidin-2-yl, H), (M-11558, CH₃, F, Cl, pyrimidin-2-yl, Cl), (M-11559, CH₃, F, Cl, pyrimidin-2-yl, F), (M-11560, CH₃, F, Cl, pyrimidin-2-yl, CF₃), (M-11561, CH₃, F, Cl, pyrimidin-2-yl, Br), (M-11562, CH₃, F, Cl, pyrimidin-2-yl, CH₃), (M-11563, CH₃, F, Cl, pyrimidin-4-yl, H), (M-11564, CH₃, F, Cl, pyrimidin-4-yl, Cl), (M-11565, CH₃, F, Cl, pyrimidin-4-yl, F), (M-11566, CH₃, F, Cl, pyrimidin-4-yl, CF₃), (M-11567, CH₃, F, Cl, pyrimidin-4-yl, Br), (M-11568, CH₃, F, Cl, pyrimidin-4-yl, CH₃), (M-11569, CH₃, F, Cl, pyrimidin-5-yl, H), (M-11570, CH₃, F, Cl, pyrimidin-5-yl, Cl), (M-11571, CH₃, F, Cl, pyrimidin-5-yl, F), (M-11572, CH₃, F, Cl, pyrimidin-5-yl, CF₃), (M-11573, CH₃, F, Cl, pyrimidin-5-yl, Br), (M-11574, CH₃, F, Cl, pyrimidin-5-yl, CH₃), (M-11575, CH₃, F, Cl, HOOCCH₂CH₂CH₂, H), (M-11576, CH₃, F, Cl, HOOCCH₂CH₂CH₂, Cl), (M-11577, CH₃, F, Cl, HOOCCH₂CH₂CH₂, F), (M-11578, CH₃, F, Cl, HOOCCH₂CH₂CH₂, CF₃), (M-11579, CH₃, F, Cl, HOOCCH₂CH₂CH₂, Br), (M-11580, CH₃, F, Cl, HOOCCH₂CH₂CH₂, CH₃), (M-11581, CH₃, F, Cl, HOOCCH₂CH₂CH₂CH₂, H), (M-11582, CH₃, F, Cl, HOOCCH₂CH₂CH₂CH₂, Cl), (M-11583, CH₃, F, Cl, HOOCCH₂CH₂CH₂CH₂, F), (M-11584, CH₃, F, Cl, HOOCCH₂CH₂CH₂CH₂, CF₃), (M-11585, CH₃, F, Cl, HOOCCH₂CH₂CH₂CH₂, Br), (M-11586, CH₃, F, Cl, HOOCCH₂CH₂CH₂CH₂, CH₃), (M-11587, CH₃, F, Cl, (Me)₂NCOCH₂CH₂CH₂CH₂, H), (M-11588, CH₃, F, Cl, (Me)₂NCOCH₂CH₂CH₂CH₂, Cl), (M-11589, CH₃, F, Cl, (Me)₂NCOCH₂CH₂CH₂CH₂, F), (M-11590, CH₃, F, Cl, (Me)₂NCOCH₂CH₂CH₂CH₂, CF₃), (M-11591, CH₃, F, Cl, (Me)₂NCOCH₂CH₂CH₂CH₂, Br), (M-11592, CH₃, F, Cl, (Me)₂NCOCH₂CH₂CH₂CH₂, CH₃), (M-11593, CH₃, F, Cl, (Me)₂NCOCH₂CH₂CH₂CH₂CH₂, H), (M-11594, CH₃, F, Cl, (Me)₂NCOCH₂CH₂CH₂CH₂CH₂, Cl), (M-11595, CH₃, F, Cl, (Me)₂NCOCH₂CH₂CH₂CH₂CH₂, F), (M-11596, CH₃, F, Cl, (Me)₂NCOCH₂CH₂CH₂CH₂CH₂, CF₃), (M-11597, CH₃, F, Cl, (Me)₂NCOCH₂CH₂CH₂CH₂CH₂, Br), (M-11598, CH₃, F, Cl, (Me)₂NCOCH₂CH₂CH₂CH₂CH₂, CH₃), (M-11599, CH₃, F, Cl, MeOCH₂, H), (M-11600, CH₃, F, Cl, MeOCH₂, Cl), (M-11601, CH₃, F, Cl, MeOCH₂, F), (M-11602, CH₃, F, Cl, MeOCH₂, CF₃), (M-11603, CH₃, F, Cl, MeOCH₂, Br), (M-11604, CH₃, F, Cl, MeOCH₂, CH₃), (M-11605, CH₃, F, Cl, EtOCH₂, H), (M-11606, CH₃, F, Cl, EtOCH₂, Cl), (M-11607, CH₃, F, Cl, EtOCH₂, F), (M-11608, CH₃, F, Cl, EtOCH₂, CF₃), (M-11609, CH₃, F, Cl, EtOCH₂, Br), (M-11610, CH₃, F, Cl, EtOCH₂, CH₃), (M-11611, CH₃, F, Cl, EtOCH₂CH₂, H), (M-11612, CH₃, F, Cl, EtOCH₂CH₂, Cl), (M-11613, CH₃, F, Cl, EtOCH₂CH₂, F), (M-11614, CH₃, F, Cl, EtOCH₂CH₂, CF₃), (M-11615, CH₃, F, Cl, EtOCH₂CH₂, Br), (M-11616, CH₃, F, Cl, EtOCH₂CH₂, CH₃), (M-11617, CH₃, F, Cl, MeOCH₂CH₂OCH₂CH₂, H), (M-11618, CH₃, F, Cl, MeOCH₂CH₂OCH₂CH₂, Cl), (M-11619, CH₃, F, Cl, MeOCH₂CH₂OCH₂CH₂, F), (M-11620, CH₃, F, Cl, MeOCH₂CH₂OCH₂CH₂, CF₃), (M-11621, CH₃, F, Cl, MeOCH₂CH₂OCH₂CH₂, Br), (M-11622, CH₃, F, Cl, MeOCH₂CH₂OCH₂CH₂, CH₃), (M-11623, CH₃, F, Cl, MeOCH₂CH₂, H), (M-11624, CH₃, F, Cl, MeOCH₂CH₂, Cl), (M-11625, CH₃, F, Cl, MeOCH₂CH₂, F), (M-11626, CH₃, F, Cl, MeOCH₂CH₂, CF₃), (M-11627, CH₃, F, Cl, MeOCH₂CH₂, Br), (M-11628, CH₃, F, Cl, MeOCH₂CH₂, CH₃), (M-11629, CH₃, F, Cl, HOCH₂, H), (M-11630, CH₃, F, Cl, HOCH₂, Cl), (M-11631, CH₃, F, Cl, HOCH₂, F), (M-11632, CH₃, F, Cl, HOCH₂, CF₃), (M-11633, CH₃, F, Cl, HOCH₂, Br), (M-11634, CH₃, F, Cl, HOCH₂, CH₃), (M-11635, CH₃, F, Cl, HOCH₂CH₂, H), (M-11636, CH₃, F, Cl, HOCH₂CH₂, Cl), (M-11637, CH₃, F, Cl, HOCH₂CH₂, F), (M-11638, CH₃, F, Cl, HOCH₂CH₂, CF₃), (M-11639, CH₃, F, Cl, HOCH₂CH₂, Br), (M-11640, CH₃, F, Cl, HOCH₂CH₂, CH₃), (M-11641, CH₃, F, Cl, HOCH₂CH₂CH₂, H), (M-11642, CH₃, F, Cl, HOCH₂CH₂CH₂, Cl), (M-11643, CH₃, F, Cl, HOCH₂CH₂CH₂, F), (M-11644, CH₃, F, Cl, HOCH₂CH₂CH₂, CF₃), (M-11645, CH₃, F, Cl, HOCH₂CH₂CH₂, Br), (M-11646, CH₃, F, Cl, HOCH₂CH₂CH₂, CH₃), (M-11647, CH₃, F, Cl, HOCH₂CH₂CH₂CH₂, H), (M-11648, CH₃, F, Cl, HOCH₂CH₂CH₂CH₂, Cl), (M-11649, CH₃, F, Cl, HOCH₂CH₂CH₂CH₂, F), (M-11650, CH₃, F, Cl, HOCH₂CH₂CH₂CH₂, CF₃), (M-11651, CH₃, F, Cl, HOCH₂CH₂CH₂CH₂, Br), (M-11652, CH₃, F, Cl, HOCH₂CH₂CH₂CH₂, CH₃), (M-11653, CH₃, F, Cl, HOCH₂CH₂CH₂CH₂CH₂, H), (M-11654, CH₃, F, Cl, HOCH₂CH₂CH₂CH₂CH₂, Cl), (M-11655, CH₃, F, Cl, HOCH₂CH₂CH₂CH₂CH₂, F), (M-11656, CH₃, F, Cl, HOCH₂CH₂CH₂CH₂CH₂, CH₃), (M-11657, CH₃F, Cl, HOCH₂CH₂CH₂CH₂CH₂, Br), (M-11658, CH₃, F, Cl, HOCH₂CH₂CH₂CH₂CH₂, CH₃), (M-11659, CH₃, F, Cl, HOCH₂CH₂OCH₂CH₂, H), (M-11660, CH₃, F, Cl, HOCH₂CH₂OCH₂CH₂, Cl), (M-11661, CH₃, F, Cl, HOCH₂CH₂O CH₂CH₂, F), (M-11662, CH₃, F, Cl, HOCH₂CH₂O CH₂CH₂, CF₃), (M-11663, CH₃, F, Cl, HOCH₂CH₂OCH₂CH₂, Br), (M-11664, CH₃, F, Cl, HOCH₂CH₂O CH₂CH₂, CH₃), (M-11665, CH₃, F, Cl, (Me)₂N, H), (M-11666, CH₃, F, Cl, (Me)₂N, Cl), (M-11667, CH₃, F, Cl, (Me)₂N, F), (M-11668, CH₃, F, Cl, (Me)₂N, CF₃), (M-11669, CH₃, F, Cl, (Me)₂N, Br), (M-11670, CH₃, F, Cl, (Me)₂N, CH₃), (M-11671, CH₃, F, Cl, piperidin-4-yl-methyl, H), (M-11672, CH₃, F, Cl, piperidin-4-yl-methyl, Cl), (M-11673, CH₃, F, Cl, piperidin-4-yl-methyl, F), (M-11674, CH₃, F, Cl, piperidin-4-yl-methyl, CF₃), (M-11675, CH₃, F, Cl, piperidin-4-yl-methyl, Br), (M-11676, CH₃, F, Cl, piperidin-4-yl-methyl, CH₃), (M-11677, CH₃, F, Cl, cyclohexylmethyl, H), (M-11678, CH₃, F, Cl, cyclohexylmethyl, Cl), (M-11679, CH₃, F, Cl, cyclohexylmethyl, F), (M-11680, CH₃, F, Cl, cyclohexylmethyl, CF₃), (M-11681, CH₃, F, Cl, cyclohexylmethyl, Br), (M-11682, CH₃, F, Cl, cyclohexylmethyl, CH₃), (M-11683, CH₃, CH₃, H, H, H), (M-11684, CH₃, CH₃, H, H, Cl), (M-11685, CH₃, CH₃, H, H, F), (M-11686, CH₃, CH₃, H, H, CF₃), (M-11687, CH₃, CH₃, H, H, Br), (M-11688, CH₃, CH₃, H, H, CH₃), (M-11689, CH₃, CH₃, H, F, H), (M-11690, CH₃, CH₃, H, F, Cl), (M-11691, CH₃, CH₃, H, F, F), (M-11692, CH₃, CH₃, H, F, CF₃), (M-11693, CH₃, CH₃, H, F, Br), (M-11694, CH₃, CH₃, H, F, CH₃), (M-11695, CH₃, CH₃, H, Cl, H), (M-11696, CH₃, CH₃, H, Cl, Cl), (M-11697, CH₃, CH₃, H, Cl, F), (M-11698, CH₃, CH₃, H, Cl, CF₃), (M-11699, CH₃, CH₃, H, Cl, Br), (M-11700, CH₃, CH₃, H, Cl, CH₃), (M-11701, CH₃, CH₃, H, CH₃, H), (M-11702, CH₃, CH₃, H, CH₃, Cl), (M-11703, CH₃, CH₃, H, CH₃, F), (M-11704, CH₃, CH₃, H, CH₃, CF₃), (M-11705, CH₃, CH₃, H, CH₃, Br), (M-11706, CH₃, CH₃, H, CH₃, CH₃), (M-11707, CH₃, CH₃, H, Et, H), (M-11708, CH₃, CH₃, H, Et, Cl), (M-11709, CH₃, CH₃, H, Et, F), (M-11710, CH₃, CH₃, H, Et, CF₃), (M-11711, CH₃, CH₃, H, Et, Br), (M-11712, CH₃, CH₃, H, Et, CH₃), (M-11713, CH₃, CH₃, H, n-Pr, H), (M-11714, CH₃, CH₃, H, n-Pr, Cl), (M-11715, CH₃, CH₃, H, n-Pr, F), (M-11716, CH₃, CH₃, H, n-Pr, CF₃), (M-11717, CH₃, CH₃, H, n-Pr, Br), (M-11718, CH₃, CH₃, H, n-Pr, CH₃), (M-11719, CH₃, CH₃, H, c-Pr, H), (M-11720, CH₃, CH₃, H, c-Pr, Cl), (M-11721, CH₃, CH₃, H, c-Pr, F), (M-11722, CH₃, CH₃, H, c-Pr, CF₃), (M-11723, CH₃, CH₃, H, c-Pr, Br), (M-11724, CH₃, CH₃, H, c-Pr, CH₃), (M-11725, CH₃, CH₃, H, i-Pr, H), (M-11726, CH₃, CH₃, H, i-Pr, Cl), (M-11727, CH₃, CH₃, H, i-Pr, F), (M-11728, CH₃, CH₃, H, i-Pr, CF₃), (M-11729, CH₃, CH₃, H, i-Pr, Br), (M-11730, CH₃, CH₃, H, i-Pr, CH₃), (M-11731, CH₃, CH₃, H, n-Bu, H), (M-11732, CH₃, CH₃, H, n-Bu, Cl), (M-11733, CH₃, CH₃, H, n-Bu, F), (M-11734, CH₃, CH₃, H, n-Bu, CF₃), (M-11735, CH₃, CH₃, H, n-Bu, Br), (M-11736, CH₃, CH₃, H, n-Bu, CH₃), (M-11737, CH₃, CH₃, H, i-Bu, H), (M-11738, CH₃, CH₃, H, i-Bu, Cl), (M-11739, CH₃, CH₃, H, i-Bu, F), (M-11740, CH₃, CH₃, H, i-Bu, CF₃), (M-11741, CH₃, CH₃, H, i-Bu, Br), (M-11742, CH₃, CH₃, H, i-Bu, CH₃), (M-11743, CH₃, CH₃, H, sec-Bu, H), (M-11744, CH₃, CH₃, H, sec-Bu, Cl), (M-11745, CH₃, CH₃, H, sec-Bu, F), (M-11746, CH₃, CH₃, H, sec-Bu; CF₃), (M-11747, CH₃, CH₃, H, sec-Bu, Br), (M-11748, CH₃, CH₃, H, sec-Bu, CH₃), (M-11749, CH₃, CH₃, H, n-Pen, H), (M-11750, CH₃, CH₃, H, n-Pen, Cl), (M-11751, CH₃, CH₃, H, n-Pen, F), (M-11752, CH₃, CH₃, H, n-Pen, CF₃), (M-11753, CH₃, CH₃, H, n-Pen, Br), (M-11754, CH₃, CH₃, H, n-Pen, CH₃), (M-11755, CH₃, CH₃, H, c-Pen, H), (M-11756, CH₃, CH₃, H, c-Pen, Cl), (M-11757, CH₃, CH₃, H, c-Pen, F), (M-11758, CH₃, CH₃, H, c-Pen, CF₃), (M-11759, CH₃, CH₃, H, c-Pen, Br), (M-11760, CH₃, CH₃, H, c-Pen, CH₃), (M-11761, CH₃, CH₃, H, n-Hex, H), (M-11762, CH₃, CH₃, H, n-Hex, Cl), (M-11763, CH₃, CH₃, H, n-Hex, F), (M-11764, CH₃, CH₃, H, n-Hex, CF₃), (M-11765, CH₃, CH₃, H, n-Hex, Br), (M-11766, CH₃, CH₃, H, n-Hex, CH₃), (M-11767, CH₃, CH₃, H, c-Hex, H), (M-11768, CH₃, CH₃, H, c-Hex, Cl), (M-11769, CH₃, CH₃, H, c-Hex, F), (M-11770, CH₃, CH₃, H, c-Hex, CF₃), (M-11771, CH₃, CH₃, H, c-Hex, Br), (M-11772, CH₃, H, c-Hex, CH₃), (M-11773, CH₃, CH₃, H, OH, H), (M-11774, CH₃, CH₃, H, OH, Cl), (M-11775, CH₃, CH₃, H, OH, F), (M-11776, CH₃, CH₃, H, OH, CF₃), (M-11777, CH₃, CH₃, H, OH, Br), (M-11778, CH₃, CH₃, H, OH, CH₃), (M-11779, CH₃, CH₃, H, EtO, H), (M-11780, CH₃, CH₃, H, EtO, Cl), (M-11781, CH₃, CH₃, H, EtO, F), (M-11782, CH₃, CH₃, H, EtO, CF₃), (M-11783, CH₃, CH₃, H, EtO, Br), (M-11784, CH₃, CH₃, H, EtO, CH₃), (M-11785, CH₃, CH₃, H, n-PrO, H), (M-11786, CH₃, CH₃, H, n-PrO, Cl), (M-11787, CH₃, CH₃, H, n-PrO, F), (M-11788, CH₃, CH₃, H, n-PrO, CF₃), (M-11789, CH₃, CH₃, H, n-PrO, Br), (M-11790, CH₃, CH₃, H, n-PrO, CH₃), (M-11791, CH₃, CH₃, H, PhO, H), (M-11792, CH₃, CH₃, H, PhO, Cl), (M-11793, CH₃, CH₃, H, PhO, F), (M-11794, CH₃, CH₃, H, PhO, CF₃), (M-11795, CH₃, CH₃, H, PhO, Br), (M-11796, CH₃, CH₃, H, PhO, CH₃), (M-11797, CH₃, CH₃, H, BnO, H), (M-11798, CH₃, CH₃, H, BnO, Cl), (M-11799, CH₃, CH₃, H, BnO, F), (M-11800, CH₃, CH₃, H, BnO, CF₃), (M-11801, CH₃, CH₃, H, BnO, Br), (M-11802, CH₃, CH₃, H, BnO, CH₃), (M-11803, CH₃, CH₃, H, PhCH₂CH₂O, H), (M-11804, CH₃, CH₃, H, PhCH₂CH₂O, Cl), (M-11805, CH₃, CH₃, H, PhCH₂CH₂O, F), (M-11806, CH₃, CH₃, H, PhCH₂CH₂O, CF₃), (M-11807, CH₃, CH₃, H, PhCH₂CH₂O, Br), (M-11808, CH₃, CH₃, H, PhCH₂CH₂O, CH₃), (M-11809, CH₃, CH₃, H, CF₃O, H), (M-11810, CH₃, CH₃, H, CF₃O, Cl), (M-11811, CH₃, CH₃, H, CF₃O, F), (M-11812, CH₃, CH₃, H, CF₃O, CF₃), (M-11813, CH₃, CH₃, H, CF₃O, Br), (M-11814, CH₃, CH₃, H, CF₃O, CH₃), (M-11815, CH₃, CH₃, H, Ph, H), (M-11816, CH₃, CH₃, H, Ph, Cl), (M-11817, CH₃, CH₃, H, Ph, F), (M-11818, CH₃, CH₃, H, Ph, CF₃), (M-11819, CH₃, CH₃, H, Ph, Br), (M-11820, CH₃, CH₃, H, Ph, CH₃), (M-11821, CH₃, CH₃, H, 4-F-Ph, H), (M-11822, CH₃, CH₃, H, 4-F-Ph, Cl), (M-11823, CH₃, CH₃, H, 4-F-Ph, F), (M-11824, CH₃, CH₃, H, 4-F-Ph, CF₃), (M-11825, CH₃, CH₃, H, 4-F-Ph, Br), (M-11826, CH₃, CH₃, H, 4-F-Ph, CH₃), (M-11827, CH₃, CH₃, H, 4-CF₃-Ph, H), (M-11828, CH₃, CH₃, H, 4-CF₃-Ph, Cl), (M-11829, CH₃, CH₃, H, 4-CF₃-Ph, F), (M-11830, CH₃, CH₃, H, 4-CF₃-Ph, CF₃), (M-11831, CH₃, CH₃H, 4-CF₃-Ph, Br), (M-11832, CH₃, CH₃, H, 4-CF₃-Ph, CH₃), (M-11833, CH₃, CH₃H, 4-(Me)₂N-Ph, H), (M-11834, CH₃, CH₃, H, 4-(Me)₂N-Ph, Cl), (M-11835, CH₃, CH₃, H, 4-(Me)₂N-Ph, F), (M-11836, CH₃, CH₃, H, 4-(Me)₂N-Ph, CF₃), (M-11837, CH₃, CH₃, H, 4-(Me)₂N-Ph, Br), (M-11838, CH₃, CH₃, H, 4-(Me)₂N-Ph, CH₃), (M-11839, CH₃, CH₃, H, 4-OH-Ph, H), (M-11840, CH₃, CH₃, H, 4-OH-Ph, Cl), (M-11841, CH₃, CH₃, H, 4-OH-Ph, F), (M-11842, CH₃, CH₃, H, 4-OH-Ph, CF₃), (M-11843, CH₃, CH₃, H, 4-OH-Ph, Br), (M-11844, CH₃, CH₃, H, 4-OH-Ph, CH₃), (M-11845, CH₃, CH₃, H, 3,4-di-F-Ph, H), (M-11846, CH₃, CH₃, H, 3,4-di-F-Ph, Cl), (M-11847, CH₃, CH₃, H, 3,4-di-F-Ph, F), (M-11848, CH₃, CH₃, H, 3,4-di-F-Ph, CF₃), (M-11849, CH₃, CH₃, H, 3,4-di-F-Ph, Br), (M-11850, CH₃, CH₃, H, 3,4-di-F-Ph, CH₃), (M-11851, CH₃, CH₃, H, 4-COOH-Ph, H), (M-11852, CH₃, CH₃, H, 4-COOH-Ph, Cl), (M-11853, CH₃, CH₃, H, 4-COOH-Ph, F), (M-11854, CH₃, CH₃, H, 4-COOH-Ph, CF₃), (M-11855, CH₃, CH₃, H, 4-COOH-Ph, Br), (M-11856, CH₃, CH₃, H, 4-COOH-Ph, CH₃), (M-11857, CH₃, CH₃, H, Bn, H), (M-11858, CH₃, CH₃, H, Bn, Cl), (M-11859, CH₃, CH₃, H, Bn, F), (M-11860, CH₃, CH₃, H, Bn, CF₃), (M-11861, CH₃, CH₃, H, Bn, Br), (M-11862, CH₃, CH₃, H, Bn, CH₃), (M-11863, CH₃, CH₃, H, 4-F-Bn, H), (M-11864, CH₃, CH₃, H, 4-F-Bn, Cl), (M-11865, CH₃, CH3, H, 4-F-Bn, F), (M-11866, CH₃, CH₃, H, 4-F-Bn, CF₃), (M-11867, CH₃, CH₃, H, 4-F-Bn, Br), (M-11868, CH₃, CH₃, H, 4-F-Bn, CH₃), (M-11869, CH₃, CH₃, H, 2-Py, H), (M-11870, CH₃, CH₃, H, 2-Py, Cl), (M-11871, CH₃CH₃H, 2-Py, F), (M-11872, CH₃CH₃H, 2-Py, CF₃), (M-11873, CH₃CH₃, H, 2-Py, Br), (M-11874, CH₃, CH₃, H, 2-Py, CH₃), (M-11875, CH₃, CH₃, H, 3-Py, H), (M-11876, CH₃, CH₃, H, 3-Py, Cl), (M-11877, CH₃, CH₃, H, 3-Py, F), (M-11878, CH₃, CH₃, H, 3-Py, CF₃), (M-11879, CH₃, CH₃, H, 3-Py, Br), (M-11880, CH₃, CH₃, H, 3-Py, CH₃), (M-11881, CH₃, CH₃, H, 4-Py, H), (M-11882, CH₃, CH₃, H, 4-Py, Cl), (M-11883, CH₃, CH₃, H, 4-Py, F), (M-11884, CH₃, CH₃, H, 4-Py, CF₃), (M-11885, CH₃, CH₃, H, 4-Py, Br), (M-11886, CH₃, CH3, H, 4-Py, CH₃), (M-11887, CH₃, CH₃, H, 2-Th, H), (M-11888, CH₃, CH₃, H, 2-Th, Cl), (M-11889, CH₃, CH₃, H, 2-Th, F), (M-11890, CH₃, CH₃, H, 2-Th, CF₃), (M-11891, CH₃, CH₃, H, 2-Th, Br), (M-11892, CH₃, CH₃, H, 2-Th, CH₃), (M-11893, CH₃, CH₃, H, 3-Th, H), (M-11894, CH₃, CH₃, H, 3-Th, Cl), (M-11895, CH₃, CH₃, H, 3-Th, F), (M-11896, CH₃, CH₃, H, 3-Th, CF₃), (M-11897, CH₃, CH₃, H, 3-Th, Br), (M-11898, CH₃, CH₃, H, 3-Th, CH₃), (M-11899, CH₃, CH₃, H, pyrrazol-2-yl, H), (M-11900, CH₃, CH₃, H, pyrrazol-2-yl, Cl), (M-11901, CH₃, CH₃, H, pyrrazol-2-yl, F), (M-11902, CH₃, CH₃, H, pyrrazol-2-yl, CF₃), (M-11903, CH₃, CH₃, H, pyrrazol-2-yl, Br), (M-11904, CH₃, CH₃, H, pyrrazol-2-yl, CH₃), (M-11905, CH₃, CH₃, H, pyrrazol-3-yl, H), (M-11906, CH₃, CH₃, H, pyrrazol-3-yl, Cl), (M-11907, CH₃, CH₃, H, pyrrazol-3-yl, F), (M-11908, CH₃, CH₃, H, pyrrazol-3-yl, CF₃), (M-11909, CH₃, CH₃, H, pyrrazol-3-yl, Br), (M-11910, CH₃, CH₃, H, pyrrazol-3-yl, CH₃), (M-11911, CH₃, CH₃, H, pyrimidin-2-yl, H), (M-11912, CH₃, CH₃, H, pyrimidin-2-yl, Cl), (M-11913, CH₃, CH₃, H, pyrimidin-2-yl, F), (M-11914, CH₃, CH₃, H, pyrimidin-2-yl, CF₃), (M-11915, CH₃, CH₃, H, pyrimidin-2-yl, Br), (M-11916, CH₃, CH₃, H, pyrimidin-2-yl, CH₃), (M-11917, CH₃, CH₃, H, pyrimidin-4-yl, H), (M-11918, CH₃, CH₃, H, pyrimidin-4-yl, Cl), (M-11919, CH₃, CH₃, H, pyrimidin-4-yl, F), (M-11920, CH₃, CH₃, H, pyrimidin-4-yl, CF₃), (M-11921, CH₃, CH₃, H, pyrimidin-4-yl, Br), (M-11922, CH₃, CH₃, H, pyrimidin-4-yl, CH₃), (M-11923, CH₃, CH₃, H, pyrimidin-5-yl, H), (M-11924, CH₃, CH₃, H, pyrimidin-5-yl, Cl), (M-11925, CH₃, CH₃, H, pyrimidin-5-yl, F), (M-11926, CH₃, CH₃, H, pyrimidin-5-yl, CF₃), (M-11927, CH₃, CH₃, H, pyrimidin-5-yl, Br), (M-11928, CH₃, CH₃, H, pyrimidin-5-yl, CH₃), (M-11929, CH₃, CH₃, H, HOOCCH₂CH₂CH₂, H), (M-11930, CH₃, CH₃, H, HOOCCH₂CH₂CH₂, Cl), (M-11931, CH₃, CH₃, H, HOOCCH₂CH₂CH₂, F), (M-11932, CH₃, CH₃, H, HOOCCH₂CH₂CH₂, CF₃), (M-11933, CH₃, CH₃, H, HOOCCH₂CH₂CH₂, Br), (M-11934, CH₃, CH₃, H, HOOCCH₂CH₂CH₂, CH₃), (M-11935, CH₃, CH₃, H, HOOCCH₂CH₂CH₂CH₂, H), (M-11936, CH₃, CH₃, H, HOOCCH₂CH₂CH₂CH₂, Cl), (M-11937, CH₃, CH₃, H, HOOCCH₂CH₂CH₂CH₂, F), (M-11938, CH₃, CH₃, H, HOOCCH₂CH₂CH₂CH₂, CF₃), (M-11939, CH₃, CH₃, H, HOOCCH₂CH₂CH₂CH₂, Br), (M-11940, CH₃, CH₃, H, HOOCCH₂CH₂CH₂CH₂, CH₃), (M-11941, CH₃, CH₃, H, (Me)₂NCOCH₂CH₂CH₂, H), (M-11942, CH₃, CH₃, H, (Me)₂NCOCH₂CH₂CH₂, Cl), (M-11943, CH₃, CH₃, H, (Me)₂NCOCH₂CH₂CH₂, F), (M-11944, CH₃, CH₃, H, (Me)₂NCOCH₂CH₂CH₂, CF₃), (M-11945, CH₃, CH₃, H, (Me)₂NCOCH₂CH₂CH₂, Br), (M-11946, CH₃, CH₃, H, (Me)₂NCOCH₂CH₂CH₂, CH₃), (M-11947, CH₃, CH₃, H, (Me)₂NCOCH₂CH₂CH₂CH₂, H), (M-11948, CH₃, CH₃, H, (Me)₂NCOCH₂CH₂CH₂CH₂, Cl), (M-11949, CH₃, CH₃, H, (Me)₂NCOCH₂CH₂CH₂CH₂, F), (M-11950, CH₃, CH₃, H, (Me)₂NCOCH₂CH₂CH₂CH₂, CF₃), (M-11951, CH₃, CH₃, H, (Me)₂NCOCH₂CH₂CH₂CH₂, Br), (M-11952, CH₃, CH₃, H, (Me)₂NCOCH₂CH₂CH₂CH₂, CH₃), (M-11953, CH₃, CH₃, H, MeOCH₂, H), (M-11954, CH₃, CH₃, H, MeOCH₂, Cl), (M-11955, CH₃, CH₃, H, MeOCH₂, F), (M-11956, CH₃, CH₃, H, MeOCH₂, CF₃), (M-11957, CH₃, CH₃, H, MeOCH₂, Br), (M-11958, CH₃, CH₃, H, MeOCH₂, CH₃), (M-11959, CH₃, CH₃, H, EtOCH₂, H), (M-11960, CH₃, CH₃, H, EtOCH₂, Cl), (M-11961, CH₃, CH₃, H, EtOCH₂, F), (M-11962, CH₃, CH₃, H, EtOCH₂, CF₃), (M-11963, CH₃, CH₃, H, EtOCH₂, Br), (M-11964, CH₃, CH₃, H, EtOCH₂, CH₃), (M-11965, CH₃, CH₃, H, EtOCH₂CH₂, H), (M-11966, CH₃, CH₃, H, EtOCH₂CH₂, Cl), (M-11967, CH₃, CH₃, H, EtOCH₂CH₂, F), (M-11968, CH₃, CH₃, H, EtOCH₂CH₂, CF₃), (M-11969, CH₃, CH₃, H, EtOCH₂CH₂, Br), (M-11970, CH₃, CH₃, H, EtOCH₂CH₂, CH₃), (M-11971, CH₃, CH₃, H, MeOCH₂CH₂OCH₂CH₂, H), (M-11972, CH₃, CH₃, H, MeOCH₂CH₂OCH₂CH₂, Cl), (M-11973, CH₃, CH₃, H, MeOCH₂CH₂OCH₂CH₂, F), (M-11974, CH₃, CH₃, H, MeOCH₂CH₂OCH₂CH₂, CF₃), (M-11975, CH₃, CH₃, H MeOCH₂CH₂OCH₂CH₂, Br), (M-11976, CH₃, CH₃, H, MeOCH₂CH₂OCH₂CH₂, CH₃), (M-11977, CH₃, CH₃, H, MeOCH₂CH₂, H), (M-11978, CH₃, CH₃, H, MeOCH₂CH₂, Cl), (M-11979, CH₃, CH₃, H, MeOCH₂CH₂, F), (M-11980, CH₃, CH₃, H, MeOCH₂CH₂, CF₃), (M-11981, CH₃, CH₃, H, MeOCH₂CH₂, Br), (M-11982, CH₃, CH₃, H, MeOCH₂CH₂, CH₃), (M-11983, CH₃, CH₃, H, HOCH₂, H), (M-11984, CH₃, CH₃, H, HOCH₂, Cl), (M-11985, CH₃, CH₃, H, HOCH₂, F), (M-11986, CH₃, CH₃, H, HOCH₂, CF₃), (M-11987, CH₃, CH₃, H, HOCH₂, Br), (M-11988, CH, CH₃, H, HOCH₂, CH₃), (M-11989, CH₃, CH₃, H, HOCH₂CH₂, H), (M-11990, CH₃, CH₃, H, HOCH₂CH₂, Cl), (M-11991, CH₃, CH₃, H, HOCH₂CH₂, F), (M-11992, CH₃, CH₃, H, HOCH₂CH₂, CF₃), (M-11993, CH₃, CH₃, H, HOCH₂CH₂, Br), (M-11994, CH₃, CH₃, H, HOCH₂CH₂, CH₃), (M-11995, CH₃, CH₃, H, HOCH₂CH₂CH₂, H), (M-11996, CH₃, CH₃, H, HOCH₂CH₂CH₂, Cl), (M-11997, CH₃, CH₃, H, HOCH₂CH₂CH₂, F), (M-11998, CH₃, CH₃, H, HOCH₂CH₂CH₂, CF₃), (M-11999, CH₃, CH₃, H, HOCH₂CH₂CH₂, Br), (M-12000, CH₃, CH₃, H, HOCH₂CH₂CH₂, CH₃), (M-12001, CH₃, CH₃, H, HOCH₂CH₂CH₂CH₂, H), (M-12002, CH₃, CH₃, H, HOCH₂CH₂CH₂CH₂, Cl), (M-12003, CH₃, CH₃, H, HOCH₂CH₂CH₂CH₂, F), (M-12004, CH₃, CH₃, H, HOCH₂CH₂CH₂CH₂, CF₃), (M-12005, CH₃, CH₃, H, HOCH₂CH₂CH₂CH₂, Br), (M-12006, CH₃, CH₃, H, HOCH₂CH₂CH₂CH₂, CH₃), (M-12007, CH₃, CH₃, H, HOCH₂CH₂CH₂CH₂CH₂, H), (M-12008, CH₃, CH₃, H, HOCH₂CH₂CH₂CH₂CH₂, Cl), (M-12009, CH₃, CH₃, H, HOCH₂CH₂CH₂CH₂CH₂, F), (M-12010, CH₃, CH₃, H, HOCH₂CH₂CH₂CH₂CH₂, CF₃), (M-12011, CH₃, CH₃, H, HOCH₂CH₂CH₂CH₂CH₂, Br), (M-12012, CH₃, CH₃, H, HOCH₂CH₂CH₂CH₂CH₂, CH₃), (M-12013, CH₃, CH₃, H, HOCH₂CH₂OCH₂CH₂, H), (M-12014, CH₃, CH₃, H, HOCH₂CH₂OCH₂CH₂, Cl), (M-12015, CH₃, CH₃H, HOCH₂CH₂OCH₂CH₂, F), (M-12016, CH₃, CH₃, H, HOCH₂CH₂OCH₂CH₂, CF₃), (M-12017, CH₃CH₃H, HOCH₂CH₂OCH₂CH₂, Br), (M-12018, CH₃, CH₃, H, HOCH₂CH₂OCH₂CH₂, CH₃), (M-12019, CH₃, CH₃, H, (Me)₂N, H), (M-12020, CH₃, CH₃, H, (Me)₂N, Cl), (M-12021, CH₃, CH₃, H, (Me)₂N, F), (M-12022, CH₃, CH₃, H, (Me)₂N, CF₃), (M-12023, CH₃, CH₃, H, (Me)₂N, Br), (M-12024, CH₃, CH₃, H, (Me)₂N, CH₃), (M-12025, CH₃, CH₃, H, piperidin-4-yl-methyl, H), (M-12026, CH₃, CH₃, H, piperidin-4-yl-methyl, Cl), (M-12027, CH₃, CH₃, H, piperidin-4-yl-methyl, F), (M-12028, CH₃, CH₃, H, piperidin-4-yl-methyl, CF₃), (M-12029, CH₃, CH₃, H, piperidin-4-yl-methyl, Br), (M-12030, CH₃, CH₃, H, piperidin-4-yl-methyl, CH₃), (M-12031, CH₃, CH₃, H, cyclohexylmethyl, H), (M-12032, CH₃, CH₃, H, cyclohexylmethyl, Cl), (M-12033, CH₃, CH₃, H, cyclohexylmethyl, F), (M-12034, CH₃, CH₃, H, cyclohexylmethyl, CF₃), (M-12035, CH₃, CH₃, H, cyclohexylmethyl, Br), (M-12036, CH₃, CH₃, H, cyclohexylmethyl, CH₃), (M-12037, CH₃, CH₃, F, H, H), (M-12038, CH₃, CH₃F, H, Cl), (M-12039, CH₃, CH₃, F, H, F), (M-12040, CH₃, CH₃, F, H, CF₃), (M-12041, CH₃, CH₃, F, H, Br), (M-12042, CH₃, CH₃, F, H, CH₃), (M-12043, CH₃, CH₃, F, F, H), (M-12044, CH₃, CH₃, F, F, Cl), (M-12045, CH₃, CH₃, F, F, F), (M-12046, CH₃, CH₃, F, F, CF₃), (M-12047, CH₃, CH₃, F, F, Br), (M-12048, CH₃, CH₃, F, F, CH₃), (M-12049, CH₃, CH₃, F, Cl, H), (M-12050, CH₃, CH₃, F, Cl Cl), (M-12051, CH₃, CH₃, F, Cl, F), (M-12052, CH₃, CH₃, F, Cl, CF₃), (M-12053, CH₃, CH₃, F, Cl, Br), (M-12054, CH₃, CH₃, F, Cl CH₃), (M-12055, CH₃, CH₃, F, CH₃, H), (M-12056, CH₃, CH₃, F, CH₃, Cl), (M-12057, CH₃, CH₃, F, CH₃, F), (M-12058, CH₃, CH₃, F, CH₃, CF₃), (M-12059, CH₃, CH₃, F, CH₃, Br), (M-12060, CH₃, CH₃, F, CH₃, CH₃), (M-12061, CH₃, CH₃, F, Et, H), (M-12062, CH₃, CH₃, F, Et, Cl), (M-12063, CH₃, CH₃, F, Et, F), (M-12064, CH₃, CH₃, F, Et, CF₃), (M-12065, CH₃, CH₃, F, Et, Br), (M-12066, CH₃, CH₃, F, Et, CH₃), (M-12067, CH₃, CH₃, F, n-Pr, H), (M-12068, CH₃, CH₃, F, n-Pr, Cl), (M-12069, CH₃, CH₃, F, n-Pr, F), (M-12070, CH₃, CH₃, F, n-Pr, CF₃), (M-12071, CH₃, CH₃, F, n-Pr, Br), (M-12072, CH₃, CH₃, F, n-Pr, CH₃), (M-12073, CH₃, CH₃, F, c-Pr, H), (M-12074, CH₃, CH₃, F, c-Pr, Cl), (M-12075, CH₃, CH₃, F, c-Pr, F), (M-12076, CH₃, CH₃, F, c-Pr, CF₃), (M-12077, CH₃, CH₃, F, c-Pr, Br), (M-12078, CH₃, CH₃, F, c-Pr, CH₃), (M-12079, CH₃, CH₃, F, i-Pr, H), (M-12080, CH₃, CH₃, F, i-Pr, Cl), (M-12081, CH₃, CH₃, F, i-Pr, F), (M-12082, CH₃, CH₃, F, i-Pr, CF₃), (M-12083, CH₃, CH₃, F, i-Pr, Br), (M-12084, CH₃, CH₃, F, i-Pr, CH₃), (M-12085, CH₃, CH₃, F, n-Bu, H), (M-12086, CH₃, CH₃, F, n-Bu, Cl), (M-12087, CH₃, CH₃, F, n-Bu, F), (M-12088, CH₃, CH₃, F, n-Bu, CF₃), (M-12089, CH₃, CH₃, F, n-Bu, Br), (M-12090, CH₃, CH₃, F, n-Bu, CH₃), (M-12091, CH₃, CH₃, F, i-Bu, H), (M-12092, CH₃, CH₃, F, i-Bu, Cl), (M-12093, CH₃, CH₃, F, i-Bu, F), (M-12094, CH₃, CH₃, F, i-Bu, CF₃), (M-12095, CH₃, CH₃, F, i-Bu, Br), (M-12096, CH₃, CH₃, F, i-Bu, CH₃), (M-12097, CH₃, CH₃, F, sec-Bu, H), (M-12098, CH₃, CH₃, F, sec-Bu, Cl), (M-12099, CH₃, CH₃, F, sec-Bu, F), (M-12100, CH₃, CH₃, F, sec-Bu, CF₃), (M-12101, CH₃, CH₃, F, sec-Bu, Br), (M-12102, CH₃, CH₃, F, sec-Bu, CH₃), (M-12103, CH₃, CH₃, F, n-Pen, H), (M-12104, CH₃, CH₃, F, n-Pen, Cl), (M-12105, CH₃, CH₃, F, n-Pen, F), (M-12106, CH₃, CH₃, F, n-Pen, CF₃), (M-12107, CH₃, CH₃, F, n-Pen, Br), (M-12108, CH₃, CH₃, F, n-Pen, CH₃), (M-12109, CH₃, CH₃, F, c-Pen, H), (M-12110, CH₃, CH₃, F, c-Pen, Cl), (M-12111, CH₃, CH₃, F, c-Pen, F), (M-12112, CH₃, CH₃, F, c-Pen, CF₃), (M-12113, CH₃, CH₃, F, c-Pen, Br), (M-12114, CH₃, CH₃, F, c-Pen, CH₃), (M-12115, CH₃, CH₃, F, n-Hex, H), (M-12116, CH₃, CH₃, F, n-Hex, Cl), (M-12117, CH₃, CH₃, F, n-Hex, F), (M-12118, CH₃, CH₃, F, n-Hex, CF₃), (M-12119, CH₃, CH₃, F, n-Hex, Br), (M-12120, CH₃, CH₃, F, n-Hex, CH₃), (M-12121, CH₃, CH₃, F, c-Hex, H), (M-12122, CH₃, CH₃, F, c-Hex, Cl), (M-12123, CH₃, CH₃, F, c-Hex, F), (M-12124, CH₃, CH₃, F, c-Hex, CF₃), (M-12125, CH₃, CH₃, F, c-Hex, Br), (M-12126, CH₃, CH₃, F, c-Hex, CH₃), (M-12127, CH₃, CH₃, F, OH, H), (M-12128, CH₃, CH₃, F, OH, Cl), (M-12129, CH₃, CH₃, F, OH, F), (M-12130, CH₃, CH₃, F, OH, CF₃), (M-12131, CH₃, CH₃, F, OH, Br), (M-12132, CH₃, CH₃, F, OH, CH₃), (M-12133, CH₃, CH₃, F, EtO, H), (M-12134, CH₃, CH₃, F, EtO, Cl), (M-12135, CH₃, CH₃, F, EtO, F), (M-12136, CH₃, CH₃, F, EtO, CF₃), (M-12137, CH₃, CH₃, F, EtO, Br), (M-12138, CH₃, CH₃, F, EtO, CH₃), (M-12139, CH₃, CH₃, F, n-PrO, H), (M-12140, CH₃, CH₃, F, n-PrO, Cl), (M-12141, CH₃, CH₃, F, n-PrO, F), (M-12142, CH₃, CH₃, F, n-PrO, CF₃), (M-12143, CH₃, CH₃, F, n-PrO, Br), (M-12144, CH₃, CH₃, F, n-PrO, CH₃), (M-12145, CH₃, CH₃, F, PhO, H), (M-12146, CH₃, CH₃, F, PhO, Cl), (M-12147, CH₃, CH₃, F, PhO, F), (M-12148, CH₃, CH₃, F, PhO, CF₃), (M-12149, CH₃, CH₃, F, PhO, Br), (M-12150, CH$_3$, CH$_3$, F, PhO, CH$_3$), (M-12151, CH$_3$, CH$_3$, F, BnO, H), (M-12152, CH$_3$, CH$_3$, F, BnO, Cl), (M-12153, CH$_3$, CH$_3$, F, BnO, F), (M-12154, CH$_3$, CH$_3$, F, BnO, CF$_3$), (M-12155, CH$_3$, CH$_3$, F, BnO, Br), (M-12156, CH$_3$, CH$_3$, F, BnO, CH$_3$), (M-12157, CH$_3$, CH$_3$, F, PhCH$_2$CH$_2$O, H), (M-12158, CH$_3$, CH$_3$, F, PhCH$_2$CH$_2$O, Cl), (M-12159, CH$_3$, CH$_3$, F, PhCH$_2$CH$_2$O, F), (M-12160, CH$_3$, CH$_3$, F, PhCH$_2$CH$_2$O, CF$_3$), (M-12161, CH$_3$, CH$_3$, F, PhCH$_2$CH$_2$O, Br), (M-12162, CH$_3$, CH$_3$, F, PhCH$_2$CH$_2$O, CH$_3$), (M-12163, CH$_3$, CH$_3$, F, CF$_3$O, H), (M-12164, CH$_3$, CH$_3$, F, CF$_3$O, Cl), (M-12165, CH$_3$, CH$_3$, F, CF$_3$O, F), (M-12166, CH$_3$, CH$_3$, F, CF$_3$O, CF$_3$), (M-12167, CH$_3$, CH$_3$, F, CF$_3$O, Br), (M-12168, CH$_3$, CH$_3$, F, CF$_3$O, CH$_3$), (M-12169, CH$_3$, CH$_3$, F, Ph, H), (M-12170, CH$_3$, CH$_3$, F, Ph, Cl), (M-12171, CH$_3$, CH$_3$, F, Ph, F), (M-12172, CH$_3$, CH$_3$, F, Ph, CF$_3$), (M-12173, CH$_3$, CH$_3$, F, Ph, Br), (M-12174, CH$_3$, CH$_3$, F, Ph, CH$_3$), (M-12175, CH$_3$, CH$_3$, F, 4-F-Ph, H), (M-12176, CH$_3$, CH$_3$, F, 4-F-Ph, Cl), (M-12177, CH$_3$, CH$_3$, F, 4-F-Ph, F), (M-12178, CH$_3$, CH$_3$, F, 4-F-Ph, CF$_3$), (M-12179, CH$_3$, CH$_3$, F, 4-F-Ph, Br), (M-12180, CH$_3$, CH$_3$, F, 4-F-Ph, CH$_3$), (M-12181, CH$_3$, CH$_3$, F, 4-CF$_3$-Ph, H), (M-12182, CH$_3$, CH$_3$, F, 4-CF$_3$-Ph, Cl), (M-12183, CH$_3$, CH$_3$, F, 4-CF$_3$-Ph, F), (M-12184, CH$_3$, CH$_3$, F, 4-CF$_3$-Ph, CF$_3$), (M-12185, CH$_3$, CH$_3$, F, 4-CF$_3$-Ph, Br), (M-12186, CH$_3$, CH$_3$, F, 4-CF$_3$-Ph, CH$_3$), (M-12187, CH$_3$, CH$_3$, F, 4-(Me)2N-Ph, H), (M-12188, CH$_3$, CH$_3$, F, 4-(Me)$_2$N-Ph, Cl), (M-12189, CH$_3$, CH$_3$, F, 4-(Me)$_2$N-Ph, F), (M-12190, CH$_3$, CH$_3$, F, 4-(Me)$_2$N-Ph, CF$_3$), (M-12191, CH$_3$, CH$_3$, F, 4-(Me)$_2$N-Ph, Br), (M-12192, CH$_3$, CH$_3$, F, 4-(Me)$_2$N-Ph, CH$_3$), (M-12193, CH$_3$, CH$_3$, F, 4-OH-Ph, H), (M-12194, CH$_3$, CH$_3$, F, 4-OH-Ph, Cl), (M-12195, CH$_3$, CH$_3$, F, 4-OH-Ph, F), (M-12196, CH$_3$, CH$_3$, F, 4-OH-Ph, CF$_3$), (M-12197, CH$_3$, CH$_3$, F, 4-OH-Ph, Br), (M-12198, CH$_3$, CH$_3$, F, 4-OH-Ph, CH$_3$), (M-12199, CH$_3$, CH$_3$, F, 3,4-di-F-Ph, H), (M-12200, CH$_3$, CH$_3$, F, 3,4-di-F-Ph, Cl), (M-12201, CH$_3$, CH$_3$, F, 3,4-di-F-Ph, F), (M-12202, CH$_3$, CH$_3$, F, 3,4-di-F-Ph, CF$_3$), (M-12203, CH$_3$, CH$_3$, F, 3,4-di-F-Ph, Br), (M-12204, CH$_3$, CH$_3$, F, 3,4-di-F-Ph, CH$_3$), (M-12205, CH$_3$, CH$_3$, F, 4-COOH-Ph, H), (M-12206, CH$_3$, CH$_3$, F, 4-COOH-Ph, Cl), (M-12207, CH$_3$, CH$_3$, F, 4-COOH-Ph, F), (M-12208, CH$_3$, CH$_3$, F, 4-COOH-Ph, CF$_3$), (M-12209, CH$_3$, CH$_3$, F, 4-COOH-Ph, Br), (M-12210, CH$_3$, CH$_3$, F, 4-COOH-Ph, CH$_3$), (M-12211, CH$_3$, CH$_3$, F, Bn, H), (M-12212, CH$_3$, CH$_3$, F, Bn, Cl), (M-12213, CH$_3$, CH$_3$, F, Bn, F), (M-12214, CH$_3$, CH$_3$, F, Bn, CF$_3$), (M-12215, CH$_3$, CH$_3$, F, Bn, Br), (M-12216, CH$_3$, CH$_3$, F, Bn, CH$_3$), (M-12217, CH$_3$, CH$_3$, F, 4-F-Bn, H), (M-12218, CH$_3$, CH$_3$, F, 4-F-Bn, Cl), (M-12219, CH$_3$, CH$_3$, F, 4-F-Bn, F), (M-12220, CH$_3$, CH$_3$, F, 4-F-Bn, CF$_3$), (M-12221, CH$_3$, CH$_3$, F, 4-F-Bn, Br), (M-12222, CH$_3$, CH$_3$, F, 4-F-Bn, CH$_3$), (M-12223, CH$_3$, CH$_3$, F, 2-Py, H), (M-12224, CH$_3$, CH$_3$, F, 2-Py, Cl), (M-12225, CH$_3$, CH$_3$, F, 2-Py, F), (M-12226, CH$_3$, CH$_3$, F, 2-Py, CF$_3$), (M-12227, CH$_3$, CH$_3$, F, 2-Py, Br), (M-12228, CH$_3$, CH$_3$, F, 2-Py, CH$_3$), (M-12229, CH$_3$, CH$_3$, F, 3-Py, H), (M-12230, CH$_3$, CH$_3$, F, 3-Py, Cl), (M-12231, CH$_3$, CH$_3$, F, 3-Py, F), (M-12232, CH$_3$, CH$_3$, F, 3-Py, CF$_3$), (M-12233, CH$_3$, CH$_3$, F, 3-Py, Br), (M-12234, CH$_3$, CH$_3$, F, 3-Py, CH$_3$), (M-12235, CH$_3$, CH$_3$, F, 4-Py, H), (M-12236, CH$_3$, CH$_3$, F, 4-Py, Cl), (M-12237, CH$_3$, CH$_3$, F, 4-Py, F), (M-12238, CH$_3$, CH$_3$, F, 4-Py, CF$_3$), (M-12239, CH$_3$, CH$_3$, F, 4-Py, Br), (M-12240, CH$_3$, CH$_3$, F, 4-Py, CH$_3$), (M-12241, CH$_3$, CH$_3$, F, 2-Th, H), (M-12242, CH$_3$, CH$_3$, F, 2-Th, Cl), (M-12243, CH$_3$, CH$_3$, F, 2-Th, F), (M-12244, CH$_3$, CH$_3$, F, 2-Th, CF$_3$), (M-12245, CH$_3$, CH$_3$, F, 2-Th, Br), (M-12246, CH$_3$, CH$_3$, F, 2-Th, CH$_3$), (M-12247, CH$_3$, CH$_3$, F, 3-Th, H), (M-12248, CH$_3$, CH$_3$, F, 3-Th, Cl), (M-12249, CH$_3$, CH$_3$, F, 3-Th, F), (M-12250, CH$_3$, CH$_3$, F, 3-Th, CF$_3$), (M-12251, CH$_3$, CH$_3$, F, 3-Th, Br), (M-12252, CH$_3$, CH$_3$, F, 3-Th, CH$_3$), (M-12253, CH$_3$, CH$_3$, F, pyrrazol-2-yl, H), (M-12254, CH$_3$, CH$_3$, F, pyrrazol-2-yl, Cl), (M-12255, CH$_3$, CH$_3$, F, pyrrazol-2-yl, F), (M-12256, CH$_3$, CH$_3$, F, pyrrazol-2-yl, CF$_3$), (M-12257, CH$_3$, CH$_3$, F, pyrrazol-2-yl, Br), (M-12258, CH$_3$, CH$_3$, F, pyrrazol-2-yl, CH$_3$), (M-12259, CH$_3$, CH$_3$, F, pyrrazol-3-yl, H), (M-12260, CH$_3$, CH$_3$, F, pyrrazol-3-yl, Cl), (M-12261, CH$_3$, CH$_3$, F, pyrrazol-3-yl, F), (M-12262, CH$_3$, CH$_3$, F, pyrrazol-3-yl, CF$_3$), (M-12263, CH$_3$, CH$_3$, F, pyrrazol-3-yl, Br), (M-12264, CH$_3$, CH$_3$, F, pyrrazol-3-yl, CH$_3$), (M-12265, CH$_3$, CH$_3$, F, pyrimidin-2-yl, H), (M-12266, CH$_3$, CH$_3$, F, pyrimidin-2-yl, Cl), (M-12267, CH$_3$, CH$_3$, F, pyrimidin-2-yl, F), (M-12268, CH$_3$, CH$_3$, F, pyrimidin-2-yl, CF$_3$), (M-12269, CH$_3$, CH$_3$, F, pyrimidin-2-yl, Br), (M-12270, CH$_3$, CH$_3$, F, pyrimidin-2-yl, CH$_3$), (M-12271, CH$_3$, CH$_3$, F, pyrimidin-4-yl, H), (M-12272, CH$_3$, CH$_3$, F, pyrimidin-4-yl, Cl), (M-12273, CH$_3$, CH$_3$, F, pyrimidin-4-yl, F), (M-12274, CH$_3$, CH$_3$, F, pyrimidin-4-yl, CF$_3$), (M-12275, CH$_3$, CH$_3$, F, pyrimidin-4-yl, Br), (M-12276, CH$_3$, CH$_3$, F, pyrimidin-4-yl, CH$_3$), (M-12277, CH$_3$, CH$_3$, F, pyrimidin-5-yl, H), (M-12278, CH$_3$, CH$_3$, F, pyrimidin-5-yl, Cl), (M-12279, CH$_3$, CH$_3$, F, pyrimidin-5-yl, F), (M-12280, CH$_3$, CH$_3$, F, pyrimidin5-yl, CF$_3$), (M-12281, CH$_3$, CH$_3$, F, pyrimidin-5-yl, Br), (M-12282, CH$_3$, CH$_3$, F, pyrimidin-5-yl, CH$_3$), (M-12283, CH$_3$, CH$_3$, F, HOOCCH$_2$CH$_2$, H), (M-12284, CH$_3$, CH$_3$, F, HOOCCH$_2$CH$_2$, Cl), (M-12285, CH$_3$, CH$_3$, F, HOOCCH$_2$CH$_2$, F), (M-12286, CH$_3$, CH$_3$, F, HOOCCH$_2$CH$_2$, CF$_3$), (M-12287, CH$_3$, CH$_3$, F, HOOCCH$_2$CH$_2$, Br), (M-12288, CH$_3$, CH$_3$, F, HOOCCH$_2$CH$_2$, CH$_3$), (M-12289, CH$_3$, CH$_3$, F, HOOCCH$_2$CH$_2$CH$_2$, H), (M-12290, CH$_3$, CH$_3$, F, HOOCCH$_2$CH$_2$CH$_2$, Cl), (M-12291, CH$_3$, CH$_3$, F, HOOCCH$_2$CH$_2$CH$_2$, F), (M-12292, CH$_3$, CH$_3$, F, HOOCCH$_2$CH$_2$CH$_2$, CF$_3$), (M-12293, CH$_3$, CH$_3$, F, HOOCCH$_2$CH$_2$CH$_2$, Br), (M-12294, CH$_3$, CH$_3$, F, HOOCCH$_2$CH$_2$CH$_2$, CH$_3$), (M-12295, CH$_3$, CH$_3$, F, (Me)$_2$NCOCH$_2$CH$_2$CH$_2$, H), (M-12296, CH$_3$, CH$_3$, F, (Me)$_2$NCOCH$_2$CH$_2$CH$_2$, Cl), (M-12297, CH$_3$, CH$_3$, F, (Me)$_2$NCOCH$_2$CH$_2$CH$_2$, F), (M-12298, CH$_3$, CH$_3$, F, (Me)$_2$NCOCH$_2$CH$_2$CH$_2$, CF$_3$), (M-12299, CH$_3$, CH$_3$, F, (Me)$_2$NCOCH$_2$CH$_2$CH$_2$, Br), (M-12300, CH$_3$, CH$_3$, F, (Me)$_2$NCOCH$_2$CH$_2$CH$_2$, CH$_3$), (M-12301, CH$_3$, CH$_3$, F, (Me)$_2$NCOCH$_2$CH$_2$CH$_2$CH$_2$, H), (M-12302, CH$_3$, CH$_3$, F, (Me)$_2$NCOCH$_2$CH$_2$CH$_2$CH$_2$, Cl), (M-12303, CH$_3$, CH$_3$, F, (Me)$_2$NCOCH$_2$CH$_2$CH$_2$CH$_2$, F), (M-12304, CH$_3$, CH$_3$, F, (Me)$_2$NCOCH$_2$CH$_2$CH$_2$CH$_2$, CF$_3$), (M-12305, CH$_3$, CH$_3$, F, (Me)$_2$NCOCH$_2$CH$_2$CH$_2$CH$_2$, Br), (M-12306, CH$_3$, CH$_3$, F, (Me)$_2$NCOCH$_2$CH$_2$CH$_2$CH$_2$, CH$_3$), (M-12307, CH$_3$, CH$_3$, F, MeOCH$_2$, H), (M-12308, CH$_3$, CH$_3$, F, MeOCH$_2$, Cl), (M-12309, CH$_3$, CH$_3$, F, MeOCH$_2$, F), (M-12310, CH$_3$, CH$_3$, F, MeOCH$_2$, CF$_3$), (M-12311, CH$_3$, CH$_3$, F, MeOCH$_2$, Br), (M-12312, CH$_3$, CH$_3$, F, MeOCH$_2$, CH$_3$), (M-12313, CH$_3$, CH$_3$, F, EtOCH$_2$, H), (M-12314, CH$_3$, CH$_3$, F, EtOCH$_2$, Cl), (M-12315, CH$_3$, CH$_3$, F, EtOCH$_2$, F), (M-12316, CH$_3$, CH$_3$, F, EtOCH$_2$, CF$_3$), (M-12317, CH$_3$, CH$_3$, F, EtOCH$_2$, Br), (M-12318, CH$_3$, CH$_3$, F, EtOCH$_2$, CH$_3$), (M-12319, CH$_3$, CH$_3$, F, EtOCH$_2$CH$_2$, H), (M-12320, CH$_3$, CH$_3$, F, EtOCH$_2$CH$_2$, Cl), (M-12321, CH$_3$, CH$_3$, F, EtOCH$_2$CH$_2$, F), (M-12322, CH$_3$, CH$_3$, F, EtOCH$_2$CH$_2$, CF$_3$), (M-12323, CH$_3$, CH$_3$, F, EtOCH$_2$CH$_2$, Br), (M-12324, CH$_3$, CH$_3$, F, EtOCH$_2$CH$_2$, CH$_3$), (M-12325, CH$_3$, CH$_3$, F, MeOCH$_2$CH$_2$OCH$_2$CH$_2$, H), (M-12326, CH$_3$, CH$_3$, F, MeOCH$_2$CH$_2$OCH$_2$CH$_2$, Cl), (M-12327, CH$_3$, CH$_3$, F, MeOCH$_2$CH$_2$OCH$_2$CH$_2$, F), (M-12328, CH$_3$, CH$_3$, F, MeOCH$_2$CH$_2$OCH$_2$CH$_2$, CF$_3$), (M-12329, CH$_3$, CH$_3$, F, MeOCH$_2$CH$_2$OCH$_2$CH$_2$, Br), (M-12330, CH$_3$, CH$_3$, F, MeOCH$_2$CH$_2$OCH$_2$CH$_2$, CH$_3$), (M-12331, CH$_3$, CH$_3$, F, MeOCH₂CH₂, H), (M-12332, CH₃, CH₃, F, MeOCH₂CH₂, Cl), (M-12333, CH₃, CH₃, F, MeOCH₂CH₂, F), (M-12334, CH₃, CH₃, F, MeOCH₂CH₂, CF₃), (M-12335, CH₃, CH₃, F, MeOCH₂CH₂, Br), (M-12336, CH₃, CH₃, F, MeOCH₂CH₂, CH₃), (M-12337, CH₃, CH₃, F, HOCH₂, H), (M-12338, CH₃, CH₃, F, HOCH₂, Cl), (M-12339, CH₃, CH₃, F, HOCH₂, F), (M-12340, CH₃, CH₃, F, HOCH₂, CF₃), (M-12341, CH₃, CH₃, F, HOCH₂, Br), (M-12342, CH₃, CH₃, F, HOCH₂, CH₃), (M-12343, CH₃, CH₃, F, HOCH₂CH₂, H), (M-12344, CH₃, CH₃, F, HOCH₂CH₂, Cl), (M-12345, CH₃, CH₃, F, HOCH₂CH₂, F), (M-12346, CH₃, CH₃, F, HOCH₂CH₂, CF₃), (M-12347, CH₃, CH₃, F, HOCH₂CH₂, Br), (M-12348, CH₃, CH₃, F, HOCH₂CH₂, CH₃), (M-12349, CH₃, CH₃, F, HOCH₂CH₂CH₂, H), (M-12350, CH₃, CH₃, F, HOCH₂CH₂CH₂, Cl), (M-12351, CH₃, CH₃, F, HOCH₂CH₂CH₂, F), (M-12352, CH₃, CH₃, F, HOCH₂CH₂CH₂, CF₃), (M-12353, CH₃, CH₃, F, HOCH₂CH₂CH₂, Br), (M-12354, CH₃, CH₃, F, HOCH₂CH₂CH₂, CH₃), (M-12355, CH₃, CH₃, F, HOCH₂CH₂CH₂CH₂, H), (M-12356, CH₃, CH₃, F, HOCH₂CH₂CH₂CH₂, Cl), (M-12357, CH₃, CH₃, F, HOCH₂CH₂CH₂CH₂, F), (M-12358, CH₃, CH₃, F, HOCH₂CH₂CH₂CH₂CF₃), (M-12359, CH₃, CH₃F, HOCH₂CH₂CH₂CH₂, Br), (M-12360, CH₃, CH₃, F, HOCH₂CH₂CH₂CH₂, CH₃), (M-12361, CH₃, CH₃, F, HOCH₂CH₂CH₂CH₂CH₂, H), (M-12362, CH₃CH₃F, HOCH₂CH₂CH₂CH₂CH₂Cl), (M-12363, CH₃, CH₃, F, HOCH₂CH₂CH₂CH₂CH₂F), (M-12364, CH₃, CH₃, F, HOCH₂CH₂CH₂CH₂CH₂, CF₃), (M-12365, CH₃, CH₃, F, HOCH₂CH₂CH₂CH₂CH₂, Br), (M-12366, CH₃CH₃, F, HOCH₂CH₂CH₂CH₂CH₂, CH₃), (M-12367, CH₃, CH₃F, HOCH₂CH₂OCH₂CH₂, H), (M-12368, CH₃CH₃, F, HOCH₂CH₂OCH₂CH₂, Cl), (M-12369, CH₃CH₃F, HOCH₂CH₂OCH₂CH₂, (M-12370, CH₃, CH₃, F, HOCH₂CH₂OCH₂CH₂, CF₃), (M-12371, CH₃, CH₃, F, HOCH₂CH₂OCH₂CH₂, Br), (M-12372, CH₃CH₃, F, HOCH₂CH₂OCH₂CH₂, CH (M-12373, CH₃, CH₃, F, (Me)₂N, H), (M-12374, CH₃, CH₃, F, (Me)₂N, Cl), (M-12375, CH₃, CH₃, F, (Me)₂N, F), (M-12376, CH₃, CH₃, F, (Me)₂N, CF₃), (M-12377, CH₃, CH₃, F, (Me)₂N, Br), (M-12378, CH₃, CH₃, F, (Me)₂N, CH₃), (M-12379, CH₃, CH₃, F, piperidin-4-yl-methyl, H), (M-12380, CH₃, CH₃, F, piperidin-4-yl-methyl, Cl), (M-12381, CH₃, CH₃, F, piperidin-4-yl-methyl, F), (M-12382, CH₃, CH₃, F, piperidin-4-yl-methyl, CF₃), (M-12383, CH₃, CH₃, F, piperidin-4-yl-methyl, Br), (M-12384, CH₃, CH₃, F, piperidin-4-yl-methyl, CH₃), (M-12385, CH₃, CH₃, F, cyclohexylmethyl, H), (M-12386, CH₃, CH₃, F, cyclohexylmethyl, Cl), (M-12387, CH₃, CH₃, F, cyclohexylmethyl, F), (M-12388, CH₃, CH₃, F, cyclohexylmethyl, CF₃), (M-12389, CH₃, CH₃, F, cyclohexylmethyl, Br), (M-12390, CH₃, CH₃, F, cyclohexylmethyl, CH₃), (M-12391, CH₃, CH₃, Cl, H, H), (M-12392, CH₃, CH₃, Cl, H, Cl), (M-12393, CH₃, CH₃, Cl, H, F), (M-12394, CH₃, CH₃, Cl, H, CF₃), (M-12395, CH₃, CH₃, Cl, H, Br), (M-12396, CH₃, CH₃, Cl, H, CH₃), (M-12397, CH₃, CH₃, Cl, F, H), (M-12398, CH₃, CH₃, Cl, F, Cl), (M-12399, CH₃, CH₃, Cl, F, F), (M-12400, CH₃, CH₃, Cl, F, CF₃), (M-12401, CH₃, CH₃, Cl, F, Br), (M-12402, CH₃, CH₃, Cl, F, CH₃), (M-12403, CH₃, CH₃, Cl, Cl, H), (M-12404, CH₃, CH₃, Cl, Cl, Cl), (M-12405, CH₃, CH₃, Cl, Cl, F), (M-12406, CH₃, CH₃, Cl, Cl, CF₃), (M-12407, CH₃, CH₃, Cl, Cl, Br), (M-12408, CH₃, CH₃, Cl, Cl, CH₃), (M-12409, CH₃, CH₃, Cl, CH₃, H), (M-12410, CH₃, CH₃, Cl, CH₃, Cl), (M-12411, CH₃, CH₃, Cl, CH₃, F), (M-12412, CH₃, CH₃, Cl, CH₃, CF₃), (M-12413, CH₃, CH₃, Cl, CH₃, Br), (M-12414, CH₃, CH₃, Cl, CH₃, CH₃), (M-12415, CH₃, CH₃, Cl, Et, H), (M-12416, CH₃, CH₃, Cl, Et, Cl), (M-12417, CH₃, CH₃, Cl, Et, F), (M-12418, CH₃, CH₃, Cl, Et, CF₃), (M-12419, CH₃, CH₃, Cl, Et, Br), (M-12420, CH₃, CH₃, Cl, Et, CH₃), (M-12421, CH₃, CH₃, Cl, n-Pr, H), (M-12422, CH₃, CH₃, Cl, n-Pr, Cl), (M-12423, CH₃, CH₃, Cl, n-Pr, F), (M-12424, CH₃, CH₃, Cl, n-Pr, CF₃), (M-12425, CH₃, CH₃, Cl, n-Pr, Br), (M-12426, CH₃, CH₃, Cl, n-Pr, CH₃), (M-12427, CH₃, CH₃, Cl, c-Pr, H), (M-12428, CH₃, CH₃, Cl, c-Pr, Cl), (M-12429, CH₃, CH₃, Cl, c-Pr, F), (M-12430, CH₃, CH₃, Cl, c-Pr, CF₃), (M-12431, CH₃, CH₃, Cl, c-Pr, Br), (M-12432, CH₃, CH₃, Cl, c-Pr, CH₃), (M-12433, CH₃, CH₃, Cl, i-Pr, H), (M-12434, CH₃, CH₃, Cl, i-Pr, Cl), (M-12435, CH₃, CH₃, Cl, i-Pr, F), (M-12436, CH₃, CH₃, Cl, i-Pr, CF₃), (M-12437, CH₃, CH₃, Cl, i-Pr, Br ), (M-12438, CH₃, CH₃, Cl, i-Pr, CH₃), (M-12439, CH₃, CH₃, Cl, n-Bu, H), (M-124403, CH₃, Cl, n-Bu, Cl), (M-12441, CH₃, CH₃, Cl, n-Bu, F), (M-12442, CH₃, CH₃, Cl, n-Bu, CF₃), (M-12443, CH₃, CH₃, Cl, n-Bu, Br), (M-12444, CH₃, CH₃, Cl, n-Bu, CH₃), (M-12445, CH₃, CH₃, Cl, n-Bu, H), (M-12446, CH₃, CH₃, Cl, i-Bu, Cl), (M-12447, CH₃, CH₃, Cl, i-Bu, F), (M-12448, CH₃, C₃, Cl, i-Bu, CF₃), (M-12449, CH₃, CH₃, Cl, i-Bu, Br), (M-12450, CH₃, CH₃, Cl, i-Bu, CH₃), (M-12451, CH₃, CH₃, Cl, sec-Bu, H), (M-12452, CH₃, CH₃, Cl, sec-Bu, Cl), (M-12453, CH₃, CH₃, Cl, sec-Bu, F), (M-12454, CH₃, CH₃, Cl, sec-Bu, CF₃), (M-12455, CH₃, CH₃, Cl, sec-Bu, Br), (M-12456, CH₃, CH₃, Cl, sec-Bu, CH₃), (M-12457, CH₃, CH₃, Cl, n-Pen, H), (M-12458, CH₃, CH₃, Cl, n-Pen, Cl), (M-12459, CH₃, CH₃, Cl, n-Pen, F), (M-12460, CH₃, CH₃, Cl, n-Pen, CF₃), (M-12461, CH₃, CH₃, Cl, n-Pen, Br), (M-12462, CH₃, CH₃, Cl, n-Pen, CH₃), (M-12463, CH₃, CH₃, Cl, c-Pen, H), (M-12464, CH₃, CH₃, Cl, c-Pen, Cl), (M-12465, CH₃, CH₃, Cl, c-Pen, F), (M-12466, CH₃, CH₃, Cl, c-Pen, CF₃), (M-12467, CH₃, CH₃, Cl, c-Pen, Br), (M-12468, CH₃, CH₃, Cl, c-Pen, CH₃), (M-12469, CH₃, CH₃, Cl, n-Hex, ), (M-12470, CH₃, CH₃, Cl, n-Hex, Cl), (M-12471, CH₃, CH₃, Cl, n-Hex, F), (M-12472, CH₃, CH₃, Cl, n-Hex, CF₃), (M-12473, CH₃, CH₃, Cl, a-Hex, Br), (M-12474, CH₃, CH₃, Cl, n-Hex, CH₃), (M-12475, CH₃, CH₃, Cl, c-Hex, H), (M-12476, CH₃, CH₃, Cl, n-Hex, Cl), (M-12477, CH₃, CH₃, Cl, c-Hex, F), (M-12478, CH₃, CH₃, Cl, c-Hex, CF₃), (M-12479, CH₃, CH₃, Cl, c-Hex, Br), (M-12480, CH₃, CH₃, Cl, c-Hex, CH₃), (M-12481, CH₃, CH₃, Cl, OH, H), (M-12482, CH₃, CH₃, Cl, OH, Cl), (M-12483, CH₃, CH₃, Cl, OH, F), (M-12484, CH₃, CH₃, Cl, OH, CF₃), (M-12485, CH₃, CH₃, Cl, OH, Br), (M-12486, CH₃, CH₃, Cl, OH, CH₃), (M-12487, CH₃, CH₃, Cl, EtO, H), (M-12488, CH₃, CH₃, Cl, EtO, Cl), (M-12489, CH₃, CH₃, Cl, EtO, F), (M-12490, CH₃, CH₃, Cl, EtO, CF₃), (M-12491, CH₃, CH₃, Cl, EtO, Br), (M-12492, CH₃, CH₃, Cl, EtO, CH₃), (M-12493, CH₃, CH₃, Cl, n-PrO, H), (M-12494, CH₃, CH₃, Cl, n-PrO, Cl), (M-12495, CH₃, CH₃, Cl, n-PrO, F), (M-12496, CH₃, CH₃, Cl, n-PrO, CF₃), (M-12497, CH₃, CH₃, C, n-PrO, Br), (M-12498, CH₃, CH₃, Cl, n-PrO, CH₃), (M-12499, CH₃, CH₃, Cl, PhO, H), (M-12500, CH₃, CH₃, Cl, PhO, Cl), (M-12501, CH₃, CH₃, Cl, PhO, F), (M-12502, CH₃, CH₃, Cl, PhO, CF₃), (M-12503, CH₃, CH₃, Cl, PhO, Br), (M-12504, CH₃, CH₃, Cl, PhO, CH₃), (M-12505, CH₃, CH₃, Cl, BnO, H), (M-12506, CH₃, CH₃, Cl, BnO, Cl), (M-12507, CH₃, CH₃, Cl, BnO, F), (M-12508, CH₃, CH₃, Cl, BnO, CF₃), (M-12509, CH₃, CH₃, Cl, BnO, Br), (M-12510, CH₃, CH₃, Cl, BnO, CH₃), (M-12511, CH₃, CH₃, Cl, PhCH₂CH₂O, H), (M-12512, CH₃, CH₃, Cl, PhCH₂CH₂O, Cl), (M-12513, CH₃, CH₃, Cl, PhCH₂CH₂O, F), (M-12514, CH₃, CH₃, Cl, PhCH₂CH₂O, CF₃), (M-12515, CH₃, CH₃, Cl, PhCH₂CH₂O, Br), (M-12516, CH₃, CH₃, Cl, PhCH₂CH₂O, CH₃), (M-12517, CH₃, CH₃, Cl, CF₃O, H), (M-12518, CH₃, CH₃, Cl, CF₃O, Cl), (M-12519, CH₃, CH₃, Cl, CF₃O, F), (M-12520, CH₃, CH₃Cl, CF₃O, CF₃), (M-12521, CH₃CH₃, Cl, CF₃O, Br), (M-12522, CH₃, CH₃, Cl, CF₃O, CH₃)

(M-12523, CH₃, CH₃, Cl, Ph, H), (M-12524, CH₃, CH₃, Cl, Ph, Cl), (M-12525, CH₃, CH₃, Cl, Ph, F), (M-12526, CH₃, CH₃, Cl, Ph, CF₃), (M-12527, CH₃, CH₃, Cl, Ph, Br), (M-12528, CH₃, CH₃, Cl, Ph, CH₃), (M-12529, CH₃, CH₃, Cl, 4-F-Ph, H), (M-12530, CH₃, CH₃, Cl, 4-F-Ph, Cl), (M-12531, CH₃, CH₃, Cl, 4-F-Ph, F), (M-12532, CH₃, CH₃, Cl, 4-F-Ph, CF₃), (M-12533, CH₃, CH₃, Cl, 4-F-Ph, Br), (M-12534, CH₃, CH₃, Cl, 4-F-Ph, CH₃), (M-12535, CH₃, CH₃, Cl, 4-CF₃-Ph, H), (M-12536, CH₃, CH₃, Cl, 4-CF₃-Ph, Cl), (M-12537, CH₃, CH₃, Cl, 4-CF₃-Ph, F), (M-12538, CH₃, CH₃, Cl, 4-CF₃-Ph, CF₃), (M-12539, CH₃, CH₃, Cl, 4-CF₃-Ph, Br), (M-12540, CH₃, CH₃, Cl, 4-CF₃-Ph, CH₃), (M-12541, CH₃, CH₃, Cl, 4-(Me)₂N-Ph, H), (M-12542, CH₃, CH₃, Cl, 4-(Me)₂N-Ph, Cl), (M-12543, CH₃, CH₃, Cl, 4-(Me)₂N-Ph, F), (M-12544, CH₃, CH₃, Cl, 4-(Me)₂N -Ph, CF₃), (M-12545, CH₃, CH₃, Cl, 4-(Me)₂N -Ph, Br), (M-12546, CH₃, CH₃, Cl, 4-(Me)₂N-Ph, CH₃), (M-12547, CH₃, CH₃, Cl, 4-OH-Ph, H), (M-12548, CH₃, CH₃, Cl, 4-OH-Ph, Cl), (M-12549, CH₃, CH₃, Cl, 4-OH-Ph, F), (M-12550, CH₃, CH₃, Cl, 4-OH-Ph, CF₃), (M-12551, CH₃, CH₃, Cl, 4-OH-Ph, Br), (M-12552, CH₃, CH₃, Cl, 4-OH-Ph, CH₃), (M-12551, CH₃, CH₃, Cl, 3,4-di-F-Ph, H), (M-12554, CH₃, CH₃, Cl, 3,4-di-F-Ph, Cl), (M-12555, CH₃, CH₃, Cl, 3,4-di-F-Ph, F), (M-12556, CH₃, CH₃, Cl, 3,4-di-F-Ph, CF₃), (M-12557, CH₃, CH₃, Cl, 3,4-di-F-Ph, Br), (M-12558, CH₃, CH₃, Cl, 3,4-di-F-Ph, CH₃), (M-12559, CH₃, CH₃, Cl, 4-COOH-Ph, H), (M-12560, CH₃, CH₃, Cl, 4-COOH-Ph, Cl), (M-12561, CH₃, CH₃, Cl, 4-COOH -Ph, F), (M-12562, CH₃, CH₃, Cl, 4-COOH -Ph, CF₃), (M-12563, CH₃, CH₃, Cl, 4-COOH-Ph, Br), (M-12564, CH₃, CH₃, Cl, 4-COOH-Ph, CH₃), (M-12565 CH₃, CH₃, Cl, Bn, H), (M-12566, CH₃, CH₃, Cl, Bn, Cl), (M-12567, CH₃, CH₃, Cl, Bn, F), (M-12568, CH₃, CH₃, Cl, Bn, CF₃), (M-12569, CH₃, CH₃, Cl, Bn Br ), (M-12570, CH₃, CH₃, Cl, Bn, CH₃), (M-12571, CH₃, CH₃, Cl, 4-F-Bn, H), (M-12572, CH₃, CH₃, Cl, 4-F-Bn, Cl), (M-12573, CH₃, CH₃, Cl, 4-F-Bn, F), (M-12574, CH₃, CH₃, Cl, 4-F-Bn, CF₃), (M-12575, CH₃, CH₃, Cl, 4-F-Bn, Br), (M-12576, CH₃, CH₃, Cl, 4-F-Bn, CH₃), (M-12577, CH₃, CH₃, Cl, 2-Py, Br), (M-12578, CH₃, CH₃, Cl, 2-Py, Cl), (M-12579, CH₃, CH₃, Cl, 2-Py, F), (M-12580, CH₃, CH₃, Cl, 2-Py, CF₃), (M-12581, CH₃, CH₃, Cl, 2-Py, Br), (M-12582, CH₃, CH₃, Cl, 2-Py, CH₃), (M-12583, CH₃, CH₃, Cl, 3-Py, H), (M-12684, CH₃, CH₃, Cl, 3-Py, Cl), (M-12585, CH₃, CH₃, Cl, 3-Py, F), (M-12586, C₃, CH₃, Cl, 3-Py, CF₃), (M-12587, CH₃, CH₃, Cl, 3-Py, Br), (M-12588, CH₃, CH₃, Cl, 3-Py, CH₃), (M-12589, CH₃, CH₃, Cl, 4-Py, H), (M-12590, CH₃, CH₃, Cl, 4-Py, Cl), (M-12591, CH₃, CH₃, Cl, 4-Py, F), (M-12592, CH₃, CH₃, Cl, 4-Py, CF₃), (M-12593, CH₃, CH₃, Cl, 4-Py, Br), (M-12594, CH₃, CH₃, Cl, 4-Py, CH₃), (M-12595, CH₃, CH₃, Cl, 2-Th, H), (M-12596, CH₃, CH₃, Cl, 2-Th, Cl), (M-12597, CH₃, CH₃, Cl, 2-Th, F), (M-12598, CH₃, CH₃, Cl, 2-Th, CF₃), (M-12599, CH₃, CH₃, Cl, 2-Th, Br), (M-12600, CH₃, CH₃, Cl, 2-Th, CH₃), (M-12601, CH₃, CH₃, Cl, 3-Th, H), (M-12602, CH₃, CH₃, Cl, 3-Th, Cl), (M-12603, CH₃, CH₃, Cl, 3-Th, F), (M-12604, CH₃, CH₃, Cl, 3-Th, CF₃), (M-12605, CH₃, CH₃, Cl, 3-Th, Br), (M-12606, CH₃, CH₃, Cl, 3-Th, CH₃), (M-12607, CH₃, CH₃, Cl, pyrrazol-2-yl, H), (M-12608, CH₃, CH₃, Cl, pyrrazol-2-yl, Cl), (M-12609, CH₃, CH₃, Cl, pyrrazol-2-yl, F), (M-12610, CH₃, CH₃, Cl, pyrrazol-2-yl, CF₃), (M-12611, CH₃, CH₃, Cl, pyrrazol-2-yl, Br), (M-12612, CH₃, CH₃, Cl, pyrrazol-2-yl, CH₃), (M-12613, CH₃, CH₃, Cl, pyrrazol-3-yl, H), (M-12614, CH₃, CH₃, Cl, pyrrazol-3-yl, Cl), (M-12615, CH₃, CH₃, Cl, pyrrazol-3-yl, F), (M-12616, CH₃, CH₃, Cl, pyrrazol-3-yl, CF₃), (M-12617, CH₃, CH₃, Cl, pyrrazol-3-yl, Br), (M-12618, CH₃, CH₃, Cl, pyrrazol-3-yl, CH₃), (M-12619, CH₃, CH₃, Cl, pyrimidin-2-yl, H), (M-12620, CH₃, CH₃, Cl, pyrimidin-2-yl, Cl), (M-12621, CH₃, CH₃, Cl, pyrimidin-2-yl, F), (M-12622, CH₃, CH₃, Cl, pyrimidin-2-yl, CF₃), (M-12623, CH₃, CH₃, Cl, pyrimidin-2-yl, Br), (M-12624, CH₃, CH₃, Cl, pyrimidin-2-yl, CH₃), (M-12625, CH₃, CH₃, Cl, pyrimidin-4-yl, H), (M-12626, CH₃, CH₃, Cl, pyrimidin-4-yl, Cl), (M-12627, CH₃, CH₃, Cl, pyrimidin-4-yl, F), (M-12628, CH₃, CH₃, Cl, pyrimidin-4-yl, CF₃), (M-12629, CH₃, CH₃, Cl, pyrimidin-4-yl, Br), (M-12630, CH₃, CH₃, Cl, pyrimidin-4-yl, CH₃), (M-12631, CH₃, CH₃, Cl, pyrimidin-5-yl, H), (M-12632, CH₃, CH₃, Cl, pyrimidin-5-yl, Cl), (M-12633, CH₃, CH₃, Cl, pyrimidin-5-yl, F), (M-12634, CH₃, CH₃, Cl, pyrimidin-5-yl, CF₃), (M-12635, CH₃, CH₃, Cl, pyrimidin-5-yl, Br), (M-12636, CH₃, CH₃, Cl, pyrimidin-5-yl, CH₃), (M-12637, CH₃, CH₃, Cl, HOOCCH₂CH₂CH₂, H), (M-12638, CH₃, CH₃, Cl, HOOCCH₂CH₂CH₂, Cl), (M-12639, CH₃, CH₃, Cl, HOOCCH₂CH₂CH₂, F), (M-12640, CH₃, CH₃, Cl, HOOCCH₂CH₂CH₂, CF₃), (M-12641, CH₃, CH₃, Cl, HOOCCH₂CH₂CH₂, Br), (M-12642, CH₃, CH₃, Cl, HOOCCH₂CH₂CH₂, CH₃), (M-12643, CH₃, CH₃, Cl, HOOCCH₂CH₂CH₂CH₂, H), (M-12644, CH₃, CH₃, Cl, HOOCCH₂CH₂CH₂CH₂, Cl), (M-12645, CH₃, CH₃, Cl, HOOCCH₂CH₂CH₂CH₂, F), (M-12646, CH₃, CH₃, Cl, HOOCCH₂CH₂CH₂CH₂, CF₃), (M-12647, CH₃, CH₃, Cl, HOOCCH₂CH₂CH₂CH₂, Br), (M-12648, CH₃, CH₃, Cl, HOOCCH₂CH₂CH₂CH₂, CH₃), (M-12649, CH₃, CH₃, Cl, (Me)₂NCOCH₂CH₂CH₂, H), (M-12650, CH₃, CH₃, Cl, (Me)₂NCOCH₂CH₂CH₂, Cl), (M-12651, CH₃, CH₃, Cl, (Me)₂NCOCH₂CH₂CH₂, F), (M-12652, CH₃, CH₃, Cl, (Me)₂NCOCH₂CH₂CH₂, CF₃), (M-12653, CH₃, CH₃, Cl, (Me)₂NCOCH₂CH₂CH₂, Br), (M-12654, CH₃, CH₃, Cl, (Me)₂NCOCH₂CH₂CH₂, CH₃), (M-12655, CH₃, CH₃, Cl, (Me)₂NCOCH₂CH₂CH₂CH₂, H), (M-12656, CH₃, CH₃, Cl, (Me)₂NCOCH₂CH₂CH₂CH₂, Cl), (M-12657, CH₃, CH₃, Cl, (Me)₂NCOCH₂CH₂CH₂CH₂, F), (M-12658, CH₃, CH₃, Cl, (Me)₂NCOCH₂CH₂CH₂CH₂, CF₃), (M-12659, CH₃, CH₃, Cl, (Me)₂NCOCH₂CH₂CH₂CH₂, Br), (M-12660, CH₃, CH₃, Cl, (Me)₂NCOCH₂CH₂CH₂CH₂, CH₃), (M-12661, CH₃, CH₃, Cl, MeOCH₂, H), (M-12662, CH₃, CH₃, Cl, MeOCH₂, Cl), (M-12663, CH₃, CH₃, Cl, MeOCH₂, F), (M-12664, CH₃, CH₃, Cl, MeOCH₂, CF₃), (M-12665, CH₃, CH₃, Cl, MeOCH₂, Br), (M-12666, CH₃, CH₃, Cl, MeOCH₂, CH₃), (M-12667, CH₃, CH₃, Cl, EtOCH₂, H), (M-12668, CH₃, CH₃, Cl, EtOCH₂, Cl), (M-12669, CH₃, CH₃, Cl, EtOCH₂, F), (M-12670, CH₃, CH₃, Cl, EtOCH₂, CF₃), (M-12671, CH₃, CH₃, Cl, EtOCH₂, Br), (M-12672, CH₃, CH₃, Cl, EtOCH₂, CH₃), (M-12673, CH₃, CH₃, Cl, EtOCH₂CH₂, H), (M-12674, CH₃, CH₃, Cl, EtOCH₂CH₂, Cl), (M-12675, CH₃, CH₃, Cl, EtOCH₂CH₂, F), (M-12676, CH₃, CH₃, Cl, EtOCH₂CH₂, CF₃), (M-12677, CH₃, CH₃, Cl, EtOCH₂CH₂, Br), (M-12678, CH₃, CH₃, Cl, EtOCH₂CH₂, CH₃), (M-12679, CH₃, CH₃, Cl, MeOCH₂CH₂OCH₂CH₂, H), (M-12680, CH₃, CH₃, Cl, MeOCH₂CH₂OCH₂CH₂, Cl), (M-12681, CH₃, CH₃, Cl, MeOCH₂CH₂OCH₂CH₂, F), (M-12682, CH₃, CH₃Cl, MeOCH₂CH₂OCH₂CH₂, CF₃), (M-12683, CH₃CF₃, Cl, MeOCH₂CH₂OCH₂CH₂, Br), (M-12684, CH₃, CH₃, Cl, MeOCH₂CH₂OCH₂CH₂, CH₃), (M-12685, CH₃, CH₃, Cl, MeOCH₂CH₂, H), (M-12686, CH₃, C₃, Cl, MeOCH₂CH₂, Cl), (M-12687, CH₃, CH₃, Cl, MeOCH₂CH₂, F), (M-12688, CH₃, CH₃, Cl, MeOCH₂CH₂, CF₃), (M-12689, CH₃, CH₃, Cl, MeOCH₂CH₂, Br), (M-12690, CH₃, CH₃, Cl, MeOCH₂CH₂, CH₃), (M-12691, CH₃, CH₃, Cl, HOCH₂, H), (M-12692, CH₃, CH₃, Cl, HOCH₂, Cl), (M-12693, CH₃, CH₃, Cl, HOCH₂, F), (M-12694, CH₃, CH₃, Cl, HOCH₂, CF₃), (M-12695, CH₃, CH₃, Cl, HOCH₂, Br), (M-12696, CH₃, CH₃, Cl, HOCH₂, CH₃), (M-12697, CH₃, CH₃, Cl, HOCH₂CH₂, H), (M-12698, CH₃, CH₃, Cl, HOCH₂CH₂, Cl), (M-12699, CH₃, CH₃, Cl, HOCH₂CH₂, F), (M-12700, CH₃, CH₃, Cl, HOCH₂CH₂, CF₃), (M-12701, CH₃, CH₃, Cl, HOCH₂CH₂, Br), (M-12702, CH₃, CH₃, Cl, HOCH₂CH₂, CH₃), (M-12703, CH₃, CH₃, Cl, HOCH₂CH₂CH₂, H), (M-12704, CH₃, CH₃, Cl, HOCH₂CH₂CH₂, Cl), (M-12705, CH₃, CH₃, Cl, HOCH₂CH₂CH₂, F), (M-12706, CH₃, CH₃, Cl, HOCH₂CH₂CH₂, CF₃), (M-12707, CH₃, CH₃, Cl, HOCH₂CH₂CH₂, Br), (M-12708, CH₃, CH₃, Cl, HOCH₂CH₂CH₂, CH₃), (M-12709, CH₃, CH₃, Cl, HOCH₂CH₂CH₂CH₂, H), (M-12710, CH₃, CH₃, Cl, HOCH₂CH₂CH₂CH₂, Cl), (M-12711, CH₃, CH₃, Cl, HOCH₂CH₂CH₂CH₂, F), (M-12712, CH₃, CH₃, Cl, HOCH₂CH₂CH₂CH₂, CF₃), (M-12713, CH₃, CH₃, Cl, HOCH₂CH₂CH₂CH₂, Br), (M-12714, CH₃, CH₃, Cl, HOCH₂CH₂CH₂CH₂, CH₃), (M-12715, CH₃, CH₃, Cl, HOCH₂CH₂CH₂CH₂CH₂, H), (M-12716, CH₃, CH₃, Cl, HOCH₂CH₂CH₂CH₂CH₂, Cl), (M-12717, CH₃, CH₃, Cl, HOCH₂CH₂CH₂CH₂CH₂, F), (M-12718, CH₃, CH₃, Cl, HOCH₂CH₂CH₂CH₂CH₂, CF₃), (M-12719, CH₃, CH₃, Cl, HOCH₂CH₂CH₂CH₂CH₂, Br), (M-12720, CH₃, CH₃, Cl, HOCH₂CH₂CH₂CH₂CH₂, CH₃), (M-12721, CH₃, CH₃, Cl, HOCH₂CH₂OCH₂CH₂H), (M-12722, CH₃, CH₃, Cl, HOCH₂CH₂OCH₂CH₂, Cl), (M-12723, CH₃, CH₃, Cl, HOCH₂CH₂OCH₂CH₂, F), (M-12724, CH₃, CH₃, Cl, HOCH₂CH₂CH₂CH₂, CF₃), (M-12725, CH₃, CH₃, Cl, HOCH₂CH₂OCH₂CH₂, Br), (M-12726, CH₃, CH₃, Cl, HOCH₂CH₂OCH₂CH₂, CH₃), (M-12727, CH₃, CH₃, Cl, (Me)₂N, H), (M-12728, CH₃, CH₃, Cl, (Me)₂N, Cl), (M-12729, CH₃, CH₃, Cl, (Me)₂N, F), (M-12730, CH₃, CH₃, Cl, (Me)₂N, CF₃), (M-12731, CH₃, CH₃, Cl, (Me)₂N, Br), (M-12732, CH₃, CH₃, Cl, (Me)₂N, CH₃), (M-12733, CH₃, CH₃, Cl, piperidin-4-yl-methyl, H), (M-12734, CH₃, CH₃, Cl, piperidin-4-yl-methyl, Cl), (M-12735, CH₃, CH₃, Cl, piperidin-4-yl-methyl, F), (M-12736, CH₃, CH₃, Cl, piperidin-4-yl-methyl, CF₃), (M-12737, CH₃, CH₃, Cl, piperidin-4-yl-methyl, Br), (M-12738, CH₃, CH₃, Cl, piperidin-4-yl-methyl, CH₃), (M-12739, CH₃, CH₃, Cl, cyclohexylmethyl, H), (M-12740, CH₃, CH₃, Cl, cyclohexylmethyl, Cl), (M-12741, CH₃, CH₃, Cl, cyclohexylmethyl, F), (M-12742, CH₃, CH₃, Cl, cyclohexylmethyl, CF₃), (M-12743, CH₃, CH₃, Cl, cyclohexylmethyl, Br), (M-12744, CH₃, CH₃, Cl, cyclohexylmethyl, CH₃), (M-12745, H, H, H, CF₃, H), (M-12746, H, H, H, CF₃, Cl), (M-12747, H, H, H, CF₃, F), (M-12748, H, H, H, CF₃, CF₃), (M-12749, H, H, H, CF₃, Br), (M-12750, H, H, H, CF₃, CH₃), (M-12751, H, H, F, CF₃, H), (M-12752, H, H, F, CF₃, Cl), (M-12753, H, H, F, CF₃, F), (M-12754, H, H, F, CF₃, CF₃), (M-12755, H, H, F, CF₃, Br), (M-12756, H, H, F, CF₃, CH₃), (M-12757, H, H, Cl, CF₃, H), (M-12758, H, H, Cl, CF₃, Cl), (M-12759, H, H, Cl, CF₃, F), (M-12760, H, H, Cl, CF₃, CF₃), (M-12761, H, H, Cl, CF₃, Br), (M-12762, H, H, Cl, CF₃, CH₃), (M-12763, H, F, H, CF₃, H), (M-12764, H, F, H, CF₃, Cl), (M-12765, H, F, H, CF₃, F), (M-12766, H, F, H, CF₃, CF₃), (M-12767, H, F, H, CF₃, Br), (M-12768, H, F, H, CF₃, CH₃), (M-12769, H, F, F, CF₃, H), (M-12770, H, F, F, CF₃, Cl), (M-12771, H, F, F, CF₃, F), (M-12772, H, F, F, CF₃, CF₃), (M-12773, H, F, F, CF₃, Br), (M-12774, H, F, F, CF₃, CH₃), (M-12775, H, F, Cl, CF₃, H), (M-12776, H, F, Cl, CF₃, Cl), (M-12777, H, F, Cl, CF₃, F), (M-12778, H, F, Cl, CF₃, CF₃), (M-12779, H, F, Cl, CF₃, Br), (M-12780, H, F, Cl, CF₃, CH₃), (M-12781, H, CH₃, H, CF₃, H), (M-12782, H, CH₃, H, CF₃, Cl), (M-12783, H, CH₃, H, CF₃, F), (M-12784, H, CH₃, H, CF₃, CF₃), (M-12785, H, CH₃, H, CF₃, Br), (M-12786, H, CH₃, H, CF₃, CH₃), (M-12787, H, CH₃, F, CF₃, H), (M-12788, H, CH₃, F, CF₃, Cl), (M-12789, H, CH₃, F, CF₃, F), (M-12790, H, CH₃, F, CF₃, CF₃), (M-12791, H, CH₃, F, CF₃, Br), (M-12792, H, CH₃, F, CF₃, CH₃), (M-12793, H, CH₃, Cl, CF₃, H), (M-12794, H, CH₃, Cl, CF₃, Cl), (M-12795, H, CH₃, Cl, CF₃, F), (M-12796, H, CH₃, Cl, CF₃, CF₃), (M-12797, H, CH₃, Cl, CF₃, Br), (M-12798, H, CH₃, Cl, CF₃, CH₃), (M-12799, F, H, H, CF₃, i-Pr), (M-12800, F, H, H, CF₃, Cl), (M-12801, F, H, H, CF₃, F), (M-12802, F, H, H, CF₃, CF₃), (M-12803, F, H, H, CF₃, Br), (M-12804, F, H, H, CF₃, CH₃), (M-12805, F, H, F, CF₃, H), (M-12806, F, H, F, CF₃, Cl), (M-12807, F, H, F, CF₃, F), (M-12808, F, H, F, CF₃, CF₃), (M-12809, F, H, F, CF₃, Br), (M-12810, F, H, F, CF₃, CH₃), (M-12811, F, H, CT, CF₃, H), (M-12812, F, H, Cl, CF₃, Cl), (M-12813, F, H, Cl, CF₃, F), (M-12814, F, H, Cl, CF₃, CF₃), (M-12815, F, H, Cl, CF₃, Br), (M-12816, F, H, Cl, CF₃, CH₃), (M-12817, F, F, H, CF₃, H), (M-12818, F, F, H, CF₃, Cl), (M-12819, F, F, H, CF₃, F), (M-12820, F, F, H, CF₃, CF₃), (M-12821, F, F, H, CF₃, Br), (M-12822, F, F, H, CF₃, CH₃), (M-12823, F, F, F, CF₃, H), (M-12824, F, F, F, CF₃, Cl), (M-12825, F, F, F, CF₃, F), (M-12826, F, F, F, CF₃, CF₃), (M-12827, F, F, F, CF₃, Br), (M-12828, F, F, F, CF₃, CH₃), (M-12829, F, F, Cl, CF₃, H), (M-12830, F, F, Cl, CF₃, Cl), (M-12831, F, F, Cl, CF₃, F), (M-12832, F, F, Cl, CF₃, CF₃), (M-12833, F, F, Cl, CF₃, Br), (M-12834, F, F, Cl, CF₃, CH₃), (M-12835, F, CH₃, H, CF₃, H), (M-12836, F, CH₃, H, CF₃, Cl), (M-12837, F, CH₃, H, CF₃, F), (M-12838, F, CH₃, H, CF₃, CF₃), (M-12839, F, CH₃, H, CF₃, Br), (M-12840, F, CH₃, H, CF₃, CH₃), (M-12841, F, CH₃, F, CF₃, H), (M-12842, F, CH₃, F, CF₃, Cl), (M-12843, F, CH₃, F, CF₃, F), (M-12844, F, CH₃, F, CF₃, CF₃), (M-12845, F, CH₃, F, CF₃, Br), (M-12846, F, CH₃, F, CF₃, CH₃), (M-12847, F, CH₃, Cl, CF₃, H), (M-12848, F, CH₃, Cl, CF₃, CT), (M-12849, F, CH₃, Cl, CF₃, F), (M-12850, F, CH₃, Cl, CF₃, CF₃), (M-12851, F, CH₃, Cl, CF₃, Br), (M-12852, F, CH₃, Cl, CF₃, CH₃), (M-12853, Cl, H, H, CF₃, i-Pr), (M-12854, Cl, H, H, CF₃, Cl), (M-12855, Cl, H, H, CF₃, F), (M-12856, Cl, H, H, CF₃, CF₃), (M-12857, Cl, H, H, CF₃, Br), (M-12858, Cl, H, H, CF₃, CH₃), (M-12859, Cl, H, F, CF₃, i-Pr), (M-12860, Cl, H, F, CF₃, Cl), (M-12861, Cl, H, F, CF₃, F), (M-12862, Cl, H, F, CF₃, CF₃), (M-12863, Cl, H, F, CF₃, Br), (M-12864, Cl, H, F, CF₃, CH₃), (M-12865, Cl, H, Cl, CF₃, H), (M-12866, Cl, H, Cl, CF₃, Cl), (M-12867, Cl, H, Cl, CF₃, F), (M-12868, Cl, H, Cl, CF₃, CF₃), (M-12869, Cl, H, Cl, CF₃, Br), (M-12870, Cl, H, Cl, CF₃, CH₃), (M-12871, Cl, F, H, CF₃, i-Pr), (M-12872, Cl, F, H, CF₃, Cl), (M-12873, Cl, F, H, CF₃, F), (M-12874, Cl, F, H, CF₃, CF₃), (M-12875, Cl, F, H, CF₃, Br), (M-12876, Cl, F, H, CF₃, CH₃), (M-12877, Cl, F, F, CF₃, H), (M-12878, Cl, F, F, CF₃, Cl), (M-12879, Cl, F, F, CF₃, F), (M-12880, Cl, F, F, CF₃, CF₃), (M-12881, Cl, F, F, CF₃, Br), (M-12882, Cl, F, F, CF₃, CH₃), (M-12883, Cl, F, Cl, CF₃, H), (M-12884, Cl, F, Cl, CF₃, Cl), (M-12885, Cl, F, Cl, CF₃, F), (M-12886, Cl, F, Cl, CF₃, CF₃), (M-12887, Cl, F, Cl, CF₃, Br), (M-12888, Cl, F, Cl, CF₃, CH₃), (M-12889, Cl, CH₃, H, CF₃, i-Pr), (M-12890, Cl, CH₃, H, CF₃, Cl), (M-12891, Cl, CH₃, H, CF₃, F), (M-12892, Cl, CH₃, H, CF₃, CF₃), (M-12893, Cl, CH₃, H, CF₃, Br), (M-12894, Cl, CH₃, H, CF₃, CH₃), (M-12895, Cl, CH₃, F, CF₃, i-Pr), (M-12896, Cl, CH₃, F, CF₃, Cl), (M-12897, Cl, CH₃, F, CF₃, F), (M-12898, Cl, CH₃, F, CF₃, CF₃), (M-12899, Cl, CH₃, F, CF₃, Br), (M-12900, Cl, CH₃, F, CF₃, CH₃), (M-12901, Cl, CH₃, Cl, CF₃, H), (M-12902, Cl, CH₃, Cl, CF₃, Cl), (M-12903, Cl, CH₃, Cl, CF₃, F), (M-12904, Cl, CH₃, Cl, CF₃, CF₃), (M-12905, Cl, CH₃, Cl, CF₃, Br), (M-12906, Cl, CH₃, Cl, CF₃, CH₃), (M-12907, CH₃, H, H, CF₃, i-Pr), (M-12908, CH₃, H, H, CF₃, Cl), (M-12909, CH₃, H, H, CF₃, F), (M-12910, CH₃, H, H, CF₃, CF₃), (M-12911, CH₃, H, H, CF₃, Br), (M-12912, CH₃, H, H, CF₃, CH₃), (M-12913, CH₃, H, F, CF₃, H), (M-12914, CH₃, H, F, CF₃, Cl), (M-12915, CH₃, H, F, CF₃, F), (M-12916, CH₃, H, F, CF₃, CF₃), (M-12917, CH₃, H, F, CF₃, Br), (M-12918, CH₃, H, F, CF₃, CH$_3$), (M-12919, CH$_3$, H, Cl, CF$_3$, H), (M-12920, CH$_3$, H, Cl, CF$_3$, Cl), (M-12921, CH$_3$, H, Cl, CF$_3$, F), (M-12922, CH$_3$, H, Cl, CF$_3$, CF$_3$), (M-12923, CH$_3$, H, Cl, CF$_3$, Br), (M-12924, CH$_3$, H, Cl, CF$_3$, CH$_3$), (M-12925, CH$_3$, F, H, CF$_3$, H), (M-12926, CH$_3$, F, H, CF$_3$, Cl), (M-12927, CH$_3$, F, H, CF$_3$, F), (M-12928, CH$_3$, F, H, CF$_3$, CF$_3$), (M-12929, CH$_3$, F, H, CF$_3$, Br), (M-12930, CH$_3$, F, H, CF$_3$, CH$_3$), (M-12931, CH$_3$, F, F, CF$_3$, H), (M-12932, CH$_3$, F, F, CF$_3$, Cl), (M-12933, CH$_3$, F, F, CF$_3$, F), (M-12934, CH$_3$, F, F, CF$_3$, CF$_3$), (M-12935, CH$_3$, F, F, CF$_3$, Br), (M-12936, CH$_3$, F, F, CF$_3$, CH$_3$), (M-12937, CH$_3$, F, Cl, CF$_3$, H), (M-12938, CH$_3$, F, Cl, CF$_3$, Cl), (M-12939, CH$_3$, F, Cl, CF$_3$, F), (M-12940, CH$_3$, F, Cl, CF$_3$, CF$_3$), (M-12941, CH$_3$, F, Cl, CF$_3$, Br), (M-12942, CH$_3$, F, Cl, CF$_3$, CH$_3$), (M-12943, CH$_3$, CH$_3$, H, CF$_3$H), (M-12944, CH$_3$, CH$_3$, CF$_3$, Cl), (M-12945,-CH$_3$, CH$_3$, H, CF$_3$, F), (M-12946, CH$_3$, CH$_3$, H, CF$_3$, CF$_3$), (M-12947, CH$_3$, CH$_3$, H, CF$_3$, Br), (M-12948, CH$_3$, CH$_3$, H, CF$_3$, CH$_3$), (M-12949, CH$_3$, CH$_3$, F, CF$_3$, H), (M-12950, CH$_3$, CH$_3$, F, CF$_3$, Cl), (M-12951, CH$_3$, CH$_3$, F, CF$_3$, F), (M-12952, CH$_3$, CH$_3$, F, CF$_3$, CF$_3$), (M-12953, CH$_3$, CH$_3$, F, CF$_3$, Br), (M-12954, CH$_3$, CH$_3$, F, CF$_3$, CH$_3$), (M-12955, CH$_3$, CH$_3$, Cl, CF$_3$, H), (M-12956, CH$_3$, CH$_3$, Cl, CF$_3$, Cl), (M-12957, CH$_3$, CH$_3$, Cl, CF$_3$, F), (M-12958, CH$_3$, CH$_3$, Cl, CF$_3$, CF$_3$), (M-12959, CH$_3$, CH$_3$, Cl, CF$_3$, Br), (M-12960, CH$_3$, CH$_3$, Cl, CF$_3$CH$_3$)

Test Examples

Test Example 1

Isolation and Purification of Thrombopoietin (TPO)

Human TPO (hTPO) and murine TPO (mTPO) were purchased from R&D Systems.

Test Example 2

The Increasing Effect in Vitro of the Megakaryocyte Colonies with the Compound (B-1)

We examined the ability of the compound in promoting differentiation of human hematopoietic progenitor cells into mature megakaryocytes. Human bone marrow cells (2.2×10$^5$ cells) were plated in 3-cm dishes and cultured in methylcellulose in Iscove's Modified Dulbecco's medium in the presence of 1% of the compound dissolved in 10% ethanol. After incubation at 37° C. for 7 days in the 5% CO$_2$ incubator, the megakaryocyte colonies were counted. The results are shown in FIG. 1.

Test Example 3

The Thrombopoietic Activity of the Compound (B-1)

Figure 2:
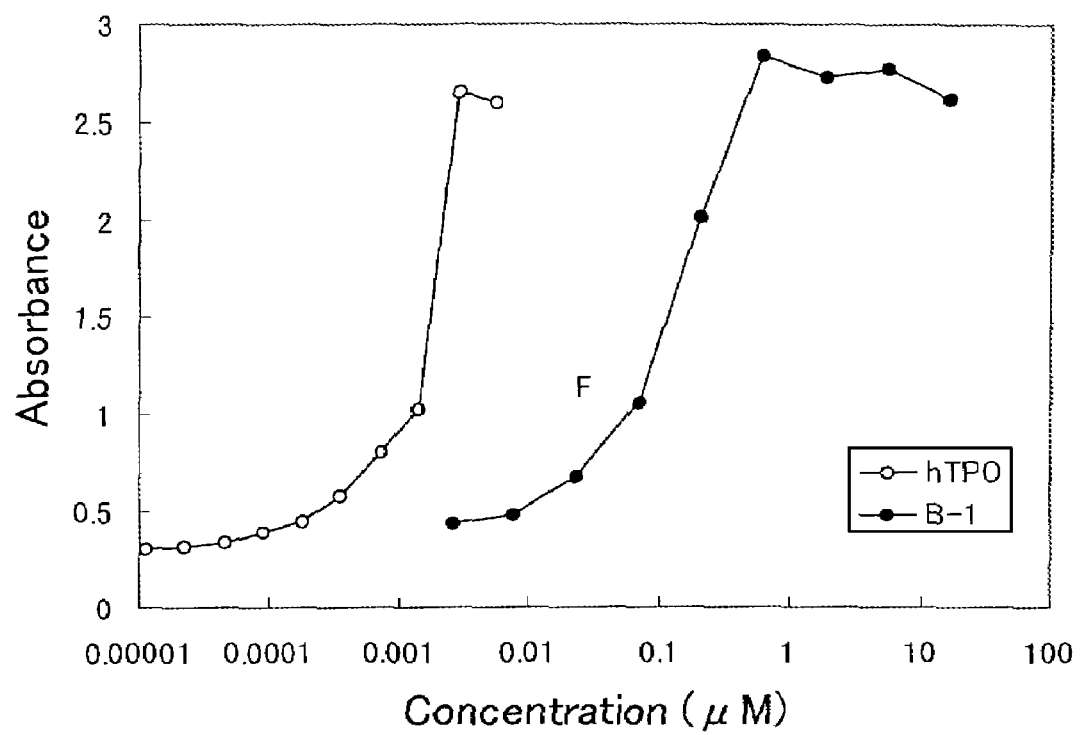
FIG. 2: The chart represents proliferation of the human TPO dependent cells bearing human TPO receptors by the present invention compound, wherein the x-axis is concentration of the present invention compound, and the y-axis is the absorbance as an indicator of cell proliferation. Open circles indicate a response of human TPO, and closed circles indicate a response of the compound (B-1).
Figure 3:
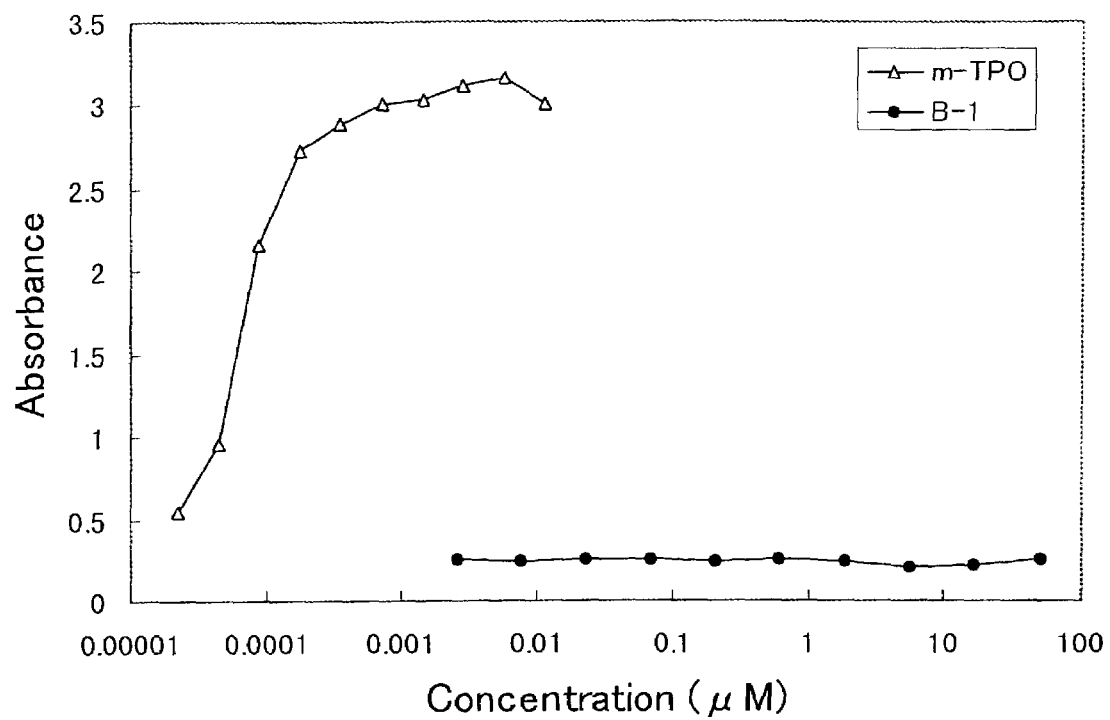
FIG. 3: The chart represents proliferation of the human TPO independent cells bearing no human TPO receptor by the present invention compound, wherein the x-axis is a concentration of the present invention compound, and the y-axis is absorbance as an indicator of cell proliferation. Open triangles indicate a response of human TPO, and closed circles indicate a response of the compound (B-1).

The TPO dependent BaF/hTPOR cell line which was established by introducing human TPO receptor (hTPOR) into BaF-B03 cells according to Collins et al (J. Cell. Physiol., 137:293-298 (1988)) was used to test the thrombopoietic activity of the present compound. The DNA sequences and encoded peptide sequences for human hTPOR have been described by Vigon et al (Proc. Natl. Acad. Sci. USA, 89:5640-5644 (1992)). TPO dose not have any ability to support proliferation of interlukin-3 dependent parental cell line BaF-B03. BAF/hTPOR cells were maintained in RPMI medium and WEHI-3B conditioned medium as a source of murine interleukin-3 (IL-3). These cells were washed and resuspended in RPMI medium without a source of murine IL-3 and seeded into each well of 96-well microtiter plates at a density of 5 X10$^4$ cells per well in the absence or presence of various concentration of hTPO or the present compound. After incubation at 37° C. for 20 hours in the 5% CO$_2$ incubator, 10% WST-1 reagent (Takara Biomedicals, Japan) was added to each wells and the cells were further incubated for 4 hours. The absorbance at 450 nm was measured and the results are shown in FIG. 2. Effect of the present compound on the growth of BAF/mTPOR cell line which was established by introducing murine TPO receptor (mTPOR) into BAF-B03 cells is shown in FIG. 3. Table 8 exemplifies the ED$_{50}$ for tested compounds of the present invention, wherein the ED$_{50}$ is the half concentration of the concentration showing the maximum thrombopoietic activity.

TABLE 33

| Compound No. | ED$_{50}$ (μM) |
|---|---|
| A-1 | 0.117 |
| A-2 | 0.066 |
| A-3 | 0.218 |
| A-4 | 0.124 |
| A-5 | 0.984 |
| A-6 | 0.248 |
| A-8 | 0.529 |
| A-9 | 0.504 |
| A-10 | 0.365 |
| A-11 | 0.0335 |
| A-14 | 0.017 |
| A-17 | 0.864 |
| A-18 | 0.132 |
| A-19 | 0.170 |
| A-20 | 0.610 |
| A-23 | 0.337 |
| A-24 | 0.288 |
| A-25 | 0.150 |
| A-26 | 0.098 |
| A-27 | 0.193 |
| A-28 | 0.099 |
| A-29 | 0.289 |
| A-30 | 0.274 |
| A-31 | 0.056 |
| A-32 | 0.040 |
| A-35 | 0.096 |
| A-36 | 0.095 |
| A-37 | 0.096 |
| A-38 | 0.245 |
| A-39 | 0.044 |
| A-40 | 0.047 |
| A-41 | 0.039 |
| A-42 | 0.050 |
| A-43 | 0.071 |
| A-44 | 0.227 |
| A-45 | 0.203 |
| A-46 | 0.263 |
| A-47 | 0.512 |
| A-48 | 0.473 |
| A-49 | 0.116 |
| A-50 | 0.113 |
| A-51 | 0.568 |
| A-52 | 0.425 |
| A-54 | 0.065 |
| A-55 | 0.037 |
| A-56 | 0.066 |
| A-57 | 0.019 |
| A-58 | 0.497 |
| A-59 | 0.164 |
| A-60 | 0.023 |
| A-61 | 0.207 |
| A-62 | 0.101 |
| A-63 | 0.025 |
| A-64 | 0.204 |
| A-65 | 0.028 |
| A-66 | 0.211 |
| A-68 | 0.222 |

TABLE 33-continued

| Compound No. | ED$_{50}$ (μM) |
|---|---|
| A-69 | 0.071 |
| A-70 | 0.089 |
| A-72 | 0.119 |
| A-73 | 0.075 |
| A-74 | 0.472 |
| A-75 | 0.073 |
| A-76 | 0.205 |
| A-77 | 0.110 |
| A-78 | 0.408 |
| A-79 | 0.410 |
| A-80 | 0.066 |
| A-81 | 0.071 |
| A-82 | 0.199 |
| A-83 | 0.077 |
| A-84 | 0.023 |
| A-85 | 0.026 |
| A-86 | 0.243 |
| A-87 | 0.710 |
| A-88 | 0.028 |
| A-89 | 0.072 |
| A-90 | 0.805 |
| A-91 | 0.076 |
| A-92 | 0.178 |
| A-93 | 0.008 |
| B-1 | 0.081 |
| B-2 | 0.257 |
| B-3 | 0.156 |
| B-4 | 0.089 |
| B-5 | 0.123 |
| B-6 | 0.084 |
| B-7 | 0.059 |
| B-8 | 0.378 |
| B-9 | 0.082 |
| B-11 | 0.236 |
| B-12 | 0.207 |
| B-13 | 0.213 |
| B-14 | 0.305 |
| B-15 | 0.197 |
| B-16 | 0.182 |
| B-17 | 0.244 |
| B-18 | 0.15 |
| B-19 | 0.15 |
| B-20 | 0.425 |
| B-25 | 0.367 |
| B-26 | 0.346 |
| B-27 | 0.707 |
| B-28 | 0.565 |
| B-29 | 0.181 |
| B-30 | 0.177 |
| B-31 | 0.178 |
| B-32 | 0.123 |
| B-33 | 0.372 |
| B-34 | 0.398 |
| B-35 | 0.186 |
| B-36 | 0.163 |
| B-37 | 0.139 |
| B-38 | 0.239 |
| B-39 | 0.729 |
| B-40 | 0.201 |
| B-41 | 0.19 |
| B-42 | 0.236 |
| B-43 | 0.303 |
| B-46 | 0.213 |
| C-4 | 0.922 |
| D-1 | 0.276 |
| F-1 | 0.174 |
| F-2 | 0.144 |
| F-3 | 0.198 |
| G-1 | 0.261 |
| G-2 | 0.299 |
| G-3 | 0.430 |
| G-4 | 0.240 |
| G-5 | 0.260 |
| G-6 | 0.370 |
| G-7 | 0.400 |
| G-8 | 0.360 |
| H-7 | 0.038 |
| H-8 | 0.250 |
| J-11 | 0.311 |
| J-12 | 0.107 |
| J-13 | 0.116 |
| J-14 | 0.036 |
| J-15 | 0.011 |
| K-1 | 0.189 |
| K-2 | 0.975 |
| K-3 | 0.693 |
| K-5 | 0.403 |
| K-6 | 0.077 |
| K-10 | 0.475 |
| K-11 | 0.373 |
| K-12 | 0.208 |
| K-13 | 0.260 |
| K-15 | 0.465 |
| L-1 | 0.208 |
| L-2 | 0.143 |
| L-3 | 0.321 |
| L-4 | 0.256 |

As shown in FIG. 1, addition of the compounds of the present invention induced forming megakaryocyte colonies and the number of colonies increased depending on the concentration of the compounds. This result revealed that the compounds of the present invention induced the differentiation of human bone marrow cells and produced megakaryocytes having ability of producing platelet.

The compound supported the proliferation of TPO-dependent BaF/hTPOR in a dose-dependent manner as shown in FIG. 2. BaF/mTPOR expressing murine TPOR was not induced the proliferation by compounds as shown in FIG. 3. These results suggest that the compound of the present invention exert the thrombopoietic activity by interacting with hTPOR because it is active only in cells expressing hTPOR.

Formulation Example

Formulation Example 1

Granules are prepared using the following ingredients.

| Ingredients | |
|---|---|
| The compound represented by the formula (I) | 10 mg |
| Lactose | 700 mg |
| Corn starch | 274 mg |
| HPC-L | 16 mg |
| | 1000 mg |

The compound represented by the formula (I) and lactose are made pass through a 60 mesh sieve. Corn starch is made pass through a 120 mesh sieve. They are mixed by a twin shell blender. An aqueous solution of HPC-L (low mucosity hydroxypropylcellulose) is added to the mixture and the resulting mixture is kneaded, granulated (by the extrusion with pore size 0.5 to 1 mm mesh), and dried. The dried granules thus obtained are sieved by a swing sieve (12/60 mesh) to yield the granules.

Formulation 2

Powders for filling capsules are prepared using the following ingredients.

| Ingredients | |
| --- | --- |
| The compound represented by the formula (I) | 10 mg |
| Lactose | 79 mg |
| Corn starch | 10 mg |
| Magnesium stearate | 1 mg |
| | 100 mg |

The compound represented by the formula (I) and lactose are made pass through a 60 mesh sieve. Corn starch is made pass through a 120 mesh sieve. These ingredients and magnesium stearate are mixed by a twin shell blender. 100 mg of the 10-fold trituration is filled into a No. 5 hard gelatin capsule.

Formulation 3

Granules for filling capsules are prepared using the following ingredients.

| Ingredients | |
| --- | --- |
| The compound represented by the formula (I) | 15 mg |
| Lactose | 90 mg |
| Corn starch | 42 mg |
| HPC-L | 3 mg |
| | 150 mg |

The compound represented by the formula (I) and lactose are made pass through a 60 mesh sieve. Corn starch is made pass through a 120 mesh sieve. After mixing them, an aqueous solution of HPC-L is added to the mixture and the resulting mixture is kneaded, granulated, and dried. After the dried granules are lubricated, 150 mg of that are filled into a No. 4 hard gelatin capsule.

Formulation 4

Tablets are prepared using the following ingredients.

| Ingredients | |
| --- | --- |
| The compound represented by the formula (I) | 10 mg |
| Lactose | 90 mg |
| Microcrystal cellulose | 30 mg |
| CMC-Na | 15 mg |
| Magnesium stearate | 5 mg |
| | 150 mg |

The compound represented by the formula (I), lactose, microcrystal cellulose, and CMC-Na (carboxymethylcellulose sodium salt) are made pass through a 60 mesh sieve and then mixed. The resulting mixture is mixed with magnesium stearate to obtain the mixed powder for the tablet formulation. The mixed powder is compressed to yield tablets of 150 mg.

Formulation 5

Intravenous formulations are prepared using the following ingredients.

Ingredients The compound represented by the formula (I) 100 mg

| Saturated fattyacid glyceride | 1000 ml |
| --- | --- |

Usually a solution of ingredients above described is administered intravenously to a patient by the speed of 1 ml/min.

INDUSTRIAL APPLICABILITY

The compounds of the present invention have thrombopoietin receptor agonism and are useful as the treating or preventing agent for hemopathy accompanied with unusual count of platelet, for example, thrombocytopenia and the like

The invention claimed is:

1. A compound represented by the general formula (III):

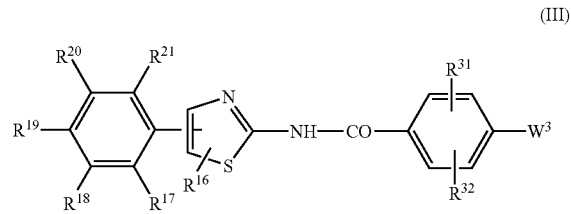

(III)

wherein $R^{16}$ is a hydrogen atom, optionally substituted lower alkyl, carboxy, lower alkyloxycarbonyl, halogen atom, or optionally substituted aminocarbonyl;

$R^{17}, R^{18}, R^{19}, R^{20}$, and $R^{21}$ are each independently a hydrogen atom, optionally substituted lower alkyl by one or more substituent(s) selected from substituent group B, cycloalkyl, optionally substituted alkyoxy by one or more substituent(s) selected from substituent group B, alkylthio, halogen atom, optionally substituted phenyl by one or more halogen atoms, optionally substituted heteroaryl by one or more halogen atoms, or optionally substituted nonaromatic heterocyclic group by one or more halogen atoms;

substituent group B consists of hydroxy, alkyloxy, halogen atom, carboxy, lower alkyloxycarbonyl, aryloxycarbonyl, optionally substituted amino wherein the substituent is an alkyl, phenyl, non-aromatic heterocyclic group, or heteroaryl; or $R^{16}$ and $R^{17}$ taken together may form —$CH_2$—, —$CH_2CH_2$—, —$CH_2CH_2CH_2$—, —$OCH_2$—, or —$SCH_2$—;

$R^{31}$ and $R^{32}$ are each independently a hydrogen atom, lower alkyl, halogen atom, halo(lower)alkyl, lower alkyloxy, halo(lower)alkyloxy, or hydroxy;

$W^3$ is represented by the formula:

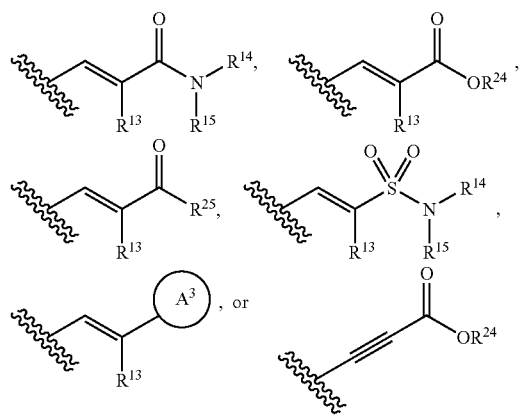

wherein $R^{13}$ is a hydrogen atom, lower alkyl, lower alkyloxy, lower alkylthio, or halogen atom;
$R^{14}$ and $R^{15}$ are each independently a hydrogen atom, or optionally substituted lower alkyl, optionally substituted lower alkenyl, optionally substituted lower alkynyl, optionally substituted cycloalkyl, optionally substituted aryl, optionally substituted aralkyl, optionally substituted heteroaryl, optionally substituted heteroarylalkyl, or optionally substituted non-aromatic heterocyclic group, each substituted by one or more substituent(s) selected from substituent group A;
substituent group A consists of a halogen atom, halo(lower)alkyl, optionally substituted amino, carboxy, lower alkylthio, lower alkylsilyl, or lower alkyloxy;
$R^{24}$ is a hydrogen atom or lower alkyl;
$R^{25}$ is lower alkyl, optionally substituted aryl, or optionally substituted non-aromatic heterocyclic group;
$A^3$ is heteroaryl;
or pharmaceutically acceptable salts thereof.

2. A compound represented by the general formula (IV-A):

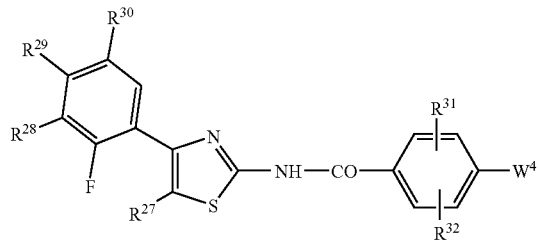

wherein $R^{27}$ is a hydrogen atom, C1-C3 alkyl, trifluoromethyl, or halogen atom;
$R^{28}$, $R^{29}$, and $R^{30}$ are independently a hydrogen atom, optionally substituted lower alkyl by one or more substituent(s) selected from substituent group B, cycloalkyl, optionally substituted alkyoxy by one or more substituent(s) selected from substituent group B, alkylthio, halogen atom, optionally substituted phenyl by one or more halogen atoms, optionally substituted heteroaryl by one or more halogen atoms, or optionally substituted nonaromatic heterocyclic group by one or more halogen atoms;
substituent group B consists of hydroxy, alkyloxy, halogen atom, carboxy, lower alkyloxycarbonyl, aryloxycarbonyl, optionally substituted amino wherein the substituent is an alkyl, phenyl, non-aromatic heterocyclic group, or heteroaryl;
$R^{31}$ and $R^{32}$ are each independently a hydrogen atom, lower alkyl, halogen atom, halo(lower)alkyl, lower alkyloxy, halo(lower)alkyloxy, or hydroxy;
$W^4$ is a group represented by the formula:

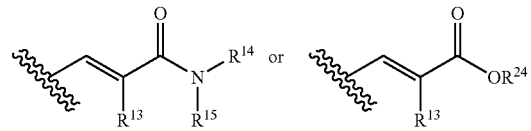

wherein $R^{13}$ is a hydrogen atom, lower alkyl, lower alkyloxy, lower alkylthie, or halogen atom;
$R^{14}$ and $R^{15}$ are each independently a hydrogen atom, optionally substituted lower alkyl, optionally substituted lower alkenyl, optionally substituted lower alkynyl, optionally substituted cycloalkyl, optionally substituted aryl, optionally substituted aralkyl, optionally substituted heteroaryl, optionally substituted heteroarylalkyl, or optionally substituted non-aromatic heterocyclic group, each substituted by one or more substituent(s) selected from substituent group A,
substituent group A consists of a halogen atom, halo(lower)alkyl, optionally substituted amino, carboxy, lower alkylthio, lower alkylsilyl, or lower alkyloxy;
$R^{24}$ is a hydrogen atom or lower alkyl;
or pharmaceutically acceptable salts thereof.

3. A pharmaceutical composition containing as the active ingredient a compound of any one of claims 1, or 2.

4. A pharmaceutical composition containing as the active ingredient a compound of any one of claims 1 or 2, which is exhibiting thrombopoietin receptor agon ism.

5. A pharmaceutical composition for platelet production modification, comprising at least one compound according to any one of claims 1 or 2 and at least one of an excipient, binder, penetrant, disintegrator, or lubricant.

6. A method for modifiering a platelet production of a mammal, including a human, which comprises administration to said mammal of a compound of any one of claims 1 or 2 in a pharmaceutically effective amount.

* * * * *

UNITED STATES PATENT AND TRADEMARK OFFICE
CERTIFICATE OF CORRECTION

PATENT NO. : 7,582,665 B2 Page 1 of 1
APPLICATION NO. : 10/169362
DATED : September 1, 2009
INVENTOR(S) : Takemoto et al.

It is certified that error appears in the above-identified patent and that said Letters Patent is hereby corrected as shown below:

In claim 2, column 224, line 27, "alkylthie," should read --alkylthio,--.

In claim 4, column 224, line 46, "agon ism." should read --agonism.--.

In claim 6, column 224, line 51, "modifiering" should read --modifying--.

Signed and Sealed this

Twenty-fourth Day of November, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,582,665 B2 | Page 1 of 1 |
| APPLICATION NO. | : 10/169362 | |
| DATED | : September 1, 2009 | |
| INVENTOR(S) | : Hiroshi Takemoto et al. | |

It is certified that error appears in the above-identified patent and that said Letters Patent is hereby corrected as shown below:

On the Title page,

[*] Notice:    Subject to any disclaimer, the term of this patent is extended or adjusted under 35 U.S.C. 154(b) by 403 days Delete the phrase "by 403 days" and insert -- by 641 days --

Signed and Sealed this

Twenty-second Day of June, 2010

David J. Kappos
*Director of the United States Patent and Trademark Office*